(12) United States Patent
Mosyak et al.

(10) Patent No.: US 7,555,415 B2
(45) Date of Patent: Jun. 30, 2009

(54) METHODS FOR THE DESIGN OF ESTROGEN RECEPTOR LIGANDS

(75) Inventors: Lidia Mosyak, Newton, MA (US);
Zhang Bao Xu, Tewksbury, MA (US);
Mark Stahl, Lexington, MA (US);
Wah-Tung Hum, Acton, MA (US);
William Stuart Somers, Lexington, MA (US); Eric Steven Manas, Lafayette Hill, PA (US)

(73) Assignee: Wyeth, Madison, NJ (US)

( * ) Notice: Subject to any disclaimer, the term of this patent is extended or adjusted under 35 U.S.C. 154(b) by 135 days.

(21) Appl. No.: 11/334,982

(22) Filed: Jan. 18, 2006

(65) Prior Publication Data

US 2006/0160836 A1    Jul. 20, 2006

Related U.S. Application Data

(60) Provisional application No. 60/644,897, filed on Jan. 19, 2005.

(51) Int. Cl.
*G06G 7/48* (2006.01)
*G01N 33/50* (2006.01)
*G06F 19/00* (2006.01)

(52) U.S. Cl. .............................. 703/11; 702/19; 702/27

(58) Field of Classification Search ................. 703/11
See application file for complete search history.

(56) References Cited

U.S. PATENT DOCUMENTS

2004/0167155 A1   8/2004   Molinari et al.

FOREIGN PATENT DOCUMENTS

WO   WO 98/56812 A    12/1998
WO   WO 2004/031159 A   4/2004

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol., 61, pp. 525-536.*
Cudney R. Protein Crystallization and Dumb Luck. The Rigaku Journal. 1999. vol. 16, No. 1, pp. 1-7.*
Ginalski et al., Comparative Modeling for Protein Structure Prediction. Current Opinion in Structural Biololgy, 2006. vol. 16, pp. 172-177.*
Goodsell et al., Journal of Molecular Recognition, 1996, vol. 9, pp. 1-5.*
Böhm et al., Journal of Computer-Aided Molecular Design, 1992, vol. 6, pp. 61-78.*
Dean et al. BioEssays, 1994, 16(9):683-687.*
Egner et al., "Different Ligands-Different Receptor Conformations: Modeling of the hERα LBD in Complex with Agonists and Antagonists" *Med. Res. Reviews* 21(6):523-539 (2001).

(Continued)

*Primary Examiner*—Suzanne M. Noakes
(74) *Attorney, Agent, or Firm*—Lowrie, Lando & Anastasi, LLP

(57) ABSTRACT

Estrogen receptor ligands, estrogen receptor polypeptide/ligand complexes, crystals of estrogen receptor polypeptide/ligand complexes, and related methods and software systems are disclosed.

28 Claims, 6 Drawing Sheets

OTHER PUBLICATIONS

Klebe, "Recent developments in structure-based drug design" *J. Mol. Med.* 78:269-281 (2000).

Olivier et al., "Raloxifene-induced myeloma cell apoptosis: a study of nuclear factor-kappaB inhibition and gene expression signature," *Mol. Pharmacol.* 69:1615-1623 (2006) (Abstract only).

Somjen et al., ""Non-hypercalcemic" analogs of 1α,25 dihydrozy vitamin D augment the induction of creatine kinase B by estrogen and selective estrogen receptor moduclators (SERMS) in osteolbast-like cells and rat skeletal organs" *J. Steroid Biochem. & Mol. Biol.* 72:79-88 (2000).

Wurtz et al., "Three-Dimensional Models of Estrogen Receptor Ligand Binding Domain Complexes, Based on Related Crystal Structures and Mutational and Structure-Activity Relationship Data" *J. Med. Chem.* 41:1803-1814 (1998).

Brzozowski et al., "Molecular basis of agonism and antagonism in the oestrogen receptor" *Nature* 389:753-758 (1997).

Shiau et al., "The Structural Basis of Estrogen Receptor/Coactivator Recognition and the Antagonism of This Interaction by Tamoxifen" *Cell* 95:927-937 (1998).

Brzozowski et al., "Molecular basis of agonism and antagonism in the oestrogen receptor" *Nature* 389:753-758 (1997).

Kim et al., "Estrogen Receptor Ligands. II. Discovery of Benzoxathiins as Potent, Selective Estrogen Receptor α Modulators" *J. Med. Chem.* 47(9):2171-2175 (2004).

Kong et al., "Structure and mechanism of the oestrogen receptor" *Biochem. Soc. Transactions* 31(1):56-59 (2002).

Leduc et al., "Helix-stabilized cyclic peptides as selective inhibitors of steroid receptor-coactivator interactions" *PNAS* 100(20):11273-11278 (2003).

Ruff et al., "Estrogen receptor transcription and transactivation Structure-function relationship in DNA- and ligand-binding domains of estrogen receptors" *Breast Cancer Res.* 2:353-359 (2000).

Shiau et al., "Structural characterization of a subtype-selective ligand reveals a novel mode of estrogen receptor antagonism" *Nature Structural Biol.* 9(5):359-363 (2002).

Shiau et al., "The Structural Basis of Estrogen Receptor/Coactivator Recognition and the Antagonism of This Interaction by Tamoxifen" *Cell* 95:927-937 (1998).

Um et al., "Synthesis of Novel Quinolinecarboxamide Derivatives with Estrogenic Activity" *Bull. Korean Chem. Soc.* 24(5):677-680 (2003).

Waernmark et al., "Interaction of Transcriptional Intermediary Factor 2 Nuclear Receptor Box Peptides with the Coactivator Binding Site of Estrogen Receptor α" *J. biol. Chem.* 277(24):21862-21868 (2002).

\* cited by examiner

```
  1  MTMTLHTKASGMALLHQIQGNELEPLNRPQLKIPLERPLGEVYLDSSKPA
 51  VYNYPEGAAYEFNAAAAANAQVYGQTGLPYGPGSEAAAFGSNGLGGFPPL
101  NSVSPSPLMLLHPPPQLSPFLQPHGQQVPYYLENEPSGYTVREAGPPAFY
151  RPNSDNRRQGGRERLASTNDKGSMAMESAKETRYCAVCNDYASGYHYGVW
201  SCEGCKAFFKRSIQGHNDYMCPATNQCTIDKNRRKSCQACRLRKCYEVGM
251  MKGGIRKDRRGGRMLKHKRQRDDGEGRGEVGSAGDMRAANLWPSPLMIKR
301  SKKNSLALSLTADQMVSALLDAEPPILYSEYDPTRPFSEASMMGLLTNLA
351  DRELVHMINWAKRVPGFVDLTLHDQVHLLECAWLEILMIGLVWRSMEHPV
401  KLLFAPNLLLDRNQGKCVEGMVEIFDMLLATSSRFRMMNLQGEEFVCLKS
451  IILLNSGVYTFLSSTLKSLEEKDHIHRVLDKITDTLIHLMAKAGLTLQQQ
501  HQRLAQLLLILSHIRHMSNKGMEHLYSMKCKNVVPLYDLLLEMLDAHRLH
551  APTSRGGASVEETDQSHLATAGSTSSHSLQKYYITGEAEGFPATV
```

(SEQ ID NO:1)

FIG. 6

```
                        SEQUENCE LISTING

<160> NUMBER OF SEQ ID NOS: 1

<210> SEQ ID NO 1
<211> LENGTH: 595
<212> TYPE: PRT
<213> ORGANISM: Homo sapiens

<400> SEQUENCE: 1

Met Thr Met Thr Leu His Thr Lys Ala Ser Gly Met Ala Leu Leu His
 1               5                  10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
```

-continued

```
            210                 215                 220
Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
                450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
                515                 520                 525

Lys Cys Lys Asn Val Val Pro Leu Tyr Asp Leu Leu Leu Glu Met Leu
                530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
                595
```

METHODS FOR THE DESIGN OF ESTROGEN RECEPTOR LIGANDS

RELATED APPLICATIONS

This application claims the benefit of U.S. Provisional Application No. 60/644,897, filed Jan. 19, 2005, which is incorporated herein by reference in its entirety.

TECHNICAL FIELD

This invention relates to estrogen receptor ligands, estrogen receptor polypeptide/ligand complexes, crystals of estrogen receptor polypeptide/ligand complexes, and related methods and software systems.

BACKGROUND

17β-estradiol (E2) is a steroidal hormone that regulates a variety of biological processes. Many of the physiological effects of E2 are mediated by estrogen receptors (ERs), such as estrogen receptor alpha and estrogen receptor beta. Interaction of E2 with an estrogen receptor can cause activation of the receptor, which results in its transport from the cytoplasm into the nucleus where it can function as a transcriptional activator.

E2, through its interaction with estrogen receptor alpha (ERalpha) regulates the differentiation and maintenance of different tissues including reproductive tissues. E2 can also inhibit IL-1β induced NF-κB reporter activity and IL-6 expression in an estrogen receptor-dependent manner. This activity correlates with an anti-inflammatory activity of E2 in vivo.

SUMMARY

In one aspect the invention features a crystallized polypeptide-ligand complex that includes an estrogen receptor polypeptide and a ligand having a fused ring system. The fused ring system includes at least two fused rings, at least one of which includes at least one nitrogen.

In another aspect, the invention features a crystallized polypeptide-ligand complex that includes an estrogen receptor polypeptide and a ligand having a fused ring system having at least two fused rings, at least one of which includes at least two heteroatoms.

In a further aspect the invention features a crystallized polypeptide-ligand complex that includes an estrogen receptor polypeptide and a ligand. The ligand inhibits NFκB transcriptional activity and does not stimulate proliferation of mouse or human uterine tissue.

In another aspect, the invention features a composition including a crystal. The crystal includes an estrogen receptor polypeptide and a ligand having a fused ring system including at least two fused rings, at least one of which includes at least one nitrogen.

In another aspect, the invention features a composition including a crystal that includes an estrogen receptor polypeptide and a ligand having a fused ring system. The fused ring system includes at least two fused rings, at least one of which includes at least two heteroatoms.

In another aspect the invention features a composition including a crystal that includes an estrogen receptor polypeptide and a ligand. The ligand inhibits NFκB transcriptional activity and does not stimulate proliferation of mouse or human uterine tissue.

In another aspect, the invention features a method that includes using a three-dimensional model of a complex to design an agent that interacts with the estrogen receptor polypeptide. The complex includes an estrogen receptor polypeptide bound to a ligand, and the ligand bound to the estrogen receptor polypeptide has a fused ring system that includes at least two fused rings. At least one of the at least two fused rings includes at least one nitrogen.

In another aspect, the invention features a method that includes using a three-dimensional model of a complex to design an agent that interacts with an estrogen receptor polypeptide. The complex includes an estrogen receptor polypeptide bound to a ligand, and the ligand bound to the estrogen receptor polypeptide has a fused ring system that includes at least two fused rings. At least one of the at least two fused rings includes at least two heteroatoms.

In another aspect, the invention features a method that includes using a three-dimensional model of a complex to design an agent that interacts with an estrogen receptor polypeptide. The complex includes an estrogen receptor polypeptide bound to a ligand, and the ligand bound to the estrogen receptor polypeptide inhibits NFκB transcriptional activity and does not stimulate proliferation of mouse or uterine tissue.

In another aspect, the invention features a method that includes using a three-dimensional model of an estrogen receptor polypeptide to design an agent that interacts with the estrogen receptor polypeptide.

In another aspect, the invention features a method that includes selecting an agent by performing rational drug design with a three-dimensional structure of a crystalline complex that includes an estrogen receptor polypeptide. The method includes contacting the agent with an estrogen receptor polypeptide and detecting the ability of the agent to bind the estrogen receptor polypeptide.

In another aspect, the invention features a method that includes contacting an estrogen receptor polypeptide with a ligand to form a composition and crystallizing the composition to form a crystalline complex in which the ligand is bound to the estrogen receptor polypeptide. The ligand has a fused ring system including at least two fused rings, at least one of which includes at least one nitrogen. The crystalline complex diffracts X-rays to a resolution of at least about 3.5 Å.

In another aspect, the invention features a method that includes contacting an estrogen receptor polypeptide with a ligand to form a composition and crystallizing the composition to form a crystalline complex in which the ligand is bound to the estrogen receptor polypeptide. The ligand has a fused ring system including at least two fused rings, at least one of which includes at least two heteroatoms. The crystalline complex diffracts X-rays to a resolution of at least about 3.5 Å.

In another aspect, the invention features a method that includes contacting an estrogen receptor polypeptide with a ligand to form a composition, and crystallizing the composition to form a crystalline complex in which the ligand is bound to the estrogen receptor polypeptide. The ligand inhibits NFκB transcriptional activity and does not stimulate proliferation of mouse or uterine tissue. The crystalline complex diffracts X-rays to a resolution of at least about 3.5 Å.

In yet another aspect, the invention features a software system that includes instructions for causing a computer system to accept information relating to the structure of an estrogen receptor polypeptide bound to a ligand and information relating to a candidate agent. From this information, the computer system can determine binding characteristics of the candidate agent to the estrogen receptor polypeptide. The ligand bound to the estrogen receptor polypeptide has a fused ring system including at least two fused rings, at least one of which includes at least one nitrogen.

In another aspect, the invention features a software system that includes instructions for causing a computer system to accept information relating to the structure of an estrogen receptor polypeptide bound to a ligand and information relating to a candidate agent. From this information, the computer system can determine the binding characteristics of the candidate agent to the estrogen receptor polypeptide. The ligand bound to the estrogen receptor polypeptide has a fused ring system including at least two fused rings, at least one of which has at least two heteroatoms.

In another aspect, the invention features a software system that includes instructions for causing a computer system to accept information relating to the structure of an estrogen receptor polypeptide bound to a ligand and information relating to a candidate agent. From this information, the computer system can determine the binding characteristics of the candidate agent to the estrogen receptor polypeptide. The ligand bound to the estrogen receptor polypeptide inhibits NFκB transcriptional activity and does not stimulate proliferation of mouse or uterine tissue.

In another aspect, the invention features a computer program residing on a computer readable medium on which a plurality of instructions is stored. When the instructions are executed by one or more processors, the one or more processors accept information relating to the structure of a complex that includes an estrogen receptor polypeptide bound to a ligand and information relating to a candidate agent. From this information, the one or more processors determine binding characteristics of the candidate agent to the estrogen receptor polypeptide. The ligand bound to the estrogen receptor polypeptide has a fused ring system including at least two fused rings, at least one of which includes at least one nitrogen.

In another aspect, the invention features a computer program residing on a computer readable medium on which a plurality of instructions is stored. When the instructions are executed by one or more processors, the one or more processors accept information relating to the structure of a complex that includes an estrogen receptor polypeptide bound to a ligand and information relating to a candidate agent. From this information the one or more processors determine binding characteristics of the candidate agent to the estrogen receptor polypeptide. The ligand bound to the estrogen receptor polypeptide has a fused ring system including at least two fused rings, at least one of which includes at least two heteroatoms.

In another aspect, the invention features a computer program residing on a computer readable medium on which a plurality of instructions is stored. When the instructions are executed by one or more processors, the one or more processors accept information relating to the structure of a complex that includes an estrogen receptor polypeptide bound to a ligand and information relating to a candidate agent. From this information, the one or more processors determine binding characteristics of the candidate agent to the estrogen receptor polypeptide. The ligand bound to the estrogen receptor polypeptide inhibits NFκB transcriptional activity and does not stimulate proliferation of mouse or uterine tissue.

In one aspect, the invention features a method that includes accepting information relating to the structure of a complex that includes an estrogen receptor polypeptide bound to a ligand and modeling the binding characteristics of an ERalpha polypeptide with a candidate agent. The ligand bound the estrogen receptor polypeptide has a fused ring system that includes at least two fused rings, at least one of which includes at least one nitrogen. The method is implemented by a software system.

In one aspect, the invention features a method that includes accepting information relating to the structure of a complex that includes an estrogen receptor polypeptide bound to a ligand and modeling the binding characteristics of an ERalpha polypeptide with a candidate agent. The ligand bound the estrogen receptor polypeptide has a fused ring system that includes at least two fused rings, at least one of which includes at least two heteroatoms. Furthermore, the method is implemented by a software system.

In one aspect, the invention features a method that includes accepting information relating to the structure of a complex that includes an estrogen receptor polypeptide bound to a ligand and modeling the binding characteristics of an ERalpha polypeptide with a candidate agent. The ligand bound to the estrogen receptor polypeptide inhibits NFκB transcriptional activity and does not stimulate proliferation of mouse or uterine tissue. The method is implemented by a software system.

In another aspect, the invention features a computer program residing on a computer readable medium on which a plurality of instructions is stored. When the instructions are executed by one or more processors, the one or more processors will accept information relating to a structure of a complex that includes an estrogen receptor polypeptide bound to a ligand and model the binding characteristics of the estrogen receptor polypeptide with a candidate agent. The ligand bound to the estrogen receptor polypeptide has a fused ring system including at least two fused rings, at least one of which includes at least one nitrogen.

In another aspect, the invention features a computer program residing on a computer readable medium on which a plurality of instructions is stored. When the instructions are executed by one or more processors, the one or more processors will accept information relating to a structure of a complex that includes an estrogen receptor polypeptide bound to a ligand and model the binding characteristics of the estrogen receptor polypeptide with a candidate agent. The ligand bound to the estrogen receptor polypeptide has a fused ring system including at least two fused rings, at least one of which includes at least two heteroatoms.

In another aspect, the invention features a computer program residing on a computer readable medium on which a plurality of instructions is stored. When the instructions are executed by one or more processors, the one or more processors will accept information relating to a structure of a complex that includes an estrogen receptor polypeptide bound to a ligand and model the binding characteristics of the estrogen receptor polypeptide with a candidate agent. The ligand inhibits NFκB transcriptional activity and does not stimulate proliferation of mouse or uterine tissue.

In another aspect, the invention features a software system that includes instructions for causing a computer system to accept information relating to the structure of a complex that includes an estrogen receptor polypeptide bound to a ligand and model the binding characteristics of the estrogen receptor polypeptide with a candidate agent. The ligand bound to the estrogen receptor polypeptide has a fused ring system including at least two fused rings, at least one of which includes at least one nitrogen.

In another aspect, the invention features a software system that includes instructions for causing a computer system to accept information relating to the structure of a complex that includes an estrogen receptor polypeptide bound to a ligand and model the binding characteristics of the estrogen receptor polypeptide with a candidate agent. The ligand bound to the estrogen receptor polypeptide has a fused ring system including at least two fused rings, at least one of which includes at least two heteroatoms.

In another aspect, the invention features a software system that includes instructions for causing a computer system to accept information relating to the structure of a complex that includes an estrogen receptor polypeptide bound to a ligand and model the binding characteristics of the estrogen receptor polypeptide with a candidate agent. The ligand inhibits NFκB transcriptional activity and does not stimulate proliferation of mouse or uterine tissue.

In another aspect, the invention features a method of modulating ERalpha activity in a subject. The method includes using rational drug design to select an agent that is capable of modulating ERalpha activity and administering a therapeutically effective amount of the agent to the subject.

In another aspect, the invention features a method of treating a subject having a condition associated with ERalpha activity. The method includes using rational drug design to select an agent that is capable of effecting ERalpha activity and administering a therapeutically effective amount of the agent to a subject in need thereof.

In another aspect, the invention features a method of prophylactically treating a subject susceptible to a condition associated with ERalpha activity. The method includes determining that the subject is susceptible to the condition associated with ERalpha activity, using rational drug design to select an agent that is capable of effecting ERalpha activity, and administering a therapeutically effective amount of the agent to the subject.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 6 is the amino acid sequence of human ERalpha receptor (SEQ ID NO:1). The sequence used for crystallization (the ERalpha ligand binding domain) is indicated by underlining.

Like reference symbols in the various drawings indicate like elements.

DETAILED DESCRIPTION

Figure 1:
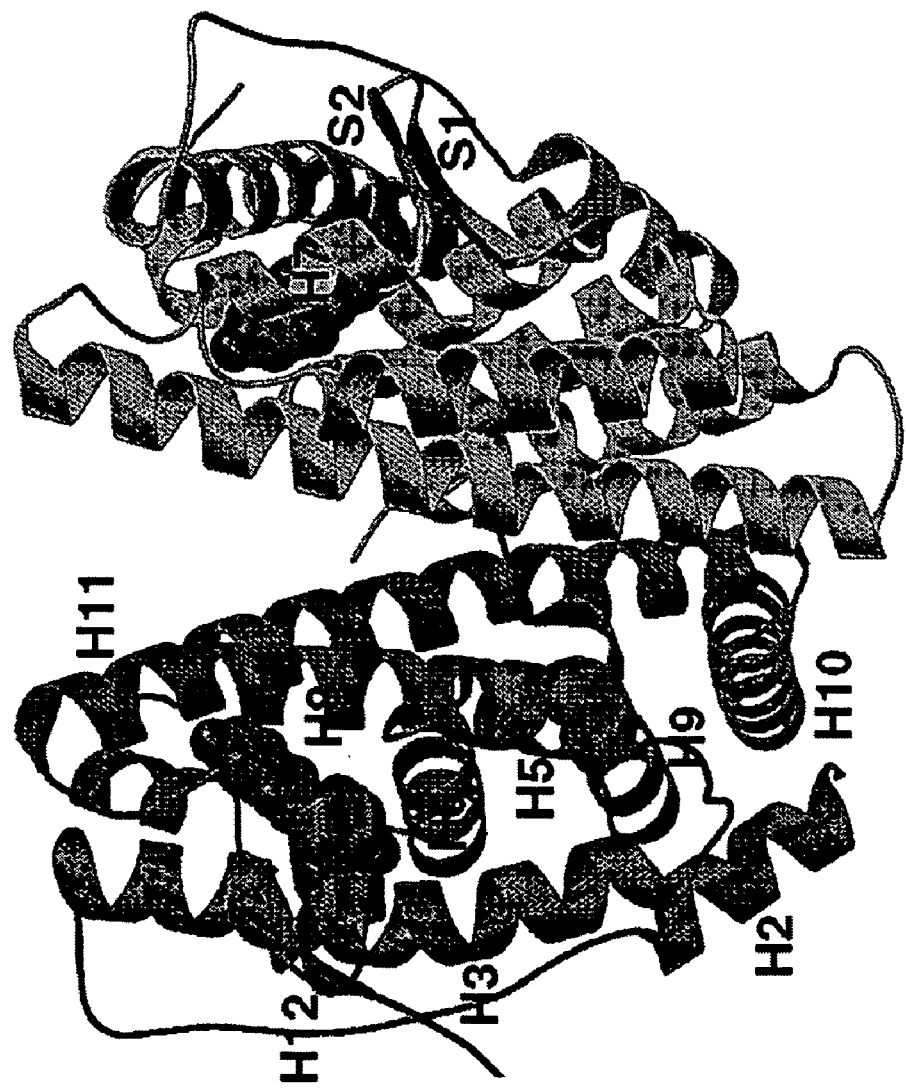
FIG. 1 is a ribbon diagram illustrating the structure of an ERalpha dimer complexed with ligands representative of Compound 1, Compound 2 or 17β-estradiol. Structural helices are identified by "H2," "H3," etc. Structural sheets are indicated by S1 and S2.
Figure 2:
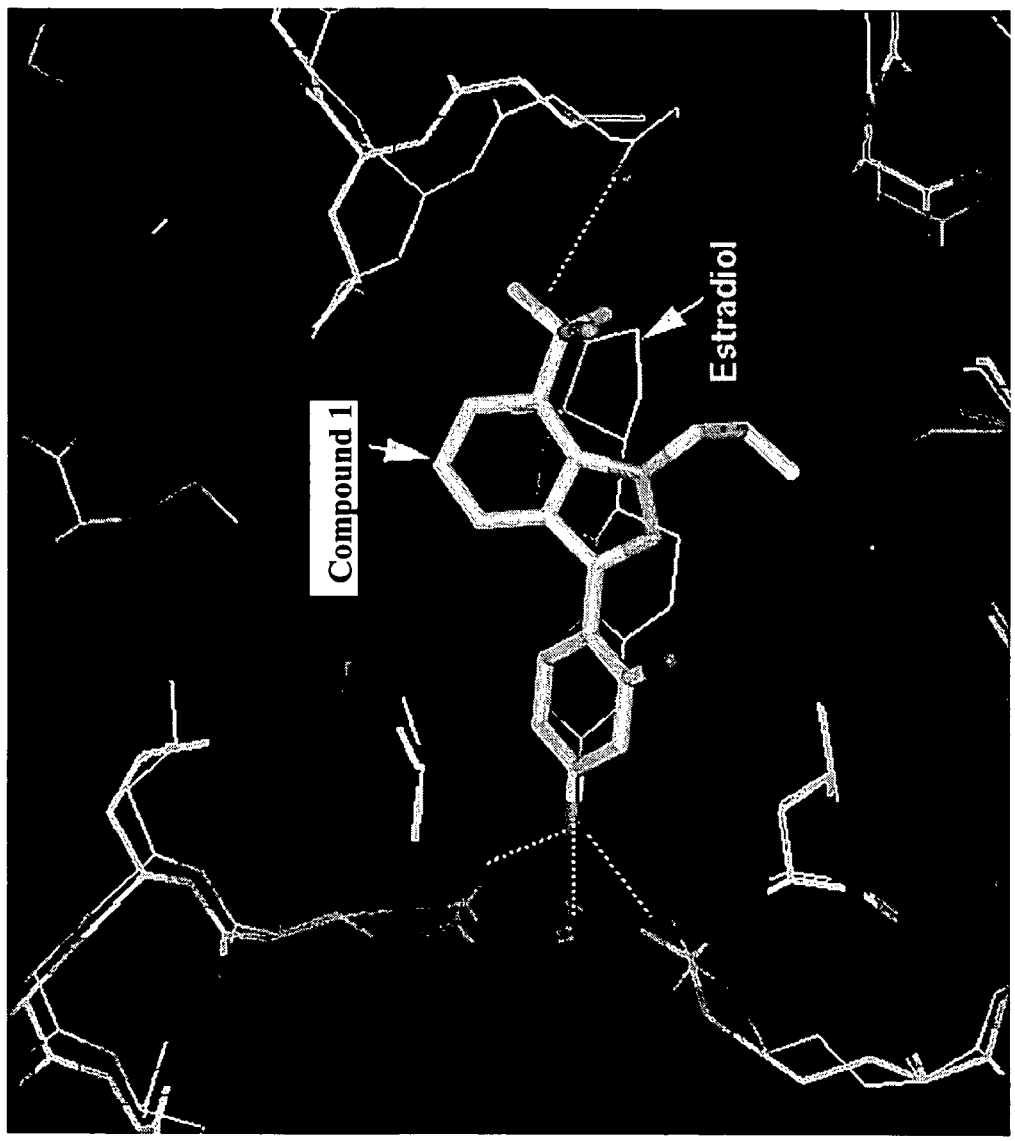
FIG. 2 is a stick model comparing the structures of 17β-estradiol and Compound 1 bound to ERalpha.
Figure 3:
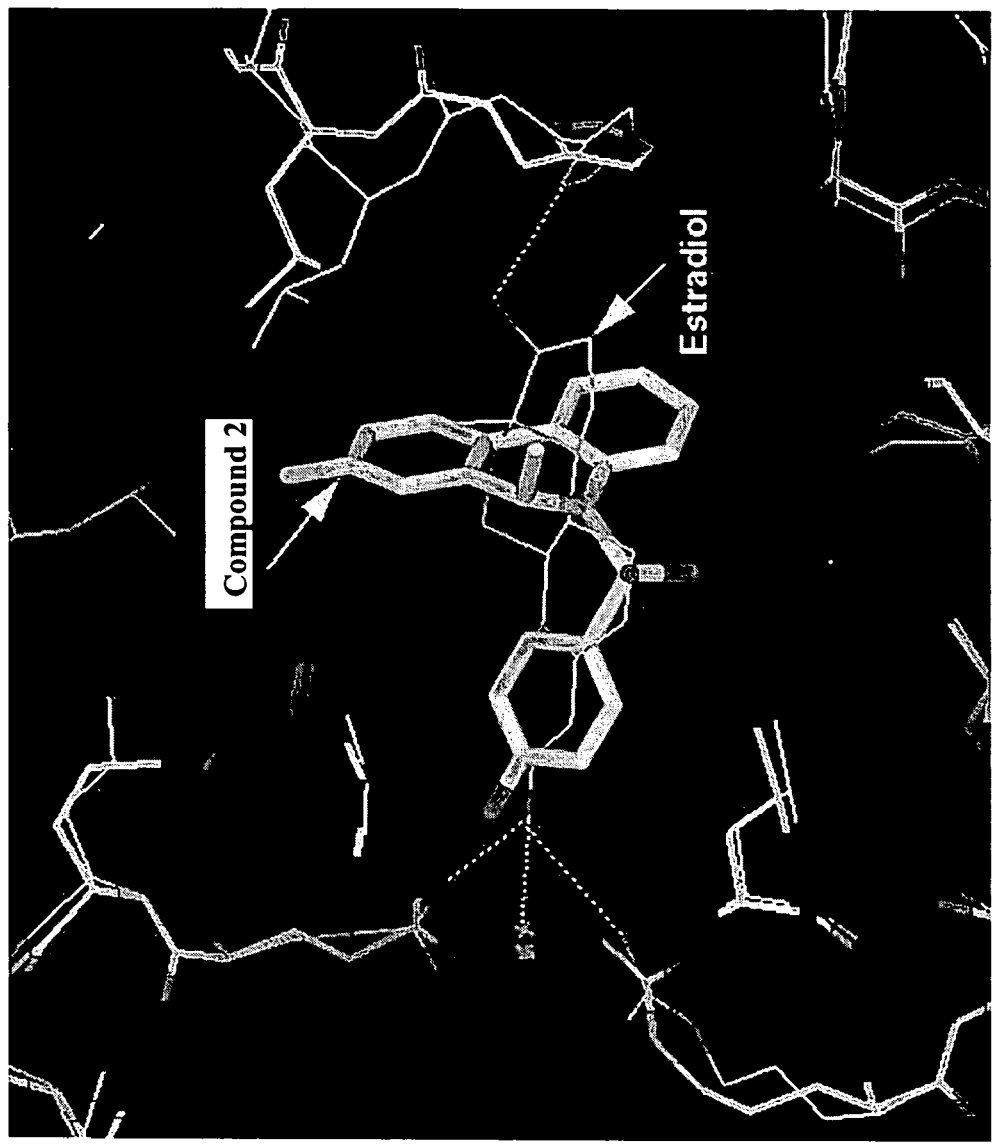
FIG. 3 is a stick model comparing the structures of 17β-estradiol and Compound 2 bound to ERalpha.
Figure 4:
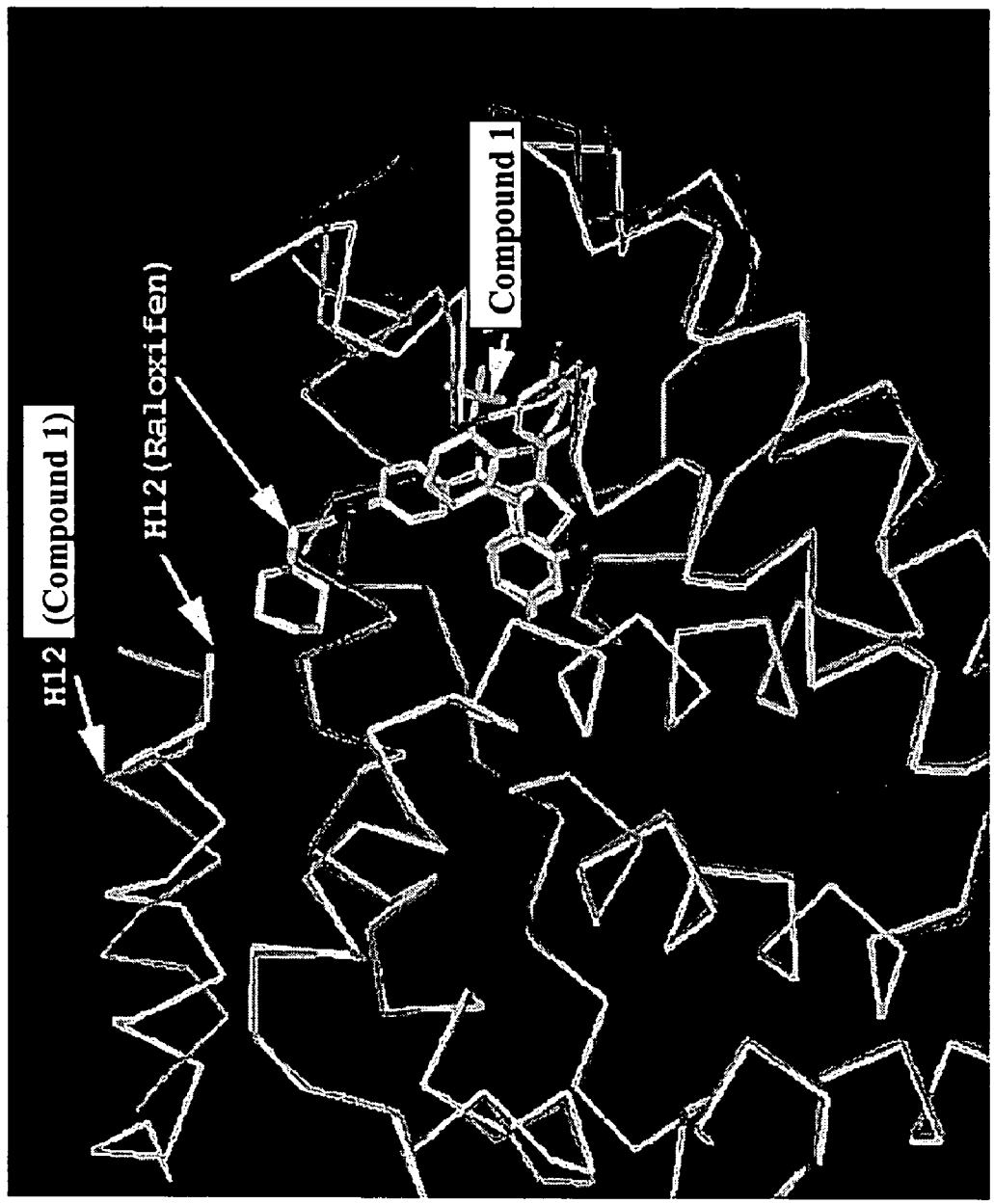
FIG. 4 is a stick model comparing the structures of Raloxifene and Compound 1 bound to ERalpha. Parenthesis indicate positions of helix 12 (H12) when Compound 1 and Raloxifen are bound to ERalpha.

The structures of the human estrogen receptor alpha ligand binding domain (ERalpha-LBD) bound to each of the non-steroidal hormones Compound 1 (IUPAC name: 4-[1-allyl-7-(trifluoromethyl)-1H-indazol-3-yl]benzene-1,3-diol) and Compound 2 (IUPAC name: 4-[(8-Fluoro-6-methylphenanthridin-5(6H)-yl)sulfonyl]phenol) were determined by X-ray crystallography and are described herein. FIG. 1 is a ribbon diagram illustrating the structure of an ERalpha dimer complexed with ligands representative of Compound 1, Compound 2, or the natural receptor ligand, 17β-estradiol (E2). FIGS. 2 and 3 are stick diagrams illustrating a comparison between the binding of Compound 1 and Compound 2, respectively, to ERalpha-LBD and the binding of E2. The ribbon and stick diagrams indicate that the tertiary structure of Compound 1 or Compound 2 bound to the human ERalpha-LBD is similar to the tertiary structure of E2 bound to the ERalpha-LBD. It is therefore believed that the crystal structures of the human ERalpha-LBD/Compound 1 complex and the human ERalpha-LBD/Compound 2 complex (see Tables 9 and 10, respectively, below) can be useful for designing or identifying other ligands, such as, for example, non-steroidal ligands, that can also interact with an ERalpha-LBD.

The chemical structure of Compound 1 is given by:

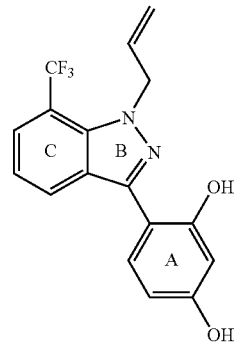

The chemical structure of Compound 2 is given by:

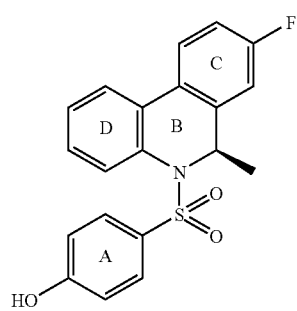

Like E2, Compound 1 and Compound 2 can bind ERalpha and inhibit nuclear factor-kappaB (NFκB)-induced inflammatory events. However, unlike, E2, binding of Compound 1 or Compound 2 to ERalpha does not stimulate feminizing effects. For example, administration of Compound 1 or Compound 2 does not stimulate proliferation of uterine or breast tissue.

In general, a complex of the human ERalpha-LBD bound to Compound 1 or Compound 2 can be prepared as desired. In some embodiments, such a complex can be prepared as follows. The human ERalpha-LBD is expressed from a DNA plasmid. The expression can be driven by a promoter, such as an inducible promoter. The human ERalpha-LBD can be expressed as a fusion protein with a suitable tag, such as a glutathione-S-transferase (GST), myc, HA, hexahistidine (SEQ ID NO: 9), or FLAG tag. The tag can facilitate isolation of the human ERalpha-LBD from cells. A fusion protein can be cleaved at a protease site engineered into the fusion protein, such as at or near the site of fusion between the polypeptide and the tag. Following cleavage and purification, the human ERalpha-LBD can be contacted with Compound 1 or Compound 2. For example, the human ERalpha-LBD can be mixed with Compound 1 or Compound 2 prior to purification (e.g., prior to cleavage of a polypeptide tag), or the human ERalpha-LBD can be mixed with either of the two compounds after purification. In some embodiments, Compound 1 or Compound 2 can be mixed with the human ERalpha-LBD prior to purification and again following purification. In certain embodiments, the structure of the human ERalpha-LBD can be assessed in the absence of ligand.

The human ERalpha-LBD and Compound 1 or Compound 2 compounds can be combined in a solution for collecting spectral data for a human ERalpha-LBD/Compound 1 complex or a human ERalpha-LBD/Compound 2 complex, NMR data for either of these two complexes, or for growing a crystal of either of these two complexes. For example, the human ERalpha-LBD/Compound 1 complex or human ERalpha-LBD/Compound 2 complex can be crystallized in the presence of a salt (e.g., a sodium salt), a polymer (e.g., polyethylene glycol (PEG)), and/or an organic solvent. Crystals can be grown by various methods, such as, for example, sitting or hanging drop vapor diffusion. In general, crystallization can be performed at a temperature of from about 4° C. to about 60° C. (e.g., from about 4° C. to about 45° C., such as at about 4° C., about 15° C., about 18° C., about 20° C., about 25° C., about 30° C., about 32° C., about 35° C., about 37° C.).

In general, a crystal of the human ERalpha-LBD bound to Compound 1 or Compound 2 can diffract X-rays to a resolution of about 3.5 Å or less (e.g., about 3.2 Å or less, about 3.0 Å or less, about 2.5 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, or about 1.4 Å or less). In some embodiments, a crystal of the human ERalpha-LBD bound to Compound 1 or Compound 2 can diffract X-rays to a resolution of from about 1.7 Å to about 2.5 Å (e.g., the crystal of ERalpha-LBD bound to Compound 1 can diffract X-rays to about 2.4 Å).

In one embodiment, a crystal of the human ERalpha-LBD bound to Compound 1 belongs to space group C2 with unit cell parameters a=104.80 Å, b=54.12 Å, c=97.10 Å, $\alpha=\gamma=90°$, $\beta=113.67°$. In another embodiment, a crystal of the human ERalpha-LBD bound to Compound 2 belongs to space group C2 with unit cell parameters a=104.80 Å, b=54.12 Å, c=97.10 Å, $\alpha=\gamma=90°$, $\beta=113.67°$. The space group refers to the overall symmetry of the crystal, and includes point symmetry and space symmetry. In certain embodiments, a crystal of the human ERalpha-LBD bound to Compound 1 or Compound 2 can contain two molecules of the human ERalpha-LBD in the asymmetric unit. The asymmetric unit is the smallest unit from which the crystal structure can be generated by making use of the symmetry operations of the space group. A crystal is generally made up of the motif defined by the space-group symmetry operations on the asymmetric units, and a translation of that motif through the crystal lattice.

Structural data describing a crystal can be obtained, for example, by X-ray diffraction. X-ray diffraction data can be collected by a variety of sources, X-ray wavelengths and detectors. In some embodiments, rotating anodes and synchrotron sources (e.g., Advanced Light Source (ALS), Berkeley, Calif.; or Advanced Photon Source (APS), Argonne, Ill.) can be used as the source(s) of X-rays. In certain embodiments, X-rays for generating diffraction data can have a wavelength of from about 0.5 Å to about 1.6 Å (e.g., about 0.7 Å, about 0.9 Å, about 1.0 Å, about 1.1 Å, about 1.3 Å, about 1.4 Å, about 1.5 Å, or about 1.6 Å). In some embodiments, area detectors and/or charge-couple devices (CCDs) can be used as the detector(s).

X-ray diffraction data of a crystal of a complex of the human ERalpha-LBD bound to Compound 1 or Compound 2 can be used to obtain the structural coordinates of the atoms in the complex. The structural coordinates are Cartesian coordinates that describe the location of atoms in three-dimensional space in relation to other atoms in the complex. For example, the structural coordinates listed in Tables 9 and 10 are the structural coordinates of a crystalline complex of the human ERalpha-LBD bound to Compound 1 and Compound 2, respectively. These structural coordinates describe the location of atoms of the human ERalpha-LBD in relation to each other, the location of atoms in the human ERalpha-LBD in relation to the atoms in Compound 1 or Compound 2, and the location of atoms in Compound 1 or Compound 2 in relation to each other. The structural coordinates of the complex can be modified by mathematical manipulation, such as by inversion or integer additions or subtractions. As such, structural coordinates are relative coordinates. For example, structural coordinates describing the location of atoms in an ERalpha-LBD bound to Compound 1 or Compound 2 are not specifically limited by the actual x, y, and z coordinates of Table 9 and Table 10, respectively.

The structural coordinates of a complex of the human ERalpha-LBD bound to Compound 1 or Compound 2 can be used to derive a representation (e.g., a two dimensional representation or three dimensional representation) of the complex, a fragment of the complex, the ERalpha-LBD or a fragment of the ERalpha-LBD. Such a representation can be useful for a number of applications, including, for example, the visualization, identification and characterization of an active site of the polypeptide. In certain embodiments, a three-dimensional representation can include the structural coordinates of the human ERalpha-LBD according to Tables 9 or 10, ± a root mean square (rms) deviation from the alpha carbon atoms of amino acids of not more than about 1.5 Å (e.g., not more than about 1.0 Å, not more than about 0.5 Å). RMS deviation is the square root of the arithmetic mean of the squares of the deviations from the mean, and is a way of expressing deviation or variation from structural coordinates. Conservative substitutions (see discussion below) of amino acids can result in a molecular representation having structural coordinates within the stated rms deviation. For example, two molecular models of polypeptides that differ from one another by conservative amino acid substitutions can have coordinates of backbone atoms within a stated rms deviation, such as less than about 1.5 Å (e.g., less than about 1.0 Å, less than about 0.5 Å). Backbone atoms of a polypeptide include the alpha carbon ($C_\alpha$ or CA) atoms, carbonyl carbon (C) atoms, and amide nitrogen (N) atoms.

Various software programs allow for the graphical representation of a set of structural coordinates to obtain a representation of a complex of the human ERalpha-LBD bound to Compound 1 or Compound 2, or a fragment of one of these complexes. In general, such a representation should accurately reflect (relatively and/or absolutely) structural coordinates, or information derived from structural coordinates, such as distances or angles between features. In some embodiments, the representation is a two-dimensional figure, such as a stereoscopic two-dimensional figure. In certain embodiments, the representation is an interactive two-dimensional display, such as an interactive stereoscopic two-dimensional display. An interactive two-dimensional display can be, for example, a computer display that can be rotated to show different faces of a polypeptide, a fragment of a polypeptide, a complex and/or a fragment of a complex. In some embodiments, the representation is a three-dimensional representation. As an example, a three-dimensional model can be a physical model of a molecular structure (e.g., a ball-and-stick model). As another example, a three dimensional representation can be a graphical representation of a molecular structure (e.g., a drawing or a figure presented on a computer display). A two-dimensional graphical representation (e.g., a drawing) can correspond to a three-dimensional representation when the two-dimensional representation reflects three-dimensional information, for example, through the use of perspective, shading, or the obstruction of features more distant from the viewer by features closer to the viewer. In some embodiments, a representation can be modeled at more than one level. As an example, when the three-dimensional representation includes a polypeptide, such as a complex of the human ERalpha-LBD bound to Compound 1 or Compound 2, the polypeptide can be represented at one or more different levels of structure, such as primary (amino acid sequence), secondary (e.g., α-helices and β-sheets), tertiary (overall fold), and quaternary (oligomerization state) structure. A representation can include different levels of detail. For example, the representation can include the relative locations of secondary structural features of a protein without specifying the positions of atoms. A more detailed representation could, for example, include the positions of atoms.

In some embodiments, a representation can include information in addition to the structural coordinates of the atoms in a complex of the human ERalpha-LBD bound to Compound 1 or Compound 2. For example, a representation can provide information regarding the shape of a solvent accessible surface, the van der Waals radii of the atoms of the model, and the van der Waals radius of a solvent (e.g., water). Other features that can be derived from a representation include, for example, electrostatic potential, the location of voids or pockets within a macromolecular structure, and the location of hydrogen bonds and salt bridges.

An agent that interacts with a human ERalpha-LBD can be identified or designed by a method that includes using a representation of the human ERalpha-LBD or a fragment thereof, or a complex of human ERalpha-LBD bound to Compound 1 or Compound 2 or a fragment of either one of these complexes. Exemplary types of representations include the representations discussed above. In some embodiments, the representation can be of an analog polypeptide, polypeptide fragment, complex or fragment of a complex. A candidate agent that interacts with the representation can be designed or identified by performing computer fitting analysis of the candidate agent with the representation. In general, an agent is a molecule. Examples of agents include polypeptides, nucleic acids (including DNA or RNA), steroids and non-steroidal organic compounds. An agent that interacts with a polypeptide (e.g., an ERalpha polypeptide) can interact transiently or stably with the polypeptide. The interaction can be mediated by any of the forces noted herein, including, for example, hydrogen bonding, electrostatic forces, hydrophobic interactions, and van der Waals interactions.

As noted above, X-ray crystallography can be used to obtain structural coordinates of a complex of human ERalpha-LBD bound to Compound 1 or Compound 2. However, such structural coordinates can be obtained using other techniques including NMR techniques. Additional structural information can be obtained from spectral techniques (e.g., optical rotary dispersion (ORD), circular dichroism (CD)), homology modeling, and computational methods (e.g., computational methods that can include data from molecular mechanics, computational methods that include data from dynamics assays).

In some embodiments, the X-ray diffraction data can be used to construct an electron density map of a complex of human ERalpha-LBD bound to Compound 1 or Compound 2 or a fragment thereof, and the electron density map can be used to derive a representation (e.g., a two dimensional representation, a three dimensional representation) of human ERalpha-LBD bound to Compound 1 or Compound 2 or a fragment thereof. Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data include, for example, multiwavelength anomalous dispersion (MAD), multiple isomorphous replacement (MIR), multiple isomorphous replacement with anomalous scattering (MIRAS), single isomorphous replacement with anomalous scattering (SIRAS), reciprocal space solvent flattening, molecular replacement, or any combination thereof. Upon determination of the phase, an electron density map can be constructed. The electron density map can be used to derive a representation of the complex or a fragment thereof by aligning a three-dimensional model of a previously known polypeptide or a previously known complex (e.g., a complex containing a polypeptide bound to a ligand) with the electron density map. For example, the electron density map corresponding to a human ERalpha-LBD/Compound 1 complex or human ERalpha-LBD/Compound 2 complex can be aligned with the electron density map corresponding to human ERalpha-LBD complexed to another compound, such as an agonist (e.g., diethylstilbestrol (Protein Databank Identification No. 2erd)). In other embodiments, a human ERalpha-LBD/Compound 1 complex or human ERalpha-LBD/Compound 2 complex can be aligned with the electron density map corresponding to human ERalpha-LBD complexed to the natural ligand 17β-estradiol (Protein Databank Identification No. 1a52) or to an antagonist, such as 4-hydroxytamoxifen (Protein Databank Identification No. 3ert).

The alignment process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, 10 cycles) to generate a better fit with the electron density map. A software program such as CNS (Brunger et al., *Acta Crystallogr*. D54:905-921, 1998) can be used to refine the model. The quality of fit in the comparative model can be measured by, for example, an $R_{work}$ or $R_{free}$ value. A smaller value of $R_{work}$ or $R_{free}$ generally indicates a better fit. Misalignments in the comparative model can be adjusted to provide a modified comparative model and a lower $R_{work}$ or $R_{free}$ value. The adjustments can be based on information (e.g., sequence information) relating to human ERalpha-LBD, Compound 1 or Compound 2, the previously known polypeptide and/or the previously known complex. As an example, in embodiments in which a model of a previously known complex of a polypeptide bound to a ligand is used, an adjustment can include replacing the ligand in the previously known complex with Compound 1 or Compound 2. As another example, in certain embodiments, an adjustment can include replacing an amino acid in the previously known polypeptide with the amino acid in the corresponding site of human ERalpha-LBD. When adjustments to the modified comparative model satisfy a best fit to the electron density map, the resulting model is that which is determined to describe the polypeptide or complex from which the X-ray data was derived (e.g., the human ERalpha-LBD/Compound 1 complex or the human ERalpha-LBD/Compound 2 complex). Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

Discussed above is a method of deriving a representation of a complex by aligning a three-dimensional model of a previously known polypeptide or a previously known complex with a newly calculated electron density map corresponding to a crystal of the complex. One adjustment that can be used in this modeling process can include replacing the compound in the representation of the previously known complex with Compound 1 or Compound 2.

A machine, such as a computer, can be programmed in memory with the structural coordinates of a complex of the human ERalpha-LBD bound to Compound 1 or Compound 2, together with a program capable of generating a graphical representation of the structural coordinates on a display connected to the machine. Alternatively or additionally, a software system can be designed and/or utilized to accept and store the structural coordinates. The software system can be capable of generating a graphical representation of the structural coordinates. The software system can also be capable of accessing external databases to identify compounds (e.g., polypeptides) with similar structural features as human ERalpha-LBD, and/or to identify one or more candidate agents with characteristics that may render the candidate agent(s) likely to interact with human ERalpha-LBD.

A machine having a memory containing structure data or a software system containing such data can aid in the rational design or selection of ERalpha agonists and/or ERalpha antagonists. For example, such a machine or software system can aid in the evaluation of the ability of an agent to associate with a complex of the human ERalpha-LBD bound to Compound 1 or Compound 2, or can aid in the modeling of compounds or proteins related by structural or sequence homology to an ERalpha-LBD. As used herein, an agonist refers to a compound that mimics or enhances at least one activity of E2, and an antagonist refers to a compound that inhibits at least one activity, or has an opposite activity, of E2. It is possible that one compound can act as an agonist in one respect and an antagonist in another respect, or that one compound can act as an agonist or antagonist in one respect and can have no effect (neither a positive nor negative effect) in another respect. For example, a compound, such as Compound 1 or Compound 2 can function as an agonist of the ERalpha-LBD by inhibiting estrogen receptor-dependent NFκB-induced inflammatory events, and can also function as an antagonist by inhibiting estrogen receptor-dependent feminizing events, such as stimulating the proliferation of breast or uterine tissue. Alternatively, a compound, such as Compound 1 or Compound 2 may act as an agonist by mimicking the activity of the ERalpha-LBD with respect to its inhibition of estrogen receptor-dependent NFκB-induced inflammatory events (by mimic is meant that the compound has the same or nearly the same activity), and may have no effect (neither negative nor positive) with respect to estrogen receptor-dependent feminizing events.

The machine can produce a representation (e.g., a two dimensional representation, a three dimensional representation) of a complex of the human ERalpha-LBD bound to Compound 1 or Compound 2 or a fragment thereof. A software system, for example, can cause the machine to produce such information. The machine can include a machine-readable data storage medium including a data storage material encoded with machine-readable data. The machine-readable data can include structural coordinates of atoms of a complex of the human ERalpha-LBD bound to Compound 1 or Compound 2, or a fragment thereof. Machine-readable storage media (e.g., data storage material) include, for example, conventional computer hard drives, floppy disks, DAT tape, CD-ROM, DVD, and other magnetic, magneto-optical, optical, and other media which may be adapted for use with a machine (e.g., a computer). The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. A display can be connected to the CPU so that the three-dimensional representation can be visualized by the user. Accordingly, when used with a machine programmed with instructions for using the data (e.g., a computer loaded with one or more programs of the sort described herein) the machine is capable of displaying a graphical representation (e.g., a two dimensional graphical representation, a three-dimensional graphical representation) of any of the polypeptides, polypeptide fragments, complexes, or complex fragments described herein.

A display (e.g., a computer display) can show a representation of a complex of human ERalpha-LBD bound to Compound 1 or Compound 2, or a fragment of either of these complexes. The user can inspect the representation and, using information gained from the representation, generate a model of a complex or fragment thereof that includes an agent other than Compound 1 or Compound 2. The model can be generated, for example, by altering a previously existing representation of a human ERalpha-LBD/Compound 1 complex or a human ERalpha-LBD/Compound 2 complex. Optionally, the user can superimpose a three-dimensional model of an agent on the representation of human ERalpha-LBD bound to Compound 1 or Compound 2. The agent can be an agonist (e.g., a candidate agonist) of human ERalpha-LBD or an antagonist (e.g., a candidate antagonist) of human ERalpha-LBD. In some embodiments, the agent can be a known compound or fragment of a compound. In certain embodiments, the agent can be a previously unknown compound, or a fragment of a previously unknown compound.

It can be desirable for the agent to have a shape that complements the shape of the active site. There can be a preferred distance, or range of distances, between atoms of the agent and atoms of the ERalpha polypeptide. Distances longer than a preferred distance may be associated with a weak interaction between the agent and active site (e.g., human ERalpha-LBD). Distances shorter than a preferred distance may be associated with repulsive forces that can weaken the interaction between the agent and the polypeptide. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to the ERalpha polypeptide (e.g., a rigid body translation or rotation of the agent), until the steric clash is relieved. The user can adjust the conformation of the agent or of the ERalpha polypeptide in the vicinity of the agent in order to relieve a steric clash. Steric clashes can also be removed by altering the structure of the agent, for example, by changing a "bulky group," such as an aromatic ring, to a smaller group, such as to a methyl or hydroxyl group, or by changing a rigid group to a flexible group that can accommodate a conformation that does not produce a steric clash. Electrostatic forces can also influence an interaction between an agent and a ligand-binding domain. For example, electrostatic properties can be associated with repulsive forces that can weaken the interaction between the agent and the ERalpha polypeptide. Electrostatic repulsion can be relieved by altering the charge of the agent, e.g., by replacing a positively charged group with a neutral group.

Forces that influence binding strength between Compound 1 or Compound 2 and human ERalpha-LBD can be evaluated in the polypeptide/agent model. These can include, for example, hydrogen bonding, electrostatic forces, hydrophobic interactions, van der Waals interactions, dipole-dipole interactions, π-stacking forces, and cation-π interactions. The user can evaluate these forces visually, for example by noting a hydrogen bond donor/acceptor pair arranged with a distance and angle suitable for a hydrogen bond. Based on the evaluation, the user can alter the model to find a more favorable interaction between the ERalpha polypeptide and the agent. Altering the model can include changing the three-dimensional structure of the polypeptide without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding, or removing groups. For example, if a hydrogen bond donor on the ERalpha polypeptide is located near a hydrogen bond donor on the agent, the user can replace the hydrogen bond donor on the agent with a hydrogen bond acceptor.

The relative locations of an agent and the ERalpha polypeptide, or their conformations, can be adjusted to find an optimized binding geometry for a particular agent to the ERalpha polypeptide. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for an ERalpha polypeptide/agent complex. An optimized geometry can be determined, for example, through molecular mechanics or molecular dynamics calculations.

A series of representations of complexes of human ERalpha-LBD bound to Compound 1, or Compound 2, having different bound agents can be generated. A score can be calculated for each representation. The score can describe, for example, an expected strength of interaction between human ERalpha-LBD and the agent. The score can reflect one of the factors described above that influence binding strength. The score can be an aggregate score that reflects more than one of the factors. The different agents can be ranked according to their scores.

Steps in the design of the agent can be carried out in an automated fashion by a machine. For example, a representation of ERalpha-LBD can be programmed in the machine, along with representations of candidate agents. The machine can find an optimized binding geometry for each of the candidate agents to the active site, and calculate a score to determine which of the agents in the series is likely to interact most strongly with human ERalpha-LBD.

A software system can be designed and/or implemented to facilitate these steps. Software systems (e.g., computer programs) used to generate representations or perform the fitting analyses include, for example: MCSS, Ludi, QUANTA, Insight II, Cerius2, CHARMm, and Modeler from Accelrys, Inc. (San Diego, Calif.); SYBYL, Unity, FleXX, and LEAP-FROG from TRIPOS, Inc. (St. Louis, Mo.); AUTODOCK (Scripps Research Institute, La Jolla, Calif.); GRID (Oxford University, Oxford, UK); DOCK (University of California, San Francisco, Calif.); and Flo+ and Flo99 (Thistlesoft, Morris Township, N.J.). Other useful programs include ROCS, ZAP, FRED, Vida, and Szybki from Openeye Scientific Software (Santa Fe, N. Mex.); Maestro, Macromodel, and Glide from Schrodinger, LLC (Portland, Oreg.); MOE (Chemical Computing Group, Montreal, Quebec), Allegrow (Boston De Novo, Boston, Mass.), and GOLD (Jones et al., *J. Mol. Biol.* 245:43-53, 1995). The structural coordinates can also be used to visualize the three-dimensional structure of an ERalpha polypeptide using MOLSCRIPT, RASTER3D, or PyMOL (Kraulis, *J. Appl. Crystallogr.* 24: 946-950, 1991; Bacon and Anderson, *J. Mol. Graph.* 6: 219-220, 1998; DeLano, The PyMOL Molecular Graphics System (2002) DeLano Scientific, San Carlos, Calif.).

The agent can, for example, be selected by screening an appropriate database, can be designed de novo by analyzing the steric configurations and charge potentials of unbound human ERalpha-LBD in conjunction with the appropriate software systems, and/or can be designed using characteristics of known ligands of progesterone receptors or other hormone receptors. The method can be used to design or select agonists or antagonists of human ERalpha-LBD. A software system can be designed and/or implemented to facilitate database searching, and/or agent selection and design.

Once an agent has been designed or identified, it can be obtained or synthesized and further evaluated for its effect on human ERalpha-LBD activity. For example, the agent can be evaluated by contacting it with human ERalpha-LBD and measuring the effect of the agent on polypeptide activity. A method for evaluating the agent can include an activity assay performed in vitro or in vivo. An activity assay can be a cell-based assay, for example. Depending upon the action of the agent on human ERalpha-LBD, the agent can act either as an agonist or antagonist of human ERalpha-LBD activity. The agent also can be contacted with the polypeptide in the presence of progesterone in order to determine whether or not the agent inhibits binding of progesterone to the polypeptide. A crystal containing human ERalpha-LBD bound to the identified agent can be grown and the structure determined by X-ray crystallography. A second agent can be designed or identified based on the interaction of the first agent with human ERalpha-LBD.

Various molecular analysis and rational drug design techniques are further disclosed in, for example, U.S. Pat. Nos. 5,834,228, 5,939,528 and 5,856,116, as well as in PCT Application No. PCT/US98/16879, published as WO 99/09148.

While certain embodiments have been described, other embodiments are also contemplated.

As an example, while embodiments involving the human ERalpha-LBD and Compound 1 or Compound 2 have been described, the description herein is more generally directed to any estrogen receptor polypeptide and any ligand having at least two fused rings where at least one of the fused rings includes a heteroatom.

An estrogen receptor polypeptide can be a full-length, mature polypeptide, including the full-length amino acid sequence of any isoform of an ERalpha polypeptide. An isoform is any of several multiple forms of a protein that differ in their primary structure.

An estrogen receptor polypeptide can be a fragment of an ERalpha, such as a ligand binding domain, a DNA-binding domain, a protein-interaction domain (e.g., an activation domain), or a combination thereof.

An estrogen receptor polypeptide can have an active site. In general, an active site can include a site of ligand binding, or a site of phosphorylation, glycosylation, alkylation, acylation, or other covalent modification. A ligand binding site can include accessory binding sites adjacent or proximal to the actual site of binding that may affect activity upon interaction with the ligand. An active site of an estrogen receptor polypeptide can include amino acids of SEQ ID NO:1 (FIG. 6). For example, an active site of an ERalpha-polypeptide can include one or more of amino acids Glu353, Arg394, Phe404, Met421, Leu425, and His524 as defined by the amino acid positions of SEQ ID NO:1.

The numbering of the amino acids of an ERalpha polypeptide may be different than that set forth herein, and the sequence of the ERalpha polypeptide may contain certain conservative amino acid substitutions that yield the same three-dimensional structure. For example, the numbering of an ERalpha-LBD may be different than that set forth in FIG. 6, and the sequence of the ERalpha-LBD may contain conservative amino acid substitutions but yield the same structure as that defined by the coordinates of Tables 9 and 10 and illustrated in FIGS. 1-4. Corresponding amino acids and conservative substitutions in other isoforms or analogs are easily identified by visual inspection of the relevant amino acid sequences or by using commercially available homology software programs (e.g., MODELLAR, MSI, San Diego, Calif.).

An analog is a polypeptide having conservative amino acid substitutions. A conservative substitution can include switching one amino acid for another with similar polarity, steric arrangement, or of the same class (e.g., hydrophobic, acidic or basic), and includes substitutions having an inconsequential effect on the three-dimensional structure of the ERalpha polypeptide with respect to identification and design of agents that interact with the polypeptide (e.g., an ERalpha-LBD), as well as for molecular replacement analyses and/or for homology modeling.

An estrogen receptor polypeptide, such as an ERalpha polypeptide, can originate from a nonmammalian or mammalian species. A mammalian estrogen receptor polypeptide can originate from a human, for example. Exemplary nonhuman mammals include a nonhuman primate (such as a monkey or ape), a mouse, rat, goat, cow, bull, pig, horse, sheep, wild boar, sea otter, cat, and dog. Exemplary nonmammalian species include chicken, turkey, shrimp, alligator, and fish.

As another example, while embodiments have been described in which Compound 1 or Compound 2 is a ligand, more generally other compounds may also be used as ligands. For example, based on a representation of the human ERalpha-LBD bound to Compound 1, or human ERalpha-LBD bound to Compound 2, derived from the structure of the crystalline complex, and without wishing to be bound by theory, it is believed that: the hydroxyl group of the A ring of Compound 1 forms hydrogen bonds with the side chains of Glu353 and Arg394 of the human ERalpha-LBD (as defined by the amino acid positions of SEQ ID NO:1) and a conserved water molecule that lies between these two amino acids; the hydroxyl group of the A ring of Compound 2 forms hydrogen bonds with the side chain of Glu353 of the human ERalpha-LBD and a conserved water molecule that lies between Glu353 and Arg394, but may not interact with Arg394; the phenyl group of Compound 1 and Compound 2 interacts with Phe404 and may contribute to pi-edge stacking in this region of the ERalpha-LBD binding pocket; Compound 1 and Compound 2 interact indirectly with His524, Leu425, and Met421 or ERalpha; the indazole group of Compound 1 and the phenanthridine group of Compound 2 form hydrophobic interactions with the binding pocket; and the allyl group of Compound 1 and the phenanthroline group of Compound 2 sit deeply in the binding pocket of ERalpha-LBD, in the region of Met421.

Based on this information, and without wishing to be bound by theory, it is believed that other compounds capable of having one or more similar interactions with the human ERalpha-LBD may also be capable of acting as ligands for the human ERalpha-LBD. Such compounds may have the structure:

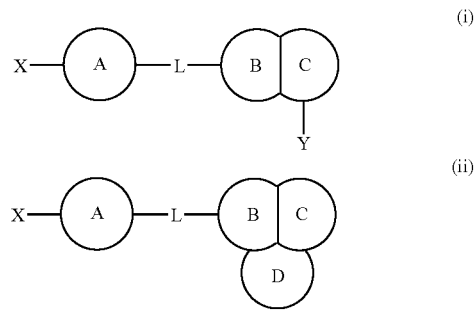

where A, B, C and D represent ring systems; B and C of compound (i) are fused rings; B, C, and D of compound (ii) are fused rings; L is a linker moiety, and X is a substituent. Y of compound (i) includes a carbon chain of not more than ten carbon atoms. In the B/C/D ring system of compound (ii), ring B is fused to ring C and ring C is fused to ring D, or ring C and ring D are each fused to ring B.

In general, rings A, B, and C of compounds (i) and (ii), and ring D of compound (ii) are each independently formed of at least four atoms (e.g., five atoms, six atoms, seven atoms, eight atoms, nine atoms, ten atoms, 11 atoms, 12 atoms, 13 atoms, 14 atoms). One or more atoms (e.g., one atom, two atoms, three atoms, four atoms) in rings A, B, C, and/or D can independently be heteroatoms (e.g., N, S, O). For example, in some embodiments, ring B can include one or two nitrogen atoms. In compound (i), the B and C rings can form an indazole. In compound (ii), the B, C, and D rings can form a phenanthridine. In some embodiments, ring A can be a phenyl, thiophene, pyrrole, or methyl-pyrrol. In general, X can be a hydroxy substituent, amino substituent, cyano substituent, nitro substituent, mercapto substituent, thiol substituent, amido substituent, or oxo substituent. The position of X on the A ring can vary. For example, if the A ring is a phenol, the X can be in the para or meta position. A second substituent can occupy any position on the A ring. The second substituent can be, for example a hydroxy substituent, amino substituent, cyano substituent, nitro substituent, mercapto substituent, thiol substituent, amido substituent, oxo substituent, or halogen (e.g., fluorine, chlorine, bromine, iodine).

In some embodiments, the A ring may be fused with another ring to form a bicyclic structure.

In some embodiments, rings A, B, and C of compounds (i) and (ii), and ring D of compound (ii) can each independently include one or more (e.g., one, two, three, four) substituents (e.g., one or more substituents that provide favorable interaction with the human ERalpha-LBD, such as, for example, through hydrogen bonding, hydrophobic interaction and/or electrostatic interaction). While in some embodiments, a substituent itself may be a hydrogen bond donor or acceptor with the human ERalpha-LBD, in other embodiments, the substituent may form a hydrogen bond with a portion of the human ERalpha-LBD through one or more solvent molecules such as water.

The B/C fused ring system of compound (i) and the B/C/D fused ring system of compound (ii) can form hydrophobic interactions with an ERalpha polypeptide in the region of Met421, His524, and Leu425. Optionally, the fused ring systems can interact directly or indirectly with Met421, and the interaction can be mediated by a heteroatom of one of the rings, or by a substituent on one of the rings. The substituents on rings B and C of compounds (i) and (ii), and ring D of compound (ii) can be hydrophobic. A substituent (Y) on a ring of the B/C ring system of compound (i), and particularly on ring C of compound (i) will not include more than 10 carbon atoms, and a substituent on a ring of the B/C/D ring system of compound (ii) will not include more than 5 carbon atoms.

In general, L can be a direct chemical bond, or L can be formed of a chemical moiety, such as, for example, a sulfonyl moiety, an alkyl moiety, an alkenyl moiety, an alkynyl moiety, an ether moiety, a thioether moiety, an amido moiety, or a carbonyl moiety. In some embodiments, L can be formed of multiple moieties (e.g., a sulfonyl moiety bonded to an alkyl moiety).

It is believed that a ligand having the properties described above can have a physiological effect similar to Compound 1 or Compound 2. For example, it is believed that the ligand can inhibit nuclear factor-kappaB (NFκB)-induced inflammatory events, but may not have the feminizing effects characteristic of the natural ERalpha ligand 17β-estradiol.

The following examples are illustrative and not intended as limiting.

EXAMPLES

Example 1

Synthesis of 4-[1-allyl-7-(trifluoromethyl)-1H-indazol-3-yl]benzene-1,3-diol (Compound 1)

Step 1: Synthesis of 1-allyl-3-(2,4-dimethoxyphenyl)-7-(trifluoromethyl)-1H-indazole A solution of (2-fluoro-3-substituted-phenyl)(4-methoxy-2-substituted-phenyl)methanone (1 equivalent), hydrazine hydrate (10 eq.) and DMAP (1 eq.) in pyridine was heated at 100° C. for 24-48 hrs. The cooled reaction mixture was partitioned with EtOAc and 1 N HCl. The organic phase was washed with brine and dried ($Na_2SO_4$). The resulting residue was purified by flash chromatography to give the intermediate 3-(4-methoxyphenyl)-7-substituted-1-1H-indazole.

A solution of the intermediate 3-(2,4-methoxyphenyl)-7-trifluoromethyl-1H-indazole (0.52 g, 1.6 mmol) in DMF was added to sodium hydride (60% in oil, 0.065 g, 1.6 mmol). After the gas evolution ceased, allyl bromide (0.138 mL, 1.6 mmol) was added and the reaction was stirred at ambient to 50° C. overnight. The cool reaction mixture was partitioned with EtOAc and 1 N HCl. The organic phase was washed with brine and dried ($Na_2SO_4$). The resulting residue was purified by flash chromatography or by HPLC chromatography through silica gel columns 150×12 mm (Biotage) at 10 mL/min with methyl-t-butyl ether/hexane (gradient elution 1:9 to 1:1) to give 1-allyl-3-(2,4-dimethoxyphenyl)-7-(trifluoromethyl)-1H-indazole (0.26 g) as a white solid. $^1$H NMR (DMSO-$d_6$): δ3.73 (s, 3H), 3.80 (s, 3H), 4.85 (dd, 1H, J=1.5 and 14.65), 5.1 (m, 3H), 5.97-6.05 (m, 1H), 6.39 (dd, 1H, J=2.32 and 6.14), 6.64 (s, 1H), 7.25 (t, 1H), 7.35 (d, 1H), 7.85-7.87 (m, 2H)).

MS (ESI) m/z 363 [M+H]+.

Step 2: 4-[1-allyl-7-(trifluoromethyl)-1H-indazol-3-yl]benzene-1,3-diol 1-allyl-3-(2,4-dimethoxyphenyl)-7-(trifluoromethyl)-1H-indazole (0.065 g, 0.18 mmol) in $CH_2Cl_2$ containing 1.0 mL of cyclohexene at −78° C. was treated with boron tribromide (0.136 mL, 1.4 mmol) and slowly allowed to warm to ambient temperature. The reaction was quenched by dropwise edition of $CH_3OH$ to the cooled reaction. The solvent was removed in vacuo and the residue partitioned with EtOAc and 1 N HCl. The organic phase was washed with brine and dried ($Na_2SO_4$). Removal of the solvent in vacuo afforded the crude product. Pure product was obtained by crystallization or flash chromatography through water deactivated silica gel. A sample of 0.066 g was obtained as a white solid.

HPLC retention times were obtained using the following conditions:

| | |
|---|---|
| Column: | Keystone Aquasil C18 (50 × 2 mm, 5 u), |
| Solvent System: | A: 95% 10 mM $NH_4OAc$/5% acetonitrile |
| | B: 95% acetonitrile 5% 10 mM $NH_4OAc$, |
| Gradient: | 0% B to 100% B over 0-15 minutes, |
| Flow: | 0.8 mL/min |
| Detection: | UV (various wavelengths) |

Product Characteristics:

Melting point: 114-115° C.; $^1$H NMR (DMSO-$d_6$): δ 4.87 (dd, 1H, J=1.37 and 17.10 Hz), 5.31-5.08 (m, 3H), 6.01-6.08 (m, H), 6.39 (dd, 1H, J=2.44 and 8.40 Hz), 6.46 (s, 1H), 7.30 (t, 1H), 3.78 (d, 1H), 7.85-7.87 (m, 1H), 8.14-8.19 (m, 1H), 9.59 (broad s, 1H), 9.82 (broad s, 1H) MS (ESI) m/z 335 [M+H]+. Anal. calcd for $C_{17}H_{13}F_3N_2O_2$: C, 61.08; H, 3.92; N, 8.38; Found: C:61.02; H:3.76, N:8.28.

Example 2

Compound 1 has Anti-rheumatic Activity in Mice

The compound Compound 1 was tested in an assay in HAECT-1 cells (immortalized human aortic endothelial cell line). HAECT-1 cells were transfected with two plasmids, one expressing the human ERalpha gene and one expressing a reporter gene, NFκB-luciferase. The reporter gene promoter included three copies of the major histocompatability complex class I promoter NF-κB binding site. The cells were then treated for 16-18 hours with IL-1beta and Compound 1. The level of transcription of NFκB was directly proportional to the amount of luciferase present. Classical estrogenic activity is characterized by ER mediated gene expression and a lack of creatine kinase (CK) activity in vitro. Compound 1 inhibited the expression of the NFκB-luciferase reporter to a similar extent as did 17β-estradiol. The compound did not effect creatine kinase levels.

Classical estrogenic activity is characterized by stimulation of uterine proliferation in vivo. To assay the effect of Compound 1 in vivo, C57BL/6 mice were subjected to a high fat diet for five weeks. The expression of NFκB target genes MHC, VCAM-1, RANTES, and TNF-alpha was measured by TAC-Man assay. Expression of all four genes was inhibited when the mice were fed Compound 1 at 10 or 5 mg/kg/day for five weeks (Table 1).

TABLE 1

Effect of 17α-ethinylestradiol and Compound 1 on NFκB target gene expression

| Concentration (mg/kg/day) | RANTES[a] (% EE)[b] | VCAM-1[a] (% EE)[b] | TNF-alpha[a] (% EE)[b] | MHC[a] (% EE)[b] |
|---|---|---|---|---|
| 10 | 41 (100%) | 28 (100%) | 42 (93%) | 38 (84%) |
| 5 | 58 (100%) | 38 (94%) | 42 (96%) | 38 (103%) |
| 2.5 | 0 | 0 | 44 (92%) | 0 |

[a]percent inhibition of expression
[b]percent inhibition of expression as compared to inhibition by EE fed at 0.01 mg/kg/day Compound 1 did not cause an increase in uterine wet weight in the mice described in Table 1.

In a disease model for Adjuvant Induced Arthritis (AIA), Compound 1 was found to be orally active in a dose dependent fashion. Rats were injected with Complete Freund's Adjuvant (CFA), and synovitis in the tarsal joints was monitored. The mice were treated orally for two weeks with Compound 1 beginning on day 8 after injection. Tarsal joints returned to normal after six days of dosing at 1 or 0.3 mg/kg/day. A 0.1 mg/kg/day dose was active, which is indicated in the histological scoring of Table 2 (see also Table 4 below).

TABLE 2

Histological scoring of Synovitis in tarsal joints of animals with Adjuvant-Induced Arthritis treated orally for two weeks with Compound 1

| Dose (mg/kg, p.o.) | Synovial Structure (0-3) | Fibroplasia (0-3) | Inflammatory Cells (0-3) | Pannus (0-2) | Total Score (0-10) |
|---|---|---|---|---|---|
| Vehicle | 2.92 +/− 0.21 | 2.67 +/− 0.41 | 2.92 +/− 0.3 | 2.00 +/− 0 | 10.50 +/− 0.63 |
| 1 | 2.08 +/− 0.20 | 1.58 +/− 0.38 | 1.33 +/− 0.41 | 0.83 +/− 0.98 | 5.83 +/− 1.78 |
| 0.3 | 2.33 +/− 0.41 | 2.33 +/− 0.52 | 1.58 +/− 0.38 | 1.17 +/− 0.75 | 7.42 +/− 1.88 |
| 0.1 | 2.17 +/− 0.68 | 1.92 +/− 0.49 | 1.50 +/− 0.45 | 0.83 +/− 0.98 | 6.42 +/− 2.9 |

Example 3

Synthesis of 4-[(8-Fluoro-6-methylphenanthridin-5 (6H)-yl)sulfonyl]phenol (Compound 2)

Step 1: N-(4'-Fluorobiphenyl-2-yl)acetamide

A stirred solution of 2-iodoaniline (32.6 g, 149 mmol) and 4-fluorophenylboronic acid (20.8 g, 149 mmol) in tetrahydrofuran (1.5 L) was treated under nitrogen with [1,1'-bis(diphenylphosphino)ferrocene]dichloropalladium (II) complex with dichloromethane (2.20 g, 2.69 mmol) and a 5 N sodium hydroxide solution (60 mL). The reaction mixture was heated at reflux for twelve hours, cooled to room temperature, and the solvent removed in vacuo. The residue was dissolved in ethyl acetate (250 mL) and extracted with a saturated, aqueous, sodium chloride solution (100 mL). The aqueous phase was further extracted with ethyl acetate (2×50 mL). The combined organic phase was dried over anhydrous magnesium sulfate, filtered, and concentrated in vacuo to a brown oil. The brown oil was filtered through a short column of silica gel, and eluted with a mixture of ethyl acetate-hexane (1:4). After evaporation of the solvent in vacuo, a solution of the crude 4'-fluoro-biphenyl-2-ylamine in dichloromethane (75 mL) was treated with pyridine (27.7 mL, 343 mmol), acetic anhydride (15.5 mL, 164 mmol), and 4-(N,N-dimethylamino)pyridine (0.55 g, 4.5 mmol). After stirring for twelve hours at room temperature, the reaction was quenched with a saturated, aqueous, ammonium chloride solution (250 mL). The separated aqueous phase was extracted with dichloromethane (3×75 mL), and the combined organic phase washed sequentially with a 0.1 N hydrochloric acid solution (2×50 mL), and a saturated, aqueous, sodium bicarbonate solution (50 mL). The organic phase was dried over anhydrous sodium sulfate, filtered and concentrated in vacuo to a second brown oil. After toluene was added and removed in vacuo (3×), the resulting brown solid was crystallized from ethyl acetate-hexane to yield a first crop of the desired product (19.0 g). The mother liquor was concentrated and purified by flash column chromatography on silica gel, eluting with ethyl acetate-hexane (1:4), to obtain a second crop (5.0 g).

The combined crops afforded the title compound as a homogeneous, colorless, crystalline, solid (24.0 g, 70%).

Melting Point: 123-124° C.; MS [(+ESI), m/z]: 230 [M+H]$^+$; $^1$H NMR (500 MHz, DMSO-d$_6$) δ: 9.24 (s, 1H), 7.44-7.23 (m, 8H), 1.87 (s, 3H); Anal. calcd for C$_{14}$H$_{12}$FNO: C, 73.35; H, 5.28; N, 6.11. Found: C, 73.09; H, 5.20; N, 5.89.

Step 2: 8-Fluoro-6-methylphenanthridine

The N-(4'-fluorobiphenyl-2-yl)acetamide (18.5 g, 80.7 mmol) was mixed with polyphosphoric acid (250 g) and heated at 120° C. with vigorous stirring for 48 hours. The hot reaction mixture was poured onto ice and stirred vigorously until homogeneous. Ammonium hydroxide (28-30%, aqueous) was added until the pH was greater than eight. A white precipitate was filtered, dissolved in ethyl acetate (250 mL), and re-filtered. The combined filtrate was washed with a saturated, aqueous, sodium chloride solution, dried over anhydrous sodium sulfate, filtered, and evaporated in vacuo to a brown solid. The brown solid was purified by crystallization from a mixture of ethyl acetate-hexane to yield the title compound as a white, crystalline solid (15.9 g, 94%).

Melting point: 92-93° C.; MS [(+ESI), m/z]: 212 [M+H]$^+$; $^1$H NMR (500 MHz, CDCl$_3$) δ: 8.63 (dd, J=9.0, 5.4 Hz, 1H), 8.49 (dd, J=8.2, 1.0 Hz, 1H), 8.10 (dd, J=8.1, 1.1 Hz, 1H), 7.84 (dd, J=9.6, 2.6 Hz, 1H), 7.71 (m, 1H), 7.65-7.57 (m, 2H), 3.01 (s, 3H); $^1$H NMR (400 MHz, DMSO-d$_6$) δ: 8.89 (dd, J=9.1, 5.6 Hz, 1H), 8.70 (dd, J=8.1, 1.3 Hz, 1H), 8.05 (dd, J=10.1, 2.5 Hz, 1H), 7.97 (dd, J=8.1, 1.3 Hz, 1H), 7.80 (m, 1H), 7.70 (m, 1H), 7.63 (m, 1H), 3.01 (s, 3H); Anal. calcd for $C_{14}H_{10}FN$ $0.10H_2O$: C, 78.93; H, 4.83; N, 6.57. Found: C, 78.90; H, 4.57; N, 6.58.

Step 3: 4-(Chlorosulfonyl)phenyl ethyl carbonate

A solution of sodium 4-hydroxybenzenesulfonate dihydrate (50.0 g, 215 mmol) in 1.25 N aqueous sodium hydroxide (170 mL, 213 mmol) was treated drop-wise with ethyl chloroformate (20.6 mL, 215 mmol). The reaction mixture was stirred for twelve hours at room temperature. After cooling the mixture to 0° C., a white precipitate, which formed under the reaction conditions, was filtered. The solid was dried in vacuo at 70° C. The white solid (40.0 g) was suspended in toluene (350 mL) and treated with N,N-dimethylformamide (6.0 mL) and thionyl chloride (22.0 mL, 298 mmol), and the resulting mixture was heated at 100° C. for twelve hours. After cooling to room temperature, the reaction mixture was filtered through diatomaceous earth. The filtrate was concentrated in vacuo, and the resulting oil solidified upon standing. The solidified oil was dissolved in ethyl acetate-hexane (1:4), filtered through a short column of silica gel, and the solvent removed in vacuo to yield the sulfonyl chloride as a white solid (34.8 g, 61%).

Melting point: 74-76° C.; $^1$H NMR (400 MHz, DMSO-$d_6$) δ: 7.60 (d, J=8.7 Hz, 2H), 7.14 (d, J=8.8 Hz, 2H), 4.23 (q, J=7.1 Hz, 2H), 1.26 (t, J=7.1 Hz, 3H).

Step 4: Ethyl 4-[(8-fluoro-6-methylphenanthridin-5 (6H)-yl)sulfonyl]phenyl carbonate A stirred solution of 8-fluoro-6-methylphenanthridine (8.00 g, 37.9 mmol) in tetrahydrofuran (152 mL) was treated with freshly crushed sodium borohydride (7.16 g, 189 mmol). Trifluoroacetic acid (11.7 mL, 152 mmol) was added dropwise at a rate suitable to control gas evolution and exothermic reaction conditions. After the trifluoroacetic acid addition was completed, the heterogeneous reaction mixture was stirred until the reaction returned to room temperature; then was re-heated to reflux for 14 hours. After cooling to room temperature, a saturated, aqueous, sodium bicarbonate solution (250 mL) was slowly added. The mixture was filtered through a plug of glass wool, and extracted with diethyl ether (4×75 mL). The combined organic extract was dried over anhydrous sodium sulfate, filtered, and concentrated in vacuo to afford the dihydrophenanthridine as a light-brown paste. A solution of the crude dihydrophenanthridine in dichloromethane (38 mL) was treated with triethylamine (31.7 mL, 227 mmol) and 4-(chlorosulfonyl)phenyl ethyl carbonate (12.0 g, 45.3 mmol), and stirred at room temperature for 14 hours. The reaction was quenched with a 0.1 N sodium hydroxide solution (150 mL) and extracted with dichloromethane (6×50 mL). The combined organic extract was washed with a 2 N hydrochloric acid solution (2×40 mL), dried over anhydrous sodium sulfate, filtered, and concentrated in vacuo to a viscous, brown oil. The brown oil was triturated with hexane (25 mL) to afford a light-brown solid. The light-brown solid was purified by crystallization from a mixture of ethyl acetate-hexane to yield a first crop of the desired product. The mother liquor was concentrated in vacuo, and purified by filtration through a plug of silica gel, eluting with ethyl acetate-hexane (1:4), to obtain a second crop. The combined crops afforded the title compound as a white, crystalline solid (15.2 g, 91%).

Melting point: 136-138° C.; MS [(+ESI), m/z]: 442 $[M+H]^+$; $^1$H NMR (500 MHz, DMSO-$d_6$) δ: 7.77 (d, J=7.6 Hz, 1H), 7.63 (d, J=7.8 Hz, 1H), 7.48-7.39 (m, 3H), 7.19 (dd, J=9.0, 2.6 Hz, 1H), 7.09 (d, J=8.7 Hz, 2H), 6.98 (d, J=8.7 Hz, 2H), 6.93 (td, J=8.7, 2.6 Hz, 1H), 5.48 (q, J=7.0 Hz, 1H), 4.21 (q, J=7.1 Hz, 2H), 1.25 (t, J=7.1 Hz, 3H), 1.15 (t, J=7.0 Hz, 3H); Anal. calcd for $C_{23}H_{20}FNO_5S$: C, 62.57; H, 4.57; N, 3.17. Found: C, 62.51; H, 4.47; N, 2.96.

Step 5: 4-[(8-Fluoro-6-methylphenanthridin-5(6H)-yl)sulfonyl]phenol

A solution of ethyl 4-[(8-fluoro-6-methylphenanthridin-5 (6H)-yl)sulfonyl]phenyl carbonate (0.45 g, 1.02 mmol) in methanol (5.0 mL) was treated with a 1 N sodium hydroxide (5.1 mL) solution, and heated at 75° C. for 14 hours. After cooling to room temperature, the methanol was evaporated in vacuo. The resulting aqueous mixture was acidified with a 1 N hydrochloric acid solution, diluted with a saturated, aqueous, sodium chloride solution (100 mL), and extracted with dichloromethane (5×15 mL). The combined organic phase was dried over anhydrous sodium sulfate, filtered, and concentrated in vacuo to a white solid. The solid was purified by filtration through a short column of silica gel, eluting with ethyl acetate, to yield the title compound as a homogeneous, white, crystalline, solid (0.34 g, 89%).

Melting point: 188° C.; MS [(−ESI), m/z]: 368 $[M-H]^-$; $^1$H NMR (500 MHz, DMSO-$d_6$) δ: 10.24 (br s, 1H), 7.76 (dd, J=7.6 Hz, 1.5, 1H), 7.60 (dd, J=7.8, 1.4 Hz, 1H), 7.52 (dd, J=8.7, 5.0 Hz, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H); Anal. calcd for $C_{20}H_{16}FNO_3S$: C, 65.03; H, 4.37; N, 3.79. Found: C, 64.77; H, 4.31; N, 3.76.

Example 4

Compound 2 has Anti-Rheumatic Activity

Forty-two male, 8-10 weeks old, Lewis rats were housed according to standard facility operating procedures. They received a standard regimen of food and water ad libitum. Each animal was identified by a cage card indicating the project group and animal number. Each rat number was marked by indelible ink marker on the tail. Freund's Adjuvant-Complete (Sigma Immuno Chemicals, St. Louis, Mo.) was used to induce arthritis. Each mL contained 1 mg *Mycobacterium tuberculosis* heat killed and dried, 0.85 mL mineral oil and 0.15 mL mannide monooleate (Lot No. 084H8800).

The rats were injected intradermally with 0.1 mL of Freund's Adjuvant-Complete at the base of the tail. The animals were randomized to seven groups, each group containing six rats. The groups received vehicle (2% Tween 80, 0.5% methylcellulose), or the Compound 2 compound at 1.0 mg/kg, 0.3 mg/kg, or 0.1 mg/kg orally each day. The rats began treatment on Day 8 after adjuvant injection.

The degree of arthritis severity was monitored daily in terms of the following disease indices: Hindpaw erythema, hindpaw swelling, tenderness of the joints, and movements and posture. An integer scale of 0 to 3 was used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day was 12 (Table 3).

TABLE 3

Effect of Compound 2 on paw swelling

| Day | Vehicle | 1 mg/kg | 0.3 mg/kg | 0.3 mg/kg |
|---|---|---|---|---|
| 8 | 11 | 11.3 | 11.5 | 11.3 |
| 9 | 11 | 8.8 | 9.8 | 10.7 |
| 10 | 11.5 | 7 | 7.3 | 9.3 |
| 11 | 11.7 | 6 | 7 | 9.7 |
| 12 | 11.7 | 5 | 6.7 | 10 |
| 13 | 11.7 | 1.7 | 3.7 | 4.2 |
| 14 | 11.7 | 1.3 | 3 | 3.5 |
| 15 | 11.7 | 1.3 | 3.7 | 3.5 |
| 16 | 11.7 | 1.2 | 2.3 | 3.3 |
| 17 | 11.7 | 1.2 | 2.3 | 3.3 |
| 18 | 11.7 | 1.2 | 2.3 | 3.3 |
| 19 | 11.7 | 1.2 | 2 | 3 |
| 20 | 11.7 | 1.2 | 2 | 2.8 |
| 21 | 11.7 | 1.2 | 1.7 | 2.5 |
| 22 | 12 | 1.2 | 1.7 | 2.5 |
| 23 | 12 | 1 | 1 | 1.2 |
| 24 | 11.7 | 0.8 | 1.3 | 1.3 |

Statistical analysis was performed using Abacus Concepts SuperANOVA. (Abacus Concepts, Inc., Berkeley, Calif.). All of the parameters of interest were subjected to Analysis of Variance with Duncan's new multiple range post hoc testing between groups. Data are expressed throughout as mean± standard deviation (SD), and differences were deemed significant if $p<0.05$.

For the joint scores, the results of the dose response studies for each compound are seen in Table 3. Decreases in paw swelling and redness were observed following treatment with Compound 2. There appeared to be a dose response. Vehicle-treated rats revealed severe arthritis with paw swelling and redness.

At the end of the study the rats were euthanized with $CO_2$, hindlimbs were removed at necropsy and fixed in 10% buffered formalin, and the tarsal joints were decalcified and embedded in paraffin. Histologic sections were stained with Hemotoxylin and Eosin or Saffranin O-Fast Green stain.

Slides were coded so that the examiner was blind to the treatment groups. Synovial tissue from tarsal joints were evaluated based on synovial hyperplasia, inflammatory cell infiltration, and pannus formation (see Table 4). Articular cartilage and bone was evaluated using Mankin's histological grading system. Biochemical and metabolic abnormalities in articular cartilage was assessed as from osteoarthritic human hip (see J. Bone Joint Surg (AM) 53A:152-153) (Table 5).

TABLE 4

Synovitis Score

| Category | Grade |
|---|---|
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. Villus present | 3 |
| 2. Fibroplasia | |
| a. No change | 0 |
| b. Fibroplasia present under lining cells. | 1 |
| c. Small areas of areolar tissue replaced by fibrous tissue | 2 |
| d. Replacement of areolar tissue by fibrous tissue | 3 |

TABLE 4-continued

Synovitis Score

| Category | Grade |
|---|---|
| 3. Inflammatory Cells | |
| a. Occasionally seen, scattered throughout selection | 0 |
| b. Cells present in small numbers in or just under lining cell layer and/or around blood vessels. | 1 |
| c. Small focal collection of cells may be present. | 2 |
| d. Large numbers of cells present in capsule and in or under lining cell layers. Large foci often seen. | 3 |
| 4. Pannus | |
| a. Not detectable | 0 |
| b. Pannus detectable | 1 |

TABLE 5

Mankin Score

| Category | Grade |
|---|---|
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O Staining | |
| a. Normal | 0 |
| b. Slight reduction | 1 |
| c. Modest reduction | 2 |
| d. Severe reduction | 3 |
| e. No dye noted | 4 |
| 4. Tidemark Integrity | |
| a. Intact | 0 |
| b. Crossed by blood vessels | 1 |

As shown in the Tables 6 and 7 below, an improvement in both synovitis and cartilage scores was observed following treatment with the compound. Compound 2 significantly improved the overall synovitis and cartilage scores at all concentrations tested (down to 0.1 mg/kg). This demonstrates that the compound can function as a disease-modifying anti-rheumatic drugs (DMARD) which is an important component of arthritis therapy.

TABLE 6

Histological scoring of Cartilage Changes (Mankin Score) in the tarsal joints from animals with adjuvant-induced arthritis treated orally for 2 weeks with Compound 2 beginning on day 8 after CFA injection.

| Group | Cartilage Structure[a] (0-6) | Cartilage Cells[a] (0-3) | Saffranin-O/ Fast Green Staining[a] (0-4) | Tidemark Integrity[a] (0-1) | Total Mankin Score[a] (0-14) |
|---|---|---|---|---|---|
| Vehicle | 3.25 ± 0.42 | 2.33 ± 0.41 | 3.00 ± 0 | 0 | 8.58 ± 0.74 |
| 1 mg/kg | 1.25 ± 0.27*# | 1.17 ± 0.26*t | 2.17 ± 0.26* | 0 | 4.58 ± 0.74*t |
| 0.3 mg/kg | 1.75 ± 0.42* | 1.50 ± 0.32* | 2.17 ± 0.26* | 0 | 5.42 ± 0.74*t |
| 0.1 mg/kg | 2.33 ± 0.68* | 1.92 ± 0.21 | 2.42 ± 0.67* | 0 | 6.83 ± 1.25* |

[a]Means ± SD
*sig < vehicle
sig < Compound 2, 0.1 mg/kg
tsig < Compound 2, 0.1 mg/kg

TABLE 7

Histological scoring of Synovitis in the tarsal joints from animals with adjuvant-induced arthritis treated orally for 2 weeks with Compound 2 beginning on day 8 after CFA injection.

| Group | Synovial Structure[a] (0-3) | Fibroplasia[a] (0-3) | Inflammatory Cells[a] (0-3) | Pannus[a] (0-2) | Total Synovitis Score[a] (0-10) |
|---|---|---|---|---|---|
| Vehicle | 2.92 ± 0.21 | 2.67 ± 0.41 | 2.92 ± 0.21 | 2.00 ± 0 | 10.50 ± 0.63 |
| 1 mg/kg | 1.42 ± 0.38*# | 1.33 ± 0.41*t | 1.17 ± 0.26*# | 0.25 ± 0.42*# | 4.17 ± 1.21*#t |
| 0.3 mg/kg | 1.58 ± 0.38*# | 1.67 ± 0.26*t | 1.25 ± 0.27*# | 0.50 ± 0.84*# | 5.00 ± 1.30*#t |
| 0.1 mg/kg | 2.33 ± 0.75 | 1.75 ± 0.42* | 1.83 ± 0.52* | 1.50 ± 0.84 | 7.42 ± 2.25* |

[a]Means ± SD
*sig < vehicle
sig < Compound 2, 0.1 mg/kg
tsig < Compound 2, 0.1 mg/kg Evaluation in the Collagen Induced Arthritis Models.

Compound 2 was evaluated in BALB/c mice, 6-8 weeks of age, in which arthritis was induced by monoclonal antibodies raised against type II collagen, plus lipopolysaccharide (LPS). The animals were administered intravenously with a combination of four different mAbs totaling 4 mg/mouse on day 0, and followed by intravenous administration of 25 mg of LPS 72 hours later (day 3). From day 3, one hour after LPS application, tested compounds were given orally once daily for 15 days. For each animal, an increase in volume of both hind paws was measured using a plethysmometer with water cell (12 mm diameter) on days 0, 5, 7, 10, 14 and 17. Percent inhibition of increase in volume was calculated. Reduction of edema in the hind paws by 30% or more was considered significant.

The compound Compound 2 significantly inhibited paw edema >30% over the course of the experiment when given orally at 2.5 mg/kg.

Example 5

Compound 2 Does not Affect Uterine Wet Weights

Figure 5:
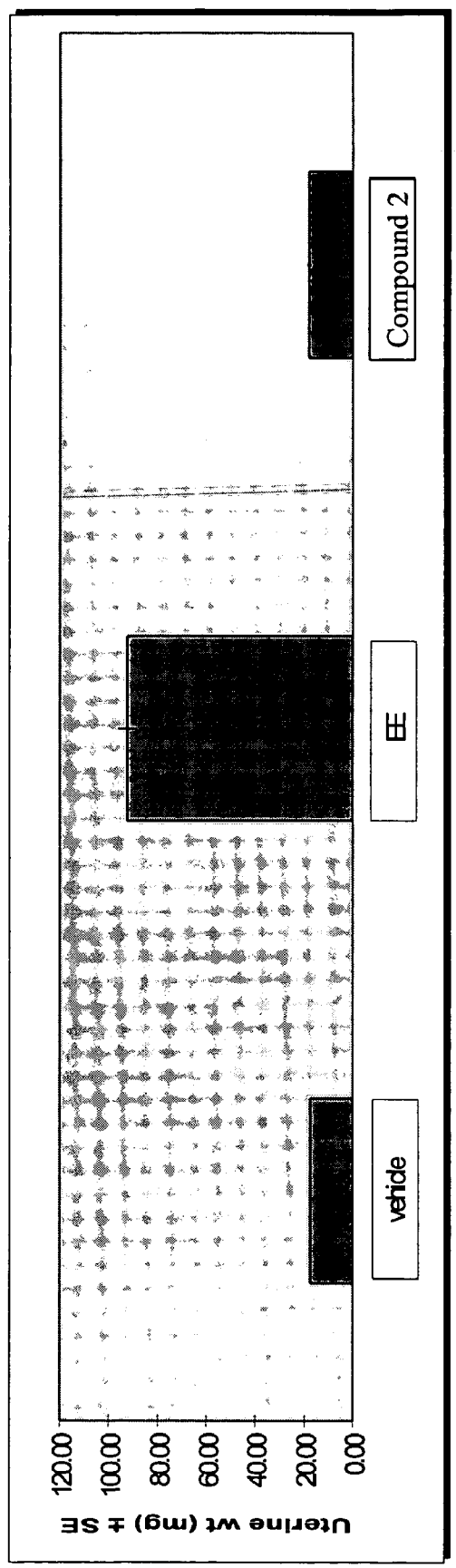
FIG. 5 is a graph illustrating a comparison of uterine weight (mg) versus vehicle, 17α-ethinylestradiol (EE), or Compound 2.

As a control to demonstrate the selectivity of the compound, Compound 2 was given orally to immature female rats (n=6/treatment) at a concentration of 50 mg/kg in a vehicle of 2.0% Tween 80 (w/v)/0.5% methyl cellulose (w/v). Animals were treated once per day by gavage for three days. Following euthanasia on day four (24 hours after the last dose) the uteri were removed, stripped of remaining fat and mesentery and weighed. The dose of the compound (50 mg/kg) was 500 fold higher than the efficacious dose in the above experiments. As shown in the graph of FIG. 5, Compound 2 demonstrated no increase in uterine wet weights while 17α-ethinylestradiol (EE) given at 1.5 mg/kg (EC80) significantly stimulated uterine weight.

Example 6

The Crystal Structures of ERalpha-LBD/Compound 1 and ERalpha-LBD/Compound 2 were Determined Human ERalpha-LBD (FIG. 6) was cloned into the pET16b expression vector (Novagen, Inc., Madison, Wis.), and the protein was overexpressed from a high density culture of *E. coli* BL21 DE3-RP cells (Stratagene, La Jolla, Calif.) in a Biostat C-10 bioreactor (B. Braun Biotech, Allentown, Pa.). Cultures were induced with 1.0 mM IPTG (final concentration) for 3 hours at 37° C. Cell pellets were quick-frozen in liquid nitrogen prior to storage at −80° C.

Cell pellets were resuspended in a buffer of 100 mM Tris-HCl pH 8.5, 100 mM KCl, 1 mM EDTA and 4 mM DTT. The cell suspension was disrupted by passing through a microfluidizer five times (Model 110Y, Microfluidics Corpt, Newton, Mass.). After centrifugation (13,000×g) for 30 min at 4° C., the pellet was extracted with 4 M urea in the same buffer. After centrifugation, the urea extract was applied to a column of estradiol-Sepharose Fast Flow. The column was first washed with 1 M urea in the above buffer, then sequentially washed with: 1) 50 mM Tris-HCl, pH 8.5, 700 mM KCl, 1 mM EDTA & 1 mM DTT; 2) 50 mM Tris-HCl, pH 8.5, 250 mM NaSCN, 1 mM EDTA, and 1 mM DTT in 10% dimethylformamide; and 3) 10 mM Tris-HCl, pH 8.0. While the ERalpha-LBD was still bound to the estradiol-affinity column, carboxymethylation was performed by equilibrating the column with 5 mM iodoacetic acid in 10 mM Tris-HCl, pH 8.0, overnight at 4° C. The carboxymethylated ERalpha-LBD was eluted with a ligand in the NaSCN-containing buffer. Different ligand-containing elution buffers included 100 μM 17β-estradiol, or 200 μM Compound 1 or 200 μM Compound 2. The presence of the receptor bound to ligand was determined by SDS-PAGE. Fractions containing ERalpha-LBD bound to ligand were pooled and concentrated by a Millipore Ultrafree centrifugal filtration device. The concentrated solution containing ERalpha-LBD bound to ligand was desalted with a BioRad disposable desalting column equilibrated with 50 mM ammonium bicarbonate, pH 7.5, and was used for crystallization trials.

Crystallization conditions for ERalpha-LBD complexed with ligand were determined using Hampton crystallization screens (Hampton Research, Aliso Viejo, Calif.). In one screen, 3 ml of protein solution (at 10 mg/ml) were mixed with 3 ml of precipitant (20% PEG3350, 0.15 M Lithium chloride, 0.1 M Hepes at pH 7.5, and 4% Benzamidine HCl) and equilibrated against 1 mL of the precipitant solution at 18° C. Crystals began to appear after three days and grew to the maximum size of 0.3×0.2×0.08 mm$^3$.

Resolution data at 30.0-2.4 Å were collected using Quantum 4 CCD area detector at Advanced Light Source (ALS) (Berkeley, Calif.). The data were collected at −130° C. and were processed using DENZO and SCALEPACK (Otwinowski and Minor, *Methods Enzymol.* 276: 307-326, 1997). Both ERalpha/Compound 1 and ERalpha/Compound 2 co-crystals belong to space group C2 with two molecules per asymmetric unit.

The ERalpha molecule was located using a dimer model from 2erd.pdb (Shiau et al., *Cell* 95:927-37, 1998) in rotation and translation searches with AmoRe (Navaza, *Acta Crystallogr.* A50:157-163, 1994). The structural refinement was carried out by CNS (Brunger et al., *Acta Crystallogr.* D54: 905-921, 1998) using all data from 30 to 2.4 Å resolution. In both structures, the position of the ligand and the Helix 12 position was identified using the 3Fo-2Fc and Fo-Fc electron density maps. After cycles of rebuilding, minimization, and individual B factor refinements, the $R_{work}$ and $R_{free}$ factors converged to 24.1% and 27.5% for the ERalpha-LBD/Compound 1 complex structure, and to 26.7% and 30.5% for the ERalpha-LBD/Compound 2 complex structure. The final model contains two copies of protein (residues 307-546, of which residues 333-340, 459-471 and 528-535 have been omitted due to disorder), two ligands, and water molecules. Table 8 summarizes the data collection parameters and results.

TABLE 8

Statistics of X-Ray Diffraction Data Collection for Compound 1 and Compound 2[d]

| Data Collection: | |
|---|---|
| Crystal System | monoclinic |
| Space Group | C2 |
| Unit Cell Dimensions | Compound 1: A = 104.803 Å, b = 54.124 Å, c = 97.102 Å, α = γ = 90°, β = 113.668° |
| | Compound 2: A = 105.128 Å, b = 52.927 Å, c = 95.534 Å, α = γ = 90°, β = 113.247° |
| Data Collection Temperature | −130° C. |
| Number of crystals | 1 |
| Radiation Source | Quantum 4 CCD area detector at ALS (Berkeley, CA) |
| X-ray wavelength | 1.0 Å |
| Resolution range of data | 30.0-2.4 Å |
| Maximum Resolution | 2.4 Å |
| $R_{merge}$[a] | Compound 1: 9.0%; Compound 2: 7.7% |
| Completeness | Compound 1: 98.7%; Compound 2: 99.4% |
| Total reflections | Compound 1: 70450 |
| | Compound 2: 68760 |
| Unique reflections | Compound 1: 19,668 |
| | Compound 2: 19,085 |
| I/σ(I) | Compound 1: 14.49 |
| | Compound 2: 16.69 |
| Phasing and Refinement | |
| Model for molecular refinement | 2erd.pdb (ERalpha-LBD/diethylstilbestrol) |
| Construct (amino acids) | ERalpha-LBD (301-554) |
| Compounds (ligands) | Compound 1 and Compound 2 |
| ERalpha-LBD molecules per asymmetric unit | 2 |
| Resolution range of refinement | 30.0-2.4 Å |
| $R_{work}$ | Compound 1: 24.1% |
| | Compound 2: 26.7% |
| $R_{free}$ | Compound 1: 27.5% |
| | Compound 2: 30.5% |
| Number of non-hydrogen protein atoms (in a dimer structure) | Compound 1: 3281 |
| | Compound 2: 3309 |
| Number of water molecules | Compound 1: 161; Compound 2: 225 |
| RMS deviations from ideal bond lengths | Compound 1: 0.0085; Compound 2: 0.0099 |
| RMS deviations from ideal bond angles | Compound 1: 1.313; Compound 2: 1.371 |

[a] $R_{merge} = |I_h - \langle I_h \rangle|/I_h$, where $\langle I_h \rangle$ is the average intensity over symmetry equivalents. Numbers in parentheses reflect statistics for the last shell.
[b] $R_{work} = ||F_{obs}| - |F_{calc}||/|F_{obs}|$
[c] $R_{free}$ is equivalent to $R_{work}$, but calculated for a randomly chosen 5% of reflections omitted from the refinement process.
[d] Except where otherwise indicated, parameters were the same for Compounds 1 and 2.

The overall structure of ERalpha in complex with Compound 1 and Compound 2 is very similar to previously reported ERalpha structures (Brzozowski et al., Nature 389: 753-8, 1997). It is formed by three layers of anti-parallel α-helices and a short β-ribbon (FIG. 1). In both structures, ligands are located in the hydrophobic cavity formed by side chains of helices H3, H6, H7, H8, H11, and strand S1. A non-crystallographic dimer has a large interface formed by helices H10 and H11. Five residues at the N-terminus (H1) and the loop connecting H11 and H12 are invisible in the electron density maps.

FIGS. 2 and 3 demonstrate the similarity and difference in the binding modes of Compound 1 and Compound 2 and ERalpha's natural ligand, 17β-estradiol. In all co-structures, ligands are oriented in such a way that their phenols make hydrogen bonds with the Glu353 salt bridge, and a structurally conserved water molecule at one end of the cavity. Compound 1 also forms a hydrogen bond with the Arg394 salt bridge near the distal end of the cavity. However, near helix H11, Compound 1 and Compound 2 lack hydrogen bonding to the imidazole side chain of His524, even though the trifluoromethyl group of Compound 1 and the fluoro group of Compound 2 point directly to His524. The conformation of amino acid residues involved in hydrophobic interaction with the ligands is otherwise close to that seen for the ERalpha/17β-estradiol complex.

Comparison with the ERalpha/Raloxifene structure (FIG. 4) shows that, unlike Raloxifene which sterically prevents the correct assembly of H12 and the NR-box binding, the binding modes of Compound 1 and Compound 2 do not reveal any obvious direct steric hindrance. Nevertheless, helix H12 is shifted away from its characteristic position over the ligand-binding site and occupies the co-activator peptide binding site. Thus, from the structural point of view, it appears that these two ligands induce H12 to adopt an antagonist-like position.

TABLE 9

Structure coordinates for ERalpha-LBD/Compound 1 complex
(Table discloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 1 | CB | LEU | A | 306 | 6.089 | 4.195 | −2.131 | 1.00 | 70.29 | A |
| ATOM | 2 | CG | LEU | A | 306 | 4.711 | 4.600 | −2.688 | 1.00 | 71.26 | A |
| ATOM | 3 | CD1 | LEU | A | 306 | 3.861 | 5.247 | −1.603 | 1.00 | 71.77 | A |
| ATOM | 4 | CD2 | LEU | A | 306 | 4.891 | 5.548 | −3.869 | 1.00 | 71.39 | A |
| ATOM | 5 | C | LEU | A | 306 | 6.619 | 6.151 | −0.638 | 1.00 | 68.48 | A |
| ATOM | 6 | O | LEU | A | 306 | 6.020 | 7.216 | −0.844 | 1.00 | 68.38 | A |
| ATOM | 7 | N | LEU | A | 306 | 8.431 | 4.668 | −1.441 | 1.00 | 69.12 | A |
| ATOM | 8 | CA | LEU | A | 306 | 7.118 | 5.289 | −1.800 | 1.00 | 69.34 | A |
| ATOM | 9 | N | ALA | A | 307 | 6.867 | 5.678 | 0.582 | 1.00 | 66.71 | A |
| ATOM | 10 | CA | ALA | A | 307 | 6.475 | 6.396 | 1.785 | 1.00 | 64.54 | A |
| ATOM | 11 | CB | ALA | A | 307 | 6.612 | 5.484 | 2.996 | 1.00 | 65.30 | A |
| ATOM | 12 | C | ALA | A | 307 | 7.381 | 7.628 | 1.926 | 1.00 | 63.23 | A |
| ATOM | 13 | O | ALA | A | 307 | 7.362 | 8.333 | 2.936 | 1.00 | 62.08 | A |
| ATOM | 14 | N | LEU | A | 308 | 8.174 | 7.867 | 0.886 | 1.00 | 61.54 | A |
| ATOM | 15 | CA | LEU | A | 308 | 9.089 | 9.000 | 0.813 | 1.00 | 59.95 | A |
| ATOM | 16 | CB | LEU | A | 308 | 10.280 | 8.648 | −0.077 | 1.00 | 60.61 | A |
| ATOM | 17 | CG | LEU | A | 308 | 11.628 | 8.391 | 0.593 | 1.00 | 61.40 | A |
| ATOM | 18 | CD1 | LEU | A | 308 | 12.606 | 7.803 | −0.416 | 1.00 | 60.53 | A |
| ATOM | 19 | CD2 | LEU | A | 308 | 12.152 | 9.698 | 1.176 | 1.00 | 61.54 | A |
| ATOM | 20 | C | LEU | A | 308 | 8.336 | 10.154 | 0.178 | 1.00 | 58.61 | A |
| ATOM | 21 | O | LEU | A | 308 | 8.749 | 11.316 | 0.253 | 1.00 | 57.46 | A |
| ATOM | 22 | N | SER | A | 309 | 7.218 | 9.803 | −0.450 | 1.00 | 57.23 | A |
| ATOM | 23 | CA | SER | A | 309 | 6.376 | 10.759 | −1.155 | 1.00 | 55.79 | A |
| ATOM | 24 | CB | SER | A | 309 | 5.795 | 10.103 | −2.412 | 1.00 | 55.78 | A |
| ATOM | 25 | OG | SER | A | 309 | 6.731 | 9.216 | −2.998 | 1.00 | 56.19 | A |
| ATOM | 26 | C | SER | A | 309 | 5.237 | 11.276 | −0.292 | 1.00 | 53.92 | A |
| ATOM | 27 | O | SER | A | 309 | 4.448 | 12.114 | −0.748 | 1.00 | 53.00 | A |
| ATOM | 28 | N | LEU | A | 310 | 5.146 | 10.770 | 0.939 | 1.00 | 51.27 | A |
| ATOM | 29 | CA | LEU | A | 310 | 4.084 | 11.193 | 1.849 | 1.00 | 49.15 | A |
| ATOM | 30 | CB | LEU | A | 310 | 4.083 | 10.351 | 3.124 | 1.00 | 48.88 | A |
| ATOM | 31 | CG | LEU | A | 310 | 3.705 | 8.875 | 2.983 | 1.00 | 48.47 | A |
| ATOM | 32 | CD1 | LEU | A | 310 | 3.536 | 8.303 | 4.377 | 1.00 | 47.61 | A |
| ATOM | 33 | CD2 | LEU | A | 310 | 2.413 | 8.711 | 2.189 | 1.00 | 47.02 | A |
| ATOM | 34 | C | LEU | A | 310 | 4.174 | 12.655 | 2.231 | 1.00 | 47.54 | A |
| ATOM | 35 | O | LEU | A | 310 | 5.221 | 13.279 | 2.116 | 1.00 | 47.44 | A |
| ATOM | 36 | N | THR | A | 311 | 3.058 | 13.204 | 2.677 | 1.00 | 46.21 | A |
| ATOM | 37 | CA | THR | A | 311 | 3.035 | 14.595 | 3.081 | 1.00 | 45.84 | A |
| ATOM | 38 | CB | THR | A | 311 | 1.726 | 15.276 | 2.623 | 1.00 | 46.24 | A |
| ATOM | 39 | OG1 | THR | A | 311 | 0.654 | 14.911 | 3.498 | 1.00 | 46.74 | A |
| ATOM | 40 | CG2 | THR | A | 311 | 1.378 | 14.836 | 1.209 | 1.00 | 45.98 | A |
| ATOM | 41 | C | THR | A | 311 | 3.149 | 14.657 | 4.607 | 1.00 | 45.34 | A |
| ATOM | 42 | O | THR | A | 311 | 3.064 | 13.634 | 5.281 | 1.00 | 45.28 | A |
| ATOM | 43 | N | ALA | A | 312 | 3.348 | 15.850 | 5.150 | 1.00 | 44.23 | A |
| ATOM | 44 | CA | ALA | A | 312 | 3.453 | 15.994 | 6.591 | 1.00 | 43.39 | A |
| ATOM | 45 | CB | ALA | A | 312 | 3.671 | 17.463 | 6.965 | 1.00 | 43.01 | A |
| ATOM | 46 | C | ALA | A | 312 | 2.179 | 15.470 | 7.242 | 1.00 | 43.02 | A |
| ATOM | 47 | O | ALA | A | 312 | 2.214 | 14.816 | 8.288 | 1.00 | 42.00 | A |
| ATOM | 48 | N | ASP | A | 313 | 1.045 | 15.746 | 6.611 | 1.00 | 43.60 | A |
| ATOM | 49 | CA | ASP | A | 313 | −0.221 | 15.300 | 7.163 | 1.00 | 44.10 | A |
| ATOM | 50 | CB | ASP | A | 313 | −1.367 | 16.091 | 6.548 | 1.00 | 46.83 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 51 | CG | ASP | A | 313 | −1.504 | 17.455 | 7.169 | 1.00 | 49.87 | A |
| ATOM | 52 | OD1 | ASP | A | 313 | −1.414 | 17.535 | 8.415 | 1.00 | 51.53 | A |
| ATOM | 53 | OD2 | ASP | A | 313 | −1.704 | 18.440 | 6.427 | 1.00 | 52.51 | A |
| ATOM | 54 | C | ASP | A | 313 | −0.480 | 13.806 | 7.055 | 1.00 | 42.83 | A |
| ATOM | 1 | CB | LEU | A | 306 | 6.089 | 4.195 | −2.131 | 1.00 | 70.29 | A |
| ATOM | 2 | CG | LEU | A | 306 | 4.711 | 4.600 | −2.688 | 1.00 | 71.26 | A |
| ATOM | 3 | CD1 | LEU | A | 306 | 3.861 | 5.247 | −1.603 | 1.00 | 71.77 | A |
| ATOM | 4 | CD2 | LEU | A | 306 | 4.891 | 5.548 | −3.869 | 1.00 | 71.39 | A |
| ATOM | 5 | C | LEU | A | 306 | 6.619 | 6.151 | −0.638 | 1.00 | 68.48 | A |
| ATOM | 6 | O | LEU | A | 306 | 6.020 | 7.216 | −0.844 | 1.00 | 68.38 | A |
| ATOM | 7 | N | LEU | A | 306 | 8.431 | 4.668 | −1.441 | 1.00 | 69.12 | A |
| ATOM | 8 | CA | LEU | A | 306 | 7.118 | 5.289 | −1.800 | 1.00 | 69.34 | A |
| ATOM | 9 | N | ALA | A | 307 | 6.867 | 5.678 | 0.582 | 1.00 | 66.71 | A |
| ATOM | 10 | CA | ALA | A | 307 | 6.475 | 6.396 | 1.785 | 1.00 | 64.54 | A |
| ATOM | 11 | CB | ALA | A | 307 | 6.612 | 5.484 | 2.996 | 1.00 | 65.30 | A |
| ATOM | 12 | C | ALA | A | 307 | 7.381 | 7.628 | 1.926 | 1.00 | 63.23 | A |
| ATOM | 13 | O | ALA | A | 307 | 7.362 | 8.333 | 2.936 | 1.00 | 62.08 | A |
| ATOM | 14 | N | LEU | A | 308 | 8.174 | 7.867 | 0.886 | 1.00 | 61.54 | A |
| ATOM | 15 | CA | LEU | A | 308 | 9.089 | 9.000 | 0.813 | 1.00 | 59.95 | A |
| ATOM | 16 | CB | LEU | A | 308 | 10.280 | 8.648 | −0.077 | 1.00 | 60.61 | A |
| ATOM | 17 | CG | LEU | A | 308 | 11.628 | 8.391 | 0.593 | 1.00 | 61.40 | A |
| ATOM | 18 | CD1 | LEU | A | 308 | 12.606 | 7.803 | −0.416 | 1.00 | 60.53 | A |
| ATOM | 19 | CD2 | LEU | A | 308 | 12.152 | 9.698 | 1.176 | 1.00 | 61.54 | A |
| ATOM | 20 | C | LEU | A | 308 | 8.336 | 10.154 | 0.178 | 1.00 | 58.61 | A |
| ATOM | 21 | O | LEU | A | 308 | 8.749 | 11.316 | 0.253 | 1.00 | 57.46 | A |
| ATOM | 22 | N | SER | A | 309 | 7.218 | 9.803 | −0.450 | 1.00 | 57.23 | A |
| ATOM | 23 | CA | SER | A | 309 | 6.376 | 10.759 | −1.155 | 1.00 | 55.79 | A |
| ATOM | 24 | CB | SER | A | 309 | 5.795 | 10.103 | −2.412 | 1.00 | 55.78 | A |
| ATOM | 25 | OG | SER | A | 309 | 6.731 | 9.216 | −2.998 | 1.00 | 56.19 | A |
| ATOM | 26 | C | SER | A | 309 | 5.237 | 11.276 | −0.292 | 1.00 | 53.92 | A |
| ATOM | 27 | O | SER | A | 309 | 4.448 | 12.114 | −0.748 | 1.00 | 53.00 | A |
| ATOM | 28 | N | LEU | A | 310 | 5.146 | 10.770 | 0.939 | 1.00 | 51.27 | A |
| ATOM | 29 | CA | LEU | A | 310 | 4.084 | 11.193 | 1.849 | 1.00 | 49.15 | A |
| ATOM | 30 | CB | LEU | A | 310 | 4.083 | 10.351 | 3.124 | 1.00 | 48.88 | A |
| ATOM | 31 | CG | LEU | A | 310 | 3.705 | 8.875 | 2.983 | 1.00 | 48.47 | A |
| ATOM | 32 | CD1 | LEU | A | 310 | 3.536 | 8.303 | 4.377 | 1.00 | 47.61 | A |
| ATOM | 33 | CD2 | LEU | A | 310 | 2.413 | 8.711 | 2.189 | 1.00 | 47.02 | A |
| ATOM | 34 | C | LEU | A | 310 | 4.174 | 12.655 | 2.231 | 1.00 | 47.54 | A |
| ATOM | 35 | O | LEU | A | 310 | 5.221 | 13.279 | 2.116 | 1.00 | 47.44 | A |
| ATOM | 36 | N | THR | A | 311 | 3.058 | 13.204 | 2.677 | 1.00 | 46.21 | A |
| ATOM | 37 | CA | THR | A | 311 | 3.035 | 14.595 | 3.081 | 1.00 | 45.84 | A |
| ATOM | 38 | CB | THR | A | 311 | 1.726 | 15.276 | 2.623 | 1.00 | 46.24 | A |
| ATOM | 39 | OG1 | THR | A | 311 | 0.654 | 14.911 | 3.498 | 1.00 | 46.74 | A |
| ATOM | 40 | CG2 | THR | A | 311 | 1.378 | 14.836 | 1.209 | 1.00 | 45.98 | A |
| ATOM | 41 | C | THR | A | 311 | 3.149 | 14.657 | 4.607 | 1.00 | 45.34 | A |
| ATOM | 42 | O | THR | A | 311 | 3.064 | 13.634 | 5.281 | 1.00 | 45.28 | A |
| ATOM | 43 | N | ALA | A | 312 | 3.348 | 15.850 | 5.150 | 1.00 | 44.23 | A |
| ATOM | 44 | CA | ALA | A | 312 | 3.453 | 15.994 | 6.591 | 1.00 | 43.39 | A |
| ATOM | 45 | CB | ALA | A | 312 | 3.671 | 17.463 | 6.965 | 1.00 | 43.01 | A |
| ATOM | 46 | C | ALA | A | 312 | 2.179 | 15.470 | 7.242 | 1.00 | 43.02 | A |
| ATOM | 47 | O | ALA | A | 312 | 2.214 | 14.816 | 8.288 | 1.00 | 42.00 | A |
| ATOM | 48 | N | ASP | A | 313 | 1.045 | 15.746 | 6.611 | 1.00 | 43.60 | A |
| ATOM | 49 | CA | ASP | A | 313 | −0.221 | 15.300 | 7.163 | 1.00 | 44.10 | A |
| ATOM | 50 | CB | ASP | A | 313 | −1.367 | 16.091 | 6.548 | 1.00 | 46.83 | A |
| ATOM | 51 | CG | ASP | A | 313 | −1.504 | 17.455 | 7.169 | 1.00 | 49.87 | A |
| ATOM | 52 | OD1 | ASP | A | 313 | −1.414 | 17.535 | 8.415 | 1.00 | 51.53 | A |
| ATOM | 53 | OD2 | ASP | A | 313 | −1.704 | 18.440 | 6.427 | 1.00 | 52.51 | A |
| ATOM | 54 | C | ASP | A | 313 | −0.480 | 13.806 | 7.055 | 1.00 | 42.83 | A |
| ATOM | 55 | O | ASP | A | 313 | −1.098 | 13.226 | 7.950 | 1.00 | 42.39 | A |
| ATOM | 56 | N | GLN | A | 314 | −0.009 | 13.182 | 5.979 | 1.00 | 41.06 | A |
| ATOM | 57 | CA | GLN | A | 314 | −0.192 | 11.744 | 5.810 | 1.00 | 40.27 | A |
| ATOM | 58 | CB | GLN | A | 314 | 0.051 | 11.337 | 4.351 | 1.00 | 41.15 | A |
| ATOM | 59 | CG | GLN | A | 314 | −0.865 | 12.064 | 3.366 | 1.00 | 42.44 | A |
| ATOM | 60 | CD | GLN | A | 314 | −0.574 | 11.742 | 1.911 | 1.00 | 43.63 | A |
| ATOM | 61 | OE1 | GLN | A | 314 | 0.583 | 11.675 | 1.492 | 1.00 | 43.95 | A |
| ATOM | 62 | NE2 | GLN | A | 314 | −1.631 | 11.564 | 1.127 | 1.00 | 44.85 | A |
| ATOM | 63 | C | GLN | A | 314 | 0.780 | 11.011 | 6.736 | 1.00 | 39.60 | A |
| ATOM | 64 | O | GLN | A | 314 | 0.511 | 9.894 | 7.177 | 1.00 | 38.98 | A |
| ATOM | 65 | N | MET | A | 315 | 1.918 | 11.644 | 7.019 | 1.00 | 39.06 | A |
| ATOM | 66 | CA | MET | A | 315 | 2.915 | 11.067 | 7.917 | 1.00 | 37.89 | A |
| ATOM | 67 | CB | MET | A | 315 | 4.160 | 11.965 | 7.970 | 1.00 | 39.72 | A |
| ATOM | 68 | CG | MET | A | 315 | 5.236 | 11.536 | 8.979 | 1.00 | 41.31 | A |
| ATOM | 69 | SD | MET | A | 315 | 5.795 | 9.823 | 8.749 | 1.00 | 46.32 | A |
| ATOM | 70 | CE | MET | A | 315 | 7.266 | 10.031 | 7.763 | 1.00 | 44.10 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 71 | C | MET | A | 315 | 2.279 | 10.960 | 9.309 | 1.00 | 37.33 | A |
| ATOM | 72 | O | MET | A | 315 | 2.357 | 9.924 | 9.971 | 1.00 | 36.52 | A |
| ATOM | 73 | N | VAL | A | 316 | 1.614 | 12.035 | 9.715 | 1.00 | 36.05 | A |
| ATOM | 74 | CA | VAL | A | 316 | 0.970 | 12.116 | 11.009 | 1.00 | 36.43 | A |
| ATOM | 75 | CB | VAL | A | 316 | 0.511 | 13.564 | 11.292 | 1.00 | 36.61 | A |
| ATOM | 76 | CG1 | VAL | A | 316 | −0.093 | 13.662 | 12.677 | 1.00 | 36.31 | A |
| ATOM | 77 | CG2 | VAL | A | 316 | 1.698 | 14.510 | 11.168 | 1.00 | 36.83 | A |
| ATOM | 78 | C | VAL | A | 316 | −0.212 | 11.168 | 11.166 | 1.00 | 37.58 | A |
| ATOM | 79 | O | VAL | A | 316 | −0.363 | 10.531 | 12.217 | 1.00 | 37.84 | A |
| ATOM | 80 | N | SER | A | 317 | −1.054 | 11.092 | 10.136 | 1.00 | 37.40 | A |
| ATOM | 81 | CA | SER | A | 317 | −2.213 | 10.204 | 10.148 | 1.00 | 36.66 | A |
| ATOM | 82 | CB | SER | A | 317 | −3.000 | 10.293 | 8.826 | 1.00 | 38.21 | A |
| ATOM | 83 | OG | SER | A | 317 | −3.477 | 11.603 | 8.575 | 1.00 | 39.53 | A |
| ATOM | 84 | C | SER | A | 317 | −1.685 | 8.793 | 10.285 | 1.00 | 35.25 | A |
| ATOM | 85 | O | SER | A | 317 | −2.179 | 8.007 | 11.080 | 1.00 | 35.71 | A |
| ATOM | 86 | N | ALA | A | 318 | −0.679 | 8.483 | 9.480 | 1.00 | 34.47 | A |
| ATOM | 87 | CA | ALA | A | 318 | −0.063 | 7.165 | 9.488 | 1.00 | 34.73 | A |
| ATOM | 88 | CB | ALA | A | 318 | 1.088 | 7.123 | 8.491 | 1.00 | 33.40 | A |
| ATOM | 89 | C | ALA | A | 318 | 0.440 | 6.833 | 10.890 | 1.00 | 34.79 | A |
| ATOM | 90 | O | ALA | A | 318 | 0.079 | 5.811 | 11.467 | 1.00 | 34.60 | A |
| ATOM | 91 | N | LEU | A | 319 | 1.267 | 7.714 | 11.438 | 1.00 | 35.57 | A |
| ATOM | 92 | CA | LEU | A | 319 | 1.817 | 7.512 | 12.776 | 1.00 | 35.86 | A |
| ATOM | 93 | CB | LEU | A | 319 | 2.729 | 8.683 | 13.141 | 1.00 | 35.48 | A |
| ATOM | 94 | CG | LEU | A | 319 | 4.030 | 8.656 | 12.338 | 1.00 | 35.44 | A |
| ATOM | 95 | CD1 | LEU | A | 319 | 4.975 | 9.737 | 12.835 | 1.00 | 35.34 | A |
| ATOM | 96 | CD2 | LEU | A | 319 | 4.676 | 7.279 | 12.474 | 1.00 | 36.39 | A |
| ATOM | 97 | C | LEU | A | 319 | 0.744 | 7.302 | 13.848 | 1.00 | 35.84 | A |
| ATOM | 98 | O | LEU | A | 319 | 0.775 | 6.299 | 14.571 | 1.00 | 34.75 | A |
| ATOM | 99 | N | LEU | A | 320 | −0.202 | 8.233 | 13.935 | 1.00 | 35.72 | A |
| ATOM | 100 | CA | LEU | A | 320 | −1.281 | 8.136 | 14.915 | 1.00 | 36.90 | A |
| ATOM | 101 | CB | LEU | A | 320 | −2.214 | 9.345 | 14.810 | 1.00 | 37.27 | A |
| ATOM | 102 | CG | LEU | A | 320 | −1.703 | 10.711 | 15.262 | 1.00 | 37.80 | A |
| ATOM | 103 | CD1 | LEU | A | 320 | −2.751 | 11.784 | 14.950 | 1.00 | 37.24 | A |
| ATOM | 104 | CD2 | LEU | A | 320 | −1.388 | 10.666 | 16.743 | 1.00 | 36.80 | A |
| ATOM | 105 | C | LEU | A | 320 | −2.119 | 6.860 | 14.786 | 1.00 | 36.87 | A |
| ATOM | 106 | O | LEU | A | 320 | −2.582 | 6.317 | 15.786 | 1.00 | 38.16 | A |
| ATOM | 107 | N | ASP | A | 321 | −2.318 | 6.391 | 13.564 | 0.50 | 35.72 | A |
| ATOM | 108 | CA | ASP | A | 321 | −3.101 | 5.188 | 13.336 | 0.50 | 35.16 | A |
| ATOM | 109 | CB | ASP | A | 321 | −3.469 | 5.104 | 11.851 | 0.50 | 36.67 | A |
| ATOM | 110 | CG | ASP | A | 321 | −4.415 | 3.970 | 11.549 | 0.50 | 37.25 | A |
| ATOM | 111 | OD1 | ASP | A | 321 | −5.441 | 3.843 | 12.247 | 0.50 | 37.63 | A |
| ATOM | 112 | OD2 | ASP | A | 321 | −4.134 | 3.209 | 10.606 | 0.50 | 38.60 | A |
| ATOM | 113 | C | ASP | A | 321 | −2.327 | 3.943 | 13.780 | 0.50 | 34.60 | A |
| ATOM | 114 | O | ASP | A | 321 | −2.912 | 2.917 | 14.120 | 0.50 | 33.87 | A |
| ATOM | 115 | N | ALA | A | 322 | −1.004 | 4.053 | 13.791 | 1.00 | 34.26 | A |
| ATOM | 116 | CA | ALA | A | 322 | −0.130 | 2.956 | 14.196 | 1.00 | 34.17 | A |
| ATOM | 117 | CB | ALA | A | 322 | 1.224 | 3.069 | 13.480 | 1.00 | 32.11 | A |
| ATOM | 118 | C | ALA | A | 322 | 0.090 | 2.901 | 15.718 | 1.00 | 34.22 | A |
| ATOM | 119 | O | ALA | A | 322 | 0.702 | 1.958 | 16.219 | 1.00 | 34.25 | A |
| ATOM | 120 | N | GLU | A | 323 | −0.407 | 3.895 | 16.452 | 1.00 | 33.73 | A |
| ATOM | 121 | CA | GLU | A | 323 | −0.226 | 3.904 | 17.902 | 1.00 | 34.12 | A |
| ATOM | 122 | CB | GLU | A | 323 | −0.970 | 5.072 | 18.545 | 1.00 | 33.40 | A |
| ATOM | 123 | CG | GLU | A | 323 | −0.181 | 6.373 | 18.611 | 1.00 | 33.21 | A |
| ATOM | 124 | CD | GLU | A | 323 | 1.137 | 6.228 | 19.359 | 1.00 | 33.38 | A |
| ATOM | 125 | OE1 | GLU | A | 323 | 2.140 | 5.805 | 18.739 | 1.00 | 32.84 | A |
| ATOM | 126 | OE2 | GLU | A | 323 | 1.164 | 6.526 | 20.572 | 1.00 | 32.63 | A |
| ATOM | 127 | C | GLU | A | 323 | −0.673 | 2.615 | 18.568 | 1.00 | 34.89 | A |
| ATOM | 128 | O | GLU | A | 323 | −1.739 | 2.080 | 18.261 | 1.00 | 35.11 | A |
| ATOM | 129 | N | PRO | A | 324 | 0.144 | 2.100 | 19.498 | 1.00 | 35.22 | A |
| ATOM | 130 | CD | PRO | A | 324 | 1.451 | 2.652 | 19.888 | 1.00 | 35.42 | A |
| ATOM | 131 | CA | PRO | A | 324 | −0.143 | 0.863 | 20.236 | 1.00 | 33.88 | A |
| ATOM | 132 | CB | PRO | A | 324 | 1.221 | 0.453 | 20.813 | 1.00 | 36.00 | A |
| ATOM | 133 | CG | PRO | A | 324 | 2.238 | 1.402 | 20.152 | 1.00 | 36.95 | A |
| ATOM | 134 | C | PRO | A | 324 | −1.130 | 1.153 | 21.355 | 1.00 | 33.37 | A |
| ATOM | 135 | O | PRO | A | 324 | −1.354 | 2.305 | 21.706 | 1.00 | 32.85 | A |
| ATOM | 136 | N | PRO | A | 325 | −1.740 | 0.110 | 21.927 | 1.00 | 33.20 | A |
| ATOM | 137 | CD | PRO | A | 325 | −1.777 | −1.315 | 21.538 | 1.00 | 31.90 | A |
| ATOM | 138 | CA | PRO | A | 325 | −2.680 | 0.387 | 23.012 | 1.00 | 31.36 | A |
| ATOM | 139 | CB | PRO | A | 325 | −3.584 | −0.839 | 23.002 | 1.00 | 31.78 | A |
| ATOM | 140 | CG | PRO | A | 325 | −2.624 | −1.935 | 22.623 | 1.00 | 30.50 | A |
| ATOM | 141 | C | PRO | A | 325 | −1.907 | 0.523 | 24.317 | 1.00 | 32.06 | A |
| ATOM | 142 | O | PRO | A | 325 | −0.738 | 0.144 | 24.402 | 1.00 | 31.44 | A |
| ATOM | 143 | N | ILE | A | 326 | −2.570 | 1.070 | 25.325 | 1.00 | 33.22 | A |
| ATOM | 144 | CA | ILE | A | 326 | −1.977 | 1.256 | 26.643 | 1.00 | 33.88 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 145 | CB | ILE | A | 326 | −2.567 | 2.526 | 27.325 | 1.00 | 33.33 | A |
| ATOM | 146 | CG2 | ILE | A | 326 | −2.171 | 2.595 | 28.795 | 1.00 | 34.18 | A |
| ATOM | 147 | CG1 | ILE | A | 326 | −2.065 | 3.768 | 26.584 | 1.00 | 33.99 | A |
| ATOM | 148 | CD1 | ILE | A | 326 | −2.765 | 5.044 | 26.981 | 1.00 | 34.87 | A |
| ATOM | 149 | C | ILE | A | 326 | −2.294 | 0.000 | 27.437 | 1.00 | 34.76 | A |
| ATOM | 150 | O | ILE | A | 326 | −3.440 | −0.217 | 27.836 | 1.00 | 35.42 | A |
| ATOM | 151 | N | LEU | A | 327 | −1.288 | −0.842 | 27.643 | 1.00 | 35.10 | A |
| ATOM | 152 | CA | LEU | A | 327 | −1.513 | −2.084 | 28.370 | 1.00 | 37.25 | A |
| ATOM | 153 | CB | LEU | A | 327 | −0.391 | −3.084 | 28.086 | 1.00 | 35.63 | A |
| ATOM | 154 | CG | LEU | A | 327 | −0.093 | −3.493 | 26.638 | 1.00 | 35.01 | A |
| ATOM | 155 | CD1 | LEU | A | 327 | 0.779 | −4.736 | 26.669 | 1.00 | 33.87 | A |
| ATOM | 156 | CD2 | LEU | A | 327 | −1.378 | −3.766 | 25.861 | 1.00 | 33.84 | A |
| ATOM | 157 | C | LEU | A | 327 | −1.663 | −1.896 | 29.879 | 1.00 | 39.72 | A |
| ATOM | 158 | O | LEU | A | 327 | −1.351 | −0.838 | 30.423 | 1.00 | 40.77 | A |
| ATOM | 159 | N | TYR | A | 328 | −2.165 | −2.933 | 30.541 | 1.00 | 42.81 | A |
| ATOM | 160 | CA | TYR | A | 328 | −2.370 | −2.931 | 31.988 | 1.00 | 45.06 | A |
| ATOM | 161 | CB | TYR | A | 328 | −3.821 | −3.253 | 32.323 | 1.00 | 44.29 | A |
| ATOM | 162 | CG | TYR | A | 328 | −4.733 | −2.067 | 32.387 | 1.00 | 44.05 | A |
| ATOM | 163 | CD1 | TYR | A | 328 | −5.121 | −1.389 | 31.227 | 1.00 | 43.98 | A |
| ATOM | 164 | CE1 | TYR | A | 328 | −6.001 | −0.313 | 31.291 | 1.00 | 43.84 | A |
| ATOM | 165 | CD2 | TYR | A | 328 | −5.240 | −1.637 | 33.611 | 1.00 | 43.03 | A |
| ATOM | 166 | CE2 | TYR | A | 328 | −6.111 | −0.565 | 33.688 | 1.00 | 43.28 | A |
| ATOM | 167 | CZ | TYR | A | 328 | −6.488 | 0.091 | 32.526 | 1.00 | 43.91 | A |
| ATOM | 168 | OH | TYR | A | 328 | −7.343 | 1.159 | 32.601 | 1.00 | 45.28 | A |
| ATOM | 169 | C | TYR | A | 328 | −1.497 | −3.970 | 32.682 | 1.00 | 47.17 | A |
| ATOM | 170 | O | TYR | A | 328 | −1.108 | −4.980 | 32.085 | 1.00 | 45.72 | A |
| ATOM | 171 | N | SER | A | 329 | −1.204 | −3.726 | 33.954 | 1.00 | 50.66 | A |
| ATOM | 172 | CA | SER | A | 329 | −0.393 | −4.665 | 34.722 | 1.00 | 54.37 | A |
| ATOM | 173 | CB | SER | A | 329 | 0.458 | −3.926 | 35.763 | 1.00 | 54.65 | A |
| ATOM | 174 | OG | SER | A | 329 | −0.327 | −3.048 | 36.548 | 1.00 | 57.57 | A |
| ATOM | 175 | C | SER | A | 329 | −1.318 | −5.671 | 35.400 | 1.00 | 56.02 | A |
| ATOM | 176 | O | SER | A | 329 | −2.452 | −5.342 | 35.760 | 1.00 | 55.43 | A |
| ATOM | 177 | N | GLU | A | 330 | −0.826 | −6.897 | 35.554 | 1.00 | 59.06 | A |
| ATOM | 178 | CA | GLU | A | 330 | −1.591 | −7.982 | 36.169 | 1.00 | 61.96 | A |
| ATOM | 179 | CB | GLU | A | 330 | −0.650 | −9.135 | 36.534 | 1.00 | 63.49 | A |
| ATOM | 180 | CG | GLU | A | 330 | −1.369 | −10.418 | 36.921 | 1.00 | 65.80 | A |
| ATOM | 181 | CD | GLU | A | 330 | −0.413 | −11.562 | 37.209 | 1.00 | 66.67 | A |
| ATOM | 182 | OE1 | GLU | A | 330 | 0.547 | −11.761 | 36.430 | 1.00 | 67.20 | A |
| ATOM | 183 | OE2 | GLU | A | 330 | −0.630 | −12.272 | 38.212 | 1.00 | 67.92 | A |
| ATOM | 184 | C | GLU | A | 330 | −2.361 | −7.531 | 37.414 | 1.00 | 62.81 | A |
| ATOM | 185 | O | GLU | A | 330 | −1.838 | −6.776 | 38.239 | 1.00 | 63.06 | A |
| ATOM | 186 | N | ALA | A | 331 | −3.602 | −7.995 | 37.547 | 1.00 | 63.57 | A |
| ATOM | 187 | CA | ALA | A | 331 | −4.429 | −7.629 | 38.696 | 1.00 | 64.38 | A |
| ATOM | 188 | CB | ALA | A | 331 | −5.860 | −7.339 | 38.247 | 1.00 | 64.46 | A |
| ATOM | 189 | C | ALA | A | 331 | −4.427 | −8.735 | 39.747 | 1.00 | 64.72 | A |
| ATOM | 190 | O | ALA | A | 331 | −4.601 | −9.909 | 39.422 | 1.00 | 65.20 | A |
| ATOM | 191 | N | SER | A | 341 | 8.152 | −8.728 | 44.111 | 1.00 | 99.94 | A |
| ATOM | 192 | CA | SER | A | 341 | 9.147 | −7.926 | 43.409 | 1.00 | 99.76 | A |
| ATOM | 193 | CB | SER | A | 341 | 10.167 | −8.832 | 42.708 | 1.00 | 99.69 | A |
| ATOM | 194 | OG | SER | A | 341 | 9.560 | −9.567 | 41.658 | 1.00 | 99.66 | A |
| ATOM | 195 | C | SER | A | 341 | 8.478 | −7.017 | 42.383 | 1.00 | 99.48 | A |
| ATOM | 196 | O | SER | A | 341 | 7.886 | −7.487 | 41.410 | 1.00 | 99.65 | A |
| ATOM | 197 | N | MET | A | 342 | 8.576 | −5.712 | 42.617 | 1.00 | 98.93 | A |
| ATOM | 198 | CA | MET | A | 342 | 7.999 | −4.705 | 41.734 | 1.00 | 97.85 | A |
| ATOM | 199 | CB | MET | A | 342 | 8.048 | −3.333 | 42.407 | 1.00 | 98.51 | A |
| ATOM | 200 | CG | MET | A | 342 | 7.202 | −3.224 | 43.662 | 1.00 | 99.39 | A |
| ATOM | 201 | SD | MET | A | 342 | 5.447 | −3.464 | 43.307 | 1.00 | 100.00 | A |
| ATOM | 202 | CE | MET | A | 342 | 4.970 | −1.796 | 42.798 | 1.00 | 100.00 | A |
| ATOM | 203 | C | MET | A | 342 | 8.769 | −4.634 | 40.425 | 1.00 | 96.76 | A |
| ATOM | 204 | O | MET | A | 342 | 8.470 | −3.812 | 39.562 | 1.00 | 96.74 | A |
| ATOM | 205 | N | MET | A | 343 | 9.766 | −5.498 | 40.289 | 1.00 | 95.49 | A |
| ATOM | 206 | CA | MET | A | 343 | 10.598 | −5.524 | 39.098 | 1.00 | 94.07 | A |
| ATOM | 207 | CB | MET | A | 343 | 12.043 | −5.829 | 39.492 | 1.00 | 95.21 | A |
| ATOM | 208 | CG | MET | A | 343 | 13.090 | −5.393 | 38.478 | 1.00 | 96.46 | A |
| ATOM | 209 | SD | MET | A | 343 | 13.048 | −3.619 | 38.081 | 1.00 | 97.70 | A |
| ATOM | 210 | CE | MET | A | 343 | 13.295 | −3.690 | 36.314 | 1.00 | 97.02 | A |
| ATOM | 211 | C | MET | A | 343 | 10.083 | −6.577 | 38.130 | 1.00 | 92.31 | A |
| ATOM | 212 | O | MET | A | 343 | 10.487 | −6.618 | 36.967 | 1.00 | 92.72 | A |
| ATOM | 213 | N | GLY | A | 344 | 9.192 | −7.431 | 38.620 | 1.00 | 89.88 | A |
| ATOM | 214 | CA | GLY | A | 344 | 8.629 | −8.466 | 37.778 | 1.00 | 86.93 | A |
| ATOM | 215 | C | GLY | A | 344 | 7.409 | −7.929 | 37.059 | 1.00 | 84.99 | A |
| ATOM | 216 | O | GLY | A | 344 | 6.985 | −8.464 | 36.031 | 1.00 | 84.70 | A |
| ATOM | 217 | N | LEU | A | 345 | 6.847 | −6.854 | 37.604 | 1.00 | 82.82 | A |
| ATOM | 218 | CA | LEU | A | 345 | 5.662 | −6.232 | 37.026 | 1.00 | 80.42 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 219 | CB | LEU | A | 345 | 4.914 | −5.407 | 38.074 | 1.00 | 79.95 | A |
| ATOM | 220 | CG | LEU | A | 345 | 4.085 | −6.148 | 39.125 | 1.00 | 79.50 | A |
| ATOM | 221 | CD1 | LEU | A | 345 | 3.434 | −5.124 | 40.037 | 1.00 | 79.15 | A |
| ATOM | 222 | CD2 | LEU | A | 345 | 3.027 | −7.020 | 38.457 | 1.00 | 79.18 | A |
| ATOM | 223 | C | LEU | A | 345 | 5.992 | −5.339 | 35.851 | 1.00 | 78.76 | A |
| ATOM | 224 | O | LEU | A | 345 | 5.235 | −5.270 | 34.890 | 1.00 | 79.25 | A |
| ATOM | 225 | N | LEU | A | 346 | 7.121 | −4.648 | 35.936 | 1.00 | 76.55 | A |
| ATOM | 226 | CA | LEU | A | 346 | 7.542 | −3.751 | 34.873 | 1.00 | 74.27 | A |
| ATOM | 227 | CB | LEU | A | 346 | 8.573 | −2.768 | 35.420 | 1.00 | 74.52 | A |
| ATOM | 228 | CG | LEU | A | 346 | 8.178 | −2.163 | 36.770 | 1.00 | 74.13 | A |
| ATOM | 229 | CD1 | LEU | A | 346 | 9.423 | −1.711 | 37.502 | 1.00 | 74.56 | A |
| ATOM | 230 | CD2 | LEU | A | 346 | 7.208 | −1.016 | 36.578 | 1.00 | 74.15 | A |
| ATOM | 231 | C | LEU | A | 346 | 8.133 | −4.556 | 33.718 | 1.00 | 72.69 | A |
| ATOM | 232 | O | LEU | A | 346 | 8.140 | −4.102 | 32.573 | 1.00 | 72.63 | A |
| ATOM | 233 | N | THR | A | 347 | 8.628 | −5.751 | 34.023 | 1.00 | 70.54 | A |
| ATOM | 234 | CA | THR | A | 347 | 9.208 | −6.615 | 33.003 | 1.00 | 68.45 | A |
| ATOM | 235 | CB | THR | A | 347 | 10.251 | −7.585 | 33.607 | 1.00 | 68.28 | A |
| ATOM | 236 | OG1 | THR | A | 347 | 10.693 | −8.501 | 32.601 | 1.00 | 67.95 | A |
| ATOM | 237 | CG2 | THR | A | 347 | 9.653 | −8.375 | 34.740 | 1.00 | 68.63 | A |
| ATOM | 238 | C | THR | A | 347 | 8.089 | −7.411 | 32.341 | 1.00 | 67.14 | A |
| ATOM | 239 | O | THR | A | 347 | 8.125 | −7.671 | 31.139 | 1.00 | 67.14 | A |
| ATOM | 240 | N | ASN | A | 348 | 7.096 | −7.795 | 33.138 | 1.00 | 65.58 | A |
| ATOM | 241 | CA | ASN | A | 348 | 5.943 | −8.538 | 32.636 | 1.00 | 63.69 | A |
| ATOM | 242 | CB | ASN | A | 348 | 5.022 | −8.931 | 33.794 | 1.00 | 64.78 | A |
| ATOM | 243 | CG | ASN | A | 348 | 3.701 | −9.533 | 33.326 | 1.00 | 65.84 | A |
| ATOM | 244 | OD1 | ASN | A | 348 | 2.665 | −9.339 | 33.966 | 1.00 | 67.16 | A |
| ATOM | 245 | ND2 | ASN | A | 348 | 3.734 | −10.277 | 32.222 | 1.00 | 65.18 | A |
| ATOM | 246 | C | ASN | A | 348 | 5.211 | −7.581 | 31.707 | 1.00 | 61.91 | A |
| ATOM | 247 | O | ASN | A | 348 | 4.853 | −7.936 | 30.582 | 1.00 | 61.85 | A |
| ATOM | 248 | N | LEU | A | 349 | 4.999 | −6.361 | 32.199 | 1.00 | 59.21 | A |
| ATOM | 249 | CA | LEU | A | 349 | 4.331 | −5.303 | 31.440 | 1.00 | 56.42 | A |
| ATOM | 250 | CB | LEU | A | 349 | 4.256 | −4.025 | 32.275 | 1.00 | 55.23 | A |
| ATOM | 251 | CG | LEU | A | 349 | 3.735 | −2.772 | 31.574 | 1.00 | 54.12 | A |
| ATOM | 252 | CD1 | LEU | A | 349 | 2.318 | −3.003 | 31.081 | 1.00 | 53.10 | A |
| ATOM | 253 | CD2 | LEU | A | 349 | 3.783 | −1.602 | 32.541 | 1.00 | 54.25 | A |
| ATOM | 254 | C | LEU | A | 349 | 5.102 | −5.010 | 30.158 | 1.00 | 54.87 | A |
| ATOM | 255 | O | LEU | A | 349 | 4.535 | −4.985 | 29.064 | 1.00 | 54.49 | A |
| ATOM | 256 | N | ALA | A | 350 | 6.403 | −4.794 | 30.313 | 1.00 | 53.04 | A |
| ATOM | 257 | CA | ALA | A | 350 | 7.282 | −4.505 | 29.199 | 1.00 | 51.54 | A |
| ATOM | 258 | CB | ALA | A | 350 | 8.671 | −4.170 | 29.719 | 1.00 | 51.22 | A |
| ATOM | 259 | C | ALA | A | 350 | 7.350 | −5.653 | 28.186 | 1.00 | 50.70 | A |
| ATOM | 260 | O | ALA | A | 350 | 7.561 | −5.413 | 26.998 | 1.00 | 49.56 | A |
| ATOM | 261 | N | ASP | A | 351 | 7.179 | −6.893 | 28.643 | 1.00 | 50.40 | A |
| ATOM | 262 | CA | ASP | A | 351 | 7.211 | −8.036 | 27.725 | 1.00 | 50.42 | A |
| ATOM | 263 | CB | ASP | A | 351 | 7.257 | −9.363 | 28.478 | 1.00 | 52.78 | A |
| ATOM | 264 | CG | ASP | A | 351 | 8.635 | −9.674 | 29.030 | 1.00 | 54.93 | A |
| ATOM | 265 | OD1 | ASP | A | 351 | 9.640 | −9.366 | 28.345 | 1.00 | 55.76 | A |
| ATOM | 266 | OD2 | ASP | A | 351 | 8.711 | −10.246 | 30.144 | 1.00 | 56.77 | A |
| ATOM | 267 | C | ASP | A | 351 | 5.994 | −8.043 | 26.818 | 1.00 | 49.27 | A |
| ATOM | 268 | O | ASP | A | 351 | 6.081 | −8.412 | 25.649 | 1.00 | 48.59 | A |
| ATOM | 269 | N | ARG | A | 352 | 4.857 | −7.637 | 27.368 | 1.00 | 48.06 | A |
| ATOM | 270 | CA | ARG | A | 352 | 3.631 | −7.588 | 26.598 | 1.00 | 48.21 | A |
| ATOM | 271 | CB | ARG | A | 352 | 2.421 | −7.567 | 27.534 | 1.00 | 48.11 | A |
| ATOM | 272 | CG | ARG | A | 352 | 2.149 | −8.921 | 28.174 | 1.00 | 48.68 | A |
| ATOM | 273 | CD | ARG | A | 352 | 0.915 | −8.925 | 29.062 | 1.00 | 48.67 | A |
| ATOM | 274 | NE | ARG | A | 352 | 1.145 | −8.302 | 30.362 | 1.00 | 50.72 | A |
| ATOM | 275 | CZ | ARG | A | 352 | 0.635 | −7.130 | 30.730 | 1.00 | 51.48 | A |
| ATOM | 276 | NH1 | ARG | A | 352 | −0.135 | −6.445 | 29.892 | 1.00 | 51.46 | A |
| ATOM | 277 | NH2 | ARG | A | 352 | 0.883 | −6.650 | 31.941 | 1.00 | 51.32 | A |
| ATOM | 278 | C | ARG | A | 352 | 3.619 | −6.379 | 25.669 | 1.00 | 47.92 | A |
| ATOM | 279 | O | ARG | A | 352 | 3.039 | −6.418 | 24.582 | 1.00 | 48.55 | A |
| ATOM | 280 | N | GLU | A | 353 | 4.264 | −5.298 | 26.082 | 1.00 | 46.89 | A |
| ATOM | 281 | CA | GLU | A | 353 | 4.301 | −4.123 | 25.234 | 1.00 | 45.30 | A |
| ATOM | 282 | CB | GLU | A | 353 | 4.863 | −2.948 | 26.005 | 1.00 | 45.26 | A |
| ATOM | 283 | CG | GLU | A | 353 | 3.896 | −2.377 | 27.003 | 1.00 | 44.73 | A |
| ATOM | 284 | CD | GLU | A | 353 | 4.473 | −1.168 | 27.704 | 1.00 | 44.66 | A |
| ATOM | 285 | OE1 | GLU | A | 353 | 5.395 | −1.351 | 28.525 | 1.00 | 41.52 | A |
| ATOM | 286 | OE2 | GLU | A | 353 | 4.013 | −0.039 | 27.419 | 1.00 | 45.15 | A |
| ATOM | 287 | C | GLU | A | 353 | 5.139 | −4.371 | 23.991 | 1.00 | 44.89 | A |
| ATOM | 288 | O | GLU | A | 353 | 4.799 | −3.922 | 22.899 | 1.00 | 44.10 | A |
| ATOM | 289 | N | LEU | A | 354 | 6.235 | −5.100 | 24.171 | 1.00 | 44.50 | A |
| ATOM | 290 | CA | LEU | A | 354 | 7.144 | −5.415 | 23.080 | 1.00 | 45.02 | A |
| ATOM | 291 | CB | LEU | A | 354 | 8.183 | −6.442 | 23.542 | 1.00 | 47.15 | A |
| ATOM | 292 | CG | LEU | A | 354 | 9.168 | −5.988 | 24.625 | 1.00 | 49.47 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 293 | CD1 | LEU | A | 354 | 9.983 | −7.174 | 25.133 | 1.00 | 49.79 | A |
| ATOM | 294 | CD2 | LEU | A | 354 | 10.081 | −4.906 | 24.050 | 1.00 | 49.84 | A |
| ATOM | 295 | C | LEU | A | 354 | 6.421 | −5.950 | 21.856 | 1.00 | 44.21 | A |
| ATOM | 296 | O | LEU | A | 354 | 6.698 | −5.532 | 20.732 | 1.00 | 43.98 | A |
| ATOM | 297 | N | VAL | A | 355 | 5.502 | −6.881 | 22.083 | 1.00 | 43.63 | A |
| ATOM | 298 | CA | VAL | A | 355 | 4.754 | −7.501 | 21.001 | 1.00 | 42.69 | A |
| ATOM | 299 | CB | VAL | A | 355 | 3.737 | −8.539 | 21.554 | 1.00 | 43.62 | A |
| ATOM | 300 | CG1 | VAL | A | 355 | 3.109 | −9.296 | 20.403 | 1.00 | 41.72 | A |
| ATOM | 301 | CG2 | VAL | A | 355 | 4.430 | −9.508 | 22.520 | 1.00 | 42.26 | A |
| ATOM | 302 | C | VAL | A | 355 | 4.020 | −6.474 | 20.146 | 1.00 | 42.48 | A |
| ATOM | 303 | O | VAL | A | 355 | 4.018 | −6.561 | 18.917 | 1.00 | 43.12 | A |
| ATOM | 304 | N | HIS | A | 356 | 3.392 | −5.502 | 20.796 | 1.00 | 41.82 | A |
| ATOM | 305 | CA | HIS | A | 356 | 2.679 | −4.451 | 20.078 | 1.00 | 40.85 | A |
| ATOM | 306 | CB | HIS | A | 356 | 1.705 | −3.744 | 21.015 | 1.00 | 41.93 | A |
| ATOM | 307 | CG | HIS | A | 356 | 0.613 | −4.631 | 21.522 | 1.00 | 43.22 | A |
| ATOM | 308 | CD2 | HIS | A | 356 | 0.627 | −5.922 | 21.926 | 1.00 | 44.75 | A |
| ATOM | 309 | ND1 | HIS | A | 356 | −0.685 | −4.202 | 21.664 | 1.00 | 44.13 | A |
| ATOM | 310 | CE1 | HIS | A | 356 | −1.427 | −5.189 | 22.134 | 1.00 | 44.12 | A |
| ATOM | 311 | NE2 | HIS | A | 356 | −0.654 | −6.244 | 22.301 | 1.00 | 45.14 | A |
| ATOM | 312 | C | HIS | A | 356 | 3.637 | −3.432 | 19.460 | 1.00 | 40.57 | A |
| ATOM | 313 | O | HIS | A | 356 | 3.312 | −2.791 | 18.457 | 1.00 | 40.98 | A |
| ATOM | 314 | N | MET | A | 357 | 4.816 | −3.288 | 20.063 | 1.00 | 39.68 | A |
| ATOM | 315 | CA | MET | A | 357 | 5.833 | −2.360 | 19.573 | 1.00 | 38.05 | A |
| ATOM | 316 | CB | MET | A | 357 | 7.071 | −2.401 | 20.468 | 1.00 | 36.05 | A |
| ATOM | 317 | CG | MET | A | 357 | 8.125 | −1.372 | 20.087 | 1.00 | 33.20 | A |
| ATOM | 318 | SD | MET | A | 357 | 9.610 | −1.454 | 21.095 | 1.00 | 31.84 | A |
| ATOM | 319 | CE | MET | A | 357 | 9.006 | −0.930 | 22.668 | 1.00 | 26.35 | A |
| ATOM | 320 | C | MET | A | 357 | 6.237 | −2.760 | 18.165 | 1.00 | 38.63 | A |
| ATOM | 321 | O | MET | A | 357 | 6.418 | −1.913 | 17.290 | 1.00 | 37.84 | A |
| ATOM | 322 | N | ILE | A | 358 | 6.384 | −4.065 | 17.966 | 1.00 | 39.42 | A |
| ATOM | 323 | CA | ILE | A | 358 | 6.762 | −4.612 | 16.676 | 1.00 | 40.33 | A |
| ATOM | 324 | CB | ILE | A | 358 | 7.065 | −6.116 | 16.772 | 1.00 | 41.29 | A |
| ATOM | 325 | CG2 | ILE | A | 358 | 7.274 | −6.681 | 15.371 | 1.00 | 43.30 | A |
| ATOM | 326 | CG1 | ILE | A | 358 | 8.306 | −6.341 | 17.649 | 1.00 | 42.20 | A |
| ATOM | 327 | CD1 | ILE | A | 358 | 8.581 | −7.796 | 18.014 | 1.00 | 43.03 | A |
| ATOM | 328 | C | ILE | A | 358 | 5.662 | −4.379 | 15.653 | 1.00 | 41.11 | A |
| ATOM | 329 | O | ILE | A | 358 | 5.951 | −4.094 | 14.491 | 1.00 | 41.95 | A |
| ATOM | 330 | N | ASN | A | 359 | 4.402 | −4.502 | 16.062 | 1.00 | 40.96 | A |
| ATOM | 331 | CA | ASN | A | 359 | 3.333 | −4.244 | 15.108 | 1.00 | 41.07 | A |
| ATOM | 332 | CB | ASN | A | 359 | 1.944 | −4.533 | 15.698 | 1.00 | 43.05 | A |
| ATOM | 333 | CG | ASN | A | 359 | 1.638 | −6.023 | 15.791 | 1.00 | 45.28 | A |
| ATOM | 334 | OD1 | ASN | A | 359 | 2.123 | −6.825 | 14.984 | 1.00 | 46.57 | A |
| ATOM | 335 | ND2 | ASN | A | 359 | 0.807 | −6.397 | 16.766 | 1.00 | 45.25 | A |
| ATOM | 336 | C | ASN | A | 359 | 3.428 | −2.776 | 14.721 | 1.00 | 39.72 | A |
| ATOM | 337 | O | ASN | A | 359 | 3.267 | −2.424 | 13.552 | 1.00 | 39.49 | A |
| ATOM | 338 | N | TRP | A | 360 | 3.693 | −1.928 | 15.715 | 1.00 | 38.38 | A |
| ATOM | 339 | CA | TRP | A | 360 | 3.831 | −0.486 | 15.503 | 1.00 | 36.05 | A |
| ATOM | 340 | CB | TRP | A | 360 | 4.067 | 0.216 | 16.833 | 1.00 | 32.77 | A |
| ATOM | 341 | CG | TRP | A | 360 | 4.583 | 1.618 | 16.690 | 1.00 | 30.37 | A |
| ATOM | 342 | CD2 | TRP | A | 360 | 5.950 | 2.045 | 16.807 | 1.00 | 27.85 | A |
| ATOM | 343 | CE2 | TRP | A | 360 | 5.971 | 3.443 | 16.593 | 1.00 | 27.73 | A |
| ATOM | 344 | CE3 | TRP | A | 360 | 7.155 | 1.384 | 17.080 | 1.00 | 28.17 | A |
| ATOM | 345 | CD1 | TRP | A | 360 | 3.853 | 2.744 | 16.413 | 1.00 | 29.00 | A |
| ATOM | 346 | NE1 | TRP | A | 360 | 4.678 | 3.842 | 16.354 | 1.00 | 26.89 | A |
| ATOM | 347 | CZ2 | TRP | A | 360 | 7.159 | 4.195 | 16.641 | 1.00 | 27.24 | A |
| ATOM | 348 | CZ3 | TRP | A | 360 | 8.339 | 2.130 | 17.131 | 1.00 | 28.06 | A |
| ATOM | 349 | CH2 | TRP | A | 360 | 8.328 | 3.524 | 16.913 | 1.00 | 26.37 | A |
| ATOM | 350 | C | TRP | A | 360 | 4.975 | −0.151 | 14.547 | 1.00 | 36.27 | A |
| ATOM | 351 | O | TRP | A | 360 | 4.769 | 0.541 | 13.564 | 1.00 | 35.91 | A |
| ATOM | 352 | N | ALA | A | 361 | 6.177 | −0.633 | 14.853 | 1.00 | 37.51 | A |
| ATOM | 353 | CA | ALA | A | 361 | 7.361 | −0.393 | 14.021 | 1.00 | 38.29 | A |
| ATOM | 354 | CB | ALA | A | 361 | 8.521 | −1.255 | 14.503 | 1.00 | 38.01 | A |
| ATOM | 355 | C | ALA | A | 361 | 7.047 | −0.721 | 12.567 | 1.00 | 39.46 | A |
| ATOM | 356 | O | ALA | A | 361 | 7.366 | 0.050 | 11.657 | 1.00 | 39.37 | A |
| ATOM | 357 | N | LYS | A | 362 | 6.431 | −1.886 | 12.366 | 1.00 | 40.06 | A |
| ATOM | 358 | CA | LYS | A | 362 | 6.030 | −2.342 | 11.042 | 1.00 | 40.11 | A |
| ATOM | 359 | CB | LYS | A | 362 | 5.126 | −3.570 | 11.144 | 1.00 | 43.05 | A |
| ATOM | 360 | CG | LYS | A | 362 | 5.794 | −4.917 | 11.398 | 1.00 | 45.82 | A |
| ATOM | 361 | CD | LYS | A | 362 | 4.672 | −5.948 | 11.545 | 1.00 | 49.57 | A |
| ATOM | 362 | CE | LYS | A | 362 | 5.135 | −7.390 | 11.436 | 1.00 | 51.65 | A |
| ATOM | 363 | NZ | LYS | A | 362 | 3.952 | −8.304 | 11.496 | 1.00 | 52.76 | A |
| ATOM | 364 | C | LYS | A | 362 | 5.256 | −1.248 | 10.306 | 1.00 | 38.75 | A |
| ATOM | 365 | O | LYS | A | 362 | 5.391 | −1.100 | 9.096 | 1.00 | 40.27 | A |
| ATOM | 366 | N | ARG | A | 363 | 4.452 | −0.483 | 11.035 | 0.50 | 36.28 | A |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 367 | CA | ARG | A | 363 | 3.653 | 0.566 | 10.422 | 0.50 | 33.60 | A |
| ATOM | 368 | CB | ARG | A | 363 | 2.321 | 0.701 | 11.156 | 0.50 | 32.62 | A |
| ATOM | 369 | CG | ARG | A | 363 | 1.551 | −0.596 | 11.232 | 0.50 | 30.36 | A |
| ATOM | 370 | CD | ARG | A | 363 | 0.328 | −0.468 | 12.111 | 0.50 | 29.70 | A |
| ATOM | 371 | NE | ARG | A | 363 | −0.734 | 0.309 | 11.482 | 0.50 | 28.80 | A |
| ATOM | 372 | CZ | ARG | A | 363 | −1.931 | 0.499 | 12.027 | 0.50 | 28.88 | A |
| ATOM | 373 | NH1 | ARG | A | 363 | −2.211 | −0.028 | 13.212 | 0.50 | 28.99 | A |
| ATOM | 374 | NH2 | ARG | A | 363 | −2.855 | 1.192 | 11.383 | 0.50 | 28.23 | A |
| ATOM | 375 | C | ARG | A | 363 | 4.333 | 1.926 | 10.343 | 0.50 | 33.88 | A |
| ATOM | 376 | O | ARG | A | 363 | 3.721 | 2.902 | 9.905 | 0.50 | 32.04 | A |
| ATOM | 377 | N | VAL | A | 364 | 5.590 | 2.009 | 10.767 | 1.00 | 34.14 | A |
| ATOM | 378 | CA | VAL | A | 364 | 6.281 | 3.287 | 10.674 | 1.00 | 35.09 | A |
| ATOM | 379 | CB | VAL | A | 364 | 7.502 | 3.391 | 11.630 | 1.00 | 35.10 | A |
| ATOM | 380 | CG1 | VAL | A | 364 | 8.272 | 4.678 | 11.347 | 1.00 | 34.01 | A |
| ATOM | 381 | CG2 | VAL | A | 364 | 7.041 | 3.368 | 13.078 | 1.00 | 33.72 | A |
| ATOM | 382 | C | VAL | A | 364 | 6.759 | 3.445 | 9.233 | 1.00 | 36.75 | A |
| ATOM | 383 | O | VAL | A | 364 | 7.469 | 2.581 | 8.703 | 1.00 | 37.10 | A |
| ATOM | 384 | N | PRO | A | 365 | 6.346 | 4.538 | 8.574 | 1.00 | 37.52 | A |
| ATOM | 385 | CD | PRO | A | 365 | 5.400 | 5.551 | 9.086 | 1.00 | 37.38 | A |
| ATOM | 386 | CA | PRO | A | 365 | 6.721 | 4.827 | 7.190 | 1.00 | 38.09 | A |
| ATOM | 387 | CB | PRO | A | 365 | 6.294 | 6.278 | 7.028 | 1.00 | 38.30 | A |
| ATOM | 388 | CG | PRO | A | 365 | 5.008 | 6.312 | 7.824 | 1.00 | 38.44 | A |
| ATOM | 389 | C | PRO | A | 365 | 8.202 | 4.604 | 6.868 | 1.00 | 40.56 | A |
| ATOM | 390 | O | PRO | A | 365 | 9.082 | 5.269 | 7.418 | 1.00 | 39.82 | A |
| ATOM | 391 | N | GLY | A | 366 | 8.457 | 3.648 | 5.973 | 1.00 | 42.97 | A |
| ATOM | 392 | CA | GLY | A | 366 | 9.809 | 3.330 | 5.552 | 1.00 | 43.78 | A |
| ATOM | 393 | C | GLY | A | 366 | 10.479 | 2.205 | 6.313 | 1.00 | 46.30 | A |
| ATOM | 394 | O | GLY | A | 366 | 11.467 | 1.645 | 5.836 | 1.00 | 47.57 | A |
| ATOM | 395 | N | PHE | A | 367 | 9.958 | 1.860 | 7.487 | 1.00 | 47.60 | A |
| ATOM | 396 | CA | PHE | A | 367 | 10.567 | 0.807 | 8.288 | 1.00 | 48.71 | A |
| ATOM | 397 | CB | PHE | A | 367 | 9.792 | 0.587 | 9.588 | 1.00 | 48.35 | A |
| ATOM | 398 | CG | PHE | A | 367 | 10.499 | −0.321 | 10.560 | 1.00 | 47.50 | A |
| ATOM | 399 | CD1 | PHE | A | 367 | 11.649 | 0.110 | 11.221 | 1.00 | 47.31 | A |
| ATOM | 400 | CD2 | PHE | A | 367 | 10.030 | −1.609 | 10.801 | 1.00 | 46.46 | A |
| ATOM | 401 | CE1 | PHE | A | 367 | 12.323 | −0.732 | 12.113 | 1.00 | 46.44 | A |
| ATOM | 402 | CE2 | PHE | A | 367 | 10.694 | −2.455 | 11.685 | 1.00 | 46.51 | A |
| ATOM | 403 | CZ | PHE | A | 367 | 11.844 | −2.015 | 12.344 | 1.00 | 45.69 | A |
| ATOM | 404 | C | PHE | A | 367 | 10.634 | −0.507 | 7.535 | 1.00 | 50.28 | A |
| ATOM | 405 | O | PHE | A | 367 | 11.670 | −1.173 | 7.517 | 1.00 | 50.59 | A |
| ATOM | 406 | N | VAL | A | 368 | 9.517 | −0.882 | 6.925 | 1.00 | 51.97 | A |
| ATOM | 407 | CA | VAL | A | 368 | 9.437 | −2.131 | 6.177 | 1.00 | 53.67 | A |
| ATOM | 408 | CB | VAL | A | 368 | 7.963 | −2.489 | 5.885 | 1.00 | 53.91 | A |
| ATOM | 409 | CG1 | VAL | A | 368 | 7.284 | −2.936 | 7.183 | 1.00 | 53.39 | A |
| ATOM | 410 | CG2 | VAL | A | 368 | 7.233 | −1.277 | 5.291 | 1.00 | 54.22 | A |
| ATOM | 411 | C | VAL | A | 368 | 10.260 | −2.145 | 4.881 | 1.00 | 54.44 | A |
| ATOM | 412 | O | VAL | A | 368 | 10.567 | −3.208 | 4.346 | 1.00 | 54.46 | A |
| ATOM | 413 | N | ASP | A | 369 | 10.625 | −0.969 | 4.380 | 1.00 | 55.93 | A |
| ATOM | 414 | CA | ASP | A | 369 | 11.445 | −0.883 | 3.174 | 1.00 | 57.25 | A |
| ATOM | 415 | CB | ASP | A | 369 | 11.450 | 0.544 | 2.611 | 1.00 | 56.53 | A |
| ATOM | 416 | CG | ASP | A | 369 | 10.113 | 0.955 | 2.044 | 1.00 | 56.64 | A |
| ATOM | 417 | OD1 | ASP | A | 369 | 9.499 | 0.137 | 1.331 | 1.00 | 56.80 | A |
| ATOM | 418 | OD2 | ASP | A | 369 | 9.684 | 2.100 | 2.293 | 1.00 | 57.07 | A |
| ATOM | 419 | C | ASP | A | 369 | 12.876 | −1.271 | 3.545 | 1.00 | 58.64 | A |
| ATOM | 420 | O | ASP | A | 369 | 13.803 | −1.103 | 2.752 | 1.00 | 58.95 | A |
| ATOM | 421 | N | LEU | A | 370 | 13.045 | −1.783 | 4.761 | 1.00 | 60.10 | A |
| ATOM | 422 | CA | LEU | A | 370 | 14.353 | −2.190 | 5.266 | 1.00 | 61.53 | A |
| ATOM | 423 | CB | LEU | A | 370 | 14.615 | −1.523 | 6.619 | 1.00 | 61.57 | A |
| ATOM | 424 | CG | LEU | A | 370 | 15.410 | −0.211 | 6.690 | 1.00 | 62.39 | A |
| ATOM | 425 | CD1 | LEU | A | 370 | 14.959 | 0.779 | 5.622 | 1.00 | 62.33 | A |
| ATOM | 426 | CD2 | LEU | A | 370 | 15.229 | 0.377 | 8.090 | 1.00 | 62.65 | A |
| ATOM | 427 | C | LEU | A | 370 | 14.456 | −3.702 | 5.421 | 1.00 | 62.50 | A |
| ATOM | 428 | O | LEU | A | 370 | 13.456 | −4.378 | 5.648 | 1.00 | 62.63 | A |
| ATOM | 429 | N | THR | A | 371 | 15.671 | −4.228 | 5.295 | 1.00 | 63.88 | A |
| ATOM | 430 | CA | THR | A | 371 | 15.889 | −5.660 | 5.434 | 1.00 | 65.64 | A |
| ATOM | 431 | CB | THR | A | 371 | 17.343 | −6.053 | 5.121 | 1.00 | 66.29 | A |
| ATOM | 432 | OG1 | THR | A | 371 | 18.225 | −5.030 | 5.586 | 1.00 | 67.23 | A |
| ATOM | 433 | CG2 | THR | A | 371 | 17.540 | −6.260 | 3.635 | 1.00 | 66.69 | A |
| ATOM | 434 | C | THR | A | 371 | 15.580 | −6.100 | 6.853 | 1.00 | 66.50 | A |
| ATOM | 435 | O | THR | A | 371 | 15.703 | −5.321 | 7.794 | 1.00 | 66.83 | A |
| ATOM | 436 | N | LEU | A | 372 | 15.189 | −7.363 | 6.990 | 1.00 | 67.73 | A |
| ATOM | 437 | CA | LEU | A | 372 | 14.849 | −7.957 | 8.278 | 1.00 | 68.07 | A |
| ATOM | 438 | CB | LEU | A | 372 | 14.684 | −9.471 | 8.119 | 1.00 | 68.61 | A |
| ATOM | 439 | CG | LEU | A | 372 | 14.296 | −10.260 | 9.370 | 1.00 | 68.81 | A |
| ATOM | 440 | CD1 | LEU | A | 372 | 12.925 | −9.814 | 9.848 | 1.00 | 69.54 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 441 | CD2 | LEU | A | 372 | 14.289 | −11.743 | 9.052 | 1.00 | 69.69 | A |
| ATOM | 442 | C | LEU | A | 372 | 15.897 | −7.685 | 9.344 | 1.00 | 67.91 | A |
| ATOM | 443 | O | LEU | A | 372 | 15.569 | −7.305 | 10.468 | 1.00 | 67.73 | A |
| ATOM | 444 | N | HIS | A | 373 | 17.159 | −7.885 | 8.980 | 1.00 | 68.15 | A |
| ATOM | 445 | CA | HIS | A | 373 | 18.264 | −7.689 | 9.905 | 1.00 | 68.30 | A |
| ATOM | 446 | CB | HIS | A | 373 | 19.566 | −8.108 | 9.234 | 1.00 | 71.16 | A |
| ATOM | 447 | CG | HIS | A | 373 | 19.555 | −9.528 | 8.763 | 1.00 | 74.03 | A |
| ATOM | 448 | CD2 | HIS | A | 373 | 19.490 | −10.056 | 7.516 | 1.00 | 75.36 | A |
| ATOM | 449 | ND1 | HIS | A | 373 | 19.555 | −10.599 | 9.632 | 1.00 | 75.22 | A |
| ATOM | 450 | CE1 | HIS | A | 373 | 19.489 | −11.724 | 8.942 | 1.00 | 76.23 | A |
| ATOM | 451 | NE2 | HIS | A | 373 | 19.449 | −11.422 | 7.655 | 1.00 | 76.54 | A |
| ATOM | 452 | C | HIS | A | 373 | 18.361 | −6.265 | 10.427 | 1.00 | 66.92 | A |
| ATOM | 453 | O | HIS | A | 373 | 18.667 | −6.056 | 11.601 | 1.00 | 66.70 | A |
| ATOM | 454 | N | ASP | A | 374 | 18.096 | −5.287 | 9.564 | 1.00 | 65.09 | A |
| ATOM | 455 | CA | ASP | A | 374 | 18.144 | −3.893 | 9.986 | 1.00 | 63.18 | A |
| ATOM | 456 | CB | ASP | A | 374 | 18.098 | −2.962 | 8.783 | 1.00 | 64.80 | A |
| ATOM | 457 | CG | ASP | A | 374 | 19.318 | −3.092 | 7.908 | 1.00 | 67.04 | A |
| ATOM | 458 | OD1 | ASP | A | 374 | 20.442 | −3.145 | 8.457 | 1.00 | 67.56 | A |
| ATOM | 459 | OD2 | ASP | A | 374 | 19.159 | −3.134 | 6.669 | 1.00 | 68.35 | A |
| ATOM | 460 | C | ASP | A | 374 | 16.985 | −3.569 | 10.909 | 1.00 | 61.11 | A |
| ATOM | 461 | O | ASP | A | 374 | 17.155 | −2.876 | 11.918 | 1.00 | 60.05 | A |
| ATOM | 462 | N | GLN | A | 375 | 15.809 | −4.081 | 10.558 | 1.00 | 58.41 | A |
| ATOM | 463 | CA | GLN | A | 375 | 14.614 | −3.850 | 11.348 | 1.00 | 56.07 | A |
| ATOM | 464 | CB | GLN | A | 375 | 13.400 | −4.492 | 10.691 | 1.00 | 55.68 | A |
| ATOM | 465 | CG | GLN | A | 375 | 13.256 | −4.202 | 9.218 | 1.00 | 55.38 | A |
| ATOM | 466 | CD | GLN | A | 375 | 11.887 | −4.593 | 8.709 | 1.00 | 55.23 | A |
| ATOM | 467 | OE1 | GLN | A | 375 | 11.354 | −5.634 | 9.088 | 1.00 | 55.60 | A |
| ATOM | 468 | NE2 | GLN | A | 375 | 11.312 | −3.765 | 7.843 | 1.00 | 54.64 | A |
| ATOM | 469 | C | GLN | A | 375 | 14.807 | −4.453 | 12.722 | 1.00 | 54.65 | A |
| ATOM | 470 | O | GLN | A | 375 | 14.336 | −3.916 | 13.718 | 1.00 | 54.46 | A |
| ATOM | 471 | N | VAL | A | 376 | 15.503 | −5.580 | 12.767 | 1.00 | 53.60 | A |
| ATOM | 472 | CA | VAL | A | 376 | 15.755 | −6.258 | 14.031 | 1.00 | 53.50 | A |
| ATOM | 473 | CB | VAL | A | 376 | 16.214 | −7.714 | 13.799 | 1.00 | 52.93 | A |
| ATOM | 474 | CG1 | VAL | A | 376 | 16.647 | −8.333 | 15.100 | 1.00 | 52.31 | A |
| ATOM | 475 | CG2 | VAL | A | 376 | 15.081 | −8.520 | 13.204 | 1.00 | 52.87 | A |
| ATOM | 476 | C | VAL | A | 376 | 16.816 | −5.505 | 14.829 | 1.00 | 53.05 | A |
| ATOM | 477 | O | VAL | A | 376 | 16.707 | −5.351 | 16.043 | 1.00 | 52.91 | A |
| ATOM | 478 | N | HIS | A | 377 | 17.842 | −5.036 | 14.131 | 1.00 | 53.24 | A |
| ATOM | 479 | CA | HIS | A | 377 | 18.916 | −4.283 | 14.760 | 1.00 | 52.89 | A |
| ATOM | 480 | CB | HIS | A | 377 | 20.024 | −4.015 | 13.735 | 1.00 | 53.99 | A |
| ATOM | 481 | CG | HIS | A | 377 | 21.069 | −3.049 | 14.205 | 1.00 | 56.67 | A |
| ATOM | 482 | CD2 | HIS | A | 377 | 21.317 | −1.764 | 13.851 | 1.00 | 57.57 | A |
| ATOM | 483 | ND1 | HIS | A | 377 | 22.008 | −3.370 | 15.164 | 1.00 | 57.68 | A |
| ATOM | 484 | CE1 | HIS | A | 377 | 22.789 | −2.325 | 15.379 | 1.00 | 57.93 | A |
| ATOM | 485 | NE2 | HIS | A | 377 | 22.391 | −1.338 | 14.595 | 1.00 | 58.11 | A |
| ATOM | 486 | C | HIS | A | 377 | 18.363 | −2.960 | 15.307 | 1.00 | 52.32 | A |
| ATOM | 487 | O | HIS | A | 377 | 18.730 | −2.525 | 16.402 | 1.00 | 52.04 | A |
| ATOM | 488 | N | LEU | A | 378 | 17.473 | −2.323 | 14.548 | 1.00 | 50.95 | A |
| ATOM | 489 | CA | LEU | A | 378 | 16.900 | −1.057 | 14.981 | 1.00 | 49.45 | A |
| ATOM | 490 | CB | LEU | A | 378 | 16.042 | −0.446 | 13.874 | 1.00 | 49.71 | A |
| ATOM | 491 | CG | LEU | A | 378 | 16.791 | 0.229 | 12.724 | 1.00 | 49.28 | A |
| ATOM | 492 | CD1 | LEU | A | 378 | 15.796 | 0.881 | 11.773 | 1.00 | 49.26 | A |
| ATOM | 493 | CD2 | LEU | A | 378 | 17.748 | 1.266 | 13.284 | 1.00 | 49.22 | A |
| ATOM | 494 | C | LEU | A | 378 | 16.076 | −1.184 | 16.250 | 1.00 | 48.59 | A |
| ATOM | 495 | O | LEU | A | 378 | 16.269 | −0.422 | 17.196 | 1.00 | 48.45 | A |
| ATOM | 496 | N | LEU | A | 379 | 15.155 | −2.141 | 16.269 | 1.00 | 47.50 | A |
| ATOM | 497 | CA | LEU | A | 379 | 14.307 | −2.351 | 17.436 | 1.00 | 46.44 | A |
| ATOM | 498 | CB | LEU | A | 379 | 13.261 | −3.426 | 17.141 | 1.00 | 46.43 | A |
| ATOM | 499 | CG | LEU | A | 379 | 12.166 | −2.959 | 16.180 | 1.00 | 46.10 | A |
| ATOM | 500 | CD1 | LEU | A | 379 | 11.385 | −4.142 | 15.601 | 1.00 | 44.95 | A |
| ATOM | 501 | CD2 | LEU | A | 379 | 11.251 | −1.994 | 16.942 | 1.00 | 45.32 | A |
| ATOM | 502 | C | LEU | A | 379 | 15.151 | −2.757 | 18.620 | 1.00 | 45.73 | A |
| ATOM | 503 | O | LEU | A | 379 | 14.883 | −2.359 | 19.750 | 1.00 | 45.84 | A |
| ATOM | 504 | N | GLU | A | 380 | 16.180 | −3.546 | 18.343 | 1.00 | 45.74 | A |
| ATOM | 505 | CA | GLU | A | 380 | 17.096 | −4.021 | 19.370 | 1.00 | 46.28 | A |
| ATOM | 506 | CB | GLU | A | 380 | 18.167 | −4.906 | 18.736 | 1.00 | 48.78 | A |
| ATOM | 507 | CG | GLU | A | 380 | 18.762 | −5.918 | 19.688 | 1.00 | 54.81 | A |
| ATOM | 508 | CD | GLU | A | 380 | 19.715 | −6.877 | 18.993 | 1.00 | 58.54 | A |
| ATOM | 509 | OE1 | GLU | A | 380 | 19.508 | −7.151 | 17.786 | 1.00 | 60.65 | A |
| ATOM | 510 | OE2 | GLU | A | 380 | 20.661 | −7.368 | 19.657 | 1.00 | 61.12 | A |
| ATOM | 511 | C | GLU | A | 380 | 17.755 | −2.838 | 20.074 | 1.00 | 44.32 | A |
| ATOM | 512 | O | GLU | A | 380 | 17.866 | −2.814 | 21.298 | 1.00 | 44.13 | A |
| ATOM | 513 | N | CYS | A | 381 | 18.179 | −1.856 | 19.287 | 1.00 | 41.77 | A |
| ATOM | 514 | CA | CYS | A | 381 | 18.825 | −0.662 | 19.811 | 1.00 | 40.34 | A |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 515 | CB | CYS | A | 381 | 19.572 | 0.062 | 18.681 | 1.00 | 40.59 | A |
| ATOM | 516 | SG | CYS | A | 381 | 21.039 | −0.799 | 18.041 | 1.00 | 43.99 | A |
| ATOM | 517 | C | CYS | A | 381 | 17.888 | 0.341 | 20.496 | 1.00 | 39.27 | A |
| ATOM | 518 | O | CYS | A | 381 | 18.273 | 0.991 | 21.466 | 1.00 | 37.32 | A |
| ATOM | 519 | N | ALA | A | 382 | 16.653 | 0.450 | 20.012 | 1.00 | 37.92 | A |
| ATOM | 520 | CA | ALA | A | 382 | 15.731 | 1.440 | 20.553 | 1.00 | 36.27 | A |
| ATOM | 521 | CB | ALA | A | 382 | 15.142 | 2.252 | 19.403 | 1.00 | 36.01 | A |
| ATOM | 522 | C | ALA | A | 382 | 14.601 | 0.997 | 21.458 | 1.00 | 35.52 | A |
| ATOM | 523 | O | ALA | A | 382 | 13.883 | 1.848 | 21.982 | 1.00 | 36.92 | A |
| ATOM | 524 | N | TRP | A | 383 | 14.434 | −0.300 | 21.675 | 1.00 | 33.25 | A |
| ATOM | 525 | CA | TRP | A | 383 | 13.303 | −0.745 | 22.479 | 1.00 | 31.24 | A |
| ATOM | 526 | CB | TRP | A | 383 | 13.339 | −2.267 | 22.666 | 1.00 | 31.41 | A |
| ATOM | 527 | CG | TRP | A | 383 | 14.316 | −2.775 | 23.679 | 1.00 | 32.84 | A |
| ATOM | 528 | CD2 | TRP | A | 383 | 14.071 | −2.969 | 25.078 | 1.00 | 32.21 | A |
| ATOM | 529 | CE2 | TRP | A | 383 | 15.261 | −3.490 | 25.643 | 1.00 | 32.75 | A |
| ATOM | 530 | CE3 | TRP | A | 383 | 12.964 | −2.750 | 25.910 | 1.00 | 32.32 | A |
| ATOM | 531 | CD1 | TRP | A | 383 | 15.607 | −3.169 | 23.456 | 1.00 | 32.32 | A |
| ATOM | 532 | NE1 | TRP | A | 383 | 16.180 | −3.604 | 24.631 | 1.00 | 33.55 | A |
| ATOM | 533 | CZ2 | TRP | A | 383 | 15.375 | −3.797 | 27.006 | 1.00 | 32.26 | A |
| ATOM | 534 | CZ3 | TRP | A | 383 | 13.077 | −3.054 | 27.268 | 1.00 | 32.83 | A |
| ATOM | 535 | CH2 | TRP | A | 383 | 14.278 | −3.573 | 27.800 | 1.00 | 32.99 | A |
| ATOM | 536 | C | TRP | A | 383 | 13.044 | −0.054 | 23.825 | 1.00 | 30.23 | A |
| ATOM | 537 | O | TRP | A | 383 | 11.911 | 0.350 | 24.095 | 1.00 | 29.04 | A |
| ATOM | 538 | N | LEU | A | 384 | 14.068 | 0.107 | 24.664 | 1.00 | 30.20 | A |
| ATOM | 539 | CA | LEU | A | 384 | 13.853 | 0.738 | 25.966 | 1.00 | 28.01 | A |
| ATOM | 540 | CB | LEU | A | 384 | 15.049 | 0.485 | 26.897 | 1.00 | 29.25 | A |
| ATOM | 541 | CG | LEU | A | 384 | 14.941 | 0.884 | 28.386 | 1.00 | 28.52 | A |
| ATOM | 542 | CD1 | LEU | A | 384 | 13.685 | 0.298 | 29.010 | 1.00 | 26.50 | A |
| ATOM | 543 | CD2 | LEU | A | 384 | 16.180 | 0.397 | 29.137 | 1.00 | 28.14 | A |
| ATOM | 544 | C | LEU | A | 384 | 13.574 | 2.228 | 25.845 | 1.00 | 27.82 | A |
| ATOM | 545 | O | LEU | A | 384 | 12.775 | 2.772 | 26.596 | 1.00 | 28.06 | A |
| ATOM | 546 | N | GLU | A | 385 | 14.229 | 2.897 | 24.906 | 1.00 | 28.73 | A |
| ATOM | 547 | CA | GLU | A | 385 | 13.986 | 4.325 | 24.709 | 1.00 | 28.94 | A |
| ATOM | 548 | CB | GLU | A | 385 | 14.901 | 4.894 | 23.618 | 1.00 | 31.71 | A |
| ATOM | 549 | CG | GLU | A | 385 | 16.338 | 5.171 | 24.029 | 1.00 | 32.54 | A |
| ATOM | 550 | CD | GLU | A | 385 | 17.218 | 5.470 | 22.822 | 1.00 | 34.29 | A |
| ATOM | 551 | OE1 | GLU | A | 385 | 17.737 | 4.501 | 22.239 | 1.00 | 36.35 | A |
| ATOM | 552 | OE2 | GLU | A | 385 | 17.384 | 6.658 | 22.440 | 1.00 | 33.93 | A |
| ATOM | 553 | C | GLU | A | 385 | 12.536 | 4.497 | 24.274 | 1.00 | 28.42 | A |
| ATOM | 554 | O | GLU | A | 385 | 11.863 | 5.455 | 24.677 | 1.00 | 27.77 | A |
| ATOM | 555 | N | ILE | A | 386 | 12.057 | 3.558 | 23.451 | 1.00 | 28.39 | A |
| ATOM | 556 | CA | ILE | A | 386 | 10.677 | 3.604 | 22.955 | 1.00 | 28.15 | A |
| ATOM | 557 | CB | ILE | A | 386 | 10.364 | 2.445 | 21.944 | 1.00 | 28.00 | A |
| ATOM | 558 | CG2 | ILE | A | 386 | 8.944 | 2.577 | 21.426 | 1.00 | 26.76 | A |
| ATOM | 559 | CG1 | ILE | A | 386 | 11.321 | 2.489 | 20.741 | 1.00 | 28.96 | A |
| ATOM | 560 | CD1 | ILE | A | 386 | 11.232 | 3.747 | 19.911 | 1.00 | 29.08 | A |
| ATOM | 561 | C | ILE | A | 386 | 9.712 | 3.492 | 24.132 | 1.00 | 28.99 | A |
| ATOM | 562 | O | ILE | A | 386 | 8.766 | 4.289 | 24.279 | 1.00 | 28.51 | A |
| ATOM | 563 | N | LEU | A | 387 | 9.950 | 2.497 | 24.976 | 1.00 | 30.46 | A |
| ATOM | 564 | CA | LEU | A | 387 | 9.089 | 2.302 | 26.133 | 1.00 | 31.12 | A |
| ATOM | 565 | CB | LEU | A | 387 | 9.490 | 1.047 | 26.912 | 1.00 | 31.66 | A |
| ATOM | 566 | CG | LEU | A | 387 | 9.149 | −0.310 | 26.285 | 1.00 | 32.95 | A |
| ATOM | 567 | CD1 | LEU | A | 387 | 9.584 | −1.418 | 27.244 | 1.00 | 31.70 | A |
| ATOM | 568 | CD2 | LEU | A | 387 | 7.640 | −0.388 | 25.972 | 1.00 | 31.02 | A |
| ATOM | 569 | C | LEU | A | 387 | 9.145 | 3.507 | 27.048 | 1.00 | 30.81 | A |
| ATOM | 570 | O | LEU | A | 387 | 8.103 | 3.982 | 27.511 | 1.00 | 29.88 | A |
| ATOM | 571 | N | MET | A | 388 | 10.357 | 4.007 | 27.291 | 1.00 | 31.08 | A |
| ATOM | 572 | CA | MET | A | 388 | 10.545 | 5.154 | 28.173 | 1.00 | 31.95 | A |
| ATOM | 573 | CB | MET | A | 388 | 12.036 | 5.400 | 28.436 | 1.00 | 34.35 | A |
| ATOM | 574 | CG | MET | A | 388 | 12.712 | 4.303 | 29.267 | 1.00 | 35.09 | A |
| ATOM | 575 | SD | MET | A | 388 | 14.496 | 4.523 | 29.396 | 1.00 | 36.94 | A |
| ATOM | 576 | CE | MET | A | 388 | 14.662 | 4.919 | 31.132 | 1.00 | 38.07 | A |
| ATOM | 577 | C | MET | A | 388 | 9.893 | 6.433 | 27.681 | 1.00 | 31.68 | A |
| ATOM | 578 | O | MET | A | 388 | 9.312 | 7.172 | 28.482 | 1.00 | 32.04 | A |
| ATOM | 579 | N | ILE | A | 389 | 9.971 | 6.719 | 26.382 | 1.00 | 31.37 | A |
| ATOM | 580 | CA | ILE | A | 389 | 9.327 | 7.941 | 25.919 | 1.00 | 30.99 | A |
| ATOM | 581 | CB | ILE | A | 389 | 9.763 | 8.364 | 24.473 | 1.00 | 31.38 | A |
| ATOM | 582 | CG2 | ILE | A | 389 | 9.245 | 7.373 | 23.425 | 1.00 | 29.47 | A |
| ATOM | 583 | CG1 | ILE | A | 389 | 9.271 | 9.808 | 24.219 | 1.00 | 31.17 | A |
| ATOM | 584 | CD1 | ILE | A | 389 | 9.597 | 10.394 | 22.866 | 1.00 | 29.20 | A |
| ATOM | 585 | C | ILE | A | 389 | 7.820 | 7.739 | 25.999 | 1.00 | 30.71 | A |
| ATOM | 586 | O | ILE | A | 389 | 7.064 | 8.695 | 26.183 | 1.00 | 31.71 | A |
| ATOM | 587 | N | GLY | A | 390 | 7.392 | 6.482 | 25.863 | 1.00 | 30.95 | A |
| ATOM | 588 | CA | GLY | A | 390 | 5.984 | 6.159 | 25.968 | 1.00 | 30.22 | A |

TABLE 9-continued

Structure coordinates for ERalpha-LBD/Compound 1 complex
(Table dicloses SEQ ID NOS 2-8, respectively, in order of appearance)

|      | #   | Name | Res. | Chain | Res # | X      | Y      | Z      | occ  | B     | SegID |
|------|-----|------|------|-------|-------|--------|--------|--------|------|-------|-------|
| ATOM | 589 | C    | GLY  | A     | 390   | 5.564  | 6.422  | 27.405 | 1.00 | 31.18 | A     |
| ATOM | 590 | O    | GLY  | A     | 390   | 4.535  | 7.055  | 27.661 | 1.00 | 30.45 | A     |
| ATOM | 591 | N    | LEU  | A     | 391   | 6.365  | 5.936  | 28.352 | 1.00 | 32.37 | A     |
| ATOM | 592 | CA   | LEU  | A     | 391   | 6.073  | 6.151  | 29.770 | 1.00 | 32.95 | A     |
| ATOM | 593 | CB   | LEU  | A     | 391   | 7.166  | 5.575  | 30.673 | 1.00 | 34.03 | A     |
| ATOM | 594 | CG   | LEU  | A     | 391   | 6.963  | 6.029  | 32.129 | 1.00 | 35.41 | A     |
| ATOM | 595 | CD1  | LEU  | A     | 391   | 5.801  | 5.248  | 32.735 | 1.00 | 35.50 | A     |
| ATOM | 596 | CD2  | LEU  | A     | 391   | 8.227  | 5.838  | 32.941 | 1.00 | 35.08 | A     |
| ATOM | 597 | C    | LEU  | A     | 391   | 5.992  | 7.635  | 30.052 | 1.00 | 33.15 | A     |
| ATOM | 598 | O    | LEU  | A     | 391   | 4.991  | 8.120  | 30.589 | 1.00 | 32.02 | A     |
| ATOM | 599 | N    | VAL  | A     | 392   | 7.066  | 8.343  | 29.698 | 1.00 | 33.85 | A     |
| ATOM | 600 | CA   | VAL  | A     | 392   | 7.158  | 9.782  | 29.926 | 1.00 | 34.90 | A     |
| ATOM | 601 | CB   | VAL  | A     | 392   | 8.437  | 10.389 | 29.271 | 1.00 | 35.16 | A     |
| ATOM | 602 | CG1  | VAL  | A     | 392   | 8.306  | 11.901 | 29.158 | 1.00 | 35.11 | A     |
| ATOM | 603 | CG2  | VAL  | A     | 392   | 9.666  | 10.047 | 30.107 | 1.00 | 32.49 | A     |
| ATOM | 604 | C    | VAL  | A     | 392   | 5.937  | 10.497 | 29.397 | 1.00 | 36.51 | A     |
| ATOM | 605 | O    | VAL  | A     | 392   | 5.396  | 11.385 | 30.052 | 1.00 | 37.88 | A     |
| ATOM | 606 | N    | TRP  | A     | 393   | 5.497  | 10.094 | 28.215 | 1.00 | 37.24 | A     |
| ATOM | 607 | CA   | TRP  | A     | 393   | 4.343  | 10.700 | 27.593 | 1.00 | 38.21 | A     |
| ATOM | 608 | CB   | TRP  | A     | 393   | 4.141  | 10.107 | 26.200 | 1.00 | 38.65 | A     |
| ATOM | 609 | CG   | TRP  | A     | 393   | 2.819  | 10.448 | 25.608 | 1.00 | 38.55 | A     |
| ATOM | 610 | CD2  | TRP  | A     | 393   | 2.405  | 11.729 | 25.116 | 1.00 | 38.60 | A     |
| ATOM | 611 | CE2  | TRP  | A     | 393   | 1.073  | 11.589 | 24.656 | 1.00 | 38.37 | A     |
| ATOM | 612 | CE3  | TRP  | A     | 393   | 3.029  | 12.981 | 25.011 | 1.00 | 38.91 | A     |
| ATOM | 613 | CD1  | TRP  | A     | 393   | 1.750  | 9.606  | 25.440 | 1.00 | 38.06 | A     |
| ATOM | 614 | NE1  | TRP  | A     | 393   | 0.697  | 10.286 | 24.870 | 1.00 | 37.86 | A     |
| ATOM | 615 | CZ2  | TRP  | A     | 393   | 0.357  | 12.656 | 24.105 | 1.00 | 37.26 | A     |
| ATOM | 616 | CZ3  | TRP  | A     | 393   | 2.314  | 14.042 | 24.463 | 1.00 | 36.84 | A     |
| ATOM | 617 | CH2  | TRP  | A     | 393   | 0.996  | 13.870 | 24.016 | 1.00 | 37.48 | A     |
| ATOM | 618 | C    | TRP  | A     | 393   | 3.065  | 10.568 | 28.411 | 1.00 | 39.15 | A     |
| ATOM | 619 | O    | TRP  | A     | 393   | 2.400  | 11.569 | 28.685 | 1.00 | 40.22 | A     |
| ATOM | 620 | N    | ARG  | A     | 394   | 2.704  | 9.348  | 28.794 | 1.00 | 40.00 | A     |
| ATOM | 621 | CA   | ARG  | A     | 394   | 1.489  | 9.158  | 29.580 | 1.00 | 40.78 | A     |
| ATOM | 622 | CB   | ARG  | A     | 394   | 1.038  | 7.690  | 29.542 | 1.00 | 40.28 | A     |
| ATOM | 623 | CG   | ARG  | A     | 394   | 2.121  | 6.664  | 29.606 | 1.00 | 40.78 | A     |
| ATOM | 624 | CD   | ARG  | A     | 394   | 1.662  | 5.398  | 28.907 | 1.00 | 42.05 | A     |
| ATOM | 625 | NE   | ARG  | A     | 394   | 2.711  | 4.382  | 28.848 | 1.00 | 43.81 | A     |
| ATOM | 626 | CZ   | ARG  | A     | 394   | 3.112  | 3.685  | 29.899 | 1.00 | 44.54 | A     |
| ATOM | 627 | NH1  | ARG  | A     | 394   | 2.549  | 3.897  | 31.075 | 1.00 | 46.84 | A     |
| ATOM | 628 | NH2  | ARG  | A     | 394   | 4.066  | 2.783  | 29.782 | 1.00 | 43.75 | A     |
| ATOM | 629 | C    | ARG  | A     | 394   | 1.582  | 9.662  | 31.024 | 1.00 | 42.13 | A     |
| ATOM | 630 | O    | ARG  | A     | 394   | 0.564  | 9.987  | 31.632 | 1.00 | 41.34 | A     |
| ATOM | 631 | N    | SER  | A     | 395   | 2.799  | 9.742  | 31.564 | 1.00 | 44.31 | A     |
| ATOM | 632 | CA   | SER  | A     | 395   | 3.009  | 10.237 | 32.930 | 1.00 | 45.65 | A     |
| ATOM | 633 | CB   | SER  | A     | 395   | 4.430  | 9.923  | 33.409 | 1.00 | 44.86 | A     |
| ATOM | 634 | OG   | SER  | A     | 395   | 4.627  | 8.529  | 33.598 | 1.00 | 44.62 | A     |
| ATOM | 635 | C    | SER  | A     | 395   | 2.795  | 11.743 | 32.962 | 1.00 | 47.01 | A     |
| ATOM | 636 | O    | SER  | A     | 395   | 2.339  | 12.297 | 33.949 | 1.00 | 46.64 | A     |
| ATOM | 637 | N    | MET  | A     | 396   | 3.122  | 12.391 | 31.854 | 1.00 | 50.25 | A     |
| ATOM | 638 | CA   | MET  | A     | 396   | 2.996  | 13.840 | 31.696 | 1.00 | 53.60 | A     |
| ATOM | 639 | CB   | MET  | A     | 396   | 2.704  | 14.172 | 30.231 | 1.00 | 53.38 | A     |
| ATOM | 640 | CG   | MET  | A     | 396   | 3.766  | 14.999 | 29.540 | 1.00 | 53.37 | A     |
| ATOM | 641 | SD   | MET  | A     | 396   | 3.261  | 15.468 | 27.873 | 1.00 | 53.23 | A     |
| ATOM | 642 | CE   | MET  | A     | 396   | 2.607  | 17.110 | 28.174 | 1.00 | 54.15 | A     |
| ATOM | 643 | C    | MET  | A     | 396   | 1.967  | 14.567 | 32.569 | 1.00 | 55.56 | A     |
| ATOM | 644 | O    | MET  | A     | 396   | 2.300  | 15.542 | 33.245 | 1.00 | 56.79 | A     |
| ATOM | 645 | N    | GLU  | A     | 397   | 0.721  | 14.107 | 32.551 | 1.00 | 57.31 | A     |
| ATOM | 646 | CA   | GLU  | A     | 397   | −0.351 | 14.758 | 33.314 | 1.00 | 58.65 | A     |
| ATOM | 647 | CB   | GLU  | A     | 397   | −1.697 | 14.577 | 32.593 | 1.00 | 59.64 | A     |
| ATOM | 648 | CG   | GLU  | A     | 397   | −1.629 | 14.606 | 31.059 | 1.00 | 61.01 | A     |
| ATOM | 649 | CD   | GLU  | A     | 397   | −0.722 | 13.519 | 30.474 | 1.00 | 62.15 | A     |
| ATOM | 650 | OE1  | GLU  | A     | 397   | −0.729 | 12.372 | 30.981 | 1.00 | 61.23 | A     |
| ATOM | 651 | OE2  | GLU  | A     | 397   | −0.005 | 13.813 | 29.492 | 1.00 | 64.19 | A     |
| ATOM | 652 | C    | GLU  | A     | 397   | −0.471 | 14.217 | 34.735 | 1.00 | 58.48 | A     |
| ATOM | 653 | O    | GLU  | A     | 397   | −1.524 | 14.332 | 35.363 | 1.00 | 57.39 | A     |
| ATOM | 654 | N    | HIS  | A     | 398   | 0.608  | 13.620 | 35.228 | 1.00 | 58.98 | A     |
| ATOM | 655 | CA   | HIS  | A     | 398   | 0.637  | 13.051 | 36.575 | 1.00 | 60.04 | A     |
| ATOM | 656 | CB   | HIS  | A     | 398   | 0.570  | 11.521 | 36.518 | 1.00 | 60.49 | A     |
| ATOM | 657 | CG   | HIS  | A     | 398   | −0.681 | 10.984 | 35.895 | 1.00 | 61.83 | A     |
| ATOM | 658 | CD2  | HIS  | A     | 398   | −1.604 | 10.110 | 36.363 | 1.00 | 62.32 | A     |
| ATOM | 659 | ND1  | HIS  | A     | 398   | −1.086 | 11.319 | 34.619 | 1.00 | 62.08 | A     |
| ATOM | 660 | CE1  | HIS  | A     | 398   | −2.203 | 10.675 | 34.329 | 1.00 | 61.94 | A     |
| ATOM | 661 | NE2  | HIS  | A     | 398   | −2.538 | 9.935  | 35.370 | 1.00 | 62.02 | A     |
| ATOM | 662 | C    | HIS  | A     | 398   | 1.916  | 13.453 | 37.310 | 1.00 | 60.59 | A     |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 663 | O | HIS | A | 398 | 2.700 | 12.593 | 37.722 | 1.00 | 60.68 | A |
| ATOM | 664 | N | PRO | A | 399 | 2.140 | 14.767 | 37.485 | 1.00 | 60.99 | A |
| ATOM | 665 | CD | PRO | A | 399 | 1.206 | 15.845 | 37.120 | 1.00 | 60.79 | A |
| ATOM | 666 | CA | PRO | A | 399 | 3.322 | 15.311 | 38.172 | 1.00 | 61.05 | A |
| ATOM | 667 | CB | PRO | A | 399 | 2.988 | 16.802 | 38.313 | 1.00 | 61.04 | A |
| ATOM | 668 | CG | PRO | A | 399 | 1.476 | 16.845 | 38.190 | 1.00 | 61.11 | A |
| ATOM | 669 | C | PRO | A | 399 | 3.638 | 14.639 | 39.515 | 1.00 | 61.20 | A |
| ATOM | 670 | O | PRO | A | 399 | 2.752 | 14.457 | 40.355 | 1.00 | 61.05 | A |
| ATOM | 671 | N | VAL | A | 400 | 4.910 | 14.280 | 39.686 | 1.00 | 61.21 | A |
| ATOM | 672 | CA | VAL | A | 400 | 5.436 | 13.614 | 40.879 | 1.00 | 61.40 | A |
| ATOM | 673 | CB | VAL | A | 400 | 4.871 | 14.236 | 42.230 | 1.00 | 63.15 | A |
| ATOM | 674 | CG1 | VAL | A | 400 | 5.453 | 13.500 | 43.458 | 1.00 | 63.40 | A |
| ATOM | 675 | CG2 | VAL | A | 400 | 5.245 | 15.725 | 42.329 | 1.00 | 63.89 | A |
| ATOM | 676 | C | VAL | A | 400 | 5.154 | 12.108 | 40.835 | 1.00 | 60.50 | A |
| ATOM | 677 | O | VAL | A | 400 | 5.415 | 11.394 | 41.801 | 1.00 | 61.09 | A |
| ATOM | 678 | N | LYS | A | 401 | 4.626 | 11.620 | 39.714 | 1.00 | 59.03 | A |
| ATOM | 679 | CA | LYS | A | 401 | 4.355 | 10.186 | 39.578 | 1.00 | 56.61 | A |
| ATOM | 680 | CB | LYS | A | 401 | 2.921 | 9.838 | 40.005 | 1.00 | 56.90 | A |
| ATOM | 681 | CG | LYS | A | 401 | 2.143 | 10.934 | 40.703 | 1.00 | 58.07 | A |
| ATOM | 682 | CD | LYS | A | 401 | 0.898 | 10.359 | 41.374 | 1.00 | 58.85 | A |
| ATOM | 683 | CE | LYS | A | 401 | 1.283 | 9.342 | 42.450 | 1.00 | 59.57 | A |
| ATOM | 684 | NZ | LYS | A | 401 | 0.108 | 8.801 | 43.199 | 1.00 | 59.95 | A |
| ATOM | 685 | C | LYS | A | 401 | 4.569 | 9.657 | 38.164 | 1.00 | 54.59 | A |
| ATOM | 686 | O | LYS | A | 401 | 4.328 | 10.358 | 37.175 | 1.00 | 54.08 | A |
| ATOM | 687 | N | LEU | A | 402 | 5.021 | 8.409 | 38.087 | 1.00 | 52.31 | A |
| ATOM | 688 | CA | LEU | A | 402 | 5.247 | 7.726 | 36.821 | 1.00 | 50.15 | A |
| ATOM | 689 | CB | LEU | A | 402 | 6.624 | 7.057 | 36.810 | 1.00 | 49.38 | A |
| ATOM | 690 | CG | LEU | A | 402 | 7.832 | 7.987 | 36.671 | 1.00 | 49.36 | A |
| ATOM | 691 | CD1 | LEU | A | 402 | 9.105 | 7.165 | 36.492 | 1.00 | 48.45 | A |
| ATOM | 692 | CD2 | LEU | A | 402 | 7.636 | 8.907 | 35.476 | 1.00 | 48.80 | A |
| ATOM | 693 | C | LEU | A | 402 | 4.158 | 6.672 | 36.583 | 1.00 | 49.62 | A |
| ATOM | 694 | O | LEU | A | 402 | 4.110 | 5.641 | 37.254 | 1.00 | 48.38 | A |
| ATOM | 695 | N | LEU | A | 403 | 3.288 | 6.950 | 35.615 | 1.00 | 49.21 | A |
| ATOM | 696 | CA | LEU | A | 403 | 2.188 | 6.061 | 35.257 | 1.00 | 48.12 | A |
| ATOM | 697 | CB | LEU | A | 403 | 1.071 | 6.871 | 34.582 | 1.00 | 48.37 | A |
| ATOM | 698 | CG | LEU | A | 403 | −0.325 | 6.270 | 34.385 | 1.00 | 48.10 | A |
| ATOM | 699 | CD1 | LEU | A | 403 | −1.237 | 7.314 | 33.800 | 1.00 | 48.68 | A |
| ATOM | 700 | CD2 | LEU | A | 403 | −0.268 | 5.085 | 33.451 | 1.00 | 49.80 | A |
| ATOM | 701 | C | LEU | A | 403 | 2.687 | 4.975 | 34.314 | 1.00 | 47.40 | A |
| ATOM | 702 | O | LEU | A | 403 | 2.694 | 5.159 | 33.103 | 1.00 | 47.47 | A |
| ATOM | 703 | N | PHE | A | 404 | 3.116 | 3.853 | 34.878 | 1.00 | 46.70 | A |
| ATOM | 704 | CA | PHE | A | 404 | 3.610 | 2.723 | 34.095 | 1.00 | 45.92 | A |
| ATOM | 705 | CB | PHE | A | 404 | 4.376 | 1.757 | 35.004 | 1.00 | 45.78 | A |
| ATOM | 706 | CG | PHE | A | 404 | 5.720 | 2.268 | 35.443 | 1.00 | 46.35 | A |
| ATOM | 707 | CD1 | PHE | A | 404 | 6.887 | 1.831 | 34.811 | 1.00 | 46.03 | A |
| ATOM | 708 | CD2 | PHE | A | 404 | 5.825 | 3.184 | 36.489 | 1.00 | 46.19 | A |
| ATOM | 709 | CE1 | PHE | A | 404 | 8.143 | 2.295 | 35.216 | 1.00 | 45.65 | A |
| ATOM | 710 | CE2 | PHE | A | 404 | 7.074 | 3.657 | 36.903 | 1.00 | 46.15 | A |
| ATOM | 711 | CZ | PHE | A | 404 | 8.235 | 3.210 | 36.265 | 1.00 | 45.83 | A |
| ATOM | 712 | C | PHE | A | 404 | 2.431 | 1.994 | 33.439 | 1.00 | 45.70 | A |
| ATOM | 713 | O | PHE | A | 404 | 2.588 | 1.315 | 32.426 | 1.00 | 45.96 | A |
| ATOM | 714 | N | ALA | A | 405 | 1.258 | 2.128 | 34.048 | 1.00 | 44.63 | A |
| ATOM | 715 | CA | ALA | A | 405 | 0.027 | 1.529 | 33.555 | 1.00 | 44.17 | A |
| ATOM | 716 | CB | ALA | A | 405 | −0.002 | 0.039 | 33.838 | 1.00 | 42.99 | A |
| ATOM | 717 | C | ALA | A | 405 | −1.079 | 2.232 | 34.314 | 1.00 | 44.28 | A |
| ATOM | 718 | O | ALA | A | 405 | −0.856 | 2.720 | 35.414 | 1.00 | 43.42 | A |
| ATOM | 719 | N | PRO | A | 406 | −2.284 | 2.322 | 33.730 | 1.00 | 45.68 | A |
| ATOM | 720 | CD | PRO | A | 406 | −2.737 | 1.850 | 32.410 | 1.00 | 45.31 | A |
| ATOM | 721 | CA | PRO | A | 406 | −3.374 | 2.997 | 34.445 | 1.00 | 46.26 | A |
| ATOM | 722 | CB | PRO | A | 406 | −4.584 | 2.732 | 33.553 | 1.00 | 45.10 | A |
| ATOM | 723 | CG | PRO | A | 406 | −3.979 | 2.685 | 32.188 | 1.00 | 44.92 | A |
| ATOM | 724 | C | PRO | A | 406 | −3.568 | 2.460 | 35.867 | 1.00 | 46.73 | A |
| ATOM | 725 | O | PRO | A | 406 | −4.074 | 3.160 | 36.730 | 1.00 | 45.97 | A |
| ATOM | 726 | N | ASN | A | 407 | −3.152 | 1.219 | 36.103 | 1.00 | 48.17 | A |
| ATOM | 727 | CA | ASN | A | 407 | −3.293 | 0.609 | 37.418 | 1.00 | 50.11 | A |
| ATOM | 728 | CB | ASN | A | 407 | −4.106 | −0.684 | 37.304 | 1.00 | 49.24 | A |
| ATOM | 729 | CG | ASN | A | 407 | −3.350 | −1.784 | 36.602 | 1.00 | 48.79 | A |
| ATOM | 730 | OD1 | ASN | A | 407 | −2.496 | −1.522 | 35.756 | 1.00 | 49.21 | A |
| ATOM | 731 | ND2 | ASN | A | 407 | −3.666 | −3.025 | 36.936 | 1.00 | 47.75 | A |
| ATOM | 732 | C | ASN | A | 407 | −1.936 | 0.322 | 38.065 | 1.00 | 51.98 | A |
| ATOM | 733 | O | ASN | A | 407 | −1.813 | −0.545 | 38.932 | 1.00 | 53.19 | A |
| ATOM | 734 | N | LEU | A | 408 | −0.919 | 1.061 | 37.640 | 1.00 | 53.26 | A |
| ATOM | 735 | CA | LEU | A | 408 | 0.425 | 0.896 | 38.168 | 1.00 | 54.81 | A |
| ATOM | 736 | CB | LEU | A | 408 | 1.192 | −0.167 | 37.372 | 1.00 | 54.34 | A |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 737 | CG | LEU | A | 408 | 2.618 | −0.476 | 37.837 | 1.00 | 54.24 | A |
| ATOM | 738 | CD1 | LEU | A | 408 | 2.594 | −0.929 | 39.285 | 1.00 | 53.47 | A |
| ATOM | 739 | CD2 | LEU | A | 408 | 3.234 | −1.554 | 36.957 | 1.00 | 53.89 | A |
| ATOM | 740 | C | LEU | A | 408 | 1.111 | 2.243 | 38.055 | 1.00 | 56.44 | A |
| ATOM | 741 | O | LEU | A | 408 | 2.007 | 2.442 | 37.239 | 1.00 | 56.41 | A |
| ATOM | 742 | N | LEU | A | 409 | 0.652 | 3.168 | 38.885 | 1.00 | 58.91 | A |
| ATOM | 743 | CA | LEU | A | 409 | 1.167 | 4.527 | 38.938 | 1.00 | 61.65 | A |
| ATOM | 744 | CB | LEU | A | 409 | −0.015 | 5.492 | 38.958 | 1.00 | 61.50 | A |
| ATOM | 745 | CG | LEU | A | 409 | 0.184 | 6.958 | 39.321 | 1.00 | 62.72 | A |
| ATOM | 746 | CD1 | LEU | A | 409 | 0.569 | 7.795 | 38.103 | 1.00 | 62.84 | A |
| ATOM | 747 | CD2 | LEU | A | 409 | −1.123 | 7.462 | 39.898 | 1.00 | 63.35 | A |
| ATOM | 748 | C | LEU | A | 409 | 2.027 | 4.710 | 40.194 | 1.00 | 63.73 | A |
| ATOM | 749 | O | LEU | A | 409 | 1.506 | 4.818 | 41.304 | 1.00 | 64.00 | A |
| ATOM | 750 | N | LEU | A | 410 | 3.344 | 4.742 | 40.007 | 1.00 | 66.08 | A |
| ATOM | 751 | CA | LEU | A | 410 | 4.290 | 4.896 | 41.109 | 1.00 | 68.79 | A |
| ATOM | 752 | CB | LEU | A | 410 | 5.432 | 3.901 | 40.935 | 1.00 | 67.95 | A |
| ATOM | 753 | CG | LEU | A | 410 | 5.002 | 2.540 | 40.389 | 1.00 | 67.84 | A |
| ATOM | 754 | CD1 | LEU | A | 410 | 6.231 | 1.708 | 40.077 | 1.00 | 67.76 | A |
| ATOM | 755 | CD2 | LEU | A | 410 | 4.097 | 1.835 | 41.390 | 1.00 | 67.54 | A |
| ATOM | 756 | C | LEU | A | 410 | 4.853 | 6.315 | 41.137 | 1.00 | 71.26 | A |
| ATOM | 757 | O | LEU | A | 410 | 4.506 | 7.136 | 40.295 | 1.00 | 71.29 | A |
| ATOM | 758 | N | ASP | A | 411 | 5.724 | 6.604 | 42.103 | 1.00 | 74.84 | A |
| ATOM | 759 | CA | ASP | A | 411 | 6.315 | 7.937 | 42.198 | 1.00 | 78.08 | A |
| ATOM | 760 | CB | ASP | A | 411 | 5.306 | 8.926 | 42.789 | 1.00 | 78.59 | A |
| ATOM | 761 | CG | ASP | A | 411 | 5.007 | 8.659 | 44.240 | 1.00 | 78.89 | A |
| ATOM | 762 | OD1 | ASP | A | 411 | 4.725 | 7.498 | 44.580 | 1.00 | 80.10 | A |
| ATOM | 763 | OD2 | ASP | A | 411 | 5.041 | 9.611 | 45.043 | 1.00 | 79.01 | A |
| ATOM | 764 | C | ASP | A | 411 | 7.613 | 7.996 | 42.992 | 1.00 | 79.93 | A |
| ATOM | 765 | O | ASP | A | 411 | 8.176 | 6.972 | 43.368 | 1.00 | 79.89 | A |
| ATOM | 766 | N | ARG | A | 412 | 8.078 | 9.219 | 43.223 | 1.00 | 82.62 | A |
| ATOM | 767 | CA | ARG | A | 412 | 9.313 | 9.493 | 43.951 | 1.00 | 85.40 | A |
| ATOM | 768 | CB | ARG | A | 412 | 9.236 | 10.905 | 44.542 | 1.00 | 86.28 | A |
| ATOM | 769 | CG | ARG | A | 412 | 8.920 | 11.991 | 43.525 | 1.00 | 87.93 | A |
| ATOM | 770 | CD | ARG | A | 412 | 10.182 | 12.536 | 42.871 | 1.00 | 89.15 | A |
| ATOM | 771 | NE | ARG | A | 412 | 10.348 | 13.968 | 43.108 | 1.00 | 90.33 | A |
| ATOM | 772 | CZ | ARG | A | 412 | 11.470 | 14.524 | 43.561 | 1.00 | 91.09 | A |
| ATOM | 773 | NH1 | ARG | A | 412 | 12.529 | 13.772 | 43.832 | 1.00 | 90.87 | A |
| ATOM | 774 | NH2 | ARG | A | 412 | 11.541 | 15.837 | 43.741 | 1.00 | 91.58 | A |
| ATOM | 775 | C | ARG | A | 412 | 9.627 | 8.492 | 45.070 | 1.00 | 86.58 | A |
| ATOM | 776 | O | ARG | A | 412 | 10.615 | 7.750 | 45.011 | 1.00 | 86.87 | A |
| ATOM | 777 | N | ASN | A | 413 | 8.778 | 8.479 | 46.090 | 1.00 | 87.96 | A |
| ATOM | 778 | CA | ASN | A | 413 | 8.971 | 7.604 | 47.238 | 1.00 | 89.27 | A |
| ATOM | 779 | CB | ASN | A | 413 | 7.862 | 7.853 | 48.264 | 1.00 | 89.79 | A |
| ATOM | 780 | CG | ASN | A | 413 | 7.663 | 9.334 | 48.555 | 1.00 | 90.41 | A |
| ATOM | 781 | OD1 | ASN | A | 413 | 8.631 | 10.092 | 48.669 | 1.00 | 90.61 | A |
| ATOM | 782 | ND2 | ASN | A | 413 | 6.408 | 9.750 | 48.685 | 1.00 | 90.45 | A |
| ATOM | 783 | C | ASN | A | 413 | 9.022 | 6.124 | 46.863 | 1.00 | 89.85 | A |
| ATOM | 784 | O | ASN | A | 413 | 9.921 | 5.399 | 47.305 | 1.00 | 90.07 | A |
| ATOM | 785 | N | GLN | A | 414 | 8.070 | 5.677 | 46.049 | 1.00 | 90.10 | A |
| ATOM | 786 | CA | GLN | A | 414 | 8.032 | 4.276 | 45.642 | 1.00 | 90.63 | A |
| ATOM | 787 | CB | GLN | A | 414 | 6.770 | 3.981 | 44.828 | 1.00 | 89.76 | A |
| ATOM | 788 | CG | GLN | A | 414 | 5.647 | 4.976 | 45.025 | 1.00 | 88.62 | A |
| ATOM | 789 | CD | GLN | A | 414 | 4.281 | 4.327 | 44.962 | 1.00 | 87.74 | A |
| ATOM | 790 | OE1 | GLN | A | 414 | 3.269 | 4.987 | 44.723 | 1.00 | 86.78 | A |
| ATOM | 791 | NE2 | GLN | A | 414 | 4.245 | 3.024 | 45.200 | 1.00 | 87.72 | A |
| ATOM | 792 | C | GLN | A | 414 | 9.258 | 3.905 | 44.816 | 1.00 | 91.47 | A |
| ATOM | 793 | O | GLN | A | 414 | 9.776 | 2.794 | 44.926 | 1.00 | 91.18 | A |
| ATOM | 794 | N | GLY | A | 415 | 9.714 | 4.844 | 43.989 | 1.00 | 92.58 | A |
| ATOM | 795 | CA | GLY | A | 415 | 10.873 | 4.612 | 43.142 | 1.00 | 93.39 | A |
| ATOM | 796 | C | GLY | A | 415 | 12.092 | 4.131 | 43.901 | 1.00 | 93.91 | A |
| ATOM | 797 | O | GLY | A | 415 | 13.061 | 3.653 | 43.309 | 1.00 | 93.65 | A |
| ATOM | 798 | N | LYS | A | 416 | 12.038 | 4.262 | 45.221 | 1.00 | 94.72 | A |
| ATOM | 799 | CA | LYS | A | 416 | 13.129 | 3.836 | 46.082 | 1.00 | 95.82 | A |
| ATOM | 800 | CB | LYS | A | 416 | 13.107 | 4.647 | 47.380 | 1.00 | 96.31 | A |
| ATOM | 801 | CG | LYS | A | 416 | 14.199 | 4.276 | 48.366 | 1.00 | 96.85 | A |
| ATOM | 802 | CD | LYS | A | 416 | 14.040 | 5.051 | 49.663 | 1.00 | 97.82 | A |
| ATOM | 803 | CE | LYS | A | 416 | 15.134 | 4.690 | 50.659 | 1.00 | 98.31 | A |
| ATOM | 804 | NZ | LYS | A | 416 | 15.047 | 5.495 | 51.911 | 1.00 | 98.52 | A |
| ATOM | 805 | C | LYS | A | 416 | 12.992 | 2.347 | 46.394 | 1.00 | 96.12 | A |
| ATOM | 806 | O | LYS | A | 416 | 13.981 | 1.658 | 46.651 | 1.00 | 96.11 | A |
| ATOM | 807 | N | CYS | A | 417 | 11.755 | 1.862 | 46.363 | 1.00 | 96.40 | A |
| ATOM | 808 | CA | CYS | A | 417 | 11.467 | 0.461 | 46.650 | 1.00 | 96.64 | A |
| ATOM | 809 | CB | CYS | A | 417 | 10.016 | 0.296 | 47.126 | 1.00 | 96.50 | A |
| ATOM | 810 | SG | CYS | A | 417 | 9.643 | 0.954 | 48.769 | 1.00 | 95.65 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 811 | C | CYS | A | 417 | 11.700 | −0.457 | 45.447 | 1.00 | 96.96 | A |
| ATOM | 812 | O | CYS | A | 417 | 10.750 | −0.980 | 44.861 | 1.00 | 97.25 | A |
| ATOM | 813 | N | VAL | A | 418 | 12.962 | −0.647 | 45.078 | 1.00 | 97.01 | A |
| ATOM | 814 | CA | VAL | A | 418 | 13.322 | −1.533 | 43.971 | 1.00 | 97.01 | A |
| ATOM | 815 | CB | VAL | A | 418 | 13.147 | −0.833 | 42.592 | 1.00 | 97.37 | A |
| ATOM | 816 | CG1 | VAL | A | 418 | 13.880 | 0.495 | 42.566 | 1.00 | 97.70 | A |
| ATOM | 817 | CG2 | VAL | A | 418 | 13.640 | −1.751 | 41.476 | 1.00 | 97.47 | A |
| ATOM | 818 | C | VAL | A | 418 | 14.768 | −1.997 | 44.172 | 1.00 | 96.48 | A |
| ATOM | 819 | O | VAL | A | 418 | 15.004 | −3.161 | 44.510 | 1.00 | 96.75 | A |
| ATOM | 820 | N | GLU | A | 419 | 15.722 | −1.090 | 43.971 | 1.00 | 95.22 | A |
| ATOM | 821 | CA | GLU | A | 419 | 17.145 | −1.378 | 44.173 | 1.00 | 94.32 | A |
| ATOM | 822 | CB | GLU | A | 419 | 17.608 | −2.599 | 43.361 | 1.00 | 94.55 | A |
| ATOM | 823 | CG | GLU | A | 419 | 17.281 | −2.591 | 41.886 | 1.00 | 95.53 | A |
| ATOM | 824 | CD | GLU | A | 419 | 18.041 | −3.673 | 41.141 | 1.00 | 96.27 | A |
| ATOM | 825 | OE1 | GLU | A | 419 | 18.040 | −4.833 | 41.610 | 1.00 | 96.23 | A |
| ATOM | 826 | OE2 | GLU | A | 419 | 18.639 | −3.366 | 40.085 | 1.00 | 96.92 | A |
| ATOM | 827 | C | GLU | A | 419 | 18.016 | −0.176 | 43.841 | 1.00 | 93.26 | A |
| ATOM | 828 | O | GLU | A | 419 | 18.739 | 0.332 | 44.698 | 1.00 | 93.52 | A |
| ATOM | 829 | N | GLY | A | 420 | 17.944 | 0.273 | 42.596 | 1.00 | 91.72 | A |
| ATOM | 830 | CA | GLY | A | 420 | 18.714 | 1.424 | 42.165 | 1.00 | 89.63 | A |
| ATOM | 831 | C | GLY | A | 420 | 17.986 | 2.055 | 40.996 | 1.00 | 88.14 | A |
| ATOM | 832 | O | GLY | A | 420 | 18.414 | 1.932 | 39.852 | 1.00 | 88.14 | A |
| ATOM | 833 | N | MET | A | 421 | 16.873 | 2.724 | 41.274 | 1.00 | 86.29 | A |
| ATOM | 834 | CA | MET | A | 421 | 16.094 | 3.332 | 40.206 | 1.00 | 84.10 | A |
| ATOM | 835 | CB | MET | A | 421 | 14.880 | 2.451 | 39.882 | 1.00 | 85.14 | A |
| ATOM | 836 | CG | MET | A | 421 | 15.048 | 1.574 | 38.636 | 1.00 | 85.97 | A |
| ATOM | 837 | SD | MET | A | 421 | 16.194 | 0.181 | 38.801 | 1.00 | 87.95 | A |
| ATOM | 838 | CE | MET | A | 421 | 15.083 | −1.195 | 38.588 | 1.00 | 87.48 | A |
| ATOM | 839 | C | MET | A | 421 | 15.632 | 4.762 | 40.478 | 1.00 | 82.17 | A |
| ATOM | 840 | O | MET | A | 421 | 15.069 | 5.411 | 39.595 | 1.00 | 82.24 | A |
| ATOM | 841 | N | VAL | A | 422 | 15.872 | 5.261 | 41.685 | 1.00 | 79.30 | A |
| ATOM | 842 | CA | VAL | A | 422 | 15.469 | 6.620 | 42.027 | 1.00 | 76.42 | A |
| ATOM | 843 | CB | VAL | A | 422 | 15.802 | 6.919 | 43.506 | 1.00 | 76.78 | A |
| ATOM | 844 | CG1 | VAL | A | 422 | 17.303 | 6.789 | 43.730 | 1.00 | 76.50 | A |
| ATOM | 845 | CG2 | VAL | A | 422 | 15.300 | 8.302 | 43.895 | 1.00 | 76.31 | A |
| ATOM | 846 | C | VAL | A | 422 | 16.196 | 7.611 | 41.106 | 1.00 | 74.15 | A |
| ATOM | 847 | O | VAL | A | 422 | 15.804 | 8.772 | 40.980 | 1.00 | 73.31 | A |
| ATOM | 848 | N | GLU | A | 423 | 17.264 | 7.130 | 40.473 | 1.00 | 71.58 | A |
| ATOM | 849 | CA | GLU | A | 423 | 18.064 | 7.927 | 39.542 | 1.00 | 68.36 | A |
| ATOM | 850 | CB | GLU | A | 423 | 19.408 | 7.236 | 39.287 | 1.00 | 69.90 | A |
| ATOM | 851 | CG | GLU | A | 423 | 19.479 | 5.796 | 39.811 | 1.00 | 71.54 | A |
| ATOM | 852 | CD | GLU | A | 423 | 20.107 | 4.825 | 38.819 | 1.00 | 73.10 | A |
| ATOM | 853 | OE1 | GLU | A | 423 | 20.846 | 5.271 | 37.910 | 1.00 | 73.35 | A |
| ATOM | 854 | OE2 | GLU | A | 423 | 19.869 | 3.606 | 38.956 | 1.00 | 73.79 | A |
| ATOM | 855 | C | GLU | A | 423 | 17.283 | 7.999 | 38.239 | 1.00 | 65.11 | A |
| ATOM | 856 | O | GLU | A | 423 | 16.935 | 9.076 | 37.745 | 1.00 | 63.72 | A |
| ATOM | 857 | N | ILE | A | 424 | 17.020 | 6.816 | 37.700 | 1.00 | 61.54 | A |
| ATOM | 858 | CA | ILE | A | 424 | 16.273 | 6.649 | 36.472 | 1.00 | 58.25 | A |
| ATOM | 859 | CB | ILE | A | 424 | 16.198 | 5.167 | 36.135 | 1.00 | 56.95 | A |
| ATOM | 860 | CG2 | ILE | A | 424 | 15.301 | 4.939 | 34.944 | 1.00 | 56.83 | A |
| ATOM | 861 | CG1 | ILE | A | 424 | 17.621 | 4.660 | 35.889 | 1.00 | 56.13 | A |
| ATOM | 862 | CD1 | ILE | A | 424 | 17.734 | 3.185 | 35.659 | 1.00 | 55.74 | A |
| ATOM | 863 | C | ILE | A | 424 | 14.880 | 7.250 | 36.637 | 1.00 | 56.48 | A |
| ATOM | 864 | O | ILE | A | 424 | 14.396 | 7.946 | 35.749 | 1.00 | 55.87 | A |
| ATOM | 865 | N | PHE | A | 425 | 14.262 | 6.997 | 37.788 | 1.00 | 54.42 | A |
| ATOM | 866 | CA | PHE | A | 425 | 12.937 | 7.517 | 38.109 | 1.00 | 53.15 | A |
| ATOM | 867 | CB | PHE | A | 425 | 12.515 | 7.073 | 39.506 | 1.00 | 53.48 | A |
| ATOM | 868 | CG | PHE | A | 425 | 11.641 | 5.863 | 39.529 | 1.00 | 54.19 | A |
| ATOM | 869 | CD1 | PHE | A | 425 | 12.109 | 4.634 | 39.067 | 1.00 | 54.85 | A |
| ATOM | 870 | CD2 | PHE | A | 425 | 10.354 | 5.941 | 40.051 | 1.00 | 54.29 | A |
| ATOM | 871 | CE1 | PHE | A | 425 | 11.309 | 3.495 | 39.132 | 1.00 | 54.92 | A |
| ATOM | 872 | CE2 | PHE | A | 425 | 9.546 | 4.811 | 40.120 | 1.00 | 55.17 | A |
| ATOM | 873 | CZ | PHE | A | 425 | 10.028 | 3.582 | 39.659 | 1.00 | 55.06 | A |
| ATOM | 874 | C | PHE | A | 425 | 12.897 | 9.037 | 38.080 | 1.00 | 52.45 | A |
| ATOM | 875 | O | PHE | A | 425 | 11.980 | 9.638 | 37.504 | 1.00 | 51.78 | A |
| ATOM | 876 | N | ASP | A | 426 | 13.885 | 9.653 | 38.723 | 1.00 | 51.50 | A |
| ATOM | 877 | CA | ASP | A | 426 | 13.961 | 11.108 | 38.792 | 1.00 | 51.49 | A |
| ATOM | 878 | CB | ASP | A | 426 | 15.020 | 11.555 | 39.809 | 1.00 | 52.84 | A |
| ATOM | 879 | CG | ASP | A | 426 | 14.458 | 11.665 | 41.222 | 1.00 | 53.85 | A |
| ATOM | 880 | OD1 | ASP | A | 426 | 13.443 | 12.372 | 41.413 | 1.00 | 54.77 | A |
| ATOM | 881 | OD2 | ASP | A | 426 | 15.028 | 11.051 | 42.145 | 1.00 | 55.02 | A |
| ATOM | 882 | C | ASP | A | 426 | 14.230 | 11.740 | 37.447 | 1.00 | 49.69 | A |
| ATOM | 883 | O | ASP | A | 426 | 13.786 | 12.850 | 37.182 | 1.00 | 48.83 | A |
| ATOM | 884 | N | MET | A | 427 | 14.963 | 11.032 | 36.600 | 1.00 | 49.31 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 885 | CA | MET | A | 427 | 15.253 | 11.530 | 35.264 | 1.00 | 49.19 | A |
| ATOM | 886 | CB | MET | A | 427 | 16.327 | 10.668 | 34.601 | 1.00 | 50.89 | A |
| ATOM | 887 | CG | MET | A | 427 | 17.632 | 10.631 | 35.361 | 1.00 | 53.02 | A |
| ATOM | 888 | SD | MET | A | 427 | 19.005 | 10.179 | 34.307 | 1.00 | 56.51 | A |
| ATOM | 889 | CE | MET | A | 427 | 18.987 | 8.392 | 34.446 | 1.00 | 55.17 | A |
| ATOM | 890 | C | MET | A | 427 | 13.953 | 11.465 | 34.457 | 1.00 | 48.41 | A |
| ATOM | 891 | O | MET | A | 427 | 13.545 | 12.453 | 33.837 | 1.00 | 48.18 | A |
| ATOM | 892 | N | LEU | A | 428 | 13.308 | 10.298 | 34.498 | 1.00 | 46.07 | A |
| ATOM | 893 | CA | LEU | A | 428 | 12.053 | 10.055 | 33.798 | 1.00 | 45.37 | A |
| ATOM | 894 | CB | LEU | A | 428 | 11.543 | 8.649 | 34.123 | 1.00 | 45.07 | A |
| ATOM | 895 | CG | LEU | A | 428 | 12.467 | 7.535 | 33.624 | 1.00 | 44.77 | A |
| ATOM | 896 | CD1 | LEU | A | 428 | 11.983 | 6.176 | 34.093 | 1.00 | 43.73 | A |
| ATOM | 897 | CD2 | LEU | A | 428 | 12.526 | 7.606 | 32.109 | 1.00 | 44.99 | A |
| ATOM | 898 | C | LEU | A | 428 | 10.997 | 11.076 | 34.177 | 1.00 | 44.96 | A |
| ATOM | 899 | O | LEU | A | 428 | 10.230 | 11.541 | 33.333 | 1.00 | 44.20 | A |
| ATOM | 900 | N | LEU | A | 429 | 10.967 | 11.410 | 35.461 | 1.00 | 44.65 | A |
| ATOM | 901 | CA | LEU | A | 429 | 10.025 | 12.378 | 36.004 | 1.00 | 44.06 | A |
| ATOM | 902 | CB | LEU | A | 429 | 10.141 | 12.362 | 37.527 | 1.00 | 45.66 | A |
| ATOM | 903 | CG | LEU | A | 429 | 8.985 | 12.050 | 38.486 | 1.00 | 47.20 | A |
| ATOM | 904 | CD1 | LEU | A | 429 | 7.978 | 11.083 | 37.888 | 1.00 | 47.49 | A |
| ATOM | 905 | CD2 | LEU | A | 429 | 9.602 | 11.461 | 39.762 | 1.00 | 47.36 | A |
| ATOM | 906 | C | LEU | A | 429 | 10.316 | 13.790 | 35.469 | 1.00 | 43.79 | A |
| ATOM | 907 | O | LEU | A | 429 | 9.400 | 14.565 | 35.189 | 1.00 | 43.02 | A |
| ATOM | 908 | N | ALA | A | 430 | 11.595 | 14.124 | 35.325 | 1.00 | 42.99 | A |
| ATOM | 909 | CA | ALA | A | 430 | 11.976 | 15.447 | 34.839 | 1.00 | 42.94 | A |
| ATOM | 910 | CB | ALA | A | 430 | 13.459 | 15.669 | 35.076 | 1.00 | 44.06 | A |
| ATOM | 911 | C | ALA | A | 430 | 11.648 | 15.612 | 33.356 | 1.00 | 42.84 | A |
| ATOM | 912 | O | ALA | A | 430 | 11.054 | 16.622 | 32.939 | 1.00 | 41.23 | A |
| ATOM | 913 | N | THR | A | 431 | 12.057 | 14.614 | 32.571 | 1.00 | 42.57 | A |
| ATOM | 914 | CA | THR | A | 431 | 11.808 | 14.584 | 31.132 | 1.00 | 41.97 | A |
| ATOM | 915 | CB | THR | A | 431 | 12.258 | 13.237 | 30.523 | 1.00 | 41.25 | A |
| ATOM | 916 | OG1 | THR | A | 431 | 11.734 | 12.174 | 31.315 | 1.00 | 42.88 | A |
| ATOM | 917 | CG2 | THR | A | 431 | 13.771 | 13.114 | 30.504 | 1.00 | 40.21 | A |
| ATOM | 918 | C | THR | A | 431 | 10.304 | 14.767 | 30.898 | 1.00 | 42.54 | A |
| ATOM | 919 | O | THR | A | 431 | 9.878 | 15.511 | 30.010 | 1.00 | 42.25 | A |
| ATOM | 920 | N | SER | A | 432 | 9.505 | 14.090 | 31.716 | 1.00 | 42.90 | A |
| ATOM | 921 | CA | SER | A | 432 | 8.060 | 14.180 | 31.615 | 1.00 | 43.68 | A |
| ATOM | 922 | CB | SER | A | 432 | 7.409 | 13.194 | 32.581 | 1.00 | 43.35 | A |
| ATOM | 923 | OG | SER | A | 432 | 6.007 | 13.374 | 32.595 | 1.00 | 44.20 | A |
| ATOM | 924 | C | SER | A | 432 | 7.607 | 15.605 | 31.920 | 1.00 | 45.13 | A |
| ATOM | 925 | O | SER | A | 432 | 6.670 | 16.125 | 31.302 | 1.00 | 46.07 | A |
| ATOM | 926 | N | SER | A | 433 | 8.275 | 16.239 | 32.876 | 1.00 | 46.35 | A |
| ATOM | 927 | CA | SER | A | 433 | 7.953 | 17.615 | 33.233 | 1.00 | 47.26 | A |
| ATOM | 928 | CB | SER | A | 433 | 8.651 | 18.017 | 34.541 | 1.00 | 47.98 | A |
| ATOM | 929 | OG | SER | A | 433 | 8.039 | 17.405 | 35.665 | 1.00 | 49.46 | A |
| ATOM | 930 | C | SER | A | 433 | 8.389 | 18.547 | 32.106 | 1.00 | 47.45 | A |
| ATOM | 931 | O | SER | A | 433 | 7.693 | 19.508 | 31.778 | 1.00 | 45.99 | A |
| ATOM | 932 | N | ARG | A | 434 | 9.550 | 18.274 | 31.522 | 1.00 | 48.74 | A |
| ATOM | 933 | CA | ARG | A | 434 | 10.012 | 19.101 | 30.419 | 1.00 | 51.18 | A |
| ATOM | 934 | CB | ARG | A | 434 | 11.361 | 18.596 | 29.879 | 1.00 | 52.97 | A |
| ATOM | 935 | CG | ARG | A | 434 | 12.027 | 19.538 | 28.873 | 1.00 | 56.53 | A |
| ATOM | 936 | CD | ARG | A | 434 | 12.553 | 20.826 | 29.525 | 1.00 | 59.49 | A |
| ATOM | 937 | NE | ARG | A | 434 | 12.186 | 22.041 | 28.782 | 1.00 | 61.96 | A |
| ATOM | 938 | CZ | ARG | A | 434 | 12.688 | 22.403 | 27.600 | 1.00 | 62.85 | A |
| ATOM | 939 | NH1 | ARG | A | 434 | 13.597 | 21.649 | 26.992 | 1.00 | 62.36 | A |
| ATOM | 940 | NH2 | ARG | A | 434 | 12.283 | 23.530 | 27.023 | 1.00 | 63.75 | A |
| ATOM | 941 | C | ARG | A | 434 | 8.930 | 19.034 | 29.330 | 1.00 | 51.10 | A |
| ATOM | 942 | O | ARG | A | 434 | 8.550 | 20.064 | 28.775 | 1.00 | 51.59 | A |
| ATOM | 943 | N | PHE | A | 435 | 8.417 | 17.834 | 29.042 | 1.00 | 50.89 | A |
| ATOM | 944 | CA | PHE | A | 435 | 7.370 | 17.685 | 28.025 | 1.00 | 51.05 | A |
| ATOM | 945 | CB | PHE | A | 435 | 7.006 | 16.211 | 27.791 | 1.00 | 48.77 | A |
| ATOM | 946 | CG | PHE | A | 435 | 7.990 | 15.463 | 26.930 | 1.00 | 47.42 | A |
| ATOM | 947 | CD1 | PHE | A | 435 | 8.971 | 16.140 | 26.199 | 1.00 | 46.58 | A |
| ATOM | 948 | CD2 | PHE | A | 435 | 7.930 | 14.074 | 26.837 | 1.00 | 46.50 | A |
| ATOM | 949 | CE1 | PHE | A | 435 | 9.873 | 15.440 | 25.393 | 1.00 | 44.76 | A |
| ATOM | 950 | CE2 | PHE | A | 435 | 8.828 | 13.365 | 26.032 | 1.00 | 44.70 | A |
| ATOM | 951 | CZ | PHE | A | 435 | 9.799 | 14.050 | 25.311 | 1.00 | 44.28 | A |
| ATOM | 952 | C | PHE | A | 435 | 6.108 | 18.453 | 28.400 | 1.00 | 52.58 | A |
| ATOM | 953 | O | PHE | A | 435 | 5.425 | 18.992 | 27.523 | 1.00 | 52.32 | A |
| ATOM | 954 | N | ARG | A | 436 | 5.793 | 18.489 | 29.695 | 1.00 | 54.29 | A |
| ATOM | 955 | CA | ARG | A | 436 | 4.619 | 19.216 | 30.168 | 1.00 | 56.63 | A |
| ATOM | 956 | CB | ARG | A | 436 | 4.310 | 18.877 | 31.624 | 1.00 | 57.24 | A |
| ATOM | 957 | CG | ARG | A | 436 | 3.068 | 19.576 | 32.171 | 1.00 | 58.54 | A |
| ATOM | 958 | CD | ARG | A | 436 | 2.944 | 19.382 | 33.674 | 1.00 | 59.70 | A |

TABLE 9-continued

Structure coordinates for ERalpha-LBD/Compound 1 complex
(Table dicloses SEQ ID NOS 2-8, respectively, in order of appearance)

|      | #    | Name | Res. | Chain | Res # | X      | Y      | Z      | occ  | B     | SegID |
|------|------|------|------|-------|-------|--------|--------|--------|------|-------|-------|
| ATOM | 959  | NE   | ARG  | A     | 436   | 3.359  | 18.037 | 34.070 | 1.00 | 61.58 | A     |
| ATOM | 960  | CZ   | ARG  | A     | 436   | 4.505  | 17.756 | 34.690 | 1.00 | 62.20 | A     |
| ATOM | 961  | NH1  | ARG  | A     | 436   | 5.353  | 18.733 | 34.996 | 1.00 | 62.70 | A     |
| ATOM | 962  | NH2  | ARG  | A     | 436   | 4.814  | 16.497 | 34.985 | 1.00 | 61.68 | A     |
| ATOM | 963  | C    | ARG  | A     | 436   | 4.927  | 20.700 | 30.056 | 1.00 | 58.13 | A     |
| ATOM | 964  | O    | ARG  | A     | 436   | 4.094  | 21.487 | 29.609 | 1.00 | 58.36 | A     |
| ATOM | 965  | N    | MET  | A     | 437   | 6.131  | 21.079 | 30.474 | 1.00 | 59.78 | A     |
| ATOM | 966  | CA   | MET  | A     | 437   | 6.557  | 22.469 | 30.397 | 1.00 | 61.41 | A     |
| ATOM | 967  | CB   | MET  | A     | 437   | 8.010  | 22.614 | 30.871 | 1.00 | 65.24 | A     |
| ATOM | 968  | CG   | MET  | A     | 437   | 8.221  | 22.365 | 32.356 | 1.00 | 69.81 | A     |
| ATOM | 969  | SD   | MET  | A     | 437   | 7.212  | 23.482 | 33.361 | 1.00 | 76.59 | A     |
| ATOM | 970  | CE   | MET  | A     | 437   | 8.293  | 24.998 | 33.418 | 1.00 | 75.24 | A     |
| ATOM | 971  | C    | MET  | A     | 437   | 6.450  | 22.939 | 28.949 | 1.00 | 60.09 | A     |
| ATOM | 972  | O    | MET  | A     | 437   | 6.004  | 24.056 | 28.680 | 1.00 | 60.15 | A     |
| ATOM | 973  | N    | MET  | A     | 438   | 6.857  | 22.072 | 28.023 | 1.00 | 57.74 | A     |
| ATOM | 974  | CA   | MET  | A     | 438   | 6.827  | 22.382 | 26.596 | 1.00 | 55.60 | A     |
| ATOM | 975  | CB   | MET  | A     | 438   | 7.825  | 21.504 | 25.842 | 1.00 | 54.55 | A     |
| ATOM | 976  | CG   | MET  | A     | 438   | 9.272  | 21.818 | 26.114 | 1.00 | 54.05 | A     |
| ATOM | 977  | SD   | MET  | A     | 438   | 10.339 | 20.909 | 25.000 | 1.00 | 53.81 | A     |
| ATOM | 978  | CE   | MET  | A     | 438   | 10.393 | 21.981 | 23.612 | 1.00 | 51.91 | A     |
| ATOM | 979  | C    | MET  | A     | 438   | 5.451  | 22.215 | 25.958 | 1.00 | 54.57 | A     |
| ATOM | 980  | O    | MET  | A     | 438   | 5.212  | 22.703 | 24.852 | 1.00 | 53.64 | A     |
| ATOM | 981  | N    | ASN  | A     | 439   | 4.554  | 21.510 | 26.637 | 1.00 | 53.76 | A     |
| ATOM | 982  | CA   | ASN  | A     | 439   | 3.218  | 21.301 | 26.097 | 1.00 | 53.30 | A     |
| ATOM | 983  | CB   | ASN  | A     | 439   | 2.541  | 22.663 | 25.879 | 1.00 | 54.94 | A     |
| ATOM | 984  | CG   | ASN  | A     | 439   | 1.070  | 22.542 | 25.510 | 1.00 | 56.77 | A     |
| ATOM | 985  | OD1  | ASN  | A     | 439   | 0.365  | 21.652 | 25.990 | 1.00 | 57.73 | A     |
| ATOM | 986  | ND2  | ASN  | A     | 439   | 0.594  | 23.460 | 24.672 | 1.00 | 57.64 | A     |
| ATOM | 987  | C    | ASN  | A     | 439   | 3.340  | 20.526 | 24.784 | 1.00 | 52.01 | A     |
| ATOM | 988  | O    | ASN  | A     | 439   | 2.779  | 20.901 | 23.754 | 1.00 | 51.54 | A     |
| ATOM | 989  | N    | LEU  | A     | 440   | 4.107  | 19.443 | 24.837 | 1.00 | 50.44 | A     |
| ATOM | 990  | CA   | LEU  | A     | 440   | 4.322  | 18.586 | 23.683 | 1.00 | 48.37 | A     |
| ATOM | 991  | CB   | LEU  | A     | 440   | 5.234  | 17.419 | 24.076 | 1.00 | 47.96 | A     |
| ATOM | 992  | CG   | LEU  | A     | 440   | 5.454  | 16.293 | 23.062 | 1.00 | 47.22 | A     |
| ATOM | 993  | CD1  | LEU  | A     | 440   | 6.347  | 16.756 | 21.934 | 1.00 | 45.37 | A     |
| ATOM | 994  | CD2  | LEU  | A     | 440   | 6.069  | 15.110 | 23.780 | 1.00 | 46.55 | A     |
| ATOM | 995  | C    | LEU  | A     | 440   | 2.968  | 18.065 | 23.194 | 1.00 | 47.03 | A     |
| ATOM | 996  | O    | LEU  | A     | 440   | 2.099  | 17.724 | 23.995 | 1.00 | 46.99 | A     |
| ATOM | 997  | N    | GLN  | A     | 441   | 2.789  | 18.018 | 21.879 | 1.00 | 45.31 | A     |
| ATOM | 998  | CA   | GLN  | A     | 441   | 1.542  | 17.540 | 21.298 | 1.00 | 43.32 | A     |
| ATOM | 999  | CB   | GLN  | A     | 441   | 1.179  | 18.373 | 20.069 | 1.00 | 44.38 | A     |
| ATOM | 1000 | CG   | GLN  | A     | 441   | 0.952  | 19.851 | 20.358 | 1.00 | 44.77 | A     |
| ATOM | 1001 | CD   | GLN  | A     | 441   | −0.343 | 20.110 | 21.099 | 1.00 | 45.41 | A     |
| ATOM | 1002 | OE1  | GLN  | A     | 441   | −1.423 | 19.824 | 20.588 | 1.00 | 48.04 | A     |
| ATOM | 1003 | NE2  | GLN  | A     | 441   | −0.244 | 20.650 | 22.306 | 1.00 | 45.05 | A     |
| ATOM | 1004 | C    | GLN  | A     | 441   | 1.678  | 16.082 | 20.897 | 1.00 | 42.00 | A     |
| ATOM | 1005 | O    | GLN  | A     | 441   | 2.774  | 15.614 | 20.571 | 1.00 | 41.38 | A     |
| ATOM | 1006 | N    | GLY  | A     | 442   | 0.561  | 15.363 | 20.934 | 1.00 | 40.66 | A     |
| ATOM | 1007 | CA   | GLY  | A     | 442   | 0.570  | 13.963 | 20.552 | 1.00 | 39.25 | A     |
| ATOM | 1008 | C    | GLY  | A     | 442   | 1.124  | 13.752 | 19.154 | 1.00 | 39.23 | A     |
| ATOM | 1009 | O    | GLY  | A     | 442   | 1.729  | 12.709 | 18.893 | 1.00 | 39.29 | A     |
| ATOM | 1010 | N    | GLU  | A     | 443   | 0.920  | 14.728 | 18.260 | 1.00 | 38.89 | A     |
| ATOM | 1011 | CA   | GLU  | A     | 443   | 1.417  | 14.646 | 16.880 | 1.00 | 39.14 | A     |
| ATOM | 1012 | CB   | GLU  | A     | 443   | 0.860  | 15.779 | 16.016 | 1.00 | 41.54 | A     |
| ATOM | 1013 | CG   | GLU  | A     | 443   | −0.598 | 15.635 | 15.616 | 1.00 | 44.33 | A     |
| ATOM | 1014 | CD   | GLU  | A     | 443   | −1.542 | 15.793 | 16.790 | 1.00 | 47.26 | A     |
| ATOM | 1015 | OE1  | GLU  | A     | 443   | −1.184 | 16.519 | 17.750 | 1.00 | 48.85 | A     |
| ATOM | 1016 | OE2  | GLU  | A     | 443   | −2.650 | 15.210 | 16.748 | 1.00 | 48.90 | A     |
| ATOM | 1017 | C    | GLU  | A     | 443   | 2.937  | 14.710 | 16.826 | 1.00 | 38.13 | A     |
| ATOM | 1018 | O    | GLU  | A     | 443   | 3.568  | 14.085 | 15.972 | 1.00 | 37.33 | A     |
| ATOM | 1019 | N    | GLU  | A     | 444   | 3.517  | 15.485 | 17.734 | 1.00 | 37.27 | A     |
| ATOM | 1020 | CA   | GLU  | A     | 444   | 4.965  | 15.620 | 17.816 | 1.00 | 36.01 | A     |
| ATOM | 1021 | CB   | GLU  | A     | 444   | 5.330  | 16.854 | 18.632 | 1.00 | 37.89 | A     |
| ATOM | 1022 | CG   | GLU  | A     | 444   | 4.670  | 18.135 | 18.159 | 1.00 | 40.09 | A     |
| ATOM | 1023 | CD   | GLU  | A     | 444   | 5.074  | 19.326 | 18.998 | 1.00 | 42.03 | A     |
| ATOM | 1024 | OE1  | GLU  | A     | 444   | 4.665  | 19.404 | 20.180 | 1.00 | 43.90 | A     |
| ATOM | 1025 | OE2  | GLU  | A     | 444   | 5.814  | 20.182 | 18.477 | 1.00 | 42.69 | A     |
| ATOM | 1026 | C    | GLU  | A     | 444   | 5.508  | 14.384 | 18.513 | 1.00 | 34.67 | A     |
| ATOM | 1027 | O    | GLU  | A     | 444   | 6.552  | 13.849 | 18.148 | 1.00 | 34.38 | A     |
| ATOM | 1028 | N    | PHE  | A     | 445   | 4.781  | 13.941 | 19.530 | 1.00 | 33.60 | A     |
| ATOM | 1029 | CA   | PHE  | A     | 445   | 5.181  | 12.773 | 20.294 | 1.00 | 32.77 | A     |
| ATOM | 1030 | CB   | PHE  | A     | 445   | 4.133  | 12.442 | 21.363 | 1.00 | 32.56 | A     |
| ATOM | 1031 | CG   | PHE  | A     | 445   | 4.252  | 11.044 | 21.896 | 1.00 | 32.99 | A     |
| ATOM | 1032 | CD1  | PHE  | A     | 445   | 5.331  | 10.679 | 22.687 | 1.00 | 31.75 | A     |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1033 | CD2 | PHE | A | 445 | 3.315 | 10.069 | 21.547 | 1.00 | 32.90 | A |
| ATOM | 1034 | CE1 | PHE | A | 445 | 5.475 | 9.364 | 23.123 | 1.00 | 32.40 | A |
| ATOM | 1035 | CE2 | PHE | A | 445 | 3.457 | 8.761 | 21.975 | 1.00 | 30.87 | A |
| ATOM | 1036 | CZ | PHE | A | 445 | 4.536 | 8.406 | 22.763 | 1.00 | 30.80 | A |
| ATOM | 1037 | C | PHE | A | 445 | 5.395 | 11.547 | 19.409 | 1.00 | 32.50 | A |
| ATOM | 1038 | O | PHE | A | 445 | 6.435 | 10.880 | 19.496 | 1.00 | 32.06 | A |
| ATOM | 1039 | N | VAL | A | 446 | 4.411 | 11.243 | 18.566 | 1.00 | 31.22 | A |
| ATOM | 1040 | CA | VAL | A | 446 | 4.527 | 10.079 | 17.701 | 1.00 | 30.73 | A |
| ATOM | 1041 | CB | VAL | A | 446 | 3.186 | 9.805 | 16.926 | 1.00 | 32.26 | A |
| ATOM | 1042 | CG1 | VAL | A | 446 | 2.058 | 9.589 | 17.924 | 1.00 | 31.38 | A |
| ATOM | 1043 | CG2 | VAL | A | 446 | 2.837 | 10.959 | 16.003 | 1.00 | 31.45 | A |
| ATOM | 1044 | C | VAL | A | 446 | 5.708 | 10.223 | 16.740 | 1.00 | 31.10 | A |
| ATOM | 1045 | O | VAL | A | 446 | 6.327 | 9.224 | 16.350 | 1.00 | 31.32 | A |
| ATOM | 1046 | N | CYS | A | 447 | 6.038 | 11.465 | 16.387 | 1.00 | 29.94 | A |
| ATOM | 1047 | CA | CYS | A | 447 | 7.158 | 11.745 | 15.491 | 1.00 | 29.19 | A |
| ATOM | 1048 | CB | CYS | A | 447 | 7.145 | 13.212 | 15.054 | 1.00 | 30.16 | A |
| ATOM | 1049 | SG | CYS | A | 447 | 5.909 | 13.668 | 13.821 | 1.00 | 35.72 | A |
| ATOM | 1050 | C | CYS | A | 447 | 8.505 | 11.451 | 16.137 | 1.00 | 28.14 | A |
| ATOM | 1051 | O | CYS | A | 447 | 9.408 | 10.909 | 15.503 | 1.00 | 28.06 | A |
| ATOM | 1052 | N | LEU | A | 448 | 8.642 | 11.849 | 17.397 | 1.00 | 28.04 | A |
| ATOM | 1053 | CA | LEU | A | 448 | 9.872 | 11.641 | 18.153 | 1.00 | 26.80 | A |
| ATOM | 1054 | CB | LEU | A | 448 | 9.751 | 12.336 | 19.502 | 1.00 | 27.72 | A |
| ATOM | 1055 | CG | LEU | A | 448 | 9.598 | 13.851 | 19.398 | 1.00 | 28.44 | A |
| ATOM | 1056 | CD1 | LEU | A | 448 | 9.200 | 14.439 | 20.747 | 1.00 | 26.95 | A |
| ATOM | 1057 | CD2 | LEU | A | 448 | 10.908 | 14.442 | 18.877 | 1.00 | 28.40 | A |
| ATOM | 1058 | C | LEU | A | 448 | 10.137 | 10.146 | 18.347 | 1.00 | 26.72 | A |
| ATOM | 1059 | O | LEU | A | 448 | 11.270 | 9.673 | 18.185 | 1.00 | 26.08 | A |
| ATOM | 1060 | N | LYS | A | 449 | 9.079 | 9.410 | 18.688 | 1.00 | 25.26 | A |
| ATOM | 1061 | CA | LYS | A | 449 | 9.162 | 7.969 | 18.882 | 1.00 | 24.05 | A |
| ATOM | 1062 | CB | LYS | A | 449 | 7.756 | 7.440 | 19.173 | 1.00 | 26.01 | A |
| ATOM | 1063 | CG | LYS | A | 449 | 7.698 | 6.057 | 19.796 | 1.00 | 26.27 | A |
| ATOM | 1064 | CD | LYS | A | 449 | 6.516 | 5.946 | 20.741 | 1.00 | 26.00 | A |
| ATOM | 1065 | CE | LYS | A | 449 | 5.179 | 6.043 | 20.029 | 1.00 | 26.71 | A |
| ATOM | 1066 | NZ | LYS | A | 449 | 4.342 | 4.844 | 20.288 | 1.00 | 24.38 | A |
| ATOM | 1067 | C | LYS | A | 449 | 9.754 | 7.316 | 17.626 | 1.00 | 23.73 | A |
| ATOM | 1068 | O | LYS | A | 449 | 10.712 | 6.528 | 17.688 | 1.00 | 24.22 | A |
| ATOM | 1069 | N | SER | A | 450 | 9.195 | 7.670 | 16.479 | 1.00 | 23.25 | A |
| ATOM | 1070 | CA | SER | A | 450 | 9.666 | 7.146 | 15.208 | 1.00 | 23.25 | A |
| ATOM | 1071 | CB | SER | A | 450 | 8.735 | 7.605 | 14.082 | 1.00 | 24.72 | A |
| ATOM | 1072 | OG | SER | A | 450 | 7.426 | 7.090 | 14.299 | 1.00 | 26.69 | A |
| ATOM | 1073 | C | SER | A | 450 | 11.101 | 7.595 | 14.964 | 1.00 | 23.54 | A |
| ATOM | 1074 | O | SER | A | 450 | 11.939 | 6.795 | 14.537 | 1.00 | 22.78 | A |
| ATOM | 1075 | N | ILE | A | 451 | 11.398 | 8.865 | 15.221 | 1.00 | 23.38 | A |
| ATOM | 1076 | CA | ILE | A | 451 | 12.785 | 9.312 | 15.068 | 1.00 | 24.78 | A |
| ATOM | 1077 | CB | ILE | A | 451 | 13.004 | 10.760 | 15.583 | 1.00 | 26.04 | A |
| ATOM | 1078 | CG2 | ILE | A | 451 | 14.492 | 11.066 | 15.674 | 1.00 | 26.93 | A |
| ATOM | 1079 | CG1 | ILE | A | 451 | 12.335 | 11.759 | 14.643 | 1.00 | 27.01 | A |
| ATOM | 1080 | CD1 | ILE | A | 451 | 12.248 | 13.131 | 15.224 | 1.00 | 28.54 | A |
| ATOM | 1081 | C | ILE | A | 451 | 13.701 | 8.386 | 15.884 | 1.00 | 24.94 | A |
| ATOM | 1082 | O | ILE | A | 451 | 14.746 | 7.946 | 15.393 | 1.00 | 25.22 | A |
| ATOM | 1083 | N | ILE | A | 452 | 13.303 | 8.102 | 17.125 | 1.00 | 25.61 | A |
| ATOM | 1084 | CA | ILE | A | 452 | 14.078 | 7.239 | 18.023 | 1.00 | 27.38 | A |
| ATOM | 1085 | CB | ILE | A | 452 | 13.334 | 7.019 | 19.373 | 1.00 | 28.78 | A |
| ATOM | 1086 | CG2 | ILE | A | 452 | 13.953 | 5.862 | 20.145 | 1.00 | 28.54 | A |
| ATOM | 1087 | CG1 | ILE | A | 452 | 13.360 | 8.299 | 20.206 | 1.00 | 29.21 | A |
| ATOM | 1088 | CD1 | ILE | A | 452 | 12.557 | 8.208 | 21.503 | 1.00 | 29.11 | A |
| ATOM | 1089 | C | ILE | A | 452 | 14.343 | 5.882 | 17.396 | 1.00 | 28.71 | A |
| ATOM | 1090 | O | ILE | A | 452 | 15.461 | 5.384 | 17.433 | 1.00 | 28.82 | A |
| ATOM | 1091 | N | LEU | A | 453 | 13.295 | 5.291 | 16.825 | 1.00 | 31.75 | A |
| ATOM | 1092 | CA | LEU | A | 453 | 13.375 | 3.986 | 16.174 | 1.00 | 33.76 | A |
| ATOM | 1093 | CB | LEU | A | 453 | 12.003 | 3.603 | 15.619 | 1.00 | 33.90 | A |
| ATOM | 1094 | CG | LEU | A | 453 | 11.883 | 2.375 | 14.709 | 1.00 | 33.76 | A |
| ATOM | 1095 | CD1 | LEU | A | 453 | 12.368 | 1.098 | 15.438 | 1.00 | 30.54 | A |
| ATOM | 1096 | CD2 | LEU | A | 453 | 10.424 | 2.255 | 14.268 | 1.00 | 33.10 | A |
| ATOM | 1097 | C | LEU | A | 453 | 14.397 | 3.936 | 15.047 | 1.00 | 36.15 | A |
| ATOM | 1098 | O | LEU | A | 453 | 15.184 | 2.984 | 14.955 | 1.00 | 37.82 | A |
| ATOM | 1099 | N | LEU | A | 454 | 14.388 | 4.963 | 14.199 | 1.00 | 37.51 | A |
| ATOM | 1100 | CA | LEU | A | 454 | 15.304 | 5.036 | 13.066 | 1.00 | 39.03 | A |
| ATOM | 1101 | CB | LEU | A | 454 | 14.677 | 5.857 | 11.934 | 1.00 | 39.30 | A |
| ATOM | 1102 | CG | LEU | A | 454 | 13.289 | 5.430 | 11.451 | 1.00 | 39.56 | A |
| ATOM | 1103 | CD1 | LEU | A | 454 | 12.767 | 6.419 | 10.430 | 1.00 | 38.43 | A |
| ATOM | 1104 | CD2 | LEU | A | 454 | 13.362 | 4.041 | 10.863 | 1.00 | 39.16 | A |
| ATOM | 1105 | C | LEU | A | 454 | 16.675 | 5.612 | 13.390 | 1.00 | 40.67 | A |
| ATOM | 1106 | O | LEU | A | 454 | 17.634 | 5.331 | 12.677 | 1.00 | 40.93 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1107 | N | ASN | A | 455 | 16.785 | 6.403 | 14.457 | 1.00 | 42.96 | A |
| ATOM | 1108 | CA | ASN | A | 455 | 18.076 | 7.009 | 14.812 | 1.00 | 44.82 | A |
| ATOM | 1109 | CB | ASN | A | 455 | 17.863 | 8.413 | 15.374 | 1.00 | 44.46 | A |
| ATOM | 1110 | CG | ASN | A | 455 | 19.175 | 9.142 | 15.622 | 1.00 | 44.96 | A |
| ATOM | 1111 | OD1 | ASN | A | 455 | 19.560 | 9.383 | 16.766 | 1.00 | 43.23 | A |
| ATOM | 1112 | ND2 | ASN | A | 455 | 19.879 | 9.486 | 14.538 | 1.00 | 45.61 | A |
| ATOM | 1113 | C | ASN | A | 455 | 19.021 | 6.258 | 15.762 | 1.00 | 46.39 | A |
| ATOM | 1114 | O | ASN | A | 455 | 20.244 | 6.357 | 15.634 | 1.00 | 47.35 | A |
| ATOM | 1115 | N | SER | A | 456 | 18.482 | 5.513 | 16.717 | 1.00 | 47.89 | A |
| ATOM | 1116 | CA | SER | A | 456 | 19.339 | 4.817 | 17.673 | 1.00 | 49.27 | A |
| ATOM | 1117 | CB | SER | A | 456 | 18.483 | 4.248 | 18.809 | 1.00 | 49.26 | A |
| ATOM | 1118 | OG | SER | A | 456 | 17.748 | 5.282 | 19.447 | 1.00 | 47.80 | A |
| ATOM | 1119 | C | SER | A | 456 | 20.250 | 3.722 | 17.093 | 1.00 | 50.48 | A |
| ATOM | 1120 | O | SER | A | 456 | 21.281 | 3.397 | 17.686 | 1.00 | 50.87 | A |
| ATOM | 1121 | N | GLY | A | 457 | 19.888 | 3.172 | 15.937 | 1.00 | 51.29 | A |
| ATOM | 1122 | CA | GLY | A | 457 | 20.697 | 2.125 | 15.339 | 1.00 | 53.35 | A |
| ATOM | 1123 | C | GLY | A | 457 | 21.681 | 2.566 | 14.269 | 1.00 | 55.17 | A |
| ATOM | 1124 | O | GLY | A | 457 | 22.690 | 1.890 | 14.051 | 1.00 | 55.68 | A |
| ATOM | 1125 | N | VAL | A | 458 | 21.395 | 3.687 | 13.601 | 1.00 | 56.67 | A |
| ATOM | 1126 | CA | VAL | A | 458 | 22.265 | 4.211 | 12.543 | 1.00 | 57.94 | A |
| ATOM | 1127 | CB | VAL | A | 458 | 21.808 | 5.617 | 12.076 | 1.00 | 58.29 | A |
| ATOM | 1128 | CG1 | VAL | A | 458 | 20.411 | 5.550 | 11.486 | 1.00 | 58.32 | A |
| ATOM | 1129 | CG2 | VAL | A | 458 | 21.845 | 6.585 | 13.237 | 1.00 | 57.94 | A |
| ATOM | 1130 | C | VAL | A | 458 | 23.729 | 4.305 | 12.987 | 1.00 | 58.67 | A |
| ATOM | 1131 | O | VAL | A | 458 | 24.596 | 3.585 | 12.478 | 1.00 | 59.31 | A |
| ATOM | 1132 | N | LYS | A | 472 | 21.533 | 2.896 | 6.064 | 1.00 | 70.92 | A |
| ATOM | 1133 | CA | LYS | A | 472 | 21.667 | 3.331 | 4.679 | 1.00 | 70.54 | A |
| ATOM | 1134 | CB | LYS | A | 472 | 20.848 | 2.407 | 3.768 | 1.00 | 71.54 | A |
| ATOM | 1135 | CG | LYS | A | 472 | 19.365 | 2.327 | 4.123 | 1.00 | 72.43 | A |
| ATOM | 1136 | CD | LYS | A | 472 | 18.694 | 1.120 | 3.477 | 1.00 | 72.70 | A |
| ATOM | 1137 | CE | LYS | A | 472 | 19.213 | −0.191 | 4.068 | 1.00 | 73.50 | A |
| ATOM | 1138 | NZ | LYS | A | 472 | 18.487 | −1.396 | 3.551 | 1.00 | 73.14 | A |
| ATOM | 1139 | C | LYS | A | 472 | 21.234 | 4.789 | 4.492 | 1.00 | 69.91 | A |
| ATOM | 1140 | O | LYS | A | 472 | 20.985 | 5.507 | 5.464 | 1.00 | 69.78 | A |
| ATOM | 1141 | N | ASP | A | 473 | 21.159 | 5.223 | 3.236 | 1.00 | 68.76 | A |
| ATOM | 1142 | CA | ASP | A | 473 | 20.762 | 6.590 | 2.921 | 1.00 | 67.33 | A |
| ATOM | 1143 | CB | ASP | A | 473 | 21.243 | 6.957 | 1.512 | 1.00 | 68.51 | A |
| ATOM | 1144 | CG | ASP | A | 473 | 20.981 | 8.415 | 1.161 | 1.00 | 69.63 | A |
| ATOM | 1145 | OD1 | ASP | A | 473 | 21.399 | 9.302 | 1.937 | 1.00 | 70.55 | A |
| ATOM | 1146 | OD2 | ASP | A | 473 | 20.361 | 8.678 | 0.109 | 1.00 | 69.65 | A |
| ATOM | 1147 | C | ASP | A | 473 | 19.243 | 6.736 | 3.020 | 1.00 | 65.58 | A |
| ATOM | 1148 | O | ASP | A | 473 | 18.716 | 7.820 | 3.273 | 1.00 | 64.74 | A |
| ATOM | 1149 | N | HIS | A | 474 | 18.546 | 5.624 | 2.828 | 1.00 | 63.93 | A |
| ATOM | 1150 | CA | HIS | A | 474 | 17.092 | 5.607 | 2.888 | 1.00 | 62.21 | A |
| ATOM | 1151 | CB | HIS | A | 474 | 16.584 | 4.184 | 2.614 | 1.00 | 63.18 | A |
| ATOM | 1152 | CG | HIS | A | 474 | 15.091 | 4.063 | 2.616 | 1.00 | 64.38 | A |
| ATOM | 1153 | CD2 | HIS | A | 474 | 14.160 | 4.511 | 1.740 | 1.00 | 64.68 | A |
| ATOM | 1154 | ND1 | HIS | A | 474 | 14.394 | 3.445 | 3.633 | 1.00 | 64.68 | A |
| ATOM | 1155 | CE1 | HIS | A | 474 | 13.098 | 3.520 | 3.385 | 1.00 | 65.34 | A |
| ATOM | 1156 | NE2 | HIS | A | 474 | 12.929 | 4.163 | 2.242 | 1.00 | 65.46 | A |
| ATOM | 1157 | C | HIS | A | 474 | 16.593 | 6.100 | 4.244 | 1.00 | 60.35 | A |
| ATOM | 1158 | O | HIS | A | 474 | 15.719 | 6.967 | 4.324 | 1.00 | 59.40 | A |
| ATOM | 1159 | N | ILE | A | 475 | 17.163 | 5.544 | 5.307 | 1.00 | 58.62 | A |
| ATOM | 1160 | CA | ILE | A | 475 | 16.790 | 5.917 | 6.659 | 1.00 | 57.04 | A |
| ATOM | 1161 | CB | ILE | A | 475 | 17.658 | 5.181 | 7.703 | 1.00 | 57.65 | A |
| ATOM | 1162 | CG2 | ILE | A | 475 | 17.333 | 5.678 | 9.112 | 1.00 | 57.10 | A |
| ATOM | 1163 | CG1 | ILE | A | 475 | 17.391 | 3.678 | 7.615 | 1.00 | 58.13 | A |
| ATOM | 1164 | CD1 | ILE | A | 475 | 18.180 | 2.858 | 8.606 | 1.00 | 58.49 | A |
| ATOM | 1165 | C | ILE | A | 475 | 16.909 | 7.419 | 6.877 | 1.00 | 55.87 | A |
| ATOM | 1166 | O | ILE | A | 475 | 16.059 | 8.025 | 7.540 | 1.00 | 55.65 | A |
| ATOM | 1167 | N | HIS | A | 476 | 17.955 | 8.023 | 6.321 | 1.00 | 54.09 | A |
| ATOM | 1168 | CA | HIS | A | 476 | 18.138 | 9.459 | 6.478 | 1.00 | 52.36 | A |
| ATOM | 1169 | CB | HIS | A | 476 | 19.472 | 9.915 | 5.886 | 1.00 | 54.53 | A |
| ATOM | 1170 | CG | HIS | A | 476 | 20.637 | 9.659 | 6.787 | 1.00 | 57.03 | A |
| ATOM | 1171 | CD2 | HIS | A | 476 | 21.195 | 10.425 | 7.756 | 1.00 | 57.77 | A |
| ATOM | 1172 | ND1 | HIS | A | 476 | 21.307 | 8.453 | 6.819 | 1.00 | 57.99 | A |
| ATOM | 1173 | CE1 | HIS | A | 476 | 22.223 | 8.486 | 7.770 | 1.00 | 57.86 | A |
| ATOM | 1174 | NE2 | HIS | A | 476 | 22.175 | 9.670 | 8.354 | 1.00 | 58.34 | A |
| ATOM | 1175 | C | HIS | A | 476 | 17.004 | 10.228 | 5.843 | 1.00 | 50.17 | A |
| ATOM | 1176 | O | HIS | A | 476 | 16.511 | 11.201 | 6.418 | 1.00 | 49.50 | A |
| ATOM | 1177 | N | ARG | A | 477 | 16.586 | 9.781 | 4.662 | 1.00 | 47.83 | A |
| ATOM | 1178 | CA | ARG | A | 477 | 15.502 | 10.435 | 3.952 | 1.00 | 45.66 | A |
| ATOM | 1179 | CB | ARG | A | 477 | 15.290 | 9.783 | 2.583 | 1.00 | 48.56 | A |
| ATOM | 1180 | CG | ARG | A | 477 | 16.499 | 9.830 | 1.638 | 1.00 | 51.33 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1181 | CD | ARG | A | 477 | 16.176 | 9.120 | 0.307 | 1.00 | 55.48 | A |
| ATOM | 1182 | NE | ARG | A | 477 | 17.060 | 7.983 | 0.011 | 1.00 | 57.79 | A |
| ATOM | 1183 | CZ | ARG | A | 477 | 16.638 | 6.761 | −0.332 | 1.00 | 58.62 | A |
| ATOM | 1184 | NH1 | ARG | A | 477 | 15.339 | 6.495 | −0.422 | 1.00 | 58.70 | A |
| ATOM | 1185 | NH2 | ARG | A | 477 | 17.518 | 5.798 | −0.599 | 1.00 | 58.81 | A |
| ATOM | 1186 | C | ARG | A | 477 | 14.219 | 10.370 | 4.777 | 1.00 | 43.07 | A |
| ATOM | 1187 | O | ARG | A | 477 | 13.466 | 11.350 | 4.849 | 1.00 | 42.24 | A |
| ATOM | 1188 | N | VAL | A | 478 | 13.965 | 9.228 | 5.412 | 1.00 | 40.23 | A |
| ATOM | 1189 | CA | VAL | A | 478 | 12.759 | 9.111 | 6.228 | 1.00 | 38.22 | A |
| ATOM | 1190 | CB | VAL | A | 478 | 12.552 | 7.672 | 6.774 | 1.00 | 39.19 | A |
| ATOM | 1191 | CG1 | VAL | A | 478 | 11.159 | 7.559 | 7.438 | 1.00 | 37.61 | A |
| ATOM | 1192 | CG2 | VAL | A | 478 | 12.677 | 6.662 | 5.637 | 1.00 | 39.40 | A |
| ATOM | 1193 | C | VAL | A | 478 | 12.869 | 10.092 | 7.393 | 1.00 | 36.46 | A |
| ATOM | 1194 | O | VAL | A | 478 | 11.944 | 10.860 | 7.656 | 1.00 | 34.35 | A |
| ATOM | 1195 | N | LEU | A | 479 | 14.014 | 10.064 | 8.077 | 1.00 | 36.24 | A |
| ATOM | 1196 | CA | LEU | A | 479 | 14.293 | 10.971 | 9.196 | 1.00 | 34.49 | A |
| ATOM | 1197 | CB | LEU | A | 479 | 15.731 | 10.770 | 9.686 | 1.00 | 34.42 | A |
| ATOM | 1198 | CG | LEU | A | 479 | 15.897 | 9.579 | 10.648 | 1.00 | 34.33 | A |
| ATOM | 1199 | CD1 | LEU | A | 479 | 17.350 | 9.192 | 10.755 | 1.00 | 32.66 | A |
| ATOM | 1200 | CD2 | LEU | A | 479 | 15.310 | 9.919 | 12.020 | 1.00 | 32.48 | A |
| ATOM | 1201 | C | LEU | A | 479 | 14.074 | 12.420 | 8.776 | 1.00 | 34.03 | A |
| ATOM | 1202 | O | LEU | A | 479 | 13.434 | 13.194 | 9.482 | 1.00 | 32.51 | A |
| ATOM | 1203 | N | ASP | A | 480 | 14.596 | 12.776 | 7.608 | 1.00 | 35.91 | A |
| ATOM | 1204 | CA | ASP | A | 480 | 14.435 | 14.130 | 7.070 | 1.00 | 36.89 | A |
| ATOM | 1205 | CB | ASP | A | 480 | 15.185 | 14.266 | 5.748 | 1.00 | 36.47 | A |
| ATOM | 1206 | CG | ASP | A | 480 | 16.662 | 14.476 | 5.946 | 1.00 | 37.42 | A |
| ATOM | 1207 | OD1 | ASP | A | 480 | 17.057 | 14.806 | 7.088 | 1.00 | 36.66 | A |
| ATOM | 1208 | OD2 | ASP | A | 480 | 17.423 | 14.333 | 4.962 | 1.00 | 38.01 | A |
| ATOM | 1209 | C | ASP | A | 480 | 12.962 | 14.462 | 6.854 | 1.00 | 37.45 | A |
| ATOM | 1210 | O | ASP | A | 480 | 12.510 | 15.582 | 7.101 | 1.00 | 36.92 | A |
| ATOM | 1211 | N | LYS | A | 481 | 12.216 | 13.468 | 6.395 | 1.00 | 38.92 | A |
| ATOM | 1212 | CA | LYS | A | 481 | 10.799 | 13.632 | 6.158 | 1.00 | 40.39 | A |
| ATOM | 1213 | CB | LYS | A | 481 | 10.265 | 12.390 | 5.450 | 1.00 | 44.21 | A |
| ATOM | 1214 | CG | LYS | A | 481 | 8.823 | 12.497 | 5.024 | 1.00 | 51.50 | A |
| ATOM | 1215 | CD | LYS | A | 481 | 8.234 | 11.107 | 4.861 | 1.00 | 57.14 | A |
| ATOM | 1216 | CE | LYS | A | 481 | 6.703 | 11.145 | 4.844 | 1.00 | 61.09 | A |
| ATOM | 1217 | NZ | LYS | A | 481 | 6.097 | 9.814 | 5.199 | 1.00 | 62.76 | A |
| ATOM | 1218 | C | LYS | A | 481 | 10.098 | 13.854 | 7.507 | 1.00 | 39.34 | A |
| ATOM | 1219 | O | LYS | A | 481 | 9.158 | 14.652 | 7.607 | 1.00 | 37.53 | A |
| ATOM | 1220 | N | ILE | A | 482 | 10.554 | 13.158 | 8.553 | 1.00 | 38.87 | A |
| ATOM | 1221 | CA | ILE | A | 482 | 9.950 | 13.353 | 9.878 | 1.00 | 37.73 | A |
| ATOM | 1222 | CB | ILE | A | 482 | 10.430 | 12.303 | 10.912 | 1.00 | 38.22 | A |
| ATOM | 1223 | CG2 | ILE | A | 482 | 9.776 | 12.575 | 12.270 | 1.00 | 38.55 | A |
| ATOM | 1224 | CG1 | ILE | A | 482 | 10.021 | 10.897 | 10.466 | 1.00 | 38.51 | A |
| ATOM | 1225 | CD1 | ILE | A | 482 | 10.563 | 9.764 | 11.352 | 1.00 | 37.02 | A |
| ATOM | 1226 | C | ILE | A | 482 | 10.281 | 14.763 | 10.389 | 1.00 | 36.14 | A |
| ATOM | 1227 | O | ILE | A | 482 | 9.459 | 15.388 | 11.045 | 1.00 | 33.91 | A |
| ATOM | 1228 | N | THR | A | 483 | 11.486 | 15.249 | 10.082 | 1.00 | 35.64 | A |
| ATOM | 1229 | CA | THR | A | 483 | 11.885 | 16.602 | 10.477 | 1.00 | 36.18 | A |
| ATOM | 1230 | CB | THR | A | 483 | 13.324 | 16.952 | 10.008 | 1.00 | 36.19 | A |
| ATOM | 1231 | OG1 | THR | A | 483 | 14.259 | 16.063 | 10.617 | 1.00 | 36.01 | A |
| ATOM | 1232 | CG2 | THR | A | 483 | 13.688 | 18.387 | 10.394 | 1.00 | 35.80 | A |
| ATOM | 1233 | C | THR | A | 483 | 10.909 | 17.582 | 9.811 | 1.00 | 36.59 | A |
| ATOM | 1234 | O | THR | A | 483 | 10.408 | 18.522 | 10.449 | 1.00 | 36.56 | A |
| ATOM | 1235 | N | ASP | A | 484 | 10.642 | 17.360 | 8.526 | 1.00 | 36.62 | A |
| ATOM | 1236 | CA | ASP | A | 484 | 9.704 | 18.218 | 7.802 | 1.00 | 37.90 | A |
| ATOM | 1237 | CB | ASP | A | 484 | 9.557 | 17.772 | 6.346 | 1.00 | 37.84 | A |
| ATOM | 1238 | CG | ASP | A | 484 | 10.852 | 17.853 | 5.574 | 1.00 | 39.60 | A |
| ATOM | 1239 | OD1 | ASP | A | 484 | 11.746 | 18.648 | 5.954 | 1.00 | 41.28 | A |
| ATOM | 1240 | OD2 | ASP | A | 484 | 10.967 | 17.127 | 4.567 | 1.00 | 39.80 | A |
| ATOM | 1241 | C | ASP | A | 484 | 8.328 | 18.177 | 8.468 | 1.00 | 37.62 | A |
| ATOM | 1242 | O | ASP | A | 484 | 7.672 | 19.208 | 8.630 | 1.00 | 38.25 | A |
| ATOM | 1243 | N | THR | A | 485 | 7.893 | 16.983 | 8.858 | 1.00 | 37.35 | A |
| ATOM | 1244 | CA | THR | A | 485 | 6.592 | 16.844 | 9.503 | 1.00 | 37.94 | A |
| ATOM | 1245 | CB | THR | A | 485 | 6.271 | 15.378 | 9.886 | 1.00 | 37.24 | A |
| ATOM | 1246 | OG1 | THR | A | 485 | 6.425 | 14.521 | 8.749 | 1.00 | 38.12 | A |
| ATOM | 1247 | CG2 | THR | A | 485 | 4.853 | 15.279 | 10.384 | 1.00 | 35.56 | A |
| ATOM | 1248 | C | THR | A | 485 | 6.544 | 17.673 | 10.780 | 1.00 | 38.11 | A |
| ATOM | 1249 | O | THR | A | 485 | 5.632 | 18.480 | 10.970 | 1.00 | 39.44 | A |
| ATOM | 1250 | N | LEU | A | 486 | 7.516 | 17.460 | 11.662 | 1.00 | 37.24 | A |
| ATOM | 1251 | CA | LEU | A | 486 | 7.569 | 18.203 | 12.912 | 1.00 | 37.86 | A |
| ATOM | 1252 | CB | LEU | A | 486 | 8.870 | 17.885 | 13.653 | 1.00 | 37.14 | A |
| ATOM | 1253 | CG | LEU | A | 486 | 8.703 | 16.611 | 14.495 | 1.00 | 38.18 | A |
| ATOM | 1254 | CD1 | LEU | A | 486 | 10.073 | 16.007 | 14.841 | 1.00 | 37.49 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1255 | CD2 | LEU | A | 486 | 7.870 | 16.935 | 15.750 | 1.00 | 34.45 | A |
| ATOM | 1256 | C | LEU | A | 486 | 7.413 | 19.713 | 12.717 | 1.00 | 37.50 | A |
| ATOM | 1257 | O | LEU | A | 486 | 6.600 | 20.345 | 13.385 | 1.00 | 35.77 | A |
| ATOM | 1258 | N | ILE | A | 487 | 8.191 | 20.281 | 11.800 | 1.00 | 38.73 | A |
| ATOM | 1259 | CA | ILE | A | 487 | 8.115 | 21.707 | 11.516 | 1.00 | 40.31 | A |
| ATOM | 1260 | CB | ILE | A | 487 | 9.133 | 22.105 | 10.446 | 1.00 | 40.47 | A |
| ATOM | 1261 | CG2 | ILE | A | 487 | 8.869 | 23.536 | 9.999 | 1.00 | 40.04 | A |
| ATOM | 1262 | CG1 | ILE | A | 487 | 10.554 | 21.953 | 10.991 | 1.00 | 39.70 | A |
| ATOM | 1263 | CD1 | ILE | A | 487 | 10.923 | 22.999 | 12.019 | 1.00 | 38.92 | A |
| ATOM | 1264 | C | ILE | A | 487 | 6.718 | 22.117 | 11.033 | 1.00 | 41.58 | A |
| ATOM | 1265 | O | ILE | A | 487 | 6.155 | 23.123 | 11.498 | 1.00 | 41.49 | A |
| ATOM | 1266 | N | HIS | A | 488 | 6.166 | 21.344 | 10.101 | 1.00 | 42.46 | A |
| ATOM | 1267 | CA | HIS | A | 488 | 4.831 | 21.629 | 9.564 | 1.00 | 44.34 | A |
| ATOM | 1268 | CB | HIS | A | 488 | 4.370 | 20.508 | 8.617 | 1.00 | 46.82 | A |
| ATOM | 1269 | CG | HIS | A | 488 | 2.921 | 20.599 | 8.231 | 1.00 | 48.49 | A |
| ATOM | 1270 | CD2 | HIS | A | 488 | 1.831 | 19.940 | 8.697 | 1.00 | 48.75 | A |
| ATOM | 1271 | ND1 | HIS | A | 488 | 2.451 | 21.490 | 7.289 | 1.00 | 48.98 | A |
| ATOM | 1272 | CE1 | HIS | A | 488 | 1.137 | 21.377 | 7.193 | 1.00 | 48.58 | A |
| ATOM | 1273 | NE2 | HIS | A | 488 | 0.737 | 20.444 | 8.037 | 1.00 | 49.03 | A |
| ATOM | 1274 | C | HIS | A | 488 | 3.817 | 21.765 | 10.687 | 1.00 | 44.07 | A |
| ATOM | 1275 | O | HIS | A | 488 | 2.988 | 22.680 | 10.685 | 1.00 | 43.35 | A |
| ATOM | 1276 | N | LEU | A | 489 | 3.880 | 20.828 | 11.630 | 1.00 | 44.69 | A |
| ATOM | 1277 | CA | LEU | A | 489 | 2.979 | 20.812 | 12.772 | 1.00 | 45.27 | A |
| ATOM | 1278 | CB | LEU | A | 489 | 3.233 | 19.569 | 13.628 | 1.00 | 45.44 | A |
| ATOM | 1279 | CG | LEU | A | 489 | 3.126 | 18.187 | 12.976 | 1.00 | 46.69 | A |
| ATOM | 1280 | CD1 | LEU | A | 489 | 3.614 | 17.136 | 13.967 | 1.00 | 45.99 | A |
| ATOM | 1281 | CD2 | LEU | A | 489 | 1.682 | 17.902 | 12.561 | 1.00 | 45.94 | A |
| ATOM | 1282 | C | LEU | A | 489 | 3.224 | 22.060 | 13.606 | 1.00 | 45.79 | A |
| ATOM | 1283 | O | LEU | A | 489 | 2.333 | 22.532 | 14.313 | 1.00 | 45.11 | A |
| ATOM | 1284 | N | MET | A | 490 | 4.441 | 22.590 | 13.522 | 1.00 | 46.48 | A |
| ATOM | 1285 | CA | MET | A | 490 | 4.792 | 23.781 | 14.281 | 1.00 | 48.17 | A |
| ATOM | 1286 | CB | MET | A | 490 | 6.297 | 23.809 | 14.543 | 1.00 | 47.11 | A |
| ATOM | 1287 | CG | MET | A | 490 | 6.688 | 22.846 | 15.662 | 1.00 | 46.60 | A |
| ATOM | 1288 | SD | MET | A | 490 | 8.447 | 22.736 | 15.997 | 1.00 | 46.28 | A |
| ATOM | 1289 | CE | MET | A | 490 | 8.713 | 20.972 | 15.879 | 1.00 | 44.76 | A |
| ATOM | 1290 | C | MET | A | 490 | 4.319 | 25.039 | 13.577 | 1.00 | 48.76 | A |
| ATOM | 1291 | O | MET | A | 490 | 3.798 | 25.955 | 14.215 | 1.00 | 48.18 | A |
| ATOM | 1292 | N | ALA | A | 491 | 4.490 | 25.071 | 12.260 | 1.00 | 50.24 | A |
| ATOM | 1293 | CA | ALA | A | 491 | 4.032 | 26.196 | 11.458 | 1.00 | 51.14 | A |
| ATOM | 1294 | CB | ALA | A | 491 | 4.350 | 25.953 | 9.994 | 1.00 | 50.89 | A |
| ATOM | 1295 | C | ALA | A | 491 | 2.522 | 26.293 | 11.664 | 1.00 | 52.62 | A |
| ATOM | 1296 | O | ALA | A | 491 | 2.001 | 27.347 | 12.034 | 1.00 | 52.86 | A |
| ATOM | 1297 | N | LYS | A | 492 | 1.819 | 25.185 | 11.441 | 1.00 | 54.07 | A |
| ATOM | 1298 | CA | LYS | A | 492 | 0.373 | 25.169 | 11.623 | 1.00 | 56.12 | A |
| ATOM | 1299 | CB | LYS | A | 492 | −0.216 | 23.823 | 11.195 | 1.00 | 57.09 | A |
| ATOM | 1300 | CG | LYS | A | 492 | −0.801 | 23.823 | 9.792 | 1.00 | 58.75 | A |
| ATOM | 1301 | CD | LYS | A | 492 | −1.985 | 24.787 | 9.688 | 1.00 | 60.42 | A |
| ATOM | 1302 | CE | LYS | A | 492 | −1.704 | 25.927 | 8.713 | 1.00 | 62.09 | A |
| ATOM | 1303 | NZ | LYS | A | 492 | −2.879 | 26.832 | 8.550 | 1.00 | 62.87 | A |
| ATOM | 1304 | C | LYS | A | 492 | −0.050 | 25.468 | 13.056 | 1.00 | 56.65 | A |
| ATOM | 1305 | O | LYS | A | 492 | −1.151 | 25.956 | 13.287 | 1.00 | 58.00 | A |
| ATOM | 1306 | N | ALA | A | 493 | 0.816 | 25.179 | 14.019 | 1.00 | 57.18 | A |
| ATOM | 1307 | CA | ALA | A | 493 | 0.494 | 25.421 | 15.421 | 1.00 | 57.64 | A |
| ATOM | 1308 | CB | ALA | A | 493 | 1.559 | 24.798 | 16.330 | 1.00 | 58.12 | A |
| ATOM | 1309 | C | ALA | A | 493 | 0.409 | 26.932 | 15.668 | 1.00 | 58.06 | A |
| ATOM | 1310 | O | ALA | A | 493 | −0.359 | 27.393 | 16.510 | 1.00 | 57.43 | A |
| ATOM | 1311 | N | GLY | A | 494 | 1.205 | 27.691 | 14.923 | 1.00 | 58.65 | A |
| ATOM | 1312 | CA | GLY | A | 494 | 1.198 | 29.133 | 15.078 | 1.00 | 60.09 | A |
| ATOM | 1313 | C | GLY | A | 494 | 2.492 | 29.685 | 15.645 | 1.00 | 60.47 | A |
| ATOM | 1314 | O | GLY | A | 494 | 2.486 | 30.638 | 16.425 | 1.00 | 60.76 | A |
| ATOM | 1315 | N | LEU | A | 495 | 3.610 | 29.082 | 15.261 | 1.00 | 60.50 | A |
| ATOM | 1316 | CA | LEU | A | 495 | 4.910 | 29.529 | 15.739 | 1.00 | 60.17 | A |
| ATOM | 1317 | CB | LEU | A | 495 | 5.742 | 28.339 | 16.227 | 1.00 | 60.22 | A |
| ATOM | 1318 | CG | LEU | A | 495 | 5.367 | 27.694 | 17.560 | 1.00 | 60.65 | A |
| ATOM | 1319 | CD1 | LEU | A | 495 | 3.949 | 27.142 | 17.514 | 1.00 | 60.64 | A |
| ATOM | 1320 | CD2 | LEU | A | 495 | 6.369 | 26.591 | 17.857 | 1.00 | 61.35 | A |
| ATOM | 1321 | C | LEU | A | 495 | 5.637 | 30.217 | 14.599 | 1.00 | 59.99 | A |
| ATOM | 1322 | O | LEU | A | 495 | 5.359 | 29.940 | 13.433 | 1.00 | 60.09 | A |
| ATOM | 1323 | N | THR | A | 496 | 6.567 | 31.106 | 14.934 | 1.00 | 59.24 | A |
| ATOM | 1324 | CA | THR | A | 496 | 7.327 | 31.808 | 13.910 | 1.00 | 58.70 | A |
| ATOM | 1325 | CB | THR | A | 496 | 8.027 | 33.060 | 14.471 | 1.00 | 58.50 | A |
| ATOM | 1326 | OG1 | THR | A | 496 | 9.066 | 32.667 | 15.374 | 1.00 | 58.45 | A |
| ATOM | 1327 | CG2 | THR | A | 496 | 7.031 | 33.931 | 15.215 | 1.00 | 58.59 | A |
| ATOM | 1328 | C | THR | A | 496 | 8.381 | 30.855 | 13.394 | 1.00 | 58.40 | A |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 1329 | O | THR | A | 496 | 8.649 | 29.829 | 14.012 | 1.00 | 58.80 | A |
| ATOM | 1330 | N | LEU | A | 497 | 8.979 | 31.188 | 12.261 | 1.00 | 58.16 | A |
| ATOM | 1331 | CA | LEU | A | 497 | 10.009 | 30.338 | 11.697 | 1.00 | 58.16 | A |
| ATOM | 1332 | CB | LEU | A | 497 | 10.471 | 30.910 | 10.361 | 1.00 | 58.56 | A |
| ATOM | 1333 | CG | LEU | A | 497 | 9.714 | 30.326 | 9.172 | 1.00 | 59.36 | A |
| ATOM | 1334 | CD1 | LEU | A | 497 | 9.796 | 31.269 | 7.988 | 1.00 | 60.11 | A |
| ATOM | 1335 | CD2 | LEU | A | 497 | 10.300 | 28.955 | 8.834 | 1.00 | 60.27 | A |
| ATOM | 1336 | C | LEU | A | 497 | 11.186 | 30.179 | 12.657 | 1.00 | 58.25 | A |
| ATOM | 1337 | O | LEU | A | 497 | 12.013 | 29.277 | 12.492 | 1.00 | 57.58 | A |
| ATOM | 1338 | N | GLN | A | 498 | 11.251 | 31.052 | 13.663 | 1.00 | 57.99 | A |
| ATOM | 1339 | CA | GLN | A | 498 | 12.317 | 30.996 | 14.658 | 1.00 | 57.92 | A |
| ATOM | 1340 | CB | GLN | A | 498 | 12.638 | 32.387 | 15.205 | 1.00 | 58.69 | A |
| ATOM | 1341 | CG | GLN | A | 498 | 13.789 | 32.359 | 16.192 | 1.00 | 60.60 | A |
| ATOM | 1342 | CD | GLN | A | 498 | 14.092 | 33.712 | 16.776 | 1.00 | 61.78 | A |
| ATOM | 1343 | OE1 | GLN | A | 498 | 13.249 | 34.314 | 17.446 | 1.00 | 62.15 | A |
| ATOM | 1344 | NE2 | GLN | A | 498 | 15.304 | 34.205 | 16.530 | 1.00 | 62.42 | A |
| ATOM | 1345 | C | GLN | A | 498 | 11.899 | 30.097 | 15.812 | 1.00 | 57.17 | A |
| ATOM | 1346 | O | GLN | A | 498 | 12.685 | 29.283 | 16.303 | 1.00 | 56.73 | A |
| ATOM | 1347 | N | GLN | A | 499 | 10.656 | 30.263 | 16.245 | 1.00 | 56.36 | A |
| ATOM | 1348 | CA | GLN | A | 499 | 10.111 | 29.460 | 17.327 | 1.00 | 55.95 | A |
| ATOM | 1349 | CB | GLN | A | 499 | 8.714 | 29.950 | 17.688 | 1.00 | 56.43 | A |
| ATOM | 1350 | CG | GLN | A | 499 | 8.662 | 31.415 | 18.039 | 1.00 | 57.61 | A |
| ATOM | 1351 | CD | GLN | A | 499 | 7.256 | 31.882 | 18.310 | 1.00 | 58.62 | A |
| ATOM | 1352 | OE1 | GLN | A | 499 | 6.360 | 31.705 | 17.477 | 1.00 | 59.17 | A |
| ATOM | 1353 | NE2 | GLN | A | 499 | 7.045 | 32.481 | 19.479 | 1.00 | 58.82 | A |
| ATOM | 1354 | C | GLN | A | 499 | 10.041 | 28.005 | 16.883 | 1.00 | 55.29 | A |
| ATOM | 1355 | O | GLN | A | 499 | 9.906 | 27.104 | 17.701 | 1.00 | 55.49 | A |
| ATOM | 1356 | N | GLN | A | 500 | 10.120 | 27.787 | 15.575 | 1.00 | 54.40 | A |
| ATOM | 1357 | CA | GLN | A | 500 | 10.078 | 26.442 | 15.019 | 1.00 | 53.56 | A |
| ATOM | 1358 | CB | GLN | A | 500 | 9.674 | 26.506 | 13.542 | 1.00 | 52.90 | A |
| ATOM | 1359 | CG | GLN | A | 500 | 8.215 | 26.897 | 13.353 | 1.00 | 52.43 | A |
| ATOM | 1360 | CD | GLN | A | 500 | 7.845 | 27.179 | 11.909 | 1.00 | 51.96 | A |
| ATOM | 1361 | OE1 | GLN | A | 500 | 8.246 | 26.455 | 11.000 | 1.00 | 51.45 | A |
| ATOM | 1362 | NE2 | GLN | A | 500 | 7.060 | 28.228 | 11.696 | 1.00 | 50.72 | A |
| ATOM | 1363 | C | GLN | A | 500 | 11.437 | 25.770 | 15.184 | 1.00 | 53.08 | A |
| ATOM | 1364 | O | GLN | A | 500 | 11.532 | 24.667 | 15.730 | 1.00 | 52.62 | A |
| ATOM | 1365 | N | HIS | A | 501 | 12.482 | 26.454 | 14.724 | 1.00 | 52.52 | A |
| ATOM | 1366 | CA | HIS | A | 501 | 13.853 | 25.958 | 14.814 | 1.00 | 52.57 | A |
| ATOM | 1367 | CB | HIS | A | 501 | 14.843 | 27.019 | 14.341 | 1.00 | 56.06 | A |
| ATOM | 1368 | CG | HIS | A | 501 | 14.593 | 27.509 | 12.952 | 1.00 | 60.04 | A |
| ATOM | 1369 | CD2 | HIS | A | 501 | 13.868 | 26.987 | 11.934 | 1.00 | 61.63 | A |
| ATOM | 1370 | ND1 | HIS | A | 501 | 15.140 | 28.681 | 12.474 | 1.00 | 61.31 | A |
| ATOM | 1371 | CE1 | HIS | A | 501 | 14.761 | 28.860 | 11.221 | 1.00 | 62.24 | A |
| ATOM | 1372 | NE2 | HIS | A | 501 | 13.988 | 27.848 | 10.869 | 1.00 | 62.57 | A |
| ATOM | 1373 | C | HIS | A | 501 | 14.213 | 25.615 | 16.247 | 1.00 | 50.20 | A |
| ATOM | 1374 | O | HIS | A | 501 | 14.872 | 24.618 | 16.509 | 1.00 | 50.52 | A |
| ATOM | 1375 | N | GLN | A | 502 | 13.785 | 26.466 | 17.168 | 1.00 | 47.18 | A |
| ATOM | 1376 | CA | GLN | A | 502 | 14.085 | 26.287 | 18.573 | 1.00 | 44.51 | A |
| ATOM | 1377 | CB | GLN | A | 502 | 13.772 | 27.579 | 19.328 | 1.00 | 45.24 | A |
| ATOM | 1378 | CG | GLN | A | 502 | 14.658 | 28.738 | 18.887 | 1.00 | 45.60 | A |
| ATOM | 1379 | CD | GLN | A | 502 | 14.400 | 30.008 | 19.669 | 1.00 | 46.77 | A |
| ATOM | 1380 | OE1 | GLN | A | 502 | 13.431 | 30.093 | 20.426 | 1.00 | 46.83 | A |
| ATOM | 1381 | NE2 | GLN | A | 502 | 15.265 | 31.012 | 19.482 | 1.00 | 45.99 | A |
| ATOM | 1382 | C | GLN | A | 502 | 13.402 | 25.100 | 19.225 | 1.00 | 42.05 | A |
| ATOM | 1383 | O | GLN | A | 502 | 14.070 | 24.285 | 19.865 | 1.00 | 41.89 | A |
| ATOM | 1384 | N | ARG | A | 503 | 12.085 | 25.002 | 19.062 | 1.00 | 39.88 | A |
| ATOM | 1385 | CA | ARG | A | 503 | 11.306 | 23.890 | 19.623 | 1.00 | 37.28 | A |
| ATOM | 1386 | CB | ARG | A | 503 | 9.820 | 24.072 | 19.327 | 1.00 | 35.56 | A |
| ATOM | 1387 | CG | ARG | A | 503 | 8.916 | 23.054 | 19.998 | 1.00 | 35.65 | A |
| ATOM | 1388 | CD | ARG | A | 503 | 7.471 | 23.430 | 19.773 | 1.00 | 34.83 | A |
| ATOM | 1389 | NE | ARG | A | 503 | 6.527 | 22.449 | 20.290 | 1.00 | 35.67 | A |
| ATOM | 1390 | CZ | ARG | A | 503 | 6.261 | 22.254 | 21.579 | 1.00 | 36.98 | A |
| ATOM | 1391 | NH1 | ARG | A | 503 | 6.867 | 22.976 | 22.511 | 1.00 | 34.69 | A |
| ATOM | 1392 | NH2 | ARG | A | 503 | 5.377 | 21.327 | 21.933 | 1.00 | 38.03 | A |
| ATOM | 1393 | C | ARG | A | 503 | 11.787 | 22.574 | 19.019 | 1.00 | 35.61 | A |
| ATOM | 1394 | O | ARG | A | 503 | 11.874 | 21.559 | 19.707 | 1.00 | 34.87 | A |
| ATOM | 1395 | N | LEU | A | 504 | 12.101 | 22.609 | 17.731 | 1.00 | 33.57 | A |
| ATOM | 1396 | CA | LEU | A | 504 | 12.600 | 21.437 | 17.042 | 1.00 | 34.01 | A |
| ATOM | 1397 | CB | LEU | A | 504 | 12.864 | 21.756 | 15.567 | 1.00 | 33.94 | A |
| ATOM | 1398 | CG | LEU | A | 504 | 13.673 | 20.650 | 14.877 | 1.00 | 35.08 | A |
| ATOM | 1399 | CD1 | LEU | A | 504 | 12.829 | 19.389 | 14.831 | 1.00 | 35.05 | A |
| ATOM | 1400 | CD2 | LEU | A | 504 | 14.104 | 21.071 | 13.482 | 1.00 | 34.60 | A |
| ATOM | 1401 | C | LEU | A | 504 | 13.902 | 20.972 | 17.707 | 1.00 | 34.85 | A |
| ATOM | 1402 | O | LEU | A | 504 | 14.107 | 19.776 | 17.931 | 1.00 | 34.22 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1403 | N | ALA | A | 505 | 14.784 | 21.930 | 18.004 | 1.00 | 35.45 | A |
| ATOM | 1404 | CA | ALA | A | 505 | 16.067 | 21.649 | 18.652 | 1.00 | 34.94 | A |
| ATOM | 1405 | CB | ALA | A | 505 | 16.975 | 22.869 | 18.574 | 1.00 | 35.44 | A |
| ATOM | 1406 | C | ALA | A | 505 | 15.853 | 21.252 | 20.112 | 1.00 | 34.54 | A |
| ATOM | 1407 | O | ALA | A | 505 | 16.496 | 20.336 | 20.617 | 1.00 | 33.56 | A |
| ATOM | 1408 | N | GLN | A | 506 | 14.944 | 21.947 | 20.787 | 1.00 | 34.64 | A |
| ATOM | 1409 | CA | GLN | A | 506 | 14.651 | 21.639 | 22.178 | 1.00 | 35.67 | A |
| ATOM | 1410 | CB | GLN | A | 506 | 13.485 | 22.497 | 22.678 | 1.00 | 36.61 | A |
| ATOM | 1411 | CG | GLN | A | 506 | 13.855 | 23.935 | 22.988 | 1.00 | 39.72 | A |
| ATOM | 1412 | CD | GLN | A | 506 | 12.667 | 24.896 | 22.941 | 1.00 | 40.98 | A |
| ATOM | 1413 | OE1 | GLN | A | 506 | 11.670 | 24.726 | 23.638 | 1.00 | 42.35 | A |
| ATOM | 1414 | NE2 | GLN | A | 506 | 12.786 | 25.923 | 22.118 | 1.00 | 43.46 | A |
| ATOM | 1415 | C | GLN | A | 506 | 14.286 | 20.163 | 22.281 | 1.00 | 35.96 | A |
| ATOM | 1416 | O | GLN | A | 506 | 14.851 | 19.445 | 23.102 | 1.00 | 37.12 | A |
| ATOM | 1417 | N | LEU | A | 507 | 13.353 | 19.733 | 21.424 | 1.00 | 34.11 | A |
| ATOM | 1418 | CA | LEU | A | 507 | 12.855 | 18.365 | 21.376 | 1.00 | 32.78 | A |
| ATOM | 1419 | CB | LEU | A | 507 | 11.725 | 18.249 | 20.336 | 1.00 | 33.40 | A |
| ATOM | 1420 | CG | LEU | A | 507 | 10.445 | 19.081 | 20.507 | 1.00 | 33.52 | A |
| ATOM | 1421 | CD1 | LEU | A | 507 | 9.503 | 18.790 | 19.353 | 1.00 | 32.94 | A |
| ATOM | 1422 | CD2 | LEU | A | 507 | 9.769 | 18.759 | 21.830 | 1.00 | 31.78 | A |
| ATOM | 1423 | C | LEU | A | 507 | 13.922 | 17.319 | 21.063 | 1.00 | 32.19 | A |
| ATOM | 1424 | O | LEU | A | 507 | 13.948 | 16.251 | 21.668 | 1.00 | 31.36 | A |
| ATOM | 1425 | N | LEU | A | 508 | 14.783 | 17.620 | 20.099 | 1.00 | 31.50 | A |
| ATOM | 1426 | CA | LEU | A | 508 | 15.841 | 16.699 | 19.714 | 1.00 | 30.98 | A |
| ATOM | 1427 | CB | LEU | A | 508 | 16.494 | 17.176 | 18.424 | 1.00 | 31.37 | A |
| ATOM | 1428 | CG | LEU | A | 508 | 15.595 | 17.167 | 17.194 | 1.00 | 30.80 | A |
| ATOM | 1429 | CD1 | LEU | A | 508 | 16.413 | 17.575 | 15.977 | 1.00 | 32.13 | A |
| ATOM | 1430 | CD2 | LEU | A | 508 | 15.004 | 15.786 | 17.004 | 1.00 | 30.79 | A |
| ATOM | 1431 | C | LEU | A | 508 | 16.909 | 16.525 | 20.798 | 1.00 | 31.08 | A |
| ATOM | 1432 | O | LEU | A | 508 | 17.489 | 15.446 | 20.939 | 1.00 | 30.07 | A |
| ATOM | 1433 | N | LEU | A | 509 | 17.171 | 17.586 | 21.553 | 1.00 | 31.22 | A |
| ATOM | 1434 | CA | LEU | A | 509 | 18.154 | 17.517 | 22.623 | 1.00 | 31.62 | A |
| ATOM | 1435 | CB | LEU | A | 509 | 18.437 | 18.900 | 23.220 | 1.00 | 32.12 | A |
| ATOM | 1436 | CG | LEU | A | 509 | 19.314 | 19.762 | 22.302 | 1.00 | 33.09 | A |
| ATOM | 1437 | CD1 | LEU | A | 509 | 19.622 | 21.098 | 22.968 | 1.00 | 32.07 | A |
| ATOM | 1438 | CD2 | LEU | A | 509 | 20.614 | 19.007 | 21.980 | 1.00 | 32.81 | A |
| ATOM | 1439 | C | LEU | A | 509 | 17.614 | 16.586 | 23.677 | 1.00 | 31.57 | A |
| ATOM | 1440 | O | LEU | A | 509 | 18.346 | 15.745 | 24.188 | 1.00 | 31.39 | A |
| ATOM | 1441 | N | ILE | A | 510 | 16.330 | 16.726 | 23.997 | 1.00 | 31.81 | A |
| ATOM | 1442 | CA | ILE | A | 510 | 15.720 | 15.831 | 24.972 | 1.00 | 31.66 | A |
| ATOM | 1443 | CB | ILE | A | 510 | 14.199 | 16.062 | 25.108 | 1.00 | 31.67 | A |
| ATOM | 1444 | CG2 | ILE | A | 510 | 13.616 | 15.079 | 26.102 | 1.00 | 33.01 | A |
| ATOM | 1445 | CG1 | ILE | A | 510 | 13.919 | 17.469 | 25.630 | 1.00 | 32.02 | A |
| ATOM | 1446 | CD1 | ILE | A | 510 | 12.441 | 17.729 | 25.896 | 1.00 | 32.34 | A |
| ATOM | 1447 | C | ILE | A | 510 | 15.966 | 14.367 | 24.581 | 1.00 | 31.64 | A |
| ATOM | 1448 | O | ILE | A | 510 | 16.143 | 13.522 | 25.447 | 1.00 | 32.29 | A |
| ATOM | 1449 | N | LEU | A | 511 | 15.996 | 14.063 | 23.286 | 1.00 | 31.61 | A |
| ATOM | 1450 | CA | LEU | A | 511 | 16.228 | 12.683 | 22.857 | 1.00 | 32.45 | A |
| ATOM | 1451 | CB | LEU | A | 511 | 16.163 | 12.549 | 21.322 | 1.00 | 31.85 | A |
| ATOM | 1452 | CG | LEU | A | 511 | 14.817 | 12.821 | 20.628 | 1.00 | 32.17 | A |
| ATOM | 1453 | CD1 | LEU | A | 511 | 14.858 | 12.220 | 19.229 | 1.00 | 30.66 | A |
| ATOM | 1454 | CD2 | LEU | A | 511 | 13.660 | 12.205 | 21.427 | 1.00 | 31.15 | A |
| ATOM | 1455 | C | LEU | A | 511 | 17.570 | 12.169 | 23.356 | 1.00 | 32.97 | A |
| ATOM | 1456 | O | LEU | A | 511 | 17.772 | 10.961 | 23.511 | 1.00 | 32.86 | A |
| ATOM | 1457 | N | SER | A | 512 | 18.486 | 13.095 | 23.608 | 1.00 | 33.06 | A |
| ATOM | 1458 | CA | SER | A | 512 | 19.810 | 12.750 | 24.098 | 1.00 | 32.97 | A |
| ATOM | 1459 | CB | SER | A | 512 | 20.735 | 13.965 | 23.973 | 1.00 | 34.51 | A |
| ATOM | 1460 | OG | SER | A | 512 | 22.057 | 13.570 | 23.645 | 1.00 | 38.55 | A |
| ATOM | 1461 | C | SER | A | 512 | 19.716 | 12.298 | 25.566 | 1.00 | 32.93 | A |
| ATOM | 1462 | O | SER | A | 512 | 20.445 | 11.414 | 26.000 | 1.00 | 31.86 | A |
| ATOM | 1463 | N | HIS | A | 513 | 18.817 | 12.913 | 26.324 | 1.00 | 33.43 | A |
| ATOM | 1464 | CA | HIS | A | 513 | 18.636 | 12.548 | 27.720 | 1.00 | 35.20 | A |
| ATOM | 1465 | CB | HIS | A | 513 | 17.768 | 13.581 | 28.416 | 1.00 | 38.21 | A |
| ATOM | 1466 | CG | HIS | A | 513 | 18.370 | 14.949 | 28.429 | 1.00 | 43.36 | A |
| ATOM | 1467 | CD2 | HIS | A | 513 | 19.659 | 15.356 | 28.335 | 1.00 | 44.91 | A |
| ATOM | 1468 | ND1 | HIS | A | 513 | 17.612 | 16.095 | 28.538 | 1.00 | 45.17 | A |
| ATOM | 1469 | CE1 | HIS | A | 513 | 18.407 | 17.149 | 28.506 | 1.00 | 46.68 | A |
| ATOM | 1470 | NE2 | HIS | A | 513 | 19.654 | 16.729 | 28.385 | 1.00 | 47.58 | A |
| ATOM | 1471 | C | HIS | A | 513 | 17.967 | 11.197 | 27.773 | 1.00 | 34.88 | A |
| ATOM | 1472 | O | HIS | A | 513 | 18.284 | 10.357 | 28.634 | 1.00 | 33.62 | A |
| ATOM | 1473 | N | ILE | A | 514 | 17.038 | 11.004 | 26.835 | 1.00 | 33.54 | A |
| ATOM | 1474 | CA | ILE | A | 514 | 16.299 | 9.760 | 26.726 | 1.00 | 32.44 | A |
| ATOM | 1475 | CB | ILE | A | 514 | 15.204 | 9.851 | 25.635 | 1.00 | 32.79 | A |
| ATOM | 1476 | CG2 | ILE | A | 514 | 14.642 | 8.456 | 25.334 | 1.00 | 31.89 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1477 | CG1 | ILE | A | 514 | 14.100 | 10.797 | 26.114 | 1.00 | 32.37 | A |
| ATOM | 1478 | CD1 | ILE | A | 514 | 13.070 | 11.152 | 25.065 | 1.00 | 33.21 | A |
| ATOM | 1479 | C | ILE | A | 514 | 17.268 | 8.636 | 26.410 | 1.00 | 31.73 | A |
| ATOM | 1480 | O | ILE | A | 514 | 17.176 | 7.554 | 26.984 | 1.00 | 32.39 | A |
| ATOM | 1481 | N | ARG | A | 515 | 18.201 | 8.897 | 25.501 | 1.00 | 31.00 | A |
| ATOM | 1482 | CA | ARG | A | 515 | 19.189 | 7.898 | 25.147 | 1.00 | 30.08 | A |
| ATOM | 1483 | CB | ARG | A | 515 | 20.108 | 8.418 | 24.051 | 1.00 | 29.87 | A |
| ATOM | 1484 | CG | ARG | A | 515 | 21.221 | 7.439 | 23.695 | 1.00 | 32.25 | A |
| ATOM | 1485 | CD | ARG | A | 515 | 20.699 | 6.271 | 22.843 | 1.00 | 34.85 | A |
| ATOM | 1486 | NE | ARG | A | 515 | 20.521 | 6.684 | 21.453 | 1.00 | 35.48 | A |
| ATOM | 1487 | CZ | ARG | A | 515 | 21.366 | 6.388 | 20.473 | 1.00 | 36.35 | A |
| ATOM | 1488 | NH1 | ARG | A | 515 | 22.445 | 5.659 | 20.723 | 1.00 | 36.83 | A |
| ATOM | 1489 | NH2 | ARG | A | 515 | 21.152 | 6.853 | 19.250 | 1.00 | 37.69 | A |
| ATOM | 1490 | C | ARG | A | 515 | 20.014 | 7.586 | 26.399 | 1.00 | 31.14 | A |
| ATOM | 1491 | O | ARG | A | 515 | 20.387 | 6.437 | 26.649 | 1.00 | 30.81 | A |
| ATOM | 1492 | N | HIS | A | 516 | 20.289 | 8.625 | 27.181 | 1.00 | 31.58 | A |
| ATOM | 1493 | CA | HIS | A | 516 | 21.066 | 8.503 | 28.414 | 1.00 | 32.44 | A |
| ATOM | 1494 | CB | HIS | A | 516 | 21.278 | 9.880 | 29.041 | 1.00 | 33.26 | A |
| ATOM | 1495 | CG | HIS | A | 516 | 22.158 | 9.867 | 30.253 | 1.00 | 33.65 | A |
| ATOM | 1496 | CD2 | HIS | A | 516 | 21.860 | 9.944 | 31.573 | 1.00 | 34.21 | A |
| ATOM | 1497 | ND1 | HIS | A | 516 | 23.529 | 9.756 | 30.177 | 1.00 | 33.16 | A |
| ATOM | 1498 | CE1 | HIS | A | 516 | 24.037 | 9.768 | 31.397 | 1.00 | 34.34 | A |
| ATOM | 1499 | NE2 | HIS | A | 516 | 23.045 | 9.880 | 32.263 | 1.00 | 33.86 | A |
| ATOM | 1500 | C | HIS | A | 516 | 20.355 | 7.596 | 29.414 | 1.00 | 32.21 | A |
| ATOM | 1501 | O | HIS | A | 516 | 20.950 | 6.647 | 29.927 | 1.00 | 31.80 | A |
| ATOM | 1502 | N | MET | A | 517 | 19.086 | 7.899 | 29.686 | 1.00 | 32.70 | A |
| ATOM | 1503 | CA | MET | A | 517 | 18.280 | 7.096 | 30.604 | 1.00 | 33.72 | A |
| ATOM | 1504 | CB | MET | A | 517 | 16.852 | 7.631 | 30.705 | 1.00 | 32.60 | A |
| ATOM | 1505 | CG | MET | A | 517 | 16.741 | 9.032 | 31.255 | 1.00 | 32.08 | A |
| ATOM | 1506 | SD | MET | A | 517 | 15.034 | 9.479 | 31.566 | 1.00 | 35.80 | A |
| ATOM | 1507 | CE | MET | A | 517 | 14.358 | 9.499 | 29.857 | 1.00 | 35.01 | A |
| ATOM | 1508 | C | MET | A | 517 | 18.221 | 5.647 | 30.153 | 1.00 | 35.20 | A |
| ATOM | 1509 | O | MET | A | 517 | 18.166 | 4.731 | 30.971 | 1.00 | 36.47 | A |
| ATOM | 1510 | N | SER | A | 518 | 18.223 | 5.435 | 28.846 | 1.00 | 36.91 | A |
| ATOM | 1511 | CA | SER | A | 518 | 18.174 | 4.077 | 28.326 | 1.00 | 37.98 | A |
| ATOM | 1512 | CB | SER | A | 518 | 17.967 | 4.081 | 26.805 | 1.00 | 36.05 | A |
| ATOM | 1513 | OG | SER | A | 518 | 18.114 | 2.784 | 26.264 | 1.00 | 31.22 | A |
| ATOM | 1514 | C | SER | A | 518 | 19.468 | 3.364 | 28.673 | 1.00 | 39.60 | A |
| ATOM | 1515 | O | SER | A | 518 | 19.453 | 2.212 | 29.071 | 1.00 | 40.68 | A |
| ATOM | 1516 | N | ASN | A | 519 | 20.591 | 4.053 | 28.523 | 1.00 | 42.33 | A |
| ATOM | 1517 | CA | ASN | A | 519 | 21.879 | 3.457 | 28.829 | 1.00 | 45.21 | A |
| ATOM | 1518 | CB | ASN | A | 519 | 22.993 | 4.396 | 28.387 | 1.00 | 45.62 | A |
| ATOM | 1519 | CG | ASN | A | 519 | 23.143 | 4.440 | 26.873 | 1.00 | 46.64 | A |
| ATOM | 1520 | OD1 | ASN | A | 519 | 23.594 | 5.436 | 26.313 | 1.00 | 47.58 | A |
| ATOM | 1521 | ND2 | ASN | A | 519 | 22.773 | 3.350 | 26.207 | 1.00 | 47.26 | A |
| ATOM | 1522 | C | ASN | A | 519 | 21.987 | 3.131 | 30.311 | 1.00 | 47.72 | A |
| ATOM | 1523 | O | ASN | A | 519 | 22.540 | 2.101 | 30.685 | 1.00 | 47.22 | A |
| ATOM | 1524 | N | LYS | A | 520 | 21.459 | 4.004 | 31.163 | 1.00 | 51.68 | A |
| ATOM | 1525 | CA | LYS | A | 520 | 21.497 | 3.728 | 32.592 | 1.00 | 55.59 | A |
| ATOM | 1526 | CB | LYS | A | 520 | 21.021 | 4.932 | 33.409 | 1.00 | 56.43 | A |
| ATOM | 1527 | CG | LYS | A | 520 | 22.148 | 5.838 | 33.876 | 1.00 | 59.61 | A |
| ATOM | 1528 | CD | LYS | A | 520 | 21.768 | 6.576 | 35.164 | 1.00 | 62.57 | A |
| ATOM | 1529 | CE | LYS | A | 520 | 22.994 | 7.209 | 35.852 | 1.00 | 64.31 | A |
| ATOM | 1530 | NZ | LYS | A | 520 | 22.720 | 7.620 | 37.275 | 1.00 | 65.11 | A |
| ATOM | 1531 | C | LYS | A | 520 | 20.585 | 2.537 | 32.848 | 1.00 | 57.69 | A |
| ATOM | 1532 | O | LYS | A | 520 | 20.840 | 1.726 | 33.746 | 1.00 | 57.71 | A |
| ATOM | 1533 | N | GLY | A | 521 | 19.529 | 2.438 | 32.039 | 1.00 | 59.59 | A |
| ATOM | 1534 | CA | GLY | A | 521 | 18.574 | 1.350 | 32.169 | 1.00 | 61.93 | A |
| ATOM | 1535 | C | GLY | A | 521 | 19.176 | 0.007 | 31.803 | 1.00 | 63.75 | A |
| ATOM | 1536 | O | GLY | A | 521 | 19.062 | −0.952 | 32.561 | 1.00 | 64.14 | A |
| ATOM | 1537 | N | MET | A | 522 | 19.824 | −0.057 | 30.644 | 1.00 | 65.68 | A |
| ATOM | 1538 | CA | MET | A | 522 | 20.448 | −1.283 | 30.175 | 1.00 | 68.16 | A |
| ATOM | 1539 | CB | MET | A | 522 | 20.999 | −1.083 | 28.761 | 1.00 | 67.17 | A |
| ATOM | 1540 | CG | MET | A | 522 | 19.934 | −0.761 | 27.724 | 1.00 | 66.83 | A |
| ATOM | 1541 | SD | MET | A | 522 | 18.647 | −2.019 | 27.697 | 1.00 | 66.04 | A |
| ATOM | 1542 | CE | MET | A | 522 | 19.625 | −3.438 | 27.233 | 1.00 | 66.25 | A |
| ATOM | 1543 | C | MET | A | 522 | 21.557 | −1.733 | 31.113 | 1.00 | 70.92 | A |
| ATOM | 1544 | O | MET | A | 522 | 21.794 | −2.926 | 31.273 | 1.00 | 71.44 | A |
| ATOM | 1545 | N | GLU | A | 523 | 22.242 | −0.779 | 31.733 | 1.00 | 74.39 | A |
| ATOM | 1546 | CA | GLU | A | 523 | 23.307 | −1.116 | 32.667 | 1.00 | 77.89 | A |
| ATOM | 1547 | CB | GLU | A | 523 | 23.952 | 0.149 | 33.229 | 1.00 | 78.31 | A |
| ATOM | 1548 | CG | GLU | A | 523 | 25.026 | 0.773 | 32.362 | 1.00 | 79.52 | A |
| ATOM | 1549 | CD | GLU | A | 523 | 25.630 | 1.997 | 33.021 | 1.00 | 80.24 | A |
| ATOM | 1550 | OE1 | GLU | A | 523 | 25.915 | 1.933 | 34.236 | 1.00 | 80.64 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1551 | OE2 | GLU | A | 523 | 25.823 | 3.022 | 32.332 | 1.00 | 80.98 | A |
| ATOM | 1552 | C | GLU | A | 523 | 22.716 | −1.920 | 33.820 | 1.00 | 80.30 | A |
| ATOM | 1553 | O | GLU | A | 523 | 23.266 | −2.940 | 34.230 | 1.00 | 80.29 | A |
| ATOM | 1554 | N | HIS | A | 524 | 21.589 | −1.447 | 34.339 | 1.00 | 83.41 | A |
| ATOM | 1555 | CA | HIS | A | 524 | 20.910 | −2.107 | 35.445 | 1.00 | 87.00 | A |
| ATOM | 1556 | CB | HIS | A | 524 | 19.783 | −1.213 | 35.964 | 1.00 | 88.94 | A |
| ATOM | 1557 | CG | HIS | A | 524 | 20.105 | −0.548 | 37.265 | 1.00 | 91.72 | A |
| ATOM | 1558 | CD2 | HIS | A | 524 | 20.850 | 0.549 | 37.546 | 1.00 | 92.67 | A |
| ATOM | 1559 | ND1 | HIS | A | 524 | 19.706 | −1.061 | 38.481 | 1.00 | 92.84 | A |
| ATOM | 1560 | CE1 | HIS | A | 524 | 20.194 | −0.312 | 39.455 | 1.00 | 93.39 | A |
| ATOM | 1561 | NE2 | HIS | A | 524 | 20.893 | 0.671 | 38.914 | 1.00 | 93.40 | A |
| ATOM | 1562 | C | HIS | A | 524 | 20.375 | −3.496 | 35.105 | 1.00 | 88.62 | A |
| ATOM | 1563 | O | HIS | A | 524 | 20.632 | −4.453 | 35.835 | 1.00 | 88.85 | A |
| ATOM | 1564 | N | LEU | A | 525 | 19.629 | −3.613 | 34.009 | 1.00 | 90.21 | A |
| ATOM | 1565 | CA | LEU | A | 525 | 19.096 | −4.912 | 33.605 | 1.00 | 92.01 | A |
| ATOM | 1566 | CB | LEU | A | 525 | 18.375 | −4.822 | 32.251 | 1.00 | 91.32 | A |
| ATOM | 1567 | CG | LEU | A | 525 | 17.014 | −4.130 | 32.115 | 1.00 | 90.76 | A |
| ATOM | 1568 | CD1 | LEU | A | 525 | 17.139 | −2.928 | 31.199 | 1.00 | 90.23 | A |
| ATOM | 1569 | CD2 | LEU | A | 525 | 16.001 | −5.107 | 31.544 | 1.00 | 90.61 | A |
| ATOM | 1570 | C | LEU | A | 525 | 20.253 | −5.906 | 33.494 | 1.00 | 93.65 | A |
| ATOM | 1571 | O | LEU | A | 525 | 20.146 | −7.050 | 33.937 | 1.00 | 94.36 | A |
| ATOM | 1572 | N | TYR | A | 526 | 21.362 | −5.462 | 32.909 | 1.00 | 95.23 | A |
| ATOM | 1573 | CA | TYR | A | 526 | 22.529 | −6.321 | 32.744 | 1.00 | 97.01 | A |
| ATOM | 1574 | CB | TYR | A | 526 | 23.666 | −5.540 | 32.069 | 1.00 | 97.68 | A |
| ATOM | 1575 | CG | TYR | A | 526 | 24.881 | −6.374 | 31.713 | 1.00 | 98.91 | A |
| ATOM | 1576 | CD1 | TYR | A | 526 | 24.740 | −7.686 | 31.256 | 1.00 | 99.35 | A |
| ATOM | 1577 | CE1 | TYR | A | 526 | 25.847 | −8.442 | 30.882 | 1.00 | 99.79 | A |
| ATOM | 1578 | CD2 | TYR | A | 526 | 26.171 | −5.838 | 31.790 | 1.00 | 99.21 | A |
| ATOM | 1579 | CE2 | TYR | A | 526 | 27.287 | −6.588 | 31.416 | 1.00 | 99.81 | A |
| ATOM | 1580 | CZ | TYR | A | 526 | 27.115 | −7.890 | 30.961 | 1.00 | 99.97 | A |
| ATOM | 1581 | OH | TYR | A | 526 | 28.204 | −8.640 | 30.571 | 1.00 | 100.00 | A |
| ATOM | 1582 | C | TYR | A | 526 | 22.985 | −6.875 | 34.094 | 1.00 | 97.66 | A |
| ATOM | 1583 | O | TYR | A | 526 | 23.332 | −8.052 | 34.207 | 1.00 | 97.83 | A |
| ATOM | 1584 | N | SER | A | 527 | 22.969 | −6.028 | 35.118 | 1.00 | 98.53 | A |
| ATOM | 1585 | CA | SER | A | 527 | 23.380 | −6.443 | 36.455 | 1.00 | 99.34 | A |
| ATOM | 1586 | CB | SER | A | 527 | 23.533 | −5.219 | 37.368 | 1.00 | 99.45 | A |
| ATOM | 1587 | OG | SER | A | 527 | 24.512 | −4.318 | 36.868 | 1.00 | 99.92 | A |
| ATOM | 1588 | C | SER | A | 527 | 22.367 | −7.415 | 37.058 | 1.00 | 99.53 | A |
| ATOM | 1589 | O | SER | A | 527 | 22.745 | −8.375 | 37.733 | 1.00 | 99.93 | A |
| ATOM | 1590 | N | MET | A | 528 | 21.082 | −7.165 | 36.807 | 1.00 | 99.68 | A |
| ATOM | 1591 | CA | MET | A | 528 | 20.006 | −8.014 | 37.324 | 1.00 | 99.59 | A |
| ATOM | 1592 | CB | MET | A | 528 | 18.641 | −7.411 | 36.978 | 1.00 | 99.52 | A |
| ATOM | 1593 | CG | MET | A | 528 | 17.968 | −6.705 | 38.143 | 1.00 | 99.71 | A |
| ATOM | 1594 | SD | MET | A | 528 | 16.411 | −5.916 | 37.687 | 1.00 | 100.00 | A |
| ATOM | 1595 | CE | MET | A | 528 | 16.945 | −4.209 | 37.428 | 1.00 | 99.76 | A |
| ATOM | 1596 | C | MET | A | 528 | 20.073 | −9.444 | 36.801 | 1.00 | 99.29 | A |
| ATOM | 1597 | O | MET | A | 528 | 20.801 | −9.739 | 35.853 | 1.00 | 99.15 | A |
| ATOM | 1598 | N | PRO | A | 535 | 15.363 | −13.797 | 24.319 | 1.00 | 100.00 | A |
| ATOM | 1599 | CD | PRO | A | 535 | 16.418 | −13.504 | 25.302 | 1.00 | 100.00 | A |
| ATOM | 1600 | CA | PRO | A | 535 | 14.151 | −13.018 | 24.607 | 1.00 | 100.00 | A |
| ATOM | 1601 | CB | PRO | A | 535 | 14.490 | −12.311 | 25.924 | 1.00 | 100.00 | A |
| ATOM | 1602 | CG | PRO | A | 535 | 15.609 | −13.145 | 26.513 | 1.00 | 100.00 | A |
| ATOM | 1603 | C | PRO | A | 535 | 13.891 | −12.009 | 23.493 | 1.00 | 100.00 | A |
| ATOM | 1604 | O | PRO | A | 535 | 12.781 | −11.902 | 22.964 | 1.00 | 99.93 | A |
| ATOM | 1605 | N | LEU | A | 536 | 14.949 | −11.284 | 23.147 | 1.00 | 100.00 | A |
| ATOM | 1606 | CA | LEU | A | 536 | 14.914 | −10.250 | 22.125 | 1.00 | 100.00 | A |
| ATOM | 1607 | CB | LEU | A | 536 | 16.175 | −9.384 | 22.230 | 1.00 | 99.93 | A |
| ATOM | 1608 | CG | LEU | A | 536 | 16.660 | −8.992 | 23.632 | 1.00 | 100.00 | A |
| ATOM | 1609 | CD1 | LEU | A | 536 | 17.231 | −10.216 | 24.343 | 1.00 | 99.82 | A |
| ATOM | 1610 | CD2 | LEU | A | 536 | 17.728 | −7.908 | 23.520 | 1.00 | 100.00 | A |
| ATOM | 1611 | C | LEU | A | 536 | 14.805 | −10.791 | 20.702 | 1.00 | 100.00 | A |
| ATOM | 1612 | O | LEU | A | 536 | 14.009 | −10.301 | 19.905 | 1.00 | 99.87 | A |
| ATOM | 1613 | N | TYR | A | 537 | 15.592 | −11.812 | 20.387 | 1.00 | 100.00 | A |
| ATOM | 1614 | CA | TYR | A | 537 | 15.595 | −12.354 | 19.035 | 1.00 | 100.00 | A |
| ATOM | 1615 | CB | TYR | A | 537 | 16.963 | −12.966 | 18.731 | 1.00 | 100.00 | A |
| ATOM | 1616 | CG | TYR | A | 537 | 17.675 | −12.239 | 17.623 | 1.00 | 100.00 | A |
| ATOM | 1617 | CD1 | TYR | A | 537 | 18.163 | −10.945 | 17.818 | 1.00 | 99.89 | A |
| ATOM | 1618 | CE1 | TYR | A | 537 | 18.760 | −10.238 | 16.779 | 1.00 | 100.00 | A |
| ATOM | 1619 | CD2 | TYR | A | 537 | 17.805 | −12.814 | 16.356 | 1.00 | 100.00 | A |
| ATOM | 1620 | CE2 | TYR | A | 537 | 18.399 | −12.114 | 15.308 | 1.00 | 100.00 | A |
| ATOM | 1621 | CZ | TYR | A | 537 | 18.873 | −10.827 | 15.525 | 1.00 | 100.00 | A |
| ATOM | 1622 | OH | TYR | A | 537 | 19.446 | −10.127 | 14.484 | 1.00 | 100.00 | A |
| ATOM | 1623 | C | TYR | A | 537 | 14.509 | −13.326 | 18.582 | 1.00 | 99.97 | A |
| ATOM | 1624 | O | TYR | A | 537 | 14.260 | −13.437 | 17.381 | 1.00 | 100.00 | A |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1625 | N | ASP | A | 538 | 13.867 | −14.037 | 19.503 | 1.00 | 100.00 | A |
| ATOM | 1626 | CA | ASP | A | 538 | 12.822 | −14.981 | 19.097 | 1.00 | 100.00 | A |
| ATOM | 1627 | CB | ASP | A | 538 | 12.244 | −15.701 | 20.323 | 1.00 | 100.00 | A |
| ATOM | 1628 | CG | ASP | A | 538 | 13.219 | −16.709 | 20.926 | 1.00 | 100.00 | A |
| ATOM | 1629 | OD1 | ASP | A | 538 | 14.399 | −16.349 | 21.132 | 1.00 | 100.00 | A |
| ATOM | 1630 | OD2 | ASP | A | 538 | 12.803 | −17.858 | 21.198 | 1.00 | 99.89 | A |
| ATOM | 1631 | C | ASP | A | 538 | 11.709 | −14.273 | 18.312 | 1.00 | 98.49 | A |
| ATOM | 1632 | O | ASP | A | 538 | 11.361 | −14.687 | 17.200 | 1.00 | 99.71 | A |
| ATOM | 1633 | N | LEU | A | 539 | 11.165 | −13.202 | 18.893 | 1.00 | 96.01 | A |
| ATOM | 1634 | CA | LEU | A | 539 | 10.106 | −12.404 | 18.260 | 1.00 | 96.35 | A |
| ATOM | 1635 | CB | LEU | A | 539 | 9.621 | −11.284 | 19.194 | 1.00 | 96.38 | A |
| ATOM | 1636 | CG | LEU | A | 539 | 9.105 | −11.686 | 20.581 | 1.00 | 98.82 | A |
| ATOM | 1637 | CD1 | LEU | A | 539 | 10.241 | −12.338 | 21.396 | 1.00 | 99.85 | A |
| ATOM | 1638 | CD2 | LEU | A | 539 | 8.475 | −10.508 | 21.290 | 1.00 | 99.55 | A |
| ATOM | 1639 | C | LEU | A | 539 | 10.668 | −11.751 | 17.011 | 1.00 | 94.96 | A |
| ATOM | 1640 | O | LEU | A | 539 | 10.141 | −11.919 | 15.910 | 1.00 | 90.95 | A |
| ATOM | 1641 | N | LEU | A | 540 | 11.724 | −10.966 | 17.204 | 1.00 | 96.84 | A |
| ATOM | 1642 | CA | LEU | A | 540 | 12.370 | −10.292 | 16.089 | 1.00 | 97.12 | A |
| ATOM | 1643 | CB | LEU | A | 540 | 12.821 | −8.868 | 16.490 | 1.00 | 94.91 | A |
| ATOM | 1644 | CG | LEU | A | 540 | 13.449 | −8.519 | 17.849 | 1.00 | 91.17 | A |
| ATOM | 1645 | CD1 | LEU | A | 540 | 14.675 | −7.640 | 17.647 | 1.00 | 92.79 | A |
| ATOM | 1646 | CD2 | LEU | A | 540 | 12.428 | −7.792 | 18.717 | 1.00 | 92.95 | A |
| ATOM | 1647 | C | LEU | A | 540 | 13.556 | −11.130 | 15.599 | 1.00 | 96.06 | A |
| ATOM | 1648 | OT1 | LEU | A | 540 | 13.429 | −11.724 | 14.507 | 1.00 | 95.11 | A |
| ATOM | 1649 | OT2 | LEU | A | 540 | 14.584 | −11.215 | 16.310 | 1.00 | 95.22 | A |
| ATOM | 1650 | CB | SER | B | 309 | 25.040 | 40.843 | 26.783 | 1.00 | 89.01 | B |
| ATOM | 1651 | OG | SER | B | 309 | 25.184 | 41.416 | 28.074 | 1.00 | 88.52 | B |
| ATOM | 1652 | C | SER | B | 309 | 25.034 | 38.700 | 25.475 | 1.00 | 89.20 | B |
| ATOM | 1653 | O | SER | B | 309 | 25.847 | 37.921 | 24.970 | 1.00 | 89.70 | B |
| ATOM | 1654 | N | SER | B | 309 | 26.752 | 39.111 | 27.214 | 1.00 | 88.97 | B |
| ATOM | 1655 | CA | SER | B | 309 | 25.330 | 39.341 | 26.828 | 1.00 | 89.04 | B |
| ATOM | 1656 | N | LEU | B | 310 | 23.883 | 39.020 | 24.880 | 1.00 | 88.50 | B |
| ATOM | 1657 | CA | LEU | B | 310 | 23.528 | 38.422 | 23.595 | 1.00 | 87.30 | B |
| ATOM | 1658 | CB | LEU | B | 310 | 22.022 | 38.537 | 23.352 | 1.00 | 87.09 | B |
| ATOM | 1659 | CG | LEU | B | 310 | 21.171 | 37.732 | 24.348 | 1.00 | 86.72 | B |
| ATOM | 1660 | CD1 | LEU | B | 310 | 19.761 | 37.598 | 23.797 | 1.00 | 86.74 | B |
| ATOM | 1661 | CD2 | LEU | B | 310 | 21.775 | 36.354 | 24.577 | 1.00 | 86.32 | B |
| ATOM | 1662 | C | LEU | B | 310 | 24.325 | 38.945 | 22.403 | 1.00 | 86.61 | B |
| ATOM | 1663 | O | LEU | B | 310 | 24.642 | 40.137 | 22.304 | 1.00 | 85.95 | B |
| ATOM | 1664 | N | THR | B | 311 | 24.627 | 38.007 | 21.506 | 1.00 | 85.97 | B |
| ATOM | 1665 | CA | THR | B | 311 | 25.446 | 38.216 | 20.314 | 1.00 | 84.81 | B |
| ATOM | 1666 | CB | THR | B | 311 | 26.800 | 37.522 | 20.528 | 1.00 | 84.69 | B |
| ATOM | 1667 | OG1 | THR | B | 311 | 27.342 | 37.899 | 21.799 | 1.00 | 83.71 | B |
| ATOM | 1668 | CG2 | THR | B | 311 | 27.753 | 37.900 | 19.469 | 1.00 | 84.29 | B |
| ATOM | 1669 | C | THR | B | 311 | 24.777 | 37.617 | 19.063 | 1.00 | 84.43 | B |
| ATOM | 1670 | O | THR | B | 311 | 23.656 | 37.124 | 19.144 | 1.00 | 84.37 | B |
| ATOM | 1671 | N | ALA | B | 312 | 25.473 | 37.632 | 17.923 | 1.00 | 83.27 | B |
| ATOM | 1672 | CA | ALA | B | 312 | 24.914 | 37.094 | 16.683 | 1.00 | 82.17 | B |
| ATOM | 1673 | CB | ALA | B | 312 | 24.184 | 38.202 | 15.932 | 1.00 | 82.59 | B |
| ATOM | 1674 | C | ALA | B | 312 | 25.937 | 36.433 | 15.754 | 1.00 | 81.17 | B |
| ATOM | 1675 | O | ALA | B | 312 | 25.918 | 35.220 | 15.539 | 1.00 | 80.92 | B |
| ATOM | 1676 | N | ASP | B | 313 | 26.809 | 37.247 | 15.179 | 1.00 | 79.98 | B |
| ATOM | 1677 | CA | ASP | B | 313 | 27.835 | 36.760 | 14.269 | 1.00 | 78.33 | B |
| ATOM | 1678 | CB | ASP | B | 313 | 27.898 | 37.686 | 13.050 | 1.00 | 79.79 | B |
| ATOM | 1679 | CG | ASP | B | 313 | 28.257 | 36.953 | 11.775 | 1.00 | 80.74 | B |
| ATOM | 1680 | OD1 | ASP | B | 313 | 27.804 | 35.799 | 11.611 | 1.00 | 81.17 | B |
| ATOM | 1681 | OD2 | ASP | B | 313 | 28.971 | 37.532 | 10.926 | 1.00 | 81.92 | B |
| ATOM | 1682 | C | ASP | B | 313 | 29.135 | 36.805 | 15.068 | 1.00 | 76.55 | B |
| ATOM | 1683 | O | ASP | B | 313 | 30.177 | 36.293 | 14.648 | 1.00 | 75.57 | B |
| ATOM | 1684 | N | GLN | B | 314 | 29.032 | 37.428 | 16.241 | 1.00 | 74.53 | B |
| ATOM | 1685 | CA | GLN | B | 314 | 30.147 | 37.583 | 17.166 | 1.00 | 72.52 | B |
| ATOM | 1686 | CB | GLN | B | 314 | 29.968 | 38.851 | 18.001 | 1.00 | 72.39 | B |
| ATOM | 1687 | CG | GLN | B | 314 | 29.309 | 40.008 | 17.275 | 1.00 | 71.89 | B |
| ATOM | 1688 | CD | GLN | B | 314 | 28.633 | 40.974 | 18.229 | 1.00 | 71.44 | B |
| ATOM | 1689 | OE1 | GLN | B | 314 | 27.511 | 40.738 | 18.681 | 1.00 | 70.67 | B |
| ATOM | 1690 | NE2 | GLN | B | 314 | 29.323 | 42.062 | 18.553 | 1.00 | 71.18 | B |
| ATOM | 1691 | C | GLN | B | 314 | 30.120 | 36.367 | 18.082 | 1.00 | 71.00 | B |
| ATOM | 1692 | O | GLN | B | 314 | 31.103 | 36.062 | 18.764 | 1.00 | 71.36 | B |
| ATOM | 1693 | N | MET | B | 315 | 28.969 | 35.697 | 18.092 | 1.00 | 68.43 | B |
| ATOM | 1694 | CA | MET | B | 315 | 28.743 | 34.489 | 18.875 | 1.00 | 65.37 | B |
| ATOM | 1695 | CB | MET | B | 315 | 27.265 | 34.090 | 18.759 | 1.00 | 65.85 | B |
| ATOM | 1696 | CG | MET | B | 315 | 26.881 | 32.716 | 19.309 | 1.00 | 65.83 | B |
| ATOM | 1697 | SD | MET | B | 315 | 27.095 | 32.504 | 21.101 | 1.00 | 65.87 | B |
| ATOM | 1698 | CE | MET | B | 315 | 25.604 | 33.209 | 21.729 | 1.00 | 65.78 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1699 | C | MET | B | 315 | 29.644 | 33.398 | 18.296 | 1.00 | 63.61 | B |
| ATOM | 1700 | O | MET | B | 315 | 30.203 | 32.578 | 19.024 | 1.00 | 62.88 | B |
| ATOM | 1701 | N | VAL | B | 316 | 29.793 | 33.419 | 16.974 | 1.00 | 61.69 | B |
| ATOM | 1702 | CA | VAL | B | 316 | 30.619 | 32.451 | 16.258 | 1.00 | 59.49 | B |
| ATOM | 1703 | CB | VAL | B | 316 | 30.246 | 32.409 | 14.760 | 1.00 | 59.47 | B |
| ATOM | 1704 | CG1 | VAL | B | 316 | 30.929 | 31.224 | 14.087 | 1.00 | 59.27 | B |
| ATOM | 1705 | CG2 | VAL | B | 316 | 28.733 | 32.337 | 14.601 | 1.00 | 59.79 | B |
| ATOM | 1706 | C | VAL | B | 316 | 32.113 | 32.759 | 16.364 | 1.00 | 57.82 | B |
| ATOM | 1707 | O | VAL | B | 316 | 32.945 | 31.854 | 16.310 | 1.00 | 57.90 | B |
| ATOM | 1708 | N | SER | B | 317 | 32.448 | 34.038 | 16.493 | 1.00 | 55.68 | B |
| ATOM | 1709 | CA | SER | B | 317 | 33.837 | 34.459 | 16.608 | 1.00 | 53.60 | B |
| ATOM | 1710 | CB | SER | B | 317 | 33.961 | 35.950 | 16.302 | 1.00 | 55.25 | B |
| ATOM | 1711 | OG | SER | B | 317 | 33.403 | 36.256 | 15.036 | 1.00 | 57.05 | B |
| ATOM | 1712 | C | SER | B | 317 | 34.292 | 34.187 | 18.031 | 1.00 | 51.56 | B |
| ATOM | 1713 | O | SER | B | 317 | 35.387 | 33.681 | 18.255 | 1.00 | 50.81 | B |
| ATOM | 1714 | N | ALA | B | 318 | 33.434 | 34.538 | 18.984 | 1.00 | 49.61 | B |
| ATOM | 1715 | CA | ALA | B | 318 | 33.703 | 34.320 | 20.400 | 1.00 | 48.94 | B |
| ATOM | 1716 | CB | ALA | B | 318 | 32.485 | 34.729 | 21.236 | 1.00 | 48.82 | B |
| ATOM | 1717 | C | ALA | B | 318 | 34.007 | 32.838 | 20.614 | 1.00 | 48.46 | B |
| ATOM | 1718 | O | ALA | B | 318 | 35.028 | 32.479 | 21.215 | 1.00 | 48.31 | B |
| ATOM | 1719 | N | LEU | B | 319 | 33.114 | 31.986 | 20.111 | 1.00 | 47.23 | B |
| ATOM | 1720 | CA | LEU | B | 319 | 33.278 | 30.546 | 20.230 | 1.00 | 45.49 | B |
| ATOM | 1721 | CB | LEU | B | 319 | 32.076 | 29.820 | 19.623 | 1.00 | 44.51 | B |
| ATOM | 1722 | CG | LEU | B | 319 | 30.753 | 29.901 | 20.385 | 1.00 | 43.62 | B |
| ATOM | 1723 | CD1 | LEU | B | 319 | 29.739 | 28.979 | 19.756 | 1.00 | 42.12 | B |
| ATOM | 1724 | CD2 | LEU | B | 319 | 30.977 | 29.520 | 21.834 | 1.00 | 43.64 | B |
| ATOM | 1725 | C | LEU | B | 319 | 34.559 | 30.097 | 19.540 | 1.00 | 45.47 | B |
| ATOM | 1726 | O | LEU | B | 319 | 35.270 | 29.217 | 20.027 | 1.00 | 45.77 | B |
| ATOM | 1727 | N | LEU | B | 320 | 34.855 | 30.709 | 18.402 | 1.00 | 45.26 | B |
| ATOM | 1728 | CA | LEU | B | 320 | 36.051 | 30.365 | 17.647 | 1.00 | 44.63 | B |
| ATOM | 1729 | CB | LEU | B | 320 | 35.990 | 31.022 | 16.262 | 1.00 | 45.38 | B |
| ATOM | 1730 | CG | LEU | B | 320 | 35.139 | 30.329 | 15.192 | 1.00 | 46.02 | B |
| ATOM | 1731 | CD1 | LEU | B | 320 | 34.850 | 31.287 | 14.055 | 1.00 | 44.96 | B |
| ATOM | 1732 | CD2 | LEU | B | 320 | 35.872 | 29.090 | 14.681 | 1.00 | 45.79 | B |
| ATOM | 1733 | C | LEU | B | 320 | 37.366 | 30.736 | 18.355 | 1.00 | 43.57 | B |
| ATOM | 1734 | O | LEU | B | 320 | 38.318 | 29.955 | 18.345 | 1.00 | 43.70 | B |
| ATOM | 1735 | N | ASP | B | 321 | 37.431 | 31.915 | 18.962 | 0.50 | 42.33 | B |
| ATOM | 1736 | CA | ASP | B | 321 | 38.660 | 32.311 | 19.646 | 0.50 | 41.49 | B |
| ATOM | 1737 | CB | ASP | B | 321 | 38.626 | 33.794 | 20.040 | 0.50 | 40.67 | B |
| ATOM | 1738 | CG | ASP | B | 321 | 38.380 | 34.713 | 18.858 | 0.50 | 39.51 | B |
| ATOM | 1739 | OD1 | ASP | B | 321 | 38.990 | 34.505 | 17.785 | 0.50 | 38.12 | B |
| ATOM | 1740 | OD2 | ASP | B | 321 | 37.577 | 35.655 | 19.012 | 0.50 | 38.52 | B |
| ATOM | 1741 | C | ASP | B | 321 | 38.840 | 31.473 | 20.902 | 0.50 | 41.07 | B |
| ATOM | 1742 | O | ASP | B | 321 | 39.960 | 31.205 | 21.332 | 0.50 | 40.88 | B |
| ATOM | 1743 | N | ALA | B | 322 | 37.713 | 31.059 | 21.472 | 1.00 | 41.33 | B |
| ATOM | 1744 | CA | ALA | B | 322 | 37.683 | 30.269 | 22.694 | 1.00 | 39.63 | B |
| ATOM | 1745 | CB | ALA | B | 322 | 36.283 | 30.316 | 23.302 | 1.00 | 39.69 | B |
| ATOM | 1746 | C | ALA | B | 322 | 38.124 | 28.827 | 22.499 | 1.00 | 39.36 | B |
| ATOM | 1747 | O | ALA | B | 322 | 38.186 | 28.062 | 23.457 | 1.00 | 38.52 | B |
| ATOM | 1748 | N | GLU | B | 323 | 38.440 | 28.456 | 21.264 | 1.00 | 39.10 | B |
| ATOM | 1749 | CA | GLU | B | 323 | 38.888 | 27.096 | 20.984 | 1.00 | 38.82 | B |
| ATOM | 1750 | CB | GLU | B | 323 | 39.148 | 26.927 | 19.494 | 1.00 | 37.47 | B |
| ATOM | 1751 | CG | GLU | B | 323 | 37.931 | 26.503 | 18.690 | 1.00 | 38.56 | B |
| ATOM | 1752 | CD | GLU | B | 323 | 37.386 | 25.160 | 19.125 | 1.00 | 37.76 | B |
| ATOM | 1753 | OE1 | GLU | B | 323 | 36.526 | 25.131 | 20.028 | 1.00 | 35.73 | B |
| ATOM | 1754 | OE2 | GLU | B | 323 | 37.833 | 24.133 | 18.570 | 1.00 | 39.10 | B |
| ATOM | 1755 | C | GLU | B | 323 | 40.143 | 26.689 | 21.767 | 1.00 | 40.15 | B |
| ATOM | 1756 | O | GLU | B | 323 | 41.073 | 27.478 | 21.927 | 1.00 | 41.41 | B |
| ATOM | 1757 | N | PRO | B | 324 | 40.185 | 25.439 | 22.262 | 1.00 | 40.96 | B |
| ATOM | 1758 | CD | PRO | B | 324 | 39.086 | 24.463 | 22.298 | 1.00 | 40.49 | B |
| ATOM | 1759 | CA | PRO | B | 324 | 41.328 | 24.931 | 23.025 | 1.00 | 39.12 | B |
| ATOM | 1760 | CB | PRO | B | 324 | 40.755 | 23.735 | 23.785 | 1.00 | 39.89 | B |
| ATOM | 1761 | CG | PRO | B | 324 | 39.271 | 23.881 | 23.664 | 1.00 | 41.46 | B |
| ATOM | 1762 | C | PRO | B | 324 | 42.405 | 24.475 | 22.078 | 1.00 | 39.72 | B |
| ATOM | 1763 | O | PRO | B | 324 | 42.130 | 24.197 | 20.915 | 1.00 | 41.14 | B |
| ATOM | 1764 | N | PRO | B | 325 | 43.651 | 24.389 | 22.558 | 1.00 | 39.70 | B |
| ATOM | 1765 | CD | PRO | B | 325 | 44.159 | 24.818 | 23.873 | 1.00 | 38.95 | B |
| ATOM | 1766 | CA | PRO | B | 325 | 44.743 | 23.943 | 21.694 | 1.00 | 38.17 | B |
| ATOM | 1767 | CB | PRO | B | 325 | 45.987 | 24.380 | 22.468 | 1.00 | 38.34 | B |
| ATOM | 1768 | CG | PRO | B | 325 | 45.559 | 24.236 | 23.891 | 1.00 | 38.81 | B |
| ATOM | 1769 | C | PRO | B | 325 | 44.698 | 22.427 | 21.474 | 1.00 | 38.59 | B |
| ATOM | 1770 | O | PRO | B | 325 | 43.982 | 21.714 | 22.169 | 1.00 | 37.47 | B |
| ATOM | 1771 | N | ILE | B | 326 | 45.457 | 21.947 | 20.496 | 1.00 | 39.56 | B |
| ATOM | 1772 | CA | ILE | B | 326 | 45.526 | 20.515 | 20.227 | 1.00 | 40.30 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1773 | CB | ILE | B | 326 | 45.645 | 20.221 | 18.706 | 1.00 | 39.64 | B |
| ATOM | 1774 | CG2 | ILE | B | 326 | 45.900 | 18.731 | 18.471 | 1.00 | 38.34 | B |
| ATOM | 1775 | CG1 | ILE | B | 326 | 44.358 | 20.661 | 17.997 | 1.00 | 39.24 | B |
| ATOM | 1776 | CD1 | ILE | B | 326 | 44.397 | 20.472 | 16.495 | 1.00 | 39.88 | B |
| ATOM | 1777 | C | ILE | B | 326 | 46.772 | 20.032 | 20.952 | 1.00 | 41.88 | B |
| ATOM | 1778 | O | ILE | B | 326 | 47.893 | 20.290 | 20.513 | 1.00 | 43.76 | B |
| ATOM | 1779 | N | LEU | B | 327 | 46.579 | 19.361 | 22.082 | 1.00 | 42.63 | B |
| ATOM | 1780 | CA | LEU | B | 327 | 47.710 | 18.887 | 22.868 | 1.00 | 43.14 | B |
| ATOM | 1781 | CB | LEU | B | 327 | 47.276 | 18.592 | 24.309 | 1.00 | 41.54 | B |
| ATOM | 1782 | CG | LEU | B | 327 | 46.670 | 19.775 | 25.067 | 1.00 | 38.81 | B |
| ATOM | 1783 | CD1 | LEU | B | 327 | 46.439 | 19.391 | 26.524 | 1.00 | 37.60 | B |
| ATOM | 1784 | CD2 | LEU | B | 327 | 47.608 | 20.979 | 24.966 | 1.00 | 38.07 | B |
| ATOM | 1785 | C | LEU | B | 327 | 48.367 | 17.668 | 22.252 | 1.00 | 44.25 | B |
| ATOM | 1786 | O | LEU | B | 327 | 47.829 | 17.058 | 21.340 | 1.00 | 44.06 | B |
| ATOM | 1787 | N | TYR | B | 328 | 49.543 | 17.325 | 22.759 | 1.00 | 47.31 | B |
| ATOM | 1788 | CA | TYR | B | 328 | 50.300 | 16.191 | 22.241 | 1.00 | 50.41 | B |
| ATOM | 1789 | CB | TYR | B | 328 | 51.727 | 16.622 | 21.891 | 1.00 | 49.64 | B |
| ATOM | 1790 | CG | TYR | B | 328 | 51.906 | 17.084 | 20.473 | 1.00 | 48.87 | B |
| ATOM | 1791 | CD1 | TYR | B | 328 | 51.352 | 18.282 | 20.025 | 1.00 | 49.31 | B |
| ATOM | 1792 | CE1 | TYR | B | 328 | 51.485 | 18.679 | 18.701 | 1.00 | 49.46 | B |
| ATOM | 1793 | CD2 | TYR | B | 328 | 52.602 | 16.298 | 19.566 | 1.00 | 48.98 | B |
| ATOM | 1794 | CE2 | TYR | B | 328 | 52.741 | 16.679 | 18.247 | 1.00 | 49.97 | B |
| ATOM | 1795 | CZ | TYR | B | 328 | 52.181 | 17.867 | 17.816 | 1.00 | 50.50 | B |
| ATOM | 1796 | OH | TYR | B | 328 | 52.314 | 18.216 | 16.488 | 1.00 | 52.62 | B |
| ATOM | 1797 | C | TYR | B | 328 | 50.384 | 15.021 | 23.204 | 1.00 | 53.37 | B |
| ATOM | 1798 | O | TYR | B | 328 | 50.244 | 15.182 | 24.418 | 1.00 | 52.40 | B |
| ATOM | 1799 | N | SER | B | 329 | 50.653 | 13.850 | 22.637 | 1.00 | 57.65 | B |
| ATOM | 1800 | CA | SER | B | 329 | 50.778 | 12.621 | 23.402 | 1.00 | 62.20 | B |
| ATOM | 1801 | CB | SER | B | 329 | 50.450 | 11.406 | 22.533 | 1.00 | 62.11 | B |
| ATOM | 1802 | OG | SER | B | 329 | 50.249 | 10.236 | 23.329 | 1.00 | 62.42 | B |
| ATOM | 1803 | C | SER | B | 329 | 52.197 | 12.557 | 23.869 | 1.00 | 65.91 | B |
| ATOM | 1804 | O | SER | B | 329 | 53.114 | 12.855 | 23.109 | 1.00 | 65.97 | B |
| ATOM | 1805 | N | GLU | B | 330 | 52.394 | 12.137 | 25.103 | 1.00 | 70.75 | B |
| ATOM | 1806 | CA | GLU | B | 330 | 53.739 | 12.117 | 25.644 | 1.00 | 76.16 | B |
| ATOM | 1807 | CB | GLU | B | 330 | 53.690 | 12.129 | 27.163 | 1.00 | 76.44 | B |
| ATOM | 1808 | CG | GLU | B | 330 | 52.919 | 13.308 | 27.726 | 1.00 | 78.08 | B |
| ATOM | 1809 | CD | GLU | B | 330 | 53.746 | 14.159 | 28.669 | 1.00 | 79.27 | B |
| ATOM | 1810 | OE1 | GLU | B | 330 | 54.567 | 13.578 | 29.407 | 1.00 | 80.68 | B |
| ATOM | 1811 | OE2 | GLU | B | 330 | 53.549 | 15.392 | 28.672 | 1.00 | 79.83 | B |
| ATOM | 1812 | C | GLU | B | 330 | 54.747 | 11.056 | 25.252 | 1.00 | 79.64 | B |
| ATOM | 1813 | O | GLU | B | 330 | 55.129 | 10.253 | 26.093 | 1.00 | 80.04 | B |
| ATOM | 1814 | N | TYR | B | 331 | 55.170 | 11.004 | 24.009 | 1.00 | 83.93 | B |
| ATOM | 1815 | CA | TYR | B | 331 | 56.279 | 10.139 | 23.740 | 1.00 | 88.32 | B |
| ATOM | 1816 | CB | TYR | B | 331 | 57.485 | 10.759 | 24.416 | 1.00 | 90.22 | B |
| ATOM | 1817 | CG | TYR | B | 331 | 58.288 | 11.549 | 23.492 | 1.00 | 92.74 | B |
| ATOM | 1818 | CD1 | TYR | B | 331 | 58.820 | 12.769 | 23.907 | 1.00 | 93.87 | B |
| ATOM | 1819 | CE1 | TYR | B | 331 | 59.615 | 13.493 | 23.071 | 1.00 | 95.39 | B |
| ATOM | 1820 | CD2 | TYR | B | 331 | 58.571 | 11.077 | 22.216 | 1.00 | 93.64 | B |
| ATOM | 1821 | CE2 | TYR | B | 331 | 59.324 | 11.763 | 21.424 | 1.00 | 95.21 | B |
| ATOM | 1822 | CZ | TYR | B | 331 | 59.839 | 12.940 | 21.815 | 1.00 | 95.92 | B |
| ATOM | 1823 | OH | TYR | B | 331 | 60.529 | 13.507 | 20.821 | 1.00 | 97.06 | B |
| ATOM | 1824 | C | TYR | B | 331 | 56.281 | 8.695 | 24.187 | 1.00 | 90.32 | B |
| ATOM | 1825 | O | TYR | B | 331 | 57.367 | 8.103 | 24.271 | 1.00 | 90.72 | B |
| ATOM | 1826 | N | ASP | B | 332 | 55.123 | 8.194 | 24.576 | 1.00 | 92.63 | B |
| ATOM | 1827 | CA | ASP | B | 332 | 54.984 | 6.808 | 25.011 | 1.00 | 94.68 | B |
| ATOM | 1828 | CB | ASP | B | 332 | 53.651 | 6.344 | 24.487 | 1.00 | 96.11 | B |
| ATOM | 1829 | CG | ASP | B | 332 | 53.275 | 5.043 | 25.045 | 1.00 | 97.70 | B |
| ATOM | 1830 | OD1 | ASP | B | 332 | 53.472 | 4.808 | 26.285 | 1.00 | 98.58 | B |
| ATOM | 1831 | OD2 | ASP | B | 332 | 52.882 | 4.239 | 24.240 | 1.00 | 98.52 | B |
| ATOM | 1832 | C | ASP | B | 332 | 56.158 | 5.821 | 24.572 | 1.00 | 95.35 | B |
| ATOM | 1833 | O | ASP | B | 332 | 56.732 | 5.958 | 23.462 | 1.00 | 95.47 | B |
| ATOM | 1834 | N | PRO | B | 333 | 56.566 | 4.866 | 25.444 | 1.00 | 95.99 | B |
| ATOM | 1835 | CD | PRO | B | 333 | 56.207 | 4.632 | 26.849 | 1.00 | 96.27 | B |
| ATOM | 1836 | CA | PRO | B | 333 | 57.638 | 3.951 | 25.024 | 1.00 | 96.42 | B |
| ATOM | 1837 | CB | PRO | B | 333 | 57.742 | 2.918 | 26.184 | 1.00 | 96.55 | B |
| ATOM | 1838 | CG | PRO | B | 333 | 56.513 | 3.183 | 27.022 | 1.00 | 96.45 | B |
| ATOM | 1839 | C | PRO | B | 333 | 57.416 | 3.293 | 23.678 | 1.00 | 96.82 | B |
| ATOM | 1840 | O | PRO | B | 333 | 57.196 | 3.987 | 22.677 | 1.00 | 97.17 | B |
| ATOM | 1841 | N | PRO | B | 336 | 55.478 | −1.572 | 21.615 | 1.00 | 94.30 | B |
| ATOM | 1842 | CD | PRO | B | 336 | 56.165 | −2.857 | 21.400 | 1.00 | 94.05 | B |
| ATOM | 1843 | CA | PRO | B | 336 | 54.062 | −1.680 | 21.253 | 1.00 | 94.61 | B |
| ATOM | 1844 | CB | PRO | B | 336 | 53.876 | −3.184 | 21.065 | 1.00 | 94.22 | B |
| ATOM | 1845 | CG | PRO | B | 336 | 55.193 | −3.599 | 20.509 | 1.00 | 93.97 | B |
| ATOM | 1846 | C | PRO | B | 336 | 53.117 | −1.102 | 22.307 | 1.00 | 94.77 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1847 | O | PRO | B | 336 | 53.547 | −0.446 | 23.251 | 1.00 | 94.86 | B |
| ATOM | 1848 | N | PHE | B | 337 | 51.824 | −1.345 | 22.133 | 1.00 | 95.22 | B |
| ATOM | 1849 | CA | PHE | B | 337 | 50.833 | −0.848 | 23.072 | 1.00 | 96.01 | B |
| ATOM | 1850 | CB | PHE | B | 337 | 49.838 | 0.074 | 22.366 | 1.00 | 97.01 | B |
| ATOM | 1851 | CG | PHE | B | 337 | 50.377 | 1.440 | 22.077 | 1.00 | 98.14 | B |
| ATOM | 1852 | CD1 | PHE | B | 337 | 50.872 | 2.218 | 23.098 | 1.00 | 98.55 | B |
| ATOM | 1853 | CD2 | PHE | B | 337 | 50.374 | 1.957 | 20.786 | 1.00 | 98.44 | B |
| ATOM | 1854 | CE1 | PHE | B | 337 | 51.349 | 3.477 | 22.839 | 1.00 | 98.90 | B |
| ATOM | 1855 | CE2 | PHE | B | 337 | 50.863 | 3.235 | 20.530 | 1.00 | 98.83 | B |
| ATOM | 1856 | CZ | PHE | B | 337 | 51.348 | 3.989 | 21.559 | 1.00 | 98.90 | B |
| ATOM | 1857 | C | PHE | B | 337 | 50.067 | −1.972 | 23.746 | 1.00 | 96.04 | B |
| ATOM | 1858 | O | PHE | B | 337 | 49.711 | −2.970 | 23.117 | 1.00 | 96.22 | B |
| ATOM | 1859 | N | SER | B | 338 | 49.818 | −1.796 | 25.037 | 1.00 | 95.80 | B |
| ATOM | 1860 | CA | SER | B | 338 | 49.079 | −2.775 | 25.809 | 1.00 | 95.36 | B |
| ATOM | 1861 | CB | SER | B | 338 | 49.921 | −3.280 | 26.987 | 1.00 | 95.39 | B |
| ATOM | 1862 | OG | SER | B | 338 | 50.328 | −2.218 | 27.835 | 1.00 | 94.45 | B |
| ATOM | 1863 | C | SER | B | 338 | 47.795 | −2.135 | 26.315 | 1.00 | 95.19 | B |
| ATOM | 1864 | O | SER | B | 338 | 47.361 | −1.095 | 25.817 | 1.00 | 95.22 | B |
| ATOM | 1865 | N | GLU | B | 339 | 47.202 | −2.769 | 27.317 | 1.00 | 94.80 | B |
| ATOM | 1866 | CA | GLU | B | 339 | 45.959 | −2.315 | 27.918 | 1.00 | 94.27 | B |
| ATOM | 1867 | CB | GLU | B | 339 | 45.308 | −3.499 | 28.616 | 1.00 | 94.84 | B |
| ATOM | 1868 | CG | GLU | B | 339 | 43.873 | −3.288 | 29.012 | 1.00 | 95.83 | B |
| ATOM | 1869 | CD | GLU | B | 339 | 43.093 | −4.584 | 28.964 | 1.00 | 96.48 | B |
| ATOM | 1870 | OE1 | GLU | B | 339 | 43.613 | −5.622 | 29.433 | 1.00 | 97.03 | B |
| ATOM | 1871 | OE2 | GLU | B | 339 | 41.946 | −4.570 | 28.479 | 1.00 | 96.68 | B |
| ATOM | 1872 | C | GLU | B | 339 | 46.211 | −1.186 | 28.912 | 1.00 | 93.53 | B |
| ATOM | 1873 | O | GLU | B | 339 | 45.526 | −0.159 | 28.904 | 1.00 | 93.46 | B |
| ATOM | 1874 | N | ALA | B | 340 | 47.200 | −1.399 | 29.774 | 1.00 | 92.51 | B |
| ATOM | 1875 | CA | ALA | B | 340 | 47.585 | −0.421 | 30.781 | 1.00 | 91.25 | B |
| ATOM | 1876 | CB | ALA | B | 340 | 48.201 | −1.133 | 31.985 | 1.00 | 91.17 | B |
| ATOM | 1877 | C | ALA | B | 340 | 48.584 | 0.575 | 30.184 | 1.00 | 90.15 | B |
| ATOM | 1878 | O | ALA | B | 340 | 49.200 | 1.361 | 30.905 | 1.00 | 90.51 | B |
| ATOM | 1879 | N | SER | B | 341 | 48.749 | 0.522 | 28.865 | 1.00 | 88.21 | B |
| ATOM | 1880 | CA | SER | B | 341 | 49.656 | 1.421 | 28.160 | 1.00 | 85.89 | B |
| ATOM | 1881 | CB | SER | B | 341 | 50.603 | 0.623 | 27.262 | 1.00 | 85.69 | B |
| ATOM | 1882 | OG | SER | B | 341 | 51.535 | 1.472 | 26.619 | 1.00 | 85.40 | B |
| ATOM | 1883 | C | SER | B | 341 | 48.795 | 2.362 | 27.318 | 1.00 | 84.53 | B |
| ATOM | 1884 | O | SER | B | 341 | 49.088 | 3.551 | 27.183 | 1.00 | 84.05 | B |
| ATOM | 1885 | N | MET | B | 342 | 47.724 | 1.808 | 26.760 | 1.00 | 82.49 | B |
| ATOM | 1886 | CA | MET | B | 342 | 46.783 | 2.568 | 25.952 | 1.00 | 80.71 | B |
| ATOM | 1887 | CB | MET | B | 342 | 45.831 | 1.617 | 25.229 | 1.00 | 81.52 | B |
| ATOM | 1888 | CG | MET | B | 342 | 46.256 | 1.275 | 23.826 | 1.00 | 82.54 | B |
| ATOM | 1889 | SD | MET | B | 342 | 45.863 | 2.616 | 22.702 | 1.00 | 83.39 | B |
| ATOM | 1890 | CE | MET | B | 342 | 44.364 | 1.958 | 21.929 | 1.00 | 83.42 | B |
| ATOM | 1891 | C | MET | B | 342 | 45.981 | 3.479 | 26.869 | 1.00 | 79.03 | B |
| ATOM | 1892 | O | MET | B | 342 | 45.955 | 4.700 | 26.696 | 1.00 | 78.69 | B |
| ATOM | 1893 | N | MET | B | 343 | 45.329 | 2.864 | 27.849 | 1.00 | 76.63 | B |
| ATOM | 1894 | CA | MET | B | 343 | 44.519 | 3.593 | 28.803 | 1.00 | 73.97 | B |
| ATOM | 1895 | CB | MET | B | 343 | 43.940 | 2.628 | 29.838 | 1.00 | 74.98 | B |
| ATOM | 1896 | CG | MET | B | 343 | 42.475 | 2.880 | 30.165 | 1.00 | 76.11 | B |
| ATOM | 1897 | SD | MET | B | 343 | 41.393 | 2.591 | 28.741 | 1.00 | 77.95 | B |
| ATOM | 1898 | CE | MET | B | 343 | 41.483 | 4.186 | 27.882 | 1.00 | 76.91 | B |
| ATOM | 1899 | C | MET | B | 343 | 45.351 | 4.663 | 29.495 | 1.00 | 71.76 | B |
| ATOM | 1900 | O | MET | B | 343 | 44.870 | 5.767 | 29.746 | 1.00 | 71.19 | B |
| ATOM | 1901 | N | GLY | B | 344 | 46.603 | 4.327 | 29.796 | 1.00 | 69.40 | B |
| ATOM | 1902 | CA | GLY | B | 344 | 47.492 | 5.268 | 30.459 | 1.00 | 66.36 | B |
| ATOM | 1903 | C | GLY | B | 344 | 47.736 | 6.538 | 29.664 | 1.00 | 64.27 | B |
| ATOM | 1904 | O | GLY | B | 344 | 47.784 | 7.637 | 30.219 | 1.00 | 63.90 | B |
| ATOM | 1905 | N | LEU | B | 345 | 47.900 | 6.381 | 28.357 | 1.00 | 62.08 | B |
| ATOM | 1906 | CA | LEU | B | 345 | 48.125 | 7.512 | 27.474 | 1.00 | 60.11 | B |
| ATOM | 1907 | CB | LEU | B | 345 | 48.556 | 7.030 | 26.091 | 1.00 | 61.22 | B |
| ATOM | 1908 | CG | LEU | B | 345 | 50.054 | 7.085 | 25.799 | 1.00 | 62.66 | B |
| ATOM | 1909 | CD1 | LEU | B | 345 | 50.765 | 7.994 | 26.816 | 1.00 | 63.01 | B |
| ATOM | 1910 | CD2 | LEU | B | 345 | 50.619 | 5.687 | 25.866 | 1.00 | 63.70 | B |
| ATOM | 1911 | C | LEU | B | 345 | 46.894 | 8.399 | 27.335 | 1.00 | 58.38 | B |
| ATOM | 1912 | O | LEU | B | 345 | 46.993 | 9.621 | 27.432 | 1.00 | 57.61 | B |
| ATOM | 1913 | N | LEU | B | 346 | 45.742 | 7.773 | 27.095 | 1.00 | 56.25 | B |
| ATOM | 1914 | CA | LEU | B | 346 | 44.476 | 8.484 | 26.940 | 1.00 | 53.59 | B |
| ATOM | 1915 | CB | LEU | B | 346 | 43.357 | 7.503 | 26.569 | 1.00 | 53.61 | B |
| ATOM | 1916 | CG | LEU | B | 346 | 43.554 | 6.639 | 25.318 | 1.00 | 54.09 | B |
| ATOM | 1917 | CD1 | LEU | B | 346 | 42.213 | 5.999 | 24.937 | 1.00 | 53.36 | B |
| ATOM | 1918 | CD2 | LEU | B | 346 | 44.083 | 7.488 | 24.162 | 1.00 | 53.40 | B |
| ATOM | 1919 | C | LEU | B | 346 | 44.094 | 9.236 | 28.212 | 1.00 | 51.51 | B |
| ATOM | 1920 | O | LEU | B | 346 | 43.453 | 10.286 | 28.156 | 1.00 | 49.80 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1921 | N | THR | B | 347 | 44.488 | 8.693 | 29.359 | 1.00 | 49.70 | B |
| ATOM | 1922 | CA | THR | B | 347 | 44.184 | 9.342 | 30.617 | 1.00 | 48.28 | B |
| ATOM | 1923 | CB | THR | B | 347 | 44.375 | 8.436 | 31.793 | 1.00 | 49.32 | B |
| ATOM | 1924 | OG1 | THR | B | 347 | 43.713 | 7.185 | 31.564 | 1.00 | 51.29 | B |
| ATOM | 1925 | CG2 | THR | B | 347 | 43.789 | 9.129 | 33.009 | 1.00 | 50.31 | B |
| ATOM | 1926 | C | THR | B | 347 | 45.095 | 10.535 | 30.837 | 1.00 | 46.39 | B |
| ATOM | 1927 | O | THR | B | 347 | 44.657 | 11.589 | 31.298 | 1.00 | 45.36 | B |
| ATOM | 1928 | N | ASN | B | 348 | 46.373 | 10.355 | 30.527 | 1.00 | 44.63 | B |
| ATOM | 1929 | CA | ASN | B | 348 | 47.325 | 11.439 | 30.669 | 1.00 | 43.33 | B |
| ATOM | 1930 | CB | ASN | B | 348 | 48.715 | 10.996 | 30.213 | 1.00 | 44.89 | B |
| ATOM | 1931 | CG | ASN | B | 348 | 49.714 | 12.152 | 30.173 | 1.00 | 46.64 | B |
| ATOM | 1932 | OD1 | ASN | B | 348 | 50.578 | 12.206 | 29.296 | 1.00 | 47.56 | B |
| ATOM | 1933 | ND2 | ASN | B | 348 | 49.609 | 13.069 | 31.131 | 1.00 | 46.53 | B |
| ATOM | 1934 | C | ASN | B | 348 | 46.852 | 12.589 | 29.787 | 1.00 | 41.57 | B |
| ATOM | 1935 | O | ASN | B | 348 | 46.833 | 13.740 | 30.222 | 1.00 | 40.64 | B |
| ATOM | 1936 | N | LEU | B | 349 | 46.464 | 12.248 | 28.553 | 1.00 | 39.46 | B |
| ATOM | 1937 | CA | LEU | B | 349 | 46.003 | 13.217 | 27.569 | 1.00 | 37.82 | B |
| ATOM | 1938 | CB | LEU | B | 349 | 45.743 | 12.543 | 26.219 | 1.00 | 38.32 | B |
| ATOM | 1939 | CG | LEU | B | 349 | 45.276 | 13.485 | 25.099 | 1.00 | 39.08 | B |
| ATOM | 1940 | CD1 | LEU | B | 349 | 46.375 | 14.523 | 24.828 | 1.00 | 38.38 | B |
| ATOM | 1941 | CD2 | LEU | B | 349 | 44.946 | 12.694 | 23.830 | 1.00 | 38.41 | B |
| ATOM | 1942 | C | LEU | B | 349 | 44.745 | 13.925 | 28.026 | 1.00 | 36.81 | B |
| ATOM | 1943 | O | LEU | B | 349 | 44.682 | 15.156 | 28.004 | 1.00 | 36.72 | B |
| ATOM | 1944 | N | ALA | B | 350 | 43.757 | 13.144 | 28.448 | 1.00 | 35.38 | B |
| ATOM | 1945 | CA | ALA | B | 350 | 42.493 | 13.685 | 28.918 | 1.00 | 36.05 | B |
| ATOM | 1946 | CB | ALA | B | 350 | 41.514 | 12.547 | 29.206 | 1.00 | 35.52 | B |
| ATOM | 1947 | C | ALA | B | 350 | 42.657 | 14.566 | 30.158 | 1.00 | 37.10 | B |
| ATOM | 1948 | O | ALA | B | 350 | 41.972 | 15.587 | 30.284 | 1.00 | 37.12 | B |
| ATOM | 1949 | N | ASP | B | 351 | 43.552 | 14.177 | 31.068 | 1.00 | 37.70 | B |
| ATOM | 1950 | CA | ASP | B | 351 | 43.780 | 14.963 | 32.277 | 1.00 | 39.04 | B |
| ATOM | 1951 | CB | ASP | B | 351 | 44.741 | 14.264 | 33.245 | 1.00 | 41.03 | B |
| ATOM | 1952 | CG | ASP | B | 351 | 44.050 | 13.227 | 34.112 | 1.00 | 42.57 | B |
| ATOM | 1953 | OD1 | ASP | B | 351 | 42.873 | 13.443 | 34.481 | 1.00 | 42.24 | B |
| ATOM | 1954 | OD2 | ASP | B | 351 | 44.693 | 12.202 | 34.439 | 1.00 | 44.62 | B |
| ATOM | 1955 | C | ASP | B | 351 | 44.353 | 16.312 | 31.914 | 1.00 | 38.51 | B |
| ATOM | 1956 | O | ASP | B | 351 | 44.010 | 17.330 | 32.517 | 1.00 | 38.66 | B |
| ATOM | 1957 | N | ARG | B | 352 | 45.238 | 16.322 | 30.929 | 1.00 | 38.29 | B |
| ATOM | 1958 | CA | ARG | B | 352 | 45.833 | 17.577 | 30.493 | 1.00 | 37.95 | B |
| ATOM | 1959 | CB | ARG | B | 352 | 47.113 | 17.313 | 29.696 | 1.00 | 37.38 | B |
| ATOM | 1960 | CG | ARG | B | 352 | 48.314 | 17.039 | 30.580 | 1.00 | 36.82 | B |
| ATOM | 1961 | CD | ARG | B | 352 | 49.562 | 16.835 | 29.766 | 1.00 | 37.28 | B |
| ATOM | 1962 | NE | ARG | B | 352 | 49.477 | 15.624 | 28.962 | 1.00 | 39.53 | B |
| ATOM | 1963 | CZ | ARG | B | 352 | 49.731 | 15.578 | 27.662 | 1.00 | 39.47 | B |
| ATOM | 1964 | NH1 | ARG | B | 352 | 50.086 | 16.684 | 27.022 | 1.00 | 38.86 | B |
| ATOM | 1965 | NH2 | ARG | B | 352 | 49.624 | 14.432 | 27.009 | 1.00 | 38.94 | B |
| ATOM | 1966 | C | ARG | B | 352 | 44.858 | 18.423 | 29.676 | 1.00 | 37.73 | B |
| ATOM | 1967 | O | ARG | B | 352 | 44.911 | 19.645 | 29.731 | 1.00 | 38.37 | B |
| ATOM | 1968 | N | GLU | B | 353 | 43.962 | 17.778 | 28.931 | 1.00 | 36.72 | B |
| ATOM | 1969 | CA | GLU | B | 353 | 42.995 | 18.518 | 28.133 | 1.00 | 35.64 | B |
| ATOM | 1970 | CB | GLU | B | 353 | 42.362 | 17.615 | 27.081 | 1.00 | 35.73 | B |
| ATOM | 1971 | CG | GLU | B | 353 | 43.218 | 17.427 | 25.841 | 1.00 | 36.57 | B |
| ATOM | 1972 | CD | GLU | B | 353 | 42.599 | 16.455 | 24.850 | 1.00 | 37.33 | B |
| ATOM | 1973 | OE1 | GLU | B | 353 | 42.572 | 15.240 | 25.140 | 1.00 | 36.42 | B |
| ATOM | 1974 | OE2 | GLU | B | 353 | 42.131 | 16.906 | 23.787 | 1.00 | 37.18 | B |
| ATOM | 1975 | C | GLU | B | 353 | 41.912 | 19.160 | 28.990 | 1.00 | 35.21 | B |
| ATOM | 1976 | O | GLU | B | 353 | 41.413 | 20.238 | 28.655 | 1.00 | 35.10 | B |
| ATOM | 1977 | N | LEU | B | 354 | 41.565 | 18.519 | 30.103 | 1.00 | 33.99 | B |
| ATOM | 1978 | CA | LEU | B | 354 | 40.538 | 19.064 | 30.982 | 1.00 | 34.29 | B |
| ATOM | 1979 | CB | LEU | B | 354 | 40.292 | 18.147 | 32.184 | 1.00 | 35.93 | B |
| ATOM | 1980 | CG | LEU | B | 354 | 39.676 | 16.766 | 31.902 | 1.00 | 39.25 | B |
| ATOM | 1981 | CD1 | LEU | B | 354 | 38.846 | 16.361 | 33.098 | 1.00 | 40.74 | B |
| ATOM | 1982 | CD2 | LEU | B | 354 | 38.774 | 16.789 | 30.678 | 1.00 | 38.53 | B |
| ATOM | 1983 | C | LEU | B | 354 | 40.850 | 20.470 | 31.470 | 1.00 | 33.61 | B |
| ATOM | 1984 | O | LEU | B | 354 | 39.947 | 21.293 | 31.591 | 1.00 | 33.49 | B |
| ATOM | 1985 | N | VAL | B | 355 | 42.118 | 20.751 | 31.755 | 1.00 | 33.08 | B |
| ATOM | 1986 | CA | VAL | B | 355 | 42.494 | 22.088 | 32.217 | 1.00 | 31.58 | B |
| ATOM | 1987 | CB | VAL | B | 355 | 44.033 | 22.226 | 32.438 | 1.00 | 32.08 | B |
| ATOM | 1988 | CG1 | VAL | B | 355 | 44.323 | 23.525 | 33.189 | 1.00 | 31.10 | B |
| ATOM | 1989 | CG2 | VAL | B | 355 | 44.578 | 21.032 | 33.187 | 1.00 | 32.09 | B |
| ATOM | 1990 | C | VAL | B | 355 | 42.065 | 23.127 | 31.176 | 1.00 | 30.27 | B |
| ATOM | 1991 | O | VAL | B | 355 | 41.398 | 24.102 | 31.489 | 1.00 | 29.35 | B |
| ATOM | 1992 | N | HIS | B | 356 | 42.463 | 22.888 | 29.936 | 1.00 | 30.20 | B |
| ATOM | 1993 | CA | HIS | B | 356 | 42.150 | 23.767 | 28.825 | 1.00 | 31.35 | B |
| ATOM | 1994 | CB | HIS | B | 356 | 42.903 | 23.293 | 27.589 | 1.00 | 31.88 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 1995 | CG | HIS | B | 356 | 44.380 | 23.507 | 27.676 | 1.00 | 31.55 | B |
| ATOM | 1996 | CD2 | HIS | B | 356 | 45.401 | 22.630 | 27.827 | 1.00 | 31.60 | B |
| ATOM | 1997 | ND1 | HIS | B | 356 | 44.949 | 24.762 | 27.662 | 1.00 | 29.54 | B |
| ATOM | 1998 | CE1 | HIS | B | 356 | 46.258 | 24.649 | 27.801 | 1.00 | 30.59 | B |
| ATOM | 1999 | NE2 | HIS | B | 356 | 46.559 | 23.368 | 27.905 | 1.00 | 30.37 | B |
| ATOM | 2000 | C | HIS | B | 356 | 40.661 | 23.868 | 28.514 | 1.00 | 32.87 | B |
| ATOM | 2001 | O | HIS | B | 356 | 40.189 | 24.917 | 28.079 | 1.00 | 32.04 | B |
| ATOM | 2002 | N | MET | B | 357 | 39.941 | 22.765 | 28.739 | 1.00 | 34.29 | B |
| ATOM | 2003 | CA | MET | B | 357 | 38.501 | 22.672 | 28.512 | 1.00 | 34.07 | B |
| ATOM | 2004 | CB | MET | B | 357 | 38.039 | 21.220 | 28.640 | 1.00 | 35.95 | B |
| ATOM | 2005 | CG | MET | B | 357 | 36.556 | 20.999 | 28.338 | 1.00 | 35.65 | B |
| ATOM | 2006 | SD | MET | B | 357 | 35.942 | 19.431 | 28.981 | 1.00 | 37.38 | B |
| ATOM | 2007 | CE | MET | B | 357 | 36.869 | 18.248 | 28.048 | 1.00 | 34.07 | B |
| ATOM | 2008 | C | MET | B | 357 | 37.748 | 23.503 | 29.528 | 1.00 | 34.92 | B |
| ATOM | 2009 | O | MET | B | 357 | 36.655 | 24.008 | 29.249 | 1.00 | 35.20 | B |
| ATOM | 2010 | N | ILE | B | 358 | 38.319 | 23.611 | 30.722 | 1.00 | 35.65 | B |
| ATOM | 2011 | CA | ILE | B | 358 | 37.714 | 24.398 | 31.779 | 1.00 | 36.14 | B |
| ATOM | 2012 | CB | ILE | B | 358 | 38.370 | 24.085 | 33.142 | 1.00 | 38.47 | B |
| ATOM | 2013 | CG2 | ILE | B | 358 | 37.704 | 24.889 | 34.265 | 1.00 | 36.88 | B |
| ATOM | 2014 | CG1 | ILE | B | 358 | 38.229 | 22.587 | 33.428 | 1.00 | 38.07 | B |
| ATOM | 2015 | CD1 | ILE | B | 358 | 38.777 | 22.153 | 34.780 | 1.00 | 40.74 | B |
| ATOM | 2016 | C | ILE | B | 358 | 37.889 | 25.867 | 31.404 | 1.00 | 36.44 | B |
| ATOM | 2017 | O | ILE | B | 358 | 36.978 | 26.669 | 31.609 | 1.00 | 36.95 | B |
| ATOM | 2018 | N | ASN | B | 359 | 39.044 | 26.218 | 30.836 | 1.00 | 36.91 | B |
| ATOM | 2019 | CA | ASN | B | 359 | 39.267 | 27.597 | 30.399 | 1.00 | 37.87 | B |
| ATOM | 2020 | CB | ASN | B | 359 | 40.710 | 27.840 | 29.937 | 1.00 | 39.61 | B |
| ATOM | 2021 | CG | ASN | B | 359 | 41.702 | 27.781 | 31.064 | 1.00 | 41.84 | B |
| ATOM | 2022 | OD1 | ASN | B | 359 | 41.463 | 28.320 | 32.138 | 1.00 | 43.59 | B |
| ATOM | 2023 | ND2 | ASN | B | 359 | 42.839 | 27.131 | 30.822 | 1.00 | 44.53 | B |
| ATOM | 2024 | C | ASN | B | 359 | 38.334 | 27.861 | 29.223 | 1.00 | 37.46 | B |
| ATOM | 2025 | O | ASN | B | 359 | 37.742 | 28.938 | 29.126 | 1.00 | 38.17 | B |
| ATOM | 2026 | N | TRP | B | 360 | 38.226 | 26.881 | 28.323 | 1.00 | 37.00 | B |
| ATOM | 2027 | CA | TRP | B | 360 | 37.345 | 26.992 | 27.163 | 1.00 | 35.72 | B |
| ATOM | 2028 | CB | TRP | B | 360 | 37.399 | 25.719 | 26.291 | 1.00 | 35.20 | B |
| ATOM | 2029 | CG | TRP | B | 360 | 36.177 | 25.539 | 25.374 | 1.00 | 35.75 | B |
| ATOM | 2030 | CD2 | TRP | B | 360 | 35.021 | 24.710 | 25.620 | 1.00 | 35.68 | B |
| ATOM | 2031 | CE2 | TRP | B | 360 | 34.121 | 24.917 | 24.547 | 1.00 | 35.67 | B |
| ATOM | 2032 | CE3 | TRP | B | 360 | 34.656 | 23.823 | 26.647 | 1.00 | 35.71 | B |
| ATOM | 2033 | CD1 | TRP | B | 360 | 35.932 | 26.183 | 24.191 | 1.00 | 35.52 | B |
| ATOM | 2034 | NE1 | TRP | B | 360 | 34.704 | 25.816 | 23.690 | 1.00 | 34.76 | B |
| ATOM | 2035 | CZ2 | TRP | B | 360 | 32.878 | 24.258 | 24.465 | 1.00 | 35.67 | B |
| ATOM | 2036 | CZ3 | TRP | B | 360 | 33.416 | 23.168 | 26.565 | 1.00 | 36.14 | B |
| ATOM | 2037 | CH2 | TRP | B | 360 | 32.544 | 23.396 | 25.481 | 1.00 | 35.01 | B |
| ATOM | 2038 | C | TRP | B | 360 | 35.923 | 27.198 | 27.665 | 1.00 | 35.46 | B |
| ATOM | 2039 | O | TRP | B | 360 | 35.250 | 28.150 | 27.266 | 1.00 | 34.50 | B |
| ATOM | 2040 | N | ALA | B | 361 | 35.476 | 26.316 | 28.560 | 1.00 | 35.50 | B |
| ATOM | 2041 | CA | ALA | B | 361 | 34.109 | 26.400 | 29.081 | 1.00 | 36.31 | B |
| ATOM | 2042 | CB | ALA | B | 361 | 33.892 | 25.353 | 30.162 | 1.00 | 34.48 | B |
| ATOM | 2043 | C | ALA | B | 361 | 33.749 | 27.780 | 29.616 | 1.00 | 36.81 | B |
| ATOM | 2044 | O | ALA | B | 361 | 32.608 | 28.223 | 29.501 | 1.00 | 38.43 | B |
| ATOM | 2045 | N | LYS | B | 362 | 34.721 | 28.460 | 30.207 | 1.00 | 37.55 | B |
| ATOM | 2046 | CA | LYS | B | 362 | 34.479 | 29.785 | 30.768 | 1.00 | 37.96 | B |
| ATOM | 2047 | CB | LYS | B | 362 | 35.639 | 30.170 | 31.701 | 1.00 | 39.84 | B |
| ATOM | 2048 | CG | LYS | B | 362 | 35.561 | 29.504 | 33.076 | 1.00 | 42.29 | B |
| ATOM | 2049 | CD | LYS | B | 362 | 36.937 | 29.216 | 33.691 | 1.00 | 45.64 | B |
| ATOM | 2050 | CE | LYS | B | 362 | 37.713 | 30.473 | 34.098 | 1.00 | 48.13 | B |
| ATOM | 2051 | NZ | LYS | B | 362 | 39.094 | 30.138 | 34.608 | 1.00 | 48.92 | B |
| ATOM | 2052 | C | LYS | B | 362 | 34.251 | 30.859 | 29.707 | 1.00 | 36.96 | B |
| ATOM | 2053 | O | LYS | B | 362 | 33.437 | 31.749 | 29.902 | 1.00 | 37.29 | B |
| ATOM | 2054 | N | ARG | B | 363 | 34.956 | 30.771 | 28.583 | 0.50 | 35.80 | B |
| ATOM | 2055 | CA | ARG | B | 363 | 34.799 | 31.748 | 27.512 | 0.50 | 34.70 | B |
| ATOM | 2056 | CB | ARG | B | 363 | 36.049 | 31.764 | 26.626 | 0.50 | 34.89 | B |
| ATOM | 2057 | CG | ARG | B | 363 | 37.283 | 32.355 | 27.294 | 0.50 | 34.05 | B |
| ATOM | 2058 | CD | ARG | B | 363 | 38.377 | 32.628 | 26.270 | 0.50 | 33.96 | B |
| ATOM | 2059 | NE | ARG | B | 363 | 37.882 | 33.486 | 25.195 | 0.50 | 34.87 | B |
| ATOM | 2060 | CZ | ARG | B | 363 | 38.604 | 33.872 | 24.147 | 0.50 | 34.29 | B |
| ATOM | 2061 | NH1 | ARG | B | 363 | 39.866 | 33.481 | 24.029 | 0.50 | 32.81 | B |
| ATOM | 2062 | NH2 | ARG | B | 363 | 38.053 | 34.631 | 23.207 | 0.50 | 35.26 | B |
| ATOM | 2063 | C | ARG | B | 363 | 33.553 | 31.510 | 26.649 | 0.50 | 34.84 | B |
| ATOM | 2064 | O | ARG | B | 363 | 33.359 | 32.168 | 25.629 | 0.50 | 34.11 | B |
| ATOM | 2065 | N | VAL | B | 364 | 32.713 | 30.569 | 27.071 | 1.00 | 35.09 | B |
| ATOM | 2066 | CA | VAL | B | 364 | 31.478 | 30.234 | 26.368 | 1.00 | 35.05 | B |
| ATOM | 2067 | CB | VAL | B | 364 | 31.074 | 28.719 | 26.565 | 1.00 | 33.66 | B |
| ATOM | 2068 | CG1 | VAL | B | 364 | 29.680 | 28.469 | 26.070 | 1.00 | 31.72 | B |

TABLE 9-continued

Structure coordinates for ERalpha-LBD/Compound 1 complex
(Table discloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2069 | CG2 | VAL | B | 364 | 32.019 | 27.819 | 25.804 | 1.00 | 33.41 | B |
| ATOM | 2070 | C | VAL | B | 364 | 30.361 | 31.130 | 26.897 | 1.00 | 37.96 | B |
| ATOM | 2071 | O | VAL | B | 364 | 29.977 | 31.060 | 28.070 | 1.00 | 37.31 | B |
| ATOM | 2072 | N | PRO | B | 365 | 29.818 | 31.988 | 26.023 | 1.00 | 39.92 | B |
| ATOM | 2073 | CD | PRO | B | 365 | 30.145 | 32.046 | 24.586 | 1.00 | 39.75 | B |
| ATOM | 2074 | CA | PRO | B | 365 | 28.742 | 32.927 | 26.341 | 1.00 | 40.26 | B |
| ATOM | 2075 | CB | PRO | B | 365 | 28.139 | 33.202 | 24.971 | 1.00 | 40.09 | B |
| ATOM | 2076 | CG | PRO | B | 365 | 29.372 | 33.271 | 24.123 | 1.00 | 39.96 | B |
| ATOM | 2077 | C | PRO | B | 365 | 27.715 | 32.432 | 27.362 | 1.00 | 41.57 | B |
| ATOM | 2078 | O | PRO | B | 365 | 26.957 | 31.494 | 27.104 | 1.00 | 42.64 | B |
| ATOM | 2079 | N | GLY | B | 366 | 27.703 | 33.069 | 28.528 | 1.00 | 42.24 | B |
| ATOM | 2080 | CA | GLY | B | 366 | 26.760 | 32.696 | 29.563 | 1.00 | 42.31 | B |
| ATOM | 2081 | C | GLY | B | 366 | 27.165 | 31.563 | 30.487 | 1.00 | 43.55 | B |
| ATOM | 2082 | O | GLY | B | 366 | 26.481 | 31.336 | 31.482 | 1.00 | 42.94 | B |
| ATOM | 2083 | N | PHE | B | 367 | 28.248 | 30.843 | 30.191 | 1.00 | 44.82 | B |
| ATOM | 2084 | CA | PHE | B | 367 | 28.632 | 29.752 | 31.083 | 1.00 | 46.01 | B |
| ATOM | 2085 | CB | PHE | B | 367 | 29.818 | 28.948 | 30.554 | 1.00 | 45.17 | B |
| ATOM | 2086 | CG | PHE | B | 367 | 30.166 | 27.767 | 31.422 | 1.00 | 44.50 | B |
| ATOM | 2087 | CD1 | PHE | B | 367 | 29.346 | 26.641 | 31.455 | 1.00 | 44.34 | B |
| ATOM | 2088 | CD2 | PHE | B | 367 | 31.293 | 27.789 | 32.238 | 1.00 | 44.86 | B |
| ATOM | 2089 | CE1 | PHE | B | 367 | 29.644 | 25.554 | 32.289 | 1.00 | 43.06 | B |
| ATOM | 2090 | CE2 | PHE | B | 367 | 31.598 | 26.704 | 33.077 | 1.00 | 43.92 | B |
| ATOM | 2091 | CZ | PHE | B | 367 | 30.769 | 25.588 | 33.098 | 1.00 | 42.74 | B |
| ATOM | 2092 | C | PHE | B | 367 | 28.989 | 30.294 | 32.455 | 1.00 | 47.78 | B |
| ATOM | 2093 | O | PHE | B | 367 | 28.540 | 29.762 | 33.463 | 1.00 | 47.22 | B |
| ATOM | 2094 | N | VAL | B | 368 | 29.792 | 31.355 | 32.495 | 1.00 | 49.43 | B |
| ATOM | 2095 | CA | VAL | B | 368 | 30.180 | 31.945 | 33.770 | 1.00 | 51.80 | B |
| ATOM | 2096 | CB | VAL | B | 368 | 31.253 | 33.041 | 33.592 | 1.00 | 52.02 | B |
| ATOM | 2097 | CG1 | VAL | B | 368 | 32.423 | 32.491 | 32.800 | 1.00 | 52.53 | B |
| ATOM | 2098 | CG2 | VAL | B | 368 | 30.655 | 34.260 | 32.912 | 1.00 | 52.61 | B |
| ATOM | 2099 | C | VAL | B | 368 | 28.991 | 32.548 | 34.524 | 1.00 | 53.19 | B |
| ATOM | 2100 | O | VAL | B | 368 | 28.982 | 32.571 | 35.756 | 1.00 | 54.40 | B |
| ATOM | 2101 | N | ASP | B | 369 | 27.984 | 33.028 | 33.799 | 1.00 | 54.10 | B |
| ATOM | 2102 | CA | ASP | B | 369 | 26.821 | 33.623 | 34.455 | 1.00 | 54.70 | B |
| ATOM | 2103 | CB | ASP | B | 369 | 25.881 | 34.245 | 33.420 | 1.00 | 56.11 | B |
| ATOM | 2104 | CG | ASP | B | 369 | 26.574 | 35.304 | 32.576 | 1.00 | 58.40 | B |
| ATOM | 2105 | OD1 | ASP | B | 369 | 27.344 | 36.106 | 33.153 | 1.00 | 58.90 | B |
| ATOM | 2106 | OD2 | ASP | B | 369 | 26.350 | 35.340 | 31.344 | 1.00 | 60.00 | B |
| ATOM | 2107 | C | ASP | B | 369 | 26.078 | 32.598 | 35.301 | 1.00 | 54.25 | B |
| ATOM | 2108 | O | ASP | B | 369 | 25.110 | 32.923 | 35.986 | 1.00 | 54.44 | B |
| ATOM | 2109 | N | LEU | B | 370 | 26.544 | 31.356 | 35.254 | 1.00 | 53.65 | B |
| ATOM | 2110 | CA | LEU | B | 370 | 25.940 | 30.284 | 36.034 | 1.00 | 53.03 | B |
| ATOM | 2111 | CB | LEU | B | 370 | 26.197 | 28.925 | 35.367 | 1.00 | 53.76 | B |
| ATOM | 2112 | CG | LEU | B | 370 | 25.551 | 28.609 | 34.013 | 1.00 | 54.86 | B |
| ATOM | 2113 | CD1 | LEU | B | 370 | 26.219 | 27.385 | 33.381 | 1.00 | 53.87 | B |
| ATOM | 2114 | CD2 | LEU | B | 370 | 24.061 | 28.377 | 34.213 | 1.00 | 54.84 | B |
| ATOM | 2115 | C | LEU | B | 370 | 26.546 | 30.262 | 37.438 | 1.00 | 52.27 | B |
| ATOM | 2116 | O | LEU | B | 370 | 27.588 | 30.876 | 37.700 | 1.00 | 51.82 | B |
| ATOM | 2117 | N | THR | B | 371 | 25.880 | 29.553 | 38.339 | 1.00 | 50.82 | B |
| ATOM | 2118 | CA | THR | B | 371 | 26.370 | 29.412 | 39.695 | 1.00 | 49.47 | B |
| ATOM | 2119 | CB | THR | B | 371 | 25.375 | 28.665 | 40.585 | 1.00 | 49.14 | B |
| ATOM | 2120 | OG1 | THR | B | 371 | 25.308 | 27.300 | 40.159 | 1.00 | 48.40 | B |
| ATOM | 2121 | CG2 | THR | B | 371 | 23.982 | 29.301 | 40.502 | 1.00 | 48.68 | B |
| ATOM | 2122 | C | THR | B | 371 | 27.607 | 28.540 | 39.562 | 1.00 | 49.31 | B |
| ATOM | 2123 | O | THR | B | 371 | 27.702 | 27.730 | 38.637 | 1.00 | 49.43 | B |
| ATOM | 2124 | N | LEU | B | 372 | 28.552 | 28.700 | 40.479 | 1.00 | 48.71 | B |
| ATOM | 2125 | CA | LEU | B | 372 | 29.772 | 27.911 | 40.443 | 1.00 | 48.00 | B |
| ATOM | 2126 | CB | LEU | B | 372 | 30.693 | 28.310 | 41.603 | 1.00 | 47.96 | B |
| ATOM | 2127 | CG | LEU | B | 372 | 32.016 | 27.540 | 41.691 | 1.00 | 47.81 | B |
| ATOM | 2128 | CD1 | LEU | B | 372 | 32.784 | 27.688 | 40.384 | 1.00 | 47.52 | B |
| ATOM | 2129 | CD2 | LEU | B | 372 | 32.837 | 28.051 | 42.863 | 1.00 | 47.47 | B |
| ATOM | 2130 | C | LEU | B | 372 | 29.433 | 26.425 | 40.525 | 1.00 | 46.91 | B |
| ATOM | 2131 | O | LEU | B | 372 | 30.057 | 25.591 | 39.874 | 1.00 | 46.14 | B |
| ATOM | 2132 | N | HIS | B | 373 | 28.429 | 26.103 | 41.326 | 1.00 | 46.94 | B |
| ATOM | 2133 | CA | HIS | B | 373 | 28.010 | 24.720 | 41.477 | 1.00 | 48.26 | B |
| ATOM | 2134 | CB | HIS | B | 373 | 26.943 | 24.608 | 42.573 | 1.00 | 49.21 | B |
| ATOM | 2135 | CG | HIS | B | 373 | 26.573 | 23.198 | 42.917 | 1.00 | 50.49 | B |
| ATOM | 2136 | CD2 | HIS | B | 373 | 27.203 | 22.024 | 42.674 | 1.00 | 50.73 | B |
| ATOM | 2137 | ND1 | HIS | B | 373 | 25.417 | 22.878 | 43.597 | 1.00 | 51.21 | B |
| ATOM | 2138 | CE1 | HIS | B | 373 | 25.349 | 21.568 | 43.754 | 1.00 | 51.37 | B |
| ATOM | 2139 | NE2 | HIS | B | 373 | 26.420 | 21.026 | 43.203 | 1.00 | 51.28 | B |
| ATOM | 2140 | C | HIS | B | 373 | 27.465 | 24.153 | 40.160 | 1.00 | 48.48 | B |
| ATOM | 2141 | O | HIS | B | 373 | 27.737 | 22.997 | 39.824 | 1.00 | 48.94 | B |
| ATOM | 2142 | N | ASP | B | 374 | 26.707 | 24.959 | 39.413 | 1.00 | 47.89 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2143 | CA | ASP | B | 374 | 26.140 | 24.493 | 38.145 | 1.00 | 47.42 | B |
| ATOM | 2144 | CB | ASP | B | 374 | 25.143 | 25.512 | 37.560 | 1.00 | 48.13 | B |
| ATOM | 2145 | CG | ASP | B | 374 | 23.814 | 25.548 | 38.321 | 1.00 | 49.42 | B |
| ATOM | 2146 | OD1 | ASP | B | 374 | 23.474 | 24.540 | 38.995 | 1.00 | 48.94 | B |
| ATOM | 2147 | OD2 | ASP | B | 374 | 23.105 | 26.579 | 38.228 | 1.00 | 48.29 | B |
| ATOM | 2148 | C | ASP | B | 374 | 27.233 | 24.209 | 37.121 | 1.00 | 46.36 | B |
| ATOM | 2149 | O | ASP | B | 374 | 27.214 | 23.176 | 36.442 | 1.00 | 46.10 | B |
| ATOM | 2150 | N | GLN | B | 375 | 28.188 | 25.126 | 37.017 | 1.00 | 44.57 | B |
| ATOM | 2151 | CA | GLN | B | 375 | 29.283 | 24.970 | 36.071 | 1.00 | 42.61 | B |
| ATOM | 2152 | CB | GLN | B | 375 | 30.222 | 26.167 | 36.193 | 1.00 | 42.16 | B |
| ATOM | 2153 | CG | GLN | B | 375 | 29.478 | 27.492 | 36.198 | 1.00 | 43.04 | B |
| ATOM | 2154 | CD | GLN | B | 375 | 30.407 | 28.696 | 36.239 | 1.00 | 43.70 | B |
| ATOM | 2155 | OE1 | GLN | B | 375 | 31.577 | 28.571 | 36.579 | 1.00 | 45.66 | B |
| ATOM | 2156 | NE2 | GLN | B | 375 | 29.883 | 29.869 | 35.906 | 1.00 | 43.04 | B |
| ATOM | 2157 | C | GLN | B | 375 | 30.020 | 23.653 | 36.338 | 1.00 | 41.32 | B |
| ATOM | 2158 | O | GLN | B | 375 | 30.356 | 22.914 | 35.409 | 1.00 | 39.93 | B |
| ATOM | 2159 | N | VAL | B | 376 | 30.249 | 23.360 | 37.616 | 1.00 | 40.71 | B |
| ATOM | 2160 | CA | VAL | B | 376 | 30.928 | 22.128 | 38.017 | 1.00 | 39.56 | B |
| ATOM | 2161 | CB | VAL | B | 376 | 31.174 | 22.100 | 39.557 | 1.00 | 39.78 | B |
| ATOM | 2162 | CG1 | VAL | B | 376 | 31.583 | 20.709 | 40.007 | 1.00 | 39.54 | B |
| ATOM | 2163 | CG2 | VAL | B | 376 | 32.265 | 23.092 | 39.928 | 1.00 | 40.21 | B |
| ATOM | 2164 | C | VAL | B | 376 | 30.098 | 20.905 | 37.609 | 1.00 | 38.89 | B |
| ATOM | 2165 | O | VAL | B | 376 | 30.632 | 19.866 | 37.217 | 1.00 | 37.34 | B |
| ATOM | 2166 | N | HIS | B | 377 | 28.783 | 21.034 | 37.689 | 1.00 | 38.79 | B |
| ATOM | 2167 | CA | HIS | B | 377 | 27.948 | 19.913 | 37.327 | 1.00 | 38.58 | B |
| ATOM | 2168 | CB | HIS | B | 377 | 26.516 | 20.131 | 37.801 | 1.00 | 40.44 | B |
| ATOM | 2169 | CG | HIS | B | 377 | 25.677 | 18.895 | 37.711 | 1.00 | 43.65 | B |
| ATOM | 2170 | CD2 | HIS | B | 377 | 24.524 | 18.640 | 37.047 | 1.00 | 43.13 | B |
| ATOM | 2171 | ND1 | HIS | B | 377 | 26.031 | 17.715 | 38.331 | 1.00 | 43.90 | B |
| ATOM | 2172 | CE1 | HIS | B | 377 | 25.130 | 16.789 | 38.058 | 1.00 | 43.83 | B |
| ATOM | 2173 | NE2 | HIS | B | 377 | 24.204 | 17.325 | 37.281 | 1.00 | 44.98 | B |
| ATOM | 2174 | C | HIS | B | 377 | 27.974 | 19.664 | 35.821 | 1.00 | 38.04 | B |
| ATOM | 2175 | O | HIS | B | 377 | 28.121 | 18.514 | 35.380 | 1.00 | 38.07 | B |
| ATOM | 2176 | N | LEU | B | 378 | 27.832 | 20.735 | 35.039 | 1.00 | 35.98 | B |
| ATOM | 2177 | CA | LEU | B | 378 | 27.852 | 20.626 | 33.585 | 1.00 | 34.59 | B |
| ATOM | 2178 | CB | LEU | B | 378 | 27.635 | 21.999 | 32.931 | 1.00 | 33.19 | B |
| ATOM | 2179 | CG | LEU | B | 378 | 26.264 | 22.652 | 33.156 | 1.00 | 34.46 | B |
| ATOM | 2180 | CD1 | LEU | B | 378 | 26.169 | 23.920 | 32.329 | 1.00 | 33.64 | B |
| ATOM | 2181 | CD2 | LEU | B | 378 | 25.131 | 21.691 | 32.784 | 1.00 | 34.29 | B |
| ATOM | 2182 | C | LEU | B | 378 | 29.171 | 20.023 | 33.109 | 1.00 | 33.99 | B |
| ATOM | 2183 | O | LEU | B | 378 | 29.190 | 19.111 | 32.295 | 1.00 | 33.31 | B |
| ATOM | 2184 | N | LEU | B | 379 | 30.282 | 20.537 | 33.618 | 1.00 | 35.12 | B |
| ATOM | 2185 | CA | LEU | B | 379 | 31.575 | 20.008 | 33.215 | 1.00 | 35.52 | B |
| ATOM | 2186 | CB | LEU | B | 379 | 32.700 | 20.851 | 33.805 | 1.00 | 34.33 | B |
| ATOM | 2187 | CG | LEU | B | 379 | 32.950 | 22.104 | 32.968 | 1.00 | 34.14 | B |
| ATOM | 2188 | CD1 | LEU | B | 379 | 33.902 | 23.046 | 33.684 | 1.00 | 33.22 | B |
| ATOM | 2189 | CD2 | LEU | B | 379 | 33.503 | 21.681 | 31.611 | 1.00 | 32.36 | B |
| ATOM | 2190 | C | LEU | B | 379 | 31.708 | 18.561 | 33.649 | 1.00 | 35.89 | B |
| ATOM | 2191 | O | LEU | B | 379 | 32.215 | 17.722 | 32.907 | 1.00 | 36.10 | B |
| ATOM | 2192 | N | GLU | B | 380 | 31.236 | 18.269 | 34.851 | 1.00 | 36.49 | B |
| ATOM | 2193 | CA | GLU | B | 380 | 31.297 | 16.917 | 35.364 | 1.00 | 37.51 | B |
| ATOM | 2194 | CB | GLU | B | 380 | 30.689 | 16.872 | 36.742 | 1.00 | 38.95 | B |
| ATOM | 2195 | CG | GLU | B | 380 | 30.943 | 15.589 | 37.449 | 1.00 | 42.98 | B |
| ATOM | 2196 | CD | GLU | B | 380 | 31.055 | 15.813 | 38.932 | 1.00 | 44.83 | B |
| ATOM | 2197 | OE1 | GLU | B | 380 | 30.247 | 16.617 | 39.455 | 1.00 | 45.31 | B |
| ATOM | 2198 | OE2 | GLU | B | 380 | 31.942 | 15.192 | 39.563 | 1.00 | 46.46 | B |
| ATOM | 2199 | C | GLU | B | 380 | 30.559 | 15.942 | 34.453 | 1.00 | 37.37 | B |
| ATOM | 2200 | O | GLU | B | 380 | 31.064 | 14.850 | 34.155 | 1.00 | 36.98 | B |
| ATOM | 2201 | N | CYS | B | 381 | 29.371 | 16.347 | 34.004 | 1.00 | 36.36 | B |
| ATOM | 2202 | CA | CYS | B | 381 | 28.557 | 15.513 | 33.131 | 1.00 | 35.26 | B |
| ATOM | 2203 | CB | CYS | B | 381 | 27.109 | 15.992 | 33.141 | 1.00 | 35.90 | B |
| ATOM | 2204 | SG | CYS | B | 381 | 26.271 | 15.936 | 34.724 | 1.00 | 39.26 | B |
| ATOM | 2205 | C | CYS | B | 381 | 29.001 | 15.420 | 31.668 | 1.00 | 34.29 | B |
| ATOM | 2206 | O | CYS | B | 381 | 28.791 | 14.395 | 31.036 | 1.00 | 33.40 | B |
| ATOM | 2207 | N | ALA | B | 382 | 29.644 | 16.456 | 31.134 | 1.00 | 33.27 | B |
| ATOM | 2208 | CA | ALA | B | 382 | 29.995 | 16.438 | 29.713 | 1.00 | 31.27 | B |
| ATOM | 2209 | CB | ALA | B | 382 | 29.404 | 17.681 | 29.049 | 1.00 | 32.56 | B |
| ATOM | 2210 | C | ALA | B | 382 | 31.434 | 16.297 | 29.250 | 1.00 | 31.32 | B |
| ATOM | 2211 | O | ALA | B | 382 | 31.659 | 16.148 | 28.040 | 1.00 | 31.43 | B |
| ATOM | 2212 | N | TRP | B | 383 | 32.402 | 16.307 | 30.163 | 1.00 | 28.51 | B |
| ATOM | 2213 | CA | TRP | B | 383 | 33.792 | 16.293 | 29.721 | 1.00 | 26.37 | B |
| ATOM | 2214 | CB | TRP | B | 383 | 34.747 | 16.191 | 30.923 | 1.00 | 26.63 | B |
| ATOM | 2215 | CG | TRP | B | 383 | 34.657 | 14.895 | 31.679 | 1.00 | 26.64 | B |
| ATOM | 2216 | CD2 | TRP | B | 383 | 35.451 | 13.718 | 31.459 | 1.00 | 24.59 | B |

TABLE 9-continued

Structure coordinates for ERalpha-LBD/Compound 1 complex
(Table dicloses SEQ ID NOS 2-8, respectively, in order of appearance)

|   | # | Name | Res. | Chain | Res # | X | Y | Z | occ | B | SegID |
|---|---|---|---|---|---|---|---|---|---|---|---|
| ATOM | 2217 | CE2 | TRP | B | 383 | 35.006 | 12.738 | 32.378 | 1.00 | 24.64 | B |
| ATOM | 2218 | CE3 | TRP | B | 383 | 36.501 | 13.401 | 30.580 | 1.00 | 24.18 | B |
| ATOM | 2219 | CD1 | TRP | B | 383 | 33.784 | 14.588 | 32.686 | 1.00 | 25.63 | B |
| ATOM | 2220 | NE1 | TRP | B | 383 | 33.988 | 13.296 | 33.108 | 1.00 | 26.24 | B |
| ATOM | 2221 | CZ2 | TRP | B | 383 | 35.571 | 11.446 | 32.443 | 1.00 | 23.56 | B |
| ATOM | 2222 | CZ3 | TRP | B | 383 | 37.067 | 12.118 | 30.645 | 1.00 | 24.20 | B |
| ATOM | 2223 | CH2 | TRP | B | 383 | 36.598 | 11.156 | 31.578 | 1.00 | 22.87 | B |
| ATOM | 2224 | C | TRP | B | 383 | 34.167 | 15.273 | 28.647 | 1.00 | 25.43 | B |
| ATOM | 2225 | O | TRP | B | 383 | 34.838 | 15.616 | 27.669 | 1.00 | 23.26 | B |
| ATOM | 2226 | N | LEU | B | 384 | 33.723 | 14.030 | 28.807 | 1.00 | 26.18 | B |
| ATOM | 2227 | CA | LEU | B | 384 | 34.066 | 12.991 | 27.840 | 1.00 | 24.94 | B |
| ATOM | 2228 | CB | LEU | B | 384 | 33.783 | 11.604 | 28.431 | 1.00 | 25.45 | B |
| ATOM | 2229 | CG | LEU | B | 384 | 34.334 | 10.434 | 27.607 | 1.00 | 26.24 | B |
| ATOM | 2230 | CD1 | LEU | B | 384 | 35.866 | 10.494 | 27.558 | 1.00 | 25.22 | B |
| ATOM | 2231 | CD2 | LEU | B | 384 | 33.850 | 9.117 | 28.205 | 1.00 | 26.73 | B |
| ATOM | 2232 | C | LEU | B | 384 | 33.336 | 13.197 | 26.504 | 1.00 | 25.04 | B |
| ATOM | 2233 | O | LEU | B | 384 | 33.898 | 12.948 | 25.450 | 1.00 | 24.32 | B |
| ATOM | 2234 | N | GLU | B | 385 | 32.083 | 13.642 | 26.541 | 1.00 | 25.27 | B |
| ATOM | 2235 | CA | GLU | B | 385 | 31.372 | 13.923 | 25.302 | 1.00 | 25.78 | B |
| ATOM | 2236 | CB | GLU | B | 385 | 29.974 | 14.467 | 25.591 | 1.00 | 27.71 | B |
| ATOM | 2237 | CG | GLU | B | 385 | 28.934 | 13.434 | 25.967 | 1.00 | 29.44 | B |
| ATOM | 2238 | CD | GLU | B | 385 | 27.600 | 14.066 | 26.324 | 1.00 | 31.23 | B |
| ATOM | 2239 | OE1 | GLU | B | 385 | 27.427 | 14.490 | 27.491 | 1.00 | 33.24 | B |
| ATOM | 2240 | OE2 | GLU | B | 385 | 26.723 | 14.157 | 25.434 | 1.00 | 31.81 | B |
| ATOM | 2241 | C | GLU | B | 385 | 32.187 | 15.006 | 24.567 | 1.00 | 26.44 | B |
| ATOM | 2242 | O | GLU | B | 385 | 32.376 | 14.956 | 23.341 | 1.00 | 24.18 | B |
| ATOM | 2243 | N | ILE | B | 386 | 32.671 | 15.976 | 25.345 | 1.00 | 26.60 | B |
| ATOM | 2244 | CA | ILE | B | 386 | 33.457 | 17.082 | 24.814 | 1.00 | 26.22 | B |
| ATOM | 2245 | CB | ILE | B | 386 | 33.687 | 18.160 | 25.881 | 1.00 | 27.43 | B |
| ATOM | 2246 | CG2 | ILE | B | 386 | 34.568 | 19.277 | 25.320 | 1.00 | 27.11 | B |
| ATOM | 2247 | CG1 | ILE | B | 386 | 32.335 | 18.719 | 26.315 | 1.00 | 27.24 | B |
| ATOM | 2248 | CD1 | ILE | B | 386 | 32.403 | 19.723 | 27.385 | 1.00 | 30.37 | B |
| ATOM | 2249 | C | ILE | B | 386 | 34.787 | 16.652 | 24.233 | 1.00 | 26.29 | B |
| ATOM | 2250 | O | ILE | B | 386 | 35.158 | 17.109 | 23.157 | 1.00 | 25.33 | B |
| ATOM | 2251 | N | LEU | B | 387 | 35.505 | 15.772 | 24.924 | 1.00 | 27.46 | B |
| ATOM | 2252 | CA | LEU | B | 387 | 36.787 | 15.304 | 24.396 | 1.00 | 28.32 | B |
| ATOM | 2253 | CB | LEU | B | 387 | 37.501 | 14.395 | 25.393 | 1.00 | 27.23 | B |
| ATOM | 2254 | CG | LEU | B | 387 | 38.041 | 15.099 | 26.634 | 1.00 | 28.34 | B |
| ATOM | 2255 | CD1 | LEU | B | 387 | 38.774 | 14.082 | 27.515 | 1.00 | 25.11 | B |
| ATOM | 2256 | CD2 | LEU | B | 387 | 38.957 | 16.252 | 26.207 | 1.00 | 25.11 | B |
| ATOM | 2257 | C | LEU | B | 387 | 36.527 | 14.532 | 23.115 | 1.00 | 29.76 | B |
| ATOM | 2258 | O | LEU | B | 387 | 37.245 | 14.684 | 22.121 | 1.00 | 30.33 | B |
| ATOM | 2259 | N | MET | B | 388 | 35.482 | 13.712 | 23.151 | 1.00 | 31.29 | B |
| ATOM | 2260 | CA | MET | B | 388 | 35.087 | 12.889 | 22.016 | 1.00 | 32.05 | B |
| ATOM | 2261 | CB | MET | B | 388 | 33.946 | 11.958 | 22.426 | 1.00 | 33.40 | B |
| ATOM | 2262 | CG | MET | B | 388 | 34.339 | 10.934 | 23.490 | 1.00 | 34.81 | B |
| ATOM | 2263 | SD | MET | B | 388 | 33.021 | 9.700 | 23.828 | 1.00 | 37.10 | B |
| ATOM | 2264 | CE | MET | B | 388 | 33.999 | 8.237 | 23.858 | 1.00 | 35.72 | B |
| ATOM | 2265 | C | MET | B | 388 | 34.694 | 13.685 | 20.763 | 1.00 | 31.99 | B |
| ATOM | 2266 | O | MET | B | 388 | 35.197 | 13.407 | 19.686 | 1.00 | 32.76 | B |
| ATOM | 2267 | N | ILE | B | 389 | 33.809 | 14.670 | 20.878 | 1.00 | 31.96 | B |
| ATOM | 2268 | CA | ILE | B | 389 | 33.461 | 15.421 | 19.684 | 1.00 | 31.56 | B |
| ATOM | 2269 | CB | ILE | B | 389 | 32.337 | 16.481 | 19.943 | 1.00 | 31.58 | B |
| ATOM | 2270 | CG2 | ILE | B | 389 | 32.871 | 17.668 | 20.748 | 1.00 | 30.55 | B |
| ATOM | 2271 | CG1 | ILE | B | 389 | 31.757 | 16.939 | 18.584 | 1.00 | 32.03 | B |
| ATOM | 2272 | CD1 | ILE | B | 389 | 30.470 | 17.779 | 18.653 | 1.00 | 28.96 | B |
| ATOM | 2273 | C | ILE | B | 389 | 34.738 | 16.080 | 19.142 | 1.00 | 32.92 | B |
| ATOM | 2274 | O | ILE | B | 389 | 34.897 | 16.241 | 17.934 | 1.00 | 32.48 | B |
| ATOM | 2275 | N | GLY | B | 390 | 35.658 | 16.430 | 20.040 | 1.00 | 32.96 | B |
| ATOM | 2276 | CA | GLY | B | 390 | 36.907 | 17.024 | 19.610 | 1.00 | 33.32 | B |
| ATOM | 2277 | C | GLY | B | 390 | 37.703 | 15.993 | 18.826 | 1.00 | 34.52 | B |
| ATOM | 2278 | O | GLY | B | 390 | 38.242 | 16.281 | 17.756 | 1.00 | 32.45 | B |
| ATOM | 2279 | N | LEU | B | 391 | 37.770 | 14.778 | 19.367 | 1.00 | 36.17 | B |
| ATOM | 2280 | CA | LEU | B | 391 | 38.483 | 13.671 | 18.725 | 1.00 | 37.30 | B |
| ATOM | 2281 | CB | LEU | B | 391 | 38.345 | 12.396 | 19.568 | 1.00 | 35.96 | B |
| ATOM | 2282 | CG | LEU | B | 391 | 38.907 | 11.081 | 19.006 | 1.00 | 35.76 | B |
| ATOM | 2283 | CD1 | LEU | B | 391 | 40.420 | 11.120 | 18.971 | 1.00 | 33.35 | B |
| ATOM | 2284 | CD2 | LEU | B | 391 | 38.431 | 9.923 | 19.856 | 1.00 | 33.60 | B |
| ATOM | 2285 | C | LEU | B | 391 | 37.895 | 13.424 | 17.337 | 1.00 | 39.14 | B |
| ATOM | 2286 | O | LEU | B | 391 | 38.600 | 13.462 | 16.328 | 1.00 | 39.48 | B |
| ATOM | 2287 | N | VAL | B | 392 | 36.592 | 13.186 | 17.302 | 1.00 | 40.69 | B |
| ATOM | 2288 | CA | VAL | B | 392 | 35.885 | 12.933 | 16.057 | 1.00 | 43.81 | B |
| ATOM | 2289 | CB | VAL | B | 392 | 34.360 | 12.830 | 16.313 | 1.00 | 44.30 | B |
| ATOM | 2290 | CG1 | VAL | B | 392 | 33.594 | 12.919 | 15.010 | 1.00 | 45.12 | B |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 2291 | CG2 | VAL | B | 392 | 34.049 | 11.505 | 17.005 | 1.00 | 44.33 | B |
| ATOM | 2292 | C | VAL | B | 392 | 36.169 | 13.990 | 14.993 | 1.00 | 45.31 | B |
| ATOM | 2293 | O | VAL | B | 392 | 36.446 | 13.652 | 13.840 | 1.00 | 44.71 | B |
| ATOM | 2294 | N | TRP | B | 393 | 36.102 | 15.264 | 15.380 | 1.00 | 47.65 | B |
| ATOM | 2295 | CA | TRP | B | 393 | 36.359 | 16.371 | 14.450 | 1.00 | 50.23 | B |
| ATOM | 2296 | CB | TRP | B | 393 | 35.952 | 17.700 | 15.108 | 1.00 | 50.25 | B |
| ATOM | 2297 | CG | TRP | B | 393 | 36.540 | 18.946 | 14.500 | 1.00 | 51.71 | B |
| ATOM | 2298 | CD2 | TRP | B | 393 | 35.988 | 19.732 | 13.433 | 1.00 | 53.20 | B |
| ATOM | 2299 | CE2 | TRP | B | 393 | 36.857 | 20.834 | 13.232 | 1.00 | 53.86 | B |
| ATOM | 2300 | CE3 | TRP | B | 393 | 34.844 | 19.615 | 12.626 | 1.00 | 53.80 | B |
| ATOM | 2301 | CD1 | TRP | B | 393 | 37.689 | 19.584 | 14.887 | 1.00 | 52.43 | B |
| ATOM | 2302 | NE1 | TRP | B | 393 | 37.884 | 20.718 | 14.133 | 1.00 | 52.79 | B |
| ATOM | 2303 | CZ2 | TRP | B | 393 | 36.615 | 21.816 | 12.253 | 1.00 | 53.74 | B |
| ATOM | 2304 | CZ3 | TRP | B | 393 | 34.603 | 20.589 | 11.657 | 1.00 | 54.33 | B |
| ATOM | 2305 | CH2 | TRP | B | 393 | 35.488 | 21.676 | 11.480 | 1.00 | 54.26 | B |
| ATOM | 2306 | C | TRP | B | 393 | 37.811 | 16.424 | 13.940 | 1.00 | 51.46 | B |
| ATOM | 2307 | O | TRP | B | 393 | 38.059 | 16.799 | 12.789 | 1.00 | 51.15 | B |
| ATOM | 2308 | N | ARG | B | 394 | 38.756 | 16.038 | 14.796 | 1.00 | 52.45 | B |
| ATOM | 2309 | CA | ARG | B | 394 | 40.169 | 16.024 | 14.441 | 1.00 | 53.58 | B |
| ATOM | 2310 | CB | ARG | B | 394 | 41.043 | 15.786 | 15.676 | 1.00 | 53.45 | B |
| ATOM | 2311 | CG | ARG | B | 394 | 41.232 | 16.964 | 16.607 | 1.00 | 52.33 | B |
| ATOM | 2312 | CD | ARG | B | 394 | 42.105 | 16.531 | 17.777 | 1.00 | 52.00 | B |
| ATOM | 2313 | NE | ARG | B | 394 | 41.353 | 16.471 | 19.030 | 1.00 | 52.62 | B |
| ATOM | 2314 | CZ | ARG | B | 394 | 41.464 | 15.494 | 19.924 | 1.00 | 52.88 | B |
| ATOM | 2315 | NH1 | ARG | B | 394 | 42.288 | 14.478 | 19.716 | 1.00 | 53.33 | B |
| ATOM | 2316 | NH2 | ARG | B | 394 | 40.756 | 15.538 | 21.036 | 1.00 | 53.88 | B |
| ATOM | 2317 | C | ARG | B | 394 | 40.479 | 14.919 | 13.444 | 1.00 | 55.07 | B |
| ATOM | 2318 | O | ARG | B | 394 | 41.263 | 15.115 | 12.518 | 1.00 | 55.33 | B |
| ATOM | 2319 | N | SER | B | 395 | 39.871 | 13.753 | 13.647 | 1.00 | 56.55 | B |
| ATOM | 2320 | CA | SER | B | 395 | 40.108 | 12.599 | 12.782 | 1.00 | 57.28 | B |
| ATOM | 2321 | CB | SER | B | 395 | 40.002 | 11.319 | 13.603 | 1.00 | 57.10 | B |
| ATOM | 2322 | OG | SER | B | 395 | 39.249 | 11.548 | 14.777 | 1.00 | 57.37 | B |
| ATOM | 2323 | C | SER | B | 395 | 39.189 | 12.516 | 11.578 | 1.00 | 58.02 | B |
| ATOM | 2324 | O | SER | B | 395 | 39.087 | 11.471 | 10.938 | 1.00 | 57.97 | B |
| ATOM | 2325 | N | MET | B | 396 | 38.537 | 13.627 | 11.264 | 1.00 | 59.52 | B |
| ATOM | 2326 | CA | MET | B | 396 | 37.619 | 13.686 | 10.135 | 1.00 | 61.58 | B |
| ATOM | 2327 | CB | MET | B | 396 | 36.943 | 15.054 | 10.101 | 1.00 | 61.26 | B |
| ATOM | 2328 | CG | MET | B | 396 | 35.559 | 15.044 | 9.502 | 1.00 | 61.96 | B |
| ATOM | 2329 | SD | MET | B | 396 | 34.732 | 16.615 | 9.750 | 1.00 | 62.40 | B |
| ATOM | 2330 | CE | MET | B | 396 | 34.604 | 16.622 | 11.493 | 1.00 | 62.94 | B |
| ATOM | 2331 | C | MET | B | 396 | 38.321 | 13.418 | 8.801 | 1.00 | 62.97 | B |
| ATOM | 2332 | O | MET | B | 396 | 37.977 | 12.477 | 8.093 | 1.00 | 62.79 | B |
| ATOM | 2333 | N | GLU | B | 397 | 39.306 | 14.244 | 8.462 | 1.00 | 64.97 | B |
| ATOM | 2334 | CA | GLU | B | 397 | 40.041 | 14.080 | 7.209 | 1.00 | 66.74 | B |
| ATOM | 2335 | CB | GLU | B | 397 | 40.898 | 15.310 | 6.923 | 1.00 | 68.00 | B |
| ATOM | 2336 | CG | GLU | B | 397 | 40.528 | 16.523 | 7.727 | 1.00 | 71.05 | B |
| ATOM | 2337 | CD | GLU | B | 397 | 41.680 | 17.495 | 7.848 | 1.00 | 73.00 | B |
| ATOM | 2338 | OE1 | GLU | B | 397 | 42.743 | 17.089 | 8.375 | 1.00 | 73.30 | B |
| ATOM | 2339 | OE2 | GLU | B | 397 | 41.519 | 18.659 | 7.413 | 1.00 | 74.40 | B |
| ATOM | 2340 | C | GLU | B | 397 | 40.969 | 12.863 | 7.255 | 1.00 | 67.19 | B |
| ATOM | 2341 | O | GLU | B | 397 | 41.881 | 12.754 | 6.436 | 1.00 | 67.30 | B |
| ATOM | 2342 | N | HIS | B | 398 | 40.747 | 11.962 | 8.211 | 1.00 | 67.21 | B |
| ATOM | 2343 | CA | HIS | B | 398 | 41.574 | 10.764 | 8.349 | 1.00 | 67.02 | B |
| ATOM | 2344 | CB | HIS | B | 398 | 42.431 | 10.840 | 9.609 | 1.00 | 66.23 | B |
| ATOM | 2345 | CG | HIS | B | 398 | 43.263 | 12.081 | 9.704 | 1.00 | 66.43 | B |
| ATOM | 2346 | CD2 | HIS | B | 398 | 44.606 | 12.254 | 9.746 | 1.00 | 65.59 | B |
| ATOM | 2347 | ND1 | HIS | B | 398 | 42.713 | 13.344 | 9.770 | 1.00 | 65.99 | B |
| ATOM | 2348 | CE1 | HIS | B | 398 | 43.680 | 14.240 | 9.847 | 1.00 | 65.59 | B |
| ATOM | 2349 | NE2 | HIS | B | 398 | 44.838 | 13.605 | 9.834 | 1.00 | 65.75 | B |
| ATOM | 2350 | C | HIS | B | 398 | 40.697 | 9.521 | 8.427 | 1.00 | 68.18 | B |
| ATOM | 2351 | O | HIS | B | 398 | 40.499 | 8.952 | 9.502 | 1.00 | 68.14 | B |
| ATOM | 2352 | N | PRO | B | 399 | 40.160 | 9.082 | 7.278 | 1.00 | 68.51 | B |
| ATOM | 2353 | CD | PRO | B | 399 | 40.336 | 9.705 | 5.953 | 1.00 | 68.40 | B |
| ATOM | 2354 | CA | PRO | B | 399 | 39.293 | 7.898 | 7.197 | 1.00 | 68.76 | B |
| ATOM | 2355 | CB | PRO | B | 399 | 39.081 | 7.732 | 5.693 | 1.00 | 69.20 | B |
| ATOM | 2356 | CG | PRO | B | 399 | 39.170 | 9.153 | 5.178 | 1.00 | 68.88 | B |
| ATOM | 2357 | C | PRO | B | 399 | 39.922 | 6.655 | 7.816 | 1.00 | 68.97 | B |
| ATOM | 2358 | O | PRO | B | 399 | 41.098 | 6.386 | 7.590 | 1.00 | 68.67 | B |
| ATOM | 2359 | N | VAL | B | 400 | 39.146 | 5.910 | 8.602 | 1.00 | 69.14 | B |
| ATOM | 2360 | CA | VAL | B | 400 | 39.639 | 4.674 | 9.213 | 1.00 | 69.85 | B |
| ATOM | 2361 | CB | VAL | B | 400 | 40.289 | 3.744 | 8.107 | 1.00 | 71.32 | B |
| ATOM | 2362 | CG1 | VAL | B | 400 | 40.676 | 2.372 | 8.688 | 1.00 | 71.86 | B |
| ATOM | 2363 | CG2 | VAL | B | 400 | 39.305 | 3.564 | 6.936 | 1.00 | 71.47 | B |
| ATOM | 2364 | C | VAL | B | 400 | 40.639 | 4.914 | 10.356 | 1.00 | 69.10 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2365 | O | VAL | B | 400 | 41.255 | 3.974 | 10.873 | 1.00 | 69.11 | B |
| ATOM | 2366 | N | LYS | B | 401 | 40.784 | 6.171 | 10.766 | 1.00 | 68.34 | B |
| ATOM | 2367 | CA | LYS | B | 401 | 41.712 | 6.512 | 11.843 | 1.00 | 67.32 | B |
| ATOM | 2368 | CB | LYS | B | 401 | 43.031 | 7.040 | 11.269 | 1.00 | 68.75 | B |
| ATOM | 2369 | CG | LYS | B | 401 | 43.752 | 6.092 | 10.327 | 1.00 | 70.39 | B |
| ATOM | 2370 | CD | LYS | B | 401 | 45.215 | 6.500 | 10.169 | 1.00 | 71.35 | B |
| ATOM | 2371 | CE | LYS | B | 401 | 45.891 | 5.724 | 9.049 | 1.00 | 72.00 | B |
| ATOM | 2372 | NZ | LYS | B | 401 | 47.365 | 5.958 | 9.009 | 1.00 | 73.32 | B |
| ATOM | 2373 | C | LYS | B | 401 | 41.163 | 7.553 | 12.819 | 1.00 | 65.85 | B |
| ATOM | 2374 | O | LYS | B | 401 | 40.298 | 8.360 | 12.468 | 1.00 | 65.41 | B |
| ATOM | 2375 | N | LEU | B | 402 | 41.694 | 7.527 | 14.043 | 1.00 | 64.07 | B |
| ATOM | 2376 | CA | LEU | B | 402 | 41.307 | 8.463 | 15.098 | 1.00 | 61.75 | B |
| ATOM | 2377 | CB | LEU | B | 402 | 40.710 | 7.709 | 16.291 | 1.00 | 61.00 | B |
| ATOM | 2378 | CG | LEU | B | 402 | 39.306 | 7.132 | 16.110 | 1.00 | 59.93 | B |
| ATOM | 2379 | CD1 | LEU | B | 402 | 38.908 | 6.362 | 17.359 | 1.00 | 59.47 | B |
| ATOM | 2380 | CD2 | LEU | B | 402 | 38.321 | 8.258 | 15.830 | 1.00 | 58.54 | B |
| ATOM | 2381 | C | LEU | B | 402 | 42.517 | 9.271 | 15.565 | 1.00 | 60.37 | B |
| ATOM | 2382 | O | LEU | B | 402 | 43.456 | 8.718 | 16.148 | 1.00 | 60.09 | B |
| ATOM | 2383 | N | LEU | B | 403 | 42.487 | 10.577 | 15.311 | 1.00 | 58.18 | B |
| ATOM | 2384 | CA | LEU | B | 403 | 43.580 | 11.466 | 15.698 | 1.00 | 55.69 | B |
| ATOM | 2385 | CB | LEU | B | 403 | 43.635 | 12.683 | 14.760 | 1.00 | 55.34 | B |
| ATOM | 2386 | CG | LEU | B | 403 | 44.872 | 13.594 | 14.813 | 1.00 | 55.09 | B |
| ATOM | 2387 | CD1 | LEU | B | 403 | 45.872 | 13.182 | 13.735 | 1.00 | 54.17 | B |
| ATOM | 2388 | CD2 | LEU | B | 403 | 44.450 | 15.041 | 14.603 | 1.00 | 54.45 | B |
| ATOM | 2389 | C | LEU | B | 403 | 43.434 | 11.937 | 17.148 | 1.00 | 54.43 | B |
| ATOM | 2390 | O | LEU | B | 403 | 42.832 | 12.975 | 17.424 | 1.00 | 53.35 | B |
| ATOM | 2391 | N | PHE | B | 404 | 43.986 | 11.157 | 18.068 | 1.00 | 53.68 | B |
| ATOM | 2392 | CA | PHE | B | 404 | 43.950 | 11.488 | 19.484 | 1.00 | 53.18 | B |
| ATOM | 2393 | CB | PHE | B | 404 | 44.356 | 10.275 | 20.306 | 1.00 | 53.29 | B |
| ATOM | 2394 | CG | PHE | B | 404 | 43.348 | 9.174 | 20.282 | 1.00 | 53.97 | B |
| ATOM | 2395 | CD1 | PHE | B | 404 | 42.240 | 9.207 | 21.133 | 1.00 | 54.11 | B |
| ATOM | 2396 | CD2 | PHE | B | 404 | 43.491 | 8.107 | 19.399 | 1.00 | 54.03 | B |
| ATOM | 2397 | CE1 | PHE | B | 404 | 41.285 | 8.183 | 21.106 | 1.00 | 54.38 | B |
| ATOM | 2398 | CE2 | PHE | B | 404 | 42.547 | 7.082 | 19.361 | 1.00 | 54.61 | B |
| ATOM | 2399 | CZ | PHE | B | 404 | 41.440 | 7.119 | 20.219 | 1.00 | 54.31 | B |
| ATOM | 2400 | C | PHE | B | 404 | 44.909 | 12.637 | 19.746 | 1.00 | 52.86 | B |
| ATOM | 2401 | O | PHE | B | 404 | 44.662 | 13.491 | 20.593 | 1.00 | 52.82 | B |
| ATOM | 2402 | N | ALA | B | 405 | 46.008 | 12.637 | 19.002 | 1.00 | 52.46 | B |
| ATOM | 2403 | CA | ALA | B | 405 | 47.034 | 13.667 | 19.090 | 1.00 | 52.13 | B |
| ATOM | 2404 | CB | ALA | B | 405 | 47.961 | 13.402 | 20.285 | 1.00 | 51.21 | B |
| ATOM | 2405 | C | ALA | B | 405 | 47.803 | 13.561 | 17.777 | 1.00 | 51.81 | B |
| ATOM | 2406 | O | ALA | B | 405 | 47.815 | 12.507 | 17.151 | 1.00 | 52.37 | B |
| ATOM | 2407 | N | PRO | B | 406 | 48.451 | 14.646 | 17.342 | 1.00 | 51.97 | B |
| ATOM | 2408 | CD | PRO | B | 406 | 48.619 | 15.951 | 18.002 | 1.00 | 51.91 | B |
| ATOM | 2409 | CA | PRO | B | 406 | 49.201 | 14.593 | 16.085 | 1.00 | 52.47 | B |
| ATOM | 2410 | CB | PRO | B | 406 | 49.940 | 15.924 | 16.071 | 1.00 | 51.60 | B |
| ATOM | 2411 | CG | PRO | B | 406 | 49.027 | 16.822 | 16.860 | 1.00 | 52.18 | B |
| ATOM | 2412 | C | PRO | B | 406 | 50.157 | 13.409 | 16.053 | 1.00 | 53.51 | B |
| ATOM | 2413 | O | PRO | B | 406 | 50.445 | 12.855 | 14.989 | 1.00 | 53.54 | B |
| ATOM | 2414 | N | ASN | B | 407 | 50.632 | 13.027 | 17.236 | 1.00 | 54.61 | B |
| ATOM | 2415 | CA | ASN | B | 407 | 51.576 | 11.927 | 17.399 | 1.00 | 55.68 | B |
| ATOM | 2416 | CB | ASN | B | 407 | 52.714 | 12.368 | 18.324 | 1.00 | 55.25 | B |
| ATOM | 2417 | CG | ASN | B | 407 | 52.254 | 12.609 | 19.758 | 1.00 | 54.30 | B |
| ATOM | 2418 | OD1 | ASN | B | 407 | 51.202 | 13.207 | 20.005 | 1.00 | 52.84 | B |
| ATOM | 2419 | ND2 | ASN | B | 407 | 53.056 | 12.153 | 20.710 | 1.00 | 53.55 | B |
| ATOM | 2420 | C | ASN | B | 407 | 50.915 | 10.670 | 17.955 | 1.00 | 57.37 | B |
| ATOM | 2421 | O | ASN | B | 407 | 51.592 | 9.762 | 18.442 | 1.00 | 57.27 | B |
| ATOM | 2422 | N | LEU | B | 408 | 49.589 | 10.628 | 17.883 | 1.00 | 59.09 | B |
| ATOM | 2423 | CA | LEU | B | 408 | 48.830 | 9.483 | 18.359 | 1.00 | 61.31 | B |
| ATOM | 2424 | CB | LEU | B | 408 | 48.397 | 9.693 | 19.811 | 1.00 | 60.81 | B |
| ATOM | 2425 | CG | LEU | B | 408 | 47.922 | 8.455 | 20.572 | 1.00 | 59.84 | B |
| ATOM | 2426 | CD1 | LEU | B | 408 | 49.086 | 7.501 | 20.774 | 1.00 | 59.48 | B |
| ATOM | 2427 | CD2 | LEU | B | 408 | 47.356 | 8.869 | 21.911 | 1.00 | 59.52 | B |
| ATOM | 2428 | C | LEU | B | 408 | 47.607 | 9.312 | 17.462 | 1.00 | 63.42 | B |
| ATOM | 2429 | O | LEU | B | 408 | 46.496 | 9.716 | 17.811 | 1.00 | 62.98 | B |
| ATOM | 2430 | N | LEU | B | 409 | 47.841 | 8.725 | 16.293 | 1.00 | 66.15 | B |
| ATOM | 2431 | CA | LEU | B | 409 | 46.799 | 8.465 | 15.305 | 1.00 | 69.49 | B |
| ATOM | 2432 | CB | LEU | B | 409 | 47.262 | 8.961 | 13.932 | 1.00 | 69.38 | B |
| ATOM | 2433 | CG | LEU | B | 409 | 46.259 | 8.971 | 12.777 | 1.00 | 69.60 | B |
| ATOM | 2434 | CD1 | LEU | B | 409 | 45.174 | 9.981 | 13.072 | 1.00 | 69.11 | B |
| ATOM | 2435 | CD2 | LEU | B | 409 | 46.969 | 9.320 | 11.468 | 1.00 | 69.17 | B |
| ATOM | 2436 | C | LEU | B | 409 | 46.582 | 6.947 | 15.275 | 1.00 | 71.46 | B |
| ATOM | 2437 | O | LEU | B | 409 | 47.449 | 6.205 | 14.816 | 1.00 | 71.71 | B |
| ATOM | 2438 | N | LEU | B | 410 | 45.430 | 6.487 | 15.760 | 1.00 | 73.97 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2439 | CA | LEU | B | 410 | 45.157 | 5.053 | 15.807 | 1.00 | 76.50 | B |
| ATOM | 2440 | CB | LEU | B | 410 | 44.877 | 4.618 | 17.253 | 1.00 | 76.37 | B |
| ATOM | 2441 | CG | LEU | B | 410 | 45.844 | 5.050 | 18.363 | 1.00 | 76.90 | B |
| ATOM | 2442 | CD1 | LEU | B | 410 | 45.464 | 4.343 | 19.652 | 1.00 | 76.45 | B |
| ATOM | 2443 | CD2 | LEU | B | 410 | 47.285 | 4.720 | 17.988 | 1.00 | 76.94 | B |
| ATOM | 2444 | C | LEU | B | 410 | 44.015 | 4.560 | 14.923 | 1.00 | 78.38 | B |
| ATOM | 2445 | O | LEU | B | 410 | 42.966 | 5.200 | 14.821 | 1.00 | 78.26 | B |
| ATOM | 2446 | N | ASP | B | 411 | 44.239 | 3.406 | 14.295 | 1.00 | 80.92 | B |
| ATOM | 2447 | CA | ASP | B | 411 | 43.243 | 2.759 | 13.441 | 1.00 | 83.26 | B |
| ATOM | 2448 | CB | ASP | B | 411 | 43.920 | 2.047 | 12.256 | 1.00 | 83.25 | B |
| ATOM | 2449 | CG | ASP | B | 411 | 44.789 | 0.862 | 12.685 | 1.00 | 83.55 | B |
| ATOM | 2450 | OD1 | ASP | B | 411 | 45.569 | 0.999 | 13.650 | 1.00 | 83.29 | B |
| ATOM | 2451 | OD2 | ASP | B | 411 | 44.705 | −0.209 | 12.043 | 1.00 | 83.37 | B |
| ATOM | 2452 | C | ASP | B | 411 | 42.501 | 1.749 | 14.316 | 1.00 | 84.66 | B |
| ATOM | 2453 | O | ASP | B | 411 | 43.096 | 1.138 | 15.201 | 1.00 | 84.54 | B |
| ATOM | 2454 | N | ARG | B | 412 | 41.205 | 1.587 | 14.072 | 1.00 | 86.88 | B |
| ATOM | 2455 | CA | ARG | B | 412 | 40.373 | 0.672 | 14.850 | 1.00 | 88.87 | B |
| ATOM | 2456 | CB | ARG | B | 412 | 39.132 | 0.290 | 14.032 | 1.00 | 89.15 | B |
| ATOM | 2457 | CG | ARG | B | 412 | 38.983 | −1.188 | 13.746 | 1.00 | 89.73 | B |
| ATOM | 2458 | CD | ARG | B | 412 | 37.714 | −1.756 | 14.345 | 1.00 | 90.25 | B |
| ATOM | 2459 | NE | ARG | B | 412 | 37.617 | −3.187 | 14.082 | 1.00 | 91.08 | B |
| ATOM | 2460 | CZ | ARG | B | 412 | 36.590 | −3.954 | 14.435 | 1.00 | 91.50 | B |
| ATOM | 2461 | NH1 | ARG | B | 412 | 35.550 | −3.434 | 15.073 | 1.00 | 91.19 | B |
| ATOM | 2462 | NH2 | ARG | B | 412 | 36.608 | −5.250 | 14.148 | 1.00 | 91.69 | B |
| ATOM | 2463 | C | ARG | B | 412 | 41.109 | −0.580 | 15.335 | 1.00 | 90.21 | B |
| ATOM | 2464 | O | ARG | B | 412 | 41.066 | −0.910 | 16.523 | 1.00 | 90.43 | B |
| ATOM | 2465 | N | ASN | B | 413 | 41.787 | −1.262 | 14.412 | 1.00 | 91.72 | B |
| ATOM | 2466 | CA | ASN | B | 413 | 42.541 | −2.481 | 14.712 | 1.00 | 92.84 | B |
| ATOM | 2467 | CB | ASN | B | 413 | 43.481 | −2.809 | 13.550 | 1.00 | 93.03 | B |
| ATOM | 2468 | CG | ASN | B | 413 | 42.843 | −2.563 | 12.194 | 1.00 | 93.64 | B |
| ATOM | 2469 | OD1 | ASN | B | 413 | 42.715 | −3.477 | 11.381 | 1.00 | 94.29 | B |
| ATOM | 2470 | ND2 | ASN | B | 413 | 42.444 | −1.321 | 11.942 | 1.00 | 93.87 | B |
| ATOM | 2471 | C | ASN | B | 413 | 43.365 | −2.280 | 15.977 | 1.00 | 93.72 | B |
| ATOM | 2472 | O | ASN | B | 413 | 43.325 | −3.088 | 16.907 | 1.00 | 93.51 | B |
| ATOM | 2473 | N | GLN | B | 414 | 44.111 | −1.182 | 15.985 | 1.00 | 95.11 | B |
| ATOM | 2474 | CA | GLN | B | 414 | 44.972 | −0.797 | 17.095 | 1.00 | 96.44 | B |
| ATOM | 2475 | CB | GLN | B | 414 | 45.983 | 0.244 | 16.601 | 1.00 | 97.18 | B |
| ATOM | 2476 | CG | GLN | B | 414 | 47.039 | 0.690 | 17.606 | 1.00 | 98.58 | B |
| ATOM | 2477 | CD | GLN | B | 414 | 47.998 | −0.422 | 18.009 | 1.00 | 99.45 | B |
| ATOM | 2478 | OE1 | GLN | B | 414 | 48.256 | −1.352 | 17.241 | 1.00 | 99.77 | B |
| ATOM | 2479 | NE2 | GLN | B | 414 | 48.547 | −0.318 | 19.215 | 1.00 | 99.87 | B |
| ATOM | 2480 | C | GLN | B | 414 | 44.131 | −0.216 | 18.231 | 1.00 | 96.86 | B |
| ATOM | 2481 | O | GLN | B | 414 | 44.312 | 0.935 | 18.621 | 1.00 | 96.95 | B |
| ATOM | 2482 | N | GLY | B | 415 | 43.209 | −1.016 | 18.755 | 1.00 | 97.34 | B |
| ATOM | 2483 | CA | GLY | B | 415 | 42.359 | −0.549 | 19.834 | 1.00 | 98.09 | B |
| ATOM | 2484 | C | GLY | B | 415 | 41.789 | −1.705 | 20.627 | 1.00 | 98.73 | B |
| ATOM | 2485 | O | GLY | B | 415 | 41.205 | −1.517 | 21.697 | 1.00 | 98.62 | B |
| ATOM | 2486 | N | LYS | B | 416 | 41.956 | −2.910 | 20.090 | 1.00 | 99.27 | B |
| ATOM | 2487 | CA | LYS | B | 416 | 41.468 | −4.114 | 20.746 | 1.00 | 99.57 | B |
| ATOM | 2488 | CB | LYS | B | 416 | 41.331 | −5.255 | 19.733 | 1.00 | 99.62 | B |
| ATOM | 2489 | CG | LYS | B | 416 | 40.737 | −6.531 | 20.314 | 1.00 | 99.77 | B |
| ATOM | 2490 | CD | LYS | B | 416 | 40.711 | −7.647 | 19.283 | 1.00 | 100.00 | B |
| ATOM | 2491 | CE | LYS | B | 416 | 40.286 | −8.973 | 19.904 | 1.00 | 100.00 | B |
| ATOM | 2492 | NZ | LYS | B | 416 | 40.268 | −10.084 | 18.903 | 1.00 | 100.00 | B |
| ATOM | 2493 | C | LYS | B | 416 | 42.442 | −4.510 | 21.851 | 1.00 | 99.76 | B |
| ATOM | 2494 | O | LYS | B | 416 | 42.180 | −5.438 | 22.619 | 1.00 | 99.70 | B |
| ATOM | 2495 | N | CYS | B | 417 | 43.567 | −3.801 | 21.924 | 1.00 | 99.85 | B |
| ATOM | 2496 | CA | CYS | B | 417 | 44.574 | −4.068 | 22.946 | 1.00 | 99.88 | B |
| ATOM | 2497 | CB | CYS | B | 417 | 45.659 | −2.982 | 22.941 | 1.00 | 99.77 | B |
| ATOM | 2498 | SG | CYS | B | 417 | 46.571 | −2.787 | 21.392 | 1.00 | 100.00 | B |
| ATOM | 2499 | C | CYS | B | 417 | 43.873 | −4.065 | 24.299 | 1.00 | 100.00 | B |
| ATOM | 2500 | O | CYS | B | 417 | 44.222 | −4.835 | 25.199 | 1.00 | 99.95 | B |
| ATOM | 2501 | N | VAL | B | 418 | 42.877 | −3.188 | 24.427 | 1.00 | 100.00 | B |
| ATOM | 2502 | CA | VAL | B | 418 | 42.106 | −3.063 | 25.661 | 1.00 | 99.86 | B |
| ATOM | 2503 | CB | VAL | B | 418 | 41.944 | −1.575 | 26.070 | 1.00 | 100.00 | B |
| ATOM | 2504 | CG1 | VAL | B | 418 | 41.234 | −1.475 | 27.418 | 1.00 | 99.79 | B |
| ATOM | 2505 | CG2 | VAL | B | 418 | 43.313 | −0.905 | 26.144 | 1.00 | 99.83 | B |
| ATOM | 2506 | C | VAL | B | 418 | 40.724 | −3.716 | 25.528 | 1.00 | 99.51 | B |
| ATOM | 2507 | O | VAL | B | 418 | 40.059 | −3.607 | 24.495 | 1.00 | 99.27 | B |
| ATOM | 2508 | N | GLU | B | 419 | 40.310 | −4.393 | 26.595 | 1.00 | 99.28 | B |
| ATOM | 2509 | CA | GLU | B | 419 | 39.039 | −5.108 | 26.655 | 1.00 | 98.91 | B |
| ATOM | 2510 | CB | GLU | B | 419 | 38.769 | −5.575 | 28.092 | 1.00 | 99.44 | B |
| ATOM | 2511 | CG | GLU | B | 419 | 39.871 | −6.435 | 28.723 | 1.00 | 99.83 | B |
| ATOM | 2512 | CD | GLU | B | 419 | 40.123 | −7.741 | 27.981 | 1.00 | 100.00 | B |

TABLE 9-continued

Structure coordinates for ERalpha-LBD/Compound 1 complex
(Table dicloses SEQ ID NOS 2-8, respectively, in order of appearance)

|      | #    | Name | Res. | Chain | Res # | X      | Y      | Z      | occ  | B      | SegID |
|------|------|------|------|-------|-------|--------|--------|--------|------|--------|-------|
| ATOM | 2513 | OE1  | GLU  | B     | 419   | 40.844 | −8.601 | 28.532 | 1.00 | 100.00 | B     |
| ATOM | 2514 | OE2  | GLU  | B     | 419   | 39.610 | −7.910 | 26.851 | 1.00 | 100.00 | B     |
| ATOM | 2515 | C    | GLU  | B     | 419   | 37.818 | −4.345 | 26.148 | 1.00 | 98.05  | B     |
| ATOM | 2516 | O    | GLU  | B     | 419   | 37.541 | −3.228 | 26.581 | 1.00 | 98.05  | B     |
| ATOM | 2517 | N    | GLY  | B     | 420   | 37.093 | −4.980 | 25.231 | 1.00 | 97.30  | B     |
| ATOM | 2518 | CA   | GLY  | B     | 420   | 35.884 | −4.406 | 24.664 | 1.00 | 96.05  | B     |
| ATOM | 2519 | C    | GLY  | B     | 420   | 35.938 | −2.962 | 24.200 | 1.00 | 94.97  | B     |
| ATOM | 2520 | O    | GLY  | B     | 420   | 34.902 | −2.377 | 23.872 | 1.00 | 95.16  | B     |
| ATOM | 2521 | N    | MET  | B     | 421   | 37.132 | −2.380 | 24.163 | 1.00 | 93.30  | B     |
| ATOM | 2522 | CA   | MET  | B     | 421   | 37.276 | −0.996 | 23.735 | 1.00 | 91.27  | B     |
| ATOM | 2523 | CB   | MET  | B     | 421   | 38.669 | −0.475 | 24.079 | 1.00 | 92.07  | B     |
| ATOM | 2524 | CG   | MET  | B     | 421   | 38.882 | 0.966  | 23.648 | 1.00 | 93.11  | B     |
| ATOM | 2525 | SD   | MET  | B     | 421   | 40.485 | 1.632  | 24.113 | 1.00 | 94.66  | B     |
| ATOM | 2526 | CE   | MET  | B     | 421   | 40.231 | 1.860  | 25.855 | 1.00 | 94.29  | B     |
| ATOM | 2527 | C    | MET  | B     | 421   | 37.037 | −0.828 | 22.240 | 1.00 | 89.18  | B     |
| ATOM | 2528 | O    | MET  | B     | 421   | 36.549 | 0.210  | 21.796 | 1.00 | 88.90  | B     |
| ATOM | 2529 | N    | VAL  | B     | 422   | 37.392 | −1.853 | 21.471 | 1.00 | 86.94  | B     |
| ATOM | 2530 | CA   | VAL  | B     | 422   | 37.234 | −1.839 | 20.019 | 1.00 | 84.72  | B     |
| ATOM | 2531 | CB   | VAL  | B     | 422   | 37.526 | −3.235 | 19.416 | 1.00 | 84.59  | B     |
| ATOM | 2532 | CG1  | VAL  | B     | 422   | 36.767 | −4.307 | 20.188 | 1.00 | 83.91  | B     |
| ATOM | 2533 | CG2  | VAL  | B     | 422   | 37.130 | −3.257 | 17.945 | 1.00 | 83.84  | B     |
| ATOM | 2534 | C    | VAL  | B     | 422   | 35.855 | −1.390 | 19.548 | 1.00 | 83.29  | B     |
| ATOM | 2535 | O    | VAL  | B     | 422   | 35.724 | −0.777 | 18.490 | 1.00 | 82.76  | B     |
| ATOM | 2536 | N    | GLU  | B     | 423   | 34.827 | −1.709 | 20.328 | 1.00 | 81.74  | B     |
| ATOM | 2537 | CA   | GLU  | B     | 423   | 33.465 | −1.329 | 19.976 | 1.00 | 80.06  | B     |
| ATOM | 2538 | CB   | GLU  | B     | 423   | 32.473 | −1.909 | 20.984 | 1.00 | 81.33  | B     |
| ATOM | 2539 | CG   | GLU  | B     | 423   | 31.024 | −1.797 | 20.544 | 1.00 | 82.87  | B     |
| ATOM | 2540 | CD   | GLU  | B     | 423   | 30.060 | −2.271 | 21.611 | 1.00 | 84.55  | B     |
| ATOM | 2541 | OE1  | GLU  | B     | 423   | 30.423 | −3.213 | 22.354 | 1.00 | 85.32  | B     |
| ATOM | 2542 | OE2  | GLU  | B     | 423   | 28.939 | −1.714 | 21.702 | 1.00 | 84.87  | B     |
| ATOM | 2543 | C    | GLU  | B     | 423   | 33.346 | 0.189  | 19.964 | 1.00 | 77.77  | B     |
| ATOM | 2544 | O    | GLU  | B     | 423   | 32.881 | 0.782  | 18.991 | 1.00 | 77.07  | B     |
| ATOM | 2545 | N    | ILE  | B     | 424   | 33.776 | 0.809  | 21.058 | 1.00 | 75.46  | B     |
| ATOM | 2546 | CA   | ILE  | B     | 424   | 33.731 | 2.258  | 21.195 | 1.00 | 73.47  | B     |
| ATOM | 2547 | CB   | ILE  | B     | 424   | 34.349 | 2.690  | 22.535 | 1.00 | 73.36  | B     |
| ATOM | 2548 | CG2  | ILE  | B     | 424   | 34.402 | 4.206  | 22.622 | 1.00 | 73.44  | B     |
| ATOM | 2549 | CG1  | ILE  | B     | 424   | 33.519 | 2.115  | 23.684 | 1.00 | 73.16  | B     |
| ATOM | 2550 | CD1  | ILE  | B     | 424   | 34.045 | 2.443  | 25.053 | 1.00 | 72.96  | B     |
| ATOM | 2551 | C    | ILE  | B     | 424   | 34.470 | 2.939  | 20.047 | 1.00 | 71.89  | B     |
| ATOM | 2552 | O    | ILE  | B     | 424   | 34.036 | 3.972  | 19.533 | 1.00 | 70.85  | B     |
| ATOM | 2553 | N    | PHE  | B     | 425   | 35.586 | 2.340  | 19.650 | 1.00 | 70.38  | B     |
| ATOM | 2554 | CA   | PHE  | B     | 425   | 36.405 | 2.846  | 18.560 | 1.00 | 68.66  | B     |
| ATOM | 2555 | CB   | PHE  | B     | 425   | 37.551 | 1.881  | 18.287 | 1.00 | 69.67  | B     |
| ATOM | 2556 | CG   | PHE  | B     | 425   | 38.890 | 2.431  | 18.630 | 1.00 | 70.60  | B     |
| ATOM | 2557 | CD1  | PHE  | B     | 425   | 39.270 | 2.605  | 19.958 | 1.00 | 70.89  | B     |
| ATOM | 2558 | CD2  | PHE  | B     | 425   | 39.774 | 2.794  | 17.622 | 1.00 | 70.86  | B     |
| ATOM | 2559 | CE1  | PHE  | B     | 425   | 40.515 | 3.136  | 20.275 | 1.00 | 70.84  | B     |
| ATOM | 2560 | CE2  | PHE  | B     | 425   | 41.022 | 3.326  | 17.928 | 1.00 | 71.05  | B     |
| ATOM | 2561 | CZ   | PHE  | B     | 425   | 41.393 | 3.497  | 19.258 | 1.00 | 70.95  | B     |
| ATOM | 2562 | C    | PHE  | B     | 425   | 35.617 | 3.038  | 17.274 | 1.00 | 67.17  | B     |
| ATOM | 2563 | O    | PHE  | B     | 425   | 35.722 | 4.074  | 16.623 | 1.00 | 67.20  | B     |
| ATOM | 2564 | N    | ASP  | B     | 426   | 34.841 | 2.026  | 16.901 | 1.00 | 65.53  | B     |
| ATOM | 2565 | CA   | ASP  | B     | 426   | 34.048 | 2.092  | 15.680 | 1.00 | 64.55  | B     |
| ATOM | 2566 | CB   | ASP  | B     | 426   | 33.413 | 0.733  | 15.375 | 1.00 | 66.51  | B     |
| ATOM | 2567 | CG   | ASP  | B     | 426   | 34.447 | −0.340 | 15.076 | 1.00 | 68.35  | B     |
| ATOM | 2568 | OD1  | ASP  | B     | 426   | 35.271 | −0.135 | 14.156 | 1.00 | 68.89  | B     |
| ATOM | 2569 | OD2  | ASP  | B     | 426   | 34.432 | −1.389 | 15.760 | 1.00 | 69.02  | B     |
| ATOM | 2570 | C    | ASP  | B     | 426   | 32.967 | 3.155  | 15.779 | 1.00 | 62.93  | B     |
| ATOM | 2571 | O    | ASP  | B     | 426   | 32.692 | 3.861  | 14.808 | 1.00 | 62.66  | B     |
| ATOM | 2572 | N    | MET  | B     | 427   | 32.349 | 3.264  | 16.950 | 1.00 | 60.71  | B     |
| ATOM | 2573 | CA   | MET  | B     | 427   | 31.323 | 4.274  | 17.157 | 1.00 | 58.27  | B     |
| ATOM | 2574 | CB   | MET  | B     | 427   | 30.797 | 4.221  | 18.597 | 1.00 | 58.99  | B     |
| ATOM | 2575 | CG   | MET  | B     | 427   | 29.888 | 3.033  | 18.888 | 1.00 | 59.41  | B     |
| ATOM | 2576 | SD   | MET  | B     | 427   | 29.084 | 3.099  | 20.510 | 1.00 | 60.08  | B     |
| ATOM | 2577 | CE   | MET  | B     | 427   | 30.000 | 1.878  | 21.424 | 1.00 | 58.84  | B     |
| ATOM | 2578 | C    | MET  | B     | 427   | 31.896 | 5.663  | 16.860 | 1.00 | 56.53  | B     |
| ATOM | 2579 | O    | MET  | B     | 427   | 31.231 | 6.495  | 16.246 | 1.00 | 56.32  | B     |
| ATOM | 2580 | N    | LEU  | B     | 428   | 33.137 | 5.900  | 17.285 | 1.00 | 54.31  | B     |
| ATOM | 2581 | CA   | LEU  | B     | 428   | 33.801 | 7.186  | 17.063 | 1.00 | 52.13  | B     |
| ATOM | 2582 | CB   | LEU  | B     | 428   | 35.076 | 7.277  | 17.908 | 1.00 | 50.60  | B     |
| ATOM | 2583 | CG   | LEU  | B     | 428   | 34.829 | 7.383  | 19.421 | 1.00 | 49.60  | B     |
| ATOM | 2584 | CD1  | LEU  | B     | 428   | 36.125 | 7.143  | 20.173 | 1.00 | 49.56  | B     |
| ATOM | 2585 | CD2  | LEU  | B     | 428   | 34.244 | 8.750  | 19.766 | 1.00 | 48.60  | B     |
| ATOM | 2586 | C    | LEU  | B     | 428   | 34.131 | 7.385  | 15.593 | 1.00 | 51.32  | B     |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2587 | O | LEU | B | 428 | 33.963 | 8.478 | 15.049 | 1.00 | 50.52 | B |
| ATOM | 2588 | N | LEU | B | 429 | 34.592 | 6.316 | 14.953 | 1.00 | 50.54 | B |
| ATOM | 2589 | CA | LEU | B | 429 | 34.934 | 6.348 | 13.534 | 1.00 | 49.61 | B |
| ATOM | 2590 | CB | LEU | B | 429 | 35.622 | 5.039 | 13.159 | 1.00 | 49.40 | B |
| ATOM | 2591 | CG | LEU | B | 429 | 37.027 | 4.874 | 13.721 | 1.00 | 49.18 | B |
| ATOM | 2592 | CD1 | LEU | B | 429 | 37.449 | 3.419 | 13.644 | 1.00 | 50.73 | B |
| ATOM | 2593 | CD2 | LEU | B | 429 | 37.976 | 5.753 | 12.930 | 1.00 | 48.56 | B |
| ATOM | 2594 | C | LEU | B | 429 | 33.705 | 6.582 | 12.631 | 1.00 | 48.83 | B |
| ATOM | 2595 | O | LEU | B | 429 | 33.818 | 7.167 | 11.551 | 1.00 | 48.59 | B |
| ATOM | 2596 | N | ALA | B | 430 | 32.539 | 6.122 | 13.080 | 1.00 | 48.12 | B |
| ATOM | 2597 | CA | ALA | B | 430 | 31.297 | 6.294 | 12.331 | 1.00 | 46.98 | B |
| ATOM | 2598 | CB | ALA | B | 430 | 30.221 | 5.371 | 12.882 | 1.00 | 47.12 | B |
| ATOM | 2599 | C | ALA | B | 430 | 30.849 | 7.743 | 12.445 | 1.00 | 46.77 | B |
| ATOM | 2600 | O | ALA | B | 430 | 30.396 | 8.345 | 11.473 | 1.00 | 46.76 | B |
| ATOM | 2601 | N | THR | B | 431 | 30.976 | 8.304 | 13.643 | 1.00 | 46.76 | B |
| ATOM | 2602 | CA | THR | B | 431 | 30.593 | 9.695 | 13.866 | 1.00 | 46.58 | B |
| ATOM | 2603 | CB | THR | B | 431 | 30.832 | 10.119 | 15.335 | 1.00 | 45.27 | B |
| ATOM | 2604 | OG1 | THR | B | 431 | 30.160 | 9.208 | 16.210 | 1.00 | 44.56 | B |
| ATOM | 2605 | CG2 | THR | B | 431 | 30.290 | 11.511 | 15.587 | 1.00 | 44.36 | B |
| ATOM | 2606 | C | THR | B | 431 | 31.432 | 10.575 | 12.946 | 1.00 | 47.37 | B |
| ATOM | 2607 | O | THR | B | 431 | 30.913 | 11.461 | 12.262 | 1.00 | 46.70 | B |
| ATOM | 2608 | N | SER | B | 432 | 32.732 | 10.304 | 12.924 | 1.00 | 48.83 | B |
| ATOM | 2609 | CA | SER | B | 432 | 33.671 | 11.051 | 12.096 | 1.00 | 50.95 | B |
| ATOM | 2610 | CB | SER | B | 432 | 35.076 | 10.467 | 12.264 | 1.00 | 51.86 | B |
| ATOM | 2611 | OG | SER | B | 432 | 36.071 | 11.419 | 11.927 | 1.00 | 53.25 | B |
| ATOM | 2612 | C | SER | B | 432 | 33.243 | 10.987 | 10.626 | 1.00 | 52.47 | B |
| ATOM | 2613 | O | SER | B | 432 | 33.209 | 12.005 | 9.924 | 1.00 | 51.33 | B |
| ATOM | 2614 | N | SER | B | 433 | 32.907 | 9.784 | 10.172 | 1.00 | 54.00 | B |
| ATOM | 2615 | CA | SER | B | 433 | 32.478 | 9.588 | 8.799 | 1.00 | 55.80 | B |
| ATOM | 2616 | CB | SER | B | 433 | 32.201 | 8.107 | 8.541 | 1.00 | 56.27 | B |
| ATOM | 2617 | OG | SER | B | 433 | 33.388 | 7.339 | 8.673 | 1.00 | 57.03 | B |
| ATOM | 2618 | C | SER | B | 433 | 31.239 | 10.408 | 8.477 | 1.00 | 56.69 | B |
| ATOM | 2619 | O | SER | B | 433 | 31.141 | 10.974 | 7.390 | 1.00 | 56.87 | B |
| ATOM | 2620 | N | ARG | B | 434 | 30.304 | 10.476 | 9.425 | 1.00 | 57.75 | B |
| ATOM | 2621 | CA | ARG | B | 434 | 29.060 | 11.226 | 9.240 | 1.00 | 58.87 | B |
| ATOM | 2622 | CB | ARG | B | 434 | 28.064 | 10.928 | 10.366 | 1.00 | 60.19 | B |
| ATOM | 2623 | CG | ARG | B | 434 | 26.684 | 11.562 | 10.152 | 1.00 | 62.25 | B |
| ATOM | 2624 | CD | ARG | B | 434 | 25.812 | 10.691 | 9.248 | 1.00 | 63.89 | B |
| ATOM | 2625 | NE | ARG | B | 434 | 25.071 | 11.445 | 8.234 | 1.00 | 65.51 | B |
| ATOM | 2626 | CZ | ARG | B | 434 | 23.968 | 12.160 | 8.457 | 1.00 | 65.61 | B |
| ATOM | 2627 | NH1 | ARG | B | 434 | 23.442 | 12.244 | 9.675 | 1.00 | 65.51 | B |
| ATOM | 2628 | NH2 | ARG | B | 434 | 23.376 | 12.784 | 7.445 | 1.00 | 65.40 | B |
| ATOM | 2629 | C | ARG | B | 434 | 29.276 | 12.730 | 9.172 | 1.00 | 59.17 | B |
| ATOM | 2630 | O | ARG | B | 434 | 28.519 | 13.432 | 8.504 | 1.00 | 59.64 | B |
| ATOM | 2631 | N | PHE | B | 435 | 30.283 | 13.233 | 9.879 | 1.00 | 59.76 | B |
| ATOM | 2632 | CA | PHE | B | 435 | 30.565 | 14.669 | 9.848 | 1.00 | 60.43 | B |
| ATOM | 2633 | CB | PHE | B | 435 | 31.487 | 15.091 | 11.005 | 1.00 | 60.79 | B |
| ATOM | 2634 | CG | PHE | B | 435 | 30.781 | 15.268 | 12.329 | 1.00 | 61.72 | B |
| ATOM | 2635 | CD1 | PHE | B | 435 | 29.487 | 15.786 | 12.392 | 1.00 | 62.56 | B |
| ATOM | 2636 | CD2 | PHE | B | 435 | 31.427 | 14.947 | 13.521 | 1.00 | 62.11 | B |
| ATOM | 2637 | CE1 | PHE | B | 435 | 28.846 | 15.980 | 13.628 | 1.00 | 62.21 | B |
| ATOM | 2638 | CE2 | PHE | B | 435 | 30.797 | 15.137 | 14.758 | 1.00 | 61.93 | B |
| ATOM | 2639 | CZ | PHE | B | 435 | 29.505 | 15.654 | 14.811 | 1.00 | 61.81 | B |
| ATOM | 2640 | C | PHE | B | 435 | 31.239 | 15.003 | 8.517 | 1.00 | 60.26 | B |
| ATOM | 2641 | O | PHE | B | 435 | 31.131 | 16.122 | 8.008 | 1.00 | 59.21 | B |
| ATOM | 2642 | N | ARG | B | 436 | 31.943 | 14.012 | 7.977 | 1.00 | 60.50 | B |
| ATOM | 2643 | CA | ARG | B | 436 | 32.647 | 14.130 | 6.709 | 1.00 | 61.29 | B |
| ATOM | 2644 | CB | ARG | B | 436 | 33.591 | 12.936 | 6.552 | 1.00 | 61.63 | B |
| ATOM | 2645 | CG | ARG | B | 436 | 34.674 | 13.075 | 5.512 | 1.00 | 62.13 | B |
| ATOM | 2646 | CD | ARG | B | 436 | 35.831 | 12.163 | 5.894 | 1.00 | 63.20 | B |
| ATOM | 2647 | NE | ARG | B | 436 | 35.420 | 10.762 | 5.990 | 1.00 | 64.01 | B |
| ATOM | 2648 | CZ | ARG | B | 436 | 35.904 | 9.890 | 6.873 | 1.00 | 63.74 | B |
| ATOM | 2649 | NH1 | ARG | B | 436 | 36.819 | 10.267 | 7.754 | 1.00 | 63.46 | B |
| ATOM | 2650 | NH2 | ARG | B | 436 | 35.478 | 8.633 | 6.872 | 1.00 | 62.77 | B |
| ATOM | 2651 | C | ARG | B | 436 | 31.579 | 14.122 | 5.619 | 1.00 | 61.84 | B |
| ATOM | 2652 | O | ARG | B | 436 | 31.524 | 15.017 | 4.772 | 1.00 | 61.61 | B |
| ATOM | 2653 | N | MET | B | 437 | 30.720 | 13.108 | 5.663 | 1.00 | 62.61 | B |
| ATOM | 2654 | CA | MET | B | 437 | 29.636 | 12.978 | 4.704 | 1.00 | 62.88 | B |
| ATOM | 2655 | CB | MET | B | 437 | 28.733 | 11.797 | 5.105 | 1.00 | 64.71 | B |
| ATOM | 2656 | CG | MET | B | 437 | 27.749 | 11.302 | 4.031 | 1.00 | 67.67 | B |
| ATOM | 2657 | SD | MET | B | 437 | 26.260 | 12.324 | 3.779 | 1.00 | 71.74 | B |
| ATOM | 2658 | CE | MET | B | 437 | 24.936 | 11.291 | 4.494 | 1.00 | 70.96 | B |
| ATOM | 2659 | C | MET | B | 437 | 28.863 | 14.301 | 4.738 | 1.00 | 62.53 | B |
| ATOM | 2660 | O | MET | B | 437 | 28.548 | 14.868 | 3.691 | 1.00 | 63.40 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2661 | N | MET | B | 438 | 28.592 | 14.797 | 5.946 | 1.00 | 60.89 | B |
| ATOM | 2662 | CA | MET | B | 438 | 27.851 | 16.044 | 6.144 | 1.00 | 59.13 | B |
| ATOM | 2663 | CB | MET | B | 438 | 27.339 | 16.136 | 7.577 | 1.00 | 58.84 | B |
| ATOM | 2664 | CG | MET | B | 438 | 26.221 | 15.193 | 7.894 | 1.00 | 58.59 | B |
| ATOM | 2665 | SD | MET | B | 438 | 25.502 | 15.624 | 9.470 | 1.00 | 58.01 | B |
| ATOM | 2666 | CE | MET | B | 438 | 24.499 | 17.046 | 9.026 | 1.00 | 56.44 | B |
| ATOM | 2667 | C | MET | B | 438 | 28.607 | 17.335 | 5.844 | 1.00 | 58.63 | B |
| ATOM | 2668 | O | MET | B | 438 | 27.988 | 18.379 | 5.610 | 1.00 | 57.64 | B |
| ATOM | 2669 | N | ASN | B | 439 | 29.934 | 17.272 | 5.887 | 1.00 | 58.70 | B |
| ATOM | 2670 | CA | ASN | B | 439 | 30.774 | 18.435 | 5.627 | 1.00 | 58.41 | B |
| ATOM | 2671 | CB | ASN | B | 439 | 30.456 | 19.008 | 4.243 | 1.00 | 59.79 | B |
| ATOM | 2672 | CG | ASN | B | 439 | 31.398 | 20.122 | 3.852 | 1.00 | 61.26 | B |
| ATOM | 2673 | OD1 | ASN | B | 439 | 32.604 | 19.906 | 3.737 | 1.00 | 62.29 | B |
| ATOM | 2674 | ND2 | ASN | B | 439 | 30.859 | 21.324 | 3.649 | 1.00 | 61.74 | B |
| ATOM | 2675 | C | ASN | B | 439 | 30.573 | 19.513 | 6.695 | 1.00 | 57.25 | B |
| ATOM | 2676 | O | ASN | B | 439 | 30.384 | 20.690 | 6.382 | 1.00 | 56.83 | B |
| ATOM | 2677 | N | LEU | B | 440 | 30.614 | 19.101 | 7.958 | 1.00 | 56.54 | B |
| ATOM | 2678 | CA | LEU | B | 440 | 30.423 | 20.023 | 9.078 | 1.00 | 55.24 | B |
| ATOM | 2679 | CB | LEU | B | 440 | 30.583 | 19.267 | 10.402 | 1.00 | 54.76 | B |
| ATOM | 2680 | CG | LEU | B | 440 | 30.397 | 20.027 | 11.717 | 1.00 | 54.16 | B |
| ATOM | 2681 | CD1 | LEU | B | 440 | 28.928 | 20.373 | 11.918 | 1.00 | 52.74 | B |
| ATOM | 2682 | CD2 | LEU | B | 440 | 30.914 | 19.164 | 12.865 | 1.00 | 54.15 | B |
| ATOM | 2683 | C | LEU | B | 440 | 31.430 | 21.167 | 9.017 | 1.00 | 54.27 | B |
| ATOM | 2684 | O | LEU | B | 440 | 32.603 | 20.948 | 8.746 | 1.00 | 54.78 | B |
| ATOM | 2685 | N | GLN | B | 441 | 30.973 | 22.390 | 9.248 | 1.00 | 53.16 | B |
| ATOM | 2686 | CA | GLN | B | 441 | 31.874 | 23.532 | 9.241 | 1.00 | 52.53 | B |
| ATOM | 2687 | CB | GLN | B | 441 | 31.125 | 24.808 | 8.861 | 1.00 | 54.08 | B |
| ATOM | 2688 | CG | GLN | B | 441 | 30.690 | 24.856 | 7.419 | 1.00 | 55.17 | B |
| ATOM | 2689 | CD | GLN | B | 441 | 31.862 | 25.004 | 6.482 | 1.00 | 55.65 | B |
| ATOM | 2690 | OE1 | GLN | B | 441 | 32.394 | 26.107 | 6.304 | 1.00 | 55.51 | B |
| ATOM | 2691 | NE2 | GLN | B | 441 | 32.293 | 23.888 | 5.889 | 1.00 | 55.35 | B |
| ATOM | 2692 | C | GLN | B | 441 | 32.440 | 23.693 | 10.643 | 1.00 | 51.96 | B |
| ATOM | 2693 | O | GLN | B | 441 | 31.823 | 23.264 | 11.623 | 1.00 | 50.90 | B |
| ATOM | 2694 | N | GLY | B | 442 | 33.615 | 24.310 | 10.735 | 1.00 | 50.78 | B |
| ATOM | 2695 | CA | GLY | B | 442 | 34.217 | 24.527 | 12.032 | 1.00 | 48.56 | B |
| ATOM | 2696 | C | GLY | B | 442 | 33.265 | 25.356 | 12.860 | 1.00 | 47.91 | B |
| ATOM | 2697 | O | GLY | B | 442 | 33.164 | 25.176 | 14.070 | 1.00 | 48.24 | B |
| ATOM | 2698 | N | GLU | B | 443 | 32.545 | 26.254 | 12.192 | 1.00 | 46.85 | B |
| ATOM | 2699 | CA | GLU | B | 443 | 31.597 | 27.136 | 12.858 | 1.00 | 46.07 | B |
| ATOM | 2700 | CB | GLU | B | 443 | 31.044 | 28.181 | 11.879 | 1.00 | 47.62 | B |
| ATOM | 2701 | CG | GLU | B | 443 | 32.046 | 29.208 | 11.352 | 1.00 | 48.29 | B |
| ATOM | 2702 | CD | GLU | B | 443 | 33.095 | 28.592 | 10.455 | 1.00 | 49.55 | B |
| ATOM | 2703 | OE1 | GLU | B | 443 | 32.788 | 27.584 | 9.774 | 1.00 | 49.15 | B |
| ATOM | 2704 | OE2 | GLU | B | 443 | 34.225 | 29.128 | 10.421 | 1.00 | 51.45 | B |
| ATOM | 2705 | C | GLU | B | 443 | 30.427 | 26.380 | 13.457 | 1.00 | 44.67 | B |
| ATOM | 2706 | O | GLU | B | 443 | 29.836 | 26.820 | 14.435 | 1.00 | 44.14 | B |
| ATOM | 2707 | N | GLU | B | 444 | 30.075 | 25.255 | 12.845 | 1.00 | 44.06 | B |
| ATOM | 2708 | CA | GLU | B | 444 | 28.959 | 24.446 | 13.324 | 1.00 | 42.83 | B |
| ATOM | 2709 | CB | GLU | B | 444 | 28.378 | 23.579 | 12.193 | 1.00 | 43.50 | B |
| ATOM | 2710 | CG | GLU | B | 444 | 27.901 | 24.344 | 10.947 | 1.00 | 43.47 | B |
| ATOM | 2711 | CD | GLU | B | 444 | 27.313 | 23.419 | 9.883 | 1.00 | 44.50 | B |
| ATOM | 2712 | OE1 | GLU | B | 444 | 28.027 | 22.505 | 9.410 | 1.00 | 45.44 | B |
| ATOM | 2713 | OE2 | GLU | B | 444 | 26.135 | 23.602 | 9.518 | 1.00 | 43.71 | B |
| ATOM | 2714 | C | GLU | B | 444 | 29.488 | 23.557 | 14.437 | 1.00 | 41.64 | B |
| ATOM | 2715 | O | GLU | B | 444 | 28.792 | 23.291 | 15.413 | 1.00 | 40.63 | B |
| ATOM | 2716 | N | PHE | B | 445 | 30.732 | 23.115 | 14.275 | 1.00 | 40.15 | B |
| ATOM | 2717 | CA | PHE | B | 445 | 31.399 | 22.266 | 15.254 | 1.00 | 39.60 | B |
| ATOM | 2718 | CB | PHE | B | 445 | 32.848 | 22.039 | 14.831 | 1.00 | 39.59 | B |
| ATOM | 2719 | CG | PHE | B | 445 | 33.724 | 21.468 | 15.918 | 1.00 | 40.43 | B |
| ATOM | 2720 | CD1 | PHE | B | 445 | 33.513 | 20.178 | 16.401 | 1.00 | 40.13 | B |
| ATOM | 2721 | CD2 | PHE | B | 445 | 34.776 | 22.217 | 16.446 | 1.00 | 40.10 | B |
| ATOM | 2722 | CE1 | PHE | B | 445 | 34.335 | 19.639 | 17.389 | 1.00 | 38.96 | B |
| ATOM | 2723 | CE2 | PHE | B | 445 | 35.601 | 21.688 | 17.434 | 1.00 | 40.22 | B |
| ATOM | 2724 | CZ | PHE | B | 445 | 35.378 | 20.393 | 17.907 | 1.00 | 39.17 | B |
| ATOM | 2725 | C | PHE | B | 445 | 31.365 | 22.891 | 16.651 | 1.00 | 39.36 | B |
| ATOM | 2726 | O | PHE | B | 445 | 30.752 | 22.357 | 17.577 | 1.00 | 39.20 | B |
| ATOM | 2727 | N | VAL | B | 446 | 32.016 | 24.037 | 16.785 | 1.00 | 38.81 | B |
| ATOM | 2728 | CA | VAL | B | 446 | 32.082 | 24.730 | 18.054 | 1.00 | 37.18 | B |
| ATOM | 2729 | CB | VAL | B | 446 | 32.945 | 26.019 | 17.922 | 1.00 | 37.59 | B |
| ATOM | 2730 | CG1 | VAL | B | 446 | 34.238 | 25.665 | 17.217 | 1.00 | 36.80 | B |
| ATOM | 2731 | CG2 | VAL | B | 446 | 32.211 | 27.109 | 17.160 | 1.00 | 36.47 | B |
| ATOM | 2732 | C | VAL | B | 446 | 30.697 | 25.033 | 18.599 | 1.00 | 37.02 | B |
| ATOM | 2733 | O | VAL | B | 446 | 30.514 | 25.174 | 19.806 | 1.00 | 37.49 | B |
| ATOM | 2734 | N | CYS | B | 447 | 29.715 | 25.123 | 17.714 | 1.00 | 36.34 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2735 | CA | CYS | B | 447 | 28.342 | 25.372 | 18.141 | 1.00 | 35.45 | B |
| ATOM | 2736 | CB | CYS | B | 447 | 27.472 | 25.757 | 16.943 | 1.00 | 36.64 | B |
| ATOM | 2737 | SG | CYS | B | 447 | 27.344 | 27.540 | 16.676 | 1.00 | 40.98 | B |
| ATOM | 2738 | C | CYS | B | 447 | 27.764 | 24.127 | 18.808 | 1.00 | 34.70 | B |
| ATOM | 2739 | O | CYS | B | 447 | 27.051 | 24.222 | 19.811 | 1.00 | 33.82 | B |
| ATOM | 2740 | N | LEU | B | 448 | 28.077 | 22.966 | 18.234 | 1.00 | 34.12 | B |
| ATOM | 2741 | CA | LEU | B | 448 | 27.616 | 21.676 | 18.746 | 1.00 | 34.48 | B |
| ATOM | 2742 | CB | LEU | B | 448 | 27.907 | 20.567 | 17.728 | 1.00 | 35.17 | B |
| ATOM | 2743 | CG | LEU | B | 448 | 27.246 | 20.683 | 16.348 | 1.00 | 37.35 | B |
| ATOM | 2744 | CD1 | LEU | B | 448 | 27.761 | 19.578 | 15.437 | 1.00 | 36.87 | B |
| ATOM | 2745 | CD2 | LEU | B | 448 | 25.734 | 20.613 | 16.488 | 1.00 | 36.24 | B |
| ATOM | 2746 | C | LEU | B | 448 | 28.326 | 21.349 | 20.062 | 1.00 | 34.25 | B |
| ATOM | 2747 | O | LEU | B | 448 | 27.749 | 20.733 | 20.974 | 1.00 | 33.19 | B |
| ATOM | 2748 | N | LYS | B | 449 | 29.586 | 21.768 | 20.145 | 1.00 | 33.89 | B |
| ATOM | 2749 | CA | LYS | B | 449 | 30.398 | 21.531 | 21.327 | 1.00 | 32.47 | B |
| ATOM | 2750 | CB | LYS | B | 449 | 31.833 | 21.949 | 21.040 | 1.00 | 33.26 | B |
| ATOM | 2751 | CG | LYS | B | 449 | 32.841 | 21.021 | 21.646 | 1.00 | 33.92 | B |
| ATOM | 2752 | CD | LYS | B | 449 | 34.231 | 21.307 | 21.173 | 1.00 | 34.77 | B |
| ATOM | 2753 | CE | LYS | B | 449 | 34.700 | 22.672 | 21.612 | 1.00 | 35.87 | B |
| ATOM | 2754 | NZ | LYS | B | 449 | 36.153 | 22.828 | 21.322 | 1.00 | 37.06 | B |
| ATOM | 2755 | C | LYS | B | 449 | 29.818 | 22.295 | 22.519 | 1.00 | 31.20 | B |
| ATOM | 2756 | O | LYS | B | 449 | 29.726 | 21.767 | 23.619 | 1.00 | 31.31 | B |
| ATOM | 2757 | N | SER | B | 450 | 29.385 | 23.525 | 22.285 | 1.00 | 30.12 | B |
| ATOM | 2758 | CA | SER | B | 450 | 28.787 | 24.325 | 23.340 | 1.00 | 29.66 | B |
| ATOM | 2759 | CB | SER | B | 450 | 28.640 | 25.783 | 22.892 | 1.00 | 29.75 | B |
| ATOM | 2760 | OG | SER | B | 450 | 29.898 | 26.318 | 22.517 | 1.00 | 32.46 | B |
| ATOM | 2761 | C | SER | B | 450 | 27.420 | 23.775 | 23.712 | 1.00 | 29.23 | B |
| ATOM | 2762 | O | SER | B | 450 | 26.979 | 23.911 | 24.851 | 1.00 | 29.89 | B |
| ATOM | 2763 | N | ILE | B | 451 | 26.735 | 23.171 | 22.750 | 1.00 | 28.49 | B |
| ATOM | 2764 | CA | ILE | B | 451 | 25.433 | 22.620 | 23.040 | 1.00 | 28.19 | B |
| ATOM | 2765 | CB | ILE | B | 451 | 24.692 | 22.152 | 21.726 | 1.00 | 29.72 | B |
| ATOM | 2766 | CG2 | ILE | B | 451 | 23.560 | 21.168 | 22.066 | 1.00 | 27.71 | B |
| ATOM | 2767 | CG1 | ILE | B | 451 | 24.129 | 23.388 | 20.997 | 1.00 | 28.71 | B |
| ATOM | 2768 | CD1 | ILE | B | 451 | 23.660 | 23.137 | 19.585 | 1.00 | 27.36 | B |
| ATOM | 2769 | C | ILE | B | 451 | 25.605 | 21.479 | 24.031 | 1.00 | 26.55 | B |
| ATOM | 2770 | O | ILE | B | 451 | 24.897 | 21.430 | 25.028 | 1.00 | 26.77 | B |
| ATOM | 2771 | N | ILE | B | 452 | 26.560 | 20.591 | 23.767 | 1.00 | 26.81 | B |
| ATOM | 2772 | CA | ILE | B | 452 | 26.854 | 19.447 | 24.641 | 1.00 | 27.52 | B |
| ATOM | 2773 | CB | ILE | B | 452 | 28.078 | 18.653 | 24.120 | 1.00 | 28.00 | B |
| ATOM | 2774 | CG2 | ILE | B | 452 | 28.568 | 17.647 | 25.194 | 1.00 | 27.41 | B |
| ATOM | 2775 | CG1 | ILE | B | 452 | 27.704 | 17.958 | 22.798 | 1.00 | 26.73 | B |
| ATOM | 2776 | CD1 | ILE | B | 452 | 28.874 | 17.326 | 22.097 | 1.00 | 24.63 | B |
| ATOM | 2777 | C | ILE | B | 452 | 27.125 | 19.874 | 26.088 | 1.00 | 28.90 | B |
| ATOM | 2778 | O | ILE | B | 452 | 26.554 | 19.331 | 27.028 | 1.00 | 28.83 | B |
| ATOM | 2779 | N | LEU | B | 453 | 28.006 | 20.850 | 26.253 | 1.00 | 30.42 | B |
| ATOM | 2780 | CA | LEU | B | 453 | 28.337 | 21.369 | 27.557 | 1.00 | 31.20 | B |
| ATOM | 2781 | CB | LEU | B | 453 | 29.255 | 22.579 | 27.408 | 1.00 | 32.53 | B |
| ATOM | 2782 | CG | LEU | B | 453 | 29.445 | 23.436 | 28.676 | 1.00 | 32.13 | B |
| ATOM | 2783 | CD1 | LEU | B | 453 | 30.065 | 22.570 | 29.785 | 1.00 | 30.48 | B |
| ATOM | 2784 | CD2 | LEU | B | 453 | 30.323 | 24.655 | 28.355 | 1.00 | 30.65 | B |
| ATOM | 2785 | C | LEU | B | 453 | 27.094 | 21.802 | 28.318 | 1.00 | 33.32 | B |
| ATOM | 2786 | O | LEU | B | 453 | 26.885 | 21.411 | 29.468 | 1.00 | 33.69 | B |
| ATOM | 2787 | N | LEU | B | 454 | 26.274 | 22.623 | 27.677 | 1.00 | 35.34 | B |
| ATOM | 2788 | CA | LEU | B | 454 | 25.072 | 23.154 | 28.315 | 1.00 | 38.60 | B |
| ATOM | 2789 | CB | LEU | B | 454 | 24.623 | 24.415 | 27.567 | 1.00 | 40.03 | B |
| ATOM | 2790 | CG | LEU | B | 454 | 25.667 | 25.537 | 27.560 | 1.00 | 41.18 | B |
| ATOM | 2791 | CD1 | LEU | B | 454 | 25.417 | 26.466 | 26.386 | 1.00 | 42.68 | B |
| ATOM | 2792 | CD2 | LEU | B | 454 | 25.618 | 26.292 | 28.882 | 1.00 | 41.72 | B |
| ATOM | 2793 | C | LEU | B | 454 | 23.905 | 22.167 | 28.431 | 1.00 | 39.88 | B |
| ATOM | 2794 | O | LEU | B | 454 | 23.023 | 22.344 | 29.273 | 1.00 | 38.72 | B |
| ATOM | 2795 | N | ASN | B | 455 | 23.907 | 21.131 | 27.595 | 1.00 | 42.42 | B |
| ATOM | 2796 | CA | ASN | B | 455 | 22.841 | 20.137 | 27.607 | 1.00 | 45.22 | B |
| ATOM | 2797 | CB | ASN | B | 455 | 22.474 | 19.733 | 26.184 | 1.00 | 43.09 | B |
| ATOM | 2798 | CG | ASN | B | 455 | 21.219 | 18.878 | 26.120 | 1.00 | 42.53 | B |
| ATOM | 2799 | OD1 | ASN | B | 455 | 20.138 | 19.313 | 26.515 | 1.00 | 41.92 | B |
| ATOM | 2800 | ND2 | ASN | B | 455 | 21.354 | 17.660 | 25.616 | 1.00 | 41.49 | B |
| ATOM | 2801 | C | ASN | B | 455 | 23.221 | 18.896 | 28.400 | 1.00 | 47.65 | B |
| ATOM | 2802 | O | ASN | B | 455 | 22.389 | 18.021 | 28.621 | 1.00 | 47.83 | B |
| ATOM | 2803 | N | SER | B | 456 | 24.484 | 18.816 | 28.795 | 1.00 | 51.56 | B |
| ATOM | 2804 | CA | SER | B | 456 | 24.992 | 17.692 | 29.569 | 1.00 | 55.43 | B |
| ATOM | 2805 | CB | SER | B | 456 | 26.395 | 18.024 | 30.090 | 1.00 | 55.18 | B |
| ATOM | 2806 | OG | SER | B | 456 | 26.426 | 19.313 | 30.691 | 1.00 | 53.62 | B |
| ATOM | 2807 | C | SER | B | 456 | 24.069 | 17.376 | 30.739 | 1.00 | 58.50 | B |
| ATOM | 2808 | O | SER | B | 456 | 23.941 | 16.221 | 31.137 | 1.00 | 57.59 | B |

TABLE 9-continued

Structure coordinates for ERalpha-LBD/Compound 1 complex
(Table dicloses SEQ ID NOS 2-8, respectively, in order of appearance)

|      | #    | Name | Res. | Chain | Res # | X      | Y      | Z      | occ  | B     | SegID |
|------|------|------|------|-------|-------|--------|--------|--------|------|-------|-------|
| ATOM | 2809 | N    | GLY  | B     | 457   | 23.427 | 18.401 | 31.284 | 1.00 | 62.90 | B     |
| ATOM | 2810 | CA   | GLY  | B     | 457   | 22.537 | 18.194 | 32.407 | 1.00 | 69.16 | B     |
| ATOM | 2811 | C    | GLY  | B     | 457   | 21.167 | 18.766 | 32.119 | 1.00 | 73.81 | B     |
| ATOM | 2812 | O    | GLY  | B     | 457   | 20.174 | 18.088 | 32.363 | 1.00 | 74.45 | B     |
| ATOM | 2813 | N    | VAL  | B     | 458   | 21.139 | 20.005 | 31.610 | 1.00 | 77.96 | B     |
| ATOM | 2814 | CA   | VAL  | B     | 458   | 19.914 | 20.749 | 31.264 | 1.00 | 82.53 | B     |
| ATOM | 2815 | CB   | VAL  | B     | 458   | 18.999 | 19.940 | 30.282 | 1.00 | 82.97 | B     |
| ATOM | 2816 | CG1  | VAL  | B     | 458   | 18.306 | 18.792 | 30.987 | 1.00 | 83.71 | B     |
| ATOM | 2817 | CG2  | VAL  | B     | 458   | 17.939 | 20.839 | 29.668 | 1.00 | 83.37 | B     |
| ATOM | 2818 | C    | VAL  | B     | 458   | 19.115 | 21.076 | 32.519 | 1.00 | 85.38 | B     |
| ATOM | 2819 | O    | VAL  | B     | 458   | 18.244 | 21.949 | 32.516 | 1.00 | 85.92 | B     |
| ATOM | 2820 | N    | TYR  | B     | 459   | 19.445 | 20.383 | 33.603 | 1.00 | 88.47 | B     |
| ATOM | 2821 | CA   | TYR  | B     | 459   | 18.715 | 20.548 | 34.857 | 1.00 | 91.34 | B     |
| ATOM | 2822 | CB   | TYR  | B     | 459   | 17.318 | 19.965 | 34.679 | 1.00 | 92.80 | B     |
| ATOM | 2823 | CG   | TYR  | B     | 459   | 16.229 | 20.986 | 34.833 | 1.00 | 94.86 | B     |
| ATOM | 2824 | CD1  | TYR  | B     | 459   | 15.986 | 21.918 | 33.841 | 1.00 | 95.41 | B     |
| ATOM | 2825 | CE1  | TYR  | B     | 459   | 15.024 | 22.859 | 33.998 | 1.00 | 96.13 | B     |
| ATOM | 2826 | CD2  | TYR  | B     | 459   | 15.460 | 21.045 | 35.993 | 1.00 | 95.52 | B     |
| ATOM | 2827 | CE2  | TYR  | B     | 459   | 14.496 | 21.988 | 36.156 | 1.00 | 96.24 | B     |
| ATOM | 2828 | CZ   | TYR  | B     | 459   | 14.267 | 22.896 | 35.163 | 1.00 | 96.38 | B     |
| ATOM | 2829 | OH   | TYR  | B     | 459   | 13.267 | 23.831 | 35.316 | 1.00 | 96.37 | B     |
| ATOM | 2830 | C    | TYR  | B     | 459   | 19.424 | 19.818 | 35.980 | 1.00 | 92.41 | B     |
| ATOM | 2831 | O    | TYR  | B     | 459   | 19.141 | 18.643 | 36.241 | 1.00 | 92.73 | B     |
| ATOM | 2832 | N    | THR  | B     | 460   | 20.304 | 20.521 | 36.666 | 1.00 | 93.24 | B     |
| ATOM | 2833 | CA   | THR  | B     | 460   | 21.051 | 19.923 | 37.755 | 1.00 | 94.02 | B     |
| ATOM | 2834 | CB   | THR  | B     | 460   | 22.498 | 20.465 | 37.769 | 1.00 | 94.55 | B     |
| ATOM | 2835 | OG1  | THR  | B     | 460   | 22.725 | 21.262 | 38.942 | 1.00 | 94.61 | B     |
| ATOM | 2836 | CG2  | THR  | B     | 460   | 22.754 | 21.295 | 36.508 | 1.00 | 94.54 | B     |
| ATOM | 2837 | C    | THR  | B     | 460   | 20.415 | 20.155 | 39.125 | 1.00 | 94.26 | B     |
| ATOM | 2838 | O    | THR  | B     | 460   | 20.783 | 19.514 | 40.106 | 1.00 | 94.51 | B     |
| ATOM | 2839 | N    | LYS  | B     | 472   | 15.955 | 26.215 | 33.611 | 1.00 | 87.25 | B     |
| ATOM | 2840 | CA   | LYS  | B     | 472   | 15.643 | 26.184 | 32.175 | 1.00 | 87.36 | B     |
| ATOM | 2841 | CB   | LYS  | B     | 472   | 14.251 | 25.620 | 31.830 | 1.00 | 88.05 | B     |
| ATOM | 2842 | CG   | LYS  | B     | 472   | 13.686 | 24.522 | 32.650 | 1.00 | 89.32 | B     |
| ATOM | 2843 | CD   | LYS  | B     | 472   | 12.275 | 24.144 | 32.185 | 1.00 | 90.11 | B     |
| ATOM | 2844 | CE   | LYS  | B     | 472   | 11.874 | 22.691 | 32.544 | 1.00 | 90.70 | B     |
| ATOM | 2845 | NZ   | LYS  | B     | 472   | 11.451 | 22.428 | 33.955 | 1.00 | 90.85 | B     |
| ATOM | 2846 | C    | LYS  | B     | 472   | 15.578 | 27.555 | 31.535 | 1.00 | 86.64 | B     |
| ATOM | 2847 | O    | LYS  | B     | 472   | 15.426 | 27.627 | 30.321 | 1.00 | 87.07 | B     |
| ATOM | 2848 | N    | ASP  | B     | 473   | 15.627 | 28.648 | 32.285 | 1.00 | 85.01 | B     |
| ATOM | 2849 | CA   | ASP  | B     | 473   | 15.485 | 29.905 | 31.574 | 1.00 | 83.00 | B     |
| ATOM | 2850 | CB   | ASP  | B     | 473   | 14.790 | 30.969 | 32.437 | 1.00 | 85.00 | B     |
| ATOM | 2851 | CG   | ASP  | B     | 473   | 13.644 | 31.668 | 31.689 | 1.00 | 86.74 | B     |
| ATOM | 2852 | OD1  | ASP  | B     | 473   | 13.835 | 32.032 | 30.503 | 1.00 | 87.77 | B     |
| ATOM | 2853 | OD2  | ASP  | B     | 473   | 12.555 | 31.862 | 32.280 | 1.00 | 88.19 | B     |
| ATOM | 2854 | C    | ASP  | B     | 473   | 16.779 | 30.432 | 31.000 | 1.00 | 80.60 | B     |
| ATOM | 2855 | O    | ASP  | B     | 473   | 16.862 | 30.672 | 29.793 | 1.00 | 80.44 | B     |
| ATOM | 2856 | N    | HIS  | B     | 474   | 17.797 | 30.601 | 31.835 | 1.00 | 77.48 | B     |
| ATOM | 2857 | CA   | HIS  | B     | 474   | 19.054 | 31.121 | 31.317 | 1.00 | 74.50 | B     |
| ATOM | 2858 | CB   | HIS  | B     | 474   | 19.936 | 31.661 | 32.443 | 1.00 | 73.88 | B     |
| ATOM | 2859 | CG   | HIS  | B     | 474   | 21.070 | 32.499 | 31.948 | 1.00 | 72.78 | B     |
| ATOM | 2860 | CD2  | HIS  | B     | 474   | 21.135 | 33.817 | 31.643 | 1.00 | 72.32 | B     |
| ATOM | 2861 | ND1  | HIS  | B     | 474   | 22.293 | 31.965 | 31.606 | 1.00 | 72.74 | B     |
| ATOM | 2862 | CE1  | HIS  | B     | 474   | 23.062 | 32.917 | 31.108 | 1.00 | 73.10 | B     |
| ATOM | 2863 | NE2  | HIS  | B     | 474   | 22.383 | 34.050 | 31.118 | 1.00 | 73.07 | B     |
| ATOM | 2864 | C    | HIS  | B     | 474   | 19.825 | 30.090 | 30.490 | 1.00 | 72.91 | B     |
| ATOM | 2865 | O    | HIS  | B     | 474   | 20.278 | 30.392 | 29.379 | 1.00 | 72.78 | B     |
| ATOM | 2866 | N    | ILE  | B     | 475   | 19.969 | 28.878 | 31.020 | 1.00 | 70.10 | B     |
| ATOM | 2867 | CA   | ILE  | B     | 475   | 20.669 | 27.819 | 30.301 | 1.00 | 67.52 | B     |
| ATOM | 2868 | CB   | ILE  | B     | 475   | 20.679 | 26.500 | 31.120 | 1.00 | 67.99 | B     |
| ATOM | 2869 | CG2  | ILE  | B     | 475   | 20.973 | 25.306 | 30.205 | 1.00 | 68.09 | B     |
| ATOM | 2870 | CG1  | ILE  | B     | 475   | 21.714 | 26.581 | 32.245 | 1.00 | 67.69 | B     |
| ATOM | 2871 | CD1  | ILE  | B     | 475   | 23.134 | 26.295 | 31.807 | 1.00 | 67.42 | B     |
| ATOM | 2872 | C    | ILE  | B     | 475   | 19.990 | 27.556 | 28.950 | 1.00 | 65.72 | B     |
| ATOM | 2873 | O    | ILE  | B     | 475   | 20.659 | 27.413 | 27.927 | 1.00 | 64.04 | B     |
| ATOM | 2874 | N    | HIS  | B     | 476   | 18.661 | 27.496 | 28.955 | 1.00 | 64.15 | B     |
| ATOM | 2875 | CA   | HIS  | B     | 476   | 17.909 | 27.234 | 27.733 | 1.00 | 63.36 | B     |
| ATOM | 2876 | CB   | HIS  | B     | 476   | 16.452 | 26.905 | 28.063 | 1.00 | 65.16 | B     |
| ATOM | 2877 | CG   | HIS  | B     | 476   | 16.250 | 25.553 | 28.685 | 1.00 | 67.52 | B     |
| ATOM | 2878 | CD2  | HIS  | B     | 476   | 15.190 | 24.707 | 28.651 | 1.00 | 68.34 | B     |
| ATOM | 2879 | ND1  | HIS  | B     | 476   | 17.192 | 24.950 | 29.492 | 1.00 | 68.62 | B     |
| ATOM | 2880 | CE1  | HIS  | B     | 476   | 16.723 | 23.793 | 29.928 | 1.00 | 69.16 | B     |
| ATOM | 2881 | NE2  | HIS  | B     | 476   | 15.510 | 23.622 | 29.433 | 1.00 | 68.93 | B     |
| ATOM | 2882 | C    | HIS  | B     | 476   | 17.965 | 28.400 | 26.750 | 1.00 | 61.97 | B     |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2883 | O | HIS | B | 476 | 18.081 | 28.187 | 25.544 | 1.00 | 61.30 | B |
| ATOM | 2884 | N | ARG | B | 477 | 17.883 | 29.627 | 27.260 | 1.00 | 60.27 | B |
| ATOM | 2885 | CA | ARG | B | 477 | 17.932 | 30.815 | 26.408 | 1.00 | 58.52 | B |
| ATOM | 2886 | CB | ARG | B | 477 | 17.920 | 32.081 | 27.272 | 1.00 | 60.74 | B |
| ATOM | 2887 | CG | ARG | B | 477 | 16.980 | 33.197 | 26.783 | 1.00 | 63.09 | B |
| ATOM | 2888 | CD | ARG | B | 477 | 15.564 | 33.071 | 27.365 | 1.00 | 65.83 | B |
| ATOM | 2889 | NE | ARG | B | 477 | 14.652 | 34.104 | 26.862 | 1.00 | 67.62 | B |
| ATOM | 2890 | CZ | ARG | B | 477 | 13.414 | 34.307 | 27.313 | 1.00 | 69.17 | B |
| ATOM | 2891 | NH1 | ARG | B | 477 | 12.921 | 33.545 | 28.285 | 1.00 | 69.85 | B |
| ATOM | 2892 | NH2 | ARG | B | 477 | 12.677 | 35.291 | 26.807 | 1.00 | 69.76 | B |
| ATOM | 2893 | C | ARG | B | 477 | 19.207 | 30.774 | 25.553 | 1.00 | 56.28 | B |
| ATOM | 2894 | O | ARG | B | 477 | 19.169 | 31.010 | 24.339 | 1.00 | 56.43 | B |
| ATOM | 2895 | N | VAL | B | 478 | 20.329 | 30.471 | 26.201 | 1.00 | 52.86 | B |
| ATOM | 2896 | CA | VAL | B | 478 | 21.622 | 30.370 | 25.534 | 1.00 | 49.03 | B |
| ATOM | 2897 | CB | VAL | B | 478 | 22.737 | 30.026 | 26.536 | 1.00 | 49.86 | B |
| ATOM | 2898 | CG1 | VAL | B | 478 | 24.088 | 30.017 | 25.829 | 1.00 | 49.29 | B |
| ATOM | 2899 | CG2 | VAL | B | 478 | 22.723 | 31.019 | 27.697 | 1.00 | 49.93 | B |
| ATOM | 2900 | C | VAL | B | 478 | 21.537 | 29.247 | 24.516 | 1.00 | 46.88 | B |
| ATOM | 2901 | O | VAL | B | 478 | 22.110 | 29.326 | 23.427 | 1.00 | 46.41 | B |
| ATOM | 2902 | N | LEU | B | 479 | 20.822 | 28.190 | 24.885 | 1.00 | 44.12 | B |
| ATOM | 2903 | CA | LEU | B | 479 | 20.646 | 27.054 | 23.990 | 1.00 | 41.59 | B |
| ATOM | 2904 | CB | LEU | B | 479 | 19.960 | 25.895 | 24.729 | 1.00 | 41.48 | B |
| ATOM | 2905 | CG | LEU | B | 479 | 20.946 | 25.133 | 25.643 | 1.00 | 40.95 | B |
| ATOM | 2906 | CD1 | LEU | B | 479 | 20.206 | 24.304 | 26.673 | 1.00 | 39.58 | B |
| ATOM | 2907 | CD2 | LEU | B | 479 | 21.864 | 24.268 | 24.783 | 1.00 | 40.33 | B |
| ATOM | 2908 | C | LEU | B | 479 | 19.859 | 27.495 | 22.759 | 1.00 | 39.80 | B |
| ATOM | 2909 | O | LEU | B | 479 | 20.197 | 27.121 | 21.635 | 1.00 | 37.98 | B |
| ATOM | 2910 | N | ASP | B | 480 | 18.833 | 28.316 | 22.971 | 1.00 | 38.97 | B |
| ATOM | 2911 | CA | ASP | B | 480 | 18.048 | 28.832 | 21.858 | 1.00 | 39.52 | B |
| ATOM | 2912 | CB | ASP | B | 480 | 16.877 | 29.679 | 22.347 | 1.00 | 38.69 | B |
| ATOM | 2913 | CG | ASP | B | 480 | 15.743 | 28.849 | 22.935 | 1.00 | 39.59 | B |
| ATOM | 2914 | OD1 | ASP | B | 480 | 15.512 | 27.708 | 22.475 | 1.00 | 39.29 | B |
| ATOM | 2915 | OD2 | ASP | B | 480 | 15.061 | 29.357 | 23.850 | 1.00 | 39.79 | B |
| ATOM | 2916 | C | ASP | B | 480 | 18.946 | 29.701 | 20.990 | 1.00 | 40.46 | B |
| ATOM | 2917 | O | ASP | B | 480 | 18.875 | 29.650 | 19.762 | 1.00 | 40.27 | B |
| ATOM | 2918 | N | LYS | B | 481 | 19.797 | 30.497 | 21.633 | 1.00 | 42.00 | B |
| ATOM | 2919 | CA | LYS | B | 481 | 20.694 | 31.383 | 20.911 | 1.00 | 42.84 | B |
| ATOM | 2920 | CB | LYS | B | 481 | 21.530 | 32.202 | 21.891 | 1.00 | 45.38 | B |
| ATOM | 2921 | CG | LYS | B | 481 | 21.273 | 33.699 | 21.812 | 1.00 | 47.99 | B |
| ATOM | 2922 | CD | LYS | B | 481 | 22.194 | 34.377 | 20.811 | 1.00 | 49.92 | B |
| ATOM | 2923 | CE | LYS | B | 481 | 21.694 | 35.771 | 20.461 | 1.00 | 52.27 | B |
| ATOM | 2924 | NZ | LYS | B | 481 | 20.602 | 35.745 | 19.439 | 1.00 | 53.91 | B |
| ATOM | 2925 | C | LYS | B | 481 | 21.595 | 30.600 | 19.990 | 1.00 | 43.07 | B |
| ATOM | 2926 | O | LYS | B | 481 | 21.841 | 31.015 | 18.856 | 1.00 | 42.99 | B |
| ATOM | 2927 | N | ILE | B | 482 | 22.086 | 29.460 | 20.468 | 1.00 | 43.26 | B |
| ATOM | 2928 | CA | ILE | B | 482 | 22.967 | 28.621 | 19.655 | 1.00 | 42.92 | B |
| ATOM | 2929 | CB | ILE | B | 482 | 23.659 | 27.548 | 20.523 | 1.00 | 43.73 | B |
| ATOM | 2930 | CG2 | ILE | B | 482 | 24.788 | 26.890 | 19.748 | 1.00 | 43.13 | B |
| ATOM | 2931 | CG1 | ILE | B | 482 | 24.241 | 28.218 | 21.772 | 1.00 | 45.09 | B |
| ATOM | 2932 | CD1 | ILE | B | 482 | 24.978 | 27.284 | 22.705 | 1.00 | 46.48 | B |
| ATOM | 2933 | C | ILE | B | 482 | 22.201 | 27.969 | 18.490 | 1.00 | 42.77 | B |
| ATOM | 2934 | O | ILE | B | 482 | 22.773 | 27.710 | 17.428 | 1.00 | 41.31 | B |
| ATOM | 2935 | N | THR | B | 483 | 20.911 | 27.705 | 18.688 | 1.00 | 42.30 | B |
| ATOM | 2936 | CA | THR | B | 483 | 20.100 | 27.138 | 17.616 | 1.00 | 42.49 | B |
| ATOM | 2937 | CB | THR | B | 483 | 18.655 | 26.824 | 18.076 | 1.00 | 42.24 | B |
| ATOM | 2938 | OG1 | THR | B | 483 | 18.681 | 25.909 | 19.172 | 1.00 | 41.17 | B |
| ATOM | 2939 | CG2 | THR | B | 483 | 17.855 | 26.218 | 16.934 | 1.00 | 41.20 | B |
| ATOM | 2940 | C | THR | B | 483 | 20.020 | 28.223 | 16.533 | 1.00 | 43.48 | B |
| ATOM | 2941 | O | THR | B | 483 | 20.280 | 27.963 | 15.349 | 1.00 | 42.86 | B |
| ATOM | 2942 | N | ASP | B | 484 | 19.654 | 29.434 | 16.960 | 1.00 | 43.59 | B |
| ATOM | 2943 | CA | ASP | B | 484 | 19.541 | 30.583 | 16.063 | 1.00 | 44.52 | B |
| ATOM | 2944 | CB | ASP | B | 484 | 19.268 | 31.876 | 16.850 | 1.00 | 44.85 | B |
| ATOM | 2945 | CG | ASP | B | 484 | 17.968 | 31.826 | 17.653 | 1.00 | 46.05 | B |
| ATOM | 2946 | OD1 | ASP | B | 484 | 16.987 | 31.212 | 17.189 | 1.00 | 47.03 | B |
| ATOM | 2947 | OD2 | ASP | B | 484 | 17.920 | 32.428 | 18.750 | 1.00 | 47.47 | B |
| ATOM | 2948 | C | ASP | B | 484 | 20.838 | 30.748 | 15.284 | 1.00 | 44.42 | B |
| ATOM | 2949 | O | ASP | B | 484 | 20.829 | 31.018 | 14.078 | 1.00 | 44.07 | B |
| ATOM | 2950 | N | THR | B | 485 | 21.951 | 30.564 | 15.992 | 1.00 | 44.86 | B |
| ATOM | 2951 | CA | THR | B | 485 | 23.290 | 30.695 | 15.425 | 1.00 | 45.43 | B |
| ATOM | 2952 | CB | THR | B | 485 | 24.346 | 30.738 | 16.546 | 1.00 | 45.59 | B |
| ATOM | 2953 | OG1 | THR | B | 485 | 24.039 | 31.812 | 17.443 | 1.00 | 46.14 | B |
| ATOM | 2954 | CG2 | THR | B | 485 | 25.734 | 30.947 | 15.970 | 1.00 | 44.57 | B |
| ATOM | 2955 | C | THR | B | 485 | 23.682 | 29.607 | 14.424 | 1.00 | 46.29 | B |
| ATOM | 2956 | O | THR | B | 485 | 24.401 | 29.879 | 13.461 | 1.00 | 45.93 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 2957 | N | LEU | B | 486 | 23.235 | 28.376 | 14.652 | 1.00 | 47.04 | B |
| ATOM | 2958 | CA | LEU | B | 486 | 23.553 | 27.288 | 13.729 | 1.00 | 47.88 | B |
| ATOM | 2959 | CB | LEU | B | 486 | 23.242 | 25.931 | 14.368 | 1.00 | 46.81 | B |
| ATOM | 2960 | CG | LEU | B | 486 | 24.424 | 25.165 | 14.967 | 1.00 | 45.97 | B |
| ATOM | 2961 | CD1 | LEU | B | 486 | 23.942 | 23.821 | 15.485 | 1.00 | 46.12 | B |
| ATOM | 2962 | CD2 | LEU | B | 486 | 25.497 | 24.958 | 13.916 | 1.00 | 44.78 | B |
| ATOM | 2963 | C | LEU | B | 486 | 22.737 | 27.462 | 12.444 | 1.00 | 48.49 | B |
| ATOM | 2964 | O | LEU | B | 486 | 23.235 | 27.266 | 11.330 | 1.00 | 47.66 | B |
| ATOM | 2965 | N | ILE | B | 487 | 21.474 | 27.827 | 12.622 | 1.00 | 49.72 | B |
| ATOM | 2966 | CA | ILE | B | 487 | 20.573 | 28.059 | 11.511 | 1.00 | 52.18 | B |
| ATOM | 2967 | CB | ILE | B | 487 | 19.153 | 28.339 | 12.035 | 1.00 | 52.60 | B |
| ATOM | 2968 | CG2 | ILE | B | 487 | 18.291 | 28.934 | 10.931 | 1.00 | 53.17 | B |
| ATOM | 2969 | CG1 | ILE | B | 487 | 18.535 | 27.042 | 12.562 | 1.00 | 52.65 | B |
| ATOM | 2970 | CD1 | ILE | B | 487 | 18.281 | 25.995 | 11.478 | 1.00 | 52.50 | B |
| ATOM | 2971 | C | ILE | B | 487 | 21.081 | 29.249 | 10.696 | 1.00 | 53.41 | B |
| ATOM | 2972 | O | ILE | B | 487 | 21.265 | 29.150 | 9.481 | 1.00 | 53.05 | B |
| ATOM | 2973 | N | HIS | B | 488 | 21.316 | 30.368 | 11.382 | 1.00 | 55.45 | B |
| ATOM | 2974 | CA | HIS | B | 488 | 21.825 | 31.585 | 10.751 | 1.00 | 56.83 | B |
| ATOM | 2975 | CB | HIS | B | 488 | 22.268 | 32.589 | 11.808 | 1.00 | 57.34 | B |
| ATOM | 2976 | CG | HIS | B | 488 | 23.089 | 33.712 | 11.256 | 1.00 | 58.72 | B |
| ATOM | 2977 | CD2 | HIS | B | 488 | 24.427 | 33.925 | 11.267 | 1.00 | 59.03 | B |
| ATOM | 2978 | ND1 | HIS | B | 488 | 22.537 | 34.780 | 10.581 | 1.00 | 59.16 | B |
| ATOM | 2979 | CE1 | HIS | B | 488 | 23.499 | 35.603 | 10.203 | 1.00 | 59.29 | B |
| ATOM | 2980 | NE2 | HIS | B | 488 | 24.654 | 35.106 | 10.606 | 1.00 | 59.25 | B |
| ATOM | 2981 | C | HIS | B | 488 | 23.014 | 31.286 | 9.853 | 1.00 | 57.32 | B |
| ATOM | 2982 | O | HIS | B | 488 | 23.145 | 31.843 | 8.767 | 1.00 | 57.77 | B |
| ATOM | 2983 | N | LEU | B | 489 | 23.892 | 30.417 | 10.334 | 1.00 | 58.12 | B |
| ATOM | 2984 | CA | LEU | B | 489 | 25.070 | 30.022 | 9.586 | 1.00 | 58.78 | B |
| ATOM | 2985 | CB | LEU | B | 489 | 25.952 | 29.121 | 10.447 | 1.00 | 58.78 | B |
| ATOM | 2986 | CG | LEU | B | 489 | 26.583 | 29.756 | 11.687 | 1.00 | 59.60 | B |
| ATOM | 2987 | CD1 | LEU | B | 489 | 27.059 | 28.659 | 12.641 | 1.00 | 60.02 | B |
| ATOM | 2988 | CD2 | LEU | B | 489 | 27.733 | 30.670 | 11.265 | 1.00 | 58.77 | B |
| ATOM | 2989 | C | LEU | B | 489 | 24.650 | 29.268 | 8.336 | 1.00 | 59.51 | B |
| ATOM | 2990 | O | LEU | B | 489 | 25.198 | 29.488 | 7.259 | 1.00 | 59.96 | B |
| ATOM | 2991 | N | MET | B | 490 | 23.670 | 28.379 | 8.488 | 1.00 | 60.24 | B |
| ATOM | 2992 | CA | MET | B | 490 | 23.178 | 27.567 | 7.375 | 1.00 | 61.00 | B |
| ATOM | 2993 | CB | MET | B | 490 | 22.231 | 26.480 | 7.899 | 1.00 | 60.82 | B |
| ATOM | 2994 | CG | MET | B | 490 | 22.890 | 25.542 | 8.909 | 1.00 | 59.75 | B |
| ATOM | 2995 | SD | MET | B | 490 | 21.846 | 24.187 | 9.454 | 1.00 | 58.82 | B |
| ATOM | 2996 | CE | MET | B | 490 | 21.196 | 24.824 | 10.933 | 1.00 | 57.97 | B |
| ATOM | 2997 | C | MET | B | 490 | 22.484 | 28.401 | 6.305 | 1.00 | 61.66 | B |
| ATOM | 2998 | O | MET | B | 490 | 22.519 | 28.061 | 5.122 | 1.00 | 60.71 | B |
| ATOM | 2999 | N | ALA | B | 491 | 21.861 | 29.495 | 6.730 | 1.00 | 62.81 | B |
| ATOM | 3000 | CA | ALA | B | 491 | 21.172 | 30.392 | 5.813 | 1.00 | 64.33 | B |
| ATOM | 3001 | CB | ALA | B | 491 | 20.402 | 31.436 | 6.598 | 1.00 | 64.26 | B |
| ATOM | 3002 | C | ALA | B | 491 | 22.189 | 31.065 | 4.888 | 1.00 | 65.64 | B |
| ATOM | 3003 | O | ALA | B | 491 | 22.104 | 30.947 | 3.659 | 1.00 | 66.56 | B |
| ATOM | 3004 | N | LYS | B | 492 | 23.151 | 31.768 | 5.480 | 1.00 | 66.00 | B |
| ATOM | 3005 | CA | LYS | B | 492 | 24.175 | 32.439 | 4.694 | 1.00 | 66.49 | B |
| ATOM | 3006 | CB | LYS | B | 492 | 25.133 | 33.201 | 5.611 | 1.00 | 67.59 | B |
| ATOM | 3007 | CG | LYS | B | 492 | 24.480 | 34.401 | 6.284 | 1.00 | 70.07 | B |
| ATOM | 3008 | CD | LYS | B | 492 | 25.499 | 35.282 | 7.001 | 1.00 | 71.69 | B |
| ATOM | 3009 | CE | LYS | B | 492 | 24.884 | 36.630 | 7.393 | 1.00 | 72.49 | B |
| ATOM | 3010 | NZ | LYS | B | 492 | 25.851 | 37.532 | 8.096 | 1.00 | 72.59 | B |
| ATOM | 3011 | C | LYS | B | 492 | 24.945 | 31.441 | 3.835 | 1.00 | 66.36 | B |
| ATOM | 3012 | O | LYS | B | 492 | 25.480 | 31.797 | 2.785 | 1.00 | 66.69 | B |
| ATOM | 3013 | N | ALA | B | 493 | 24.991 | 30.189 | 4.276 | 1.00 | 65.57 | B |
| ATOM | 3014 | CA | ALA | B | 493 | 25.696 | 29.159 | 3.529 | 1.00 | 65.33 | B |
| ATOM | 3015 | CB | ALA | B | 493 | 25.787 | 27.889 | 4.352 | 1.00 | 64.78 | B |
| ATOM | 3016 | C | ALA | B | 493 | 24.935 | 28.895 | 2.237 | 1.00 | 66.07 | B |
| ATOM | 3017 | O | ALA | B | 493 | 25.431 | 28.214 | 1.327 | 1.00 | 65.85 | B |
| ATOM | 3018 | N | GLY | B | 494 | 23.723 | 29.444 | 2.167 | 1.00 | 66.03 | B |
| ATOM | 3019 | CA | GLY | B | 494 | 22.893 | 29.267 | 0.995 | 1.00 | 66.13 | B |
| ATOM | 3020 | C | GLY | B | 494 | 22.127 | 27.960 | 1.048 | 1.00 | 67.00 | B |
| ATOM | 3021 | O | GLY | B | 494 | 22.371 | 27.045 | 0.247 | 1.00 | 67.73 | B |
| ATOM | 3022 | N | LEU | B | 495 | 21.205 | 27.868 | 2.006 | 1.00 | 66.31 | B |
| ATOM | 3023 | CA | LEU | B | 495 | 20.378 | 26.678 | 2.179 | 1.00 | 64.60 | B |
| ATOM | 3024 | CB | LEU | B | 495 | 20.802 | 25.908 | 3.431 | 1.00 | 63.93 | B |
| ATOM | 3025 | CG | LEU | B | 495 | 21.482 | 24.557 | 3.192 | 1.00 | 63.52 | B |
| ATOM | 3026 | CD1 | LEU | B | 495 | 22.742 | 24.735 | 2.363 | 1.00 | 62.86 | B |
| ATOM | 3027 | CD2 | LEU | B | 495 | 21.810 | 23.924 | 4.527 | 1.00 | 64.09 | B |
| ATOM | 3028 | C | LEU | B | 495 | 18.909 | 27.062 | 2.287 | 1.00 | 64.32 | B |
| ATOM | 3029 | O | LEU | B | 495 | 18.576 | 28.154 | 2.760 | 1.00 | 63.66 | B |
| ATOM | 3030 | N | THR | B | 496 | 18.039 | 26.155 | 1.844 | 1.00 | 63.62 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3031 | CA | THR | B | 496 | 16.594 | 26.378 | 1.878 | 1.00 | 63.06 | B |
| ATOM | 3032 | CB | THR | B | 496 | 15.851 | 25.387 | 0.946 | 1.00 | 62.49 | B |
| ATOM | 3033 | OG1 | THR | B | 496 | 15.814 | 24.093 | 1.555 | 1.00 | 61.79 | B |
| ATOM | 3034 | CG2 | THR | B | 496 | 16.563 | 25.273 | −0.390 | 1.00 | 61.60 | B |
| ATOM | 3035 | C | THR | B | 496 | 16.081 | 26.170 | 3.302 | 1.00 | 63.03 | B |
| ATOM | 3036 | O | THR | B | 496 | 16.642 | 25.367 | 4.048 | 1.00 | 63.25 | B |
| ATOM | 3037 | N | LEU | B | 497 | 15.027 | 26.890 | 3.681 | 1.00 | 62.54 | B |
| ATOM | 3038 | CA | LEU | B | 497 | 14.466 | 26.734 | 5.021 | 1.00 | 62.00 | B |
| ATOM | 3039 | CB | LEU | B | 497 | 13.091 | 27.403 | 5.133 | 1.00 | 62.08 | B |
| ATOM | 3040 | CG | LEU | B | 497 | 13.068 | 28.919 | 5.349 | 1.00 | 62.89 | B |
| ATOM | 3041 | CD1 | LEU | B | 497 | 11.630 | 29.429 | 5.287 | 1.00 | 62.79 | B |
| ATOM | 3042 | CD2 | LEU | B | 497 | 13.709 | 29.256 | 6.699 | 1.00 | 62.67 | B |
| ATOM | 3043 | C | LEU | B | 497 | 14.332 | 25.251 | 5.326 | 1.00 | 61.37 | B |
| ATOM | 3044 | O | LEU | B | 497 | 14.656 | 24.811 | 6.425 | 1.00 | 61.46 | B |
| ATOM | 3045 | N | GLN | B | 498 | 13.866 | 24.481 | 4.346 | 1.00 | 60.41 | B |
| ATOM | 3046 | CA | GLN | B | 498 | 13.713 | 23.044 | 4.535 | 1.00 | 59.26 | B |
| ATOM | 3047 | CB | GLN | B | 498 | 13.076 | 22.381 | 3.311 | 1.00 | 60.41 | B |
| ATOM | 3048 | CG | GLN | B | 498 | 13.046 | 20.858 | 3.422 | 1.00 | 62.12 | B |
| ATOM | 3049 | CD | GLN | B | 498 | 12.627 | 20.171 | 2.136 | 1.00 | 63.48 | B |
| ATOM | 3050 | OE1 | GLN | B | 498 | 13.232 | 20.374 | 1.085 | 1.00 | 64.61 | B |
| ATOM | 3051 | NE2 | GLN | B | 498 | 11.594 | 19.342 | 2.216 | 1.00 | 63.66 | B |
| ATOM | 3052 | C | GLN | B | 498 | 15.065 | 22.395 | 4.783 | 1.00 | 57.66 | B |
| ATOM | 3053 | O | GLN | B | 498 | 15.200 | 21.561 | 5.666 | 1.00 | 56.65 | B |
| ATOM | 3054 | N | GLN | B | 499 | 16.060 | 22.771 | 3.989 | 1.00 | 56.43 | B |
| ATOM | 3055 | CA | GLN | B | 499 | 17.398 | 22.207 | 4.137 | 1.00 | 55.28 | B |
| ATOM | 3056 | CB | GLN | B | 499 | 18.286 | 22.634 | 2.984 | 1.00 | 54.71 | B |
| ATOM | 3057 | CG | GLN | B | 499 | 17.875 | 22.117 | 1.641 | 1.00 | 53.63 | B |
| ATOM | 3058 | CD | GLN | B | 499 | 18.813 | 22.620 | 0.579 | 1.00 | 53.10 | B |
| ATOM | 3059 | OE1 | GLN | B | 499 | 18.967 | 23.830 | 0.403 | 1.00 | 52.38 | B |
| ATOM | 3060 | NE2 | GLN | B | 499 | 19.466 | 21.702 | −0.124 | 1.00 | 51.60 | B |
| ATOM | 3061 | C | GLN | B | 499 | 18.045 | 22.660 | 5.435 | 1.00 | 54.65 | B |
| ATOM | 3062 | O | GLN | B | 499 | 18.898 | 21.965 | 5.992 | 1.00 | 54.42 | B |
| ATOM | 3063 | N | GLN | B | 500 | 17.653 | 23.842 | 5.894 | 1.00 | 53.32 | B |
| ATOM | 3064 | CA | GLN | B | 500 | 18.181 | 24.375 | 7.131 | 1.00 | 52.73 | B |
| ATOM | 3065 | CB | GLN | B | 500 | 17.692 | 25.811 | 7.355 | 1.00 | 52.72 | B |
| ATOM | 3066 | CG | GLN | B | 500 | 18.551 | 26.874 | 6.685 | 1.00 | 52.33 | B |
| ATOM | 3067 | CD | GLN | B | 500 | 17.863 | 28.221 | 6.620 | 1.00 | 52.66 | B |
| ATOM | 3068 | OE1 | GLN | B | 500 | 17.369 | 28.732 | 7.623 | 1.00 | 51.58 | B |
| ATOM | 3069 | NE2 | GLN | B | 500 | 17.832 | 28.809 | 5.430 | 1.00 | 53.59 | B |
| ATOM | 3070 | C | GLN | B | 500 | 17.713 | 23.487 | 8.269 | 1.00 | 52.30 | B |
| ATOM | 3071 | O | GLN | B | 500 | 18.523 | 22.855 | 8.954 | 1.00 | 52.51 | B |
| ATOM | 3072 | N | HIS | B | 501 | 16.400 | 23.416 | 8.456 | 1.00 | 51.27 | B |
| ATOM | 3073 | CA | HIS | B | 501 | 15.864 | 22.615 | 9.537 | 1.00 | 50.41 | B |
| ATOM | 3074 | CB | HIS | B | 501 | 14.350 | 22.887 | 9.692 | 1.00 | 52.75 | B |
| ATOM | 3075 | CG | HIS | B | 501 | 13.480 | 22.295 | 8.622 | 1.00 | 55.96 | B |
| ATOM | 3076 | CD2 | HIS | B | 501 | 13.507 | 21.089 | 8.005 | 1.00 | 56.98 | B |
| ATOM | 3077 | ND1 | HIS | B | 501 | 12.343 | 22.932 | 8.165 | 1.00 | 57.78 | B |
| ATOM | 3078 | CE1 | HIS | B | 501 | 11.706 | 22.143 | 7.316 | 1.00 | 58.34 | B |
| ATOM | 3079 | NE2 | HIS | B | 501 | 12.391 | 21.017 | 7.202 | 1.00 | 58.20 | B |
| ATOM | 3080 | C | HIS | B | 501 | 16.200 | 21.116 | 9.459 | 1.00 | 48.70 | B |
| ATOM | 3081 | O | HIS | B | 501 | 16.125 | 20.411 | 10.462 | 1.00 | 49.10 | B |
| ATOM | 3082 | N | GLN | B | 502 | 16.612 | 20.633 | 8.290 | 1.00 | 46.05 | B |
| ATOM | 3083 | CA | GLN | B | 502 | 16.976 | 19.224 | 8.151 | 1.00 | 44.47 | B |
| ATOM | 3084 | CB | GLN | B | 502 | 16.914 | 18.764 | 6.697 | 1.00 | 45.07 | B |
| ATOM | 3085 | CG | GLN | B | 502 | 15.541 | 18.682 | 6.095 | 1.00 | 45.62 | B |
| ATOM | 3086 | CD | GLN | B | 502 | 15.604 | 18.056 | 4.738 | 1.00 | 46.62 | B |
| ATOM | 3087 | OE1 | GLN | B | 502 | 16.576 | 18.244 | 4.016 | 1.00 | 46.89 | B |
| ATOM | 3088 | NE2 | GLN | B | 502 | 14.571 | 17.306 | 4.374 | 1.00 | 47.83 | B |
| ATOM | 3089 | C | GLN | B | 502 | 18.388 | 18.971 | 8.650 | 1.00 | 43.45 | B |
| ATOM | 3090 | O | GLN | B | 502 | 18.663 | 17.930 | 9.246 | 1.00 | 42.42 | B |
| ATOM | 3091 | N | ARG | B | 503 | 19.284 | 19.919 | 8.369 | 1.00 | 42.26 | B |
| ATOM | 3092 | CA | ARG | B | 503 | 20.675 | 19.820 | 8.777 | 1.00 | 39.68 | B |
| ATOM | 3093 | CB | ARG | B | 503 | 21.516 | 20.879 | 8.055 | 1.00 | 39.98 | B |
| ATOM | 3094 | CG | ARG | B | 503 | 23.028 | 20.706 | 8.232 | 1.00 | 40.98 | B |
| ATOM | 3095 | CD | ARG | B | 503 | 23.821 | 21.867 | 7.633 | 1.00 | 39.98 | B |
| ATOM | 3096 | NE | ARG | B | 503 | 25.272 | 21.720 | 7.796 | 1.00 | 39.64 | B |
| ATOM | 3097 | CZ | ARG | B | 503 | 26.002 | 20.735 | 7.276 | 1.00 | 39.14 | B |
| ATOM | 3098 | NH1 | ARG | B | 503 | 25.429 | 19.792 | 6.551 | 1.00 | 40.28 | B |
| ATOM | 3099 | NH2 | ARG | B | 503 | 27.310 | 20.694 | 7.476 | 1.00 | 38.13 | B |
| ATOM | 3100 | C | ARG | B | 503 | 20.741 | 20.028 | 10.287 | 1.00 | 38.66 | B |
| ATOM | 3101 | O | ARG | B | 503 | 21.516 | 19.368 | 10.975 | 1.00 | 38.58 | B |
| ATOM | 3102 | N | LEU | B | 504 | 19.928 | 20.946 | 10.800 | 1.00 | 36.42 | B |
| ATOM | 3103 | CA | LEU | B | 504 | 19.900 | 21.205 | 12.233 | 1.00 | 35.79 | B |
| ATOM | 3104 | CB | LEU | B | 504 | 18.894 | 22.315 | 12.560 | 1.00 | 36.53 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3105 | CG | LEU | B | 504 | 18.595 | 22.547 | 14.048 | 1.00 | 38.07 | B |
| ATOM | 3106 | CD1 | LEU | B | 504 | 19.872 | 22.990 | 14.764 | 1.00 | 38.42 | B |
| ATOM | 3107 | CD2 | LEU | B | 504 | 17.495 | 23.581 | 14.216 | 1.00 | 36.11 | B |
| ATOM | 3108 | C | LEU | B | 504 | 19.513 | 19.917 | 12.961 | 1.00 | 35.51 | B |
| ATOM | 3109 | O | LEU | B | 504 | 20.128 | 19.542 | 13.955 | 1.00 | 36.23 | B |
| ATOM | 3110 | N | ALA | B | 505 | 18.492 | 19.238 | 12.450 | 1.00 | 34.38 | B |
| ATOM | 3111 | CA | ALA | B | 505 | 18.020 | 17.992 | 13.034 | 1.00 | 32.60 | B |
| ATOM | 3112 | CB | ALA | B | 505 | 16.702 | 17.568 | 12.369 | 1.00 | 32.51 | B |
| ATOM | 3113 | C | ALA | B | 505 | 19.055 | 16.880 | 12.903 | 1.00 | 32.06 | B |
| ATOM | 3114 | O | ALA | B | 505 | 19.226 | 16.084 | 13.819 | 1.00 | 28.76 | B |
| ATOM | 3115 | N | GLN | B | 506 | 19.741 | 16.821 | 11.766 | 1.00 | 33.09 | B |
| ATOM | 3116 | CA | GLN | B | 506 | 20.749 | 15.780 | 11.562 | 1.00 | 36.15 | B |
| ATOM | 3117 | CB | GLN | B | 506 | 21.280 | 15.786 | 10.130 | 1.00 | 37.17 | B |
| ATOM | 3118 | CG | GLN | B | 506 | 20.249 | 15.461 | 9.091 | 1.00 | 41.84 | B |
| ATOM | 3119 | CD | GLN | B | 506 | 20.747 | 15.722 | 7.681 | 1.00 | 43.99 | B |
| ATOM | 3120 | OE1 | GLN | B | 506 | 21.344 | 16.769 | 7.400 | 1.00 | 44.38 | B |
| ATOM | 3121 | NE2 | GLN | B | 506 | 20.493 | 14.778 | 6.783 | 1.00 | 44.73 | B |
| ATOM | 3122 | C | GLN | B | 506 | 21.921 | 15.949 | 12.515 | 1.00 | 37.03 | B |
| ATOM | 3123 | O | GLN | B | 506 | 22.506 | 14.962 | 12.950 | 1.00 | 37.65 | B |
| ATOM | 3124 | N | LEU | B | 507 | 22.270 | 17.200 | 12.814 | 1.00 | 37.03 | B |
| ATOM | 3125 | CA | LEU | B | 507 | 23.370 | 17.500 | 13.729 | 1.00 | 37.47 | B |
| ATOM | 3126 | CB | LEU | B | 507 | 23.726 | 19.001 | 13.686 | 1.00 | 38.73 | B |
| ATOM | 3127 | CG | LEU | B | 507 | 24.335 | 19.598 | 12.406 | 1.00 | 38.76 | B |
| ATOM | 3128 | CD1 | LEU | B | 507 | 24.456 | 21.100 | 12.565 | 1.00 | 38.51 | B |
| ATOM | 3129 | CD2 | LEU | B | 507 | 25.687 | 18.977 | 12.120 | 1.00 | 36.84 | B |
| ATOM | 3130 | C | LEU | B | 507 | 22.982 | 17.114 | 15.156 | 1.00 | 36.32 | B |
| ATOM | 3131 | O | LEU | B | 507 | 23.691 | 16.364 | 15.816 | 1.00 | 35.72 | B |
| ATOM | 3132 | N | LEU | B | 508 | 21.841 | 17.617 | 15.616 | 1.00 | 35.54 | B |
| ATOM | 3133 | CA | LEU | B | 508 | 21.376 | 17.327 | 16.970 | 1.00 | 34.73 | B |
| ATOM | 3134 | CB | LEU | B | 508 | 20.086 | 18.088 | 17.263 | 1.00 | 33.75 | B |
| ATOM | 3135 | CG | LEU | B | 508 | 20.197 | 19.593 | 17.031 | 1.00 | 33.68 | B |
| ATOM | 3136 | CD1 | LEU | B | 508 | 18.917 | 20.279 | 17.449 | 1.00 | 32.64 | B |
| ATOM | 3137 | CD2 | LEU | B | 508 | 21.384 | 20.137 | 17.817 | 1.00 | 34.53 | B |
| ATOM | 3138 | C | LEU | B | 508 | 21.182 | 15.848 | 17.309 | 1.00 | 34.68 | B |
| ATOM | 3139 | O | LEU | B | 508 | 21.360 | 15.464 | 18.466 | 1.00 | 35.03 | B |
| ATOM | 3140 | N | LEU | B | 509 | 20.837 | 15.021 | 16.323 | 1.00 | 33.38 | B |
| ATOM | 3141 | CA | LEU | B | 509 | 20.633 | 13.594 | 16.571 | 1.00 | 31.90 | B |
| ATOM | 3142 | CB | LEU | B | 509 | 19.800 | 12.948 | 15.457 | 1.00 | 30.90 | B |
| ATOM | 3143 | CG | LEU | B | 509 | 18.317 | 13.354 | 15.470 | 1.00 | 30.84 | B |
| ATOM | 3144 | CD1 | LEU | B | 509 | 17.638 | 12.891 | 14.198 | 1.00 | 29.19 | B |
| ATOM | 3145 | CD2 | LEU | B | 509 | 17.622 | 12.773 | 16.707 | 1.00 | 30.18 | B |
| ATOM | 3146 | C | LEU | B | 509 | 21.952 | 12.874 | 16.724 | 1.00 | 31.96 | B |
| ATOM | 3147 | O | LEU | B | 509 | 22.013 | 11.819 | 17.361 | 1.00 | 31.22 | B |
| ATOM | 3148 | N | ILE | B | 510 | 23.003 | 13.450 | 16.138 | 1.00 | 32.50 | B |
| ATOM | 3149 | CA | ILE | B | 510 | 24.359 | 12.900 | 16.235 | 1.00 | 31.67 | B |
| ATOM | 3150 | CB | ILE | B | 510 | 25.374 | 13.676 | 15.328 | 1.00 | 33.15 | B |
| ATOM | 3151 | CG2 | ILE | B | 510 | 26.793 | 13.152 | 15.540 | 1.00 | 33.33 | B |
| ATOM | 3152 | CG1 | ILE | B | 510 | 24.987 | 13.555 | 13.853 | 1.00 | 33.34 | B |
| ATOM | 3153 | CD1 | ILE | B | 510 | 24.724 | 12.142 | 13.410 | 1.00 | 35.55 | B |
| ATOM | 3154 | C | ILE | B | 510 | 24.804 | 13.045 | 17.701 | 1.00 | 32.03 | B |
| ATOM | 3155 | O | ILE | B | 510 | 25.615 | 12.257 | 18.200 | 1.00 | 32.26 | B |
| ATOM | 3156 | N | LEU | B | 511 | 24.262 | 14.054 | 18.386 | 1.00 | 31.39 | B |
| ATOM | 3157 | CA | LEU | B | 511 | 24.599 | 14.290 | 19.782 | 1.00 | 30.66 | B |
| ATOM | 3158 | CB | LEU | B | 511 | 24.012 | 15.611 | 20.287 | 1.00 | 28.75 | B |
| ATOM | 3159 | CG | LEU | B | 511 | 24.498 | 16.862 | 19.548 | 1.00 | 30.01 | B |
| ATOM | 3160 | CD1 | LEU | B | 511 | 24.067 | 18.115 | 20.286 | 1.00 | 29.22 | B |
| ATOM | 3161 | CD2 | LEU | B | 511 | 26.007 | 16.818 | 19.418 | 1.00 | 29.19 | B |
| ATOM | 3162 | C | LEU | B | 511 | 24.082 | 13.152 | 20.626 | 1.00 | 31.80 | B |
| ATOM | 3163 | O | LEU | B | 511 | 24.642 | 12.861 | 21.689 | 1.00 | 32.93 | B |
| ATOM | 3164 | N | SER | B | 512 | 23.008 | 12.510 | 20.163 | 1.00 | 30.99 | B |
| ATOM | 3165 | CA | SER | B | 512 | 22.444 | 11.380 | 20.888 | 1.00 | 30.39 | B |
| ATOM | 3166 | CB | SER | B | 512 | 21.133 | 10.939 | 20.256 | 1.00 | 31.61 | B |
| ATOM | 3167 | OG | SER | B | 512 | 20.059 | 11.731 | 20.716 | 1.00 | 32.60 | B |
| ATOM | 3168 | C | SER | B | 512 | 23.449 | 10.239 | 20.850 | 1.00 | 31.23 | B |
| ATOM | 3169 | O | SER | B | 512 | 23.607 | 9.507 | 21.823 | 1.00 | 30.62 | B |
| ATOM | 3170 | N | HIS | B | 513 | 24.138 | 10.118 | 19.722 | 1.00 | 31.78 | B |
| ATOM | 3171 | CA | HIS | B | 513 | 25.153 | 9.090 | 19.528 | 1.00 | 33.71 | B |
| ATOM | 3172 | CB | HIS | B | 513 | 25.495 | 8.998 | 18.045 | 1.00 | 36.49 | B |
| ATOM | 3173 | CG | HIS | B | 513 | 24.322 | 8.608 | 17.198 | 1.00 | 44.57 | B |
| ATOM | 3174 | CD2 | HIS | B | 513 | 24.110 | 7.529 | 16.404 | 1.00 | 45.81 | B |
| ATOM | 3175 | ND1 | HIS | B | 513 | 23.147 | 9.333 | 17.175 | 1.00 | 45.96 | B |
| ATOM | 3176 | CE1 | HIS | B | 513 | 22.264 | 8.717 | 16.409 | 1.00 | 46.30 | B |
| ATOM | 3177 | NE2 | HIS | B | 513 | 22.823 | 7.620 | 15.930 | 1.00 | 46.66 | B |
| ATOM | 3178 | C | HIS | B | 513 | 26.407 | 9.356 | 20.356 | 1.00 | 33.52 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3179 | O | HIS | B | 513 | 27.054 | 8.424 | 20.840 | 1.00 | 32.68 | B |
| ATOM | 3180 | N | ILE | B | 514 | 26.745 | 10.631 | 20.518 | 1.00 | 32.71 | B |
| ATOM | 3181 | CA | ILE | B | 514 | 27.913 | 11.018 | 21.295 | 1.00 | 32.27 | B |
| ATOM | 3182 | CB | ILE | B | 514 | 28.293 | 12.501 | 21.018 | 1.00 | 32.10 | B |
| ATOM | 3183 | CG2 | ILE | B | 514 | 29.372 | 12.973 | 22.002 | 1.00 | 32.90 | B |
| ATOM | 3184 | CG1 | ILE | B | 514 | 28.793 | 12.630 | 19.573 | 1.00 | 32.16 | B |
| ATOM | 3185 | CD1 | ILE | B | 514 | 29.093 | 14.039 | 19.119 | 1.00 | 32.66 | B |
| ATOM | 3186 | C | ILE | B | 514 | 27.630 | 10.789 | 22.785 | 1.00 | 32.00 | B |
| ATOM | 3187 | O | ILE | B | 514 | 28.520 | 10.421 | 23.539 | 1.00 | 31.21 | B |
| ATOM | 3188 | N | ARG | B | 515 | 26.387 | 11.008 | 23.194 | 1.00 | 31.72 | B |
| ATOM | 3189 | CA | ARG | B | 515 | 25.998 | 10.786 | 24.570 | 1.00 | 33.40 | B |
| ATOM | 3190 | CB | ARG | B | 515 | 24.542 | 11.179 | 24.790 | 1.00 | 32.81 | B |
| ATOM | 3191 | CG | ARG | B | 515 | 24.042 | 10.821 | 26.173 | 1.00 | 33.31 | B |
| ATOM | 3192 | CD | ARG | B | 515 | 24.765 | 11.650 | 27.196 | 1.00 | 32.59 | B |
| ATOM | 3193 | NE | ARG | B | 515 | 24.368 | 13.036 | 27.011 | 1.00 | 33.92 | B |
| ATOM | 3194 | CZ | ARG | B | 515 | 23.303 | 13.583 | 27.578 | 1.00 | 32.64 | B |
| ATOM | 3195 | NH1 | ARG | B | 515 | 22.541 | 12.859 | 28.382 | 1.00 | 32.19 | B |
| ATOM | 3196 | NH2 | ARG | B | 515 | 22.980 | 14.840 | 27.309 | 1.00 | 32.52 | B |
| ATOM | 3197 | C | ARG | B | 515 | 26.147 | 9.295 | 24.832 | 1.00 | 36.04 | B |
| ATOM | 3198 | O | ARG | B | 515 | 26.694 | 8.868 | 25.856 | 1.00 | 37.55 | B |
| ATOM | 3199 | N | HIS | B | 516 | 25.645 | 8.505 | 23.889 | 1.00 | 37.65 | B |
| ATOM | 3200 | CA | HIS | B | 516 | 25.718 | 7.061 | 23.977 | 1.00 | 38.99 | B |
| ATOM | 3201 | CB | HIS | B | 516 | 25.115 | 6.433 | 22.717 | 1.00 | 39.79 | B |
| ATOM | 3202 | CG | HIS | B | 516 | 25.050 | 4.941 | 22.762 | 1.00 | 40.40 | B |
| ATOM | 3203 | CD2 | HIS | B | 516 | 25.713 | 3.998 | 22.053 | 1.00 | 41.19 | B |
| ATOM | 3204 | ND1 | HIS | B | 516 | 24.248 | 4.259 | 23.649 | 1.00 | 41.61 | B |
| ATOM | 3205 | CE1 | HIS | B | 516 | 24.420 | 2.960 | 23.487 | 1.00 | 41.58 | B |
| ATOM | 3206 | NE2 | HIS | B | 516 | 25.304 | 2.775 | 22.525 | 1.00 | 41.55 | B |
| ATOM | 3207 | C | HIS | B | 516 | 27.176 | 6.626 | 24.141 | 1.00 | 39.25 | B |
| ATOM | 3208 | O | HIS | B | 516 | 27.509 | 5.899 | 25.081 | 1.00 | 40.90 | B |
| ATOM | 3209 | N | MET | B | 517 | 28.039 | 7.077 | 23.232 | 1.00 | 38.86 | B |
| ATOM | 3210 | CA | MET | B | 517 | 29.459 | 6.739 | 23.290 | 1.00 | 38.85 | B |
| ATOM | 3211 | CB | MET | B | 517 | 30.235 | 7.440 | 22.161 | 1.00 | 37.93 | B |
| ATOM | 3212 | CG | MET | B | 517 | 29.933 | 6.904 | 20.761 | 1.00 | 36.24 | B |
| ATOM | 3213 | SD | MET | B | 517 | 30.966 | 7.598 | 19.430 | 1.00 | 36.70 | B |
| ATOM | 3214 | CE | MET | B | 517 | 30.185 | 9.199 | 19.186 | 1.00 | 32.94 | B |
| ATOM | 3215 | C | MET | B | 517 | 30.060 | 7.121 | 24.644 | 1.00 | 39.77 | B |
| ATOM | 3216 | O | MET | B | 517 | 30.818 | 6.353 | 25.241 | 1.00 | 39.75 | B |
| ATOM | 3217 | N | SER | B | 518 | 29.721 | 8.314 | 25.121 | 1.00 | 40.69 | B |
| ATOM | 3218 | CA | SER | B | 518 | 30.213 | 8.788 | 26.405 | 1.00 | 41.48 | B |
| ATOM | 3219 | CB | SER | B | 518 | 29.716 | 10.203 | 26.672 | 1.00 | 40.61 | B |
| ATOM | 3220 | OG | SER | B | 518 | 29.894 | 10.538 | 28.033 | 1.00 | 39.63 | B |
| ATOM | 3221 | C | SER | B | 518 | 29.752 | 7.867 | 27.531 | 1.00 | 42.45 | B |
| ATOM | 3222 | O | SER | B | 518 | 30.549 | 7.485 | 28.381 | 1.00 | 41.62 | B |
| ATOM | 3223 | N | ASN | B | 519 | 28.466 | 7.523 | 27.531 | 1.00 | 44.49 | B |
| ATOM | 3224 | CA | ASN | B | 519 | 27.890 | 6.631 | 28.543 | 1.00 | 46.70 | B |
| ATOM | 3225 | CB | ASN | B | 519 | 26.439 | 6.300 | 28.201 | 1.00 | 46.66 | B |
| ATOM | 3226 | CG | ASN | B | 519 | 25.476 | 7.371 | 28.638 | 1.00 | 47.05 | B |
| ATOM | 3227 | OD1 | ASN | B | 519 | 25.570 | 7.880 | 29.748 | 1.00 | 47.42 | B |
| ATOM | 3228 | ND2 | ASN | B | 519 | 24.524 | 7.705 | 27.774 | 1.00 | 47.40 | B |
| ATOM | 3229 | C | ASN | B | 519 | 28.659 | 5.319 | 28.668 | 1.00 | 48.13 | B |
| ATOM | 3230 | O | ASN | B | 519 | 28.973 | 4.867 | 29.772 | 1.00 | 47.81 | B |
| ATOM | 3231 | N | LYS | B | 520 | 28.944 | 4.703 | 27.526 | 1.00 | 50.06 | B |
| ATOM | 3232 | CA | LYS | B | 520 | 29.672 | 3.444 | 27.508 | 1.00 | 52.51 | B |
| ATOM | 3233 | CB | LYS | B | 520 | 29.663 | 2.848 | 26.094 | 1.00 | 53.06 | B |
| ATOM | 3234 | CG | LYS | B | 520 | 28.315 | 2.979 | 25.391 | 1.00 | 54.71 | B |
| ATOM | 3235 | CD | LYS | B | 520 | 27.892 | 1.711 | 24.654 | 1.00 | 56.59 | B |
| ATOM | 3236 | CE | LYS | B | 520 | 27.241 | 0.700 | 25.601 | 1.00 | 57.23 | B |
| ATOM | 3237 | NZ | LYS | B | 520 | 26.004 | 0.106 | 25.017 | 1.00 | 57.71 | B |
| ATOM | 3238 | C | LYS | B | 520 | 31.102 | 3.692 | 27.978 | 1.00 | 53.89 | B |
| ATOM | 3239 | O | LYS | B | 520 | 31.639 | 2.932 | 28.789 | 1.00 | 54.57 | B |
| ATOM | 3240 | N | GLY | B | 521 | 31.713 | 4.761 | 27.471 | 1.00 | 55.11 | B |
| ATOM | 3241 | CA | GLY | B | 521 | 33.065 | 5.095 | 27.875 | 1.00 | 56.13 | B |
| ATOM | 3242 | C | GLY | B | 521 | 33.150 | 5.202 | 29.385 | 1.00 | 57.13 | B |
| ATOM | 3243 | O | GLY | B | 521 | 34.117 | 4.757 | 29.990 | 1.00 | 56.41 | B |
| ATOM | 3244 | N | MET | B | 522 | 32.120 | 5.787 | 29.987 | 1.00 | 59.21 | B |
| ATOM | 3245 | CA | MET | B | 522 | 32.044 | 5.971 | 31.429 | 1.00 | 61.89 | B |
| ATOM | 3246 | CB | MET | B | 522 | 30.979 | 7.017 | 31.775 | 1.00 | 60.56 | B |
| ATOM | 3247 | CG | MET | B | 522 | 31.494 | 8.135 | 32.670 | 1.00 | 60.06 | B |
| ATOM | 3248 | SD | MET | B | 522 | 32.730 | 9.132 | 31.841 | 1.00 | 57.46 | B |
| ATOM | 3249 | CE | MET | B | 522 | 31.798 | 10.696 | 31.640 | 1.00 | 58.64 | B |
| ATOM | 3250 | C | MET | B | 522 | 31.718 | 4.648 | 32.135 | 1.00 | 64.88 | B |
| ATOM | 3251 | O | MET | B | 522 | 31.409 | 4.625 | 33.319 | 1.00 | 65.26 | B |
| ATOM | 3252 | N | GLU | B | 523 | 31.782 | 3.547 | 31.394 | 1.00 | 68.02 | B |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 3253 | CA | GLU | B | 523 | 31.528 | 2.227 | 31.945 | 1.00 | 71.06 | B |
| ATOM | 3254 | CB | GLU | B | 523 | 30.447 | 1.510 | 31.127 | 1.00 | 71.81 | B |
| ATOM | 3255 | CG | GLU | B | 523 | 29.468 | 0.716 | 31.973 | 1.00 | 73.93 | B |
| ATOM | 3256 | CD | GLU | B | 523 | 28.379 | 0.074 | 31.143 | 1.00 | 75.13 | B |
| ATOM | 3257 | OE1 | GLU | B | 523 | 27.773 | 0.808 | 30.336 | 1.00 | 75.25 | B |
| ATOM | 3258 | OE2 | GLU | B | 523 | 28.140 | −1.144 | 31.314 | 1.00 | 75.68 | B |
| ATOM | 3259 | C | GLU | B | 523 | 32.844 | 1.474 | 31.880 | 1.00 | 72.84 | B |
| ATOM | 3260 | O | GLU | B | 523 | 33.105 | 0.589 | 32.686 | 1.00 | 72.79 | B |
| ATOM | 3261 | N | HIS | B | 524 | 33.677 | 1.850 | 30.922 | 1.00 | 75.27 | B |
| ATOM | 3262 | CA | HIS | B | 524 | 34.969 | 1.208 | 30.742 | 1.00 | 78.39 | B |
| ATOM | 3263 | CB | HIS | B | 524 | 35.565 | 1.544 | 29.369 | 1.00 | 79.72 | B |
| ATOM | 3264 | CG | HIS | B | 524 | 36.845 | 0.826 | 29.060 | 1.00 | 81.96 | B |
| ATOM | 3265 | CD2 | HIS | B | 524 | 37.176 | −0.012 | 28.048 | 1.00 | 82.46 | B |
| ATOM | 3266 | ND1 | HIS | B | 524 | 37.938 | 0.872 | 29.899 | 1.00 | 82.69 | B |
| ATOM | 3267 | CE1 | HIS | B | 524 | 38.888 | 0.081 | 29.418 | 1.00 | 82.96 | B |
| ATOM | 3268 | NE2 | HIS | B | 524 | 38.447 | −0.462 | 28.302 | 1.00 | 83.10 | B |
| ATOM | 3269 | C | HIS | B | 524 | 35.928 | 1.705 | 31.807 | 1.00 | 80.35 | B |
| ATOM | 3270 | O | HIS | B | 524 | 36.880 | 1.009 | 32.180 | 1.00 | 81.18 | B |
| ATOM | 3271 | N | LEU | B | 525 | 35.648 | 2.915 | 32.291 | 1.00 | 82.33 | B |
| ATOM | 3272 | CA | LEU | B | 525 | 36.462 | 3.622 | 33.290 | 1.00 | 84.09 | B |
| ATOM | 3273 | CB | LEU | B | 525 | 36.057 | 5.096 | 33.349 | 1.00 | 83.46 | B |
| ATOM | 3274 | CG | LEU | B | 525 | 36.868 | 6.080 | 32.540 | 1.00 | 82.99 | B |
| ATOM | 3275 | CD1 | LEU | B | 525 | 36.510 | 7.504 | 32.944 | 1.00 | 82.28 | B |
| ATOM | 3276 | CD2 | LEU | B | 525 | 38.328 | 5.807 | 32.799 | 1.00 | 82.66 | B |
| ATOM | 3277 | C | LEU | B | 525 | 36.424 | 3.067 | 34.693 | 1.00 | 85.92 | B |
| ATOM | 3278 | O | LEU | B | 525 | 37.474 | 2.906 | 35.317 | 1.00 | 86.69 | B |
| ATOM | 3279 | N | TYR | B | 526 | 35.221 | 2.823 | 35.195 | 1.00 | 87.71 | B |
| ATOM | 3280 | CA | TYR | B | 526 | 35.040 | 2.280 | 36.524 | 1.00 | 90.01 | B |
| ATOM | 3281 | CB | TYR | B | 526 | 33.559 | 2.139 | 36.812 | 1.00 | 90.47 | B |
| ATOM | 3282 | CG | TYR | B | 526 | 32.878 | 3.470 | 36.756 | 1.00 | 91.61 | B |
| ATOM | 3283 | CD1 | TYR | B | 526 | 33.024 | 4.296 | 35.634 | 1.00 | 92.18 | B |
| ATOM | 3284 | CE1 | TYR | B | 526 | 32.440 | 5.558 | 35.585 | 1.00 | 92.88 | B |
| ATOM | 3285 | CD2 | TYR | B | 526 | 32.126 | 3.941 | 37.829 | 1.00 | 92.36 | B |
| ATOM | 3286 | CE2 | TYR | B | 526 | 31.539 | 5.204 | 37.788 | 1.00 | 93.17 | B |
| ATOM | 3287 | CZ | TYR | B | 526 | 31.697 | 6.005 | 36.665 | 1.00 | 93.26 | B |
| ATOM | 3288 | OH | TYR | B | 526 | 31.104 | 7.248 | 36.614 | 1.00 | 93.64 | B |
| ATOM | 3289 | C | TYR | B | 526 | 35.747 | 0.943 | 36.577 | 1.00 | 91.38 | B |
| ATOM | 3290 | O | TYR | B | 526 | 35.919 | 0.337 | 37.647 | 1.00 | 91.61 | B |
| ATOM | 3291 | N | SER | B | 527 | 36.159 | 0.494 | 35.400 | 1.00 | 92.81 | B |
| ATOM | 3292 | CA | SER | B | 527 | 36.882 | −0.751 | 35.261 | 1.00 | 94.24 | B |
| ATOM | 3293 | CB | SER | B | 527 | 36.645 | −1.344 | 33.863 | 1.00 | 94.02 | B |
| ATOM | 3294 | OG | SER | B | 527 | 35.339 | −1.916 | 33.753 | 1.00 | 93.50 | B |
| ATOM | 3295 | C | SER | B | 527 | 38.372 | −0.513 | 35.508 | 1.00 | 95.37 | B |
| ATOM | 3296 | O | SER | B | 527 | 38.887 | −0.889 | 36.558 | 1.00 | 95.47 | B |
| ATOM | 3297 | N | MET | B | 528 | 39.031 | 0.154 | 34.562 | 1.00 | 96.83 | B |
| ATOM | 3298 | CA | MET | B | 528 | 40.472 | 0.435 | 34.616 | 1.00 | 98.55 | B |
| ATOM | 3299 | CB | MET | B | 528 | 40.991 | 0.671 | 33.193 | 1.00 | 99.22 | B |
| ATOM | 3300 | CG | MET | B | 528 | 41.073 | −0.597 | 32.355 | 1.00 | 99.71 | B |
| ATOM | 3301 | SD | MET | B | 528 | 42.283 | −1.758 | 33.058 | 1.00 | 100.00 | B |
| ATOM | 3302 | CE | MET | B | 528 | 43.821 | −0.938 | 32.633 | 1.00 | 99.60 | B |
| ATOM | 3303 | C | MET | B | 528 | 40.886 | 1.587 | 35.518 | 1.00 | 99.30 | B |
| ATOM | 3304 | O | MET | B | 528 | 41.624 | 1.364 | 36.468 | 1.00 | 99.64 | B |
| ATOM | 3305 | N | LYS | B | 529 | 40.438 | 2.807 | 35.217 | 1.00 | 99.79 | B |
| ATOM | 3306 | CA | LYS | B | 529 | 40.756 | 3.960 | 36.073 | 1.00 | 100.00 | B |
| ATOM | 3307 | CB | LYS | B | 529 | 40.540 | 3.524 | 37.523 | 1.00 | 100.00 | B |
| ATOM | 3308 | CG | LYS | B | 529 | 41.266 | 4.277 | 38.601 | 1.00 | 99.93 | B |
| ATOM | 3309 | CD | LYS | B | 529 | 42.490 | 3.529 | 39.086 | 1.00 | 99.86 | B |
| ATOM | 3310 | CE | LYS | B | 529 | 42.109 | 2.514 | 40.145 | 1.00 | 99.72 | B |
| ATOM | 3311 | NZ | LYS | B | 529 | 42.348 | 1.115 | 39.692 | 1.00 | 99.87 | B |
| ATOM | 3312 | C | LYS | B | 529 | 42.139 | 4.628 | 35.928 | 1.00 | 100.00 | B |
| ATOM | 3313 | O | LYS | B | 529 | 42.935 | 4.263 | 35.029 | 1.00 | 100.00 | B |
| ATOM | 3314 | N | CYS | B | 530 | 42.447 | 5.618 | 36.772 | 1.00 | 99.99 | B |
| ATOM | 3315 | CA | CYS | B | 530 | 43.738 | 6.260 | 36.594 | 1.00 | 100.00 | B |
| ATOM | 3316 | CB | CYS | B | 530 | 43.654 | 7.139 | 35.364 | 1.00 | 100.00 | B |
| ATOM | 3317 | SG | CYS | B | 530 | 45.285 | 7.508 | 34.692 | 1.00 | 100.00 | B |
| ATOM | 3318 | C | CYS | B | 530 | 44.499 | 7.067 | 37.633 | 1.00 | 100.00 | B |
| ATOM | 3319 | O | CYS | B | 530 | 45.626 | 6.716 | 37.959 | 1.00 | 100.00 | B |
| ATOM | 3320 | N | LYS | B | 531 | 43.927 | 8.170 | 38.100 | 1.00 | 100.00 | B |
| ATOM | 3321 | CA | LYS | B | 531 | 44.670 | 9.015 | 39.012 | 1.00 | 100.00 | B |
| ATOM | 3322 | CB | LYS | B | 531 | 44.660 | 10.421 | 38.441 | 1.00 | 99.94 | B |
| ATOM | 3323 | CG | LYS | B | 531 | 45.794 | 11.319 | 38.850 | 1.00 | 99.75 | B |
| ATOM | 3324 | CD | LYS | B | 531 | 45.601 | 12.687 | 38.205 | 1.00 | 99.75 | B |
| ATOM | 3325 | CE | LYS | B | 531 | 46.859 | 13.524 | 38.365 | 1.00 | 100.00 | B |
| ATOM | 3326 | NZ | LYS | B | 531 | 46.641 | 14.935 | 37.930 | 1.00 | 100.00 | B |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 3327 | C | LYS | B | 531 | 44.166 | 9.047 | 40.445 | 1.00 | 99.98 | B |
| ATOM | 3328 | O | LYS | B | 531 | 44.882 | 9.503 | 41.372 | 1.00 | 100.00 | B |
| ATOM | 3329 | N | ASN | B | 532 | 42.953 | 8.548 | 40.639 | 1.00 | 99.44 | B |
| ATOM | 3330 | CA | ASN | B | 532 | 42.392 | 8.571 | 41.955 | 1.00 | 98.82 | B |
| ATOM | 3331 | CB | ASN | B | 532 | 42.432 | 10.010 | 42.442 | 1.00 | 99.22 | B |
| ATOM | 3332 | CG | ASN | B | 532 | 42.457 | 10.118 | 43.939 | 1.00 | 99.60 | B |
| ATOM | 3333 | OD1 | ASN | B | 532 | 43.070 | 9.291 | 44.621 | 1.00 | 100.00 | B |
| ATOM | 3334 | ND2 | ASN | B | 532 | 41.808 | 11.141 | 44.468 | 1.00 | 99.45 | B |
| ATOM | 3335 | C | ASN | B | 532 | 40.972 | 8.032 | 41.974 | 1.00 | 97.79 | B |
| ATOM | 3336 | O | ASN | B | 532 | 40.751 | 6.816 | 42.025 | 1.00 | 97.76 | B |
| ATOM | 3337 | N | VAL | B | 533 | 40.012 | 8.943 | 41.939 | 1.00 | 96.57 | B |
| ATOM | 3338 | CA | VAL | B | 533 | 38.613 | 8.564 | 41.999 | 1.00 | 95.40 | B |
| ATOM | 3339 | CB | VAL | B | 533 | 38.115 | 8.600 | 43.472 | 1.00 | 95.47 | B |
| ATOM | 3340 | CG1 | VAL | B | 533 | 37.796 | 7.186 | 43.936 | 1.00 | 95.15 | B |
| ATOM | 3341 | CG2 | VAL | B | 533 | 39.172 | 9.225 | 44.384 | 1.00 | 95.38 | B |
| ATOM | 3342 | C | VAL | B | 533 | 37.767 | 9.492 | 41.151 | 1.00 | 93.99 | B |
| ATOM | 3343 | O | VAL | B | 533 | 37.509 | 9.211 | 39.984 | 1.00 | 94.37 | B |
| ATOM | 3344 | N | VAL | B | 534 | 37.331 | 10.591 | 41.751 | 1.00 | 92.14 | B |
| ATOM | 3345 | CA | VAL | B | 534 | 36.537 | 11.576 | 41.043 | 1.00 | 90.31 | B |
| ATOM | 3346 | CB | VAL | B | 534 | 35.053 | 11.471 | 41.464 | 1.00 | 90.30 | B |
| ATOM | 3347 | CG1 | VAL | B | 534 | 34.785 | 12.351 | 42.688 | 1.00 | 90.38 | B |
| ATOM | 3348 | CG2 | VAL | B | 534 | 34.152 | 11.822 | 40.298 | 1.00 | 90.20 | B |
| ATOM | 3349 | C | VAL | B | 534 | 37.079 | 12.980 | 41.332 | 1.00 | 87.94 | B |
| ATOM | 3350 | O | VAL | B | 534 | 36.354 | 13.966 | 41.182 | 1.00 | 88.36 | B |
| ATOM | 3351 | N | ERaO | B | 535 | 38.363 | 13.095 | 41.758 | 1.00 | 85.11 | B |
| ATOM | 3352 | CD | ERaO | B | 535 | 39.310 | 12.024 | 42.097 | 1.00 | 84.68 | B |
| ATOM | 3353 | CA | ERaO | B | 535 | 38.940 | 14.414 | 42.049 | 1.00 | 83.04 | B |
| ATOM | 3354 | CB | ERaO | B | 535 | 40.432 | 14.125 | 42.294 | 1.00 | 83.25 | B |
| ATOM | 3355 | CG | ERaO | B | 535 | 40.596 | 12.684 | 42.092 | 1.00 | 83.70 | B |
| ATOM | 3356 | C | ERaO | B | 535 | 38.726 | 15.357 | 40.868 | 1.00 | 80.30 | B |
| ATOM | 3357 | O | ERaO | B | 535 | 39.235 | 16.490 | 40.835 | 1.00 | 80.54 | B |
| ATOM | 3358 | N | LEU | B | 536 | 37.952 | 14.882 | 39.898 | 1.00 | 76.70 | B |
| ATOM | 3359 | CA | LEU | B | 536 | 37.621 | 15.641 | 38.717 | 1.00 | 72.89 | B |
| ATOM | 3360 | CB | LEU | B | 536 | 36.622 | 14.875 | 37.844 | 1.00 | 73.06 | B |
| ATOM | 3361 | CG | LEU | B | 536 | 36.485 | 15.360 | 36.407 | 1.00 | 72.59 | B |
| ATOM | 3362 | CD1 | LEU | B | 536 | 35.096 | 15.904 | 36.173 | 1.00 | 72.10 | B |
| ATOM | 3363 | CD2 | LEU | B | 536 | 37.547 | 16.415 | 36.125 | 1.00 | 71.54 | B |
| ATOM | 3364 | C | LEU | B | 536 | 37.027 | 16.939 | 39.173 | 1.00 | 70.47 | B |
| ATOM | 3365 | O | LEU | B | 536 | 37.267 | 17.972 | 38.577 | 1.00 | 69.79 | B |
| ATOM | 3366 | N | TYR | B | 537 | 36.267 | 16.887 | 40.249 | 1.00 | 68.28 | B |
| ATOM | 3367 | CA | TYR | B | 537 | 35.641 | 18.091 | 40.753 | 1.00 | 66.62 | B |
| ATOM | 3368 | CB | TYR | B | 537 | 34.402 | 17.748 | 41.564 | 1.00 | 68.41 | B |
| ATOM | 3369 | CG | TYR | B | 537 | 34.679 | 17.433 | 43.006 | 1.00 | 70.11 | B |
| ATOM | 3370 | CD1 | TYR | B | 537 | 34.815 | 18.459 | 43.940 | 1.00 | 70.67 | B |
| ATOM | 3371 | CE1 | TYR | B | 537 | 35.061 | 18.187 | 45.263 | 1.00 | 71.34 | B |
| ATOM | 3372 | CD2 | TYR | B | 537 | 34.808 | 16.113 | 43.447 | 1.00 | 71.06 | B |
| ATOM | 3373 | CE2 | TYR | B | 537 | 35.059 | 15.830 | 44.775 | 1.00 | 71.35 | B |
| ATOM | 3374 | CZ | TYR | B | 537 | 35.176 | 16.868 | 45.674 | 1.00 | 71.76 | B |
| ATOM | 3375 | OH | TYR | B | 537 | 35.343 | 16.580 | 47.001 | 1.00 | 72.44 | B |
| ATOM | 3376 | C | TYR | B | 537 | 36.607 | 18.927 | 41.589 | 1.00 | 64.41 | B |
| ATOM | 3377 | O | TYR | B | 537 | 36.332 | 20.088 | 41.872 | 1.00 | 63.26 | B |
| ATOM | 3378 | N | ASP | B | 538 | 37.726 | 18.337 | 42.003 | 1.00 | 61.88 | B |
| ATOM | 3379 | CA | ASP | B | 538 | 38.705 | 19.125 | 42.763 | 1.00 | 59.84 | B |
| ATOM | 3380 | CB | ASP | B | 538 | 39.758 | 18.248 | 43.470 | 1.00 | 59.51 | B |
| ATOM | 3381 | CG | ASP | B | 538 | 39.299 | 17.774 | 44.837 | 1.00 | 58.72 | B |
| ATOM | 3382 | OD1 | ASP | B | 538 | 38.880 | 18.622 | 45.651 | 1.00 | 58.40 | B |
| ATOM | 3383 | OD2 | ASP | B | 538 | 39.360 | 16.555 | 45.098 | 1.00 | 58.80 | B |
| ATOM | 3384 | C | ASP | B | 538 | 39.391 | 20.038 | 41.766 | 1.00 | 58.67 | B |
| ATOM | 3385 | O | ASP | B | 538 | 39.591 | 21.224 | 42.033 | 1.00 | 57.67 | B |
| ATOM | 3386 | N | LEU | B | 539 | 39.742 | 19.471 | 40.614 | 1.00 | 57.69 | B |
| ATOM | 3387 | CA | LEU | B | 539 | 40.376 | 20.223 | 39.543 | 1.00 | 57.31 | B |
| ATOM | 3388 | CB | LEU | B | 539 | 40.723 | 19.284 | 38.381 | 1.00 | 56.93 | B |
| ATOM | 3389 | CG | LEU | B | 539 | 41.126 | 19.903 | 37.032 | 1.00 | 57.19 | B |
| ATOM | 3390 | CD1 | LEU | B | 539 | 42.373 | 20.761 | 37.181 | 1.00 | 56.38 | B |
| ATOM | 3391 | CD2 | LEU | B | 539 | 41.369 | 18.789 | 36.018 | 1.00 | 56.58 | B |
| ATOM | 3392 | C | LEU | B | 539 | 39.385 | 21.291 | 39.083 | 1.00 | 57.52 | B |
| ATOM | 3393 | O | LEU | B | 539 | 39.744 | 22.454 | 38.901 | 1.00 | 56.66 | B |
| ATOM | 3394 | N | LEU | B | 540 | 38.132 | 20.882 | 38.915 | 1.00 | 58.21 | B |
| ATOM | 3395 | CA | LEU | B | 540 | 37.074 | 21.784 | 38.480 | 1.00 | 59.35 | B |
| ATOM | 3396 | CB | LEU | B | 540 | 35.748 | 21.028 | 38.356 | 1.00 | 58.18 | B |
| ATOM | 3397 | CG | LEU | B | 540 | 35.666 | 19.961 | 37.256 | 1.00 | 58.26 | B |
| ATOM | 3398 | CD1 | LEU | B | 540 | 34.342 | 19.218 | 37.342 | 1.00 | 57.63 | B |
| ATOM | 3399 | CD2 | LEU | B | 540 | 35.826 | 20.618 | 35.895 | 1.00 | 57.91 | B |
| ATOM | 3400 | C | LEU | B | 540 | 36.904 | 22.947 | 39.441 | 1.00 | 60.86 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3401 | O | LEU | B | 540 | 36.638 | 24.065 | 39.018 | 1.00 | 61.08 | B |
| ATOM | 3402 | N | LEU | B | 541 | 37.074 | 22.681 | 40.733 | 1.00 | 62.85 | B |
| ATOM | 3403 | CA | LEU | B | 541 | 36.916 | 23.700 | 41.767 | 1.00 | 64.64 | B |
| ATOM | 3404 | CB | LEU | B | 541 | 36.860 | 23.040 | 43.144 | 1.00 | 64.59 | B |
| ATOM | 3405 | CG | LEU | B | 541 | 35.470 | 22.618 | 43.617 | 1.00 | 64.76 | B |
| ATOM | 3406 | CD1 | LEU | B | 541 | 35.569 | 21.938 | 44.981 | 1.00 | 64.51 | B |
| ATOM | 3407 | CD2 | LEU | B | 541 | 34.565 | 23.850 | 43.684 | 1.00 | 63.97 | B |
| ATOM | 3408 | C | LEU | B | 541 | 37.941 | 24.829 | 41.801 | 1.00 | 66.53 | B |
| ATOM | 3409 | O | LEU | B | 541 | 37.571 | 26.003 | 41.763 | 1.00 | 66.17 | B |
| ATOM | 3410 | N | GLU | B | 542 | 39.220 | 24.493 | 41.889 | 1.00 | 69.18 | B |
| ATOM | 3411 | CA | GLU | B | 542 | 40.234 | 25.534 | 41.946 | 1.00 | 72.70 | B |
| ATOM | 3412 | CB | GLU | B | 542 | 41.573 | 24.971 | 42.418 | 1.00 | 73.82 | B |
| ATOM | 3413 | CG | GLU | B | 542 | 42.219 | 24.004 | 41.455 | 1.00 | 75.29 | B |
| ATOM | 3414 | CD | GLU | B | 542 | 43.677 | 23.770 | 41.785 | 1.00 | 76.60 | B |
| ATOM | 3415 | OE1 | GLU | B | 542 | 44.322 | 22.943 | 41.103 | 1.00 | 77.50 | B |
| ATOM | 3416 | OE2 | GLU | B | 542 | 44.178 | 24.419 | 42.729 | 1.00 | 76.97 | B |
| ATOM | 3417 | C | GLU | B | 542 | 40.411 | 26.181 | 40.588 | 1.00 | 74.43 | B |
| ATOM | 3418 | O | GLU | B | 542 | 40.873 | 27.322 | 40.483 | 1.00 | 74.78 | B |
| ATOM | 3419 | N | MET | B | 543 | 40.037 | 25.444 | 39.548 | 1.00 | 76.34 | B |
| ATOM | 3420 | CA | MET | B | 543 | 40.153 | 25.935 | 38.187 | 1.00 | 78.37 | B |
| ATOM | 3421 | CB | MET | B | 543 | 40.229 | 24.753 | 37.221 | 1.00 | 80.21 | B |
| ATOM | 3422 | CG | MET | B | 543 | 41.527 | 24.657 | 36.440 | 1.00 | 82.07 | B |
| ATOM | 3423 | SD | MET | B | 543 | 41.629 | 25.933 | 35.174 | 1.00 | 85.81 | B |
| ATOM | 3424 | CE | MET | B | 543 | 43.378 | 26.238 | 35.117 | 1.00 | 85.36 | B |
| ATOM | 3425 | C | MET | B | 543 | 38.975 | 26.835 | 37.832 | 1.00 | 78.99 | B |
| ATOM | 3426 | O | MET | B | 543 | 39.105 | 27.735 | 37.004 | 1.00 | 79.10 | B |
| ATOM | 3427 | N | LEU | B | 544 | 37.829 | 26.604 | 38.466 | 1.00 | 79.67 | B |
| ATOM | 3428 | CA | LEU | B | 544 | 36.647 | 27.411 | 38.192 | 1.00 | 80.73 | B |
| ATOM | 3429 | CB | LEU | B | 544 | 35.372 | 26.598 | 38.427 | 1.00 | 79.99 | B |
| ATOM | 3430 | CG | LEU | B | 544 | 34.974 | 25.638 | 37.303 | 1.00 | 79.51 | B |
| ATOM | 3431 | CD1 | LEU | B | 544 | 33.637 | 25.009 | 37.626 | 1.00 | 79.47 | B |
| ATOM | 3432 | CD2 | LEU | B | 544 | 34.889 | 26.389 | 35.985 | 1.00 | 79.15 | B |
| ATOM | 3433 | C | LEU | B | 544 | 36.571 | 28.711 | 38.983 | 1.00 | 81.05 | B |
| ATOM | 3434 | O | LEU | B | 544 | 35.992 | 29.688 | 38.510 | 1.00 | 82.52 | B |
| ATOM | 3435 | N | ASP | B | 545 | 37.146 | 28.736 | 40.181 | 1.00 | 81.20 | B |
| ATOM | 3436 | CA | ASP | B | 545 | 37.111 | 29.954 | 40.986 | 1.00 | 82.85 | B |
| ATOM | 3437 | CB | ASP | B | 545 | 37.188 | 29.622 | 42.478 | 1.00 | 83.97 | B |
| ATOM | 3438 | CG | ASP | B | 545 | 36.057 | 30.254 | 43.272 | 1.00 | 86.54 | B |
| ATOM | 3439 | OD1 | ASP | B | 545 | 35.429 | 31.210 | 42.768 | 1.00 | 87.82 | B |
| ATOM | 3440 | OD2 | ASP | B | 545 | 35.800 | 29.801 | 44.406 | 1.00 | 87.72 | B |
| ATOM | 3441 | C | ASP | B | 545 | 38.248 | 30.903 | 40.613 | 1.00 | 82.49 | B |
| ATOM | 3442 | O | ASP | B | 545 | 38.036 | 32.114 | 40.483 | 1.00 | 79.37 | B |
| ATOM | 3443 | N | ALA | B | 546 | 39.446 | 30.343 | 40.436 | 1.00 | 83.37 | B |
| ATOM | 3444 | CA | ALA | B | 546 | 40.636 | 31.115 | 40.078 | 1.00 | 83.36 | B |
| ATOM | 3445 | CB | ALA | B | 546 | 41.839 | 30.181 | 39.950 | 1.00 | 75.47 | B |
| ATOM | 3446 | C | ALA | B | 546 | 40.462 | 31.922 | 38.786 | 1.00 | 83.38 | B |
| ATOM | 3447 | OT1 | ALA | B | 546 | 39.383 | 31.834 | 38.153 | 1.00 | 83.59 | B |
| ATOM | 3448 | OT2 | ALA | B | 546 | 41.418 | 32.641 | 38.422 | 1.00 | 83.63 | B |
| ATOM | 3449 | O | HOH | W | 1 | 50.266 | 19.793 | 27.483 | 1.00 | 14.65 | W |
| ATOM | 3450 | O | HOH | W | 2 | 44.051 | 17.820 | 22.088 | 1.00 | 22.94 | W |
| ATOM | 3451 | O | HOH | W | 3 | 0.501 | 1.364 | 30.063 | 1.00 | 32.77 | W |
| ATOM | 3452 | O | HOH | W | 4 | 36.956 | 8.601 | 10.365 | 1.00 | 41.87 | W |
| ATOM | 3453 | O | HOH | W | 5 | 30.298 | 13.174 | 29.108 | 1.00 | 15.66 | W |
| ATOM | 3454 | O | HOH | W | 6 | 1.414 | 0.430 | 27.767 | 1.00 | 25.42 | W |
| ATOM | 3455 | O | HOH | W | 7 | 47.564 | 21.014 | 30.729 | 1.00 | 49.14 | W |
| ATOM | 3456 | O | HOH | W | 8 | 1.326 | 2.082 | 25.624 | 1.00 | 34.38 | W |
| ATOM | 3457 | O | HOH | W | 9 | 45.437 | 16.597 | 10.375 | 1.00 | 54.44 | W |
| ATOM | 3458 | O | HOH | W | 10 | 16.664 | 1.752 | 24.007 | 1.00 | 29.04 | W |
| ATOM | 3459 | O | HOH | W | 11 | 31.171 | 32.763 | 30.238 | 1.00 | 34.17 | W |
| ATOM | 3460 | O | HOH | W | 12 | 17.561 | 2.288 | 16.415 | 1.00 | 44.54 | W |
| ATOM | 3461 | O | HOH | W | 13 | 37.872 | 20.321 | 25.226 | 1.00 | 29.76 | W |
| ATOM | 3462 | O | HOH | W | 14 | 50.985 | 19.134 | 24.525 | 1.00 | 23.71 | W |
| ATOM | 3463 | O | HOH | W | 15 | 42.357 | 19.339 | 21.011 | 1.00 | 39.79 | W |
| ATOM | 3464 | O | HOH | W | 16 | 42.379 | 29.269 | 20.027 | 1.00 | 43.88 | W |
| ATOM | 3465 | O | HOH | W | 17 | 5.266 | 2.346 | 19.825 | 1.00 | 24.92 | W |
| ATOM | 3466 | O | HOH | W | 18 | 6.024 | 3.086 | 24.359 | 1.00 | 21.45 | W |
| ATOM | 3467 | O | HOH | W | 19 | 40.212 | 20.652 | 26.119 | 1.00 | 35.49 | W |
| ATOM | 3468 | O | HOH | W | 20 | 16.744 | 26.036 | 20.930 | 1.00 | 28.48 | W |
| ATOM | 3469 | O | HOH | W | 21 | 37.772 | 18.811 | 22.766 | 1.00 | 30.59 | W |
| ATOM | 3470 | O | HOH | W | 22 | 62.315 | 6.425 | 26.085 | 1.00 | 56.60 | W |
| ATOM | 3471 | O | HOH | W | 23 | 23.672 | −0.414 | 20.438 | 1.00 | 43.81 | W |
| ATOM | 3472 | O | HOH | W | 24 | 38.043 | 24.839 | 14.545 | 1.00 | 52.85 | W |
| ATOM | 3473 | O | HOH | W | 25 | 25.961 | 2.819 | 29.747 | 1.00 | 57.80 | W |
| ATOM | 3474 | O | HOH | W | 26 | 38.634 | 32.019 | 30.524 | 1.00 | 32.77 | W |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3475 | O | HOH | W | 27 | 23.953 | 16.680 | 25.125 | 1.00 | 34.73 | W |
| ATOM | 3476 | O | HOH | W | 28 | 16.812 | 36.096 | 14.358 | 1.00 | 52.58 | W |
| ATOM | 3477 | O | HOH | W | 29 | 9.749 | 10.208 | −3.607 | 1.00 | 50.84 | W |
| ATOM | 3478 | O | HOH | W | 30 | 18.520 | 12.682 | 7.829 | 1.00 | 49.23 | W |
| ATOM | 3479 | O | HOH | W | 31 | 52.778 | 10.257 | 13.738 | 1.00 | 60.10 | W |
| ATOM | 3480 | O | HOH | W | 32 | 12.535 | 15.427 | 2.903 | 1.00 | 35.86 | W |
| ATOM | 3481 | O | HOH | W | 33 | 2.883 | 5.951 | 16.298 | 1.00 | 21.13 | W |
| ATOM | 3482 | O | HOH | W | 34 | 35.375 | 25.829 | 8.750 | 1.00 | 59.37 | W |
| ATOM | 3483 | O | HOH | W | 35 | 43.959 | 27.369 | 27.302 | 1.00 | 45.66 | W |
| ATOM | 3484 | O | HOH | W | 36 | 40.216 | 19.468 | 11.109 | 1.00 | 51.46 | W |
| ATOM | 3485 | O | HOH | W | 37 | 49.209 | 21.810 | 29.090 | 1.00 | 49.12 | W |
| ATOM | 3486 | O | HOH | W | 38 | 2.510 | −5.927 | 35.419 | 1.00 | 60.40 | W |
| ATOM | 3487 | O | HOH | W | 39 | −1.997 | 10.470 | 21.259 | 1.00 | 44.95 | W |
| ATOM | 3488 | O | HOH | W | 40 | 34.816 | 26.618 | 20.759 | 1.00 | 29.97 | W |
| ATOM | 3489 | O | HOH | W | 41 | 16.505 | 16.068 | 9.609 | 1.00 | 24.95 | W |
| ATOM | 3490 | O | HOH | W | 42 | 1.735 | 5.206 | 25.048 | 1.00 | 44.52 | W |
| ATOM | 3491 | O | HOH | W | 43 | 43.835 | 17.856 | 12.867 | 1.00 | 48.72 | W |
| ATOM | 3492 | O | HOH | W | 44 | 29.935 | 35.086 | 28.849 | 1.00 | 64.57 | W |
| ATOM | 3493 | O | HOH | W | 45 | −1.965 | 16.073 | 3.189 | 1.00 | 47.06 | W |
| ATOM | 3494 | O | HOH | W | 46 | 2.192 | −14.291 | 33.978 | 1.00 | 52.65 | W |
| ATOM | 3495 | O | HOH | W | 47 | 17.764 | 7.893 | 18.811 | 1.00 | 33.25 | W |
| ATOM | 3496 | O | HOH | W | 48 | 23.419 | 34.909 | 1.316 | 1.00 | 50.97 | W |
| ATOM | 3497 | O | HOH | W | 49 | 10.319 | 16.087 | 0.306 | 1.00 | 49.94 | W |
| ATOM | 3498 | O | HOH | W | 50 | 25.699 | 12.727 | 34.056 | 1.00 | 51.65 | W |
| ATOM | 3499 | O | HOH | W | 51 | −2.140 | 11.386 | 39.612 | 1.00 | 59.62 | W |
| ATOM | 3500 | O | HOH | W | 52 | 36.602 | 22.537 | 24.220 | 1.00 | 33.67 | W |
| ATOM | 3501 | O | HOH | W | 53 | 14.186 | 16.382 | 1.284 | 1.00 | 44.35 | W |
| ATOM | 3502 | O | HOH | W | 54 | 5.482 | 16.132 | 0.185 | 1.00 | 43.90 | W |
| ATOM | 3503 | O | HOH | W | 55 | 28.679 | 13.017 | 36.632 | 1.00 | 52.08 | W |
| ATOM | 3504 | O | HOH | W | 56 | 35.650 | 22.692 | 3.479 | 1.00 | 42.66 | W |
| ATOM | 3505 | O | HOH | W | 57 | 27.586 | 23.052 | 4.728 | 1.00 | 62.26 | W |
| ATOM | 3506 | O | HOH | W | 58 | −4.755 | −2.834 | 11.440 | 1.00 | 66.72 | W |
| ATOM | 3507 | O | HOH | W | 59 | 46.719 | 28.360 | 28.757 | 1.00 | 62.36 | W |
| ATOM | 3508 | O | HOH | W | 60 | −0.090 | 21.541 | 4.105 | 1.00 | 62.28 | W |
| ATOM | 3509 | O | HOH | W | 61 | 1.544 | −4.761 | 12.525 | 1.00 | 44.00 | W |
| ATOM | 3510 | O | HOH | W | 62 | 8.416 | 33.499 | 10.132 | 1.00 | 50.06 | W |
| ATOM | 3511 | O | HOH | W | 63 | −5.535 | 11.171 | 11.455 | 1.00 | 32.39 | W |
| ATOM | 3512 | O | HOH | W | 64 | 16.148 | 0.041 | 0.624 | 1.00 | 49.53 | W |
| ATOM | 3513 | O | HOH | W | 65 | 4.139 | −1.059 | 22.619 | 1.00 | 26.75 | W |
| ATOM | 3514 | O | HOH | W | 66 | 28.043 | 10.095 | 29.770 | 1.00 | 26.22 | W |
| ATOM | 3515 | O | HOH | W | 67 | 13.993 | 27.003 | 26.260 | 1.00 | 53.88 | W |
| ATOM | 3516 | O | HOH | W | 68 | −4.852 | 5.806 | 35.490 | 1.00 | 49.17 | W |
| ATOM | 3517 | O | HOH | W | 69 | −1.574 | 33.788 | 16.393 | 1.00 | 49.43 | W |
| ATOM | 3518 | O | HOH | W | 70 | 36.381 | 36.589 | 21.598 | 1.00 | 46.46 | W |
| ATOM | 3519 | O | HOH | W | 71 | 2.487 | 21.568 | 38.644 | 1.00 | 57.68 | W |
| ATOM | 3520 | O | HOH | W | 72 | 11.880 | 25.002 | 1.527 | 1.00 | 39.64 | W |
| ATOM | 3521 | O | HOH | W | 73 | 14.728 | −8.678 | 4.225 | 1.00 | 52.31 | W |
| ATOM | 3522 | O | HOH | W | 74 | 42.301 | 33.606 | 20.456 | 1.00 | 56.21 | W |
| ATOM | 3523 | O | HOH | W | 75 | 19.614 | 14.431 | 20.520 | 1.00 | 37.36 | W |
| ATOM | 3524 | O | HOH | W | 76 | 40.555 | 22.492 | 18.006 | 1.00 | 50.99 | W |
| ATOM | 3525 | O | HOH | W | 77 | −1.052 | 1.978 | 41.756 | 1.00 | 37.40 | W |
| ATOM | 3526 | O | HOH | W | 78 | 4.229 | 33.918 | 20.962 | 1.00 | 47.73 | W |
| ATOM | 3527 | O | HOH | W | 79 | 24.407 | 31.724 | −0.758 | 1.00 | 57.55 | W |
| ATOM | 3528 | O | HOH | W | 80 | 2.411 | 18.614 | 4.157 | 1.00 | 50.91 | W |
| ATOM | 3529 | O | HOH | W | 81 | 37.671 | 20.673 | 20.567 | 1.00 | 30.98 | W |
| ATOM | 3530 | O | HOH | W | 82 | 51.790 | 23.214 | 18.725 | 1.00 | 50.55 | W |
| ATOM | 3531 | O | HOH | W | 83 | 12.568 | 14.258 | 39.243 | 1.00 | 54.61 | W |
| ATOM | 3532 | O | HOH | W | 84 | 14.179 | 33.823 | 8.070 | 1.00 | 47.52 | W |
| ATOM | 3533 | O | HOH | W | 85 | 7.716 | 26.732 | 8.450 | 1.00 | 51.35 | W |
| ATOM | 3534 | O | HOH | W | 86 | 16.334 | 18.986 | 0.833 | 1.00 | 50.71 | W |
| ATOM | 3535 | O | HOH | W | 87 | 7.155 | 0.289 | 7.639 | 1.00 | 64.38 | W |
| ATOM | 3536 | O | HOH | W | 88 | 40.048 | 28.531 | 25.795 | 1.00 | 34.07 | W |
| ATOM | 3537 | O | HOH | W | 89 | 45.072 | 16.256 | 20.454 | 1.00 | 39.59 | W |
| ATOM | 3538 | O | HOH | W | 90 | 25.675 | 16.448 | 26.980 | 1.00 | 30.84 | W |
| ATOM | 3539 | O | HOH | W | 91 | 39.289 | 16.767 | 22.426 | 1.00 | 18.55 | W |
| ATOM | 3540 | O | HOH | W | 92 | −4.714 | 3.662 | 17.807 | 1.00 | 55.53 | W |
| ATOM | 3541 | O | HOH | W | 93 | −3.653 | 8.312 | 1.272 | 1.00 | 44.35 | W |
| ATOM | 3542 | O | HOH | W | 94 | 52.991 | 25.723 | 17.906 | 1.00 | 50.49 | W |
| ATOM | 3543 | O | HOH | W | 95 | 39.721 | 16.161 | 10.235 | 1.00 | 51.13 | W |
| ATOM | 3544 | O | HOH | W | 96 | 25.557 | 0.117 | 15.957 | 1.00 | 49.79 | W |
| ATOM | 3545 | O | HOH | W | 97 | 23.835 | −0.404 | 11.114 | 1.00 | 43.61 | W |
| ATOM | 3546 | O | HOH | W | 98 | 49.678 | 12.932 | 11.913 | 1.00 | 52.77 | W |
| ATOM | 3547 | O | HOH | W | 99 | 53.346 | 18.821 | 24.224 | 1.00 | 28.55 | W |
| ATOM | 3548 | O | HOH | W | 100 | 16.104 | 17.287 | 31.060 | 1.00 | 45.82 | W |

TABLE 9-continued

Structure coordinates for ERalpha-LBD/Compound 1 complex
(Table dicloses SEQ ID NOS 2-8, respectively, in order of appearance)

|  | # | Name | Res. | Chain | Res # | X | Y | Z | occ | B | SegID |
|---|---|---|---|---|---|---|---|---|---|---|---|
| ATOM | 3549 | O | HOH | W | 101 | 4.533 | 23.633 | 5.392 | 1.00 | 55.10 | W |
| ATOM | 3550 | O | HOH | W | 102 | 4.186 | 4.692 | 23.684 | 1.00 | 29.21 | W |
| ATOM | 3551 | O | HOH | W | 103 | 12.484 | −7.773 | 29.328 | 1.00 | 56.88 | W |
| ATOM | 3552 | O | HOH | W | 104 | 40.857 | 20.848 | 15.785 | 1.00 | 44.63 | W |
| ATOM | 3553 | O | HOH | W | 105 | 27.189 | 6.154 | 17.836 | 1.00 | 35.79 | W |
| ATOM | 3554 | O | HOH | W | 106 | 25.276 | 14.754 | 23.421 | 1.00 | 40.77 | W |
| ATOM | 3555 | O | HOH | W | 107 | −5.513 | 1.172 | 12.526 | 1.00 | 61.10 | W |
| ATOM | 3556 | O | HOH | W | 108 | 5.652 | 2.189 | 27.002 | 1.00 | 42.63 | W |
| ATOM | 3557 | O | HOH | W | 109 | 17.419 | −13.621 | 7.993 | 1.00 | 62.70 | W |
| ATOM | 3558 | O | HOH | W | 110 | 37.581 | 34.095 | 15.322 | 1.00 | 53.44 | W |
| ATOM | 3559 | O | HOH | W | 111 | 32.701 | 38.713 | 22.215 | 1.00 | 55.52 | W |
| ATOM | 3560 | O | HOH | W | 112 | 18.045 | 32.906 | 13.531 | 1.00 | 59.88 | W |
| ATOM | 3561 | O | HOH | W | 113 | 39.080 | −0.555 | 10.612 | 1.00 | 44.12 | W |
| ATOM | 3562 | O | HOH | W | 114 | 49.371 | 20.887 | 18.429 | 1.00 | 42.31 | W |
| ATOM | 3563 | O | HOH | W | 115 | −3.642 | 9.191 | 32.062 | 1.00 | 53.22 | W |
| ATOM | 3564 | O | HOH | W | 116 | 21.666 | −6.650 | 15.911 | 1.00 | 48.58 | W |
| ATOM | 3565 | O | HOH | W | 117 | 45.466 | −5.263 | 19.403 | 1.00 | 51.82 | W |
| ATOM | 3566 | O | HOH | W | 118 | 17.538 | 13.794 | 11.195 | 1.00 | 35.83 | W |
| ATOM | 3567 | O | HOH | W | 119 | −3.344 | 14.511 | 9.663 | 1.00 | 80.39 | W |
| ATOM | 3568 | O | HOH | W | 120 | 9.772 | −1.651 | −0.703 | 1.00 | 47.37 | W |
| ATOM | 3569 | O | HOH | W | 121 | −1.373 | 8.200 | 27.218 | 1.00 | 41.09 | W |
| ATOM | 3570 | O | HOH | W | 122 | 19.202 | 30.949 | 2.397 | 1.00 | 46.83 | W |
| ATOM | 3571 | O | HOH | W | 123 | 19.975 | 11.125 | 3.161 | 1.00 | 67.05 | W |
| ATOM | 3572 | O | HOH | W | 124 | 16.542 | 38.256 | 16.367 | 1.00 | 100.00 | W |
| ATOM | 3573 | O | HOH | W | 125 | 40.153 | 20.108 | 19.525 | 1.00 | 55.29 | W |
| ATOM | 3574 | O | HOH | W | 126 | 22.923 | 21.016 | 46.007 | 1.00 | 50.09 | W |
| ATOM | 3575 | O | HOH | W | 127 | 53.748 | 16.241 | 14.606 | 1.00 | 46.81 | W |
| ATOM | 3576 | O | HOH | W | 128 | 18.844 | −15.980 | 9.127 | 1.00 | 61.91 | W |
| ATOM | 3577 | O | HOH | W | 129 | −6.036 | 6.943 | 14.187 | 1.00 | 65.99 | W |
| ATOM | 3578 | O | HOH | W | 130 | −7.814 | 5.254 | 13.693 | 1.00 | 77.03 | W |
| ATOM | 3579 | O | HOH | W | 131 | 25.565 | 1.325 | 11.175 | 1.00 | 48.40 | W |
| ATOM | 3580 | O | HOH | W | 132 | −4.584 | −8.921 | 43.947 | 1.00 | 43.92 | W |
| ATOM | 3581 | O | HOH | W | 133 | 23.499 | 3.099 | 16.852 | 1.00 | 48.06 | W |
| ATOM | 3582 | O | HOH | W | 134 | 7.924 | −10.720 | 15.054 | 1.00 | 48.00 | W |
| ATOM | 3583 | O | HOH | W | 135 | 29.477 | −4.101 | 32.086 | 1.00 | 42.78 | W |
| ATOM | 3584 | O | HOH | W | 136 | −3.691 | 16.802 | 19.856 | 1.00 | 50.69 | W |
| ATOM | 3585 | O | HOH | W | 137 | 25.888 | −1.965 | 12.718 | 1.00 | 51.14 | W |
| ATOM | 3586 | O | HOH | W | 138 | −2.638 | 16.193 | 21.976 | 1.00 | 47.80 | W |
| ATOM | 3587 | C1 | 916 | A | 1 | 13.363 | −2.631 | 32.739 | 1.00 | 90.24 | A |
| ATOM | 3588 | C2 | 916 | A | 1 | 12.246 | −2.942 | 31.912 | 1.00 | 89.92 | A |
| ATOM | 3589 | C3 | 916 | A | 1 | 11.247 | −1.943 | 31.707 | 1.00 | 89.72 | A |
| ATOM | 3590 | C4 | 916 | A | 1 | 11.389 | −0.646 | 32.324 | 1.00 | 89.06 | A |
| ATOM | 3591 | C5 | 916 | A | 1 | 12.487 | −0.335 | 33.147 | 1.00 | 89.52 | A |
| ATOM | 3592 | C6 | 916 | A | 1 | 13.533 | −1.318 | 33.358 | 1.00 | 90.29 | A |
| ATOM | 3593 | C7 | 916 | A | 1 | 10.511 | 0.503 | 32.273 | 1.00 | 87.97 | A |
| ATOM | 3594 | N8 | 916 | A | 1 | 11.044 | 1.518 | 33.021 | 1.00 | 88.83 | A |
| ATOM | 3595 | N9 | 916 | A | 1 | 12.224 | 1.016 | 33.529 | 1.00 | 89.34 | A |
| ATOM | 3596 | C10 | 916 | A | 1 | 9.212 | 0.643 | 31.532 | 1.00 | 86.65 | A |
| ATOM | 3597 | C11 | 916 | A | 1 | 8.233 | −0.401 | 31.713 | 1.00 | 85.87 | A |
| ATOM | 3598 | C12 | 916 | A | 1 | 6.988 | −0.321 | 31.032 | 1.00 | 85.59 | A |
| ATOM | 3599 | C13 | 916 | A | 1 | 6.709 | 0.787 | 30.178 | 1.00 | 85.25 | A |
| ATOM | 3600 | C14 | 916 | A | 1 | 7.663 | 1.823 | 29.998 | 1.00 | 85.64 | A |
| ATOM | 3601 | C15 | 916 | A | 1 | 8.915 | 1.751 | 30.675 | 1.00 | 85.80 | A |
| ATOM | 3602 | O16 | 916 | A | 1 | 5.501 | 0.844 | 29.525 | 1.00 | 85.70 | A |
| ATOM | 3603 | O17 | 916 | A | 1 | 9.793 | 2.799 | 30.448 | 1.00 | 84.98 | A |
| ATOM | 3604 | C18 | 916 | A | 1 | 13.031 | 1.910 | 34.404 | 1.00 | 89.28 | A |
| ATOM | 3605 | C19 | 916 | A | 1 | 12.382 | 2.181 | 35.752 | 1.00 | 89.40 | A |
| ATOM | 3606 | C20 | 916 | A | 1 | 11.972 | 1.182 | 36.564 | 1.00 | 89.87 | A |
| ATOM | 3607 | C21 | 916 | A | 1 | 14.772 | −1.121 | 34.253 | 1.00 | 90.59 | A |
| ATOM | 3608 | F22 | 916 | A | 1 | 15.596 | −2.187 | 34.213 | 1.00 | 90.70 | A |
| ATOM | 3609 | F23 | 916 | A | 1 | 14.414 | −0.963 | 35.518 | 1.00 | 91.06 | A |
| ATOM | 3610 | F24 | 916 | A | 1 | 15.471 | −0.082 | 33.811 | 1.00 | 90.86 | A |
| ATOM | 3611 | C1 | 916 | B | 1 | 38.555 | 7.202 | 29.034 | 1.00 | 71.05 | B |
| ATOM | 3612 | C2 | 916 | B | 1 | 39.190 | 8.479 | 29.069 | 1.00 | 70.52 | B |
| ATOM | 3613 | C3 | 916 | B | 1 | 39.399 | 9.179 | 27.839 | 1.00 | 70.62 | B |
| ATOM | 3614 | C4 | 916 | B | 1 | 38.976 | 8.584 | 26.595 | 1.00 | 69.72 | B |
| ATOM | 3615 | C5 | 916 | B | 1 | 38.347 | 7.315 | 26.559 | 1.00 | 70.29 | B |
| ATOM | 3616 | C6 | 916 | B | 1 | 38.102 | 6.587 | 27.789 | 1.00 | 70.95 | B |
| ATOM | 3617 | C7 | 916 | B | 1 | 39.081 | 9.083 | 25.233 | 1.00 | 68.38 | B |
| ATOM | 3618 | N8 | 916 | B | 1 | 38.542 | 8.158 | 24.374 | 1.00 | 69.58 | B |
| ATOM | 3619 | N9 | 916 | B | 1 | 38.110 | 7.119 | 25.167 | 1.00 | 70.37 | B |
| ATOM | 3620 | C10 | 916 | B | 1 | 39.649 | 10.382 | 24.718 | 1.00 | 66.27 | B |
| ATOM | 3621 | C11 | 916 | B | 1 | 40.830 | 10.937 | 25.340 | 1.00 | 65.19 | B |
| ATOM | 3622 | C12 | 916 | B | 1 | 41.367 | 12.173 | 24.850 | 1.00 | 63.90 | B |

TABLE 9-continued

Structure coordinates for ERalpha-LBD/Compound 1 complex
(Table dicloses SEQ ID NOS 2-8, respectively, in order of appearance)

| | # | Name | Res. | Chain | Res # | X | Y | Z | occ | B | SegID |
|---|---|---|---|---|---|---|---|---|---|---|---|
| ATOM | 3623 | C13 | 916 | B | 1 | 40.741 | 12.848 | 23.753 | 1.00 | 63.08 | B |
| ATOM | 3624 | C14 | 916 | B | 1 | 39.586 | 12.305 | 23.142 | 1.00 | 64.54 | B |
| ATOM | 3625 | C15 | 916 | B | 1 | 39.043 | 11.075 | 23.626 | 1.00 | 65.25 | B |
| ATOM | 3626 | O16 | 916 | B | 1 | 41.265 | 14.032 | 23.292 | 1.00 | 62.63 | B |
| ATOM | 3627 | O17 | 916 | B | 1 | 37.910 | 10.613 | 22.977 | 1.00 | 65.28 | B |
| ATOM | 3628 | C18 | 916 | B | 1 | 37.474 | 5.962 | 24.490 | 1.00 | 70.80 | B |
| ATOM | 3629 | C19 | 916 | B | 1 | 38.455 | 5.160 | 23.654 | 1.00 | 71.45 | B |
| ATOM | 3630 | C20 | 916 | B | 1 | 38.591 | 5.361 | 22.330 | 1.00 | 71.47 | B |
| ATOM | 3631 | C21 | 916 | B | 1 | 37.440 | 5.190 | 27.892 | 1.00 | 71.34 | B |
| ATOM | 3632 | F22 | 916 | B | 1 | 37.276 | 4.811 | 29.171 | 1.00 | 71.77 | B |
| ATOM | 3633 | F23 | 916 | B | 1 | 38.186 | 4.260 | 27.305 | 1.00 | 71.88 | B |
| ATOM | 3634 | F24 | 916 | B | 1 | 36.231 | 5.232 | 27.363 | 1.00 | 72.50 | B |

TABLE 10

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 1 | N | ALA | A | 307 | 5.722 | 6.562 | 0.433 | 1.00 | 74.35 | A | N |
| ATOM | 2 | CA | ALA | A | 307 | 6.662 | 6.304 | 1.556 | 1.00 | 74.18 | A | C |
| ATOM | 3 | C | ALA | A | 307 | 7.675 | 7.446 | 1.666 | 1.00 | 73.96 | A | C |
| ATOM | 4 | O | ALA | A | 307 | 8.075 | 7.833 | 2.764 | 1.00 | 73.93 | A | O |
| ATOM | 5 | CB | ALA | A | 307 | 7.385 | 4.974 | 1.332 | 1.00 | 74.06 | A | C |
| ATOM | 6 | N | LEU | A | 308 | 8.086 | 7.981 | 0.523 | 1.00 | 73.52 | A | N |
| ATOM | 7 | CA | LEU | A | 308 | 9.043 | 9.077 | 0.498 | 1.00 | 73.25 | A | C |
| ATOM | 8 | C | LEU | A | 308 | 8.323 | 10.272 | −0.106 | 1.00 | 72.81 | A | C |
| ATOM | 9 | O | LEU | A | 308 | 8.821 | 11.406 | −0.101 | 1.00 | 72.10 | A | O |
| ATOM | 10 | CB | LEU | A | 308 | 10.241 | 8.693 | −0.364 | 1.00 | 73.86 | A | C |
| ATOM | 11 | CG | LEU | A | 308 | 11.613 | 9.214 | 0.078 | 1.00 | 74.43 | A | C |
| ATOM | 12 | CD1 | LEU | A | 308 | 12.727 | 8.465 | −0.681 | 1.00 | 74.65 | A | C |
| ATOM | 13 | CD2 | LEU | A | 308 | 11.677 | 10.720 | −0.148 | 1.00 | 74.60 | A | C |
| ATOM | 14 | N | SER | A | 309 | 7.115 | 9.993 | −0.590 | 1.00 | 72.79 | A | N |
| ATOM | 15 | CA | SER | A | 309 | 6.281 | 10.988 | −1.245 | 1.00 | 72.42 | A | C |
| ATOM | 16 | C | SER | A | 309 | 5.244 | 11.648 | −0.334 | 1.00 | 71.73 | A | C |
| ATOM | 17 | O | SER | A | 309 | 4.651 | 12.665 | −0.709 | 1.00 | 71.85 | A | O |
| ATOM | 18 | CB | SER | A | 309 | 5.593 | 10.335 | −2.453 | 1.00 | 72.66 | A | C |
| ATOM | 19 | OG | SER | A | 309 | 6.545 | 9.698 | −3.305 | 1.00 | 72.63 | A | O |
| ATOM | 20 | N | LEU | A | 310 | 5.063 | 11.085 | 0.863 | 1.00 | 70.46 | A | N |
| ATOM | 21 | CA | LEU | A | 310 | 4.088 | 11.561 | 1.858 | 1.00 | 68.84 | A | C |
| ATOM | 22 | C | LEU | A | 310 | 4.187 | 13.035 | 2.249 | 1.00 | 67.69 | A | C |
| ATOM | 23 | O | LEU | A | 310 | 5.273 | 13.602 | 2.305 | 1.00 | 67.51 | A | O |
| ATOM | 24 | CB | LEU | A | 310 | 4.189 | 10.694 | 3.115 | 1.00 | 68.67 | A | C |
| ATOM | 25 | CG | LEU | A | 310 | 4.249 | 9.184 | 2.841 | 1.00 | 68.46 | A | C |
| ATOM | 26 | CD1 | LEU | A | 310 | 4.373 | 8.427 | 4.154 | 1.00 | 68.61 | A | C |
| ATOM | 27 | CD2 | LEU | A | 310 | 3.015 | 8.738 | 2.092 | 1.00 | 68.21 | A | C |
| ATOM | 28 | N | THR | A | 311 | 3.039 | 13.658 | 2.503 | 1.00 | 66.77 | A | N |
| ATOM | 29 | CA | THR | A | 311 | 3.004 | 15.067 | 2.903 | 1.00 | 65.92 | A | C |
| ATOM | 30 | C | THR | A | 311 | 3.132 | 15.164 | 4.423 | 1.00 | 65.69 | A | C |
| ATOM | 31 | O | THR | A | 311 | 3.240 | 14.152 | 5.126 | 1.00 | 65.38 | A | O |
| ATOM | 32 | CB | THR | A | 311 | 1.672 | 15.791 | 2.480 | 1.00 | 65.38 | A | C |
| ATOM | 33 | OG1 | THR | A | 311 | 1.743 | 17.178 | 2.839 | 1.00 | 65.11 | A | O |
| ATOM | 34 | CG2 | THR | A | 311 | 0.479 | 15.196 | 3.189 | 1.00 | 64.53 | A | C |
| ATOM | 35 | N | ALA | A | 312 | 3.111 | 16.396 | 4.919 | 1.00 | 64.86 | A | N |
| ATOM | 36 | CA | ALA | A | 312 | 3.225 | 16.649 | 6.342 | 1.00 | 63.91 | A | C |
| ATOM | 37 | C | ALA | A | 312 | 2.072 | 15.994 | 7.094 | 1.00 | 63.40 | A | C |
| ATOM | 38 | O | ALA | A | 312 | 2.280 | 15.131 | 7.945 | 1.00 | 63.07 | A | O |
| ATOM | 39 | CB | ALA | A | 312 | 3.227 | 18.141 | 6.591 | 1.00 | 63.77 | A | C |
| ATOM | 40 | N | ASP | A | 313 | 0.855 | 16.403 | 6.763 | 1.00 | 63.20 | A | N |
| ATOM | 41 | CA | ASP | A | 313 | −0.329 | 15.883 | 7.413 | 1.00 | 62.88 | A | C |
| ATOM | 42 | C | ASP | A | 313 | −0.523 | 14.381 | 7.208 | 1.00 | 62.62 | A | C |
| ATOM | 43 | O | ASP | A | 313 | −1.148 | 13.724 | 8.036 | 1.00 | 62.78 | A | O |
| ATOM | 44 | CB | ASP | A | 313 | −1.531 | 16.667 | 6.922 | 1.00 | 63.96 | A | C |
| ATOM | 45 | CG | ASP | A | 313 | −1.338 | 18.166 | 7.081 | 1.00 | 65.12 | A | C |
| ATOM | 46 | OD1 | ASP | A | 313 | −1.141 | 18.618 | 8.231 | 1.00 | 66.11 | A | O |
| ATOM | 47 | OD2 | ASP | A | 313 | −1.371 | 18.898 | 6.064 | 1.00 | 65.43 | A | O |
| ATOM | 48 | N | GLN | A | 314 | 0.016 | 13.839 | 6.119 | 1.00 | 61.82 | A | N |
| ATOM | 49 | CA | GLN | A | 314 | −0.086 | 12.407 | 5.848 | 1.00 | 61.25 | A | C |
| ATOM | 50 | C | GLN | A | 314 | 0.906 | 11.597 | 6.676 | 1.00 | 60.94 | A | C |
| ATOM | 51 | O | GLN | A | 314 | 0.732 | 10.390 | 6.864 | 1.00 | 61.28 | A | O |
| ATOM | 52 | CB | GLN | A | 314 | 0.171 | 12.104 | 4.373 | 1.00 | 61.26 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 53 | CG | GLN | A | 314 | −0.960 | 12.474 | 3.433 | 1.00 | 61.25 | A | C |
| ATOM | 54 | CD | GLN | A | 314 | −0.563 | 12.288 | 1.980 | 1.00 | 60.68 | A | C |
| ATOM | 55 | OE1 | GLN | A | 314 | 0.465 | 12.808 | 1.532 | 1.00 | 59.85 | A | O |
| ATOM | 56 | NE2 | GLN | A | 314 | −1.381 | 11.549 | 1.233 | 1.00 | 60.21 | A | N |
| ATOM | 57 | N | MET | A | 315 | 1.971 | 12.249 | 7.130 | 1.00 | 60.40 | A | N |
| ATOM | 58 | CA | MET | A | 315 | 2.981 | 11.580 | 7.950 | 1.00 | 59.59 | A | C |
| ATOM | 59 | C | MET | A | 315 | 2.327 | 11.333 | 9.315 | 1.00 | 58.54 | A | C |
| ATOM | 60 | O | MET | A | 315 | 2.198 | 10.185 | 9.769 | 1.00 | 57.87 | A | O |
| ATOM | 61 | CB | MET | A | 315 | 4.219 | 12.489 | 8.091 | 1.00 | 60.37 | A | C |
| ATOM | 62 | CG | MET | A | 315 | 5.412 | 11.857 | 8.792 | 1.00 | 60.77 | A | C |
| ATOM | 63 | SD | MET | A | 315 | 5.892 | 10.265 | 8.057 | 1.00 | 62.68 | A | S |
| ATOM | 64 | CE | MET | A | 315 | 7.412 | 10.692 | 7.149 | 1.00 | 61.46 | A | C |
| ATOM | 65 | N | VAL | A | 316 | 1.900 | 12.436 | 9.932 | 1.00 | 56.76 | A | N |
| ATOM | 66 | CA | VAL | A | 316 | 1.237 | 12.440 | 11.221 | 1.00 | 55.44 | A | C |
| ATOM | 67 | C | VAL | A | 316 | 0.097 | 11.431 | 11.248 | 1.00 | 54.93 | A | C |
| ATOM | 68 | O | VAL | A | 316 | −0.055 | 10.675 | 12.216 | 1.00 | 54.73 | A | O |
| ATOM | 69 | CB | VAL | A | 316 | 0.672 | 13.838 | 11.532 | 1.00 | 55.19 | A | C |
| ATOM | 70 | CG1 | VAL | A | 316 | −0.264 | 13.770 | 12.709 | 1.00 | 55.52 | A | C |
| ATOM | 71 | CG2 | VAL | A | 316 | 1.806 | 14.791 | 11.845 | 1.00 | 55.64 | A | C |
| ATOM | 72 | N | SER | A | 317 | −0.706 | 11.425 | 10.185 | 1.00 | 53.69 | A | N |
| ATOM | 73 | CA | SER | A | 317 | −1.829 | 10.498 | 10.092 | 1.00 | 52.53 | A | C |
| ATOM | 74 | C | SER | A | 317 | −1.346 | 9.054 | 10.201 | 1.00 | 51.22 | A | C |
| ATOM | 75 | O | SER | A | 317 | −1.798 | 8.293 | 11.060 | 1.00 | 51.13 | A | O |
| ATOM | 76 | CB | SER | A | 317 | −2.572 | 10.676 | 8.760 | 1.00 | 53.02 | A | C |
| ATOM | 77 | OG | SER | A | 317 | −3.168 | 11.956 | 8.657 | 1.00 | 52.85 | A | O |
| ATOM | 78 | N | ALA | A | 318 | −0.430 | 8.686 | 9.314 | 1.00 | 49.63 | A | N |
| ATOM | 79 | CA | ALA | A | 318 | 0.125 | 7.336 | 9.285 | 1.00 | 48.78 | A | C |
| ATOM | 80 | C | ALA | A | 318 | 0.585 | 6.882 | 10.670 | 1.00 | 47.38 | A | C |
| ATOM | 81 | O | ALA | A | 318 | 0.227 | 5.789 | 11.135 | 1.00 | 46.87 | A | O |
| ATOM | 82 | CB | ALA | A | 318 | 1.302 | 7.268 | 8.289 | 1.00 | 48.64 | A | C |
| ATOM | 83 | N | LEU | A | 319 | 1.369 | 7.734 | 11.326 | 1.00 | 46.17 | A | N |
| ATOM | 84 | CA | LEU | A | 319 | 1.910 | 7.444 | 12.654 | 1.00 | 43.85 | A | C |
| ATOM | 85 | C | LEU | A | 319 | 0.803 | 7.386 | 13.705 | 1.00 | 42.39 | A | C |
| ATOM | 86 | O | LEU | A | 319 | 0.631 | 6.367 | 14.371 | 1.00 | 41.30 | A | O |
| ATOM | 87 | CB | LEU | A | 319 | 2.958 | 8.514 | 13.024 | 1.00 | 42.70 | A | C |
| ATOM | 88 | CG | LEU | A | 319 | 4.077 | 8.784 | 12.007 | 1.00 | 41.76 | A | C |
| ATOM | 89 | CD1 | LEU | A | 319 | 5.035 | 9.800 | 12.601 | 1.00 | 41.58 | A | C |
| ATOM | 90 | CD2 | LEU | A | 319 | 4.814 | 7.507 | 11.659 | 1.00 | 41.58 | A | C |
| ATOM | 91 | N | LEU | A | 320 | 0.033 | 8.469 | 13.826 | 1.00 | 41.24 | A | N |
| ATOM | 92 | CA | LEU | A | 320 | −1.058 | 8.542 | 14.809 | 1.00 | 40.03 | A | C |
| ATOM | 93 | C | LEU | A | 320 | −2.121 | 7.453 | 14.676 | 1.00 | 39.30 | A | C |
| ATOM | 94 | O | LEU | A | 320 | −2.920 | 7.307 | 15.583 | 1.00 | 39.37 | A | O |
| ATOM | 95 | CB | LEU | A | 320 | −1.795 | 9.853 | 14.725 | 1.00 | 39.39 | A | C |
| ATOM | 96 | CG | LEU | A | 320 | −1.109 | 11.155 | 15.038 | 1.00 | 39.31 | A | C |
| ATOM | 97 | CD1 | LEU | A | 320 | −2.162 | 12.265 | 15.207 | 1.00 | 38.41 | A | C |
| ATOM | 98 | CD2 | LEU | A | 320 | −0.280 | 11.003 | 16.303 | 1.00 | 38.70 | A | C |
| ATOM | 99 | N | ASP | A | 321 | −2.164 | 6.709 | 13.570 | 0.50 | 38.17 | A | N |
| ATOM | 100 | CA | ASP | A | 321 | −3.161 | 5.640 | 13.431 | 0.50 | 37.52 | A | C |
| ATOM | 101 | C | ASP | A | 321 | −2.470 | 4.286 | 13.566 | 0.50 | 36.92 | A | C |
| ATOM | 102 | O | ASP | A | 321 | −3.105 | 3.214 | 13.601 | 0.50 | 36.17 | A | O |
| ATOM | 103 | CB | ASP | A | 321 | −3.909 | 5.809 | 12.110 | 0.50 | 37.40 | A | C |
| ATOM | 104 | CG | ASP | A | 321 | −4.559 | 7.155 | 12.011 | 0.50 | 37.12 | A | C |
| ATOM | 105 | OD1 | ASP | A | 321 | −5.484 | 7.414 | 12.819 | 0.50 | 36.94 | A | O |
| ATOM | 106 | OD2 | ASP | A | 321 | −4.156 | 7.967 | 11.128 | 0.50 | 36.38 | A | O |
| ATOM | 107 | N | ALA | A | 322 | −1.146 | 4.354 | 13.672 | 1.00 | 37.03 | A | N |
| ATOM | 108 | CA | ALA | A | 322 | −0.295 | 3.170 | 13.871 | 1.00 | 36.86 | A | C |
| ATOM | 109 | C | ALA | A | 322 | 0.127 | 3.078 | 15.338 | 1.00 | 36.53 | A | C |
| ATOM | 110 | O | ALA | A | 322 | 0.749 | 2.098 | 15.733 | 1.00 | 36.37 | A | O |
| ATOM | 111 | CB | ALA | A | 322 | 0.966 | 3.282 | 12.980 | 1.00 | 36.83 | A | C |
| ATOM | 112 | N | GLU | A | 323 | −0.262 | 4.082 | 16.130 | 1.00 | 35.90 | A | N |
| ATOM | 113 | CA | GLU | A | 323 | 0.049 | 4.178 | 17.571 | 1.00 | 35.96 | A | C |
| ATOM | 114 | C | GLU | A | 323 | −0.392 | 2.985 | 18.431 | 1.00 | 35.94 | A | C |
| ATOM | 115 | O | GLU | A | 323 | −1.555 | 2.585 | 18.397 | 1.00 | 36.48 | A | O |
| ATOM | 116 | CB | GLU | A | 323 | −0.586 | 5.453 | 18.152 | 1.00 | 36.09 | A | C |
| ATOM | 117 | CG | GLU | A | 323 | 0.266 | 6.759 | 18.091 | 1.00 | 35.32 | A | C |
| ATOM | 118 | CD | GLU | A | 323 | 1.469 | 6.753 | 19.030 | 1.00 | 34.87 | A | C |
| ATOM | 119 | OE1 | GLU | A | 323 | 2.490 | 6.126 | 18.683 | 1.00 | 33.43 | A | O |
| ATOM | 120 | OE2 | GLU | A | 323 | 1.383 | 7.375 | 20.113 | 1.00 | 35.39 | A | O |
| ATOM | 121 | N | PRO | A | 324 | 0.534 | 2.419 | 19.225 | 1.00 | 36.00 | A | N |
| ATOM | 122 | CA | PRO | A | 324 | 0.210 | 1.270 | 20.086 | 1.00 | 35.15 | A | C |
| ATOM | 123 | C | PRO | A | 324 | −0.824 | 1.567 | 21.195 | 1.00 | 34.90 | A | C |
| ATOM | 124 | O | PRO | A | 324 | −1.037 | 2.721 | 21.572 | 1.00 | 34.53 | A | O |
| ATOM | 125 | CB | PRO | A | 324 | 1.576 | 0.880 | 20.672 | 1.00 | 35.92 | A | C |
| ATOM | 126 | CG | PRO | A | 324 | 2.558 | 1.339 | 19.630 | 1.00 | 36.17 | A | C |
| ATOM | 127 | CD | PRO | A | 324 | 1.987 | 2.691 | 19.230 | 1.00 | 36.12 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 128 | N | PRO | A | 325 | −1.500 | 0.520 | 21.711 | 1.00 | 35.00 | A | N |
| ATOM | 129 | CA | PRO | A | 325 | −2.484 | 0.738 | 22.772 | 1.00 | 33.66 | A | C |
| ATOM | 130 | C | PRO | A | 325 | −1.780 | 0.813 | 24.113 | 1.00 | 33.70 | A | C |
| ATOM | 131 | O | PRO | A | 325 | −0.698 | 0.248 | 24.274 | 1.00 | 33.00 | A | O |
| ATOM | 132 | CB | PRO | A | 325 | −3.384 | −0.486 | 22.659 | 1.00 | 34.10 | A | C |
| ATOM | 133 | CG | PRO | A | 325 | −2.414 | −1.544 | 22.287 | 1.00 | 34.05 | A | C |
| ATOM | 134 | CD | PRO | A | 325 | −1.578 | −0.867 | 21.213 | 1.00 | 34.35 | A | C |
| ATOM | 135 | N | ILE | A | 326 | −2.391 | 1.532 | 25.053 | 1.00 | 33.67 | A | N |
| ATOM | 136 | CA | ILE | A | 326 | −1.842 | 1.694 | 26.394 | 1.00 | 34.14 | A | C |
| ATOM | 137 | C | ILE | A | 326 | −2.154 | 0.429 | 27.165 | 1.00 | 33.53 | A | C |
| ATOM | 138 | O | ILE | A | 326 | −3.235 | 0.288 | 27.735 | 1.00 | 33.72 | A | O |
| ATOM | 139 | CB | ILE | A | 326 | −2.461 | 2.948 | 27.084 | 1.00 | 35.48 | A | C |
| ATOM | 140 | CG1 | ILE | A | 326 | −1.892 | 4.209 | 26.426 | 1.00 | 35.73 | A | C |
| ATOM | 141 | CG2 | ILE | A | 326 | −2.168 | 2.964 | 28.584 | 1.00 | 35.07 | A | C |
| ATOM | 142 | CD1 | ILE | A | 326 | −2.475 | 5.487 | 26.952 | 1.00 | 36.76 | A | C |
| ATOM | 143 | N | LEU | A | 327 | −1.200 | −0.497 | 27.165 | 1.00 | 33.49 | A | N |
| ATOM | 144 | CA | LEU | A | 327 | −1.383 | −1.783 | 27.823 | 1.00 | 34.28 | A | C |
| ATOM | 145 | C | LEU | A | 327 | −1.577 | −1.715 | 29.345 | 1.00 | 36.52 | A | C |
| ATOM | 146 | O | LEU | A | 327 | −1.266 | −0.717 | 30.012 | 1.00 | 35.42 | A | O |
| ATOM | 147 | CB | LEU | A | 327 | −0.213 | −2.720 | 27.469 | 1.00 | 31.59 | A | C |
| ATOM | 148 | CG | LEU | A | 327 | 0.060 | −2.912 | 25.961 | 1.00 | 29.67 | A | C |
| ATOM | 149 | CD1 | LEU | A | 327 | 1.033 | −4.068 | 25.706 | 1.00 | 27.23 | A | C |
| ATOM | 150 | CD2 | LEU | A | 327 | −1.253 | −3.185 | 25.246 | 1.00 | 28.49 | A | C |
| ATOM | 151 | N | TYR | A | 328 | −2.127 | −2.794 | 29.886 | 1.00 | 39.75 | A | N |
| ATOM | 152 | CA | TYR | A | 328 | −2.369 | −2.888 | 31.315 | 1.00 | 42.03 | A | C |
| ATOM | 153 | C | TYR | A | 328 | −1.449 | −3.898 | 31.979 | 1.00 | 44.12 | A | C |
| ATOM | 154 | O | TYR | A | 328 | −1.001 | −4.853 | 31.352 | 1.00 | 42.98 | A | O |
| ATOM | 155 | CB | TYR | A | 328 | −3.813 | −3.276 | 31.565 | 1.00 | 41.70 | A | C |
| ATOM | 156 | CG | TYR | A | 328 | −4.729 | −2.098 | 31.808 | 1.00 | 42.80 | A | C |
| ATOM | 157 | CD1 | TYR | A | 328 | −5.446 | −1.491 | 30.761 | 1.00 | 43.08 | A | C |
| ATOM | 158 | CD2 | TYR | A | 328 | −4.908 | −1.607 | 33.092 | 1.00 | 42.22 | A | C |
| ATOM | 159 | CE1 | TYR | A | 328 | −6.321 | −0.422 | 31.010 | 1.00 | 42.77 | A | C |
| ATOM | 160 | CE2 | TYR | A | 328 | −5.769 | −0.553 | 33.346 | 1.00 | 42.94 | A | C |
| ATOM | 161 | CZ | TYR | A | 328 | −6.471 | 0.039 | 32.313 | 1.00 | 42.69 | A | C |
| ATOM | 162 | OH | TYR | A | 328 | −7.292 | 1.105 | 32.620 | 1.00 | 42.53 | A | O |
| ATOM | 163 | N | SER | A | 329 | −1.149 | −3.672 | 33.251 | 1.00 | 47.85 | A | N |
| ATOM | 164 | CA | SER | A | 329 | −0.299 | −4.597 | 33.983 | 1.00 | 52.35 | A | C |
| ATOM | 165 | C | SER | A | 329 | −1.181 | −5.653 | 34.646 | 1.00 | 55.29 | A | C |
| ATOM | 166 | O | SER | A | 329 | −2.223 | −5.327 | 35.233 | 1.00 | 55.33 | A | O |
| ATOM | 167 | CB | SER | A | 329 | 0.546 | −3.851 | 35.029 | 1.00 | 52.75 | A | C |
| ATOM | 168 | OG | SER | A | 329 | −0.255 | −3.055 | 35.889 | 1.00 | 53.10 | A | O |
| ATOM | 169 | N | GLU | A | 330 | −0.764 | −6.915 | 34.518 | 1.00 | 58.82 | A | N |
| ATOM | 170 | CA | GLU | A | 330 | −1.460 | −8.083 | 35.078 | 1.00 | 62.13 | A | C |
| ATOM | 171 | C | GLU | A | 330 | −2.039 | −7.852 | 36.491 | 1.00 | 63.64 | A | C |
| ATOM | 172 | O | GLU | A | 330 | −1.321 | −7.499 | 37.422 | 1.00 | 63.90 | A | O |
| ATOM | 173 | CB | GLU | A | 330 | −0.480 | −9.272 | 35.059 | 1.00 | 63.61 | A | C |
| ATOM | 174 | CG | GLU | A | 330 | −0.769 | −10.380 | 36.077 | 1.00 | 66.37 | A | C |
| ATOM | 175 | CD | GLU | A | 330 | 0.110 | −11.629 | 35.882 | 1.00 | 67.90 | A | C |
| ATOM | 176 | OE1 | GLU | A | 330 | 1.331 | −11.496 | 35.603 | 1.00 | 68.18 | A | O |
| ATOM | 177 | OE2 | GLU | A | 330 | −0.428 | −12.753 | 36.016 | 1.00 | 68.82 | A | O |
| ATOM | 178 | N | TYR | A | 331 | −3.348 | −8.062 | 36.628 | 1.00 | 65.22 | A | N |
| ATOM | 179 | CA | TYR | A | 331 | −4.015 | −7.874 | 37.906 | 1.00 | 67.24 | A | C |
| ATOM | 180 | C | TYR | A | 331 | −3.736 | −9.107 | 38.737 | 1.00 | 68.60 | A | C |
| ATOM | 181 | O | TYR | A | 331 | −3.739 | −10.209 | 38.223 | 1.00 | 68.98 | A | O |
| ATOM | 182 | CB | TYR | A | 331 | −5.512 | −7.660 | 37.694 | 1.00 | 67.32 | A | C |
| ATOM | 183 | CG | TYR | A | 331 | −6.322 | −7.441 | 38.958 | 1.00 | 67.84 | A | C |
| ATOM | 184 | CD1 | TYR | A | 331 | −5.978 | −6.445 | 39.877 | 1.00 | 68.32 | A | C |
| ATOM | 185 | CD2 | TYR | A | 331 | −7.436 | −8.244 | 39.239 | 1.00 | 67.90 | A | C |
| ATOM | 186 | CE1 | TYR | A | 331 | −6.721 | −6.256 | 41.054 | 1.00 | 68.35 | A | C |
| ATOM | 187 | CE2 | TYR | A | 331 | −8.179 | −8.067 | 40.399 | 1.00 | 67.94 | A | C |
| ATOM | 188 | CZ | TYR | A | 331 | −7.823 | −7.082 | 41.304 | 1.00 | 68.17 | A | C |
| ATOM | 189 | OH | TYR | A | 331 | −8.541 | −6.937 | 42.473 | 1.00 | 67.67 | A | O |
| ATOM | 190 | N | ASP | A | 332 | −3.505 | −8.939 | 40.032 | 1.00 | 70.05 | A | N |
| ATOM | 191 | CA | ASP | A | 332 | −3.235 | −10.115 | 40.851 | 1.00 | 71.12 | A | C |
| ATOM | 192 | C | ASP | A | 332 | −3.679 | −9.961 | 42.304 | 1.00 | 70.94 | A | C |
| ATOM | 193 | O | ASP | A | 332 | −4.468 | −9.060 | 42.623 | 1.00 | 70.85 | A | O |
| ATOM | 194 | CB | ASP | A | 332 | −1.760 | −10.428 | 40.788 | 1.00 | 72.41 | A | C |
| ATOM | 195 | CG | ASP | A | 332 | −1.489 | −11.913 | 40.562 | 1.00 | 73.90 | A | C |
| ATOM | 196 | OD1 | ASP | A | 332 | −0.311 | −12.264 | 40.314 | 1.00 | 74.18 | A | O |
| ATOM | 197 | OD2 | ASP | A | 332 | −2.450 | −12.722 | 40.558 | 1.00 | 74.49 | A | O |
| ATOM | 198 | N | SER | A | 341 | 6.817 | −8.891 | 43.180 | 1.00 | 75.41 | A | N |
| ATOM | 199 | CA | SER | A | 341 | 8.015 | −8.224 | 42.704 | 1.00 | 75.27 | A | C |
| ATOM | 200 | C | SER | A | 341 | 7.677 | −7.317 | 41.535 | 1.00 | 75.47 | A | C |
| ATOM | 201 | O | SER | A | 341 | 7.266 | −7.811 | 40.474 | 1.00 | 75.71 | A | O |
| ATOM | 202 | CB | SER | A | 341 | 9.065 | −9.256 | 42.287 | 1.00 | 75.27 | A | C |

TABLE 10-continued

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 203 | OG | SER | A | 341 | 9.785 | −8.862 | 41.139 | 1.00 | 74.82 A | O |
| ATOM | 204 | N | MET | A | 342 | 7.828 | −6.002 | 41.717 | 1.00 | 75.05 A | N |
| ATOM | 205 | CA | MET | A | 342 | 7.533 | −5.057 | 40.648 | 1.00 | 74.30 A | C |
| ATOM | 206 | C | MET | A | 342 | 8.479 | −5.160 | 39.487 | 1.00 | 73.17 A | C |
| ATOM | 207 | O | MET | A | 342 | 8.142 | −4.712 | 38.399 | 1.00 | 73.48 A | O |
| ATOM | 208 | CB | MET | A | 342 | 7.557 | −3.638 | 41.180 | 1.00 | 75.39 A | C |
| ATOM | 209 | CG | MET | A | 342 | 6.309 | −3.233 | 41.906 | 1.00 | 77.43 A | C |
| ATOM | 210 | SD | MET | A | 342 | 5.940 | −1.511 | 41.585 | 1.00 | 79.78 A | S |
| ATOM | 211 | CE | MET | A | 342 | 4.147 | −1.439 | 42.012 | 1.00 | 79.87 A | C |
| ATOM | 212 | N | MET | A | 343 | 9.670 | −5.692 | 39.734 | 1.00 | 71.33 A | N |
| ATOM | 213 | CA | MET | A | 343 | 10.596 | −5.849 | 38.647 | 1.00 | 69.44 A | C |
| ATOM | 214 | C | MET | A | 343 | 9.920 | −6.797 | 37.651 | 1.00 | 67.41 A | C |
| ATOM | 215 | O | MET | A | 343 | 9.951 | −6.577 | 36.442 | 1.00 | 66.93 A | O |
| ATOM | 216 | CB | MET | A | 343 | 11.925 | −6.432 | 39.143 | 1.00 | 70.79 A | C |
| ATOM | 217 | CG | MET | A | 343 | 13.151 | −6.087 | 38.303 | 1.00 | 72.84 A | C |
| ATOM | 218 | SD | MET | A | 343 | 13.355 | −4.315 | 37.950 | 1.00 | 74.69 A | S |
| ATOM | 219 | CE | MET | A | 343 | 14.426 | −4.430 | 36.491 | 1.00 | 73.89 A | C |
| ATOM | 220 | N | GLY | A | 344 | 9.273 | −7.829 | 38.186 | 1.00 | 65.38 A | N |
| ATOM | 221 | CA | GLY | A | 344 | 8.584 | −8.807 | 37.364 | 1.00 | 62.59 A | C |
| ATOM | 222 | C | GLY | A | 344 | 7.317 | −8.313 | 36.685 | 1.00 | 60.82 A | C |
| ATOM | 223 | O | GLY | A | 344 | 6.876 | −8.894 | 35.696 | 1.00 | 60.59 A | O |
| ATOM | 224 | N | LEU | A | 345 | 6.711 | −7.255 | 37.213 | 1.00 | 59.10 A | N |
| ATOM | 225 | CA | LEU | A | 345 | 5.509 | −6.693 | 36.592 | 1.00 | 56.93 A | C |
| ATOM | 226 | C | LEU | A | 345 | 5.914 | −5.854 | 35.383 | 1.00 | 55.60 A | C |
| ATOM | 227 | O | LEU | A | 345 | 5.354 | −5.999 | 34.293 | 1.00 | 55.42 A | O |
| ATOM | 228 | CB | LEU | A | 345 | 4.743 | −5.810 | 37.577 | 1.00 | 56.72 A | C |
| ATOM | 229 | CG | LEU | A | 345 | 3.922 | −6.523 | 38.652 | 1.00 | 56.71 A | C |
| ATOM | 230 | CD1 | LEU | A | 345 | 3.157 | −5.484 | 39.458 | 1.00 | 56.72 A | C |
| ATOM | 231 | CD2 | LEU | A | 345 | 2.950 | −7.517 | 38.008 | 1.00 | 56.89 A | C |
| ATOM | 232 | N | LEU | A | 346 | 6.906 | −4.989 | 35.587 | 1.00 | 54.11 A | N |
| ATOM | 233 | CA | LEU | A | 346 | 7.408 | −4.108 | 34.540 | 1.00 | 52.76 A | C |
| ATOM | 234 | C | LEU | A | 346 | 7.994 | −4.848 | 33.344 | 1.00 | 52.03 A | C |
| ATOM | 235 | O | LEU | A | 346 | 7.768 | −4.457 | 32.200 | 1.00 | 51.64 A | O |
| ATOM | 236 | CB | LEU | A | 346 | 8.471 | −3.170 | 35.108 | 1.00 | 52.20 A | C |
| ATOM | 237 | CG | LEU | A | 346 | 8.051 | −2.276 | 36.267 | 1.00 | 51.43 A | C |
| ATOM | 238 | CD1 | LEU | A | 346 | 9.189 | −1.341 | 36.600 | 1.00 | 51.78 A | C |
| ATOM | 239 | CD2 | LEU | A | 346 | 6.813 | −1.488 | 35.896 | 1.00 | 51.39 A | C |
| ATOM | 240 | N | THR | A | 347 | 8.753 | −5.906 | 33.607 | 1.00 | 51.51 A | N |
| ATOM | 241 | CA | THR | A | 347 | 9.379 | −6.659 | 32.530 | 1.00 | 50.97 A | C |
| ATOM | 242 | C | THR | A | 347 | 8.322 | −7.439 | 31.765 | 1.00 | 50.92 A | C |
| ATOM | 243 | O | THR | A | 347 | 8.414 | −7.584 | 30.538 | 1.00 | 50.72 A | O |
| ATOM | 244 | CB | THR | A | 347 | 10.503 | −7.583 | 33.072 | 1.00 | 50.27 A | C |
| ATOM | 245 | OG1 | THR | A | 347 | 10.990 | −8.423 | 32.023 | 1.00 | 50.23 A | O |
| ATOM | 246 | CG2 | THR | A | 347 | 10.004 | −8.421 | 34.212 | 1.00 | 50.69 A | C |
| ATOM | 247 | N | ASN | A | 348 | 7.314 | −7.933 | 32.486 | 1.00 | 50.58 A | N |
| ATOM | 248 | CA | ASN | A | 348 | 6.211 | −8.651 | 31.850 | 1.00 | 49.98 A | C |
| ATOM | 249 | C | ASN | A | 348 | 5.454 | −7.611 | 31.015 | 1.00 | 49.71 A | C |
| ATOM | 250 | O | ASN | A | 348 | 4.985 | −7.906 | 29.905 | 1.00 | 49.43 A | O |
| ATOM | 251 | CB | ASN | A | 348 | 5.283 | −9.274 | 32.913 | 1.00 | 50.02 A | C |
| ATOM | 252 | CG | ASN | A | 348 | 3.849 | −9.508 | 32.402 | 1.00 | 50.37 A | C |
| ATOM | 253 | OD1 | ASN | A | 348 | 2.925 | −8.743 | 32.717 | 1.00 | 50.71 A | O |
| ATOM | 254 | ND2 | ASN | A | 348 | 3.665 | −10.562 | 31.611 | 1.00 | 49.73 A | N |
| ATOM | 255 | N | LEU | A | 349 | 5.367 | −6.391 | 31.552 | 1.00 | 49.08 A | N |
| ATOM | 256 | CA | LEU | A | 349 | 4.680 | −5.277 | 30.892 | 1.00 | 48.40 A | C |
| ATOM | 257 | C | LEU | A | 349 | 5.436 | −4.801 | 29.656 | 1.00 | 47.66 A | C |
| ATOM | 258 | O | LEU | A | 349 | 4.838 | −4.548 | 28.613 | 1.00 | 47.42 A | O |
| ATOM | 259 | CB | LEU | A | 349 | 4.508 | −4.119 | 31.876 | 1.00 | 48.93 A | C |
| ATOM | 260 | CG | LEU | A | 349 | 3.837 | −2.837 | 31.383 | 1.00 | 49.40 A | C |
| ATOM | 261 | CD1 | LEU | A | 349 | 2.520 | −3.180 | 30.703 | 1.00 | 49.41 A | C |
| ATOM | 262 | CD2 | LEU | A | 349 | 3.611 | −1.891 | 32.566 | 1.00 | 49.58 A | C |
| ATOM | 263 | N | ALA | A | 350 | 6.754 | −4.697 | 29.778 | 1.00 | 46.98 A | N |
| ATOM | 264 | CA | ALA | A | 350 | 7.601 | −4.258 | 28.679 | 1.00 | 46.89 A | C |
| ATOM | 265 | C | ALA | A | 350 | 7.617 | −5.288 | 27.556 | 1.00 | 47.01 A | C |
| ATOM | 266 | O | ALA | A | 350 | 7.753 | −4.935 | 26.376 | 1.00 | 46.55 A | O |
| ATOM | 267 | CB | ALA | A | 350 | 9.017 | −4.013 | 29.178 | 1.00 | 46.08 A | C |
| ATOM | 268 | N | ASP | A | 351 | 7.494 | −6.560 | 27.925 | 1.00 | 47.31 A | N |
| ATOM | 269 | CA | ASP | A | 351 | 7.486 | −7.628 | 26.932 | 1.00 | 48.03 A | C |
| ATOM | 270 | C | ASP | A | 351 | 6.254 | −7.524 | 26.046 | 1.00 | 47.34 A | C |
| ATOM | 271 | O | ASP | A | 351 | 6.303 | −7.807 | 24.845 | 1.00 | 46.95 A | O |
| ATOM | 272 | CB | ASP | A | 351 | 7.517 | −9.007 | 27.603 | 1.00 | 50.08 A | C |
| ATOM | 273 | CG | ASP | A | 351 | 8.889 | −9.356 | 28.170 | 1.00 | 51.40 A | C |
| ATOM | 274 | OD1 | ASP | A | 351 | 9.908 | −8.847 | 27.639 | 1.00 | 52.57 A | O |
| ATOM | 275 | OD2 | ASP | A | 351 | 8.944 | −10.152 | 29.132 | 1.00 | 51.41 A | O |
| ATOM | 276 | N | ARG | A | 352 | 5.143 | −7.108 | 26.637 | 1.00 | 46.28 A | N |
| ATOM | 277 | CA | ARG | A | 352 | 3.923 | −6.979 | 25.869 | 1.00 | 44.98 A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 278 | C | ARG | A | 352 | 3.951 | −5.718 | 25.024 | 1.00 | 44.60 | A | C |
| ATOM | 279 | O | ARG | A | 352 | 3.522 | −5.743 | 23.872 | 1.00 | 44.53 | A | O |
| ATOM | 280 | CB | ARG | A | 352 | 2.707 | −7.033 | 26.797 | 1.00 | 43.75 | A | C |
| ATOM | 281 | CG | ARG | A | 352 | 2.379 | −8.470 | 27.218 | 1.00 | 42.75 | A | C |
| ATOM | 282 | CD | ARG | A | 352 | 1.216 | −8.555 | 28.172 | 1.00 | 41.21 | A | C |
| ATOM | 283 | NE | ARG | A | 352 | 1.504 | −7.910 | 29.448 | 1.00 | 40.47 | A | N |
| ATOM | 284 | CZ | ARG | A | 352 | 0.717 | −6.992 | 30.006 | 1.00 | 40.12 | A | C |
| ATOM | 285 | NH1 | ARG | A | 352 | 1.027 | −6.457 | 31.183 | 1.00 | 38.50 | A | N |
| ATOM | 286 | NH2 | ARG | A | 352 | −0.388 | −6.614 | 29.377 | 1.00 | 39.65 | A | N |
| ATOM | 287 | N | GLU | A | 353 | 4.466 | −4.624 | 25.583 | 1.00 | 44.42 | A | N |
| ATOM | 288 | CA | GLU | A | 353 | 4.571 | −3.376 | 24.827 | 1.00 | 44.30 | A | C |
| ATOM | 289 | C | GLU | A | 353 | 5.494 | −3.580 | 23.644 | 1.00 | 44.40 | A | C |
| ATOM | 290 | O | GLU | A | 353 | 5.395 | −2.886 | 22.631 | 1.00 | 44.17 | A | O |
| ATOM | 291 | CB | GLU | A | 353 | 5.154 | −2.257 | 25.676 | 1.00 | 44.17 | A | C |
| ATOM | 292 | CG | GLU | A | 353 | 4.167 | −1.593 | 26.585 | 1.00 | 45.22 | A | C |
| ATOM | 293 | CD | GLU | A | 353 | 4.712 | −0.313 | 27.181 | 1.00 | 45.11 | A | C |
| ATOM | 294 | OE1 | GLU | A | 353 | 5.759 | −0.361 | 27.848 | 1.00 | 44.94 | A | O |
| ATOM | 295 | OE2 | GLU | A | 353 | 4.087 | 0.742 | 26.980 | 1.00 | 46.78 | A | O |
| ATOM | 296 | N | LEU | A | 354 | 6.395 | −4.549 | 23.785 | 1.00 | 44.76 | A | N |
| ATOM | 297 | CA | LEU | A | 354 | 7.379 | −4.856 | 22.754 | 1.00 | 44.53 | A | C |
| ATOM | 298 | C | LEU | A | 354 | 6.794 | −5.489 | 21.492 | 1.00 | 44.09 | A | C |
| ATOM | 299 | O | LEU | A | 354 | 7.331 | −5.301 | 20.394 | 1.00 | 44.37 | A | O |
| ATOM | 300 | CB | LEU | A | 354 | 8.466 | −5.753 | 23.349 | 1.00 | 44.93 | A | C |
| ATOM | 301 | CG | LEU | A | 354 | 9.931 | −5.411 | 23.012 | 1.00 | 46.22 | A | C |
| ATOM | 302 | CD1 | LEU | A | 354 | 10.084 | −3.981 | 22.468 | 1.00 | 45.39 | A | C |
| ATOM | 303 | CD2 | LEU | A | 354 | 10.766 | −5.589 | 24.282 | 1.00 | 46.04 | A | C |
| ATOM | 304 | N | VAL | A | 355 | 5.700 | −6.227 | 21.653 | 1.00 | 43.36 | A | N |
| ATOM | 305 | CA | VAL | A | 355 | 5.038 | −6.881 | 20.537 | 1.00 | 42.84 | A | C |
| ATOM | 306 | C | VAL | A | 355 | 4.362 | −5.828 | 19.635 | 1.00 | 43.56 | A | C |
| ATOM | 307 | O | VAL | A | 355 | 4.511 | −5.862 | 18.405 | 1.00 | 41.99 | A | O |
| ATOM | 308 | CB | VAL | A | 355 | 3.987 | −7.907 | 21.064 | 1.00 | 42.36 | A | C |
| ATOM | 309 | CG1 | VAL | A | 355 | 3.292 | −8.622 | 19.905 | 1.00 | 41.95 | A | C |
| ATOM | 310 | CG2 | VAL | A | 355 | 4.671 | −8.925 | 21.963 | 1.00 | 41.74 | A | C |
| ATOM | 311 | N | HIS | A | 356 | 3.647 | −4.882 | 20.254 | 1.00 | 44.49 | A | N |
| ATOM | 312 | CA | HIS | A | 356 | 2.942 | −3.822 | 19.525 | 1.00 | 46.19 | A | C |
| ATOM | 313 | C | HIS | A | 356 | 3.911 | −2.810 | 18.922 | 1.00 | 46.30 | A | C |
| ATOM | 314 | O | HIS | A | 356 | 3.614 | −2.161 | 17.911 | 1.00 | 46.11 | A | O |
| ATOM | 315 | CB | HIS | A | 356 | 1.937 | −3.120 | 20.449 | 1.00 | 48.12 | A | C |
| ATOM | 316 | CG | HIS | A | 356 | 0.838 | −4.020 | 20.933 | 1.00 | 51.22 | A | C |
| ATOM | 317 | ND1 | HIS | A | 356 | −0.161 | −3.594 | 21.782 | 1.00 | 52.77 | A | N |
| ATOM | 318 | CD2 | HIS | A | 356 | 0.600 | −5.337 | 20.710 | 1.00 | 52.43 | A | C |
| ATOM | 319 | CE1 | HIS | A | 356 | −0.962 | −4.608 | 22.066 | 1.00 | 53.11 | A | C |
| ATOM | 320 | NE2 | HIS | A | 356 | −0.521 | −5.678 | 21.428 | 1.00 | 53.11 | A | N |
| ATOM | 321 | N | MET | A | 357 | 5.078 | −2.692 | 19.545 | 1.00 | 46.64 | A | N |
| ATOM | 322 | CA | MET | A | 357 | 6.121 | −1.792 | 19.072 | 1.00 | 46.68 | A | C |
| ATOM | 323 | C | MET | A | 357 | 6.581 | −2.249 | 17.680 | 1.00 | 46.97 | A | C |
| ATOM | 324 | O | MET | A | 357 | 6.746 | −1.430 | 16.761 | 1.00 | 46.70 | A | O |
| ATOM | 325 | CB | MET | A | 357 | 7.310 | −1.817 | 20.036 | 1.00 | 45.87 | A | C |
| ATOM | 326 | CG | MET | A | 357 | 8.452 | −0.912 | 19.620 | 1.00 | 44.78 | A | C |
| ATOM | 327 | SD | MET | A | 357 | 9.891 | −1.126 | 20.640 | 1.00 | 43.18 | A | S |
| ATOM | 328 | CE | MET | A | 357 | 9.330 | −0.333 | 22.207 | 1.00 | 43.20 | A | C |
| ATOM | 329 | N | ILE | A | 358 | 6.793 | −3.558 | 17.538 | 1.00 | 46.91 | A | N |
| ATOM | 330 | CA | ILE | A | 358 | 7.221 | −4.112 | 16.264 | 1.00 | 47.11 | A | C |
| ATOM | 331 | C | ILE | A | 358 | 6.156 | −3.820 | 15.219 | 1.00 | 47.09 | A | C |
| ATOM | 332 | O | ILE | A | 358 | 6.478 | −3.507 | 14.072 | 1.00 | 47.29 | A | O |
| ATOM | 333 | CB | ILE | A | 358 | 7.427 | −5.635 | 16.336 | 1.00 | 47.53 | A | C |
| ATOM | 334 | CG1 | ILE | A | 358 | 8.370 | −5.981 | 17.496 | 1.00 | 47.10 | A | C |
| ATOM | 335 | CG2 | ILE | A | 358 | 7.978 | −6.129 | 14.989 | 1.00 | 48.33 | A | C |
| ATOM | 336 | CD1 | ILE | A | 358 | 8.783 | −7.427 | 17.554 | 1.00 | 47.02 | A | C |
| ATOM | 337 | N | ASN | A | 359 | 4.889 | −3.927 | 15.621 | 1.00 | 46.87 | A | N |
| ATOM | 338 | CA | ASN | A | 359 | 3.765 | −3.647 | 14.724 | 1.00 | 46.60 | A | C |
| ATOM | 339 | C | ASN | A | 359 | 3.733 | −2.189 | 14.304 | 1.00 | 45.42 | A | C |
| ATOM | 340 | O | ASN | A | 359 | 3.388 | −1.846 | 13.157 | 1.00 | 45.26 | A | O |
| ATOM | 341 | CB | ASN | A | 359 | 2.442 | −3.957 | 15.398 | 1.00 | 48.26 | A | C |
| ATOM | 342 | CG | ASN | A | 359 | 1.944 | −5.316 | 15.062 | 1.00 | 50.04 | A | C |
| ATOM | 343 | OD1 | ASN | A | 359 | 2.070 | −5.772 | 13.912 | 1.00 | 50.97 | A | O |
| ATOM | 344 | ND2 | ASN | A | 359 | 1.357 | −5.987 | 16.050 | 1.00 | 50.93 | A | N |
| ATOM | 345 | N | TRP | A | 360 | 4.044 | −1.332 | 15.268 | 1.00 | 43.19 | A | N |
| ATOM | 346 | CA | TRP | A | 360 | 4.092 | 0.090 | 15.030 | 1.00 | 40.77 | A | C |
| ATOM | 347 | C | TRP | A | 360 | 5.224 | 0.361 | 14.022 | 1.00 | 41.33 | A | C |
| ATOM | 348 | O | TRP | A | 360 | 5.039 | 1.101 | 13.049 | 1.00 | 41.40 | A | O |
| ATOM | 349 | CB | TRP | A | 360 | 4.351 | 0.789 | 16.354 | 1.00 | 36.96 | A | C |
| ATOM | 350 | CG | TRP | A | 360 | 4.780 | 2.183 | 16.193 | 1.00 | 33.14 | A | C |
| ATOM | 351 | CD1 | TRP | A | 360 | 3.985 | 3.271 | 16.000 | 1.00 | 31.03 | A | C |
| ATOM | 352 | CD2 | TRP | A | 360 | 6.120 | 2.660 | 16.230 | 1.00 | 30.92 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 353 | NE1 | TRP | A | 360 | 4.745 | 4.395 | 15.912 | 1.00 | 29.83 | A | N |
| ATOM | 354 | CE2 | TRP | A | 360 | 6.065 | 4.056 | 16.038 | 1.00 | 30.03 | A | C |
| ATOM | 355 | CE3 | TRP | A | 360 | 7.369 | 2.042 | 16.387 | 1.00 | 30.11 | A | C |
| ATOM | 356 | CZ2 | TRP | A | 360 | 7.216 | 4.863 | 16.028 | 1.00 | 28.69 | A | C |
| ATOM | 357 | CZ3 | TRP | A | 360 | 8.528 | 2.851 | 16.377 | 1.00 | 29.32 | A | C |
| ATOM | 358 | CH2 | TRP | A | 360 | 8.434 | 4.242 | 16.187 | 1.00 | 28.21 | A | C |
| ATOM | 359 | N | ALA | A | 361 | 6.378 | −0.273 | 14.242 | 1.00 | 41.58 | A | N |
| ATOM | 360 | CA | ALA | A | 361 | 7.546 | −0.104 | 13.373 | 1.00 | 42.04 | A | C |
| ATOM | 361 | C | ALA | A | 361 | 7.266 | −0.351 | 11.888 | 1.00 | 42.40 | A | C |
| ATOM | 362 | O | ALA | A | 361 | 7.659 | 0.458 | 11.036 | 1.00 | 42.25 | A | O |
| ATOM | 363 | CB | ALA | A | 361 | 8.679 | −1.010 | 13.836 | 1.00 | 41.54 | A | C |
| ATOM | 364 | N | LYS | A | 362 | 6.596 | −1.465 | 11.580 | 1.00 | 42.78 | A | N |
| ATOM | 365 | CA | LYS | A | 362 | 6.267 | −1.819 | 10.187 | 1.00 | 42.97 | A | C |
| ATOM | 366 | C | LYS | A | 362 | 5.474 | −0.701 | 9.530 | 1.00 | 42.95 | A | C |
| ATOM | 367 | O | LYS | A | 362 | 5.608 | −0.435 | 8.327 | 1.00 | 43.31 | A | O |
| ATOM | 368 | CB | LYS | A | 362 | 5.425 | −3.104 | 10.117 | 1.00 | 42.54 | A | C |
| ATOM | 369 | CG | LYS | A | 362 | 6.058 | −4.342 | 10.703 | 1.00 | 43.05 | A | C |
| ATOM | 370 | CD | LYS | A | 362 | 5.149 | −5.544 | 10.452 | 1.00 | 44.03 | A | C |
| ATOM | 371 | CE | LYS | A | 362 | 5.380 | −6.676 | 11.453 | 1.00 | 43.58 | A | C |
| ATOM | 372 | NZ | LYS | A | 362 | 4.289 | −7.693 | 11.414 | 1.00 | 44.49 | A | N |
| ATOM | 373 | N | ARG | A | 363 | 4.660 | −0.043 | 10.346 | 0.50 | 42.36 | A | N |
| ATOM | 374 | CA | ARG | A | 363 | 3.810 | 1.028 | 9.885 | 0.50 | 41.80 | A | C |
| ATOM | 375 | C | ARG | A | 363 | 4.495 | 2.389 | 9.903 | 0.50 | 42.42 | A | C |
| ATOM | 376 | O | ARG | A | 363 | 3.862 | 3.410 | 9.646 | 0.50 | 41.76 | A | O |
| ATOM | 377 | CB | ARG | A | 363 | 2.525 | 1.011 | 10.710 | 0.50 | 40.68 | A | C |
| ATOM | 378 | CG | ARG | A | 363 | 1.866 | −0.380 | 10.680 | 0.50 | 39.60 | A | C |
| ATOM | 379 | CD | ARG | A | 363 | 0.500 | −0.368 | 11.370 | 0.50 | 39.03 | A | C |
| ATOM | 380 | NE | ARG | A | 363 | −0.247 | 0.785 | 10.885 | 0.50 | 37.78 | A | N |
| ATOM | 381 | CZ | ARG | A | 363 | −1.525 | 1.042 | 11.155 | 0.50 | 37.59 | A | C |
| ATOM | 382 | NH1 | ARG | A | 363 | −2.242 | 0.219 | 11.920 | 0.50 | 37.28 | A | N |
| ATOM | 383 | NH2 | ARG | A | 363 | −2.091 | 2.142 | 10.669 | 0.50 | 37.30 | A | N |
| ATOM | 384 | N | VAL | A | 364 | 5.797 | 2.408 | 10.182 | 1.00 | 43.49 | A | N |
| ATOM | 385 | CA | VAL | A | 364 | 6.525 | 3.679 | 10.169 | 1.00 | 45.35 | A | C |
| ATOM | 386 | C | VAL | A | 364 | 6.902 | 3.979 | 8.719 | 1.00 | 47.06 | A | C |
| ATOM | 387 | O | VAL | A | 364 | 7.658 | 3.225 | 8.102 | 1.00 | 46.97 | A | O |
| ATOM | 388 | CB | VAL | A | 364 | 7.834 | 3.645 | 11.010 | 1.00 | 44.81 | A | C |
| ATOM | 389 | CG1 | VAL | A | 364 | 8.442 | 5.044 | 11.095 | 1.00 | 43.29 | A | C |
| ATOM | 390 | CG2 | VAL | A | 364 | 7.525 | 3.139 | 12.389 | 1.00 | 45.23 | A | C |
| ATOM | 391 | N | PRO | A | 365 | 6.389 | 5.088 | 8.165 | 1.00 | 48.57 | A | N |
| ATOM | 392 | CA | PRO | A | 365 | 6.664 | 5.493 | 6.785 | 1.00 | 50.04 | A | C |
| ATOM | 393 | C | PRO | A | 365 | 8.089 | 5.202 | 6.350 | 1.00 | 52.03 | A | C |
| ATOM | 394 | O | PRO | A | 365 | 9.041 | 5.770 | 6.882 | 1.00 | 51.95 | A | O |
| ATOM | 395 | CB | PRO | A | 365 | 6.353 | 6.986 | 6.797 | 1.00 | 49.68 | A | C |
| ATOM | 396 | CG | PRO | A | 365 | 5.191 | 7.067 | 7.755 | 1.00 | 49.04 | A | C |
| ATOM | 397 | CD | PRO | A | 365 | 5.606 | 6.116 | 8.878 | 1.00 | 48.81 | A | C |
| ATOM | 398 | N | GLY | A | 366 | 8.212 | 4.306 | 5.377 | 1.00 | 54.38 | A | N |
| ATOM | 399 | CA | GLY | A | 366 | 9.509 | 3.935 | 4.850 | 1.00 | 56.98 | A | C |
| ATOM | 400 | C | GLY | A | 366 | 10.219 | 2.822 | 5.609 | 1.00 | 58.61 | A | C |
| ATOM | 401 | O | GLY | A | 366 | 11.293 | 2.386 | 5.202 | 1.00 | 58.44 | A | O |
| ATOM | 402 | N | PHE | A | 367 | 9.645 | 2.336 | 6.702 | 1.00 | 60.75 | A | N |
| ATOM | 403 | CA | PHE | A | 367 | 10.330 | 1.302 | 7.458 | 1.00 | 63.25 | A | C |
| ATOM | 404 | C | PHE | A | 367 | 10.434 | −0.004 | 6.687 | 1.00 | 65.14 | A | C |
| ATOM | 405 | O | PHE | A | 367 | 11.517 | −0.358 | 6.237 | 1.00 | 65.59 | A | O |
| ATOM | 406 | CB | PHE | A | 367 | 9.653 | 1.054 | 8.801 | 1.00 | 63.02 | A | C |
| ATOM | 407 | CG | PHE | A | 367 | 10.548 | 0.361 | 9.790 | 1.00 | 62.92 | A | C |
| ATOM | 408 | CD1 | PHE | A | 367 | 11.627 | 1.030 | 10.348 | 1.00 | 63.16 | A | C |
| ATOM | 409 | CD2 | PHE | A | 367 | 10.324 | −0.961 | 10.160 | 1.00 | 62.98 | A | C |
| ATOM | 410 | CE1 | PHE | A | 367 | 12.476 | 0.392 | 11.261 | 1.00 | 63.25 | A | C |
| ATOM | 411 | CE2 | PHE | A | 367 | 11.165 | −1.618 | 11.074 | 1.00 | 62.87 | A | C |
| ATOM | 412 | CZ | PHE | A | 367 | 12.240 | −0.935 | 11.629 | 1.00 | 63.01 | A | C |
| ATOM | 413 | N | VAL | A | 368 | 9.316 | −0.714 | 6.530 | 1.00 | 67.37 | A | N |
| ATOM | 414 | CA | VAL | A | 368 | 9.299 | −2.000 | 5.810 | 1.00 | 69.31 | A | C |
| ATOM | 415 | C | VAL | A | 368 | 10.259 | −2.136 | 4.625 | 1.00 | 70.84 | A | C |
| ATOM | 416 | O | VAL | A | 368 | 10.965 | −3.141 | 4.511 | 1.00 | 71.04 | A | O |
| ATOM | 417 | CB | VAL | A | 368 | 7.898 | −2.350 | 5.285 | 1.00 | 69.16 | A | C |
| ATOM | 418 | CG1 | VAL | A | 368 | 7.113 | −3.085 | 6.360 | 1.00 | 69.26 | A | C |
| ATOM | 419 | CG2 | VAL | A | 368 | 7.180 | −1.082 | 4.849 | 1.00 | 69.03 | A | C |
| ATOM | 420 | N | ASP | A | 369 | 10.272 | −1.162 | 3.720 | 1.00 | 72.27 | A | N |
| ATOM | 421 | CA | ASP | A | 369 | 11.012 | −1.267 | 2.466 | 1.00 | 73.58 | A | C |
| ATOM | 422 | C | ASP | A | 369 | 12.504 | −1.099 | 2.715 | 1.00 | 74.57 | A | C |
| ATOM | 423 | O | ASP | A | 369 | 13.319 | −0.969 | 1.808 | 1.00 | 74.93 | A | O |
| ATOM | 424 | CB | ASP | A | 369 | 10.516 | −0.190 | 1.502 | 1.00 | 73.25 | A | C |
| ATOM | 425 | CG | ASP | A | 369 | 10.007 | 1.007 | 2.288 | 1.00 | 73.03 | A | C |
| ATOM | 426 | OD1 | ASP | A | 369 | 9.016 | 0.844 | 2.998 | 1.00 | 73.34 | A | O |
| ATOM | 427 | OD2 | ASP | A | 369 | 10.608 | 2.078 | 2.191 | 1.00 | 71.77 | A | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 428 | N | LEU | A | 370 | 12.838 | −1.053 | 4.014 | 1.00 | 75.43 | A | N |
| ATOM | 429 | CA | LEU | A | 370 | 14.237 | −1.056 | 4.399 | 1.00 | 76.56 | A | C |
| ATOM | 430 | C | LEU | A | 370 | 14.820 | −2.458 | 4.270 | 1.00 | 77.12 | A | C |
| ATOM | 431 | O | LEU | A | 370 | 14.115 | −3.443 | 4.101 | 1.00 | 76.90 | A | O |
| ATOM | 432 | CB | LEU | A | 370 | 14.333 | −0.589 | 5.850 | 1.00 | 76.70 | A | C |
| ATOM | 433 | CG | LEU | A | 370 | 15.264 | 0.612 | 6.015 | 1.00 | 76.71 | A | C |
| ATOM | 434 | CD1 | LEU | A | 370 | 14.940 | 1.737 | 5.029 | 1.00 | 76.38 | A | C |
| ATOM | 435 | CD2 | LEU | A | 370 | 15.203 | 1.234 | 7.409 | 1.00 | 76.89 | A | C |
| ATOM | 436 | N | THR | A | 371 | 16.159 | −2.520 | 4.310 | 1.00 | 77.97 | A | N |
| ATOM | 437 | CA | THR | A | 371 | 16.827 | −3.809 | 4.210 | 1.00 | 78.93 | A | C |
| ATOM | 438 | C | THR | A | 371 | 16.272 | −4.813 | 5.226 | 1.00 | 79.33 | A | C |
| ATOM | 439 | O | THR | A | 371 | 16.119 | −4.522 | 6.406 | 1.00 | 79.86 | A | O |
| ATOM | 440 | CB | THR | A | 371 | 18.316 | −3.574 | 4.451 | 1.00 | 79.10 | A | C |
| ATOM | 441 | OG1 | THR | A | 371 | 18.682 | −2.328 | 3.858 | 1.00 | 78.90 | A | O |
| ATOM | 442 | CG2 | THR | A | 371 | 19.137 | −4.688 | 3.796 | 1.00 | 79.43 | A | C |
| ATOM | 443 | N | LEU | A | 372 | 15.478 | −5.892 | 5.346 | 1.00 | 79.44 | A | N |
| ATOM | 444 | CA | LEU | A | 372 | 14.802 | −6.539 | 6.466 | 1.00 | 79.79 | A | C |
| ATOM | 445 | C | LEU | A | 372 | 15.732 | −6.722 | 7.668 | 1.00 | 80.25 | A | C |
| ATOM | 446 | O | LEU | A | 372 | 15.389 | −6.446 | 8.810 | 1.00 | 80.80 | A | O |
| ATOM | 447 | CB | LEU | A | 372 | 14.271 | −7.893 | 5.995 | 1.00 | 79.36 | A | C |
| ATOM | 448 | CG | LEU | A | 372 | 13.376 | −7.774 | 4.760 | 1.00 | 20.00 | A | C |
| ATOM | 449 | CD1 | LEU | A | 372 | 13.039 | −9.135 | 4.149 | 1.00 | 20.00 | A | C |
| ATOM | 450 | CD2 | LEU | A | 372 | 12.039 | −7.095 | 5.057 | 1.00 | 20.00 | A | C |
| ATOM | 451 | N | HIS | A | 373 | 16.939 | −7.242 | 7.380 | 1.00 | 80.16 | A | N |
| ATOM | 452 | CA | HIS | A | 373 | 17.896 | −7.481 | 8.453 | 1.00 | 79.84 | A | C |
| ATOM | 453 | C | HIS | A | 373 | 18.154 | −6.210 | 9.266 | 1.00 | 79.22 | A | C |
| ATOM | 454 | O | HIS | A | 373 | 18.226 | −6.217 | 10.488 | 1.00 | 79.19 | A | O |
| ATOM | 455 | CB | HIS | A | 373 | 19.202 | −7.971 | 7.826 | 1.00 | 80.78 | A | C |
| ATOM | 456 | CG | HIS | A | 373 | 19.402 | −9.429 | 8.148 | 1.00 | 81.48 | A | C |
| ATOM | 457 | ND1 | HIS | A | 373 | 19.282 | −9.939 | 9.399 | 1.00 | 81.67 | A | N |
| ATOM | 458 | CD2 | HIS | A | 373 | 19.766 | −10.464 | 7.281 | 1.00 | 81.72 | A | C |
| ATOM | 459 | CE1 | HIS | A | 373 | 19.567 | −11.251 | 9.286 | 1.00 | 82.16 | A | C |
| ATOM | 460 | NE2 | HIS | A | 373 | 19.861 | −11.593 | 8.029 | 1.00 | 82.17 | A | N |
| ATOM | 461 | N | ASP | A | 374 | 18.333 | −5.095 | 8.533 | 1.00 | 78.32 | A | N |
| ATOM | 462 | CA | ASP | A | 374 | 18.602 | −3.824 | 9.197 | 1.00 | 77.56 | A | C |
| ATOM | 463 | C | ASP | A | 374 | 17.523 | −3.475 | 10.226 | 1.00 | 76.59 | A | C |
| ATOM | 464 | O | ASP | A | 374 | 17.795 | −3.002 | 11.321 | 1.00 | 76.74 | A | O |
| ATOM | 465 | CB | ASP | A | 374 | 18.672 | −2.733 | 8.128 | 1.00 | 78.56 | A | C |
| ATOM | 466 | CG | ASP | A | 374 | 19.609 | −3.176 | 7.013 | 1.00 | 79.99 | A | C |
| ATOM | 467 | OD1 | ASP | A | 374 | 20.416 | −4.073 | 7.263 | 1.00 | 80.20 | A | O |
| ATOM | 468 | OD2 | ASP | A | 374 | 19.525 | −2.626 | 5.918 | 1.00 | 80.64 | A | O |
| ATOM | 469 | N | GLN | A | 375 | 16.255 | −3.680 | 9.823 | 1.00 | 74.90 | A | N |
| ATOM | 470 | CA | GLN | A | 375 | 15.156 | −3.359 | 10.727 | 1.00 | 72.71 | A | C |
| ATOM | 471 | C | GLN | A | 375 | 15.308 | −4.076 | 12.072 | 1.00 | 71.29 | A | C |
| ATOM | 472 | O | GLN | A | 375 | 15.070 | −3.515 | 13.133 | 1.00 | 71.49 | A | O |
| ATOM | 473 | CB | GLN | A | 375 | 13.848 | −3.786 | 10.059 | 1.00 | 73.19 | A | C |
| ATOM | 474 | CG | GLN | A | 375 | 13.481 | −2.900 | 8.869 | 1.00 | 73.24 | A | C |
| ATOM | 475 | CD | GLN | A | 375 | 12.234 | −3.439 | 8.208 | 1.00 | 73.44 | A | C |
| ATOM | 476 | OE1 | GLN | A | 375 | 11.761 | −2.960 | 7.190 | 1.00 | 72.70 | A | O |
| ATOM | 477 | NE2 | GLN | A | 375 | 11.688 | −4.490 | 8.853 | 1.00 | 72.86 | A | N |
| ATOM | 478 | N | ALA | A | 376 | 15.677 | −5.369 | 12.041 | 1.00 | 69.44 | A | N |
| ATOM | 479 | CA | ALA | A | 376 | 15.930 | −6.062 | 13.297 | 1.00 | 67.92 | A | C |
| ATOM | 480 | C | ALA | A | 376 | 17.024 | −5.354 | 14.099 | 1.00 | 67.05 | A | C |
| ATOM | 481 | O | ALA | A | 376 | 17.044 | −5.365 | 15.323 | 1.00 | 66.82 | A | O |
| ATOM | 482 | CB | ALA | A | 376 | 16.365 | −7.492 | 12.973 | 1.00 | 67.39 | A | C |
| ATOM | 483 | N | HIS | A | 377 | 17.925 | −4.734 | 13.348 | 1.00 | 65.80 | A | N |
| ATOM | 484 | CA | HIS | A | 377 | 19.030 | −3.938 | 13.868 | 1.00 | 64.01 | A | C |
| ATOM | 485 | C | HIS | A | 377 | 18.534 | −2.655 | 14.540 | 1.00 | 61.53 | A | C |
| ATOM | 486 | O | HIS | A | 377 | 18.781 | −2.390 | 15.709 | 1.00 | 61.59 | A | O |
| ATOM | 487 | CB | HIS | A | 377 | 19.958 | −3.591 | 12.703 | 1.00 | 66.04 | A | C |
| ATOM | 488 | CG | HIS | A | 377 | 21.100 | −2.744 | 13.203 | 1.00 | 67.77 | A | C |
| ATOM | 489 | ND1 | HIS | A | 377 | 22.074 | −3.216 | 14.021 | 1.00 | 68.47 | A | N |
| ATOM | 490 | CD2 | HIS | A | 377 | 21.362 | −1.397 | 12.933 | 1.00 | 68.06 | A | C |
| ATOM | 491 | CE1 | HIS | A | 377 | 22.904 | −2.176 | 14.233 | 1.00 | 68.86 | A | C |
| ATOM | 492 | NE2 | HIS | A | 377 | 22.502 | −1.075 | 13.595 | 1.00 | 68.70 | A | N |
| ATOM | 493 | N | LEU | A | 378 | 17.842 | −1.824 | 13.738 | 1.00 | 58.45 | A | N |
| ATOM | 494 | CA | LEU | A | 378 | 17.322 | −0.572 | 14.276 | 1.00 | 55.96 | A | C |
| ATOM | 495 | C | LEU | A | 378 | 16.544 | −0.795 | 15.574 | 1.00 | 54.80 | A | C |
| ATOM | 496 | O | LEU | A | 378 | 16.767 | −0.149 | 16.590 | 1.00 | 54.43 | A | O |
| ATOM | 497 | CB | LEU | A | 378 | 16.407 | 0.055 | 13.223 | 1.00 | 54.66 | A | C |
| ATOM | 498 | CG | LEU | A | 378 | 17.166 | 0.957 | 12.248 | 1.00 | 54.11 | A | C |
| ATOM | 499 | CD1 | LEU | A | 378 | 16.230 | 1.704 | 11.296 | 1.00 | 53.65 | A | C |
| ATOM | 500 | CD2 | LEU | A | 378 | 18.000 | 2.026 | 12.955 | 1.00 | 53.67 | A | C |
| ATOM | 501 | N | LEU | A | 379 | 15.573 | −1.724 | 15.503 | 1.00 | 52.92 | A | N |
| ATOM | 502 | CA | LEU | A | 379 | 14.757 | −2.005 | 16.678 | 1.00 | 50.53 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 503 | C | LEU | A | 379 | 15.607 | −2.490 | 17.855 | 1.00 | 49.41 | A | C |
| ATOM | 504 | O | LEU | A | 379 | 15.346 | −2.195 | 19.015 | 1.00 | 48.58 | A | O |
| ATOM | 505 | CB | LEU | A | 379 | 13.731 | −3.075 | 16.301 | 1.00 | 49.70 | A | C |
| ATOM | 506 | CG | LEU | A | 379 | 12.535 | −2.497 | 15.539 | 1.00 | 48.67 | A | C |
| ATOM | 507 | CD1 | LEU | A | 379 | 11.603 | −3.585 | 15.003 | 1.00 | 48.26 | A | C |
| ATOM | 508 | CD2 | LEU | A | 379 | 11.670 | −1.579 | 16.403 | 1.00 | 48.12 | A | C |
| ATOM | 509 | N | GLU | A | 380 | 16.634 | −3.294 | 17.524 | 1.00 | 48.90 | A | N |
| ATOM | 510 | CA | GLU | A | 380 | 17.503 | −3.820 | 18.570 | 1.00 | 48.70 | A | C |
| ATOM | 511 | C | GLU | A | 380 | 18.110 | −2.699 | 19.417 | 1.00 | 46.65 | A | C |
| ATOM | 512 | O | GLU | A | 380 | 18.199 | −2.784 | 20.635 | 1.00 | 47.04 | A | O |
| ATOM | 513 | CB | GLU | A | 380 | 18.615 | −4.632 | 17.905 | 1.00 | 50.99 | A | C |
| ATOM | 514 | CG | GLU | A | 380 | 19.357 | −5.528 | 18.897 | 1.00 | 54.85 | A | C |
| ATOM | 515 | CD | GLU | A | 380 | 19.315 | −6.958 | 18.409 | 1.00 | 56.77 | A | C |
| ATOM | 516 | OE1 | GLU | A | 380 | 19.907 | −7.242 | 17.377 | 1.00 | 57.31 | A | O |
| ATOM | 517 | OE2 | GLU | A | 380 | 18.686 | −7.782 | 19.071 | 1.00 | 58.25 | A | O |
| ATOM | 518 | N | CYS | A | 381 | 18.534 | −1.632 | 18.730 | 1.00 | 43.45 | A | N |
| ATOM | 519 | CA | CYS | A | 381 | 19.182 | −0.443 | 19.294 | 1.00 | 40.22 | A | C |
| ATOM | 520 | C | CYS | A | 381 | 18.231 | 0.593 | 19.926 | 1.00 | 37.40 | A | C |
| ATOM | 521 | O | CYS | A | 381 | 18.586 | 1.249 | 20.919 | 1.00 | 36.54 | A | O |
| ATOM | 522 | CB | CYS | A | 381 | 19.996 | 0.252 | 18.195 | 1.00 | 41.16 | A | C |
| ATOM | 523 | SG | CYS | A | 381 | 21.424 | −0.707 | 17.625 | 1.00 | 45.13 | A | S |
| ATOM | 524 | N | ALA | A | 382 | 17.028 | 0.740 | 19.363 | 1.00 | 33.71 | A | N |
| ATOM | 525 | CA | ALA | A | 382 | 16.073 | 1.721 | 19.877 | 1.00 | 29.88 | A | C |
| ATOM | 526 | C | ALA | A | 382 | 14.941 | 1.221 | 20.761 | 1.00 | 27.05 | A | C |
| ATOM | 527 | O | ALA | A | 382 | 14.192 | 2.035 | 21.318 | 1.00 | 25.77 | A | O |
| ATOM | 528 | CB | ALA | A | 382 | 15.489 | 2.523 | 18.713 | 1.00 | 29.85 | A | C |
| ATOM | 529 | N | TRP | A | 383 | 14.830 | −0.092 | 20.934 | 1.00 | 24.89 | A | N |
| ATOM | 530 | CA | TRP | A | 383 | 13.719 | −0.644 | 21.710 | 1.00 | 22.87 | A | C |
| ATOM | 531 | C | TRP | A | 383 | 13.545 | −0.091 | 23.120 | 1.00 | 21.57 | A | C |
| ATOM | 532 | O | TRP | A | 383 | 12.414 | 0.122 | 23.545 | 1.00 | 21.50 | A | O |
| ATOM | 533 | CB | TRP | A | 383 | 13.765 | −2.173 | 21.728 | 1.00 | 22.48 | A | C |
| ATOM | 534 | CG | TRP | A | 383 | 14.681 | −2.742 | 22.728 | 1.00 | 22.83 | A | C |
| ATOM | 535 | CD1 | TRP | A | 383 | 15.934 | −3.251 | 22.513 | 1.00 | 22.03 | A | C |
| ATOM | 536 | CD2 | TRP | A | 383 | 14.428 | −2.860 | 24.129 | 1.00 | 22.42 | A | C |
| ATOM | 537 | NE1 | TRP | A | 383 | 16.474 | −3.672 | 23.701 | 1.00 | 22.97 | A | N |
| ATOM | 538 | CE2 | TRP | A | 383 | 15.568 | −3.437 | 24.717 | 1.00 | 22.61 | A | C |
| ATOM | 539 | CE3 | TRP | A | 383 | 13.345 | −2.510 | 24.958 | 1.00 | 21.73 | A | C |
| ATOM | 540 | CZ2 | TRP | A | 383 | 15.658 | −3.699 | 26.092 | 1.00 | 22.41 | A | C |
| ATOM | 541 | CZ3 | TRP | A | 383 | 13.429 | −2.759 | 26.310 | 1.00 | 22.16 | A | C |
| ATOM | 542 | CH2 | TRP | A | 383 | 14.583 | −3.344 | 26.870 | 1.00 | 22.08 | A | C |
| ATOM | 543 | N | LEU | A | 384 | 14.624 | 0.152 | 23.856 | 1.00 | 20.40 | A | N |
| ATOM | 544 | CA | LEU | A | 384 | 14.435 | 0.737 | 25.185 | 1.00 | 19.80 | A | C |
| ATOM | 545 | C | LEU | A | 384 | 14.124 | 2.270 | 25.136 | 1.00 | 19.85 | A | C |
| ATOM | 546 | O | LEU | A | 384 | 13.376 | 2.765 | 25.986 | 1.00 | 18.60 | A | O |
| ATOM | 547 | CB | LEU | A | 384 | 15.653 | 0.480 | 26.087 | 1.00 | 18.28 | A | C |
| ATOM | 548 | CG | LEU | A | 384 | 15.434 | 0.907 | 27.553 | 1.00 | 16.31 | A | C |
| ATOM | 549 | CD1 | LEU | A | 384 | 14.377 | 0.029 | 28.192 | 1.00 | 14.44 | A | C |
| ATOM | 550 | CD2 | LEU | A | 384 | 16.733 | 0.813 | 28.332 | 1.00 | 14.68 | A | C |
| ATOM | 551 | N | GLU | A | 385 | 14.678 | 3.010 | 24.163 | 1.00 | 19.62 | A | N |
| ATOM | 552 | CA | GLU | A | 385 | 14.415 | 4.469 | 24.072 | 1.00 | 20.42 | A | C |
| ATOM | 553 | C | GLU | A | 385 | 12.946 | 4.642 | 23.770 | 1.00 | 20.57 | A | C |
| ATOM | 554 | O | GLU | A | 385 | 12.269 | 5.514 | 24.328 | 1.00 | 19.30 | A | O |
| ATOM | 555 | CB | GLU | A | 385 | 15.264 | 5.133 | 22.966 | 1.00 | 20.99 | A | C |
| ATOM | 556 | CG | GLU | A | 385 | 16.725 | 5.426 | 23.356 | 1.00 | 22.70 | A | C |
| ATOM | 557 | CD | GLU | A | 385 | 17.665 | 5.614 | 22.153 | 1.00 | 26.00 | A | C |
| ATOM | 558 | OE1 | GLU | A | 385 | 18.224 | 4.591 | 21.665 | 1.00 | 25.52 | A | O |
| ATOM | 559 | OE2 | GLU | A | 385 | 17.846 | 6.786 | 21.700 | 1.00 | 26.26 | A | O |
| ATOM | 560 | N | ILE | A | 386 | 12.451 | 3.760 | 22.897 | 1.00 | 21.97 | A | N |
| ATOM | 561 | CA | ILE | A | 386 | 11.040 | 3.749 | 22.482 | 1.00 | 21.59 | A | C |
| ATOM | 562 | C | ILE | A | 386 | 10.145 | 3.496 | 23.700 | 1.00 | 21.51 | A | C |
| ATOM | 563 | O | ILE | A | 386 | 9.249 | 4.298 | 24.008 | 1.00 | 20.97 | A | O |
| ATOM | 564 | CB | ILE | A | 386 | 10.775 | 2.638 | 21.412 | 1.00 | 21.07 | A | C |
| ATOM | 565 | CG1 | ILE | A | 386 | 11.737 | 2.797 | 20.230 | 1.00 | 22.11 | A | C |
| ATOM | 566 | CG2 | ILE | A | 386 | 9.360 | 2.719 | 20.898 | 1.00 | 20.16 | A | C |
| ATOM | 567 | CD1 | ILE | A | 386 | 11.637 | 4.136 | 19.513 | 1.00 | 22.59 | A | C |
| ATOM | 568 | N | LEU | A | 387 | 10.375 | 2.382 | 24.392 | 1.00 | 21.26 | A | N |
| ATOM | 569 | CA | LEU | A | 387 | 9.570 | 2.077 | 25.572 | 1.00 | 21.81 | A | C |
| ATOM | 570 | C | LEU | A | 387 | 9.578 | 3.246 | 26.562 | 1.00 | 21.32 | A | C |
| ATOM | 571 | O | LEU | A | 387 | 8.527 | 3.599 | 27.103 | 1.00 | 20.22 | A | O |
| ATOM | 572 | CB | LEU | A | 387 | 10.063 | 0.795 | 26.247 | 1.00 | 23.11 | A | C |
| ATOM | 573 | CG | LEU | A | 387 | 9.593 | −0.508 | 25.558 | 1.00 | 26.43 | A | C |
| ATOM | 574 | CD1 | LEU | A | 387 | 10.157 | −1.764 | 26.258 | 1.00 | 27.05 | A | C |
| ATOM | 575 | CD2 | LEU | A | 387 | 8.067 | −0.545 | 25.561 | 1.00 | 24.90 | A | C |
| ATOM | 576 | N | MET | A | 388 | 10.751 | 3.867 | 26.747 | 1.00 | 21.10 | A | N |
| ATOM | 577 | CA | MET | A | 388 | 10.930 | 4.999 | 27.673 | 1.00 | 21.80 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 578 | C | MET | A | 388 | 10.190 | 6.261 | 27.281 | 1.00 | 21.52 | A | C |
| ATOM | 579 | O | MET | A | 388 | 9.460 | 6.817 | 28.110 | 1.00 | 21.76 | A | O |
| ATOM | 580 | CB | MET | A | 388 | 12.416 | 5.312 | 27.878 | 1.00 | 21.78 | A | C |
| ATOM | 581 | CG | MET | A | 388 | 13.102 | 4.243 | 28.694 | 1.00 | 23.59 | A | C |
| ATOM | 582 | SD | MET | A | 388 | 14.890 | 4.326 | 28.849 | 1.00 | 26.78 | A | S |
| ATOM | 583 | CE | MET | A | 388 | 15.069 | 4.459 | 30.626 | 1.00 | 25.84 | A | C |
| ATOM | 584 | N | ILE | A | 389 | 10.366 | 6.722 | 26.040 | 1.00 | 20.92 | A | N |
| ATOM | 585 | CA | ILE | A | 389 | 9.653 | 7.914 | 25.606 | 1.00 | 20.78 | A | C |
| ATOM | 586 | C | ILE | A | 389 | 8.170 | 7.579 | 25.715 | 1.00 | 19.86 | A | C |
| ATOM | 587 | O | ILE | A | 389 | 7.340 | 8.427 | 26.091 | 1.00 | 18.87 | A | O |
| ATOM | 588 | CB | ILE | A | 389 | 10.051 | 8.338 | 24.160 | 1.00 | 20.41 | A | C |
| ATOM | 589 | CG1 | ILE | A | 389 | 9.379 | 9.661 | 23.806 | 1.00 | 20.52 | A | C |
| ATOM | 590 | CG2 | ILE | A | 389 | 9.685 | 7.261 | 23.150 | 1.00 | 20.04 | A | C |
| ATOM | 591 | CD1 | ILE | A | 389 | 10.064 | 10.383 | 22.650 | 1.00 | 20.19 | A | C |
| ATOM | 592 | N | GLY | A | 390 | 7.838 | 6.321 | 25.434 | 1.00 | 19.70 | A | N |
| ATOM | 593 | CA | GLY | A | 390 | 6.441 | 5.918 | 25.552 | 1.00 | 19.80 | A | C |
| ATOM | 594 | C | GLY | A | 390 | 6.012 | 6.171 | 26.986 | 1.00 | 19.54 | A | C |
| ATOM | 595 | O | GLY | A | 390 | 4.944 | 6.739 | 27.284 | 1.00 | 18.85 | A | O |
| ATOM | 596 | N | LEU | A | 391 | 6.869 | 5.742 | 27.898 | 1.00 | 20.11 | A | N |
| ATOM | 597 | CA | LEU | A | 391 | 6.603 | 5.940 | 29.312 | 1.00 | 21.45 | A | C |
| ATOM | 598 | C | LEU | A | 391 | 6.612 | 7.422 | 29.727 | 1.00 | 22.24 | A | C |
| ATOM | 599 | O | LEU | A | 391 | 5.751 | 7.829 | 30.512 | 1.00 | 21.67 | A | O |
| ATOM | 600 | CB | LEU | A | 391 | 7.609 | 5.176 | 30.171 | 1.00 | 21.65 | A | C |
| ATOM | 601 | CG | LEU | A | 391 | 7.254 | 5.358 | 31.647 | 1.00 | 20.94 | A | C |
| ATOM | 602 | CD1 | LEU | A | 391 | 5.875 | 4.769 | 31.890 | 1.00 | 20.63 | A | C |
| ATOM | 603 | CD2 | LEU | A | 391 | 8.329 | 4.734 | 32.532 | 1.00 | 20.53 | A | C |
| ATOM | 604 | N | VAL | A | 392 | 7.562 | 8.219 | 29.217 | 1.00 | 22.45 | A | N |
| ATOM | 605 | CA | VAL | A | 392 | 7.627 | 9.644 | 29.565 | 1.00 | 24.25 | A | C |
| ATOM | 606 | C | VAL | A | 392 | 6.441 | 10.419 | 28.986 | 1.00 | 26.41 | A | C |
| ATOM | 607 | O | VAL | A | 392 | 6.121 | 11.513 | 29.437 | 1.00 | 27.23 | A | O |
| ATOM | 608 | CB | VAL | A | 392 | 8.932 | 10.310 | 29.069 | 1.00 | 23.36 | A | C |
| ATOM | 609 | CG1 | VAL | A | 392 | 8.746 | 11.815 | 29.044 | 1.00 | 22.72 | A | C |
| ATOM | 610 | CG2 | VAL | A | 392 | 10.109 | 9.957 | 29.985 | 1.00 | 20.55 | A | C |
| ATOM | 611 | N | TRP | A | 393 | 5.791 | 9.839 | 27.981 | 1.00 | 29.14 | A | N |
| ATOM | 612 | CA | TRP | A | 393 | 4.639 | 10.456 | 27.343 | 1.00 | 30.66 | A | C |
| ATOM | 613 | C | TRP | A | 393 | 3.348 | 10.299 | 28.133 | 1.00 | 31.58 | A | C |
| ATOM | 614 | O | TRP | A | 393 | 2.623 | 11.275 | 28.327 | 1.00 | 32.47 | A | O |
| ATOM | 615 | CB | TRP | A | 393 | 4.439 | 9.899 | 25.928 | 1.00 | 32.00 | A | C |
| ATOM | 616 | CG | TRP | A | 393 | 3.166 | 10.389 | 25.285 | 1.00 | 32.65 | A | C |
| ATOM | 617 | CD1 | TRP | A | 393 | 2.048 | 9.650 | 25.009 | 1.00 | 33.42 | A | C |
| ATOM | 618 | CD2 | TRP | A | 393 | 2.858 | 11.739 | 24.904 | 1.00 | 33.17 | A | C |
| ATOM | 619 | NE1 | TRP | A | 393 | 1.060 | 10.460 | 24.484 | 1.00 | 33.75 | A | N |
| ATOM | 620 | CE2 | TRP | A | 393 | 1.534 | 11.746 | 24.409 | 1.00 | 33.21 | A | C |
| ATOM | 621 | CE3 | TRP | A | 393 | 3.574 | 12.947 | 24.936 | 1.00 | 33.59 | A | C |
| ATOM | 622 | CZ2 | TRP | A | 393 | 0.909 | 12.906 | 23.949 | 1.00 | 33.16 | A | C |
| ATOM | 623 | CZ3 | TRP | A | 393 | 2.955 | 14.100 | 24.483 | 1.00 | 33.83 | A | C |
| ATOM | 624 | CH2 | TRP | A | 393 | 1.635 | 14.071 | 23.995 | 1.00 | 34.03 | A | C |
| ATOM | 625 | N | ARG | A | 394 | 3.036 | 9.090 | 28.585 | 1.00 | 32.56 | A | N |
| ATOM | 626 | CA | ARG | A | 394 | 1.805 | 8.907 | 29.354 | 1.00 | 33.50 | A | C |
| ATOM | 627 | C | ARG | A | 394 | 1.924 | 9.432 | 30.779 | 1.00 | 34.12 | A | C |
| ATOM | 628 | O | ARG | A | 394 | 0.934 | 9.530 | 31.498 | 1.00 | 33.24 | A | O |
| ATOM | 629 | CB | ARG | A | 394 | 1.346 | 7.435 | 29.355 | 1.00 | 34.64 | A | C |
| ATOM | 630 | CG | ARG | A | 394 | 2.434 | 6.356 | 29.347 | 1.00 | 35.96 | A | C |
| ATOM | 631 | CD | ARG | A | 394 | 1.881 | 5.100 | 28.642 | 1.00 | 37.04 | A | C |
| ATOM | 632 | NE | ARG | A | 394 | 2.875 | 4.050 | 28.393 | 1.00 | 36.08 | A | N |
| ATOM | 633 | CZ | ARG | A | 394 | 3.463 | 3.366 | 29.358 | 1.00 | 36.40 | A | C |
| ATOM | 634 | NH1 | ARG | A | 394 | 3.162 | 3.635 | 30.620 | 1.00 | 36.92 | A | N |
| ATOM | 635 | NH2 | ARG | A | 394 | 4.319 | 2.401 | 29.068 | 1.00 | 36.76 | A | N |
| ATOM | 636 | N | SER | A | 395 | 3.133 | 9.810 | 31.172 | 1.00 | 35.68 | A | N |
| ATOM | 637 | CA | SER | A | 395 | 3.356 | 10.335 | 32.512 | 1.00 | 37.91 | A | C |
| ATOM | 638 | C | SER | A | 395 | 3.268 | 11.868 | 32.556 | 1.00 | 39.44 | A | C |
| ATOM | 639 | O | SER | A | 395 | 3.052 | 12.462 | 33.610 | 1.00 | 38.69 | A | O |
| ATOM | 640 | CB | SER | A | 395 | 4.716 | 9.850 | 33.023 | 1.00 | 37.28 | A | C |
| ATOM | 641 | OG | SER | A | 395 | 4.706 | 8.439 | 33.186 | 1.00 | 36.70 | A | O |
| ATOM | 642 | N | MET | A | 396 | 3.424 | 12.493 | 31.395 | 1.00 | 42.47 | A | N |
| ATOM | 643 | CA | MET | A | 396 | 3.377 | 13.948 | 31.263 | 1.00 | 45.86 | A | C |
| ATOM | 644 | C | MET | A | 396 | 2.292 | 14.632 | 32.103 | 1.00 | 47.76 | A | C |
| ATOM | 645 | O | MET | A | 396 | 2.512 | 15.706 | 32.654 | 1.00 | 47.69 | A | O |
| ATOM | 646 | CB | MET | A | 396 | 3.190 | 14.332 | 29.788 | 1.00 | 46.45 | A | C |
| ATOM | 647 | CG | MET | A | 396 | 4.388 | 15.030 | 29.166 | 1.00 | 47.75 | A | C |
| ATOM | 648 | SD | MET | A | 396 | 3.941 | 15.931 | 27.684 | 1.00 | 48.83 | A | S |
| ATOM | 649 | CE | MET | A | 396 | 2.879 | 17.183 | 28.405 | 1.00 | 48.78 | A | C |
| ATOM | 650 | N | GLU | A | 397 | 1.119 | 14.023 | 32.209 | 1.00 | 49.83 | A | N |
| ATOM | 651 | CA | GLU | A | 397 | 0.050 | 14.643 | 32.988 | 1.00 | 51.82 | A | C |
| ATOM | 652 | C | GLU | A | 397 | −0.098 | 14.152 | 34.433 | 1.00 | 51.66 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 653 | O | GLU | A | 397 | −1.136 | 14.369 | 35.056 | 1.00 | 51.57 | A | O |
| ATOM | 654 | CB | GLU | A | 397 | −1.287 | 14.503 | 32.254 | 1.00 | 53.71 | A | C |
| ATOM | 655 | CG | GLU | A | 397 | −1.292 | 15.206 | 30.904 | 1.00 | 57.70 | A | C |
| ATOM | 656 | CD | GLU | A | 397 | −0.795 | 16.646 | 31.005 | 1.00 | 59.75 | A | C |
| ATOM | 657 | OE1 | GLU | A | 397 | −1.336 | 17.388 | 31.857 | 1.00 | 61.62 | A | O |
| ATOM | 658 | OE2 | GLU | A | 397 | 0.123 | 17.037 | 30.238 | 1.00 | 59.98 | A | O |
| ATOM | 659 | N | HIS | A | 398 | 0.927 | 13.490 | 34.961 | 1.00 | 51.17 | A | N |
| ATOM | 660 | CA | HIS | A | 398 | 0.899 | 13.019 | 36.344 | 1.00 | 50.85 | A | C |
| ATOM | 661 | C | HIS | A | 398 | 2.199 | 13.460 | 36.994 | 1.00 | 50.32 | A | C |
| ATOM | 662 | O | HIS | A | 398 | 3.048 | 12.631 | 37.325 | 1.00 | 50.01 | A | O |
| ATOM | 663 | CB | HIS | A | 398 | 0.789 | 11.495 | 36.416 | 1.00 | 51.60 | A | C |
| ATOM | 664 | CG | HIS | A | 398 | −0.453 | 10.953 | 35.792 | 1.00 | 52.28 | A | C |
| ATOM | 665 | ND1 | HIS | A | 398 | −0.577 | 10.768 | 34.433 | 1.00 | 52.96 | A | N |
| ATOM | 666 | CD2 | HIS | A | 398 | −1.649 | 10.616 | 36.330 | 1.00 | 52.34 | A | C |
| ATOM | 667 | CE1 | HIS | A | 398 | −1.798 | 10.345 | 34.157 | 1.00 | 52.90 | A | C |
| ATOM | 668 | NE2 | HIS | A | 398 | −2.469 | 10.245 | 35.291 | 1.00 | 52.89 | A | N |
| ATOM | 669 | N | PRO | A | 399 | 2.368 | 14.779 | 37.192 | 1.00 | 49.84 | A | N |
| ATOM | 670 | CA | PRO | A | 399 | 3.622 | 15.280 | 37.752 | 1.00 | 49.06 | A | C |
| ATOM | 671 | C | PRO | A | 399 | 3.981 | 14.593 | 39.075 | 1.00 | 48.41 | A | C |
| ATOM | 672 | O | PRO | A | 399 | 3.164 | 14.430 | 39.972 | 1.00 | 48.58 | A | O |
| ATOM | 673 | CB | PRO | A | 399 | 3.479 | 16.787 | 37.970 | 1.00 | 49.40 | A | C |
| ATOM | 674 | CG | PRO | A | 399 | 2.109 | 17.216 | 37.455 | 1.00 | 49.89 | A | C |
| ATOM | 675 | CD | PRO | A | 399 | 1.355 | 15.812 | 37.339 | 1.00 | 50.03 | A | C |
| ATOM | 676 | N | VAL | A | 400 | 5.252 | 14.151 | 39.156 | 1.00 | 47.20 | A | N |
| ATOM | 677 | CA | VAL | A | 400 | 5.732 | 13.518 | 40.382 | 1.00 | 45.46 | A | C |
| ATOM | 678 | C | VAL | A | 400 | 5.406 | 12.023 | 40.429 | 1.00 | 44.00 | A | C |
| ATOM | 679 | O | VAL | A | 400 | 5.462 | 11.376 | 41.468 | 1.00 | 43.37 | A | O |
| ATOM | 680 | CB | VAL | A | 400 | 5.093 | 14.226 | 41.577 | 1.00 | 20.00 | A | C |
| ATOM | 681 | CG1 | VAL | A | 400 | 5.530 | 13.549 | 42.875 | 1.00 | 20.00 | A | C |
| ATOM | 682 | CG2 | VAL | A | 400 | 5.513 | 15.683 | 41.607 | 1.00 | 20.00 | A | C |
| ATOM | 683 | N | LYS | A | 401 | 5.018 | 11.480 | 39.260 | 1.00 | 42.33 | A | N |
| ATOM | 684 | CA | LYS | A | 401 | 4.663 | 10.067 | 39.214 | 1.00 | 41.33 | A | C |
| ATOM | 685 | C | LYS | A | 401 | 4.651 | 9.530 | 37.781 | 1.00 | 40.30 | A | C |
| ATOM | 686 | O | LYS | A | 401 | 4.089 | 10.125 | 36.871 | 1.00 | 39.88 | A | O |
| ATOM | 687 | CB | LYS | A | 401 | 3.280 | 9.905 | 39.845 | 1.00 | 41.39 | A | C |
| ATOM | 688 | CG | LYS | A | 401 | 2.419 | 11.160 | 39.685 | 1.00 | 41.38 | A | C |
| ATOM | 689 | CD | LYS | A | 401 | 1.107 | 11.066 | 40.466 | 1.00 | 41.19 | A | C |
| ATOM | 690 | CE | LYS | A | 401 | 0.067 | 12.087 | 39.991 | 1.00 | 41.06 | A | C |
| ATOM | 691 | NZ | LYS | A | 401 | −1.084 | 11.390 | 39.422 | 1.00 | 40.44 | A | N |
| ATOM | 692 | N | LEU | A | 402 | 5.368 | 8.414 | 37.707 | 1.00 | 40.03 | A | N |
| ATOM | 693 | CA | LEU | A | 402 | 5.545 | 7.668 | 36.461 | 1.00 | 39.54 | A | C |
| ATOM | 694 | C | LEU | A | 402 | 4.450 | 6.614 | 36.286 | 1.00 | 38.84 | A | C |
| ATOM | 695 | O | LEU | A | 402 | 4.396 | 5.624 | 37.010 | 1.00 | 38.81 | A | O |
| ATOM | 696 | CB | LEU | A | 402 | 6.914 | 6.991 | 36.429 | 1.00 | 39.78 | A | C |
| ATOM | 697 | CG | LEU | A | 402 | 8.064 | 7.971 | 36.223 | 1.00 | 40.41 | A | C |
| ATOM | 698 | CD1 | LEU | A | 402 | 9.359 | 7.218 | 35.979 | 1.00 | 40.41 | A | C |
| ATOM | 699 | CD2 | LEU | A | 402 | 7.738 | 8.872 | 35.031 | 1.00 | 40.13 | A | C |
| ATOM | 700 | N | LEU | A | 403 | 3.584 | 6.836 | 35.309 | 1.00 | 38.20 | A | N |
| ATOM | 701 | CA | LEU | A | 403 | 2.483 | 5.935 | 35.029 | 1.00 | 37.88 | A | C |
| ATOM | 702 | C | LEU | A | 403 | 2.964 | 4.790 | 34.141 | 1.00 | 37.85 | A | C |
| ATOM | 703 | O | LEU | A | 403 | 2.962 | 4.896 | 32.914 | 1.00 | 37.75 | A | O |
| ATOM | 704 | CB | LEU | A | 403 | 1.377 | 6.737 | 34.351 | 1.00 | 38.42 | A | C |
| ATOM | 705 | CG | LEU | A | 403 | 0.010 | 6.147 | 34.030 | 1.00 | 39.07 | A | C |
| ATOM | 706 | CD1 | LEU | A | 403 | −0.939 | 7.285 | 33.677 | 1.00 | 38.97 | A | C |
| ATOM | 707 | CD2 | LEU | A | 403 | 0.111 | 5.168 | 32.875 | 1.00 | 39.41 | A | C |
| ATOM | 708 | N | PHE | A | 404 | 3.404 | 3.701 | 34.764 | 1.00 | 37.48 | A | N |
| ATOM | 709 | CA | PHE | A | 404 | 3.878 | 2.541 | 34.014 | 1.00 | 37.55 | A | C |
| ATOM | 710 | C | PHE | A | 404 | 2.691 | 1.893 | 33.283 | 1.00 | 37.10 | A | C |
| ATOM | 711 | O | PHE | A | 404 | 2.845 | 1.298 | 32.212 | 1.00 | 36.43 | A | O |
| ATOM | 712 | CB | PHE | A | 404 | 4.566 | 1.557 | 34.970 | 1.00 | 38.18 | A | C |
| ATOM | 713 | CG | PHE | A | 404 | 5.913 | 2.041 | 35.472 | 1.00 | 38.44 | A | C |
| ATOM | 714 | CD1 | PHE | A | 404 | 7.094 | 1.695 | 34.808 | 1.00 | 37.72 | A | C |
| ATOM | 715 | CD2 | PHE | A | 404 | 5.999 | 2.888 | 36.574 | 1.00 | 38.63 | A | C |
| ATOM | 716 | CE1 | PHE | A | 404 | 8.331 | 2.188 | 35.233 | 1.00 | 37.07 | A | C |
| ATOM | 717 | CE2 | PHE | A | 404 | 7.241 | 3.387 | 37.001 | 1.00 | 37.81 | A | C |
| ATOM | 718 | CZ | PHE | A | 404 | 8.401 | 3.032 | 36.326 | 1.00 | 37.24 | A | C |
| ATOM | 719 | N | ALA | A | 405 | 1.508 | 2.038 | 33.871 | 1.00 | 36.69 | A | N |
| ATOM | 720 | CA | ALA | A | 405 | 0.258 | 1.533 | 33.303 | 1.00 | 37.24 | A | C |
| ATOM | 721 | C | ALA | A | 405 | −0.877 | 2.319 | 33.959 | 1.00 | 37.83 | A | C |
| ATOM | 722 | O | ALA | A | 405 | −0.676 | 3.003 | 34.960 | 1.00 | 37.26 | A | O |
| ATOM | 723 | CB | ALA | A | 405 | 0.099 | 0.041 | 33.560 | 1.00 | 37.00 | A | C |
| ATOM | 724 | N | PRO | A | 406 | −2.089 | 2.250 | 33.401 | 1.00 | 39.11 | A | N |
| ATOM | 725 | CA | PRO | A | 406 | −3.118 | 3.037 | 34.085 | 1.00 | 40.47 | A | C |
| ATOM | 726 | C | PRO | A | 406 | −3.417 | 2.505 | 35.486 | 1.00 | 41.99 | A | C |
| ATOM | 727 | O | PRO | A | 406 | −3.988 | 3.208 | 36.326 | 1.00 | 42.24 | A | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 728 | CB | PRO | A | 406 | −4.317 | 2.927 | 33.142 | 1.00 | 39.51 A | | C |
| ATOM | 729 | CG | PRO | A | 406 | −3.682 | 2.767 | 31.813 | 1.00 | 39.46 A | | C |
| ATOM | 730 | CD | PRO | A | 406 | −2.576 | 1.774 | 32.098 | 1.00 | 39.33 A | | C |
| ATOM | 731 | N | ASN | A | 407 | −3.018 | 1.262 | 35.730 | 1.00 | 43.21 A | | N |
| ATOM | 732 | CA | ASN | A | 407 | −3.251 | 0.618 | 37.015 | 1.00 | 44.68 A | | C |
| ATOM | 733 | C | ASN | A | 407 | −1.932 | 0.324 | 37.716 | 1.00 | 45.75 A | | C |
| ATOM | 734 | O | ASN | A | 407 | −1.898 | −0.447 | 38.677 | 1.00 | 46.20 A | | O |
| ATOM | 735 | CB | ASN | A | 407 | −4.011 | −0.694 | 36.802 | 1.00 | 44.11 A | | C |
| ATOM | 736 | CG | ASN | A | 407 | −3.205 | −1.708 | 36.019 | 1.00 | 43.71 A | | C |
| ATOM | 737 | OD1 | ASN | A | 407 | −2.188 | −1.370 | 35.411 | 1.00 | 43.88 A | | O |
| ATOM | 738 | ND2 | ASN | A | 407 | −3.659 | −2.956 | 36.017 | 1.00 | 42.48 A | | N |
| ATOM | 739 | N | LEU | A | 408 | −0.849 | 0.925 | 37.235 | 1.00 | 46.53 A | | N |
| ATOM | 740 | CA | LEU | A | 408 | 0.457 | 0.690 | 37.833 | 1.00 | 47.97 A | | C |
| ATOM | 741 | C | LEU | A | 408 | 1.327 | 1.919 | 37.702 | 1.00 | 49.31 A | | C |
| ATOM | 742 | O | LEU | A | 408 | 2.393 | 1.868 | 37.093 | 1.00 | 48.93 A | | O |
| ATOM | 743 | CB | LEU | A | 408 | 1.151 | −0.502 | 37.158 | 1.00 | 47.60 A | | C |
| ATOM | 744 | CG | LEU | A | 408 | 2.535 | −0.893 | 37.696 | 1.00 | 47.57 A | | C |
| ATOM | 745 | CD1 | LEU | A | 408 | 2.405 | −1.365 | 39.125 | 1.00 | 46.92 A | | C |
| ATOM | 746 | CD2 | LEU | A | 408 | 3.157 | −1.980 | 36.832 | 1.00 | 47.67 A | | C |
| ATOM | 747 | N | LEU | A | 409 | 0.866 | 3.031 | 38.259 | 1.00 | 51.80 A | | N |
| ATOM | 748 | CA | LEU | A | 409 | 1.646 | 4.253 | 38.195 | 1.00 | 54.47 A | | C |
| ATOM | 749 | C | LEU | A | 409 | 2.347 | 4.469 | 39.520 | 1.00 | 56.60 A | | C |
| ATOM | 750 | O | LEU | A | 409 | 1.720 | 4.427 | 40.579 | 1.00 | 56.80 A | | O |
| ATOM | 751 | CB | LEU | A | 409 | 0.763 | 5.458 | 37.889 | 1.00 | 54.29 A | | C |
| ATOM | 752 | CG | LEU | A | 409 | 0.070 | 6.178 | 39.041 | 1.00 | 53.73 A | | C |
| ATOM | 753 | CD1 | LEU | A | 409 | −0.071 | 7.666 | 38.706 | 1.00 | 53.54 A | | C |
| ATOM | 754 | CD2 | LEU | A | 409 | −1.271 | 5.526 | 39.306 | 1.00 | 53.76 A | | C |
| ATOM | 755 | N | LEU | A | 410 | 3.651 | 4.705 | 39.455 | 1.00 | 59.01 A | | N |
| ATOM | 756 | CA | LEU | A | 410 | 4.449 | 4.919 | 40.648 | 1.00 | 61.53 A | | C |
| ATOM | 757 | C | LEU | A | 410 | 4.916 | 6.360 | 40.739 | 1.00 | 64.02 A | | C |
| ATOM | 758 | O | LEU | A | 410 | 4.599 | 7.183 | 39.882 | 1.00 | 64.14 A | | O |
| ATOM | 759 | CB | LEU | A | 410 | 5.652 | 3.988 | 40.610 | 1.00 | 60.64 A | | C |
| ATOM | 760 | CG | LEU | A | 410 | 5.215 | 2.586 | 40.200 | 1.00 | 60.41 A | | C |
| ATOM | 761 | CD1 | LEU | A | 410 | 6.391 | 1.625 | 40.259 | 1.00 | 60.01 A | | C |
| ATOM | 762 | CD2 | LEU | A | 410 | 4.090 | 2.128 | 41.121 | 1.00 | 59.86 A | | C |
| ATOM | 763 | N | ASP | A | 411 | 5.649 | 6.673 | 41.798 | 1.00 | 67.12 A | | N |
| ATOM | 764 | CA | ASP | A | 411 | 6.181 | 8.017 | 41.959 | 1.00 | 70.06 A | | C |
| ATOM | 765 | C | ASP | A | 411 | 7.396 | 7.984 | 42.869 | 1.00 | 71.88 A | | C |
| ATOM | 766 | O | ASP | A | 411 | 7.655 | 6.989 | 43.548 | 1.00 | 72.13 A | | O |
| ATOM | 767 | CB | ASP | A | 411 | 5.123 | 8.985 | 42.518 | 1.00 | 70.27 A | | C |
| ATOM | 768 | CG | ASP | A | 411 | 4.942 | 8.871 | 44.022 | 1.00 | 70.61 A | | C |
| ATOM | 769 | OD1 | ASP | A | 411 | 4.605 | 7.767 | 44.495 | 1.00 | 71.12 A | | O |
| ATOM | 770 | OD2 | ASP | A | 411 | 5.117 | 9.892 | 44.728 | 1.00 | 70.30 A | | O |
| ATOM | 771 | N | ARG | A | 412 | 8.142 | 9.082 | 42.844 | 1.00 | 74.09 A | | N |
| ATOM | 772 | CA | ARG | A | 412 | 9.350 | 9.271 | 43.637 | 1.00 | 76.29 A | | C |
| ATOM | 773 | C | ARG | A | 412 | 9.553 | 8.244 | 44.773 | 1.00 | 77.16 A | | C |
| ATOM | 774 | O | ARG | A | 412 | 10.618 | 7.624 | 44.860 | 1.00 | 76.99 A | | O |
| ATOM | 775 | CB | ARG | A | 412 | 9.348 | 10.711 | 44.183 | 1.00 | 77.51 A | | C |
| ATOM | 776 | CG | ARG | A | 412 | 7.859 | 11.052 | 44.125 | 1.00 | 78.78 A | | C |
| ATOM | 777 | CD | ARG | A | 412 | 7.232 | 11.463 | 45.462 | 1.00 | 80.22 A | | C |
| ATOM | 778 | NE | ARG | A | 412 | 8.333 | 11.195 | 46.391 | 1.00 | 81.55 A | | N |
| ATOM | 779 | CZ | ARG | A | 412 | 9.329 | 11.929 | 45.861 | 1.00 | 82.10 A | | C |
| ATOM | 780 | NH1 | ARG | A | 412 | 9.424 | 12.750 | 44.812 | 1.00 | 81.82 A | | N |
| ATOM | 781 | NH2 | ARG | A | 412 | 10.254 | 11.947 | 46.805 | 1.00 | 82.30 A | | N |
| ATOM | 782 | N | ASN | A | 413 | 8.539 | 8.062 | 45.626 | 1.00 | 78.49 A | | N |
| ATOM | 783 | CA | ASN | A | 413 | 8.615 | 7.147 | 46.772 | 1.00 | 79.72 A | | C |
| ATOM | 784 | C | ASN | A | 413 | 8.704 | 5.662 | 46.444 | 1.00 | 80.72 A | | C |
| ATOM | 785 | O | ASN | A | 413 | 9.560 | 4.960 | 46.988 | 1.00 | 80.88 A | | O |
| ATOM | 786 | CB | ASN | A | 413 | 7.401 | 7.415 | 47.681 | 1.00 | 79.56 A | | C |
| ATOM | 787 | CG | ASN | A | 413 | 7.736 | 8.760 | 48.272 | 1.00 | 79.79 A | | C |
| ATOM | 788 | OD1 | ASN | A | 413 | 7.035 | 9.639 | 48.764 | 1.00 | 79.65 A | | O |
| ATOM | 789 | ND2 | ASN | A | 413 | 9.060 | 8.670 | 48.488 | 1.00 | 79.97 A | | N |
| ATOM | 790 | N | GLN | A | 414 | 7.814 | 5.175 | 45.583 | 1.00 | 81.95 A | | N |
| ATOM | 791 | CA | GLN | A | 414 | 7.825 | 3.758 | 45.222 | 1.00 | 83.18 A | | C |
| ATOM | 792 | C | GLN | A | 414 | 9.081 | 3.360 | 44.442 | 1.00 | 83.93 A | | C |
| ATOM | 793 | O | GLN | A | 414 | 9.586 | 2.239 | 44.574 | 1.00 | 83.87 A | | O |
| ATOM | 794 | CB | GLN | A | 414 | 6.587 | 3.406 | 44.393 | 1.00 | 83.35 A | | C |
| ATOM | 795 | CG | GLN | A | 414 | 5.297 | 3.350 | 45.192 | 1.00 | 83.39 A | | C |
| ATOM | 796 | CD | GLN | A | 414 | 4.466 | 4.609 | 45.076 | 1.00 | 83.48 A | | C |
| ATOM | 797 | OE1 | GLN | A | 414 | 3.598 | 4.716 | 44.212 | 1.00 | 83.60 A | | O |
| ATOM | 798 | NE2 | GLN | A | 414 | 4.747 | 5.584 | 45.937 | 1.00 | 83.65 A | | N |
| ATOM | 799 | N | GLY | A | 415 | 9.575 | 4.282 | 43.620 | 1.00 | 85.10 A | | N |
| ATOM | 800 | CA | GLY | A | 415 | 10.763 | 4.012 | 42.829 | 1.00 | 86.53 A | | C |
| ATOM | 801 | C | GLY | A | 415 | 11.938 | 3.652 | 43.714 | 1.00 | 87.44 A | | C |
| ATOM | 802 | O | GLY | A | 415 | 12.891 | 2.998 | 43.265 | 1.00 | 87.49 A | | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 803 | N | LYS | A | 416 | 11.880 | 4.099 | 44.967 | 1.00 | 88.29 | A | N |
| ATOM | 804 | CA | LYS | A | 416 | 12.929 | 3.809 | 45.939 | 1.00 | 89.34 | A | C |
| ATOM | 805 | C | LYS | A | 416 | 12.975 | 2.296 | 46.156 | 1.00 | 89.82 | A | C |
| ATOM | 806 | O | LYS | A | 416 | 14.048 | 1.696 | 46.223 | 1.00 | 89.87 | A | O |
| ATOM | 807 | CB | LYS | A | 416 | 12.741 | 4.617 | 47.236 | 1.00 | 89.68 | A | C |
| ATOM | 808 | CG | LYS | A | 416 | 14.130 | 4.399 | 47.838 | 1.00 | 89.91 | A | C |
| ATOM | 809 | CD | LYS | A | 416 | 14.259 | 2.974 | 48.378 | 1.00 | 89.87 | A | C |
| ATOM | 810 | CE | LYS | A | 416 | 14.159 | 2.518 | 49.838 | 1.00 | 90.10 | A | C |
| ATOM | 811 | NZ | LYS | A | 416 | 14.559 | 1.170 | 50.239 | 1.00 | 89.92 | A | N |
| ATOM | 812 | N | CYS | A | 417 | 11.797 | 1.685 | 46.260 | 1.00 | 90.18 | A | N |
| ATOM | 813 | CA | CYS | A | 417 | 11.690 | 0.245 | 46.479 | 1.00 | 90.10 | A | C |
| ATOM | 814 | C | CYS | A | 417 | 12.509 | −0.587 | 45.475 | 1.00 | 89.68 | A | C |
| ATOM | 815 | O | CYS | A | 417 | 13.150 | −1.570 | 45.861 | 1.00 | 89.83 | A | O |
| ATOM | 816 | CB | CYS | A | 417 | 10.219 | −0.171 | 46.428 | 1.00 | 90.28 | A | C |
| ATOM | 817 | SG | CYS | A | 417 | 9.198 | 0.691 | 47.659 | 1.00 | 91.20 | A | S |
| ATOM | 818 | N | VAL | A | 418 | 12.503 | −0.215 | 44.195 | 1.00 | 88.96 | A | N |
| ATOM | 819 | CA | VAL | A | 418 | 13.266 | −0.997 | 43.228 | 1.00 | 87.95 | A | C |
| ATOM | 820 | C | VAL | A | 418 | 14.787 | −0.905 | 43.483 | 1.00 | 87.56 | A | C |
| ATOM | 821 | O | VAL | A | 418 | 15.473 | −1.942 | 43.556 | 1.00 | 87.82 | A | O |
| ATOM | 822 | CB | VAL | A | 418 | 12.960 | −0.570 | 41.772 | 1.00 | 87.71 | A | C |
| ATOM | 823 | CG1 | VAL | A | 418 | 13.362 | −1.695 | 40.821 | 1.00 | 87.33 | A | C |
| ATOM | 824 | CG2 | VAL | A | 418 | 11.468 | −0.246 | 41.607 | 1.00 | 87.46 | A | C |
| ATOM | 825 | N | GLU | A | 419 | 15.302 | 0.318 | 43.647 | 1.00 | 86.73 | A | N |
| ATOM | 826 | CA | GLU | A | 419 | 16.736 | 0.560 | 43.852 | 1.00 | 85.81 | A | C |
| ATOM | 827 | C | GLU | A | 419 | 17.600 | 0.014 | 42.721 | 1.00 | 84.08 | A | C |
| ATOM | 828 | O | GLU | A | 419 | 17.448 | −1.130 | 42.302 | 1.00 | 83.79 | A | O |
| ATOM | 829 | CB | GLU | A | 419 | 17.214 | 0.031 | 45.214 | 1.00 | 87.59 | A | C |
| ATOM | 830 | CG | GLU | A | 419 | 16.741 | 0.872 | 46.405 | 1.00 | 90.11 | A | C |
| ATOM | 831 | CD | GLU | A | 419 | 16.942 | 2.367 | 46.210 | 1.00 | 91.74 | A | C |
| ATOM | 832 | OE1 | GLU | A | 419 | 18.075 | 2.797 | 45.909 | 1.00 | 92.54 | A | O |
| ATOM | 833 | OE2 | GLU | A | 419 | 15.959 | 3.128 | 46.366 | 1.00 | 93.15 | A | O |
| ATOM | 834 | N | GLY | A | 420 | 18.529 | 0.850 | 42.262 | 1.00 | 82.38 | A | N |
| ATOM | 835 | CA | GLY | A | 420 | 19.382 | 0.510 | 41.136 | 1.00 | 79.71 | A | C |
| ATOM | 836 | C | GLY | A | 420 | 18.700 | 1.295 | 40.031 | 1.00 | 77.58 | A | C |
| ATOM | 837 | O | GLY | A | 420 | 19.289 | 1.713 | 39.032 | 1.00 | 77.06 | A | O |
| ATOM | 838 | N | MET | A | 421 | 17.412 | 1.508 | 40.271 | 1.00 | 75.52 | A | N |
| ATOM | 839 | CA | MET | A | 421 | 16.555 | 2.228 | 39.373 | 1.00 | 73.39 | A | C |
| ATOM | 840 | C | MET | A | 421 | 16.448 | 3.652 | 39.838 | 1.00 | 72.00 | A | C |
| ATOM | 841 | O | MET | A | 421 | 17.076 | 4.494 | 39.236 | 1.00 | 72.23 | A | O |
| ATOM | 842 | CB | MET | A | 421 | 15.218 | 1.521 | 39.313 | 1.00 | 73.45 | A | C |
| ATOM | 843 | CG | MET | A | 421 | 15.442 | 0.082 | 38.900 | 1.00 | 73.16 | A | C |
| ATOM | 844 | SD | MET | A | 421 | 16.751 | −0.047 | 37.651 | 1.00 | 73.38 | A | S |
| ATOM | 845 | CE | MET | A | 421 | 16.039 | −1.222 | 36.527 | 1.00 | 72.60 | A | C |
| ATOM | 846 | N | VAL | A | 422 | 15.688 | 3.933 | 40.892 | 1.00 | 70.33 | A | N |
| ATOM | 847 | CA | VAL | A | 422 | 15.571 | 5.309 | 41.410 | 1.00 | 68.80 | A | C |
| ATOM | 848 | C | VAL | A | 422 | 16.287 | 6.418 | 40.580 | 1.00 | 67.65 | A | C |
| ATOM | 849 | O | VAL | A | 422 | 15.713 | 7.481 | 40.327 | 1.00 | 67.27 | A | O |
| ATOM | 850 | CB | VAL | A | 422 | 16.062 | 5.350 | 42.877 | 1.00 | 69.12 | A | C |
| ATOM | 851 | CG1 | VAL | A | 422 | 17.440 | 4.664 | 42.990 | 1.00 | 68.57 | A | C |
| ATOM | 852 | CG2 | VAL | A | 422 | 16.104 | 6.802 | 43.369 | 1.00 | 69.05 | A | C |
| ATOM | 853 | N | GLU | A | 423 | 17.544 | 6.177 | 40.202 | 1.00 | 65.87 | A | N |
| ATOM | 854 | CA | GLU | A | 423 | 18.344 | 7.082 | 39.363 | 1.00 | 63.85 | A | C |
| ATOM | 855 | C | GLU | A | 423 | 17.565 | 7.246 | 38.039 | 1.00 | 61.58 | A | C |
| ATOM | 856 | O | GLU | A | 423 | 17.131 | 8.343 | 37.676 | 1.00 | 61.03 | A | O |
| ATOM | 857 | CB | GLU | A | 423 | 19.701 | 6.405 | 39.136 | 1.00 | 64.92 | A | C |
| ATOM | 858 | CG | GLU | A | 423 | 20.677 | 7.040 | 38.163 | 1.00 | 67.03 | A | C |
| ATOM | 859 | CD | GLU | A | 423 | 21.766 | 6.034 | 37.782 | 1.00 | 68.38 | A | C |
| ATOM | 860 | OE1 | GLU | A | 423 | 21.420 | 4.981 | 37.197 | 1.00 | 68.92 | A | O |
| ATOM | 861 | OE2 | GLU | A | 423 | 22.957 | 6.267 | 38.086 | 1.00 | 68.66 | A | O |
| ATOM | 862 | N | ILE | A | 424 | 17.393 | 6.126 | 37.345 | 1.00 | 58.93 | A | N |
| ATOM | 863 | CA | ILE | A | 424 | 16.653 | 6.053 | 36.098 | 1.00 | 56.65 | A | C |
| ATOM | 864 | C | ILE | A | 424 | 15.234 | 6.610 | 36.256 | 1.00 | 55.38 | A | C |
| ATOM | 865 | O | ILE | A | 424 | 14.732 | 7.284 | 35.370 | 1.00 | 55.07 | A | O |
| ATOM | 866 | CB | ILE | A | 424 | 16.614 | 4.595 | 35.617 | 1.00 | 56.30 | A | C |
| ATOM | 867 | CG1 | ILE | A | 424 | 18.010 | 4.202 | 35.130 | 1.00 | 55.73 | A | C |
| ATOM | 868 | CG2 | ILE | A | 424 | 15.561 | 4.404 | 34.552 | 1.00 | 55.28 | A | C |
| ATOM | 869 | CD1 | ILE | A | 424 | 18.150 | 2.744 | 34.785 | 1.00 | 55.98 | A | C |
| ATOM | 870 | N | PHE | A | 425 | 14.591 | 6.325 | 37.384 | 1.00 | 53.97 | A | N |
| ATOM | 871 | CA | PHE | A | 425 | 13.246 | 6.839 | 37.658 | 1.00 | 52.45 | A | C |
| ATOM | 872 | C | PHE | A | 425 | 13.232 | 8.353 | 37.566 | 1.00 | 50.84 | A | C |
| ATOM | 873 | O | PHE | A | 425 | 12.387 | 8.943 | 36.905 | 1.00 | 50.18 | A | O |
| ATOM | 874 | CB | PHE | A | 425 | 12.797 | 6.493 | 39.073 | 1.00 | 53.62 | A | C |
| ATOM | 875 | CG | PHE | A | 425 | 11.788 | 5.415 | 39.137 | 1.00 | 54.94 | A | C |
| ATOM | 876 | CD1 | PHE | A | 425 | 12.130 | 4.114 | 38.773 | 1.00 | 55.84 | A | C |
| ATOM | 877 | CD2 | PHE | A | 425 | 10.495 | 5.688 | 39.588 | 1.00 | 55.48 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 878 | CE1 | PHE | A | 425 | 11.197 | 3.082 | 38.855 | 1.00 | 56.84 | A | C |
| ATOM | 879 | CE2 | PHE | A | 425 | 9.544 | 4.667 | 39.676 | 1.00 | 56.91 | A | C |
| ATOM | 880 | CZ | PHE | A | 425 | 9.897 | 3.351 | 39.310 | 1.00 | 57.18 | A | C |
| ATOM | 881 | N | ASP | A | 426 | 14.167 | 8.974 | 38.276 | 1.00 | 49.33 | A | N |
| ATOM | 882 | CA | ASP | A | 426 | 14.274 | 10.419 | 38.297 | 1.00 | 47.65 | A | C |
| ATOM | 883 | C | ASP | A | 426 | 14.475 | 10.925 | 36.890 | 1.00 | 46.06 | A | C |
| ATOM | 884 | O | ASP | A | 426 | 13.726 | 11.788 | 36.432 | 1.00 | 45.90 | A | O |
| ATOM | 885 | CB | ASP | A | 426 | 15.408 | 10.852 | 39.232 | 1.00 | 48.61 | A | C |
| ATOM | 886 | CG | ASP | A | 426 | 14.985 | 10.822 | 40.696 | 1.00 | 49.12 | A | C |
| ATOM | 887 | OD1 | ASP | A | 426 | 14.195 | 11.709 | 41.103 | 1.00 | 49.08 | A | O |
| ATOM | 888 | OD2 | ASP | A | 426 | 15.417 | 9.901 | 41.429 | 1.00 | 49.31 | A | O |
| ATOM | 889 | N | MET | A | 427 | 15.451 | 10.362 | 36.188 | 1.00 | 43.91 | A | N |
| ATOM | 890 | CA | MET | A | 427 | 15.704 | 10.760 | 34.806 | 1.00 | 42.29 | A | C |
| ATOM | 891 | C | MET | A | 427 | 14.426 | 10.693 | 33.951 | 1.00 | 41.26 | A | C |
| ATOM | 892 | O | MET | A | 427 | 14.209 | 11.558 | 33.094 | 1.00 | 40.83 | A | O |
| ATOM | 893 | CB | MET | A | 427 | 16.787 | 9.870 | 34.196 | 1.00 | 42.06 | A | C |
| ATOM | 894 | CG | MET | A | 427 | 18.118 | 9.923 | 34.938 | 1.00 | 41.65 | A | C |
| ATOM | 895 | SD | MET | A | 427 | 19.447 | 9.139 | 34.023 | 1.00 | 39.79 | A | S |
| ATOM | 896 | CE | MET | A | 427 | 19.347 | 7.493 | 34.616 | 1.00 | 42.01 | A | C |
| ATOM | 897 | N | LEU | A | 428 | 13.590 | 9.676 | 34.187 | 1.00 | 39.58 | A | N |
| ATOM | 898 | CA | LEU | A | 428 | 12.335 | 9.515 | 33.452 | 1.00 | 38.73 | A | C |
| ATOM | 899 | C | LEU | A | 428 | 11.361 | 10.549 | 33.973 | 1.00 | 38.75 | A | C |
| ATOM | 900 | O | LEU | A | 428 | 10.606 | 11.173 | 33.237 | 1.00 | 38.20 | A | O |
| ATOM | 901 | CB | LEU | A | 428 | 11.721 | 8.129 | 33.696 | 1.00 | 37.90 | A | C |
| ATOM | 902 | CG | LEU | A | 428 | 12.457 | 6.878 | 33.220 | 1.00 | 36.78 | A | C |
| ATOM | 903 | CD1 | LEU | A | 428 | 11.725 | 5.634 | 33.694 | 1.00 | 35.82 | A | C |
| ATOM | 904 | CD2 | LEU | A | 428 | 12.564 | 6.914 | 31.706 | 1.00 | 37.45 | A | C |
| ATOM | 905 | N | LEU | A | 429 | 11.381 | 10.703 | 35.280 | 1.00 | 39.48 | A | N |
| ATOM | 906 | CA | LEU | A | 429 | 10.508 | 11.635 | 35.943 | 1.00 | 40.31 | A | C |
| ATOM | 907 | C | LEU | A | 429 | 10.793 | 13.040 | 35.443 | 1.00 | 40.86 | A | C |
| ATOM | 908 | O | LEU | A | 429 | 9.885 | 13.829 | 35.217 | 1.00 | 40.59 | A | O |
| ATOM | 909 | CB | LEU | A | 429 | 10.774 | 11.549 | 37.439 | 1.00 | 40.87 | A | C |
| ATOM | 910 | CG | LEU | A | 429 | 9.588 | 11.540 | 38.397 | 1.00 | 41.37 | A | C |
| ATOM | 911 | CD1 | LEU | A | 429 | 8.361 | 10.937 | 37.718 | 1.00 | 40.57 | A | C |
| ATOM | 912 | CD2 | LEU | A | 429 | 10.012 | 10.766 | 39.670 | 1.00 | 40.67 | A | C |
| ATOM | 913 | N | ALA | A | 430 | 12.079 | 13.326 | 35.262 | 1.00 | 41.68 | A | N |
| ATOM | 914 | CA | ALA | A | 430 | 12.547 | 14.632 | 34.832 | 1.00 | 41.82 | A | C |
| ATOM | 915 | C | ALA | A | 430 | 12.197 | 15.005 | 33.407 | 1.00 | 42.12 | A | C |
| ATOM | 916 | O | ALA | A | 430 | 11.692 | 16.106 | 33.168 | 1.00 | 42.73 | A | O |
| ATOM | 917 | CB | ALA | A | 430 | 14.055 | 14.719 | 35.024 | 1.00 | 42.34 | A | C |
| ATOM | 918 | N | THR | A | 431 | 12.480 | 14.106 | 32.461 | 1.00 | 41.92 | A | N |
| ATOM | 919 | CA | THR | A | 431 | 12.202 | 14.386 | 31.062 | 1.00 | 40.89 | A | C |
| ATOM | 920 | C | THR | A | 431 | 10.676 | 14.475 | 30.875 | 1.00 | 41.27 | A | C |
| ATOM | 921 | O | THR | A | 431 | 10.177 | 15.172 | 29.975 | 1.00 | 40.33 | A | O |
| ATOM | 922 | CB | THR | A | 431 | 12.845 | 13.302 | 30.107 | 1.00 | 39.91 | A | C |
| ATOM | 923 | OG1 | THR | A | 431 | 12.171 | 12.059 | 30.255 | 1.00 | 39.65 | A | O |
| ATOM | 924 | CG2 | THR | A | 431 | 14.321 | 13.085 | 30.425 | 1.00 | 38.57 | A | C |
| ATOM | 925 | N | SER | A | 432 | 9.938 | 13.793 | 31.750 | 1.00 | 41.19 | A | N |
| ATOM | 926 | CA | SER | A | 432 | 8.480 | 13.814 | 31.690 | 1.00 | 42.09 | A | C |
| ATOM | 927 | C | SER | A | 432 | 8.029 | 15.230 | 32.016 | 1.00 | 42.99 | A | C |
| ATOM | 928 | O | SER | A | 432 | 6.952 | 15.675 | 31.608 | 1.00 | 43.10 | A | O |
| ATOM | 929 | CB | SER | A | 432 | 7.887 | 12.825 | 32.703 | 1.00 | 41.89 | A | C |
| ATOM | 930 | OG | SER | A | 432 | 6.472 | 12.919 | 32.755 | 1.00 | 42.50 | A | O |
| ATOM | 931 | N | SER | A | 433 | 8.871 | 15.938 | 32.757 | 1.00 | 44.02 | A | N |
| ATOM | 932 | CA | SER | A | 433 | 8.580 | 17.314 | 33.137 | 1.00 | 45.50 | A | C |
| ATOM | 933 | C | SER | A | 433 | 8.988 | 18.295 | 32.024 | 1.00 | 45.73 | A | C |
| ATOM | 934 | O | SER | A | 433 | 8.247 | 19.234 | 31.703 | 1.00 | 45.21 | A | O |
| ATOM | 935 | CB | SER | A | 433 | 9.285 | 17.643 | 34.450 | 1.00 | 45.30 | A | C |
| ATOM | 936 | OG | SER | A | 433 | 8.764 | 16.819 | 35.480 | 1.00 | 46.08 | A | O |
| ATOM | 937 | N | ARG | A | 434 | 10.164 | 18.075 | 31.447 | 1.00 | 46.02 | A | N |
| ATOM | 938 | CA | ARG | A | 434 | 10.624 | 18.908 | 30.346 | 1.00 | 47.08 | A | C |
| ATOM | 939 | C | ARG | A | 434 | 9.430 | 18.979 | 29.389 | 1.00 | 46.86 | A | C |
| ATOM | 940 | O | ARG | A | 434 | 8.901 | 20.065 | 29.120 | 1.00 | 46.50 | A | O |
| ATOM | 941 | CB | ARG | A | 434 | 11.817 | 18.241 | 29.653 | 1.00 | 48.78 | A | C |
| ATOM | 942 | CG | ARG | A | 434 | 12.639 | 19.165 | 28.770 | 1.00 | 51.43 | A | C |
| ATOM | 943 | CD | ARG | A | 434 | 13.188 | 20.338 | 29.570 | 1.00 | 53.91 | A | C |
| ATOM | 944 | NE | ARG | A | 434 | 12.709 | 21.627 | 29.071 | 1.00 | 55.91 | A | N |
| ATOM | 945 | CZ | ARG | A | 434 | 13.180 | 22.233 | 27.984 | 1.00 | 56.87 | A | C |
| ATOM | 946 | NH1 | ARG | A | 434 | 14.151 | 21.665 | 27.278 | 1.00 | 56.51 | A | N |
| ATOM | 947 | NH2 | ARG | A | 434 | 12.679 | 23.407 | 27.605 | 1.00 | 57.62 | A | N |
| ATOM | 948 | N | PHE | A | 435 | 8.998 | 17.802 | 28.915 | 1.00 | 46.49 | A | N |
| ATOM | 949 | CA | PHE | A | 435 | 7.855 | 17.671 | 28.009 | 1.00 | 46.11 | A | C |
| ATOM | 950 | C | PHE | A | 435 | 6.631 | 18.465 | 28.453 | 1.00 | 46.93 | A | C |
| ATOM | 951 | O | PHE | A | 435 | 6.091 | 19.231 | 27.678 | 1.00 | 47.29 | A | O |
| ATOM | 952 | CB | PHE | A | 435 | 7.465 | 16.200 | 27.827 | 1.00 | 43.91 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 953 | CG | PHE | A | 435 | 8.375 | 15.441 | 26.903 | 1.00 | 42.97 | A | C |
| ATOM | 954 | CD1 | PHE | A | 435 | 9.354 | 16.100 | 26.157 | 1.00 | 43.08 | A | C |
| ATOM | 955 | CD2 | PHE | A | 435 | 8.251 | 14.070 | 26.767 | 1.00 | 41.73 | A | C |
| ATOM | 956 | CE1 | PHE | A | 435 | 10.196 | 15.389 | 25.282 | 1.00 | 42.79 | A | C |
| ATOM | 957 | CE2 | PHE | A | 435 | 9.080 | 13.352 | 25.899 | 1.00 | 41.99 | A | C |
| ATOM | 958 | CZ | PHE | A | 435 | 10.059 | 14.008 | 25.156 | 1.00 | 41.78 | A | C |
| ATOM | 959 | N | ARG | A | 436 | 6.170 | 18.278 | 29.680 | 1.00 | 48.43 | A | N |
| ATOM | 960 | CA | ARG | A | 436 | 5.017 | 19.045 | 30.128 | 1.00 | 50.54 | A | C |
| ATOM | 961 | C | ARG | A | 436 | 5.337 | 20.525 | 29.977 | 1.00 | 51.71 | A | C |
| ATOM | 962 | O | ARG | A | 436 | 4.627 | 21.251 | 29.283 | 1.00 | 52.13 | A | O |
| ATOM | 963 | CB | ARG | A | 436 | 4.696 | 18.747 | 31.586 | 1.00 | 51.20 | A | C |
| ATOM | 964 | CG | ARG | A | 436 | 3.504 | 19.511 | 32.168 | 1.00 | 52.88 | A | C |
| ATOM | 965 | CD | ARG | A | 436 | 3.316 | 19.063 | 33.603 | 1.00 | 54.93 | A | C |
| ATOM | 966 | NE | ARG | A | 436 | 3.918 | 17.737 | 33.743 | 1.00 | 57.10 | A | N |
| ATOM | 967 | CZ | ARG | A | 436 | 4.838 | 17.403 | 34.647 | 1.00 | 58.02 | A | C |
| ATOM | 968 | NH1 | ARG | A | 436 | 5.268 | 18.299 | 35.530 | 1.00 | 58.02 | A | N |
| ATOM | 969 | NH2 | ARG | A | 436 | 5.369 | 16.181 | 34.632 | 1.00 | 58.36 | A | N |
| ATOM | 970 | N | MET | A | 437 | 6.421 | 20.980 | 30.601 | 1.00 | 53.21 | A | N |
| ATOM | 971 | CA | MET | A | 437 | 6.750 | 22.393 | 30.506 | 1.00 | 54.22 | A | C |
| ATOM | 972 | C | MET | A | 437 | 7.038 | 22.823 | 29.070 | 1.00 | 53.93 | A | C |
| ATOM | 973 | O | MET | A | 437 | 7.100 | 24.016 | 28.771 | 1.00 | 54.33 | A | O |
| ATOM | 974 | CB | MET | A | 437 | 7.901 | 22.766 | 31.465 | 1.00 | 55.63 | A | C |
| ATOM | 975 | CG | MET | A | 437 | 9.339 | 22.455 | 31.039 | 1.00 | 57.72 | A | C |
| ATOM | 976 | SD | MET | A | 437 | 10.481 | 23.400 | 32.143 | 1.00 | 60.04 | A | S |
| ATOM | 977 | CE | MET | A | 437 | 12.153 | 22.601 | 31.863 | 1.00 | 59.88 | A | C |
| ATOM | 978 | N | MET | A | 438 | 7.193 | 21.851 | 28.176 | 1.00 | 53.45 | A | N |
| ATOM | 979 | CA | MET | A | 438 | 7.428 | 22.142 | 26.761 | 1.00 | 53.27 | A | C |
| ATOM | 980 | C | MET | A | 438 | 6.114 | 21.989 | 26.013 | 1.00 | 52.12 | A | C |
| ATOM | 981 | O | MET | A | 438 | 6.065 | 22.097 | 24.790 | 1.00 | 52.42 | A | O |
| ATOM | 982 | CB | MET | A | 438 | 8.437 | 21.173 | 26.151 | 1.00 | 54.98 | A | C |
| ATOM | 983 | CG | MET | A | 438 | 9.882 | 21.626 | 26.194 | 1.00 | 57.45 | A | C |
| ATOM | 984 | SD | MET | A | 438 | 10.863 | 20.682 | 25.006 | 1.00 | 60.48 | A | S |
| ATOM | 985 | CE | MET | A | 438 | 10.510 | 21.576 | 23.455 | 1.00 | 59.51 | A | C |
| ATOM | 986 | N | ASN | A | 439 | 5.054 | 21.725 | 26.766 | 1.00 | 50.77 | A | N |
| ATOM | 987 | CA | ASN | A | 439 | 3.718 | 21.520 | 26.218 | 1.00 | 49.72 | A | C |
| ATOM | 988 | C | ASN | A | 439 | 3.715 | 20.644 | 24.971 | 1.00 | 48.01 | A | C |
| ATOM | 989 | O | ASN | A | 439 | 2.915 | 20.846 | 24.067 | 1.00 | 47.11 | A | O |
| ATOM | 990 | CB | ASN | A | 439 | 3.053 | 22.854 | 25.903 | 1.00 | 50.66 | A | C |
| ATOM | 991 | CG | ASN | A | 439 | 1.556 | 22.727 | 25.785 | 1.00 | 51.73 | A | C |
| ATOM | 992 | OD1 | ASN | A | 439 | 0.880 | 22.312 | 26.738 | 1.00 | 51.99 | A | O |
| ATOM | 993 | ND2 | ASN | A | 439 | 1.020 | 23.074 | 24.616 | 1.00 | 52.01 | A | N |
| ATOM | 994 | N | LEU | A | 440 | 4.610 | 19.662 | 24.957 | 1.00 | 46.89 | A | N |
| ATOM | 995 | CA | LEU | A | 440 | 4.771 | 18.717 | 23.851 | 1.00 | 46.05 | A | C |
| ATOM | 996 | C | LEU | A | 440 | 3.435 | 18.216 | 23.305 | 1.00 | 45.71 | A | C |
| ATOM | 997 | O | LEU | A | 440 | 2.523 | 17.892 | 24.064 | 1.00 | 45.56 | A | O |
| ATOM | 998 | CB | LEU | A | 440 | 5.625 | 17.529 | 24.315 | 1.00 | 44.35 | A | C |
| ATOM | 999 | CG | LEU | A | 440 | 5.999 | 16.477 | 23.271 | 1.00 | 43.17 | A | C |
| ATOM | 1000 | CD1 | LEU | A | 440 | 6.858 | 17.088 | 22.177 | 1.00 | 42.54 | A | C |
| ATOM | 1001 | CD2 | LEU | A | 440 | 6.748 | 15.360 | 23.952 | 1.00 | 42.37 | A | C |
| ATOM | 1002 | N | GLN | A | 441 | 3.323 | 18.162 | 21.982 | 1.00 | 45.47 | A | N |
| ATOM | 1003 | CA | GLN | A | 441 | 2.092 | 17.704 | 21.347 | 1.00 | 44.80 | A | C |
| ATOM | 1004 | C | GLN | A | 441 | 2.201 | 16.256 | 20.907 | 1.00 | 43.74 | A | C |
| ATOM | 1005 | O | GLN | A | 441 | 3.288 | 15.781 | 20.571 | 1.00 | 43.03 | A | O |
| ATOM | 1006 | CB | GLN | A | 441 | 1.764 | 18.582 | 20.140 | 1.00 | 45.82 | A | C |
| ATOM | 1007 | CG | GLN | A | 441 | 1.501 | 20.044 | 20.492 | 1.00 | 48.02 | A | C |
| ATOM | 1008 | CD | GLN | A | 441 | 0.399 | 20.203 | 21.523 | 1.00 | 49.16 | A | C |
| ATOM | 1009 | OE1 | GLN | A | 441 | −0.721 | 19.726 | 21.333 | 1.00 | 50.68 | A | O |
| ATOM | 1010 | NE2 | GLN | A | 441 | 0.712 | 20.876 | 22.624 | 1.00 | 49.56 | A | N |
| ATOM | 1011 | N | GLY | A | 442 | 1.070 | 15.558 | 20.922 | 1.00 | 43.00 | A | N |
| ATOM | 1012 | CA | GLY | A | 442 | 1.051 | 14.162 | 20.510 | 1.00 | 43.20 | A | C |
| ATOM | 1013 | C | GLY | A | 442 | 1.583 | 13.979 | 19.096 | 1.00 | 43.39 | A | C |
| ATOM | 1014 | O | GLY | A | 442 | 2.220 | 12.957 | 18.792 | 1.00 | 42.97 | A | O |
| ATOM | 1015 | N | GLU | A | 443 | 1.323 | 14.970 | 18.235 | 1.00 | 43.19 | A | N |
| ATOM | 1016 | CA | GLU | A | 443 | 1.782 | 14.932 | 16.846 | 1.00 | 43.12 | A | C |
| ATOM | 1017 | C | GLU | A | 443 | 3.294 | 15.115 | 16.779 | 1.00 | 41.81 | A | C |
| ATOM | 1018 | O | GLU | A | 443 | 3.949 | 14.585 | 15.871 | 1.00 | 41.76 | A | O |
| ATOM | 1019 | CB | GLU | A | 443 | 1.101 | 16.010 | 16.006 | 1.00 | 44.78 | A | C |
| ATOM | 1020 | CG | GLU | A | 443 | −0.408 | 15.891 | 15.919 | 1.00 | 48.06 | A | C |
| ATOM | 1021 | CD | GLU | A | 443 | −1.113 | 16.298 | 17.214 | 1.00 | 50.31 | A | C |
| ATOM | 1022 | OE1 | GLU | A | 443 | −0.704 | 17.310 | 17.827 | 1.00 | 50.40 | A | O |
| ATOM | 1023 | OE2 | GLU | A | 443 | −2.090 | 15.618 | 17.609 | 1.00 | 52.10 | A | O |
| ATOM | 1024 | N | GLU | A | 444 | 3.848 | 15.867 | 17.732 | 1.00 | 39.77 | A | N |
| ATOM | 1025 | CA | GLU | A | 444 | 5.299 | 16.071 | 17.782 | 1.00 | 37.68 | A | C |
| ATOM | 1026 | C | GLU | A | 444 | 5.919 | 14.824 | 18.411 | 1.00 | 35.05 | A | C |
| ATOM | 1027 | O | GLU | A | 444 | 7.013 | 14.395 | 18.042 | 1.00 | 33.92 | A | O |

TABLE 10-continued

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 1028 | CB | GLU | A | 444 | 5.635 | 17.318 | 18.611 | 1.00 | 38.23 A | C |
| ATOM | 1029 | CG | GLU | A | 444 | 5.274 | 18.610 | 17.902 | 1.00 | 39.84 A | C |
| ATOM | 1030 | CD | GLU | A | 444 | 5.507 | 19.851 | 18.739 | 1.00 | 40.64 A | C |
| ATOM | 1031 | OE1 | GLU | A | 444 | 4.978 | 19.925 | 19.868 | 1.00 | 41.46 A | O |
| ATOM | 1032 | OE2 | GLU | A | 444 | 6.207 | 20.768 | 18.257 | 1.00 | 41.37 A | O |
| ATOM | 1033 | N | PHE | A | 445 | 5.174 | 14.239 | 19.348 | 1.00 | 32.75 A | N |
| ATOM | 1034 | CA | PHE | A | 445 | 5.590 | 13.045 | 20.081 | 1.00 | 29.96 A | C |
| ATOM | 1035 | C | PHE | A | 445 | 5.875 | 11.845 | 19.194 | 1.00 | 28.42 A | C |
| ATOM | 1036 | O | PHE | A | 445 | 6.949 | 11.256 | 19.274 | 1.00 | 26.52 A | O |
| ATOM | 1037 | CB | PHE | A | 445 | 4.535 | 12.659 | 21.113 | 1.00 | 28.77 A | C |
| ATOM | 1038 | CG | PHE | A | 445 | 4.713 | 11.275 | 21.633 | 1.00 | 28.27 A | C |
| ATOM | 1039 | CD1 | PHE | A | 445 | 5.882 | 10.920 | 22.283 | 1.00 | 27.45 A | C |
| ATOM | 1040 | CD2 | PHE | A | 445 | 3.734 | 10.306 | 21.427 | 1.00 | 28.00 A | C |
| ATOM | 1041 | CE1 | PHE | A | 445 | 6.080 | 9.632 | 22.718 | 1.00 | 28.37 A | C |
| ATOM | 1042 | CE2 | PHE | A | 445 | 3.919 | 9.008 | 21.857 | 1.00 | 26.55 A | C |
| ATOM | 1043 | CZ | PHE | A | 445 | 5.093 | 8.666 | 22.505 | 1.00 | 28.23 A | C |
| ATOM | 1044 | N | VAL | A | 446 | 4.904 | 11.491 | 18.351 | 1.00 | 28.30 A | N |
| ATOM | 1045 | CA | VAL | A | 446 | 5.050 | 10.358 | 17.421 | 1.00 | 28.12 A | C |
| ATOM | 1046 | C | VAL | A | 446 | 6.214 | 10.573 | 16.467 | 1.00 | 27.37 A | C |
| ATOM | 1047 | O | VAL | A | 446 | 6.955 | 9.631 | 16.163 | 1.00 | 27.19 A | O |
| ATOM | 1048 | CB | VAL | A | 446 | 3.753 | 10.105 | 16.600 | 1.00 | 27.78 A | C |
| ATOM | 1049 | CG1 | VAL | A | 446 | 2.659 | 9.566 | 17.518 | 1.00 | 27.02 A | C |
| ATOM | 1050 | CG2 | VAL | A | 446 | 3.276 | 11.399 | 15.944 | 1.00 | 27.89 A | C |
| ATOM | 1051 | N | CYS | A | 447 | 6.385 | 11.810 | 16.010 | 1.00 | 27.22 A | N |
| ATOM | 1052 | CA | CYS | A | 447 | 7.486 | 12.132 | 15.111 | 1.00 | 27.85 A | C |
| ATOM | 1053 | C | CYS | A | 447 | 8.794 | 11.798 | 15.849 | 1.00 | 27.89 A | C |
| ATOM | 1054 | O | CYS | A | 447 | 9.697 | 11.138 | 15.290 | 1.00 | 28.19 A | O |
| ATOM | 1055 | CB | CYS | A | 447 | 7.466 | 13.631 | 14.732 | 1.00 | 28.74 A | C |
| ATOM | 1056 | SG | CYS | A | 447 | 6.040 | 14.265 | 13.729 | 1.00 | 32.55 A | S |
| ATOM | 1057 | N | LEU | A | 448 | 8.900 | 12.259 | 17.103 | 1.00 | 27.06 A | N |
| ATOM | 1058 | CA | LEU | A | 448 | 10.097 | 12.002 | 17.914 | 1.00 | 25.74 A | C |
| ATOM | 1059 | C | LEU | A | 448 | 10.331 | 10.505 | 18.067 | 1.00 | 25.16 A | C |
| ATOM | 1060 | O | LEU | A | 448 | 11.449 | 10.019 | 17.863 | 1.00 | 25.73 A | O |
| ATOM | 1061 | CB | LEU | A | 448 | 9.962 | 12.629 | 19.299 | 1.00 | 25.10 A | C |
| ATOM | 1062 | CG | LEU | A | 448 | 10.012 | 14.148 | 19.314 | 1.00 | 23.97 A | C |
| ATOM | 1063 | CD1 | LEU | A | 448 | 9.949 | 14.611 | 20.737 | 1.00 | 25.05 A | C |
| ATOM | 1064 | CD2 | LEU | A | 448 | 11.303 | 14.637 | 18.658 | 1.00 | 24.09 A | C |
| ATOM | 1065 | N | LYS | A | 449 | 9.277 | 9.777 | 18.418 | 1.00 | 23.67 A | N |
| ATOM | 1066 | CA | LYS | A | 449 | 9.389 | 8.345 | 18.583 | 1.00 | 23.65 A | C |
| ATOM | 1067 | C | LYS | A | 449 | 9.929 | 7.730 | 17.298 | 1.00 | 23.86 A | C |
| ATOM | 1068 | O | LYS | A | 449 | 10.875 | 6.941 | 17.334 | 1.00 | 23.84 A | O |
| ATOM | 1069 | CB | LYS | A | 449 | 8.026 | 7.774 | 18.944 | 1.00 | 24.01 A | C |
| ATOM | 1070 | CG | LYS | A | 449 | 8.041 | 6.338 | 19.355 | 1.00 | 24.01 A | C |
| ATOM | 1071 | CD | LYS | A | 449 | 7.000 | 6.115 | 20.436 | 1.00 | 26.60 A | C |
| ATOM | 1072 | CE | LYS | A | 449 | 5.629 | 6.683 | 20.067 | 1.00 | 28.16 A | C |
| ATOM | 1073 | NZ | LYS | A | 449 | 4.800 | 5.797 | 19.206 | 1.00 | 30.06 A | N |
| ATOM | 1074 | N | SER | A | 450 | 9.362 | 8.115 | 16.157 | 1.00 | 24.81 A | N |
| ATOM | 1075 | CA | SER | A | 450 | 9.822 | 7.588 | 14.854 | 1.00 | 25.79 A | C |
| ATOM | 1076 | C | SER | A | 450 | 11.292 | 7.916 | 14.618 | 1.00 | 25.62 A | C |
| ATOM | 1077 | O | SER | A | 450 | 12.091 | 7.040 | 14.250 | 1.00 | 24.21 A | O |
| ATOM | 1078 | CB | SER | A | 450 | 8.978 | 8.159 | 13.707 | 1.00 | 25.88 A | C |
| ATOM | 1079 | OG | SER | A | 450 | 7.588 | 8.019 | 13.980 | 1.00 | 25.51 A | O |
| ATOM | 1080 | N | ILE | A | 451 | 11.653 | 9.180 | 14.829 | 1.00 | 26.60 A | N |
| ATOM | 1081 | CA | ILE | A | 451 | 13.052 | 9.587 | 14.663 | 1.00 | 28.16 A | C |
| ATOM | 1082 | C | ILE | A | 451 | 13.952 | 8.641 | 15.443 | 1.00 | 29.54 A | C |
| ATOM | 1083 | O | ILE | A | 451 | 15.003 | 8.224 | 14.945 | 1.00 | 29.61 A | O |
| ATOM | 1084 | CB | ILE | A | 451 | 13.304 | 11.009 | 15.187 | 1.00 | 27.84 A | C |
| ATOM | 1085 | CG1 | ILE | A | 451 | 12.471 | 12.008 | 14.378 | 1.00 | 28.42 A | C |
| ATOM | 1086 | CG2 | ILE | A | 451 | 14.788 | 11.339 | 15.101 | 1.00 | 27.10 A | C |
| ATOM | 1087 | CD1 | ILE | A | 451 | 12.594 | 13.454 | 14.836 | 1.00 | 29.68 A | C |
| ATOM | 1088 | N | ILE | A | 452 | 13.540 | 8.309 | 16.666 | 1.00 | 31.41 A | N |
| ATOM | 1089 | CA | ILE | A | 452 | 14.321 | 7.399 | 17.522 | 1.00 | 33.88 A | C |
| ATOM | 1090 | C | ILE | A | 452 | 14.567 | 6.064 | 16.847 | 1.00 | 35.20 A | C |
| ATOM | 1091 | O | ILE | A | 452 | 15.662 | 5.523 | 16.913 | 1.00 | 34.91 A | O |
| ATOM | 1092 | CB | ILE | A | 452 | 13.624 | 7.135 | 18.900 | 1.00 | 34.08 A | C |
| ATOM | 1093 | CG1 | ILE | A | 452 | 13.671 | 8.412 | 19.759 | 1.00 | 33.56 A | C |
| ATOM | 1094 | CG2 | ILE | A | 452 | 14.305 | 5.953 | 19.620 | 1.00 | 32.66 A | C |
| ATOM | 1095 | CD1 | ILE | A | 452 | 12.830 | 8.352 | 21.000 | 1.00 | 33.74 A | C |
| ATOM | 1096 | N | LEU | A | 453 | 13.530 | 5.523 | 16.220 | 1.00 | 37.63 A | N |
| ATOM | 1097 | CA | LEU | A | 453 | 13.641 | 4.254 | 15.510 | 1.00 | 39.79 A | C |
| ATOM | 1098 | C | LEU | A | 453 | 14.608 | 4.363 | 14.315 | 1.00 | 41.88 A | C |
| ATOM | 1099 | O | LEU | A | 453 | 15.361 | 3.435 | 14.040 | 1.00 | 42.09 A | O |
| ATOM | 1100 | CB | LEU | A | 453 | 12.269 | 3.840 | 15.001 | 1.00 | 38.63 A | C |
| ATOM | 1101 | CG | LEU | A | 453 | 12.262 | 2.590 | 14.135 | 1.00 | 37.45 A | C |
| ATOM | 1102 | CD1 | LEU | A | 453 | 12.462 | 1.350 | 15.001 | 1.00 | 36.57 A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1103 | CD2 | LEU | A | 453 | 10.948 | 2.540 | 13.384 | 1.00 | 36.79 | A | C |
| ATOM | 1104 | N | LEU | A | 454 | 14.588 | 5.503 | 13.625 | 1.00 | 44.20 | A | N |
| ATOM | 1105 | CA | LEU | A | 454 | 15.438 | 5.731 | 12.449 | 1.00 | 47.13 | A | C |
| ATOM | 1106 | C | LEU | A | 454 | 16.858 | 6.235 | 12.719 | 1.00 | 49.20 | A | C |
| ATOM | 1107 | O | LEU | A | 454 | 17.745 | 6.094 | 11.867 | 1.00 | 49.77 | A | O |
| ATOM | 1108 | CB | LEU | A | 454 | 14.752 | 6.721 | 11.495 | 1.00 | 46.58 | A | C |
| ATOM | 1109 | CG | LEU | A | 454 | 13.402 | 6.258 | 10.953 | 1.00 | 46.01 | A | C |
| ATOM | 1110 | CD1 | LEU | A | 454 | 12.686 | 7.379 | 10.222 | 1.00 | 45.54 | A | C |
| ATOM | 1111 | CD2 | LEU | A | 454 | 13.646 | 5.050 | 10.059 | 1.00 | 46.13 | A | C |
| ATOM | 1112 | N | ASN | A | 455 | 17.082 | 6.827 | 13.886 | 1.00 | 51.37 | A | N |
| ATOM | 1113 | CA | ASN | A | 455 | 18.405 | 7.360 | 14.191 | 1.00 | 53.48 | A | C |
| ATOM | 1114 | C | ASN | A | 455 | 19.345 | 6.393 | 14.888 | 1.00 | 54.50 | A | C |
| ATOM | 1115 | O | ASN | A | 455 | 20.436 | 6.102 | 14.404 | 1.00 | 55.34 | A | O |
| ATOM | 1116 | CB | ASN | A | 455 | 18.271 | 8.617 | 15.049 | 1.00 | 54.19 | A | C |
| ATOM | 1117 | CG | ASN | A | 455 | 19.553 | 9.438 | 15.091 | 1.00 | 54.85 | A | C |
| ATOM | 1118 | OD1 | ASN | A | 455 | 19.626 | 10.463 | 15.779 | 1.00 | 54.71 | A | O |
| ATOM | 1119 | ND2 | ASN | A | 455 | 20.567 | 8.995 | 14.346 | 1.00 | 54.21 | A | N |
| ATOM | 1120 | N | SER | A | 456 | 18.901 | 5.895 | 16.030 | 1.00 | 55.55 | A | N |
| ATOM | 1121 | CA | SER | A | 456 | 19.691 | 5.009 | 16.871 | 1.00 | 56.34 | A | C |
| ATOM | 1122 | C | SER | A | 456 | 20.538 | 3.905 | 16.230 | 1.00 | 57.25 | A | C |
| ATOM | 1123 | O | SER | A | 456 | 21.726 | 3.784 | 16.529 | 1.00 | 57.47 | A | O |
| ATOM | 1124 | CB | SER | A | 456 | 18.774 | 4.417 | 17.946 | 1.00 | 56.22 | A | C |
| ATOM | 1125 | OG | SER | A | 456 | 18.187 | 5.455 | 18.724 | 1.00 | 54.51 | A | O |
| ATOM | 1126 | N | GLY | A | 457 | 19.947 | 3.105 | 15.354 | 1.00 | 58.27 | A | N |
| ATOM | 1127 | CA | GLY | A | 457 | 20.697 | 2.016 | 14.747 | 1.00 | 59.73 | A | C |
| ATOM | 1128 | C | GLY | A | 457 | 21.677 | 2.338 | 13.628 | 1.00 | 60.53 | A | C |
| ATOM | 1129 | O | GLY | A | 457 | 22.459 | 1.470 | 13.222 | 1.00 | 60.34 | A | O |
| ATOM | 1130 | N | VAL | A | 458 | 21.643 | 3.570 | 13.123 | 1.00 | 61.46 | A | N |
| ATOM | 1131 | CA | VAL | A | 458 | 22.542 | 3.978 | 12.043 | 1.00 | 62.04 | A | C |
| ATOM | 1132 | C | VAL | A | 458 | 24.010 | 3.713 | 12.418 | 1.00 | 62.53 | A | C |
| ATOM | 1133 | O | VAL | A | 458 | 24.866 | 3.506 | 11.554 | 1.00 | 62.62 | A | O |
| ATOM | 1134 | CB | VAL | A | 458 | 22.371 | 5.489 | 11.710 | 1.00 | 62.21 | A | C |
| ATOM | 1135 | CG1 | VAL | A | 458 | 20.892 | 5.820 | 11.527 | 1.00 | 61.59 | A | C |
| ATOM | 1136 | CG2 | VAL | A | 458 | 22.997 | 6.350 | 12.811 | 1.00 | 62.35 | A | C |
| ATOM | 1137 | N | LYS | A | 472 | 22.182 | 3.215 | 5.290 | 1.00 | 74.28 | A | N |
| ATOM | 1138 | CA | LYS | A | 472 | 21.878 | 3.712 | 3.952 | 1.00 | 74.48 | A | C |
| ATOM | 1139 | C | LYS | A | 472 | 21.283 | 5.116 | 3.980 | 1.00 | 74.58 | A | C |
| ATOM | 1140 | O | LYS | A | 472 | 20.775 | 5.573 | 5.005 | 1.00 | 74.11 | A | O |
| ATOM | 1141 | CB | LYS | A | 472 | 20.911 | 2.765 | 3.241 | 1.00 | 74.40 | A | C |
| ATOM | 1142 | CG | LYS | A | 472 | 19.524 | 2.694 | 3.862 | 1.00 | 73.72 | A | C |
| ATOM | 1143 | CD | LYS | A | 472 | 18.848 | 1.391 | 3.484 | 1.00 | 73.06 | A | C |
| ATOM | 1144 | CE | LYS | A | 472 | 19.713 | 0.213 | 3.925 | 1.00 | 72.45 | A | C |
| ATOM | 1145 | NZ | LYS | A | 472 | 19.241 | −1.099 | 3.420 | 1.00 | 72.10 | A | N |
| ATOM | 1146 | N | ASP | A | 473 | 21.350 | 5.788 | 2.836 | 1.00 | 75.04 | A | N |
| ATOM | 1147 | CA | ASP | A | 473 | 20.841 | 7.147 | 2.696 | 1.00 | 75.30 | A | C |
| ATOM | 1148 | C | ASP | A | 473 | 19.318 | 7.206 | 2.790 | 1.00 | 74.96 | A | C |
| ATOM | 1149 | O | ASP | A | 473 | 18.753 | 8.238 | 3.169 | 1.00 | 74.67 | A | O |
| ATOM | 1150 | CB | ASP | A | 473 | 21.314 | 7.744 | 1.358 | 1.00 | 76.30 | A | C |
| ATOM | 1151 | CG | ASP | A | 473 | 20.803 | 9.163 | 1.131 | 1.00 | 76.97 | A | C |
| ATOM | 1152 | OD1 | ASP | A | 473 | 21.002 | 10.020 | 2.017 | 1.00 | 77.61 | A | O |
| ATOM | 1153 | OD2 | ASP | A | 473 | 20.206 | 9.427 | 0.065 | 1.00 | 77.15 | A | O |
| ATOM | 1154 | N | HIS | A | 474 | 18.654 | 6.102 | 2.449 | 1.00 | 74.53 | A | N |
| ATOM | 1155 | CA | HIS | A | 474 | 17.200 | 6.045 | 2.538 | 1.00 | 73.99 | A | C |
| ATOM | 1156 | C | HIS | A | 474 | 16.706 | 6.449 | 3.928 | 1.00 | 72.44 | A | C |
| ATOM | 1157 | O | HIS | A | 474 | 15.874 | 7.330 | 4.097 | 1.00 | 71.85 | A | O |
| ATOM | 1158 | CB | HIS | A | 474 | 16.760 | 4.614 | 2.223 | 1.00 | 75.91 | A | C |
| ATOM | 1159 | CG | HIS | A | 474 | 15.257 | 4.524 | 2.295 | 1.00 | 77.65 | A | C |
| ATOM | 1160 | ND1 | HIS | A | 474 | 14.592 | 3.371 | 2.550 | 1.00 | 78.14 | A | N |
| ATOM | 1161 | CD2 | HIS | A | 474 | 14.320 | 5.549 | 2.126 | 1.00 | 78.10 | A | C |
| ATOM | 1162 | CE1 | HIS | A | 474 | 13.284 | 3.695 | 2.538 | 1.00 | 78.52 | A | C |
| ATOM | 1163 | NE2 | HIS | A | 474 | 13.092 | 4.993 | 2.287 | 1.00 | 78.57 | A | N |
| ATOM | 1164 | N | ILE | A | 475 | 17.224 | 5.737 | 4.946 | 1.00 | 70.73 | A | N |
| ATOM | 1165 | CA | ILE | A | 475 | 16.823 | 6.046 | 6.313 | 1.00 | 68.83 | A | C |
| ATOM | 1166 | C | ILE | A | 475 | 16.915 | 7.546 | 6.598 | 1.00 | 67.82 | A | C |
| ATOM | 1167 | O | ILE | A | 475 | 16.139 | 8.118 | 7.352 | 1.00 | 67.23 | A | O |
| ATOM | 1168 | CB | ILE | A | 475 | 17.738 | 5.276 | 7.267 | 1.00 | 68.30 | A | C |
| ATOM | 1169 | CG1 | ILE | A | 475 | 17.266 | 3.826 | 7.397 | 1.00 | 67.68 | A | C |
| ATOM | 1170 | CG2 | ILE | A | 475 | 17.686 | 5.915 | 8.667 | 1.00 | 67.80 | A | C |
| ATOM | 1171 | CD1 | ILE | A | 475 | 18.227 | 2.974 | 8.227 | 1.00 | 67.20 | A | C |
| ATOM | 1172 | N | HIS | A | 476 | 17.937 | 8.179 | 5.992 | 1.00 | 67.40 | A | N |
| ATOM | 1173 | CA | HIS | A | 476 | 18.111 | 9.612 | 6.190 | 1.00 | 67.37 | A | C |
| ATOM | 1174 | C | HIS | A | 476 | 16.986 | 10.411 | 5.529 | 1.00 | 66.06 | A | C |
| ATOM | 1175 | O | HIS | A | 476 | 16.495 | 11.404 | 6.050 | 1.00 | 65.66 | A | O |
| ATOM | 1176 | CB | HIS | A | 476 | 19.459 | 10.019 | 5.594 | 1.00 | 69.38 | A | C |
| ATOM | 1177 | CG | HIS | A | 476 | 19.992 | 11.217 | 6.335 | 1.00 | 71.32 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1178 | ND1 | HIS | A | 476 | 20.360 | 11.182 | 7.640 | 1.00 | 72.16 | A | N |
| ATOM | 1179 | CD2 | HIS | A | 476 | 20.171 | 12.520 | 5.858 | 1.00 | 72.01 | A | C |
| ATOM | 1180 | CE1 | HIS | A | 476 | 20.751 | 12.436 | 7.940 | 1.00 | 72.46 | A | C |
| ATOM | 1181 | NE2 | HIS | A | 476 | 20.648 | 13.258 | 6.892 | 1.00 | 72.48 | A | N |
| ATOM | 1182 | N | ARG | A | 477 | 16.608 | 9.966 | 4.317 | 1.00 | 64.81 | A | N |
| ATOM | 1183 | CA | ARG | A | 477 | 15.529 | 10.643 | 3.610 | 1.00 | 63.21 | A | C |
| ATOM | 1184 | C | ARG | A | 477 | 14.269 | 10.738 | 4.473 | 1.00 | 60.98 | A | C |
| ATOM | 1185 | O | ARG | A | 477 | 13.696 | 11.802 | 4.666 | 1.00 | 59.65 | A | O |
| ATOM | 1186 | CB | ARG | A | 477 | 15.227 | 9.857 | 2.333 | 1.00 | 65.16 | A | C |
| ATOM | 1187 | CG | ARG | A | 477 | 16.445 | 9.749 | 1.416 | 1.00 | 66.69 | A | C |
| ATOM | 1188 | CD | ARG | A | 477 | 16.062 | 9.857 | −0.065 | 1.00 | 68.12 | A | C |
| ATOM | 1189 | NE | ARG | A | 477 | 17.105 | 9.270 | −0.911 | 1.00 | 68.99 | A | N |
| ATOM | 1190 | CZ | ARG | A | 477 | 16.875 | 8.042 | −1.411 | 1.00 | 69.49 | A | C |
| ATOM | 1191 | NH1 | ARG | A | 477 | 15.742 | 7.416 | −1.142 | 1.00 | 69.63 | A | N |
| ATOM | 1192 | NH2 | ARG | A | 477 | 17.798 | 7.459 | −2.182 | 1.00 | 69.46 | A | N |
| ATOM | 1193 | N | VAL | A | 478 | 13.820 | 9.594 | 4.985 | 1.00 | 58.85 | A | N |
| ATOM | 1194 | CA | VAL | A | 478 | 12.630 | 9.565 | 5.832 | 1.00 | 56.99 | A | C |
| ATOM | 1195 | C | VAL | A | 478 | 12.866 | 10.533 | 6.988 | 1.00 | 56.11 | A | C |
| ATOM | 1196 | O | VAL | A | 478 | 12.061 | 11.444 | 7.240 | 1.00 | 55.25 | A | O |
| ATOM | 1197 | CB | VAL | A | 478 | 12.381 | 8.162 | 6.438 | 1.00 | 56.50 | A | C |
| ATOM | 1198 | CG1 | VAL | A | 478 | 11.040 | 8.152 | 7.156 | 1.00 | 55.45 | A | C |
| ATOM | 1199 | CG2 | VAL | A | 478 | 12.434 | 7.090 | 5.352 | 1.00 | 55.63 | A | C |
| ATOM | 1200 | N | LEU | A | 479 | 13.986 | 10.302 | 7.682 | 1.00 | 55.45 | A | N |
| ATOM | 1201 | CA | LEU | A | 479 | 14.426 | 11.104 | 8.818 | 1.00 | 54.55 | A | C |
| ATOM | 1202 | C | LEU | A | 479 | 14.354 | 12.573 | 8.475 | 1.00 | 54.13 | A | C |
| ATOM | 1203 | O | LEU | A | 479 | 14.057 | 13.407 | 9.328 | 1.00 | 53.53 | A | O |
| ATOM | 1204 | CB | LEU | A | 479 | 15.859 | 10.743 | 9.184 | 1.00 | 54.28 | A | C |
| ATOM | 1205 | CG | LEU | A | 479 | 15.985 | 10.029 | 10.520 | 1.00 | 54.08 | A | C |
| ATOM | 1206 | CD1 | LEU | A | 479 | 17.361 | 9.403 | 10.645 | 1.00 | 54.28 | A | C |
| ATOM | 1207 | CD2 | LEU | A | 479 | 15.708 | 11.026 | 11.627 | 1.00 | 53.52 | A | C |
| ATOM | 1208 | N | ASP | A | 480 | 14.636 | 12.881 | 7.213 | 1.00 | 53.92 | A | N |
| ATOM | 1209 | CA | ASP | A | 480 | 14.583 | 14.258 | 6.741 | 1.00 | 53.86 | A | C |
| ATOM | 1210 | C | ASP | A | 480 | 13.111 | 14.674 | 6.530 | 1.00 | 53.31 | A | C |
| ATOM | 1211 | O | ASP | A | 480 | 12.720 | 15.809 | 6.823 | 1.00 | 53.07 | A | O |
| ATOM | 1212 | CB | ASP | A | 480 | 15.405 | 14.401 | 5.444 | 1.00 | 54.23 | A | C |
| ATOM | 1213 | CG | ASP | A | 480 | 16.879 | 13.987 | 5.620 | 1.00 | 54.10 | A | C |
| ATOM | 1214 | OD1 | ASP | A | 480 | 17.389 | 13.988 | 6.766 | 1.00 | 53.75 | A | O |
| ATOM | 1215 | OD2 | ASP | A | 480 | 17.539 | 13.675 | 4.603 | 1.00 | 54.36 | A | O |
| ATOM | 1216 | N | LYS | A | 481 | 12.282 | 13.750 | 6.051 | 1.00 | 52.71 | A | N |
| ATOM | 1217 | CA | LYS | A | 481 | 10.871 | 14.071 | 5.846 | 1.00 | 51.51 | A | C |
| ATOM | 1218 | C | LYS | A | 481 | 10.178 | 14.373 | 7.186 | 1.00 | 49.90 | A | C |
| ATOM | 1219 | O | LYS | A | 481 | 9.314 | 15.250 | 7.260 | 1.00 | 49.38 | A | O |
| ATOM | 1220 | CB | LYS | A | 481 | 10.174 | 12.923 | 5.097 | 1.00 | 52.15 | A | C |
| ATOM | 1221 | CG | LYS | A | 481 | 8.639 | 13.046 | 4.980 | 1.00 | 53.76 | A | C |
| ATOM | 1222 | CD | LYS | A | 481 | 8.133 | 14.436 | 4.525 | 1.00 | 53.79 | A | C |
| ATOM | 1223 | CE | LYS | A | 481 | 8.491 | 14.744 | 3.068 | 1.00 | 54.31 | A | C |
| ATOM | 1224 | NZ | LYS | A | 481 | 8.104 | 16.135 | 2.667 | 1.00 | 54.63 | A | N |
| ATOM | 1225 | N | ILE | A | 482 | 10.570 | 13.663 | 8.244 | 1.00 | 48.62 | A | N |
| ATOM | 1226 | CA | ILE | A | 482 | 9.992 | 13.882 | 9.577 | 1.00 | 47.41 | A | C |
| ATOM | 1227 | C | ILE | A | 482 | 10.364 | 15.261 | 10.117 | 1.00 | 46.93 | A | C |
| ATOM | 1228 | O | ILE | A | 482 | 9.599 | 15.883 | 10.868 | 1.00 | 45.83 | A | O |
| ATOM | 1229 | CB | ILE | A | 482 | 10.483 | 12.829 | 10.588 | 1.00 | 47.12 | A | C |
| ATOM | 1230 | CG1 | ILE | A | 482 | 10.063 | 11.436 | 10.135 | 1.00 | 46.42 | A | C |
| ATOM | 1231 | CG2 | ILE | A | 482 | 9.900 | 13.110 | 11.966 | 1.00 | 47.21 | A | C |
| ATOM | 1232 | CD1 | ILE | A | 482 | 10.567 | 10.353 | 11.040 | 1.00 | 46.70 | A | C |
| ATOM | 1233 | N | THR | A | 483 | 11.551 | 15.729 | 9.733 | 1.00 | 47.40 | A | N |
| ATOM | 1234 | CA | THR | A | 483 | 12.045 | 17.037 | 10.157 | 1.00 | 47.60 | A | C |
| ATOM | 1235 | C | THR | A | 483 | 11.111 | 18.061 | 9.517 | 1.00 | 48.57 | A | C |
| ATOM | 1236 | O | THR | A | 483 | 10.657 | 19.018 | 10.166 | 1.00 | 47.79 | A | O |
| ATOM | 1237 | CB | THR | A | 483 | 13.507 | 17.255 | 9.684 | 1.00 | 46.95 | A | C |
| ATOM | 1238 | OG1 | THR | A | 483 | 14.273 | 16.069 | 9.933 | 1.00 | 45.26 | A | C |
| ATOM | 1239 | CG2 | THR | A | 483 | 14.144 | 18.402 | 10.426 | 1.00 | 45.84 | A | C |
| ATOM | 1240 | N | ASP | A | 484 | 10.799 | 17.832 | 8.242 | 1.00 | 49.97 | A | N |
| ATOM | 1241 | CA | ASP | A | 484 | 9.895 | 18.724 | 7.523 | 1.00 | 51.56 | A | C |
| ATOM | 1242 | C | ASP | A | 484 | 8.533 | 18.684 | 8.197 | 1.00 | 51.61 | A | C |
| ATOM | 1243 | O | ASP | A | 484 | 7.937 | 19.730 | 8.469 | 1.00 | 51.69 | A | O |
| ATOM | 1244 | CB | ASP | A | 484 | 9.775 | 18.305 | 6.053 | 1.00 | 52.55 | A | C |
| ATOM | 1245 | CG | ASP | A | 484 | 11.122 | 18.288 | 5.344 | 1.00 | 53.37 | A | C |
| ATOM | 1246 | OD1 | ASP | A | 484 | 12.073 | 18.904 | 5.880 | 1.00 | 52.52 | A | O |
| ATOM | 1247 | OD2 | ASP | A | 484 | 11.225 | 17.667 | 4.258 | 1.00 | 53.86 | A | O |
| ATOM | 1248 | N | THR | A | 485 | 8.050 | 17.475 | 8.477 | 1.00 | 51.86 | A | N |
| ATOM | 1249 | CA | THR | A | 485 | 6.759 | 17.310 | 9.142 | 1.00 | 52.08 | A | C |
| ATOM | 1250 | C | THR | A | 485 | 6.739 | 18.156 | 10.422 | 1.00 | 52.95 | A | C |
| ATOM | 1251 | O | THR | A | 485 | 5.919 | 19.064 | 10.568 | 1.00 | 52.85 | A | O |
| ATOM | 1252 | CB | THR | A | 485 | 6.508 | 15.835 | 9.524 | 1.00 | 51.23 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1253 | OG1 | THR | A | 485 | 6.756 | 14.994 | 8.387 | 1.00 | 50.47 | A | O |
| ATOM | 1254 | CG2 | THR | A | 485 | 5.069 | 15.650 | 9.998 | 1.00 | 49.62 | A | C |
| ATOM | 1255 | N | LEU | A | 486 | 7.659 | 17.860 | 11.339 | 1.00 | 54.02 | A | N |
| ATOM | 1256 | CA | LEU | A | 486 | 7.750 | 18.589 | 12.605 | 1.00 | 55.02 | A | C |
| ATOM | 1257 | C | LEU | A | 486 | 7.713 | 20.107 | 12.465 | 1.00 | 55.65 | A | C |
| ATOM | 1258 | O | LEU | A | 486 | 6.982 | 20.767 | 13.202 | 1.00 | 55.02 | A | O |
| ATOM | 1259 | CB | LEU | A | 486 | 9.009 | 18.175 | 13.379 | 1.00 | 54.73 | A | C |
| ATOM | 1260 | CG | LEU | A | 486 | 8.862 | 16.962 | 14.302 | 1.00 | 53.87 | A | C |
| ATOM | 1261 | CD1 | LEU | A | 486 | 10.207 | 16.622 | 14.899 | 1.00 | 53.99 | A | C |
| ATOM | 1262 | CD2 | LEU | A | 486 | 7.861 | 17.270 | 15.406 | 1.00 | 53.25 | A | C |
| ATOM | 1263 | N | ILE | A | 487 | 8.495 | 20.670 | 11.543 | 1.00 | 57.00 | A | N |
| ATOM | 1264 | CA | ILE | A | 487 | 8.469 | 22.124 | 11.375 | 1.00 | 58.40 | A | C |
| ATOM | 1265 | C | ILE | A | 487 | 7.072 | 22.527 | 10.912 | 1.00 | 59.59 | A | C |
| ATOM | 1266 | O | ILE | A | 487 | 6.532 | 23.543 | 11.360 | 1.00 | 59.37 | A | O |
| ATOM | 1267 | CB | ILE | A | 487 | 9.514 | 22.639 | 10.343 | 1.00 | 58.15 | A | C |
| ATOM | 1268 | CG1 | ILE | A | 487 | 10.923 | 22.603 | 10.941 | 1.00 | 57.04 | A | C |
| ATOM | 1269 | CG2 | ILE | A | 487 | 9.200 | 24.101 | 9.968 | 1.00 | 58.59 | A | C |
| ATOM | 1270 | CD1 | ILE | A | 487 | 11.196 | 23.738 | 11.919 | 1.00 | 56.27 | A | C |
| ATOM | 1271 | N | HIS | A | 488 | 6.477 | 21.733 | 10.024 | 1.00 | 61.17 | A | N |
| ATOM | 1272 | CA | HIS | A | 488 | 5.132 | 22.060 | 9.563 | 1.00 | 62.90 | A | C |
| ATOM | 1273 | C | HIS | A | 488 | 4.168 | 22.166 | 10.744 | 1.00 | 63.48 | A | C |
| ATOM | 1274 | O | HIS | A | 488 | 3.465 | 23.176 | 10.883 | 1.00 | 63.31 | A | O |
| ATOM | 1275 | CB | HIS | A | 488 | 4.599 | 21.011 | 8.585 | 1.00 | 64.03 | A | C |
| ATOM | 1276 | CG | HIS | A | 488 | 3.140 | 21.178 | 8.269 | 1.00 | 65.25 | A | C |
| ATOM | 1277 | ND1 | HIS | A | 488 | 2.627 | 22.331 | 7.713 | 1.00 | 65.47 | A | N |
| ATOM | 1278 | CD2 | HIS | A | 488 | 2.083 | 20.351 | 8.460 | 1.00 | 65.58 | A | C |
| ATOM | 1279 | CE1 | HIS | A | 488 | 1.318 | 22.206 | 7.574 | 1.00 | 65.67 | A | C |
| ATOM | 1280 | NE2 | HIS | A | 488 | 0.963 | 21.014 | 8.021 | 1.00 | 65.58 | A | N |
| ATOM | 1281 | N | LEU | A | 489 | 4.132 | 21.117 | 11.576 | 1.00 | 63.89 | A | N |
| ATOM | 1282 | CA | LEU | A | 489 | 3.259 | 21.066 | 12.757 | 1.00 | 64.38 | A | C |
| ATOM | 1283 | C | LEU | A | 489 | 3.489 | 22.294 | 13.620 | 1.00 | 64.61 | A | C |
| ATOM | 1284 | O | LEU | A | 489 | 2.592 | 22.772 | 14.315 | 1.00 | 64.14 | A | O |
| ATOM | 1285 | CB | LEU | A | 489 | 3.557 | 19.823 | 13.593 | 1.00 | 64.43 | A | C |
| ATOM | 1286 | CG | LEU | A | 489 | 3.437 | 18.466 | 12.906 | 1.00 | 64.95 | A | C |
| ATOM | 1287 | CD1 | LEU | A | 489 | 3.933 | 17.389 | 13.861 | 1.00 | 65.34 | A | C |
| ATOM | 1288 | CD2 | LEU | A | 489 | 1.992 | 18.208 | 12.494 | 1.00 | 64.75 | A | C |
| ATOM | 1289 | N | MET | A | 490 | 4.720 | 22.786 | 13.575 | 1.00 | 65.24 | A | N |
| ATOM | 1290 | CA | MET | A | 490 | 5.106 | 23.960 | 14.329 | 1.00 | 65.71 | A | C |
| ATOM | 1291 | C | MET | A | 490 | 4.685 | 25.198 | 13.543 | 1.00 | 66.38 | A | C |
| ATOM | 1292 | O | MET | A | 490 | 4.366 | 26.241 | 14.121 | 1.00 | 66.50 | A | O |
| ATOM | 1293 | CB | MET | A | 490 | 6.618 | 23.924 | 14.569 | 1.00 | 64.96 | A | C |
| ATOM | 1294 | CG | MET | A | 490 | 7.035 | 22.776 | 15.490 | 1.00 | 63.83 | A | C |
| ATOM | 1295 | SD | MET | A | 490 | 8.799 | 22.671 | 15.803 | 1.00 | 62.05 | A | S |
| ATOM | 1296 | CE | MET | A | 490 | 9.159 | 21.009 | 15.275 | 1.00 | 62.59 | A | C |
| ATOM | 1297 | N | ALA | A | 491 | 4.675 | 25.071 | 12.220 | 1.00 | 66.95 | A | N |
| ATOM | 1298 | CA | ALA | A | 491 | 4.263 | 26.165 | 11.358 | 1.00 | 67.52 | A | C |
| ATOM | 1299 | C | ALA | A | 491 | 2.774 | 26.413 | 11.620 | 1.00 | 68.38 | A | C |
| ATOM | 1300 | O | ALA | A | 491 | 2.388 | 27.480 | 12.108 | 1.00 | 67.98 | A | O |
| ATOM | 1301 | CB | ALA | A | 491 | 4.495 | 25.793 | 9.896 | 1.00 | 67.24 | A | C |
| ATOM | 1302 | N | LYS | A | 492 | 1.952 | 25.407 | 11.314 | 1.00 | 69.36 | A | N |
| ATOM | 1303 | CA | LYS | A | 492 | 0.499 | 25.482 | 11.505 | 1.00 | 70.20 | A | C |
| ATOM | 1304 | C | LYS | A | 492 | 0.067 | 25.843 | 12.919 | 1.00 | 70.33 | A | C |
| ATOM | 1305 | O | LYS | A | 492 | −1.056 | 26.299 | 13.127 | 1.00 | 70.56 | A | O |
| ATOM | 1306 | CB | LYS | A | 492 | −0.173 | 24.149 | 11.131 | 1.00 | 71.02 | A | C |
| ATOM | 1307 | CG | LYS | A | 492 | −0.467 | 23.932 | 9.648 | 1.00 | 72.29 | A | C |
| ATOM | 1308 | CD | LYS | A | 492 | −1.554 | 24.877 | 9.105 | 1.00 | 73.15 | A | C |
| ATOM | 1309 | CE | LYS | A | 492 | −1.005 | 26.273 | 8.798 | 1.00 | 73.66 | A | C |
| ATOM | 1310 | NZ | LYS | A | 492 | −2.054 | 27.214 | 8.327 | 1.00 | 74.06 | A | N |
| ATOM | 1311 | N | ALA | A | 493 | 0.945 | 25.632 | 13.893 | 1.00 | 70.50 | A | N |
| ATOM | 1312 | CA | ALA | A | 493 | 0.619 | 25.924 | 15.288 | 1.00 | 70.74 | A | C |
| ATOM | 1313 | C | ALA | A | 493 | 0.713 | 27.410 | 15.631 | 1.00 | 71.22 | A | C |
| ATOM | 1314 | O | ALA | A | 493 | 0.243 | 27.843 | 16.686 | 1.00 | 71.04 | A | O |
| ATOM | 1315 | CB | ALA | A | 493 | 1.523 | 25.112 | 16.207 | 1.00 | 70.39 | A | C |
| ATOM | 1316 | N | GLY | A | 494 | 1.319 | 28.187 | 14.741 | 1.00 | 71.78 | A | N |
| ATOM | 1317 | CA | GLY | A | 494 | 1.440 | 29.612 | 14.985 | 1.00 | 72.69 | A | C |
| ATOM | 1318 | C | GLY | A | 494 | 2.747 | 30.057 | 15.620 | 1.00 | 73.13 | A | C |
| ATOM | 1319 | O | GLY | A | 494 | 2.760 | 30.982 | 16.432 | 1.00 | 73.02 | A | O |
| ATOM | 1320 | N | LEU | A | 495 | 3.846 | 29.401 | 15.260 | 1.00 | 73.78 | A | N |
| ATOM | 1321 | CA | LEU | A | 495 | 5.152 | 29.765 | 15.798 | 1.00 | 74.44 | A | C |
| ATOM | 1322 | C | LEU | A | 495 | 6.008 | 30.396 | 14.706 | 1.00 | 74.84 | A | C |
| ATOM | 1323 | O | LEU | A | 495 | 5.992 | 29.948 | 13.553 | 1.00 | 74.86 | A | O |
| ATOM | 1324 | CB | LEU | A | 495 | 5.872 | 28.537 | 16.365 | 1.00 | 74.50 | A | C |
| ATOM | 1325 | CG | LEU | A | 495 | 5.189 | 27.827 | 17.533 | 1.00 | 74.79 | A | C |
| ATOM | 1326 | CD1 | LEU | A | 495 | 4.046 | 26.958 | 17.016 | 1.00 | 74.96 | A | C |
| ATOM | 1327 | CD2 | LEU | A | 495 | 6.205 | 26.979 | 18.266 | 1.00 | 74.98 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1328 | N | THR | A | 496 | 6.752 | 31.437 | 15.075 | 1.00 | 75.04 | A | N |
| ATOM | 1329 | CA | THR | A | 496 | 7.618 | 32.140 | 14.131 | 1.00 | 75.07 | A | C |
| ATOM | 1330 | C | THR | A | 496 | 8.583 | 31.166 | 13.482 | 1.00 | 74.93 | A | C |
| ATOM | 1331 | O | THR | A | 496 | 8.656 | 30.004 | 13.875 | 1.00 | 75.16 | A | O |
| ATOM | 1332 | CB | THR | A | 496 | 8.460 | 33.219 | 14.826 | 1.00 | 75.24 | A | C |
| ATOM | 1333 | OG1 | THR | A | 496 | 9.374 | 32.584 | 15.725 | 1.00 | 75.69 | A | O |
| ATOM | 1334 | CG2 | THR | A | 496 | 7.571 | 34.194 | 15.604 | 1.00 | 74.65 | A | C |
| ATOM | 1335 | N | LEU | A | 497 | 9.323 | 31.644 | 12.487 | 1.00 | 74.72 | A | N |
| ATOM | 1336 | CA | LEU | A | 497 | 10.293 | 30.800 | 11.808 | 1.00 | 74.84 | A | C |
| ATOM | 1337 | C | LEU | A | 497 | 11.492 | 30.641 | 12.733 | 1.00 | 74.79 | A | C |
| ATOM | 1338 | O | LEU | A | 497 | 12.452 | 29.925 | 12.421 | 1.00 | 74.84 | A | O |
| ATOM | 1339 | CB | LEU | A | 497 | 10.707 | 31.426 | 10.475 | 1.00 | 74.94 | A | C |
| ATOM | 1340 | CG | LEU | A | 497 | 10.148 | 30.709 | 9.239 | 1.00 | 74.85 | A | C |
| ATOM | 1341 | CD1 | LEU | A | 497 | 10.308 | 31.585 | 8.001 | 1.00 | 74.62 | A | C |
| ATOM | 1342 | CD2 | LEU | A | 497 | 10.862 | 29.371 | 9.069 | 1.00 | 74.30 | A | C |
| ATOM | 1343 | N | GLN | A | 498 | 11.420 | 31.326 | 13.874 | 1.00 | 74.36 | A | N |
| ATOM | 1344 | CA | GLN | A | 498 | 12.461 | 31.263 | 14.894 | 1.00 | 73.62 | A | C |
| ATOM | 1345 | C | GLN | A | 498 | 11.964 | 30.240 | 15.916 | 1.00 | 72.94 | A | C |
| ATOM | 1346 | O | GLN | A | 498 | 12.624 | 29.228 | 16.176 | 1.00 | 73.02 | A | O |
| ATOM | 1347 | CB | GLN | A | 498 | 12.659 | 32.641 | 15.561 | 1.00 | 73.61 | A | C |
| ATOM | 1348 | CG | GLN | A | 498 | 13.885 | 32.735 | 16.485 | 1.00 | 73.40 | A | C |
| ATOM | 1349 | CD | GLN | A | 498 | 14.202 | 34.165 | 16.940 | 1.00 | 73.40 | A | C |
| ATOM | 1350 | OE1 | GLN | A | 498 | 13.413 | 34.805 | 17.642 | 1.00 | 72.83 | A | O |
| ATOM | 1351 | NE2 | GLN | A | 498 | 15.370 | 34.666 | 16.539 | 1.00 | 73.45 | A | N |
| ATOM | 1352 | N | GLN | A | 499 | 10.782 | 30.503 | 16.468 | 1.00 | 72.04 | A | N |
| ATOM | 1353 | CA | GLN | A | 499 | 10.166 | 29.622 | 17.449 | 1.00 | 70.94 | A | C |
| ATOM | 1354 | C | GLN | A | 499 | 10.059 | 28.193 | 16.908 | 1.00 | 70.32 | A | C |
| ATOM | 1355 | O | GLN | A | 499 | 9.722 | 27.269 | 17.648 | 1.00 | 70.61 | A | O |
| ATOM | 1356 | CB | GLN | A | 499 | 8.768 | 30.142 | 17.829 | 1.00 | 70.93 | A | C |
| ATOM | 1357 | CG | GLN | A | 499 | 8.744 | 31.545 | 18.448 | 1.00 | 70.33 | A | C |
| ATOM | 1358 | CD | GLN | A | 499 | 7.337 | 32.010 | 18.822 | 1.00 | 70.02 | A | C |
| ATOM | 1359 | OE1 | GLN | A | 499 | 6.419 | 31.964 | 18.001 | 1.00 | 70.12 | A | O |
| ATOM | 1360 | NE2 | GLN | A | 499 | 7.167 | 32.468 | 20.061 | 1.00 | 69.21 | A | N |
| ATOM | 1361 | N | GLN | A | 500 | 10.346 | 28.017 | 15.620 | 1.00 | 69.23 | A | N |
| ATOM | 1362 | CA | GLN | A | 500 | 10.290 | 26.702 | 14.989 | 1.00 | 68.35 | A | C |
| ATOM | 1363 | C | GLN | A | 500 | 11.632 | 25.989 | 15.051 | 1.00 | 67.47 | A | C |
| ATOM | 1364 | O | GLN | A | 500 | 11.692 | 24.805 | 15.375 | 1.00 | 67.81 | A | O |
| ATOM | 1365 | CB | GLN | A | 500 | 9.856 | 26.825 | 13.527 | 1.00 | 68.80 | A | C |
| ATOM | 1366 | CG | GLN | A | 500 | 8.369 | 27.062 | 13.322 | 1.00 | 68.85 | A | C |
| ATOM | 1367 | CD | GLN | A | 500 | 8.058 | 27.577 | 11.929 | 1.00 | 68.84 | A | C |
| ATOM | 1368 | OE1 | GLN | A | 500 | 8.496 | 27.000 | 10.930 | 1.00 | 69.48 | A | O |
| ATOM | 1369 | NE2 | GLN | A | 500 | 7.297 | 28.664 | 11.855 | 1.00 | 67.60 | A | N |
| ATOM | 1370 | N | HIS | A | 501 | 12.709 | 26.704 | 14.733 | 1.00 | 66.33 | A | N |
| ATOM | 1371 | CA | HIS | A | 501 | 14.045 | 26.104 | 14.760 | 1.00 | 65.01 | A | C |
| ATOM | 1372 | C | HIS | A | 501 | 14.422 | 25.762 | 16.197 | 1.00 | 62.84 | A | C |
| ATOM | 1373 | O | HIS | A | 501 | 15.001 | 24.711 | 16.467 | 1.00 | 62.35 | A | O |
| ATOM | 1374 | CB | HIS | A | 501 | 15.093 | 27.058 | 14.163 | 1.00 | 66.42 | A | C |
| ATOM | 1375 | CG | HIS | A | 501 | 14.793 | 27.491 | 12.758 | 1.00 | 67.57 | A | C |
| ATOM | 1376 | ND1 | HIS | A | 501 | 15.636 | 28.310 | 12.037 | 1.00 | 68.20 | A | N |
| ATOM | 1377 | CD2 | HIS | A | 501 | 13.725 | 27.255 | 11.958 | 1.00 | 67.89 | A | C |
| ATOM | 1378 | CE1 | HIS | A | 501 | 15.098 | 28.561 | 10.856 | 1.00 | 68.23 | A | C |
| ATOM | 1379 | NE2 | HIS | A | 501 | 13.938 | 27.934 | 10.783 | 1.00 | 67.64 | A | N |
| ATOM | 1380 | N | GLN | A | 502 | 14.073 | 26.653 | 17.117 | 1.00 | 60.30 | A | N |
| ATOM | 1381 | CA | GLN | A | 502 | 14.371 | 26.444 | 18.525 | 1.00 | 57.84 | A | C |
| ATOM | 1382 | C | GLN | A | 502 | 13.708 | 25.186 | 19.070 | 1.00 | 55.86 | A | C |
| ATOM | 1383 | O | GLN | A | 502 | 14.382 | 24.344 | 19.667 | 1.00 | 55.41 | A | O |
| ATOM | 1384 | CB | GLN | A | 502 | 13.915 | 27.644 | 19.343 | 1.00 | 58.11 | A | C |
| ATOM | 1385 | CG | GLN | A | 502 | 14.402 | 28.974 | 18.810 | 1.00 | 58.18 | A | C |
| ATOM | 1386 | CD | GLN | A | 502 | 14.644 | 29.974 | 19.919 | 1.00 | 58.46 | A | C |
| ATOM | 1387 | OE1 | GLN | A | 502 | 13.789 | 30.183 | 20.785 | 1.00 | 58.16 | A | O |
| ATOM | 1388 | NE2 | GLN | A | 502 | 15.816 | 30.602 | 19.899 | 1.00 | 58.79 | A | N |
| ATOM | 1389 | N | ARG | A | 503 | 12.394 | 25.067 | 18.858 | 1.00 | 53.42 | A | N |
| ATOM | 1390 | CA | ARG | A | 503 | 11.627 | 23.915 | 19.330 | 1.00 | 51.15 | A | C |
| ATOM | 1391 | C | ARG | A | 503 | 12.090 | 22.636 | 18.633 | 1.00 | 50.16 | A | C |
| ATOM | 1392 | O | ARG | A | 503 | 12.072 | 21.547 | 19.208 | 1.00 | 49.32 | A | O |
| ATOM | 1393 | CB | ARG | A | 503 | 10.124 | 24.144 | 19.100 | 1.00 | 50.05 | A | C |
| ATOM | 1394 | CG | ARG | A | 503 | 9.215 | 23.115 | 19.781 | 1.00 | 48.24 | A | C |
| ATOM | 1395 | CD | ARG | A | 503 | 7.780 | 23.602 | 19.840 | 1.00 | 46.68 | A | C |
| ATOM | 1396 | NE | ARG | A | 503 | 6.843 | 22.613 | 20.384 | 1.00 | 45.00 | A | N |
| ATOM | 1397 | CZ | ARG | A | 503 | 6.684 | 22.330 | 21.677 | 1.00 | 43.84 | A | C |
| ATOM | 1398 | NH1 | ARG | A | 503 | 7.393 | 22.949 | 22.603 | 1.00 | 43.49 | A | N |
| ATOM | 1399 | NH2 | ARG | A | 503 | 5.798 | 21.424 | 22.050 | 1.00 | 43.84 | A | N |
| ATOM | 1400 | N | LEU | A | 504 | 12.522 | 22.770 | 17.392 | 1.00 | 49.11 | A | N |
| ATOM | 1401 | CA | LEU | A | 504 | 12.993 | 21.605 | 16.679 | 1.00 | 49.12 | A | C |
| ATOM | 1402 | C | LEU | A | 504 | 14.311 | 21.143 | 17.304 | 1.00 | 49.89 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1403 | O | LEU | A | 504 | 14.610 | 19.949 | 17.329 | 1.00 | 50.24 | A | O |
| ATOM | 1404 | CB | LEU | A | 504 | 13.219 | 21.943 | 15.213 | 1.00 | 47.84 | A | C |
| ATOM | 1405 | CG | LEU | A | 504 | 13.945 | 20.867 | 14.413 | 1.00 | 47.29 | A | C |
| ATOM | 1406 | CD1 | LEU | A | 504 | 13.043 | 19.673 | 14.219 | 1.00 | 46.69 | A | C |
| ATOM | 1407 | CD2 | LEU | A | 504 | 14.369 | 21.430 | 13.075 | 1.00 | 47.39 | A | C |
| ATOM | 1408 | N | ALA | A | 505 | 15.094 | 22.095 | 17.813 | 1.00 | 50.20 | A | N |
| ATOM | 1409 | CA | ALA | A | 505 | 16.394 | 21.797 | 18.417 | 1.00 | 49.72 | A | C |
| ATOM | 1410 | C | ALA | A | 505 | 16.218 | 21.282 | 19.831 | 1.00 | 49.72 | A | C |
| ATOM | 1411 | O | ALA | A | 505 | 16.896 | 20.331 | 20.237 | 1.00 | 49.69 | A | O |
| ATOM | 1412 | CB | ALA | A | 505 | 17.275 | 23.037 | 18.427 | 1.00 | 49.36 | A | C |
| ATOM | 1413 | N | GLN | A | 506 | 15.312 | 21.911 | 20.576 | 1.00 | 50.27 | A | N |
| ATOM | 1414 | CA | GLN | A | 506 | 15.052 | 21.506 | 21.951 | 1.00 | 50.66 | A | C |
| ATOM | 1415 | C | GLN | A | 506 | 14.629 | 20.029 | 22.004 | 1.00 | 50.07 | A | C |
| ATOM | 1416 | O | GLN | A | 506 | 15.179 | 19.237 | 22.768 | 1.00 | 50.60 | A | O |
| ATOM | 1417 | CB | GLN | A | 506 | 13.973 | 22.414 | 22.563 | 1.00 | 51.74 | A | C |
| ATOM | 1418 | CG | GLN | A | 506 | 14.208 | 23.911 | 22.368 | 1.00 | 54.10 | A | C |
| ATOM | 1419 | CD | GLN | A | 506 | 13.252 | 24.756 | 23.205 | 1.00 | 55.30 | A | C |
| ATOM | 1420 | OE1 | GLN | A | 506 | 12.061 | 24.430 | 23.352 | 1.00 | 56.05 | A | O |
| ATOM | 1421 | NE2 | GLN | A | 506 | 13.764 | 25.850 | 23.748 | 1.00 | 56.15 | A | N |
| ATOM | 1422 | N | LEU | A | 507 | 13.672 | 19.657 | 21.160 | 1.00 | 48.67 | A | N |
| ATOM | 1423 | CA | LEU | A | 507 | 13.170 | 18.278 | 21.113 | 1.00 | 46.61 | A | C |
| ATOM | 1424 | C | LEU | A | 507 | 14.275 | 17.298 | 20.774 | 1.00 | 45.04 | A | C |
| ATOM | 1425 | O | LEU | A | 507 | 14.376 | 16.220 | 21.350 | 1.00 | 44.81 | A | O |
| ATOM | 1426 | CB | LEU | A | 507 | 12.040 | 18.144 | 20.074 | 1.00 | 47.02 | A | C |
| ATOM | 1427 | CG | LEU | A | 507 | 10.809 | 19.004 | 20.359 | 1.00 | 47.08 | A | C |
| ATOM | 1428 | CD1 | LEU | A | 507 | 10.005 | 19.229 | 19.085 | 1.00 | 48.13 | A | C |
| ATOM | 1429 | CD2 | LEU | A | 507 | 9.965 | 18.332 | 21.427 | 1.00 | 46.59 | A | C |
| ATOM | 1430 | N | LEU | A | 508 | 15.120 | 17.682 | 19.836 | 1.00 | 42.89 | A | N |
| ATOM | 1431 | CA | LEU | A | 508 | 16.201 | 16.803 | 19.439 | 1.00 | 41.86 | A | C |
| ATOM | 1432 | C | LEU | A | 508 | 17.269 | 16.659 | 20.537 | 1.00 | 40.71 | A | C |
| ATOM | 1433 | O | LEU | A | 508 | 17.936 | 15.621 | 20.633 | 1.00 | 40.21 | A | O |
| ATOM | 1434 | CB | LEU | A | 508 | 16.826 | 17.302 | 18.131 | 1.00 | 41.66 | A | C |
| ATOM | 1435 | CG | LEU | A | 508 | 15.834 | 17.499 | 16.977 | 1.00 | 41.75 | A | C |
| ATOM | 1436 | CD1 | LEU | A | 508 | 16.584 | 17.936 | 15.719 | 1.00 | 41.79 | A | C |
| ATOM | 1437 | CD2 | LEU | A | 508 | 15.073 | 16.217 | 16.726 | 1.00 | 41.67 | A | C |
| ATOM | 1438 | N | LEU | A | 509 | 17.425 | 17.691 | 21.367 | 1.00 | 39.34 | A | N |
| ATOM | 1439 | CA | LEU | A | 509 | 18.406 | 17.639 | 22.447 | 1.00 | 37.48 | A | C |
| ATOM | 1440 | C | LEU | A | 509 | 17.823 | 16.704 | 23.487 | 1.00 | 36.41 | A | C |
| ATOM | 1441 | O | LEU | A | 509 | 18.512 | 15.799 | 23.967 | 1.00 | 36.13 | A | O |
| ATOM | 1442 | CB | LEU | A | 509 | 18.676 | 19.034 | 23.029 | 1.00 | 36.93 | A | C |
| ATOM | 1443 | CG | LEU | A | 509 | 19.436 | 19.952 | 22.050 | 1.00 | 36.54 | A | C |
| ATOM | 1444 | CD1 | LEU | A | 509 | 19.714 | 21.301 | 22.696 | 1.00 | 35.21 | A | C |
| ATOM | 1445 | CD2 | LEU | A | 509 | 20.734 | 19.279 | 21.625 | 1.00 | 36.01 | A | C |
| ATOM | 1446 | N | ILE | A | 510 | 16.542 | 16.884 | 23.799 | 1.00 | 34.80 | A | N |
| ATOM | 1447 | CA | ILE | A | 510 | 15.904 | 16.003 | 24.754 | 1.00 | 33.75 | A | C |
| ATOM | 1448 | C | ILE | A | 510 | 16.016 | 14.544 | 24.313 | 1.00 | 33.78 | A | C |
| ATOM | 1449 | O | ILE | A | 510 | 15.859 | 13.642 | 25.125 | 1.00 | 34.66 | A | O |
| ATOM | 1450 | CB | ILE | A | 510 | 14.436 | 16.338 | 24.926 | 1.00 | 32.85 | A | C |
| ATOM | 1451 | CG1 | ILE | A | 510 | 14.299 | 17.714 | 25.559 | 1.00 | 32.18 | A | C |
| ATOM | 1452 | CG2 | ILE | A | 510 | 13.766 | 15.302 | 25.802 | 1.00 | 32.45 | A | C |
| ATOM | 1453 | CD1 | ILE | A | 510 | 12.860 | 18.070 | 25.859 | 1.00 | 32.29 | A | C |
| ATOM | 1454 | N | LEU | A | 511 | 16.304 | 14.306 | 23.037 | 1.00 | 33.41 | A | N |
| ATOM | 1455 | CA | LEU | A | 511 | 16.414 | 12.936 | 22.540 | 1.00 | 33.11 | A | C |
| ATOM | 1456 | C | LEU | A | 511 | 17.760 | 12.300 | 22.898 | 1.00 | 32.78 | A | C |
| ATOM | 1457 | O | LEU | A | 511 | 17.876 | 11.080 | 23.030 | 1.00 | 32.92 | A | O |
| ATOM | 1458 | CB | LEU | A | 511 | 16.193 | 12.891 | 21.017 | 1.00 | 32.40 | A | C |
| ATOM | 1459 | CG | LEU | A | 511 | 14.853 | 13.367 | 20.425 | 1.00 | 32.21 | A | C |
| ATOM | 1460 | CD1 | LEU | A | 511 | 14.863 | 13.062 | 18.934 | 1.00 | 31.45 | A | C |
| ATOM | 1461 | CD2 | LEU | A | 511 | 13.648 | 12.675 | 21.076 | 1.00 | 31.12 | A | C |
| ATOM | 1462 | N | SER | A | 512 | 18.779 | 13.134 | 23.043 | 1.00 | 32.64 | A | N |
| ATOM | 1463 | CA | SER | A | 512 | 20.123 | 12.686 | 23.416 | 1.00 | 31.33 | A | C |
| ATOM | 1464 | C | SER | A | 512 | 20.134 | 12.248 | 24.906 | 1.00 | 30.79 | A | C |
| ATOM | 1465 | O | SER | A | 512 | 20.918 | 11.394 | 25.321 | 1.00 | 28.79 | A | O |
| ATOM | 1466 | CB | SER | A | 512 | 21.101 | 13.837 | 23.169 | 1.00 | 31.44 | A | C |
| ATOM | 1467 | OG | SER | A | 512 | 22.264 | 13.732 | 23.968 | 1.00 | 32.56 | A | O |
| ATOM | 1468 | N | HIS | A | 513 | 19.243 | 12.838 | 25.695 | 1.00 | 31.04 | A | N |
| ATOM | 1469 | CA | HIS | A | 513 | 19.119 | 12.503 | 27.102 | 1.00 | 32.54 | A | C |
| ATOM | 1470 | C | HIS | A | 513 | 18.422 | 11.156 | 27.213 | 1.00 | 31.63 | A | C |
| ATOM | 1471 | O | HIS | A | 513 | 18.703 | 10.367 | 28.130 | 1.00 | 30.82 | A | O |
| ATOM | 1472 | CB | HIS | A | 513 | 18.286 | 13.559 | 27.850 | 1.00 | 34.55 | A | C |
| ATOM | 1473 | CG | HIS | A | 513 | 18.944 | 14.905 | 27.934 | 1.00 | 37.80 | A | C |
| ATOM | 1474 | ND1 | HIS | A | 513 | 18.302 | 16.019 | 28.438 | 1.00 | 39.70 | A | N |
| ATOM | 1475 | CD2 | HIS | A | 513 | 20.182 | 15.317 | 27.574 | 1.00 | 38.70 | A | C |
| ATOM | 1476 | CE1 | HIS | A | 513 | 19.117 | 17.058 | 28.386 | 1.00 | 40.14 | A | C |
| ATOM | 1477 | NE2 | HIS | A | 513 | 20.265 | 16.659 | 27.866 | 1.00 | 40.21 | A | N |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1478 | N | ILE | A | 514 | 17.495 | 10.920 | 26.284 | 1.00 | 30.59 | A | N |
| ATOM | 1479 | CA | ILE | A | 514 | 16.739 | 9.688 | 26.251 | 1.00 | 29.03 | A | C |
| ATOM | 1480 | C | ILE | A | 514 | 17.695 | 8.556 | 25.907 | 1.00 | 28.28 | A | C |
| ATOM | 1481 | O | ILE | A | 514 | 17.604 | 7.452 | 26.461 | 1.00 | 27.99 | A | O |
| ATOM | 1482 | CB | ILE | A | 514 | 15.605 | 9.773 | 25.221 | 1.00 | 29.56 | A | C |
| ATOM | 1483 | CG1 | ILE | A | 514 | 14.629 | 10.859 | 25.669 | 1.00 | 29.73 | A | C |
| ATOM | 1484 | CG2 | ILE | A | 514 | 14.916 | 8.401 | 25.062 | 1.00 | 28.41 | A | C |
| ATOM | 1485 | CD1 | ILE | A | 514 | 13.270 | 10.833 | 24.966 | 1.00 | 31.20 | A | C |
| ATOM | 1486 | N | ARG | A | 515 | 18.629 | 8.841 | 25.007 | 1.00 | 26.93 | A | N |
| ATOM | 1487 | CA | ARG | A | 515 | 19.614 | 7.840 | 24.629 | 1.00 | 26.44 | A | C |
| ATOM | 1488 | C | ARG | A | 515 | 20.449 | 7.512 | 25.876 | 1.00 | 26.35 | A | C |
| ATOM | 1489 | O | ARG | A | 515 | 20.974 | 6.380 | 26.046 | 1.00 | 24.85 | A | O |
| ATOM | 1490 | CB | ARG | A | 515 | 20.521 | 8.404 | 23.533 | 1.00 | 24.91 | A | C |
| ATOM | 1491 | CG | ARG | A | 515 | 21.797 | 7.610 | 23.304 | 1.00 | 26.65 | A | C |
| ATOM | 1492 | CD | ARG | A | 515 | 21.566 | 6.305 | 22.520 | 1.00 | 27.40 | A | C |
| ATOM | 1493 | NE | ARG | A | 515 | 21.108 | 6.590 | 21.153 | 1.00 | 30.25 | A | N |
| ATOM | 1494 | CZ | ARG | A | 515 | 21.747 | 6.226 | 20.044 | 1.00 | 31.39 | A | C |
| ATOM | 1495 | NH1 | ARG | A | 515 | 22.885 | 5.546 | 20.093 | 1.00 | 32.16 | A | N |
| ATOM | 1496 | NH2 | ARG | A | 515 | 21.247 | 6.571 | 18.869 | 1.00 | 34.89 | A | N |
| ATOM | 1497 | N | HIS | A | 516 | 20.567 | 8.524 | 26.739 | 1.00 | 26.22 | A | N |
| ATOM | 1498 | CA | HIS | A | 516 | 21.367 | 8.400 | 27.950 | 1.00 | 26.52 | A | C |
| ATOM | 1499 | C | HIS | A | 516 | 20.687 | 7.503 | 28.958 | 1.00 | 26.41 | A | C |
| ATOM | 1500 | O | HIS | A | 516 | 21.317 | 6.581 | 29.482 | 1.00 | 26.35 | A | O |
| ATOM | 1501 | CB | HIS | A | 516 | 21.629 | 9.767 | 28.574 | 1.00 | 26.31 | A | C |
| ATOM | 1502 | CG | HIS | A | 516 | 22.533 | 9.720 | 29.765 | 1.00 | 26.04 | A | C |
| ATOM | 1503 | ND1 | HIS | A | 516 | 23.900 | 9.591 | 29.656 | 1.00 | 26.42 | A | N |
| ATOM | 1504 | CD2 | HIS | A | 516 | 22.262 | 9.756 | 31.094 | 1.00 | 26.70 | A | C |
| ATOM | 1505 | CE1 | HIS | A | 516 | 24.433 | 9.551 | 30.866 | 1.00 | 26.99 | A | C |
| ATOM | 1506 | NE2 | HIS | A | 516 | 23.460 | 9.650 | 31.756 | 1.00 | 26.53 | A | N |
| ATOM | 1507 | N | MET | A | 517 | 19.412 | 7.785 | 29.226 | 1.00 | 26.44 | A | N |
| ATOM | 1508 | CA | MET | A | 517 | 18.631 | 6.978 | 30.155 | 1.00 | 27.05 | A | C |
| ATOM | 1509 | C | MET | A | 517 | 18.650 | 5.530 | 29.662 | 1.00 | 27.96 | A | C |
| ATOM | 1510 | O | MET | A | 517 | 18.816 | 4.611 | 30.455 | 1.00 | 28.79 | A | O |
| ATOM | 1511 | CB | MET | A | 517 | 17.187 | 7.476 | 30.237 | 1.00 | 25.07 | A | C |
| ATOM | 1512 | CG | MET | A | 517 | 17.078 | 8.899 | 30.707 | 1.00 | 25.93 | A | C |
| ATOM | 1513 | SD | MET | A | 517 | 15.376 | 9.441 | 30.880 | 1.00 | 28.87 | A | S |
| ATOM | 1514 | CE | MET | A | 517 | 14.780 | 9.322 | 29.104 | 1.00 | 27.81 | A | C |
| ATOM | 1515 | N | SER | A | 518 | 18.485 | 5.347 | 28.352 | 1.00 | 28.58 | A | N |
| ATOM | 1516 | CA | SER | A | 518 | 18.490 | 4.025 | 27.743 | 1.00 | 28.93 | A | C |
| ATOM | 1517 | C | SER | A | 518 | 19.829 | 3.358 | 27.996 | 1.00 | 29.23 | A | C |
| ATOM | 1518 | O | SER | A | 518 | 19.876 | 2.190 | 28.364 | 1.00 | 29.00 | A | O |
| ATOM | 1519 | CB | SER | A | 518 | 18.197 | 4.116 | 26.227 | 1.00 | 28.47 | A | C |
| ATOM | 1520 | OG | SER | A | 518 | 18.762 | 3.029 | 25.509 | 1.00 | 26.57 | A | O |
| ATOM | 1521 | N | ASN | A | 519 | 20.920 | 4.092 | 27.822 | 1.00 | 30.10 | A | N |
| ATOM | 1522 | CA | ASN | A | 519 | 22.230 | 3.503 | 28.070 | 1.00 | 31.57 | A | C |
| ATOM | 1523 | C | ASN | A | 519 | 22.374 | 3.056 | 29.537 | 1.00 | 31.55 | A | C |
| ATOM | 1524 | O | ASN | A | 519 | 22.859 | 1.957 | 29.810 | 1.00 | 30.74 | A | O |
| ATOM | 1525 | CB | ASN | A | 519 | 23.348 | 4.494 | 27.701 | 1.00 | 32.63 | A | C |
| ATOM | 1526 | CG | ASN | A | 519 | 23.584 | 4.602 | 26.181 | 1.00 | 34.07 | A | C |
| ATOM | 1527 | OD1 | ASN | A | 519 | 24.136 | 5.603 | 25.695 | 1.00 | 33.89 | A | O |
| ATOM | 1528 | ND2 | ASN | A | 519 | 23.193 | 3.567 | 25.435 | 1.00 | 32.74 | A | N |
| ATOM | 1529 | N | LYS | A | 520 | 21.948 | 3.901 | 30.471 | 1.00 | 32.38 | A | N |
| ATOM | 1530 | CA | LYS | A | 520 | 22.047 | 3.583 | 31.895 | 1.00 | 34.65 | A | C |
| ATOM | 1531 | CB | LYS | A | 520 | 21.763 | 4.829 | 32.736 | 1.00 | 34.41 | A | C |
| ATOM | 1532 | C | LYS | A | 520 | 21.054 | 2.478 | 32.245 | 1.00 | 36.48 | A | C |
| ATOM | 1533 | O | LYS | A | 520 | 21.343 | 1.598 | 33.079 | 1.00 | 35.73 | A | O |
| ATOM | 1534 | N | GLY | A | 521 | 19.885 | 2.537 | 31.598 | 1.00 | 38.14 | A | N |
| ATOM | 1535 | CA | GLY | A | 521 | 18.841 | 1.553 | 31.820 | 1.00 | 40.31 | A | C |
| ATOM | 1536 | C | GLY | A | 521 | 19.292 | 0.164 | 31.399 | 1.00 | 42.00 | A | C |
| ATOM | 1537 | O | GLY | A | 521 | 19.025 | −0.829 | 32.071 | 1.00 | 41.49 | A | O |
| ATOM | 1538 | N | MET | A | 522 | 19.992 | 0.100 | 30.277 | 1.00 | 44.09 | A | N |
| ATOM | 1539 | CA | MET | A | 522 | 20.483 | −1.168 | 29.773 | 1.00 | 46.49 | A | C |
| ATOM | 1540 | C | MET | A | 522 | 21.501 | −1.730 | 30.753 | 1.00 | 48.37 | A | C |
| ATOM | 1541 | O | MET | A | 522 | 21.476 | −2.922 | 31.063 | 1.00 | 48.55 | A | O |
| ATOM | 1542 | CB | MET | A | 522 | 21.126 | −0.969 | 28.406 | 1.00 | 46.13 | A | C |
| ATOM | 1543 | CG | MET | A | 522 | 20.802 | −2.071 | 27.443 | 1.00 | 48.00 | A | C |
| ATOM | 1544 | SD | MET | A | 522 | 19.030 | −2.228 | 27.175 | 1.00 | 49.07 | A | S |
| ATOM | 1545 | CE | MET | A | 522 | 18.928 | −1.787 | 25.378 | 1.00 | 49.57 | A | C |
| ATOM | 1546 | N | GLU | A | 523 | 22.387 | −0.861 | 31.236 | 1.00 | 50.86 | A | N |
| ATOM | 1547 | CA | GLU | A | 523 | 23.429 | −1.238 | 32.187 | 1.00 | 53.74 | A | C |
| ATOM | 1548 | C | GLU | A | 523 | 22.889 | −2.019 | 33.383 | 1.00 | 55.48 | A | C |
| ATOM | 1549 | O | GLU | A | 523 | 23.520 | −2.964 | 33.858 | 1.00 | 55.26 | A | O |
| ATOM | 1550 | CB | GLU | A | 523 | 24.153 | 0.013 | 32.698 | 1.00 | 54.37 | A | C |
| ATOM | 1551 | CG | GLU | A | 523 | 25.207 | 0.563 | 31.752 | 1.00 | 55.27 | A | C |
| ATOM | 1552 | CD | GLU | A | 523 | 25.967 | 1.736 | 32.343 | 1.00 | 55.66 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1553 | OE1 | GLU | A | 523 | 26.305 | 1.687 | 33.548 | 1.00 | 55.66 | A | O |
| ATOM | 1554 | OE2 | GLU | A | 523 | 26.233 | 2.700 | 31.594 | 1.00 | 55.90 | A | O |
| ATOM | 1555 | N | HIS | A | 524 | 21.723 | −1.620 | 33.872 | 1.00 | 57.62 | A | N |
| ATOM | 1556 | CA | HIS | A | 524 | 21.139 | −2.296 | 35.014 | 1.00 | 60.01 | A | C |
| ATOM | 1557 | C | HIS | A | 524 | 20.433 | −3.604 | 34.670 | 1.00 | 61.43 | A | C |
| ATOM | 1558 | O | HIS | A | 524 | 20.426 | −4.534 | 35.480 | 1.00 | 60.80 | A | O |
| ATOM | 1559 | CB | HIS | A | 524 | 20.215 | −1.337 | 35.749 | 1.00 | 60.34 | A | C |
| ATOM | 1560 | CG | HIS | A | 524 | 20.931 | −0.126 | 36.263 | 1.00 | 61.66 | A | C |
| ATOM | 1561 | ND1 | HIS | A | 524 | 22.304 | −0.073 | 36.382 | 1.00 | 62.07 | A | N |
| ATOM | 1562 | CD2 | HIS | A | 524 | 20.469 | 1.078 | 36.680 | 1.00 | 61.88 | A | C |
| ATOM | 1563 | CE1 | HIS | A | 524 | 22.657 | 1.114 | 36.849 | 1.00 | 62.12 | A | C |
| ATOM | 1564 | NE2 | HIS | A | 524 | 21.562 | 1.829 | 37.039 | 1.00 | 61.47 | A | N |
| ATOM | 1565 | N | LEU | A | 525 | 19.845 | −3.687 | 33.480 | 1.00 | 63.70 | A | N |
| ATOM | 1566 | CA | LEU | A | 525 | 19.184 | −4.925 | 33.074 | 1.00 | 66.43 | A | C |
| ATOM | 1567 | C | LEU | A | 525 | 20.236 | −6.025 | 33.068 | 1.00 | 68.43 | A | C |
| ATOM | 1568 | O | LEU | A | 525 | 19.996 | −7.121 | 33.567 | 1.00 | 69.08 | A | O |
| ATOM | 1569 | CB | LEU | A | 525 | 18.576 | −4.816 | 31.664 | 1.00 | 66.06 | A | C |
| ATOM | 1570 | CG | LEU | A | 525 | 17.137 | −4.343 | 31.437 | 1.00 | 65.91 | A | C |
| ATOM | 1571 | CD1 | LEU | A | 525 | 17.029 | −2.841 | 31.665 | 1.00 | 65.65 | A | C |
| ATOM | 1572 | CD2 | LEU | A | 525 | 16.721 | −4.701 | 30.009 | 1.00 | 65.53 | A | C |
| ATOM | 1573 | N | TYR | A | 526 | 21.401 | −5.722 | 32.497 | 1.00 | 70.79 | A | N |
| ATOM | 1574 | CA | TYR | A | 526 | 22.503 | −6.684 | 32.423 | 1.00 | 73.16 | A | C |
| ATOM | 1575 | C | TYR | A | 526 | 23.254 | −6.785 | 33.757 | 1.00 | 73.57 | A | C |
| ATOM | 1576 | O | TYR | A | 526 | 24.487 | −6.915 | 33.797 | 1.00 | 73.97 | A | O |
| ATOM | 1577 | CB | TYR | A | 526 | 23.472 | −6.307 | 31.291 | 1.00 | 74.97 | A | C |
| ATOM | 1578 | CG | TYR | A | 526 | 22.915 | −6.507 | 29.886 | 1.00 | 77.35 | A | C |
| ATOM | 1579 | CD1 | TYR | A | 526 | 21.658 | −7.096 | 29.673 | 1.00 | 78.41 | A | C |
| ATOM | 1580 | CD2 | TYR | A | 526 | 23.657 | −6.125 | 28.762 | 1.00 | 78.03 | A | C |
| ATOM | 1581 | CE1 | TYR | A | 526 | 21.156 | −7.300 | 28.366 | 1.00 | 78.99 | A | C |
| ATOM | 1582 | CE2 | TYR | A | 526 | 23.168 | −6.324 | 27.457 | 1.00 | 78.62 | A | C |
| ATOM | 1583 | CZ | TYR | A | 526 | 21.919 | −6.911 | 27.265 | 1.00 | 79.11 | A | C |
| ATOM | 1584 | OH | TYR | A | 526 | 21.442 | −7.097 | 25.979 | 1.00 | 79.32 | A | O |
| ATOM | 1585 | N | SER | A | 527 | 22.484 | −6.720 | 34.842 | 1.00 | 73.92 | A | N |
| ATOM | 1586 | CA | SER | A | 527 | 22.998 | −6.815 | 36.204 | 1.00 | 74.08 | A | C |
| ATOM | 1587 | C | SER | A | 527 | 21.893 | −7.466 | 37.035 | 1.00 | 74.14 | A | C |
| ATOM | 1588 | O | SER | A | 527 | 22.054 | −7.731 | 38.222 | 1.00 | 74.38 | A | O |
| ATOM | 1589 | CB | SER | A | 527 | 23.325 | −5.420 | 36.759 | 1.00 | 74.19 | A | C |
| ATOM | 1590 | OG | SER | A | 527 | 24.300 | −4.750 | 35.973 | 1.00 | 74.33 | A | O |
| ATOM | 1591 | N | LEU | A | 536 | 14.872 | −11.530 | 21.199 | 1.00 | 89.64 | A | N |
| ATOM | 1592 | CA | LEU | A | 536 | 15.161 | −10.304 | 20.463 | 1.00 | 90.15 | A | C |
| ATOM | 1593 | CB | LEU | A | 536 | 16.409 | −9.632 | 21.027 | 1.00 | 89.70 | A | C |
| ATOM | 1594 | C | LEU | A | 536 | 15.350 | −10.572 | 18.957 | 1.00 | 90.42 | A | C |
| ATOM | 1595 | O | LEU | A | 536 | 14.546 | −10.137 | 18.121 | 1.00 | 90.38 | A | O |
| ATOM | 1596 | N | TYR | A | 537 | 16.440 | −11.259 | 18.612 | 1.00 | 90.87 | A | N |
| ATOM | 1597 | CA | TYR | A | 537 | 16.748 | −11.593 | 17.217 | 1.00 | 90.92 | A | C |
| ATOM | 1598 | CB | TYR | A | 537 | 18.066 | −12.332 | 17.130 | 1.00 | 90.61 | A | C |
| ATOM | 1599 | C | TYR | A | 537 | 15.625 | −12.487 | 16.726 | 1.00 | 90.99 | A | C |
| ATOM | 1600 | O | TYR | A | 537 | 15.253 | −12.472 | 15.542 | 1.00 | 91.03 | A | O |
| ATOM | 1601 | N | ASP | A | 538 | 15.075 | −13.261 | 17.654 | 1.00 | 91.01 | A | N |
| ATOM | 1602 | CA | ASP | A | 538 | 13.990 | −14.175 | 17.337 | 1.00 | 90.93 | A | C |
| ATOM | 1603 | CB | ASP | A | 538 | 13.853 | −15.197 | 18.463 | 1.00 | 90.98 | A | C |
| ATOM | 1604 | C | ASP | A | 538 | 12.657 | −13.466 | 17.099 | 1.00 | 90.82 | A | C |
| ATOM | 1605 | O | ASP | A | 538 | 12.019 | −13.689 | 16.062 | 1.00 | 90.46 | A | O |
| ATOM | 1606 | N | LEU | A | 539 | 12.264 | −12.617 | 18.056 | 1.00 | 90.56 | A | N |
| ATOM | 1607 | CA | LEU | A | 539 | 11.003 | −11.891 | 17.987 | 1.00 | 90.40 | A | C |
| ATOM | 1608 | CB | LEU | A | 539 | 10.696 | −11.235 | 19.323 | 1.00 | 89.66 | A | C |
| ATOM | 1609 | C | LEU | A | 539 | 10.946 | −10.842 | 16.881 | 1.00 | 90.52 | A | C |
| ATOM | 1610 | O | LEU | A | 539 | 9.904 | −10.689 | 16.238 | 1.00 | 90.67 | A | O |
| ATOM | 1611 | N | LEU | A | 540 | 12.038 | −10.103 | 16.683 | 1.00 | 90.71 | A | N |
| ATOM | 1612 | CA | LEU | A | 540 | 12.077 | −9.074 | 15.655 | 1.00 | 90.83 | A | C |
| ATOM | 1613 | CB | LEU | A | 540 | 13.363 | −8.252 | 15.768 | 1.00 | 90.69 | A | C |
| ATOM | 1614 | C | LEU | A | 540 | 12.032 | −9.805 | 14.326 | 1.00 | 90.75 | A | C |
| ATOM | 1615 | O | LEU | A | 540 | 11.430 | −9.334 | 13.351 | 1.00 | 90.60 | A | O |
| ATOM | 1616 | N | LEU | A | 541 | 12.672 | −10.975 | 14.306 | 1.00 | 90.53 | A | N |
| ATOM | 1617 | CA | LEU | A | 541 | 12.739 | −11.805 | 13.106 | 1.00 | 90.17 | A | C |
| ATOM | 1618 | CB | LEU | A | 541 | 13.652 | −13.016 | 13.352 | 1.00 | 89.86 | A | C |
| ATOM | 1619 | C | LEU | A | 541 | 11.340 | −12.263 | 12.685 | 1.00 | 89.91 | A | C |
| ATOM | 1620 | O | LEU | A | 541 | 10.893 | −11.950 | 11.578 | 1.00 | 90.08 | A | O |
| ATOM | 1621 | N | GLU | A | 542 | 10.649 | −12.988 | 13.562 | 1.00 | 89.61 | A | N |
| ATOM | 1622 | CA | GLU | A | 542 | 9.313 | −13.496 | 13.255 | 1.00 | 89.39 | A | C |
| ATOM | 1623 | CB | GLU | A | 542 | 8.787 | −14.313 | 14.438 | 1.00 | 89.03 | A | C |
| ATOM | 1624 | C | GLU | A | 542 | 8.291 | −12.409 | 12.890 | 1.00 | 89.33 | A | C |
| ATOM | 1625 | O | GLU | A | 542 | 7.485 | −12.597 | 11.965 | 1.00 | 89.57 | A | O |
| ATOM | 1626 | N | MET | A | 543 | 8.298 | −11.305 | 13.639 | 1.00 | 89.08 | A | N |
| ATOM | 1627 | CA | MET | A | 543 | 7.378 | −10.203 | 13.415 | 1.00 | 89.04 | A | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1628 | CB | MET | A | 543 | 7.553 | −9.175 | 14.528 | 1.00 | 88.58 | A | C |
| ATOM | 1629 | C | MET | A | 543 | 7.576 | −9.563 | 12.027 | 1.00 | 89.36 | A | C |
| ATOM | 1630 | O | MET | A | 543 | 6.599 | −9.311 | 11.326 | 1.00 | 89.39 | A | O |
| ATOM | 1631 | N | LEU | A | 544 | 8.831 | −9.329 | 11.634 | 1.00 | 89.73 | A | N |
| ATOM | 1632 | CA | LEU | A | 544 | 9.164 | −8.703 | 10.352 | 1.00 | 90.06 | A | C |
| ATOM | 1633 | CB | LEU | A | 544 | 10.655 | −8.481 | 10.271 | 1.00 | 89.96 | A | C |
| ATOM | 1634 | C | LEU | A | 544 | 8.677 | −9.422 | 9.098 | 1.00 | 90.11 | A | C |
| ATOM | 1635 | O | LEU | A | 544 | 8.171 | −8.714 | 8.196 | 1.00 | 89.96 | A | O |
| ATOM | 1636 | OXT | LEU | A | 544 | 8.818 | −10.671 | 9.028 | 1.00 | 90.26 | A | O |
| TER | 1637 | | LEU | A | 544 | | | | | | | |
| ATOM | 1638 | N | LEU | B | 310 | 24.759 | 40.530 | 22.425 | 1.00 | 79.63 | B | N |
| ATOM | 1639 | CA | LEU | B | 310 | 25.486 | 39.468 | 21.669 | 1.00 | 79.88 | B | C |
| ATOM | 1640 | C | LEU | B | 310 | 24.713 | 39.043 | 20.419 | 1.00 | 79.89 | B | C |
| ATOM | 1641 | O | LEU | B | 310 | 23.530 | 38.723 | 20.503 | 1.00 | 80.07 | B | O |
| ATOM | 1642 | CB | LEU | B | 310 | 25.707 | 38.256 | 22.577 | 1.00 | 79.85 | B | C |
| ATOM | 1643 | CG | LEU | B | 310 | 27.163 | 37.810 | 22.726 | 1.00 | 79.72 | B | C |
| ATOM | 1644 | CD1 | LEU | B | 310 | 27.246 | 36.695 | 23.755 | 1.00 | 79.83 | B | C |
| ATOM | 1645 | CD2 | LEU | B | 310 | 27.711 | 37.355 | 21.372 | 1.00 | 79.33 | B | C |
| ATOM | 1646 | N | THR | B | 311 | 25.382 | 39.042 | 19.266 | 1.00 | 79.81 | B | N |
| ATOM | 1647 | CA | THR | B | 311 | 24.750 | 38.652 | 18.008 | 1.00 | 79.68 | B | C |
| ATOM | 1648 | C | THR | B | 311 | 25.410 | 37.418 | 17.426 | 1.00 | 79.69 | B | C |
| ATOM | 1649 | O | THR | B | 311 | 26.448 | 36.981 | 17.910 | 1.00 | 79.67 | B | O |
| ATOM | 1650 | CB | THR | B | 311 | 24.816 | 39.789 | 16.955 | 1.00 | 79.88 | B | C |
| ATOM | 1651 | OG1 | THR | B | 311 | 25.332 | 39.282 | 15.714 | 1.00 | 79.99 | B | O |
| ATOM | 1652 | CG2 | THR | B | 311 | 25.699 | 40.916 | 17.443 | 1.00 | 79.69 | B | C |
| ATOM | 1653 | N | ALA | B | 312 | 24.804 | 36.867 | 16.380 | 1.00 | 79.76 | B | N |
| ATOM | 1654 | CA | ALA | B | 312 | 25.319 | 35.674 | 15.723 | 1.00 | 80.22 | B | C |
| ATOM | 1655 | C | ALA | B | 312 | 26.780 | 35.773 | 15.284 | 1.00 | 80.74 | B | C |
| ATOM | 1656 | O | ALA | B | 312 | 27.601 | 34.934 | 15.659 | 1.00 | 81.11 | B | O |
| ATOM | 1657 | CB | ALA | B | 312 | 24.453 | 35.337 | 14.531 | 1.00 | 79.78 | B | C |
| ATOM | 1658 | N | ASP | B | 313 | 27.104 | 36.786 | 14.483 | 1.00 | 81.36 | B | N |
| ATOM | 1659 | CA | ASP | B | 313 | 28.471 | 36.962 | 13.989 | 1.00 | 81.61 | B | C |
| ATOM | 1660 | C | ASP | B | 313 | 29.495 | 37.113 | 15.095 | 1.00 | 81.17 | B | C |
| ATOM | 1661 | O | ASP | B | 313 | 30.655 | 36.732 | 14.935 | 1.00 | 80.74 | B | O |
| ATOM | 1662 | CB | ASP | B | 313 | 28.546 | 38.170 | 13.060 | 1.00 | 82.68 | B | C |
| ATOM | 1663 | CG | ASP | B | 313 | 28.052 | 37.852 | 11.667 | 1.00 | 83.77 | B | C |
| ATOM | 1664 | OD1 | ASP | B | 313 | 26.887 | 37.418 | 11.543 | 1.00 | 84.26 | B | O |
| ATOM | 1665 | OD2 | ASP | B | 313 | 28.828 | 38.029 | 10.699 | 1.00 | 84.44 | B | O |
| ATOM | 1666 | N | GLN | B | 314 | 29.056 | 37.681 | 16.211 | 1.00 | 80.93 | B | N |
| ATOM | 1667 | CA | GLN | B | 314 | 29.915 | 37.885 | 17.369 | 1.00 | 80.84 | B | C |
| ATOM | 1668 | C | GLN | B | 314 | 30.013 | 36.579 | 18.159 | 1.00 | 80.32 | B | C |
| ATOM | 1669 | O | GLN | B | 314 | 30.985 | 36.339 | 18.877 | 1.00 | 80.48 | B | O |
| ATOM | 1670 | CB | GLN | B | 314 | 29.336 | 38.983 | 18.269 | 1.00 | 81.32 | B | C |
| ATOM | 1671 | CG | GLN | B | 314 | 29.111 | 40.326 | 17.578 | 1.00 | 81.93 | B | C |
| ATOM | 1672 | CD | GLN | B | 314 | 28.704 | 41.425 | 18.556 | 1.00 | 82.45 | B | C |
| ATOM | 1673 | OE1 | GLN | B | 314 | 27.688 | 41.316 | 19.248 | 1.00 | 82.72 | B | O |
| ATOM | 1674 | NE2 | GLN | B | 314 | 29.501 | 42.489 | 18.618 | 1.00 | 82.29 | B | N |
| ATOM | 1675 | N | MET | B | 315 | 28.990 | 35.741 | 18.011 | 1.00 | 79.53 | B | N |
| ATOM | 1676 | CA | MET | B | 315 | 28.912 | 34.454 | 18.695 | 1.00 | 78.36 | B | C |
| ATOM | 1677 | C | MET | B | 315 | 29.839 | 33.414 | 18.062 | 1.00 | 77.51 | B | C |
| ATOM | 1678 | O | MET | B | 315 | 30.350 | 32.539 | 18.757 | 1.00 | 77.58 | B | O |
| ATOM | 1679 | CB | MET | B | 315 | 27.462 | 33.947 | 18.672 | 1.00 | 78.46 | B | C |
| ATOM | 1680 | CG | MET | B | 315 | 27.183 | 32.673 | 19.471 | 1.00 | 77.97 | B | C |
| ATOM | 1681 | SD | MET | B | 315 | 27.380 | 32.846 | 21.262 | 1.00 | 77.84 | B | S |
| ATOM | 1682 | CE | MET | B | 315 | 26.373 | 34.304 | 21.600 | 1.00 | 77.38 | B | C |
| ATOM | 1683 | N | VAL | B | 316 | 30.064 | 33.505 | 16.755 | 1.00 | 76.51 | B | N |
| ATOM | 1684 | CA | VAL | B | 316 | 30.935 | 32.542 | 16.088 | 1.00 | 75.97 | B | C |
| ATOM | 1685 | C | VAL | B | 316 | 32.407 | 32.924 | 16.209 | 1.00 | 75.64 | B | C |
| ATOM | 1686 | O | VAL | B | 316 | 33.293 | 32.092 | 16.008 | 1.00 | 75.76 | B | O |
| ATOM | 1687 | CB | VAL | B | 316 | 30.592 | 32.413 | 14.594 | 1.00 | 75.86 | B | C |
| ATOM | 1688 | CG1 | VAL | B | 316 | 31.434 | 31.313 | 13.958 | 1.00 | 75.54 | B | C |
| ATOM | 1689 | CG2 | VAL | B | 316 | 29.117 | 32.120 | 14.429 | 1.00 | 75.80 | B | C |
| ATOM | 1690 | N | SER | B | 317 | 32.659 | 34.185 | 16.542 | 1.00 | 75.08 | B | N |
| ATOM | 1691 | CA | SER | B | 317 | 34.023 | 34.687 | 16.685 | 1.00 | 74.13 | B | C |
| ATOM | 1692 | C | SER | B | 317 | 34.558 | 34.373 | 18.076 | 1.00 | 72.90 | B | C |
| ATOM | 1693 | O | SER | B | 317 | 35.714 | 33.983 | 18.233 | 1.00 | 72.66 | B | O |
| ATOM | 1694 | CB | SER | B | 317 | 34.042 | 36.200 | 16.456 | 1.00 | 74.85 | B | C |
| ATOM | 1695 | OG | SER | B | 317 | 33.286 | 36.548 | 15.305 | 1.00 | 75.82 | B | O |
| ATOM | 1696 | N | ALA | B | 318 | 33.704 | 34.553 | 19.080 | 1.00 | 71.61 | B | N |
| ATOM | 1697 | CA | ALA | B | 318 | 34.060 | 34.291 | 20.471 | 1.00 | 70.39 | B | C |
| ATOM | 1698 | C | ALA | B | 318 | 34.387 | 32.815 | 20.664 | 1.00 | 69.37 | B | C |
| ATOM | 1699 | O | ALA | B | 318 | 35.277 | 32.465 | 21.442 | 1.00 | 69.51 | B | O |
| ATOM | 1700 | CB | ALA | B | 318 | 32.911 | 34.695 | 21.396 | 1.00 | 70.08 | B | C |
| ATOM | 1701 | N | LEU | B | 319 | 33.665 | 31.954 | 19.950 | 1.00 | 68.23 | B | N |
| ATOM | 1702 | CA | LEU | B | 319 | 33.875 | 30.510 | 20.044 | 1.00 | 66.95 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1703 | C | LEU | B | 319 | 35.064 | 30.045 | 19.195 | 1.00 | 65.49 B | | C |
| ATOM | 1704 | O | LEU | B | 319 | 35.588 | 28.943 | 19.382 | 1.00 | 65.99 B | | O |
| ATOM | 1705 | CB | LEU | B | 319 | 32.614 | 29.743 | 19.604 | 1.00 | 67.04 B | | C |
| ATOM | 1706 | CG | LEU | B | 319 | 31.259 | 30.009 | 20.270 | 1.00 | 66.89 B | | C |
| ATOM | 1707 | CD1 | LEU | B | 319 | 30.249 | 29.024 | 19.713 | 1.00 | 66.60 B | | C |
| ATOM | 1708 | CD2 | LEU | B | 319 | 31.354 | 29.870 | 21.778 | 1.00 | 66.77 B | | C |
| ATOM | 1709 | N | LEU | B | 320 | 35.493 | 30.870 | 18.252 | 1.00 | 63.35 B | | N |
| ATOM | 1710 | CA | LEU | B | 320 | 36.616 | 30.471 | 17.425 | 1.00 | 60.59 B | | C |
| ATOM | 1711 | C | LEU | B | 320 | 37.959 | 30.843 | 18.056 | 1.00 | 58.59 B | | C |
| ATOM | 1712 | O | LEU | B | 320 | 38.948 | 30.136 | 17.869 | 1.00 | 57.65 B | | O |
| ATOM | 1713 | CB | LEU | B | 320 | 36.454 | 31.074 | 16.032 | 1.00 | 60.58 B | | C |
| ATOM | 1714 | CG | LEU | B | 320 | 35.394 | 30.343 | 15.198 | 1.00 | 59.85 B | | C |
| ATOM | 1715 | CD1 | LEU | B | 320 | 34.928 | 31.206 | 14.031 | 1.00 | 59.76 B | | C |
| ATOM | 1716 | CD2 | LEU | B | 320 | 35.977 | 29.028 | 14.709 | 1.00 | 59.06 B | | C |
| ATOM | 1717 | N | ASP | B | 321 | 37.987 | 31.937 | 18.814 | 0.50 | 56.39 B | | N |
| ATOM | 1718 | CA | ASP | B | 321 | 39.216 | 32.363 | 19.470 | 0.50 | 54.75 B | | C |
| ATOM | 1719 | C | ASP | B | 321 | 39.366 | 31.616 | 20.781 | 0.50 | 53.84 B | | C |
| ATOM | 1720 | O | ASP | B | 321 | 40.413 | 31.675 | 21.428 | 0.50 | 53.75 B | | O |
| ATOM | 1721 | CB | ASP | B | 321 | 39.206 | 33.865 | 19.741 | 0.50 | 54.18 B | | C |
| ATOM | 1722 | CG | ASP | B | 321 | 38.971 | 34.677 | 18.491 | 0.50 | 53.59 B | | C |
| ATOM | 1723 | OD1 | ASP | B | 321 | 39.629 | 34.409 | 17.459 | 0.50 | 52.98 B | | O |
| ATOM | 1724 | OD2 | ASP | B | 321 | 38.125 | 35.591 | 18.545 | 0.50 | 53.70 B | | O |
| ATOM | 1725 | N | ALA | B | 322 | 38.303 | 30.922 | 21.174 | 1.00 | 52.90 B | | N |
| ATOM | 1726 | CA | ALA | B | 322 | 38.318 | 30.133 | 22.404 | 1.00 | 51.31 B | | C |
| ATOM | 1727 | C | ALA | B | 322 | 38.632 | 28.670 | 22.064 | 1.00 | 50.14 B | | C |
| ATOM | 1728 | O | ALA | B | 322 | 38.535 | 27.790 | 22.916 | 1.00 | 50.55 B | | O |
| ATOM | 1729 | CB | ALA | B | 322 | 36.972 | 30.247 | 23.135 | 1.00 | 51.25 B | | C |
| ATOM | 1730 | N | GLU | B | 323 | 39.011 | 28.417 | 20.815 | 1.00 | 48.79 B | | N |
| ATOM | 1731 | CA | GLU | B | 323 | 39.366 | 27.070 | 20.389 | 1.00 | 48.05 B | | C |
| ATOM | 1732 | C | GLU | B | 323 | 40.642 | 26.601 | 21.087 | 1.00 | 47.38 B | | C |
| ATOM | 1733 | O | GLU | B | 323 | 41.666 | 27.277 | 21.026 | 1.00 | 47.65 B | | O |
| ATOM | 1734 | CB | GLU | B | 323 | 39.600 | 27.022 | 18.878 | 1.00 | 48.01 B | | C |
| ATOM | 1735 | CG | GLU | B | 323 | 38.445 | 26.479 | 18.051 | 1.00 | 47.34 B | | C |
| ATOM | 1736 | CD | GLU | B | 323 | 38.101 | 25.044 | 18.389 | 1.00 | 47.02 B | | C |
| ATOM | 1737 | OE1 | GLU | B | 323 | 37.370 | 24.834 | 19.386 | 1.00 | 45.60 B | | O |
| ATOM | 1738 | OE2 | GLU | B | 323 | 38.569 | 24.137 | 17.654 | 1.00 | 46.60 B | | O |
| ATOM | 1739 | N | PRO | B | 324 | 40.587 | 25.439 | 21.769 | 1.00 | 46.79 B | | N |
| ATOM | 1740 | CA | PRO | B | 324 | 41.707 | 24.820 | 22.498 | 1.00 | 45.90 B | | C |
| ATOM | 1741 | C | PRO | B | 324 | 42.789 | 24.261 | 21.569 | 1.00 | 44.59 B | | C |
| ATOM | 1742 | O | PRO | B | 324 | 42.490 | 23.704 | 20.522 | 1.00 | 44.17 B | | O |
| ATOM | 1743 | CB | PRO | B | 324 | 41.029 | 23.697 | 23.285 | 1.00 | 46.07 B | | C |
| ATOM | 1744 | CG | PRO | B | 324 | 39.632 | 24.222 | 23.494 | 1.00 | 46.40 B | | C |
| ATOM | 1745 | CD | PRO | B | 324 | 39.312 | 24.798 | 22.145 | 1.00 | 46.21 B | | C |
| ATOM | 1746 | N | PRO | B | 325 | 44.068 | 24.402 | 21.945 | 1.00 | 44.17 B | | N |
| ATOM | 1747 | CA | PRO | B | 325 | 45.130 | 23.872 | 21.080 | 1.00 | 43.79 B | | C |
| ATOM | 1748 | C | PRO | B | 325 | 45.069 | 22.358 | 20.890 | 1.00 | 43.35 B | | C |
| ATOM | 1749 | O | PRO | B | 325 | 44.337 | 21.660 | 21.584 | 1.00 | 42.57 B | | O |
| ATOM | 1750 | CB | PRO | B | 325 | 46.405 | 24.304 | 21.801 | 1.00 | 43.45 B | | C |
| ATOM | 1751 | CG | PRO | B | 325 | 45.984 | 24.356 | 23.241 | 1.00 | 43.26 B | | C |
| ATOM | 1752 | CD | PRO | B | 325 | 44.640 | 25.038 | 23.144 | 1.00 | 43.73 B | | C |
| ATOM | 1753 | N | ILE | B | 326 | 45.829 | 21.865 | 19.922 | 1.00 | 43.82 B | | N |
| ATOM | 1754 | CA | ILE | B | 326 | 45.909 | 20.432 | 19.656 | 1.00 | 44.23 B | | C |
| ATOM | 1755 | C | ILE | B | 326 | 47.180 | 20.028 | 20.374 | 1.00 | 44.73 B | | C |
| ATOM | 1756 | O | ILE | B | 326 | 48.226 | 20.625 | 20.135 | 1.00 | 44.97 B | | O |
| ATOM | 1757 | CB | ILE | B | 326 | 46.101 | 20.132 | 18.148 | 1.00 | 44.23 B | | C |
| ATOM | 1758 | CG1 | ILE | B | 326 | 44.842 | 20.527 | 17.372 | 1.00 | 44.36 B | | C |
| ATOM | 1759 | CG2 | ILE | B | 326 | 46.434 | 18.649 | 17.938 | 1.00 | 43.21 B | | C |
| ATOM | 1760 | CD1 | ILE | B | 326 | 44.931 | 20.244 | 15.864 | 1.00 | 44.53 B | | C |
| ATOM | 1761 | N | LEU | B | 327 | 47.117 | 19.038 | 21.255 | 1.00 | 44.84 B | | N |
| ATOM | 1762 | CA | LEU | B | 327 | 48.334 | 18.656 | 21.957 | 1.00 | 45.24 B | | C |
| ATOM | 1763 | C | LEU | B | 327 | 49.012 | 17.446 | 21.311 | 1.00 | 45.94 B | | C |
| ATOM | 1764 | O | LEU | B | 327 | 48.504 | 16.890 | 20.328 | 1.00 | 45.90 B | | O |
| ATOM | 1765 | CB | LEU | B | 327 | 48.028 | 18.405 | 23.438 | 1.00 | 44.53 B | | C |
| ATOM | 1766 | CG | LEU | B | 327 | 47.236 | 19.497 | 24.191 | 1.00 | 43.75 B | | C |
| ATOM | 1767 | CD1 | LEU | B | 327 | 47.183 | 19.129 | 25.665 | 1.00 | 44.16 B | | C |
| ATOM | 1768 | CD2 | LEU | B | 327 | 47.868 | 20.860 | 24.033 | 1.00 | 42.94 B | | C |
| ATOM | 1769 | N | TYR | B | 328 | 50.166 | 17.057 | 21.857 | 1.00 | 46.89 B | | N |
| ATOM | 1770 | CA | TYR | B | 328 | 50.951 | 15.926 | 21.345 | 1.00 | 47.79 B | | C |
| ATOM | 1771 | C | TYR | B | 328 | 51.047 | 14.696 | 22.255 | 1.00 | 49.38 B | | C |
| ATOM | 1772 | O | TYR | B | 328 | 50.838 | 14.769 | 23.465 | 1.00 | 48.77 B | | O |
| ATOM | 1773 | CB | TYR | B | 328 | 52.368 | 16.390 | 21.014 | 1.00 | 46.66 B | | C |
| ATOM | 1774 | CG | TYR | B | 328 | 52.536 | 16.958 | 19.618 | 1.00 | 46.07 B | | C |
| ATOM | 1775 | CD1 | TYR | B | 328 | 52.071 | 18.238 | 19.284 | 1.00 | 45.64 B | | C |
| ATOM | 1776 | CD2 | TYR | B | 328 | 53.141 | 16.197 | 18.621 | 1.00 | 45.29 B | | C |
| ATOM | 1777 | CE1 | TYR | B | 328 | 52.209 | 18.734 | 17.987 | 1.00 | 45.11 B | | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1778 | CE2 | TYR | B | 328 | 53.282 | 16.672 | 17.335 | 1.00 | 45.31 B | | C |
| ATOM | 1779 | CZ | TYR | B | 328 | 52.815 | 17.938 | 17.016 | 1.00 | 45.71 B | | C |
| ATOM | 1780 | OH | TYR | B | 328 | 52.944 | 18.367 | 15.711 | 1.00 | 46.04 B | | O |
| ATOM | 1781 | N | SER | B | 329 | 51.379 | 13.558 | 21.661 | 1.00 | 52.09 B | | N |
| ATOM | 1782 | CA | SER | B | 329 | 51.515 | 12.321 | 22.422 | 1.00 | 54.91 B | | C |
| ATOM | 1783 | C | SER | B | 329 | 52.806 | 12.331 | 23.233 | 1.00 | 56.48 B | | C |
| ATOM | 1784 | O | SER | B | 329 | 53.900 | 12.229 | 22.671 | 1.00 | 55.78 B | | O |
| ATOM | 1785 | CB | SER | B | 329 | 51.525 | 11.116 | 21.486 | 1.00 | 54.77 B | | C |
| ATOM | 1786 | OG | SER | B | 329 | 51.866 | 9.941 | 22.206 | 1.00 | 55.61 B | | O |
| ATOM | 1787 | N | GLU | B | 330 | 52.675 | 12.441 | 24.553 | 1.00 | 58.82 B | | N |
| ATOM | 1788 | CA | GLU | B | 330 | 53.843 | 12.475 | 25.424 | 1.00 | 61.63 B | | C |
| ATOM | 1789 | C | GLU | B | 330 | 54.629 | 11.172 | 25.415 | 1.00 | 63.10 B | | C |
| ATOM | 1790 | O | GLU | B | 330 | 54.260 | 10.208 | 26.086 | 1.00 | 63.55 B | | O |
| ATOM | 1791 | CB | GLU | B | 330 | 53.440 | 12.812 | 26.859 | 1.00 | 62.10 B | | C |
| ATOM | 1792 | CG | GLU | B | 330 | 54.203 | 13.998 | 27.428 | 1.00 | 62.69 B | | C |
| ATOM | 1793 | CD | GLU | B | 330 | 54.483 | 13.843 | 28.909 | 1.00 | 63.24 B | | C |
| ATOM | 1794 | OE1 | GLU | B | 330 | 53.521 | 13.699 | 29.693 | 1.00 | 63.16 B | | O |
| ATOM | 1795 | OE2 | GLU | B | 330 | 55.670 | 13.867 | 29.292 | 1.00 | 63.55 B | | O |
| ATOM | 1796 | N | TYR | B | 331 | 55.717 | 11.169 | 24.649 | 1.00 | 65.09 B | | N |
| ATOM | 1797 | CA | TYR | B | 331 | 56.617 | 10.024 | 24.506 | 1.00 | 66.88 B | | C |
| ATOM | 1798 | C | TYR | B | 331 | 56.420 | 8.848 | 25.462 | 1.00 | 67.01 B | | C |
| ATOM | 1799 | O | TYR | B | 331 | 56.940 | 7.752 | 25.224 | 1.00 | 66.71 B | | O |
| ATOM | 1800 | CB | TYR | B | 331 | 58.057 | 10.514 | 24.601 | 1.00 | 68.82 B | | C |
| ATOM | 1801 | CG | TYR | B | 331 | 58.620 | 10.888 | 23.260 | 1.00 | 71.02 B | | C |
| ATOM | 1802 | CD1 | TYR | B | 331 | 59.129 | 9.908 | 22.408 | 1.00 | 71.76 B | | C |
| ATOM | 1803 | CD2 | TYR | B | 331 | 58.619 | 12.213 | 22.825 | 1.00 | 71.84 B | | C |
| ATOM | 1804 | CE1 | TYR | B | 331 | 59.632 | 10.233 | 21.154 | 1.00 | 73.06 B | | C |
| ATOM | 1805 | CE2 | TYR | B | 331 | 59.117 | 12.555 | 21.566 | 1.00 | 73.02 B | | C |
| ATOM | 1806 | CZ | TYR | B | 331 | 59.625 | 11.558 | 20.736 | 1.00 | 73.54 B | | C |
| ATOM | 1807 | OH | TYR | B | 331 | 60.142 | 11.878 | 19.498 | 1.00 | 74.27 B | | O |
| ATOM | 1808 | N | PRO | B | 336 | 55.927 | −1.392 | 20.801 | 1.00 | 82.30 B | | N |
| ATOM | 1809 | CA | PRO | B | 336 | 54.493 | −1.563 | 20.554 | 1.00 | 82.66 B | | C |
| ATOM | 1810 | C | PRO | B | 336 | 53.633 | −1.131 | 21.742 | 1.00 | 83.13 B | | C |
| ATOM | 1811 | O | PRO | B | 336 | 54.163 | −0.689 | 22.758 | 1.00 | 83.10 B | | O |
| ATOM | 1812 | CB | PRO | B | 336 | 54.386 | −3.048 | 20.243 | 1.00 | 82.47 B | | C |
| ATOM | 1813 | CG | PRO | B | 336 | 55.656 | −3.294 | 19.480 | 1.00 | 82.39 B | | C |
| ATOM | 1814 | CD | PRO | B | 336 | 56.683 | −2.563 | 20.324 | 1.00 | 82.19 B | | C |
| ATOM | 1815 | N | PHE | B | 337 | 52.311 | −1.270 | 21.615 | 1.00 | 83.77 B | | N |
| ATOM | 1816 | CA | PHE | B | 337 | 51.379 | −0.855 | 22.670 | 1.00 | 84.41 B | | C |
| ATOM | 1817 | C | PHE | B | 337 | 50.490 | −1.927 | 23.298 | 1.00 | 84.45 B | | C |
| ATOM | 1818 | O | PHE | B | 337 | 49.733 | −2.614 | 22.609 | 1.00 | 84.72 B | | O |
| ATOM | 1819 | CB | PHE | B | 337 | 50.477 | 0.258 | 22.143 | 1.00 | 85.16 B | | C |
| ATOM | 1820 | CG | PHE | B | 337 | 51.210 | 1.513 | 21.792 | 1.00 | 85.96 B | | C |
| ATOM | 1821 | CD1 | PHE | B | 337 | 51.683 | 2.362 | 22.790 | 1.00 | 86.45 B | | C |
| ATOM | 1822 | CD2 | PHE | B | 337 | 51.452 | 1.838 | 20.461 | 1.00 | 86.27 B | | C |
| ATOM | 1823 | CE1 | PHE | B | 337 | 52.391 | 3.523 | 22.467 | 1.00 | 86.87 B | | C |
| ATOM | 1824 | CE2 | PHE | B | 337 | 52.160 | 2.994 | 20.125 | 1.00 | 86.86 B | | C |
| ATOM | 1825 | CZ | PHE | B | 337 | 52.631 | 3.839 | 21.131 | 1.00 | 86.91 B | | C |
| ATOM | 1826 | N | SER | B | 338 | 50.573 | −2.039 | 24.620 | 1.00 | 84.47 B | | N |
| ATOM | 1827 | CA | SER | B | 338 | 49.359 | −2.534 | 23.976 | 1.00 | 84.19 B | | C |
| ATOM | 1828 | C | SER | B | 338 | 48.079 | −2.172 | 24.754 | 1.00 | 84.08 B | | C |
| ATOM | 1829 | O | SER | B | 338 | 47.190 | −1.524 | 24.236 | 1.00 | 84.07 B | | O |
| ATOM | 1830 | CB | SER | B | 338 | 49.467 | −4.057 | 23.780 | 1.00 | 84.17 B | | C |
| ATOM | 1831 | OG | SER | B | 338 | 49.756 | −4.710 | 25.016 | 1.00 | 83.80 B | | O |
| ATOM | 1832 | N | GLU | B | 339 | 47.950 | −2.700 | 25.994 | 1.00 | 83.92 B | | N |
| ATOM | 1833 | CA | GLU | B | 339 | 46.938 | −2.133 | 26.893 | 1.00 | 83.52 B | | C |
| ATOM | 1834 | C | GLU | B | 339 | 47.470 | −1.006 | 27.798 | 1.00 | 82.82 B | | C |
| ATOM | 1835 | O | GLU | B | 339 | 47.038 | 0.141 | 27.742 | 1.00 | 82.70 B | | O |
| ATOM | 1836 | CB | GLU | B | 339 | 46.344 | −3.250 | 27.738 | 1.00 | 84.09 B | | C |
| ATOM | 1837 | CG | GLU | B | 339 | 44.829 | −3.096 | 27.900 | 1.00 | 85.09 B | | C |
| ATOM | 1838 | CD | GLU | B | 339 | 44.387 | −3.833 | 29.140 | 1.00 | 85.54 B | | C |
| ATOM | 1839 | OE1 | GLU | B | 339 | 44.778 | −3.416 | 30.229 | 1.00 | 85.65 B | | O |
| ATOM | 1840 | OE2 | GLU | B | 339 | 43.617 | −4.788 | 29.016 | 1.00 | 85.76 B | | O |
| ATOM | 1841 | N | ALA | B | 340 | 48.440 | −1.395 | 28.666 | 1.00 | 82.08 B | | N |
| ATOM | 1842 | CA | ALA | B | 340 | 48.872 | −0.560 | 29.807 | 1.00 | 81.00 B | | C |
| ATOM | 1843 | C | ALA | B | 340 | 49.621 | 0.730 | 29.442 | 1.00 | 80.25 B | | C |
| ATOM | 1844 | O | ALA | B | 340 | 50.094 | 1.483 | 30.283 | 1.00 | 80.39 B | | O |
| ATOM | 1845 | CB | ALA | B | 340 | 49.739 | −1.430 | 30.713 | 1.00 | 80.78 B | | C |
| ATOM | 1846 | N | SER | B | 341 | 49.828 | 0.531 | 28.143 | 1.00 | 79.23 B | | N |
| ATOM | 1847 | CA | SER | B | 341 | 50.757 | 1.342 | 27.357 | 1.00 | 78.08 B | | C |
| ATOM | 1848 | C | SER | B | 341 | 49.891 | 2.314 | 26.557 | 1.00 | 77.81 B | | C |
| ATOM | 1849 | O | SER | B | 341 | 50.228 | 3.492 | 26.383 | 1.00 | 77.39 B | | O |
| ATOM | 1850 | CB | SER | B | 341 | 51.549 | 0.452 | 26.404 | 1.00 | 77.54 B | | C |
| ATOM | 1851 | OG | SER | B | 341 | 52.422 | 1.220 | 25.603 | 1.00 | 76.48 B | | O |
| ATOM | 1852 | N | MET | B | 342 | 48.772 | 1.779 | 26.071 | 1.00 | 77.44 B | | N |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 1853 | CA | MET | B | 342 | 47.777 | 2.523 | 25.317 | 1.00 | 76.92 | B | C |
| ATOM | 1854 | C | MET | B | 342 | 46.960 | 3.294 | 26.321 | 1.00 | 76.04 | B | C |
| ATOM | 1855 | O | MET | B | 342 | 46.913 | 4.523 | 26.298 | 1.00 | 75.98 | B | O |
| ATOM | 1856 | CB | MET | B | 342 | 46.836 | 1.565 | 24.609 | 1.00 | 78.20 | B | C |
| ATOM | 1857 | CG | MET | B | 342 | 47.106 | 1.396 | 23.156 | 1.00 | 79.58 | B | C |
| ATOM | 1858 | SD | MET | B | 342 | 46.337 | 2.715 | 22.233 | 1.00 | 81.24 | B | S |
| ATOM | 1859 | CE | MET | B | 342 | 44.837 | 1.859 | 21.657 | 1.00 | 81.19 | B | C |
| ATOM | 1860 | N | MET | B | 343 | 46.290 | 2.545 | 27.193 | 1.00 | 74.77 | B | N |
| ATOM | 1861 | CA | MET | B | 343 | 45.461 | 3.154 | 28.224 | 1.00 | 73.23 | B | C |
| ATOM | 1862 | C | MET | B | 343 | 46.290 | 4.236 | 28.914 | 1.00 | 71.77 | B | C |
| ATOM | 1863 | O | MET | B | 343 | 45.774 | 5.302 | 29.252 | 1.00 | 71.76 | B | O |
| ATOM | 1864 | CB | MET | B | 343 | 45.026 | 2.116 | 29.259 | 1.00 | 73.59 | B | C |
| ATOM | 1865 | CG | MET | B | 343 | 43.691 | 2.412 | 29.907 | 1.00 | 73.83 | B | C |
| ATOM | 1866 | SD | MET | B | 343 | 42.384 | 2.218 | 28.685 | 1.00 | 74.19 | B | S |
| ATOM | 1867 | CE | MET | B | 343 | 41.888 | 3.784 | 28.650 | 1.00 | 74.35 | B | C |
| ATOM | 1868 | N | GLY | B | 344 | 47.580 | 3.955 | 29.102 | 1.00 | 69.68 | B | N |
| ATOM | 1869 | CA | GLY | B | 344 | 48.471 | 4.903 | 29.744 | 1.00 | 67.32 | B | C |
| ATOM | 1870 | C | GLY | B | 344 | 48.699 | 6.177 | 28.950 | 1.00 | 65.42 | B | C |
| ATOM | 1871 | O | GLY | B | 344 | 48.581 | 7.277 | 29.490 | 1.00 | 65.71 | B | O |
| ATOM | 1872 | N | LEU | B | 345 | 49.013 | 6.045 | 27.667 | 1.00 | 63.53 | B | N |
| ATOM | 1873 | CA | LEU | B | 345 | 49.262 | 7.220 | 26.842 | 1.00 | 61.53 | B | C |
| ATOM | 1874 | C | LEU | B | 345 | 48.016 | 8.061 | 26.559 | 1.00 | 59.65 | B | C |
| ATOM | 1875 | O | LEU | B | 345 | 48.100 | 9.291 | 26.518 | 1.00 | 59.21 | B | O |
| ATOM | 1876 | CB | LEU | B | 345 | 49.909 | 6.815 | 25.518 | 1.00 | 62.06 | B | C |
| ATOM | 1877 | CG | LEU | B | 345 | 50.590 | 7.947 | 24.730 | 1.00 | 62.82 | B | C |
| ATOM | 1878 | CD1 | LEU | B | 345 | 51.359 | 7.345 | 23.559 | 1.00 | 62.76 | B | C |
| ATOM | 1879 | CD2 | LEU | B | 345 | 49.570 | 8.970 | 24.233 | 1.00 | 62.79 | B | C |
| ATOM | 1880 | N | LEU | B | 346 | 46.877 | 7.401 | 26.346 | 1.00 | 57.59 | B | N |
| ATOM | 1881 | CA | LEU | B | 346 | 45.624 | 8.094 | 26.073 | 1.00 | 55.54 | B | C |
| ATOM | 1882 | C | LEU | B | 346 | 45.034 | 8.706 | 27.338 | 1.00 | 54.78 | B | C |
| ATOM | 1883 | O | LEU | B | 346 | 44.130 | 9.555 | 27.269 | 1.00 | 54.69 | B | O |
| ATOM | 1884 | CB | LEU | B | 346 | 44.606 | 7.144 | 25.437 | 1.00 | 55.00 | B | C |
| ATOM | 1885 | CG | LEU | B | 346 | 44.958 | 6.525 | 24.079 | 1.00 | 55.02 | B | C |
| ATOM | 1886 | CD1 | LEU | B | 346 | 43.711 | 6.581 | 23.212 | 1.00 | 55.55 | B | C |
| ATOM | 1887 | CD2 | LEU | B | 346 | 46.082 | 7.265 | 23.377 | 1.00 | 54.35 | B | C |
| ATOM | 1888 | N | THR | B | 347 | 45.534 | 8.271 | 28.498 | 1.00 | 53.38 | B | N |
| ATOM | 1889 | CA | THR | B | 347 | 45.063 | 8.829 | 29.765 | 1.00 | 51.68 | B | C |
| ATOM | 1890 | C | THR | B | 347 | 45.935 | 10.047 | 30.012 | 1.00 | 50.14 | B | C |
| ATOM | 1891 | O | THR | B | 347 | 45.487 | 11.050 | 30.568 | 1.00 | 49.33 | B | O |
| ATOM | 1892 | CB | THR | B | 347 | 45.223 | 7.854 | 30.961 | 1.00 | 51.77 | B | C |
| ATOM | 1893 | OG1 | THR | B | 347 | 44.457 | 6.664 | 30.726 | 1.00 | 52.06 | B | O |
| ATOM | 1894 | CG2 | THR | B | 347 | 44.714 | 8.520 | 32.247 | 1.00 | 51.72 | B | C |
| ATOM | 1895 | N | ASN | B | 348 | 47.186 | 9.942 | 29.577 | 1.00 | 48.79 | B | N |
| ATOM | 1896 | CA | ASN | B | 348 | 48.138 | 11.030 | 29.712 | 1.00 | 48.19 | B | C |
| ATOM | 1897 | C | ASN | B | 348 | 47.585 | 12.181 | 28.866 | 1.00 | 47.40 | B | C |
| ATOM | 1898 | O | ASN | B | 348 | 47.593 | 13.347 | 29.288 | 1.00 | 47.52 | B | O |
| ATOM | 1899 | CB | ASN | B | 348 | 49.507 | 10.603 | 29.173 | 1.00 | 48.24 | B | C |
| ATOM | 1900 | CG | ASN | B | 348 | 50.618 | 11.583 | 29.543 | 1.00 | 49.23 | B | C |
| ATOM | 1901 | OD1 | ASN | B | 348 | 51.696 | 11.576 | 28.935 | 1.00 | 49.11 | B | O |
| ATOM | 1902 | ND2 | ASN | B | 348 | 50.368 | 12.421 | 30.558 | 1.00 | 49.69 | B | N |
| ATOM | 1903 | N | LEU | B | 349 | 47.084 | 11.828 | 27.678 | 1.00 | 46.30 | B | N |
| ATOM | 1904 | CA | LEU | B | 349 | 46.523 | 12.792 | 26.737 | 1.00 | 44.55 | B | C |
| ATOM | 1905 | C | LEU | B | 349 | 45.238 | 13.463 | 27.200 | 1.00 | 43.86 | B | C |
| ATOM | 1906 | O | LEU | B | 349 | 45.124 | 14.686 | 27.136 | 1.00 | 44.25 | B | O |
| ATOM | 1907 | CB | LEU | B | 349 | 46.264 | 12.134 | 25.391 | 1.00 | 43.22 | B | C |
| ATOM | 1908 | CG | LEU | B | 349 | 45.990 | 13.138 | 24.273 | 1.00 | 41.87 | B | C |
| ATOM | 1909 | CD1 | LEU | B | 349 | 47.272 | 13.876 | 23.952 | 1.00 | 40.50 | B | C |
| ATOM | 1910 | CD2 | LEU | B | 349 | 45.473 | 12.415 | 23.042 | 1.00 | 41.65 | B | C |
| ATOM | 1911 | N | ALA | B | 350 | 44.271 | 12.683 | 27.661 | 1.00 | 42.87 | B | N |
| ATOM | 1912 | CA | ALA | B | 350 | 43.019 | 13.273 | 28.101 | 1.00 | 43.17 | B | C |
| ATOM | 1913 | C | ALA | B | 350 | 43.190 | 14.211 | 29.304 | 1.00 | 43.66 | B | C |
| ATOM | 1914 | O | ALA | B | 350 | 42.685 | 15.344 | 29.291 | 1.00 | 43.26 | B | O |
| ATOM | 1915 | CB | ALA | B | 350 | 42.000 | 12.171 | 28.417 | 1.00 | 42.81 | B | C |
| ATOM | 1916 | N | ASP | B | 351 | 43.899 | 13.747 | 30.338 | 1.00 | 44.35 | B | N |
| ATOM | 1917 | CA | ASP | B | 351 | 44.121 | 14.559 | 31.545 | 1.00 | 44.19 | B | C |
| ATOM | 1918 | C | ASP | B | 351 | 44.741 | 15.895 | 31.183 | 1.00 | 43.36 | B | C |
| ATOM | 1919 | O | ASP | B | 351 | 44.466 | 16.919 | 31.815 | 1.00 | 42.79 | B | O |
| ATOM | 1920 | CB | ASP | B | 351 | 45.038 | 13.843 | 32.545 | 1.00 | 44.89 | B | C |
| ATOM | 1921 | CG | ASP | B | 351 | 44.398 | 12.609 | 33.150 | 1.00 | 45.26 | B | C |
| ATOM | 1922 | OD1 | ASP | B | 351 | 43.211 | 12.686 | 33.560 | 1.00 | 45.95 | B | O |
| ATOM | 1923 | OD2 | ASP | B | 351 | 45.093 | 11.569 | 33.223 | 1.00 | 44.50 | B | O |
| ATOM | 1924 | N | ARG | B | 352 | 45.594 | 15.875 | 30.170 | 1.00 | 42.96 | B | N |
| ATOM | 1925 | CA | ARG | B | 352 | 46.229 | 17.101 | 29.716 | 1.00 | 42.66 | B | C |
| ATOM | 1926 | C | ARG | B | 352 | 45.228 | 17.939 | 28.921 | 1.00 | 42.60 | B | C |
| ATOM | 1927 | O | ARG | B | 352 | 45.240 | 19.164 | 29.009 | 1.00 | 42.66 | B | O |

TABLE 10-continued

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 1928 | CB | ARG | B | 352 | 47.466 | 16.780 | 28.882 | 1.00 | 41.61 B | C |
| ATOM | 1929 | CG | ARG | B | 352 | 48.663 | 16.444 | 29.725 | 1.00 | 40.82 B | C |
| ATOM | 1930 | CD | ARG | B | 352 | 49.890 | 16.382 | 28.880 | 1.00 | 40.90 B | C |
| ATOM | 1931 | NE | ARG | B | 352 | 49.861 | 15.217 | 28.013 | 1.00 | 42.68 B | N |
| ATOM | 1932 | CZ | ARG | B | 352 | 50.434 | 15.164 | 26.817 | 1.00 | 43.80 B | C |
| ATOM | 1933 | NH1 | ARG | B | 352 | 51.084 | 16.228 | 26.350 | 1.00 | 44.85 B | N |
| ATOM | 1934 | NH2 | ARG | B | 352 | 50.351 | 14.053 | 26.085 | 1.00 | 43.08 B | N |
| ATOM | 1935 | N | GLU | B | 353 | 44.345 | 17.287 | 28.168 | 1.00 | 42.28 B | N |
| ATOM | 1936 | CA | GLU | B | 353 | 43.351 | 18.027 | 27.410 | 1.00 | 41.93 B | C |
| ATOM | 1937 | C | GLU | B | 353 | 42.218 | 18.494 | 28.305 | 1.00 | 41.31 B | C |
| ATOM | 1938 | O | GLU | B | 353 | 41.566 | 19.482 | 28.000 | 1.00 | 41.39 B | O |
| ATOM | 1939 | CB | GLU | B | 353 | 42.809 | 17.198 | 26.258 | 1.00 | 42.09 B | C |
| ATOM | 1940 | CG | GLU | B | 353 | 43.745 | 17.160 | 25.070 | 1.00 | 44.35 B | C |
| ATOM | 1941 | CD | GLU | B | 353 | 43.059 | 16.668 | 23.801 | 1.00 | 46.59 B | C |
| ATOM | 1942 | OE1 | GLU | B | 353 | 42.704 | 15.473 | 23.723 | 1.00 | 46.04 B | O |
| ATOM | 1943 | OE2 | GLU | B | 353 | 42.863 | 17.490 | 22.874 | 1.00 | 48.40 B | O |
| ATOM | 1944 | N | LEU | B | 354 | 41.988 | 17.812 | 29.423 | 1.00 | 41.14 B | N |
| ATOM | 1945 | CA | LEU | B | 354 | 40.924 | 18.249 | 30.311 | 1.00 | 42.05 B | C |
| ATOM | 1946 | C | LEU | B | 354 | 41.199 | 19.608 | 30.925 | 1.00 | 42.04 B | C |
| ATOM | 1947 | O | LEU | B | 354 | 40.276 | 20.278 | 31.396 | 1.00 | 42.65 B | O |
| ATOM | 1948 | CB | LEU | B | 354 | 40.684 | 17.256 | 31.439 | 1.00 | 42.47 B | C |
| ATOM | 1949 | CG | LEU | B | 354 | 39.442 | 16.413 | 31.173 | 1.00 | 43.87 B | C |
| ATOM | 1950 | CD1 | LEU | B | 354 | 39.819 | 15.268 | 30.229 | 1.00 | 43.97 B | C |
| ATOM | 1951 | CD2 | LEU | B | 354 | 38.886 | 15.876 | 32.477 | 1.00 | 44.01 B | C |
| ATOM | 1952 | N | VAL | B | 355 | 42.471 | 20.000 | 30.935 | 1.00 | 42.15 B | N |
| ATOM | 1953 | CA | VAL | B | 355 | 42.912 | 21.289 | 31.482 | 1.00 | 41.15 B | C |
| ATOM | 1954 | C | VAL | B | 355 | 42.559 | 22.404 | 30.499 | 1.00 | 40.58 B | C |
| ATOM | 1955 | O | VAL | B | 355 | 42.043 | 23.446 | 30.890 | 1.00 | 40.04 B | O |
| ATOM | 1956 | CB | VAL | B | 355 | 44.468 | 21.293 | 31.729 | 1.00 | 41.68 B | C |
| ATOM | 1957 | CG1 | VAL | B | 355 | 44.931 | 22.667 | 32.196 | 1.00 | 40.27 B | C |
| ATOM | 1958 | CG2 | VAL | B | 355 | 44.851 | 20.213 | 32.770 | 1.00 | 40.71 B | C |
| ATOM | 1959 | N | HIS | B | 356 | 42.844 | 22.167 | 29.221 | 1.00 | 40.74 B | N |
| ATOM | 1960 | CA | HIS | B | 356 | 42.559 | 23.133 | 28.165 | 1.00 | 41.86 B | C |
| ATOM | 1961 | C | HIS | B | 356 | 41.058 | 23.326 | 27.985 | 1.00 | 41.41 B | C |
| ATOM | 1962 | O | HIS | B | 356 | 40.591 | 24.427 | 27.657 | 1.00 | 41.34 B | O |
| ATOM | 1963 | CB | HIS | B | 356 | 43.178 | 22.673 | 26.841 | 1.00 | 43.39 B | C |
| ATOM | 1964 | CG | HIS | B | 356 | 44.649 | 22.934 | 26.743 | 1.00 | 45.78 B | C |
| ATOM | 1965 | ND1 | HIS | B | 356 | 45.195 | 24.184 | 26.948 | 1.00 | 47.21 B | N |
| ATOM | 1966 | CD2 | HIS | B | 356 | 45.686 | 22.114 | 26.452 | 1.00 | 46.52 B | C |
| ATOM | 1967 | CE1 | HIS | B | 356 | 46.506 | 24.123 | 26.787 | 1.00 | 47.57 B | C |
| ATOM | 1968 | NE2 | HIS | B | 356 | 46.829 | 22.877 | 26.484 | 1.00 | 47.38 B | N |
| ATOM | 1969 | N | MET | B | 357 | 40.311 | 22.249 | 28.223 | 1.00 | 40.39 B | N |
| ATOM | 1970 | CA | MET | B | 357 | 38.862 | 22.249 | 28.088 | 1.00 | 39.00 B | C |
| ATOM | 1971 | C | MET | B | 357 | 38.163 | 23.140 | 29.116 | 1.00 | 39.03 B | C |
| ATOM | 1972 | O | MET | B | 357 | 37.105 | 23.711 | 28.836 | 1.00 | 38.28 B | O |
| ATOM | 1973 | CB | MET | B | 357 | 38.350 | 20.815 | 28.214 | 1.00 | 37.56 B | C |
| ATOM | 1974 | CG | MET | B | 357 | 36.875 | 20.626 | 27.910 | 1.00 | 36.34 B | C |
| ATOM | 1975 | SD | MET | B | 357 | 36.234 | 19.065 | 28.592 | 1.00 | 33.82 B | S |
| ATOM | 1976 | CE | MET | B | 357 | 37.058 | 17.840 | 27.485 | 1.00 | 34.93 B | C |
| ATOM | 1977 | N | ILE | B | 358 | 38.749 | 23.248 | 30.307 | 1.00 | 39.05 B | N |
| ATOM | 1978 | CA | ILE | B | 358 | 38.155 | 24.055 | 31.355 | 1.00 | 39.74 B | C |
| ATOM | 1979 | C | ILE | B | 358 | 38.260 | 25.552 | 31.045 | 1.00 | 41.29 B | C |
| ATOM | 1980 | O | ILE | B | 358 | 37.322 | 26.306 | 31.326 | 1.00 | 41.40 B | O |
| ATOM | 1981 | CB | ILE | B | 358 | 38.788 | 23.744 | 32.741 | 1.00 | 39.00 B | C |
| ATOM | 1982 | CG1 | ILE | B | 358 | 38.589 | 22.255 | 33.080 | 1.00 | 38.84 B | C |
| ATOM | 1983 | CG2 | ILE | B | 358 | 38.137 | 24.609 | 33.822 | 1.00 | 38.39 B | C |
| ATOM | 1984 | CD1 | ILE | B | 358 | 39.025 | 21.843 | 34.491 | 1.00 | 37.62 B | C |
| ATOM | 1985 | N | ASN | B | 359 | 39.384 | 26.000 | 30.477 | 1.00 | 42.58 B | N |
| ATOM | 1986 | CA | ASN | B | 359 | 39.510 | 27.428 | 30.132 | 1.00 | 43.34 B | C |
| ATOM | 1987 | C | ASN | B | 359 | 38.564 | 27.706 | 28.981 | 1.00 | 43.96 B | C |
| ATOM | 1988 | O | ASN | B | 359 | 37.865 | 28.723 | 28.974 | 1.00 | 44.04 B | O |
| ATOM | 1989 | CB | ASN | B | 359 | 40.934 | 27.809 | 29.706 | 1.00 | 43.11 B | C |
| ATOM | 1990 | CG | ASN | B | 359 | 41.901 | 27.847 | 30.870 | 1.00 | 43.39 B | C |
| ATOM | 1991 | OD1 | ASN | B | 359 | 41.594 | 28.386 | 31.944 | 1.00 | 42.71 B | O |
| ATOM | 1992 | ND2 | ASN | B | 359 | 43.085 | 27.285 | 30.662 | 1.00 | 42.85 B | N |
| ATOM | 1993 | N | TRP | B | 360 | 38.557 | 26.790 | 28.011 | 1.00 | 44.94 B | N |
| ATOM | 1994 | CA | TRP | B | 360 | 37.686 | 26.875 | 26.841 | 1.00 | 45.92 B | C |
| ATOM | 1995 | C | TRP | B | 360 | 36.262 | 27.153 | 27.323 | 1.00 | 46.70 B | C |
| ATOM | 1996 | O | TRP | B | 360 | 35.610 | 28.106 | 26.882 | 1.00 | 46.56 B | O |
| ATOM | 1997 | CB | TRP | B | 360 | 37.740 | 25.543 | 26.088 | 1.00 | 46.36 B | C |
| ATOM | 1998 | CG | TRP | B | 360 | 36.605 | 25.277 | 25.126 | 1.00 | 47.06 B | C |
| ATOM | 1999 | CD1 | TRP | B | 360 | 36.571 | 25.577 | 23.794 | 1.00 | 47.04 B | C |
| ATOM | 2000 | CD2 | TRP | B | 360 | 35.366 | 24.599 | 25.417 | 1.00 | 46.75 B | C |
| ATOM | 2001 | NE1 | TRP | B | 360 | 35.396 | 25.124 | 23.236 | 1.00 | 47.01 B | N |
| ATOM | 2002 | CE2 | TRP | B | 360 | 34.639 | 24.528 | 24.205 | 1.00 | 46.91 B | C |

TABLE 10-continued

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 2003 | CE3 | TRP | B | 360 | 34.806 | 24.055 | 26.578 | 1.00 | 46.23 B | C |
| ATOM | 2004 | CZ2 | TRP | B | 360 | 33.375 | 23.923 | 24.125 | 1.00 | 46.64 B | C |
| ATOM | 2005 | CZ3 | TRP | B | 360 | 33.550 | 23.457 | 26.497 | 1.00 | 46.72 B | C |
| ATOM | 2006 | CH2 | TRP | B | 360 | 32.848 | 23.398 | 25.275 | 1.00 | 46.61 B | C |
| ATOM | 2007 | N | ALA | B | 361 | 35.806 | 26.323 | 28.257 | 1.00 | 47.26 B | N |
| ATOM | 2008 | CA | ALA | B | 361 | 34.464 | 26.427 | 28.817 | 1.00 | 48.06 B | C |
| ATOM | 2009 | C | ALA | B | 361 | 34.198 | 27.739 | 29.563 | 1.00 | 48.72 B | C |
| ATOM | 2010 | O | ALA | B | 361 | 33.047 | 28.094 | 29.822 | 1.00 | 49.07 B | O |
| ATOM | 2011 | CB | ALA | B | 361 | 34.193 | 25.220 | 29.749 | 1.00 | 47.65 B | C |
| ATOM | 2012 | N | LYS | B | 362 | 35.247 | 28.463 | 29.913 | 1.00 | 49.37 B | N |
| ATOM | 2013 | CA | LYS | B | 362 | 35.051 | 29.705 | 30.639 | 1.00 | 50.16 B | C |
| ATOM | 2014 | C | LYS | B | 362 | 34.925 | 30.865 | 29.652 | 1.00 | 50.22 B | C |
| ATOM | 2015 | O | LYS | B | 362 | 34.462 | 31.942 | 30.005 | 1.00 | 49.93 B | O |
| ATOM | 2016 | CB | LYS | B | 362 | 36.213 | 29.908 | 31.628 | 1.00 | 50.93 B | C |
| ATOM | 2017 | CG | LYS | B | 362 | 36.244 | 28.867 | 32.765 | 1.00 | 51.70 B | C |
| ATOM | 2018 | CD | LYS | B | 362 | 37.648 | 28.681 | 33.378 | 1.00 | 52.68 B | C |
| ATOM | 2019 | CE | LYS | B | 362 | 38.152 | 29.924 | 34.112 | 1.00 | 53.14 B | C |
| ATOM | 2020 | NZ | LYS | B | 362 | 39.565 | 29.754 | 34.562 | 1.00 | 53.44 B | N |
| ATOM | 2021 | N | ARG | B | 363 | 35.330 | 30.634 | 28.410 | 0.50 | 50.91 B | N |
| ATOM | 2022 | CA | ARG | B | 363 | 35.230 | 31.667 | 27.391 | 0.50 | 51.63 B | C |
| ATOM | 2023 | C | ARG | B | 363 | 33.979 | 31.462 | 26.539 | 0.50 | 52.62 B | C |
| ATOM | 2024 | O | ARG | B | 363 | 33.704 | 32.233 | 25.621 | 0.50 | 52.43 B | O |
| ATOM | 2025 | CB | ARG | B | 363 | 36.489 | 31.676 | 26.519 | 0.50 | 51.13 B | C |
| ATOM | 2026 | CG | ARG | B | 363 | 37.703 | 32.277 | 27.221 | 0.50 | 50.41 B | C |
| ATOM | 2027 | CD | ARG | B | 363 | 38.815 | 32.577 | 26.237 | 0.50 | 50.15 B | C |
| ATOM | 2028 | NE | ARG | B | 363 | 38.348 | 33.404 | 25.127 | 0.50 | 49.84 B | N |
| ATOM | 2029 | CZ | ARG | B | 363 | 39.082 | 33.706 | 24.059 | 0.50 | 49.73 B | C |
| ATOM | 2030 | NH1 | ARG | B | 363 | 40.324 | 33.254 | 23.958 | 0.50 | 49.31 B | N |
| ATOM | 2031 | NH2 | ARG | B | 363 | 38.566 | 34.441 | 23.081 | 0.50 | 49.52 B | N |
| ATOM | 2032 | N | VAL | B | 364 | 33.220 | 30.417 | 26.861 | 1.00 | 54.24 B | N |
| ATOM | 2033 | CA | VAL | B | 364 | 31.977 | 30.094 | 26.157 | 1.00 | 55.87 B | C |
| ATOM | 2034 | C | VAL | B | 364 | 30.898 | 31.003 | 26.719 | 1.00 | 56.96 B | C |
| ATOM | 2035 | O | VAL | B | 364 | 30.472 | 30.852 | 27.867 | 1.00 | 57.52 B | O |
| ATOM | 2036 | CB | VAL | B | 364 | 31.558 | 28.617 | 26.381 | 1.00 | 55.98 B | C |
| ATOM | 2037 | CG1 | VAL | B | 364 | 30.169 | 28.373 | 25.831 | 1.00 | 56.38 B | C |
| ATOM | 2038 | CG2 | VAL | B | 364 | 32.542 | 27.687 | 25.689 | 1.00 | 56.57 B | C |
| ATOM | 2039 | N | PRO | B | 365 | 30.430 | 31.958 | 25.908 | 1.00 | 57.68 B | N |
| ATOM | 2040 | CA | PRO | B | 365 | 29.397 | 32.899 | 26.345 | 1.00 | 58.13 B | C |
| ATOM | 2041 | C | PRO | B | 365 | 28.338 | 32.292 | 27.267 | 1.00 | 58.29 B | C |
| ATOM | 2042 | O | PRO | B | 365 | 27.716 | 31.283 | 26.937 | 1.00 | 58.05 B | O |
| ATOM | 2043 | CB | PRO | B | 365 | 28.827 | 33.408 | 25.021 | 1.00 | 58.33 B | C |
| ATOM | 2044 | CG | PRO | B | 365 | 30.059 | 33.425 | 24.133 | 1.00 | 58.08 B | C |
| ATOM | 2045 | CD | PRO | B | 365 | 30.687 | 32.087 | 24.460 | 1.00 | 57.95 B | C |
| ATOM | 2046 | N | GLY | B | 366 | 28.168 | 32.902 | 28.438 | 1.00 | 58.79 B | N |
| ATOM | 2047 | CA | GLY | B | 366 | 27.170 | 32.442 | 29.390 | 1.00 | 59.17 B | C |
| ATOM | 2048 | C | GLY | B | 366 | 27.513 | 31.326 | 30.370 | 1.00 | 59.55 B | C |
| ATOM | 2049 | O | GLY | B | 366 | 26.741 | 31.091 | 31.303 | 1.00 | 59.53 B | O |
| ATOM | 2050 | N | PHE | B | 367 | 28.633 | 30.626 | 30.176 | 1.00 | 59.49 B | N |
| ATOM | 2051 | CA | PHE | B | 367 | 29.013 | 29.540 | 31.092 | 1.00 | 59.21 B | C |
| ATOM | 2052 | C | PHE | B | 367 | 29.453 | 30.104 | 32.430 | 1.00 | 59.44 B | C |
| ATOM | 2053 | O | PHE | B | 367 | 28.925 | 29.731 | 33.482 | 1.00 | 58.99 B | O |
| ATOM | 2054 | CB | PHE | B | 367 | 30.163 | 28.714 | 30.526 | 1.00 | 58.38 B | C |
| ATOM | 2055 | CG | PHE | B | 367 | 30.495 | 27.497 | 31.345 | 1.00 | 57.61 B | C |
| ATOM | 2056 | CD1 | PHE | B | 367 | 29.742 | 26.339 | 31.223 | 1.00 | 57.71 B | C |
| ATOM | 2057 | CD2 | PHE | B | 367 | 31.552 | 27.511 | 32.247 | 1.00 | 57.60 B | C |
| ATOM | 2058 | CE1 | PHE | B | 367 | 30.030 | 25.216 | 31.983 | 1.00 | 57.54 B | C |
| ATOM | 2059 | CE2 | PHE | B | 367 | 31.849 | 26.393 | 33.014 | 1.00 | 57.29 B | C |
| ATOM | 2060 | CZ | PHE | B | 367 | 31.088 | 25.244 | 32.881 | 1.00 | 57.65 B | C |
| ATOM | 2061 | N | VAL | B | 368 | 30.425 | 31.009 | 32.385 | 1.00 | 60.04 B | N |
| ATOM | 2062 | CA | VAL | B | 368 | 30.945 | 31.613 | 33.604 | 1.00 | 61.19 B | C |
| ATOM | 2063 | C | VAL | B | 368 | 29.843 | 32.255 | 34.439 | 1.00 | 61.94 B | C |
| ATOM | 2064 | O | VAL | B | 368 | 30.026 | 32.494 | 35.640 | 1.00 | 62.13 B | O |
| ATOM | 2065 | CB | VAL | B | 368 | 32.020 | 32.669 | 33.279 | 1.00 | 61.31 B | C |
| ATOM | 2066 | CG1 | VAL | B | 368 | 32.764 | 33.091 | 34.559 | 1.00 | 61.34 B | C |
| ATOM | 2067 | CG2 | VAL | B | 368 | 32.985 | 32.101 | 32.257 | 1.00 | 61.15 B | C |
| ATOM | 2068 | N | ASP | B | 369 | 28.704 | 32.525 | 33.799 | 1.00 | 62.71 B | N |
| ATOM | 2069 | CA | ASP | B | 369 | 27.548 | 33.146 | 34.458 | 1.00 | 63.16 B | C |
| ATOM | 2070 | C | ASP | B | 369 | 26.790 | 32.149 | 35.334 | 1.00 | 62.58 B | C |
| ATOM | 2071 | O | ASP | B | 369 | 25.857 | 32.508 | 36.058 | 1.00 | 62.36 B | O |
| ATOM | 2072 | CB | ASP | B | 369 | 26.598 | 33.744 | 33.405 | 1.00 | 64.67 B | C |
| ATOM | 2073 | CG | ASP | B | 369 | 27.193 | 34.969 | 32.705 | 1.00 | 66.39 B | C |
| ATOM | 2074 | OD1 | ASP | B | 369 | 27.693 | 35.863 | 33.422 | 1.00 | 67.02 B | O |
| ATOM | 2075 | OD2 | ASP | B | 369 | 27.161 | 35.038 | 31.450 | 1.00 | 67.07 B | O |
| ATOM | 2076 | N | LEU | B | 370 | 27.208 | 30.892 | 35.262 | 1.00 | 61.72 B | N |
| ATOM | 2077 | CA | LEU | B | 370 | 26.582 | 29.844 | 36.044 | 1.00 | 60.70 B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2078 | C | LEU | B | 370 | 27.145 | 29.834 | 37.446 | 1.00 | 60.00 | B | C |
| ATOM | 2079 | O | LEU | B | 370 | 28.119 | 30.520 | 37.753 | 1.00 | 59.45 | B | O |
| ATOM | 2080 | CB | LEU | B | 370 | 26.819 | 28.472 | 35.401 | 1.00 | 60.41 | B | C |
| ATOM | 2081 | CG | LEU | B | 370 | 25.998 | 28.185 | 34.146 | 1.00 | 60.30 | B | C |
| ATOM | 2082 | CD1 | LEU | B | 370 | 26.392 | 26.844 | 33.564 | 1.00 | 60.40 | B | C |
| ATOM | 2083 | CD2 | LEU | B | 370 | 24.525 | 28.200 | 34.506 | 1.00 | 60.43 | B | C |
| ATOM | 2084 | N | THR | B | 371 | 26.497 | 29.056 | 38.298 | 1.00 | 59.38 | B | N |
| ATOM | 2085 | CA | THR | B | 371 | 26.947 | 28.902 | 39.656 | 1.00 | 58.57 | B | C |
| ATOM | 2086 | C | THR | B | 371 | 28.151 | 27.989 | 39.468 | 1.00 | 58.19 | B | C |
| ATOM | 2087 | O | THR | B | 371 | 28.163 | 27.147 | 38.564 | 1.00 | 57.65 | B | O |
| ATOM | 2088 | CB | THR | B | 371 | 25.913 | 28.163 | 40.512 | 1.00 | 58.85 | B | C |
| ATOM | 2089 | OG1 | THR | B | 371 | 25.986 | 26.759 | 40.228 | 1.00 | 58.98 | B | O |
| ATOM | 2090 | CG2 | THR | B | 371 | 24.510 | 28.658 | 40.200 | 1.00 | 58.63 | B | C |
| ATOM | 2091 | N | LEU | B | 372 | 29.161 | 28.167 | 40.311 | 1.00 | 57.82 | B | N |
| ATOM | 2092 | CA | LEU | B | 372 | 30.373 | 27.361 | 40.247 | 1.00 | 56.89 | B | C |
| ATOM | 2093 | C | LEU | B | 372 | 29.957 | 25.902 | 40.225 | 1.00 | 55.99 | B | C |
| ATOM | 2094 | O | LEU | B | 372 | 30.516 | 25.089 | 39.487 | 1.00 | 55.93 | B | O |
| ATOM | 2095 | CB | LEU | B | 372 | 31.229 | 27.632 | 41.482 | 1.00 | 56.93 | B | C |
| ATOM | 2096 | CG | LEU | B | 372 | 32.746 | 27.628 | 41.316 | 1.00 | 57.07 | B | C |
| ATOM | 2097 | CD1 | LEU | B | 372 | 33.174 | 28.628 | 40.231 | 1.00 | 56.76 | B | C |
| ATOM | 2098 | CD2 | LEU | B | 372 | 33.373 | 27.987 | 42.662 | 1.00 | 57.59 | B | C |
| ATOM | 2099 | N | HIS | B | 373 | 28.956 | 25.594 | 41.042 | 1.00 | 54.89 | B | N |
| ATOM | 2100 | CA | HIS | B | 373 | 28.431 | 24.249 | 41.151 | 1.00 | 54.14 | B | C |
| ATOM | 2101 | C | HIS | B | 373 | 27.806 | 23.757 | 39.843 | 1.00 | 53.63 | B | C |
| ATOM | 2102 | O | HIS | B | 373 | 27.882 | 22.571 | 39.535 | 1.00 | 53.94 | B | O |
| ATOM | 2103 | CB | HIS | B | 373 | 27.395 | 24.188 | 42.265 | 1.00 | 54.37 | B | C |
| ATOM | 2104 | CG | HIS | B | 373 | 26.883 | 22.810 | 42.537 | 1.00 | 54.25 | B | C |
| ATOM | 2105 | ND1 | HIS | B | 373 | 25.643 | 22.577 | 43.089 | 1.00 | 54.53 | B | N |
| ATOM | 2106 | CD2 | HIS | B | 373 | 27.449 | 21.594 | 42.352 | 1.00 | 54.55 | B | C |
| ATOM | 2107 | CE1 | HIS | B | 373 | 25.464 | 21.275 | 43.231 | 1.00 | 54.77 | B | C |
| ATOM | 2108 | NE2 | HIS | B | 373 | 26.545 | 20.657 | 42.791 | 1.00 | 54.88 | B | N |
| ATOM | 2109 | N | ASP | B | 374 | 27.177 | 24.641 | 39.074 | 1.00 | 52.60 | B | N |
| ATOM | 2110 | CA | ASP | B | 374 | 26.601 | 24.188 | 37.809 | 1.00 | 51.62 | B | C |
| ATOM | 2111 | C | ASP | B | 374 | 27.720 | 23.981 | 36.796 | 1.00 | 50.76 | B | C |
| ATOM | 2112 | O | ASP | B | 374 | 27.710 | 23.018 | 36.025 | 1.00 | 51.02 | B | O |
| ATOM | 2113 | CB | ASP | B | 374 | 25.575 | 25.191 | 37.260 | 1.00 | 51.97 | B | C |
| ATOM | 2114 | CG | ASP | B | 374 | 24.244 | 25.157 | 38.022 | 1.00 | 52.73 | B | C |
| ATOM | 2115 | OD1 | ASP | B | 374 | 23.765 | 24.040 | 38.338 | 1.00 | 53.14 | B | O |
| ATOM | 2116 | OD2 | ASP | B | 374 | 23.666 | 26.242 | 38.289 | 1.00 | 52.10 | B | O |
| ATOM | 2117 | N | GLN | B | 375 | 28.700 | 24.879 | 36.816 | 1.00 | 49.65 | B | N |
| ATOM | 2118 | CA | GLN | B | 375 | 29.829 | 24.795 | 35.903 | 1.00 | 48.36 | B | C |
| ATOM | 2119 | C | GLN | B | 375 | 30.579 | 23.473 | 36.046 | 1.00 | 47.32 | B | C |
| ATOM | 2120 | O | GLN | B | 375 | 31.017 | 22.893 | 35.055 | 1.00 | 46.40 | B | O |
| ATOM | 2121 | CB | GLN | B | 375 | 30.800 | 25.937 | 36.169 | 1.00 | 49.17 | B | C |
| ATOM | 2122 | CG | GLN | B | 375 | 30.146 | 27.298 | 36.343 | 1.00 | 50.22 | B | C |
| ATOM | 2123 | CD | GLN | B | 375 | 31.175 | 28.418 | 36.366 | 1.00 | 50.13 | B | C |
| ATOM | 2124 | OE1 | GLN | B | 375 | 32.223 | 28.298 | 36.996 | 1.00 | 50.21 | B | O |
| ATOM | 2125 | NE2 | GLN | B | 375 | 30.876 | 29.510 | 35.678 | 1.00 | 50.32 | B | N |
| ATOM | 2126 | N | VAL | B | 376 | 30.737 | 23.022 | 37.291 | 1.00 | 46.41 | B | N |
| ATOM | 2127 | CA | VAL | B | 376 | 31.446 | 21.778 | 37.604 | 1.00 | 45.56 | B | C |
| ATOM | 2128 | C | VAL | B | 376 | 30.644 | 20.572 | 37.155 | 1.00 | 45.22 | B | C |
| ATOM | 2129 | O | VAL | B | 376 | 31.194 | 19.557 | 36.735 | 1.00 | 44.72 | B | O |
| ATOM | 2130 | CB | VAL | B | 376 | 31.719 | 21.637 | 39.135 | 1.00 | 44.84 | B | C |
| ATOM | 2131 | CG1 | VAL | B | 376 | 32.305 | 20.264 | 39.444 | 1.00 | 42.98 | B | C |
| ATOM | 2132 | CG2 | VAL | B | 376 | 32.683 | 22.716 | 39.592 | 1.00 | 44.26 | B | C |
| ATOM | 2133 | N | HIS | B | 377 | 29.330 | 20.699 | 37.246 | 1.00 | 45.20 | B | N |
| ATOM | 2134 | CA | HIS | B | 377 | 28.444 | 19.622 | 36.865 | 1.00 | 45.00 | B | C |
| ATOM | 2135 | C | HIS | B | 377 | 28.406 | 19.417 | 35.353 | 1.00 | 43.82 | B | C |
| ATOM | 2136 | O | HIS | B | 377 | 28.518 | 18.283 | 34.871 | 1.00 | 43.35 | B | O |
| ATOM | 2137 | CB | HIS | B | 377 | 27.055 | 19.911 | 37.390 | 1.00 | 46.84 | B | C |
| ATOM | 2138 | CG | HIS | B | 377 | 26.127 | 18.746 | 37.287 | 1.00 | 49.60 | B | C |
| ATOM | 2139 | ND1 | HIS | B | 377 | 26.432 | 17.507 | 37.811 | 1.00 | 49.88 | B | N |
| ATOM | 2140 | CD2 | HIS | B | 377 | 24.891 | 18.636 | 36.740 | 1.00 | 49.89 | B | C |
| ATOM | 2141 | CE1 | HIS | B | 377 | 25.420 | 16.685 | 37.594 | 1.00 | 50.76 | B | C |
| ATOM | 2142 | NE2 | HIS | B | 377 | 24.473 | 17.345 | 36.946 | 1.00 | 50.43 | B | N |
| ATOM | 2143 | N | LEU | B | 378 | 28.254 | 20.506 | 34.603 | 1.00 | 42.19 | B | N |
| ATOM | 2144 | CA | LEU | B | 378 | 28.218 | 20.402 | 33.149 | 1.00 | 40.34 | B | C |
| ATOM | 2145 | C | LEU | B | 378 | 29.535 | 19.832 | 32.645 | 1.00 | 39.00 | B | C |
| ATOM | 2146 | O | LEU | B | 378 | 29.556 | 19.026 | 31.714 | 1.00 | 38.08 | B | O |
| ATOM | 2147 | CB | LEU | B | 378 | 27.949 | 21.765 | 32.509 | 1.00 | 40.27 | B | C |
| ATOM | 2148 | CG | LEU | B | 378 | 26.639 | 22.434 | 32.931 | 1.00 | 40.99 | B | C |
| ATOM | 2149 | CD1 | LEU | B | 378 | 26.383 | 23.656 | 32.058 | 1.00 | 40.23 | B | C |
| ATOM | 2150 | CD2 | LEU | B | 378 | 25.486 | 21.440 | 32.811 | 1.00 | 40.59 | B | C |
| ATOM | 2151 | N | LEU | B | 379 | 30.634 | 20.236 | 33.269 | 1.00 | 37.65 | B | N |
| ATOM | 2152 | CA | LEU | B | 379 | 31.933 | 19.725 | 32.858 | 1.00 | 37.38 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2153 | C | LEU | B | 379 | 32.038 | 18.260 | 33.246 | 1.00 | 37.89 | B | C |
| ATOM | 2154 | O | LEU | B | 379 | 32.585 | 17.442 | 32.506 | 1.00 | 37.82 | B | O |
| ATOM | 2155 | CB | LEU | B | 379 | 33.079 | 20.508 | 33.510 | 1.00 | 35.33 | B | C |
| ATOM | 2156 | CG | LEU | B | 379 | 33.505 | 21.848 | 32.901 | 1.00 | 34.47 | B | C |
| ATOM | 2157 | CD1 | LEU | B | 379 | 34.862 | 22.236 | 33.502 | 1.00 | 34.31 | B | C |
| ATOM | 2158 | CD2 | LEU | B | 379 | 33.614 | 21.760 | 31.381 | 1.00 | 32.75 | B | C |
| ATOM | 2159 | N | GLU | B | 380 | 31.506 | 17.929 | 34.416 | 1.00 | 38.61 | B | N |
| ATOM | 2160 | CA | GLU | B | 380 | 31.556 | 16.557 | 34.898 | 1.00 | 38.76 | B | C |
| ATOM | 2161 | C | GLU | B | 380 | 30.768 | 15.610 | 33.991 | 1.00 | 37.40 | B | C |
| ATOM | 2162 | O | GLU | B | 380 | 31.198 | 14.482 | 33.742 | 1.00 | 36.97 | B | O |
| ATOM | 2163 | CB | GLU | B | 380 | 31.030 | 16.476 | 36.336 | 1.00 | 39.83 | B | C |
| ATOM | 2164 | CG | GLU | B | 380 | 31.359 | 15.161 | 37.026 | 1.00 | 42.68 | B | C |
| ATOM | 2165 | CD | GLU | B | 380 | 31.533 | 15.329 | 38.530 | 1.00 | 45.31 | B | C |
| ATOM | 2166 | OE1 | GLU | B | 380 | 30.548 | 15.713 | 39.200 | 1.00 | 47.13 | B | O |
| ATOM | 2167 | OE2 | GLU | B | 380 | 32.656 | 15.088 | 39.042 | 1.00 | 45.85 | B | O |
| ATOM | 2168 | N | CYS | B | 381 | 29.629 | 16.072 | 33.482 | 1.00 | 36.19 | B | N |
| ATOM | 2169 | CA | CYS | B | 381 | 28.812 | 15.230 | 32.610 | 1.00 | 35.43 | B | C |
| ATOM | 2170 | C | CYS | B | 381 | 29.292 | 15.154 | 31.148 | 1.00 | 34.31 | B | C |
| ATOM | 2171 | O | CYS | B | 381 | 29.123 | 14.123 | 30.487 | 1.00 | 33.34 | B | O |
| ATOM | 2172 | CB | CYS | B | 381 | 27.348 | 15.698 | 32.646 | 1.00 | 35.83 | B | C |
| ATOM | 2173 | SG | CYS | B | 381 | 26.506 | 15.547 | 34.279 | 1.00 | 34.36 | B | S |
| ATOM | 2174 | N | ALA | B | 382 | 29.943 | 16.212 | 30.663 | 1.00 | 33.30 | B | N |
| ATOM | 2175 | CA | ALA | B | 382 | 30.363 | 16.249 | 29.262 | 1.00 | 31.40 | B | C |
| ATOM | 2176 | C | ALA | B | 382 | 31.822 | 16.235 | 28.838 | 1.00 | 30.29 | B | C |
| ATOM | 2177 | O | ALA | B | 382 | 32.090 | 16.340 | 27.637 | 1.00 | 29.96 | B | O |
| ATOM | 2178 | CB | ALA | B | 382 | 29.691 | 17.423 | 28.593 | 1.00 | 31.84 | B | C |
| ATOM | 2179 | N | TRP | B | 383 | 32.766 | 16.071 | 29.760 | 1.00 | 27.88 | B | N |
| ATOM | 2180 | CA | TRP | B | 383 | 34.166 | 16.118 | 29.339 | 1.00 | 26.01 | B | C |
| ATOM | 2181 | C | TRP | B | 383 | 34.549 | 15.071 | 28.288 | 1.00 | 25.27 | B | C |
| ATOM | 2182 | O | TRP | B | 383 | 35.319 | 15.375 | 27.372 | 1.00 | 24.07 | B | O |
| ATOM | 2183 | CB | TRP | B | 383 | 35.118 | 15.994 | 30.537 | 1.00 | 24.72 | B | C |
| ATOM | 2184 | CG | TRP | B | 383 | 35.010 | 14.662 | 31.233 | 1.00 | 25.25 | B | C |
| ATOM | 2185 | CD1 | TRP | B | 383 | 34.113 | 14.318 | 32.215 | 1.00 | 24.14 | B | C |
| ATOM | 2186 | CD2 | TRP | B | 383 | 35.772 | 13.470 | 30.947 | 1.00 | 23.68 | B | C |
| ATOM | 2187 | NE1 | TRP | B | 383 | 34.274 | 12.996 | 32.553 | 1.00 | 23.01 | B | N |
| ATOM | 2188 | CE2 | TRP | B | 383 | 35.283 | 12.452 | 31.801 | 1.00 | 22.91 | B | C |
| ATOM | 2189 | CE3 | TRP | B | 383 | 36.820 | 13.168 | 30.056 | 1.00 | 23.81 | B | C |
| ATOM | 2190 | CZ2 | TRP | B | 383 | 35.802 | 11.141 | 31.791 | 1.00 | 22.21 | B | C |
| ATOM | 2191 | CZ3 | TRP | B | 383 | 37.344 | 11.852 | 30.044 | 1.00 | 24.12 | B | C |
| ATOM | 2192 | CH2 | TRP | B | 383 | 36.827 | 10.861 | 30.917 | 1.00 | 23.13 | B | C |
| ATOM | 2193 | N | LEU | B | 384 | 34.013 | 13.849 | 28.401 | 1.00 | 25.19 | B | N |
| ATOM | 2194 | CA | LEU | B | 384 | 34.378 | 12.791 | 27.450 | 1.00 | 24.05 | B | C |
| ATOM | 2195 | C | LEU | B | 384 | 33.724 | 12.947 | 26.068 | 1.00 | 24.39 | B | C |
| ATOM | 2196 | O | LEU | B | 384 | 34.283 | 12.492 | 25.051 | 1.00 | 23.13 | B | O |
| ATOM | 2197 | CB | LEU | B | 384 | 34.069 | 11.403 | 28.037 | 1.00 | 22.98 | B | C |
| ATOM | 2198 | CG | LEU | B | 384 | 34.568 | 10.177 | 27.249 | 1.00 | 22.44 | B | C |
| ATOM | 2199 | CD1 | LEU | B | 384 | 36.060 | 10.284 | 26.953 | 1.00 | 20.30 | B | C |
| ATOM | 2200 | CD2 | LEU | B | 384 | 34.268 | 8.908 | 28.052 | 1.00 | 22.11 | B | C |
| ATOM | 2201 | N | GLU | B | 385 | 32.548 | 13.582 | 26.038 | 1.00 | 24.79 | B | N |
| ATOM | 2202 | CA | GLU | B | 385 | 31.836 | 13.819 | 24.780 | 1.00 | 25.16 | B | C |
| ATOM | 2203 | C | GLU | B | 385 | 32.639 | 14.824 | 23.998 | 1.00 | 24.28 | B | C |
| ATOM | 2204 | O | GLU | B | 385 | 32.799 | 14.720 | 22.785 | 1.00 | 25.02 | B | O |
| ATOM | 2205 | CB | GLU | B | 385 | 30.450 | 14.398 | 25.045 | 1.00 | 27.15 | B | C |
| ATOM | 2206 | CG | GLU | B | 385 | 29.352 | 13.354 | 25.109 | 1.00 | 29.72 | B | C |
| ATOM | 2207 | CD | GLU | B | 385 | 28.142 | 13.842 | 25.879 | 1.00 | 31.48 | B | C |
| ATOM | 2208 | OE1 | GLU | B | 385 | 28.334 | 14.246 | 27.049 | 1.00 | 33.06 | B | O |
| ATOM | 2209 | OE2 | GLU | B | 385 | 27.009 | 13.812 | 25.329 | 1.00 | 32.34 | B | O |
| ATOM | 2210 | N | ILE | B | 386 | 33.168 | 15.784 | 24.735 | 1.00 | 22.80 | B | N |
| ATOM | 2211 | CA | ILE | B | 386 | 33.961 | 16.857 | 24.184 | 1.00 | 21.33 | B | C |
| ATOM | 2212 | C | ILE | B | 386 | 35.309 | 16.376 | 23.673 | 1.00 | 20.65 | B | C |
| ATOM | 2213 | O | ILE | B | 386 | 35.767 | 16.808 | 22.610 | 1.00 | 20.78 | B | O |
| ATOM | 2214 | CB | ILE | B | 386 | 34.081 | 17.973 | 25.235 | 1.00 | 20.68 | B | C |
| ATOM | 2215 | CG1 | ILE | B | 386 | 32.688 | 18.625 | 25.381 | 1.00 | 21.95 | B | C |
| ATOM | 2216 | CG2 | ILE | B | 386 | 35.151 | 18.949 | 24.846 | 1.00 | 18.52 | B | C |
| ATOM | 2217 | CD1 | ILE | B | 386 | 32.426 | 19.421 | 26.680 | 1.00 | 22.67 | B | C |
| ATOM | 2218 | N | LEU | B | 387 | 35.949 | 15.471 | 24.400 | 1.00 | 20.54 | B | N |
| ATOM | 2219 | CA | LEU | B | 387 | 37.224 | 14.936 | 23.934 | 1.00 | 20.84 | B | C |
| ATOM | 2220 | C | LEU | B | 387 | 36.953 | 14.132 | 22.663 | 1.00 | 21.44 | B | C |
| ATOM | 2221 | O | LEU | B | 387 | 37.732 | 14.182 | 21.714 | 1.00 | 21.79 | B | O |
| ATOM | 2222 | CB | LEU | B | 387 | 37.863 | 14.036 | 24.992 | 1.00 | 21.02 | B | C |
| ATOM | 2223 | CG | LEU | B | 387 | 38.565 | 14.720 | 26.168 | 1.00 | 21.58 | B | C |
| ATOM | 2224 | CD1 | LEU | B | 387 | 38.913 | 13.688 | 27.227 | 1.00 | 20.76 | B | C |
| ATOM | 2225 | CD2 | LEU | B | 387 | 39.832 | 15.428 | 25.669 | 1.00 | 20.57 | B | C |
| ATOM | 2226 | N | MET | B | 388 | 35.842 | 13.399 | 22.643 | 1.00 | 22.73 | B | N |
| ATOM | 2227 | CA | MET | B | 388 | 35.491 | 12.604 | 21.474 | 1.00 | 24.76 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2228 | C | MET | B | 388 | 35.124 | 13.477 | 20.260 | 1.00 | 24.59 B | | C |
| ATOM | 2229 | O | MET | B | 388 | 35.690 | 13.304 | 19.183 | 1.00 | 23.10 B | | O |
| ATOM | 2230 | CB | MET | B | 388 | 34.371 | 11.612 | 21.826 | 1.00 | 25.69 B | | C |
| ATOM | 2231 | CG | MET | B | 388 | 34.845 | 10.527 | 22.810 | 1.00 | 27.65 B | | C |
| ATOM | 2232 | SD | MET | B | 388 | 33.569 | 9.299 | 23.353 | 1.00 | 30.15 B | | S |
| ATOM | 2233 | CE | MET | B | 388 | 34.425 | 7.787 | 22.986 | 1.00 | 28.32 B | | C |
| ATOM | 2234 | N | ILE | B | 389 | 34.223 | 14.443 | 20.433 | 1.00 | 26.00 B | | N |
| ATOM | 2235 | CA | ILE | B | 389 | 33.856 | 15.304 | 19.307 | 1.00 | 27.85 B | | C |
| ATOM | 2236 | C | ILE | B | 389 | 35.098 | 15.982 | 18.725 | 1.00 | 29.04 B | | C |
| ATOM | 2237 | O | ILE | B | 389 | 35.257 | 16.090 | 17.493 | 1.00 | 28.26 B | | O |
| ATOM | 2238 | CB | ILE | B | 389 | 32.782 | 16.364 | 19.704 | 1.00 | 28.26 B | | C |
| ATOM | 2239 | CG1 | ILE | B | 389 | 32.321 | 17.106 | 18.442 | 1.00 | 28.50 B | | C |
| ATOM | 2240 | CG2 | ILE | B | 389 | 33.306 | 17.313 | 20.776 | 1.00 | 27.42 B | | C |
| ATOM | 2241 | CD1 | ILE | B | 389 | 30.940 | 17.784 | 18.590 | 1.00 | 27.63 B | | C |
| ATOM | 2242 | N | GLY | B | 390 | 36.000 | 16.391 | 19.617 | 1.00 | 30.17 B | | N |
| ATOM | 2243 | CA | GLY | B | 390 | 37.235 | 17.010 | 19.177 | 1.00 | 31.30 B | | C |
| ATOM | 2244 | C | GLY | B | 390 | 38.102 | 15.996 | 18.456 | 1.00 | 32.32 B | | C |
| ATOM | 2245 | O | GLY | B | 390 | 38.667 | 16.299 | 17.395 | 1.00 | 31.53 B | | O |
| ATOM | 2246 | N | LEU | B | 391 | 38.213 | 14.792 | 19.019 | 1.00 | 33.20 B | | N |
| ATOM | 2247 | CA | LEU | B | 391 | 39.020 | 13.748 | 18.387 | 1.00 | 35.38 B | | C |
| ATOM | 2248 | C | LEU | B | 391 | 38.533 | 13.469 | 16.976 | 1.00 | 37.35 B | | C |
| ATOM | 2249 | O | LEU | B | 391 | 39.329 | 13.384 | 16.034 | 1.00 | 37.31 B | | O |
| ATOM | 2250 | CB | LEU | B | 391 | 38.965 | 12.435 | 19.175 | 1.00 | 34.27 B | | C |
| ATOM | 2251 | CG | LEU | B | 391 | 39.640 | 11.281 | 18.422 | 1.00 | 33.87 B | | C |
| ATOM | 2252 | CD1 | LEU | B | 391 | 41.062 | 11.659 | 18.100 | 1.00 | 32.80 B | | C |
| ATOM | 2253 | CD2 | LEU | B | 391 | 39.598 | 9.991 | 19.240 | 1.00 | 34.22 B | | C |
| ATOM | 2254 | N | VAL | B | 392 | 37.218 | 13.316 | 16.843 | 1.00 | 40.20 B | | N |
| ATOM | 2255 | CA | VAL | B | 392 | 36.605 | 13.030 | 15.549 | 1.00 | 43.01 B | | C |
| ATOM | 2256 | C | VAL | B | 392 | 36.784 | 14.179 | 14.563 | 1.00 | 45.30 B | | C |
| ATOM | 2257 | O | VAL | B | 392 | 37.003 | 13.946 | 13.377 | 1.00 | 45.34 B | | O |
| ATOM | 2258 | CB | VAL | B | 392 | 35.106 | 12.665 | 15.712 | 1.00 | 42.36 B | | C |
| ATOM | 2259 | CG1 | VAL | B | 392 | 34.372 | 12.851 | 14.411 | 1.00 | 42.21 B | | C |
| ATOM | 2260 | CG2 | VAL | B | 392 | 34.986 | 11.206 | 16.164 | 1.00 | 41.37 B | | C |
| ATOM | 2261 | N | TRP | B | 393 | 36.719 | 15.413 | 15.058 | 1.00 | 48.41 B | | N |
| ATOM | 2262 | CA | TRP | B | 393 | 36.905 | 16.587 | 14.208 | 1.00 | 51.26 B | | C |
| ATOM | 2263 | C | TRP | B | 393 | 38.330 | 16.712 | 13.662 | 1.00 | 52.21 B | | C |
| ATOM | 2264 | O | TRP | B | 393 | 38.534 | 17.238 | 12.565 | 1.00 | 52.29 B | | O |
| ATOM | 2265 | CB | TRP | B | 393 | 36.545 | 17.856 | 14.971 | 1.00 | 53.34 B | | C |
| ATOM | 2266 | CG | TRP | B | 393 | 37.033 | 19.125 | 14.322 | 1.00 | 56.05 B | | C |
| ATOM | 2267 | CD1 | TRP | B | 393 | 38.228 | 19.750 | 14.541 | 1.00 | 56.84 B | | C |
| ATOM | 2268 | CD2 | TRP | B | 393 | 36.336 | 19.921 | 13.346 | 1.00 | 57.66 B | | C |
| ATOM | 2269 | NE1 | TRP | B | 393 | 38.322 | 20.888 | 13.765 | 1.00 | 58.37 B | | N |
| ATOM | 2270 | CE2 | TRP | B | 393 | 37.174 | 21.013 | 13.017 | 1.00 | 58.55 B | | C |
| ATOM | 2271 | CE3 | TRP | B | 393 | 35.089 | 19.812 | 12.709 | 1.00 | 58.02 B | | C |
| ATOM | 2272 | CZ2 | TRP | B | 393 | 36.801 | 22.001 | 12.085 | 1.00 | 58.41 B | | C |
| ATOM | 2273 | CZ3 | TRP | B | 393 | 34.719 | 20.791 | 11.782 | 1.00 | 58.78 B | | C |
| ATOM | 2274 | CH2 | TRP | B | 393 | 35.576 | 21.869 | 11.478 | 1.00 | 58.58 B | | C |
| ATOM | 2275 | N | ARG | B | 394 | 39.314 | 16.239 | 14.423 | 1.00 | 52.95 B | | N |
| ATOM | 2276 | CA | ARG | B | 394 | 40.693 | 16.319 | 13.977 | 1.00 | 53.47 B | | C |
| ATOM | 2277 | C | ARG | B | 394 | 40.931 | 15.240 | 12.945 | 1.00 | 54.35 B | | C |
| ATOM | 2278 | O | ARG | B | 394 | 41.434 | 15.503 | 11.856 | 1.00 | 54.58 B | | O |
| ATOM | 2279 | CB | ARG | B | 394 | 41.675 | 16.074 | 15.124 | 1.00 | 52.95 B | | C |
| ATOM | 2280 | CG | ARG | B | 394 | 41.402 | 16.776 | 16.439 | 1.00 | 51.97 B | | C |
| ATOM | 2281 | CD | ARG | B | 394 | 42.480 | 16.330 | 17.429 | 1.00 | 51.10 B | | C |
| ATOM | 2282 | NE | ARG | B | 394 | 42.044 | 16.360 | 18.825 | 1.00 | 50.12 B | | N |
| ATOM | 2283 | CZ | ARG | B | 394 | 42.268 | 15.376 | 19.692 | 1.00 | 49.31 B | | C |
| ATOM | 2284 | NH1 | ARG | B | 394 | 42.920 | 14.289 | 19.306 | 1.00 | 48.22 B | | N |
| ATOM | 2285 | NH2 | ARG | B | 394 | 41.835 | 15.475 | 20.943 | 1.00 | 50.19 B | | N |
| ATOM | 2286 | N | SER | B | 395 | 40.560 | 14.017 | 13.308 | 1.00 | 55.87 B | | N |
| ATOM | 2287 | CA | SER | B | 395 | 40.758 | 12.851 | 12.452 | 1.00 | 57.54 B | | C |
| ATOM | 2288 | C | SER | B | 395 | 39.831 | 12.732 | 11.251 | 1.00 | 58.74 B | | C |
| ATOM | 2289 | O | SER | B | 395 | 39.828 | 11.709 | 10.566 | 1.00 | 58.79 B | | O |
| ATOM | 2290 | CB | SER | B | 395 | 40.666 | 11.576 | 13.291 | 1.00 | 57.33 B | | C |
| ATOM | 2291 | OG | SER | B | 395 | 39.543 | 11.628 | 14.145 | 1.00 | 57.45 B | | O |
| ATOM | 2292 | N | MET | B | 396 | 39.049 | 13.768 | 10.989 | 1.00 | 59.94 B | | N |
| ATOM | 2293 | CA | MET | B | 396 | 38.148 | 13.735 | 9.849 | 1.00 | 61.64 B | | C |
| ATOM | 2294 | C | MET | B | 396 | 38.923 | 13.378 | 8.586 | 1.00 | 63.02 B | | C |
| ATOM | 2295 | O | MET | B | 396 | 38.869 | 12.242 | 8.095 | 1.00 | 63.12 B | | O |
| ATOM | 2296 | CB | MET | B | 396 | 37.500 | 15.099 | 9.672 | 1.00 | 61.51 B | | C |
| ATOM | 2297 | CG | MET | B | 396 | 35.995 | 15.072 | 9.643 | 1.00 | 61.53 B | | C |
| ATOM | 2298 | SD | MET | B | 396 | 35.374 | 16.739 | 9.837 | 1.00 | 61.61 B | | S |
| ATOM | 2299 | CE | MET | B | 396 | 34.982 | 16.752 | 11.540 | 1.00 | 61.70 B | | C |
| ATOM | 2300 | N | GLU | B | 397 | 39.651 | 14.371 | 8.085 | 1.00 | 64.44 B | | N |
| ATOM | 2301 | CA | GLU | B | 397 | 40.468 | 14.264 | 6.880 | 1.00 | 66.00 B | | C |
| ATOM | 2302 | C | GLU | B | 397 | 41.541 | 13.173 | 6.911 | 1.00 | 66.43 B | | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2303 | O | GLU | B | 397 | 42.557 | 13.283 | 6.221 | 1.00 | 66.60 | B | O |
| ATOM | 2304 | CB | GLU | B | 397 | 41.130 | 15.610 | 6.627 | 1.00 | 67.46 | B | C |
| ATOM | 2305 | CG | GLU | B | 397 | 40.913 | 16.582 | 7.778 | 1.00 | 70.18 | B | C |
| ATOM | 2306 | CD | GLU | B | 397 | 42.090 | 17.513 | 7.994 | 1.00 | 71.76 | B | C |
| ATOM | 2307 | OE1 | GLU | B | 397 | 43.207 | 17.007 | 8.255 | 1.00 | 72.53 | B | O |
| ATOM | 2308 | OE2 | GLU | B | 397 | 41.896 | 18.747 | 7.905 | 1.00 | 72.63 | B | O |
| ATOM | 2309 | N | HIS | B | 398 | 41.318 | 12.132 | 7.713 | 1.00 | 66.40 | B | N |
| ATOM | 2310 | CA | HIS | B | 398 | 42.242 | 11.001 | 7.827 | 1.00 | 66.22 | B | C |
| ATOM | 2311 | C | HIS | B | 398 | 41.432 | 9.703 | 7.785 | 1.00 | 66.18 | B | C |
| ATOM | 2312 | O | HIS | B | 398 | 41.256 | 9.037 | 8.801 | 1.00 | 66.39 | B | O |
| ATOM | 2313 | CB | HIS | B | 398 | 43.033 | 11.071 | 9.136 | 1.00 | 65.58 | B | C |
| ATOM | 2314 | CG | HIS | B | 398 | 43.849 | 12.315 | 9.276 | 1.00 | 65.28 | B | C |
| ATOM | 2315 | ND1 | HIS | B | 398 | 43.282 | 13.568 | 9.364 | 1.00 | 65.13 | B | N |
| ATOM | 2316 | CD2 | HIS | B | 398 | 45.188 | 12.504 | 9.307 | 1.00 | 65.02 | B | C |
| ATOM | 2317 | CE1 | HIS | B | 398 | 44.237 | 14.477 | 9.441 | 1.00 | 64.84 | B | C |
| ATOM | 2318 | NE2 | HIS | B | 398 | 45.403 | 13.857 | 9.409 | 1.00 | 64.81 | B | N |
| ATOM | 2319 | N | PRO | B | 399 | 40.935 | 9.333 | 6.594 | 1.00 | 66.26 | B | N |
| ATOM | 2320 | CA | PRO | B | 399 | 40.127 | 8.145 | 6.283 | 1.00 | 65.72 | B | C |
| ATOM | 2321 | C | PRO | B | 399 | 40.477 | 6.863 | 7.038 | 1.00 | 64.93 | B | C |
| ATOM | 2322 | O | PRO | B | 399 | 41.550 | 6.292 | 6.841 | 1.00 | 64.84 | B | O |
| ATOM | 2323 | CB | PRO | B | 399 | 40.328 | 7.986 | 4.780 | 1.00 | 66.30 | B | C |
| ATOM | 2324 | CG | PRO | B | 399 | 40.404 | 9.400 | 4.320 | 1.00 | 66.75 | B | C |
| ATOM | 2325 | CD | PRO | B | 399 | 41.305 | 10.044 | 5.354 | 1.00 | 66.71 | B | C |
| ATOM | 2326 | N | VAL | B | 400 | 39.558 | 6.413 | 7.889 | 1.00 | 64.02 | B | N |
| ATOM | 2327 | CA | VAL | B | 400 | 39.768 | 5.191 | 8.650 | 1.00 | 63.20 | B | C |
| ATOM | 2328 | C | VAL | B | 400 | 40.885 | 5.211 | 9.680 | 1.00 | 62.52 | B | C |
| ATOM | 2329 | O | VAL | B | 400 | 41.473 | 4.169 | 9.975 | 1.00 | 62.37 | B | O |
| ATOM | 2330 | CB | VAL | B | 400 | 40.038 | 4.054 | 7.632 | 1.00 | 20.00 | B | C |
| ATOM | 2331 | CG1 | VAL | B | 400 | 40.229 | 2.722 | 8.351 | 1.00 | 20.00 | B | C |
| ATOM | 2332 | CG2 | VAL | B | 400 | 38.876 | 3.927 | 6.654 | 1.00 | 20.00 | B | C |
| ATOM | 2333 | N | LYS | B | 401 | 41.173 | 6.392 | 10.227 | 1.00 | 61.89 | B | N |
| ATOM | 2334 | CA | LYS | B | 401 | 42.222 | 6.567 | 11.235 | 1.00 | 60.77 | B | C |
| ATOM | 2335 | C | LYS | B | 401 | 41.867 | 7.725 | 12.191 | 1.00 | 60.10 | B | C |
| ATOM | 2336 | O | LYS | B | 401 | 41.293 | 8.743 | 11.775 | 1.00 | 59.99 | B | O |
| ATOM | 2337 | CB | LYS | B | 401 | 43.521 | 6.888 | 10.522 | 1.00 | 60.27 | B | C |
| ATOM | 2338 | CG | LYS | B | 401 | 44.063 | 5.694 | 9.729 | 1.00 | 20.00 | B | C |
| ATOM | 2339 | CD | LYS | B | 401 | 45.188 | 6.446 | 9.014 | 1.00 | 20.00 | B | C |
| ATOM | 2340 | CE | LYS | B | 401 | 46.536 | 5.881 | 8.555 | 1.00 | 20.00 | B | C |
| ATOM | 2341 | NZ | LYS | B | 401 | 47.321 | 4.857 | 9.243 | 1.00 | 20.00 | B | N |
| ATOM | 2342 | N | LEU | B | 402 | 42.192 | 7.556 | 13.474 | 1.00 | 59.15 | B | N |
| ATOM | 2343 | CA | LEU | B | 402 | 41.903 | 8.575 | 14.485 | 1.00 | 57.95 | B | C |
| ATOM | 2344 | C | LEU | B | 402 | 43.127 | 9.393 | 14.832 | 1.00 | 56.96 | B | C |
| ATOM | 2345 | O | LEU | B | 402 | 44.193 | 8.852 | 15.118 | 1.00 | 56.90 | B | O |
| ATOM | 2346 | CB | LEU | B | 402 | 41.360 | 7.940 | 15.765 | 1.00 | 57.73 | B | C |
| ATOM | 2347 | CG | LEU | B | 402 | 39.944 | 7.387 | 15.704 | 1.00 | 57.99 | B | C |
| ATOM | 2348 | CD1 | LEU | B | 402 | 39.574 | 6.822 | 17.072 | 1.00 | 57.79 | B | C |
| ATOM | 2349 | CD2 | LEU | B | 402 | 38.972 | 8.490 | 15.278 | 1.00 | 57.69 | B | C |
| ATOM | 2350 | N | LEU | B | 403 | 42.960 | 10.707 | 14.826 | 1.00 | 56.05 | B | N |
| ATOM | 2351 | CA | LEU | B | 403 | 44.056 | 11.611 | 15.128 | 1.00 | 55.10 | B | C |
| ATOM | 2352 | C | LEU | B | 403 | 43.981 | 12.026 | 16.593 | 1.00 | 54.63 | B | C |
| ATOM | 2353 | O | LEU | B | 403 | 43.374 | 13.047 | 16.931 | 1.00 | 54.31 | B | O |
| ATOM | 2354 | CB | LEU | B | 403 | 43.959 | 12.836 | 14.222 | 1.00 | 54.49 | B | C |
| ATOM | 2355 | CG | LEU | B | 403 | 45.192 | 13.699 | 13.989 | 1.00 | 54.37 | B | C |
| ATOM | 2356 | CD1 | LEU | B | 403 | 46.200 | 12.960 | 13.131 | 1.00 | 54.33 | B | C |
| ATOM | 2357 | CD2 | LEU | B | 403 | 44.760 | 14.977 | 13.288 | 1.00 | 55.03 | B | C |
| ATOM | 2358 | N | PHE | B | 404 | 44.574 | 11.211 | 17.460 | 1.00 | 54.32 | B | N |
| ATOM | 2359 | CA | PHE | B | 404 | 44.594 | 11.499 | 18.891 | 1.00 | 54.56 | B | C |
| ATOM | 2360 | C | PHE | B | 404 | 45.531 | 12.680 | 19.078 | 1.00 | 54.97 | B | C |
| ATOM | 2361 | O | PHE | B | 404 | 45.231 | 13.633 | 19.804 | 1.00 | 55.39 | B | O |
| ATOM | 2362 | CB | PHE | B | 404 | 45.113 | 10.287 | 19.680 | 1.00 | 54.43 | B | C |
| ATOM | 2363 | CG | PHE | B | 404 | 44.110 | 9.172 | 19.816 | 1.00 | 54.27 | B | C |
| ATOM | 2364 | CD1 | PHE | B | 404 | 43.032 | 9.292 | 20.692 | 1.00 | 53.98 | B | C |
| ATOM | 2365 | CD2 | PHE | B | 404 | 44.221 | 8.018 | 19.045 | 1.00 | 54.08 | B | C |
| ATOM | 2366 | CE1 | PHE | B | 404 | 42.079 | 8.281 | 20.793 | 1.00 | 54.44 | B | C |
| ATOM | 2367 | CE2 | PHE | B | 404 | 43.269 | 6.999 | 19.139 | 1.00 | 54.38 | B | C |
| ATOM | 2368 | CZ | PHE | B | 404 | 42.196 | 7.131 | 20.014 | 1.00 | 54.42 | B | C |
| ATOM | 2369 | N | ALA | B | 405 | 46.676 | 12.607 | 18.409 | 1.00 | 54.74 | B | N |
| ATOM | 2370 | CA | ALA | B | 405 | 47.671 | 13.671 | 18.460 | 1.00 | 54.52 | B | C |
| ATOM | 2371 | C | ALA | B | 405 | 48.433 | 13.638 | 17.133 | 1.00 | 54.36 | B | C |
| ATOM | 2372 | O | ALA | B | 405 | 48.549 | 12.589 | 16.499 | 1.00 | 53.96 | B | O |
| ATOM | 2373 | CB | ALA | B | 405 | 48.626 | 13.459 | 19.647 | 1.00 | 53.99 | B | C |
| ATOM | 2374 | N | PRO | B | 406 | 48.952 | 14.792 | 16.692 | 1.00 | 54.37 | B | N |
| ATOM | 2375 | CA | PRO | B | 406 | 49.693 | 14.857 | 15.429 | 1.00 | 54.78 | B | C |
| ATOM | 2376 | C | PRO | B | 406 | 50.690 | 13.725 | 15.319 | 1.00 | 55.62 | B | C |
| ATOM | 2377 | O | PRO | B | 406 | 50.975 | 13.228 | 14.228 | 1.00 | 55.60 | B | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2378 | CB | PRO | B | 406 | 50.370 | 16.218 | 15.500 | 1.00 | 53.94 B | | C |
| ATOM | 2379 | CG | PRO | B | 406 | 49.382 | 17.031 | 16.281 | 1.00 | 54.18 B | | C |
| ATOM | 2380 | CD | PRO | B | 406 | 48.966 | 16.092 | 17.384 | 1.00 | 54.12 B | | C |
| ATOM | 2381 | N | ASN | B | 407 | 51.213 | 13.326 | 16.471 | 1.00 | 57.35 B | | N |
| ATOM | 2382 | CA | ASN | B | 407 | 52.196 | 12.254 | 16.567 | 1.00 | 58.78 B | | C |
| ATOM | 2383 | C | ASN | B | 407 | 51.538 | 10.982 | 17.093 | 1.00 | 60.17 B | | C |
| ATOM | 2384 | O | ASN | B | 407 | 52.213 | 10.072 | 17.571 | 1.00 | 60.46 B | | O |
| ATOM | 2385 | CB | ASN | B | 407 | 53.336 | 12.686 | 17.497 | 1.00 | 58.14 B | | C |
| ATOM | 2386 | CG | ASN | B | 407 | 52.854 | 13.024 | 18.904 | 1.00 | 58.14 B | | C |
| ATOM | 2387 | OD1 | ASN | B | 407 | 51.703 | 13.428 | 19.108 | 1.00 | 57.79 B | | O |
| ATOM | 2388 | ND2 | ASN | B | 407 | 53.743 | 12.876 | 19.881 | 1.00 | 58.15 B | | N |
| ATOM | 2389 | N | LEU | B | 408 | 50.215 | 10.926 | 16.998 | 1.00 | 61.64 B | | N |
| ATOM | 2390 | CA | LEU | B | 408 | 49.472 | 9.768 | 17.463 | 1.00 | 63.13 B | | C |
| ATOM | 2391 | C | LEU | B | 408 | 48.261 | 9.513 | 16.573 | 1.00 | 64.43 B | | C |
| ATOM | 2392 | O | LEU | B | 408 | 47.151 | 9.964 | 16.867 | 1.00 | 64.54 B | | O |
| ATOM | 2393 | CB | LEU | B | 408 | 49.024 | 9.985 | 18.907 | 1.00 | 63.08 B | | C |
| ATOM | 2394 | CG | LEU | B | 408 | 48.629 | 8.720 | 19.665 | 1.00 | 62.74 B | | C |
| ATOM | 2395 | CD1 | LEU | B | 408 | 49.819 | 7.773 | 19.707 | 1.00 | 61.80 B | | C |
| ATOM | 2396 | CD2 | LEU | B | 408 | 48.163 | 9.085 | 21.073 | 1.00 | 62.26 B | | C |
| ATOM | 2397 | N | LEU | B | 409 | 48.492 | 8.788 | 15.484 | 1.00 | 66.24 B | | N |
| ATOM | 2398 | CA | LEU | B | 409 | 47.440 | 8.452 | 14.530 | 1.00 | 68.42 B | | C |
| ATOM | 2399 | C | LEU | B | 409 | 47.304 | 6.931 | 14.508 | 1.00 | 70.09 B | | C |
| ATOM | 2400 | O | LEU | B | 409 | 48.201 | 6.222 | 14.031 | 1.00 | 70.50 B | | O |
| ATOM | 2401 | CB | LEU | B | 409 | 47.816 | 8.979 | 13.139 | 1.00 | 68.24 B | | C |
| ATOM | 2402 | CG | LEU | B | 409 | 46.789 | 9.048 | 12.002 | 1.00 | 68.41 B | | C |
| ATOM | 2403 | CD1 | LEU | B | 409 | 45.621 | 9.948 | 12.390 | 1.00 | 68.64 B | | C |
| ATOM | 2404 | CD2 | LEU | B | 409 | 47.469 | 9.592 | 10.758 | 1.00 | 67.59 B | | C |
| ATOM | 2405 | N | LEU | B | 410 | 46.190 | 6.433 | 15.041 | 1.00 | 71.90 B | | N |
| ATOM | 2406 | CA | LEU | B | 410 | 45.947 | 4.991 | 15.094 | 1.00 | 73.78 B | | C |
| ATOM | 2407 | C | LEU | B | 410 | 44.825 | 4.534 | 14.163 | 1.00 | 75.32 B | | C |
| ATOM | 2408 | O | LEU | B | 410 | 43.858 | 5.266 | 13.929 | 1.00 | 75.78 B | | O |
| ATOM | 2409 | CB | LEU | B | 410 | 45.608 | 4.559 | 16.527 | 1.00 | 73.40 B | | C |
| ATOM | 2410 | CG | LEU | B | 410 | 46.635 | 4.847 | 17.626 | 1.00 | 73.20 B | | C |
| ATOM | 2411 | CD1 | LEU | B | 410 | 46.225 | 4.145 | 18.920 | 1.00 | 72.32 B | | C |
| ATOM | 2412 | CD2 | LEU | B | 410 | 48.005 | 4.373 | 17.172 | 1.00 | 72.63 B | | C |
| ATOM | 2413 | N | ASP | B | 411 | 44.973 | 3.319 | 13.640 | 1.00 | 77.01 B | | N |
| ATOM | 2414 | CA | ASP | B | 411 | 43.992 | 2.708 | 12.750 | 1.00 | 78.91 B | | C |
| ATOM | 2415 | C | ASP | B | 411 | 43.240 | 1.646 | 13.562 | 1.00 | 80.14 B | | C |
| ATOM | 2416 | O | ASP | B | 411 | 43.859 | 0.911 | 14.326 | 1.00 | 80.42 B | | O |
| ATOM | 2417 | CB | ASP | B | 411 | 44.702 | 2.090 | 11.530 | 1.00 | 79.26 B | | C |
| ATOM | 2418 | CG | ASP | B | 411 | 45.757 | 1.045 | 11.907 | 1.00 | 80.06 B | | C |
| ATOM | 2419 | OD1 | ASP | B | 411 | 46.621 | 1.329 | 12.770 | 1.00 | 80.68 B | | O |
| ATOM | 2420 | OD2 | ASP | B | 411 | 45.734 | −0.063 | 11.321 | 1.00 | 80.41 B | | O |
| ATOM | 2421 | N | ARG | B | 412 | 41.914 | 1.585 | 13.408 | 1.00 | 81.67 B | | N |
| ATOM | 2422 | CA | ARG | B | 412 | 41.058 | 0.643 | 14.146 | 1.00 | 83.01 B | | C |
| ATOM | 2423 | C | ARG | B | 412 | 41.766 | −0.670 | 14.492 | 1.00 | 84.23 B | | C |
| ATOM | 2424 | O | ARG | B | 412 | 41.641 | −1.182 | 15.608 | 1.00 | 84.18 B | | O |
| ATOM | 2425 | CB | ARG | B | 412 | 39.766 | 0.369 | 13.350 | 1.00 | 82.96 B | | C |
| ATOM | 2426 | CG | ARG | B | 412 | 39.656 | −1.002 | 12.692 | 1.00 | 82.50 B | | C |
| ATOM | 2427 | CD | ARG | B | 412 | 38.641 | −1.887 | 13.401 | 1.00 | 81.71 B | | C |
| ATOM | 2428 | NE | ARG | B | 412 | 38.471 | −3.159 | 12.704 | 1.00 | 81.48 B | | N |
| ATOM | 2429 | CZ | ARG | B | 412 | 37.624 | −4.113 | 13.077 | 1.00 | 81.11 B | | C |
| ATOM | 2430 | NH1 | ARG | B | 412 | 36.864 | −3.942 | 14.150 | 1.00 | 80.69 B | | N |
| ATOM | 2431 | NH2 | ARG | B | 412 | 37.537 | −5.239 | 12.375 | 1.00 | 80.81 B | | N |
| ATOM | 2432 | N | ASN | B | 413 | 42.512 | −1.199 | 13.527 | 1.00 | 85.72 B | | N |
| ATOM | 2433 | CA | ASN | B | 413 | 43.272 | −2.433 | 13.699 | 1.00 | 87.20 B | | C |
| ATOM | 2434 | C | ASN | B | 413 | 44.061 | −2.388 | 15.019 | 1.00 | 87.97 B | | C |
| ATOM | 2435 | O | ASN | B | 413 | 44.061 | −3.331 | 15.817 | 1.00 | 88.12 B | | O |
| ATOM | 2436 | CB | ASN | B | 413 | 44.246 | −2.583 | 12.522 | 1.00 | 87.55 B | | C |
| ATOM | 2437 | CG | ASN | B | 413 | 45.016 | −3.892 | 12.556 | 1.00 | 88.23 B | | C |
| ATOM | 2438 | OD1 | ASN | B | 413 | 44.425 | −4.974 | 12.508 | 1.00 | 88.77 B | | O |
| ATOM | 2439 | ND2 | ASN | B | 413 | 46.345 | −3.801 | 12.628 | 1.00 | 88.33 B | | N |
| ATOM | 2440 | N | GLN | B | 414 | 44.733 | −1.267 | 15.234 | 1.00 | 88.62 B | | N |
| ATOM | 2441 | CA | GLN | B | 414 | 45.559 | −1.054 | 16.413 | 1.00 | 89.04 B | | C |
| ATOM | 2442 | C | GLN | B | 414 | 44.762 | −0.453 | 17.586 | 1.00 | 89.18 B | | C |
| ATOM | 2443 | O | GLN | B | 414 | 45.119 | 0.595 | 18.126 | 1.00 | 89.28 B | | O |
| ATOM | 2444 | CB | GLN | B | 414 | 46.715 | −0.137 | 16.003 | 1.00 | 89.12 B | | C |
| ATOM | 2445 | CG | GLN | B | 414 | 47.796 | 0.074 | 17.026 | 1.00 | 89.66 B | | C |
| ATOM | 2446 | CD | GLN | B | 414 | 48.815 | 1.084 | 16.548 | 1.00 | 90.22 B | | C |
| ATOM | 2447 | OE1 | GLN | B | 414 | 49.830 | 1.316 | 17.204 | 1.00 | 90.51 B | | O |
| ATOM | 2448 | NE2 | GLN | B | 414 | 48.547 | 1.697 | 15.394 | 1.00 | 90.68 B | | N |
| ATOM | 2449 | N | GLY | B | 415 | 43.681 | −1.119 | 17.979 | 1.00 | 89.39 B | | N |
| ATOM | 2450 | CA | GLY | B | 415 | 42.869 | −0.611 | 19.070 | 1.00 | 89.64 B | | C |
| ATOM | 2451 | C | GLY | B | 415 | 42.343 | −1.700 | 19.983 | 1.00 | 89.97 B | | C |
| ATOM | 2452 | O | GLY | B | 415 | 42.082 | −1.460 | 21.164 | 1.00 | 90.10 B | | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2453 | N | LYS | B | 416 | 42.177 | −2.902 | 19.442 | 1.00 | 90.11 | B | N |
| ATOM | 2454 | CA | LYS | B | 416 | 41.684 | −4.006 | 20.250 | 1.00 | 90.17 | B | C |
| ATOM | 2455 | C | LYS | B | 416 | 42.794 | −4.529 | 21.158 | 1.00 | 90.25 | B | C |
| ATOM | 2456 | O | LYS | B | 416 | 42.629 | −5.552 | 21.825 | 1.00 | 90.56 | B | O |
| ATOM | 2457 | CB | LYS | B | 416 | 41.129 | −5.128 | 19.360 | 1.00 | 89.94 | B | C |
| ATOM | 2458 | CG | LYS | B | 416 | 40.660 | −6.388 | 20.114 | 1.00 | 89.20 | B | C |
| ATOM | 2459 | CD | LYS | B | 416 | 39.914 | −6.098 | 21.430 | 1.00 | 88.65 | B | C |
| ATOM | 2460 | CE | LYS | B | 416 | 38.689 | −5.208 | 21.264 | 1.00 | 88.49 | B | C |
| ATOM | 2461 | NZ | LYS | B | 416 | 37.414 | −5.952 | 21.506 | 1.00 | 87.94 | B | N |
| ATOM | 2462 | N | CYS | B | 417 | 43.930 | −3.833 | 21.187 | 1.00 | 90.02 | B | N |
| ATOM | 2463 | CA | CYS | B | 417 | 45.022 | −4.247 | 22.064 | 1.00 | 89.65 | B | C |
| ATOM | 2464 | C | CYS | B | 417 | 44.484 | −4.191 | 23.507 | 1.00 | 89.56 | B | C |
| ATOM | 2465 | O | CYS | B | 417 | 45.035 | −4.821 | 24.420 | 1.00 | 89.49 | B | O |
| ATOM | 2466 | CB | CYS | B | 417 | 46.246 | −3.332 | 21.889 | 1.00 | 89.12 | B | C |
| ATOM | 2467 | SG | CYS | B | 417 | 45.940 | −1.575 | 22.128 | 1.00 | 88.19 | B | S |
| ATOM | 2468 | N | VAL | B | 418 | 43.394 | −3.438 | 23.687 | 1.00 | 89.27 | B | N |
| ATOM | 2469 | CA | VAL | B | 418 | 42.716 | −3.300 | 24.977 | 1.00 | 88.86 | B | C |
| ATOM | 2470 | C | VAL | B | 418 | 41.267 | −3.775 | 24.814 | 1.00 | 88.83 | B | C |
| ATOM | 2471 | O | VAL | B | 418 | 40.586 | −3.443 | 23.836 | 1.00 | 88.73 | B | O |
| ATOM | 2472 | CB | VAL | B | 418 | 42.689 | −1.831 | 25.481 | 1.00 | 88.52 | B | C |
| ATOM | 2473 | CG1 | VAL | B | 418 | 42.059 | −1.765 | 26.875 | 1.00 | 88.48 | B | C |
| ATOM | 2474 | CG2 | VAL | B | 418 | 44.086 | −1.251 | 25.488 | 1.00 | 88.16 | B | C |
| ATOM | 2475 | N | GLU | B | 419 | 40.815 | −4.549 | 25.794 | 1.00 | 88.86 | B | N |
| ATOM | 2476 | CA | GLU | B | 419 | 39.475 | −5.128 | 25.827 | 1.00 | 88.83 | B | C |
| ATOM | 2477 | C | GLU | B | 419 | 38.336 | −4.291 | 25.230 | 1.00 | 88.34 | B | C |
| ATOM | 2478 | O | GLU | B | 419 | 38.181 | −3.112 | 25.553 | 1.00 | 88.39 | B | O |
| ATOM | 2479 | CB | GLU | B | 419 | 39.136 | −5.505 | 27.275 | 1.00 | 89.24 | B | C |
| ATOM | 2480 | CG | GLU | B | 419 | 40.129 | −6.482 | 27.909 | 1.00 | 89.89 | B | C |
| ATOM | 2481 | CD | GLU | B | 419 | 40.260 | −7.784 | 27.130 | 1.00 | 90.20 | B | C |
| ATOM | 2482 | OE1 | GLU | B | 419 | 41.005 | −8.676 | 27.588 | 1.00 | 90.68 | B | O |
| ATOM | 2483 | OE2 | GLU | B | 419 | 39.622 | −7.918 | 26.063 | 1.00 | 90.58 | B | O |
| ATOM | 2484 | N | GLY | B | 420 | 37.551 | −4.930 | 24.359 | 1.00 | 87.76 | B | N |
| ATOM | 2485 | CA | GLY | B | 420 | 36.400 | −4.308 | 23.711 | 1.00 | 86.73 | B | C |
| ATOM | 2486 | C | GLY | B | 420 | 36.466 | −2.823 | 23.412 | 1.00 | 85.95 | B | C |
| ATOM | 2487 | O | GLY | B | 420 | 35.437 | −2.136 | 23.359 | 1.00 | 86.05 | B | O |
| ATOM | 2488 | N | MET | B | 421 | 37.684 | −2.336 | 23.210 | 1.00 | 84.88 | B | N |
| ATOM | 2489 | CA | MET | B | 421 | 37.938 | −0.936 | 22.912 | 1.00 | 83.85 | B | C |
| ATOM | 2490 | C | MET | B | 421 | 37.761 | −0.646 | 21.431 | 1.00 | 82.46 | B | C |
| ATOM | 2491 | O | MET | B | 421 | 37.595 | 0.509 | 21.025 | 1.00 | 82.29 | B | O |
| ATOM | 2492 | CB | MET | B | 421 | 39.359 | −0.593 | 23.324 | 1.00 | 84.78 | B | C |
| ATOM | 2493 | CG | MET | B | 421 | 40.000 | 0.501 | 22.505 | 1.00 | 86.03 | B | C |
| ATOM | 2494 | SD | MET | B | 421 | 41.642 | 0.839 | 23.152 | 1.00 | 88.25 | B | S |
| ATOM | 2495 | CE | MET | B | 421 | 41.288 | 1.012 | 24.974 | 1.00 | 87.71 | B | C |
| ATOM | 2496 | N | VAL | B | 422 | 37.829 | −1.699 | 20.626 | 1.00 | 80.59 | B | N |
| ATOM | 2497 | CA | VAL | B | 422 | 37.660 | −1.558 | 19.193 | 1.00 | 78.79 | B | C |
| ATOM | 2498 | C | VAL | B | 422 | 36.227 | −1.110 | 18.893 | 1.00 | 77.53 | B | C |
| ATOM | 2499 | O | VAL | B | 422 | 35.994 | −0.327 | 17.970 | 1.00 | 77.46 | B | O |
| ATOM | 2500 | CB | VAL | B | 422 | 37.934 | −2.882 | 18.476 | 1.00 | 78.73 | B | C |
| ATOM | 2501 | CG1 | VAL | B | 422 | 36.937 | −3.935 | 18.935 | 1.00 | 78.90 | B | C |
| ATOM | 2502 | CG2 | VAL | B | 422 | 37.848 | −2.678 | 16.978 | 1.00 | 78.94 | B | C |
| ATOM | 2503 | N | GLU | B | 423 | 35.272 | −1.607 | 19.678 | 1.00 | 75.92 | B | N |
| ATOM | 2504 | CA | GLU | B | 423 | 33.871 | −1.237 | 19.499 | 1.00 | 74.48 | B | C |
| ATOM | 2505 | CB | GLU | B | 423 | 33.009 | −1.864 | 20.604 | 1.00 | 74.25 | B | C |
| ATOM | 2506 | C | GLU | B | 423 | 33.767 | 0.287 | 19.549 | 1.00 | 73.54 | B | C |
| ATOM | 2507 | O | GLU | B | 423 | 33.092 | 0.909 | 18.724 | 1.00 | 73.44 | B | O |
| ATOM | 2508 | N | ILE | B | 424 | 34.460 | 0.878 | 20.519 | 1.00 | 72.33 | B | N |
| ATOM | 2509 | CA | ILE | B | 424 | 34.464 | 2.324 | 20.714 | 1.00 | 70.90 | B | C |
| ATOM | 2510 | C | ILE | B | 424 | 35.246 | 3.043 | 19.629 | 1.00 | 69.83 | B | C |
| ATOM | 2511 | O | ILE | B | 424 | 34.984 | 4.208 | 19.327 | 1.00 | 69.74 | B | O |
| ATOM | 2512 | CB | ILE | B | 424 | 35.046 | 2.678 | 22.098 | 1.00 | 71.02 | B | C |
| ATOM | 2513 | CG1 | ILE | B | 424 | 34.178 | 2.030 | 23.182 | 1.00 | 71.23 | B | C |
| ATOM | 2514 | CG2 | ILE | B | 424 | 35.095 | 4.188 | 22.280 | 1.00 | 70.92 | B | C |
| ATOM | 2515 | CD1 | ILE | B | 424 | 34.645 | 2.278 | 24.584 | 1.00 | 72.14 | B | C |
| ATOM | 2516 | N | PHE | B | 425 | 36.200 | 2.334 | 19.040 | 1.00 | 68.63 | B | N |
| ATOM | 2517 | CA | PHE | B | 425 | 37.024 | 2.883 | 17.977 | 1.00 | 67.36 | B | C |
| ATOM | 2518 | C | PHE | B | 425 | 36.210 | 3.170 | 16.717 | 1.00 | 66.14 | B | C |
| ATOM | 2519 | O | PHE | B | 425 | 36.227 | 4.282 | 16.181 | 1.00 | 65.94 | B | O |
| ATOM | 2520 | CB | PHE | B | 425 | 38.148 | 1.908 | 17.640 | 1.00 | 68.29 | B | C |
| ATOM | 2521 | CG | PHE | B | 425 | 39.511 | 2.457 | 17.881 | 1.00 | 69.28 | B | C |
| ATOM | 2522 | CD1 | PHE | B | 425 | 39.970 | 2.649 | 19.180 | 1.00 | 70.09 | B | C |
| ATOM | 2523 | CD2 | PHE | B | 425 | 40.296 | 2.893 | 16.814 | 1.00 | 69.81 | B | C |
| ATOM | 2524 | CE1 | PHE | B | 425 | 41.212 | 3.245 | 19.417 | 1.00 | 70.70 | B | C |
| ATOM | 2525 | CE2 | PHE | B | 425 | 41.535 | 3.488 | 17.031 | 1.00 | 69.92 | B | C |
| ATOM | 2526 | CZ | PHE | B | 425 | 41.989 | 3.682 | 18.337 | 1.00 | 70.36 | B | C |
| ATOM | 2527 | N | ASP | B | 426 | 35.489 | 2.158 | 16.250 | 1.00 | 64.72 | B | N |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2528 | CA | ASP | B | 426 | 34.686 | 2.288 | 15.042 | 1.00 | 63.14 | B | C |
| ATOM | 2529 | C | ASP | B | 426 | 33.526 | 3.249 | 15.230 | 1.00 | 62.02 | B | C |
| ATOM | 2530 | O | ASP | B | 426 | 33.078 | 3.890 | 14.276 | 1.00 | 62.27 | B | O |
| ATOM | 2531 | CB | ASP | B | 426 | 34.185 | 0.915 | 14.615 | 1.00 | 63.38 | B | C |
| ATOM | 2532 | CG | ASP | B | 426 | 35.315 | −0.099 | 14.513 | 1.00 | 63.68 | B | C |
| ATOM | 2533 | OD1 | ASP | B | 426 | 36.198 | 0.073 | 13.642 | 1.00 | 64.11 | B | O |
| ATOM | 2534 | OD2 | ASP | B | 426 | 35.330 | −1.059 | 15.315 | 1.00 | 63.57 | B | O |
| ATOM | 2535 | N | MET | B | 427 | 33.030 | 3.354 | 16.457 | 1.00 | 60.10 | B | N |
| ATOM | 2536 | CA | MET | B | 427 | 31.950 | 4.283 | 16.707 | 1.00 | 58.26 | B | C |
| ATOM | 2537 | C | MET | B | 427 | 32.522 | 5.673 | 16.446 | 1.00 | 57.88 | B | C |
| ATOM | 2538 | O | MET | B | 427 | 31.816 | 6.571 | 15.989 | 1.00 | 57.74 | B | O |
| ATOM | 2539 | CB | MET | B | 427 | 31.458 | 4.171 | 18.149 | 1.00 | 57.66 | B | C |
| ATOM | 2540 | CG | MET | B | 427 | 30.805 | 2.831 | 18.487 | 1.00 | 56.82 | B | C |
| ATOM | 2541 | SD | MET | B | 427 | 29.910 | 2.866 | 20.063 | 1.00 | 54.60 | B | S |
| ATOM | 2542 | CE | MET | B | 427 | 31.097 | 2.032 | 21.173 | 1.00 | 55.52 | B | C |
| ATOM | 2543 | N | LEU | B | 428 | 33.813 | 5.847 | 16.728 | 1.00 | 57.13 | B | N |
| ATOM | 2544 | CA | LEU | B | 428 | 34.457 | 7.139 | 16.499 | 1.00 | 56.42 | B | C |
| ATOM | 2545 | C | LEU | B | 428 | 34.718 | 7.305 | 15.007 | 1.00 | 56.60 | B | C |
| ATOM | 2546 | O | LEU | B | 428 | 34.433 | 8.355 | 14.421 | 1.00 | 55.91 | B | O |
| ATOM | 2547 | CB | LEU | B | 428 | 35.770 | 7.245 | 17.285 | 1.00 | 54.64 | B | C |
| ATOM | 2548 | CG | LEU | B | 428 | 35.653 | 7.483 | 18.795 | 1.00 | 53.10 | B | C |
| ATOM | 2549 | CD1 | LEU | B | 428 | 37.039 | 7.586 | 19.399 | 1.00 | 51.72 | B | C |
| ATOM | 2550 | CD2 | LEU | B | 428 | 34.864 | 8.757 | 19.063 | 1.00 | 51.79 | B | C |
| ATOM | 2551 | N | LEU | B | 429 | 35.253 | 6.256 | 14.392 | 1.00 | 57.04 | B | N |
| ATOM | 2552 | CA | LEU | B | 429 | 35.525 | 6.302 | 12.965 | 1.00 | 57.74 | B | C |
| ATOM | 2553 | C | LEU | B | 429 | 34.252 | 6.673 | 12.198 | 1.00 | 58.40 | B | C |
| ATOM | 2554 | O | LEU | B | 429 | 34.276 | 7.503 | 11.285 | 1.00 | 58.77 | B | O |
| ATOM | 2555 | CB | LEU | B | 429 | 36.065 | 4.951 | 12.497 | 1.00 | 56.80 | B | C |
| ATOM | 2556 | CG | LEU | B | 429 | 37.430 | 4.633 | 13.107 | 1.00 | 56.48 | B | C |
| ATOM | 2557 | CD1 | LEU | B | 429 | 38.017 | 3.395 | 12.451 | 1.00 | 56.68 | B | C |
| ATOM | 2558 | CD2 | LEU | B | 429 | 38.365 | 5.819 | 12.899 | 1.00 | 56.43 | B | C |
| ATOM | 2559 | N | ALA | B | 430 | 33.138 | 6.070 | 12.595 | 1.00 | 58.94 | B | N |
| ATOM | 2560 | CA | ALA | B | 430 | 31.854 | 6.334 | 11.962 | 1.00 | 59.49 | B | C |
| ATOM | 2561 | C | ALA | B | 430 | 31.456 | 7.804 | 12.043 | 1.00 | 59.98 | B | C |
| ATOM | 2562 | O | ALA | B | 430 | 31.122 | 8.420 | 11.031 | 1.00 | 59.85 | B | O |
| ATOM | 2563 | CB | ALA | B | 430 | 30.779 | 5.478 | 12.611 | 1.00 | 59.12 | B | C |
| ATOM | 2564 | N | THR | B | 431 | 31.487 | 8.358 | 13.252 | 1.00 | 61.05 | B | N |
| ATOM | 2565 | CA | THR | B | 431 | 31.098 | 9.749 | 13.464 | 1.00 | 62.40 | B | C |
| ATOM | 2566 | C | THR | B | 431 | 31.884 | 10.733 | 12.576 | 1.00 | 63.70 | B | C |
| ATOM | 2567 | O | THR | B | 431 | 31.320 | 11.698 | 12.052 | 1.00 | 63.96 | B | O |
| ATOM | 2568 | CB | THR | B | 431 | 31.259 | 10.148 | 14.968 | 1.00 | 61.79 | B | C |
| ATOM | 2569 | OG1 | THR | B | 431 | 30.711 | 9.115 | 15.795 | 1.00 | 61.56 | B | O |
| ATOM | 2570 | CG2 | THR | B | 431 | 30.507 | 11.450 | 15.273 | 1.00 | 61.11 | B | C |
| ATOM | 2571 | N | SER | B | 432 | 33.180 | 10.495 | 12.401 | 1.00 | 65.11 | B | N |
| ATOM | 2572 | CA | SER | B | 432 | 33.990 | 11.386 | 11.572 | 1.00 | 66.21 | B | C |
| ATOM | 2573 | C | SER | B | 432 | 33.458 | 11.314 | 10.134 | 1.00 | 66.92 | B | C |
| ATOM | 2574 | O | SER | B | 432 | 33.351 | 12.325 | 9.432 | 1.00 | 66.42 | B | O |
| ATOM | 2575 | CB | SER | B | 432 | 35.459 | 10.953 | 11.629 | 1.00 | 66.23 | B | C |
| ATOM | 2576 | OG | SER | B | 432 | 36.325 | 12.057 | 11.433 | 1.00 | 66.55 | B | O |
| ATOM | 2577 | N | SER | B | 433 | 33.102 | 10.099 | 9.727 | 1.00 | 67.98 | B | N |
| ATOM | 2578 | CA | SER | B | 433 | 32.573 | 9.833 | 8.399 | 1.00 | 68.95 | B | C |
| ATOM | 2579 | C | SER | B | 433 | 31.279 | 10.593 | 8.132 | 1.00 | 69.92 | B | C |
| ATOM | 2580 | O | SER | B | 433 | 31.029 | 11.030 | 7.008 | 1.00 | 69.90 | B | O |
| ATOM | 2581 | CB | SER | B | 433 | 32.337 | 8.333 | 8.236 | 1.00 | 68.57 | B | C |
| ATOM | 2582 | OG | SER | B | 433 | 33.558 | 7.627 | 8.376 | 1.00 | 68.32 | B | O |
| ATOM | 2583 | N | ARG | B | 434 | 30.463 | 10.753 | 9.168 | 1.00 | 70.94 | B | N |
| ATOM | 2584 | CA | ARG | B | 434 | 29.197 | 11.459 | 9.030 | 1.00 | 72.58 | B | C |
| ATOM | 2585 | C | ARG | B | 434 | 29.408 | 12.970 | 9.058 | 1.00 | 73.62 | B | C |
| ATOM | 2586 | O | ARG | B | 434 | 28.557 | 13.735 | 8.604 | 1.00 | 73.86 | B | O |
| ATOM | 2587 | CB | ARG | B | 434 | 28.235 | 11.048 | 10.148 | 1.00 | 72.73 | B | C |
| ATOM | 2588 | CG | ARG | B | 434 | 26.801 | 11.504 | 9.926 | 1.00 | 73.63 | B | C |
| ATOM | 2589 | CD | ARG | B | 434 | 26.120 | 10.723 | 8.806 | 1.00 | 74.39 | B | C |
| ATOM | 2590 | NE | ARG | B | 434 | 25.277 | 11.580 | 7.972 | 1.00 | 76.05 | B | N |
| ATOM | 2591 | CZ | ARG | B | 434 | 24.283 | 12.346 | 8.422 | 1.00 | 76.46 | B | C |
| ATOM | 2592 | NH1 | ARG | B | 434 | 23.978 | 12.380 | 9.717 | 1.00 | 76.39 | B | N |
| ATOM | 2593 | NH2 | ARG | B | 434 | 23.594 | 13.094 | 7.569 | 1.00 | 76.64 | B | N |
| ATOM | 2594 | N | PHE | B | 435 | 30.539 | 13.399 | 9.604 | 1.00 | 75.10 | B | N |
| ATOM | 2595 | CA | PHE | B | 435 | 30.847 | 14.818 | 9.658 | 1.00 | 76.67 | B | C |
| ATOM | 2596 | C | PHE | B | 435 | 31.457 | 15.259 | 8.332 | 1.00 | 77.65 | B | C |
| ATOM | 2597 | O | PHE | B | 435 | 31.208 | 16.374 | 7.864 | 1.00 | 77.32 | B | O |
| ATOM | 2598 | CB | PHE | B | 435 | 31.841 | 15.121 | 10.782 | 1.00 | 77.15 | B | C |
| ATOM | 2599 | CG | PHE | B | 435 | 31.212 | 15.275 | 12.134 | 1.00 | 77.68 | B | C |
| ATOM | 2600 | CD1 | PHE | B | 435 | 30.138 | 16.145 | 12.327 | 1.00 | 77.99 | B | C |
| ATOM | 2601 | CD2 | PHE | B | 435 | 31.719 | 14.583 | 13.227 | 1.00 | 77.54 | B | C |
| ATOM | 2602 | CE1 | PHE | B | 435 | 29.579 | 16.324 | 13.593 | 1.00 | 77.62 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2603 | CE2 | PHE | B | 435 | 31.171 | 14.753 | 14.496 | 1.00 | 77.59 | B | C |
| ATOM | 2604 | CZ | PHE | B | 435 | 30.098 | 15.626 | 14.679 | 1.00 | 77.60 | B | C |
| ATOM | 2605 | N | ARG | B | 436 | 32.266 | 14.385 | 7.733 | 1.00 | 78.90 | B | N |
| ATOM | 2606 | CA | ARG | B | 436 | 32.902 | 14.723 | 6.468 | 1.00 | 80.43 | B | C |
| ATOM | 2607 | C | ARG | B | 436 | 31.987 | 14.412 | 5.292 | 1.00 | 80.60 | B | C |
| ATOM | 2608 | O | ARG | B | 436 | 32.129 | 15.003 | 4.224 | 1.00 | 81.03 | B | O |
| ATOM | 2609 | CB | ARG | B | 436 | 34.261 | 14.011 | 6.319 | 1.00 | 81.54 | B | C |
| ATOM | 2610 | CG | ARG | B | 436 | 34.230 | 12.531 | 5.935 | 1.00 | 83.32 | B | C |
| ATOM | 2611 | CD | ARG | B | 436 | 35.655 | 11.959 | 5.964 | 1.00 | 84.63 | B | C |
| ATOM | 2612 | NE | ARG | B | 436 | 35.826 | 10.728 | 5.192 | 1.00 | 86.14 | B | N |
| ATOM | 2613 | CZ | ARG | B | 436 | 36.981 | 10.344 | 4.646 | 1.00 | 87.10 | B | C |
| ATOM | 2614 | NH1 | ARG | B | 436 | 38.068 | 11.093 | 4.789 | 1.00 | 87.37 | B | N |
| ATOM | 2615 | NH2 | ARG | B | 436 | 37.049 | 9.217 | 3.946 | 1.00 | 87.74 | B | N |
| ATOM | 2616 | N | MET | B | 437 | 31.051 | 13.487 | 5.476 | 1.00 | 80.25 | B | N |
| ATOM | 2617 | CA | MET | B | 437 | 30.115 | 13.194 | 4.405 | 1.00 | 79.87 | B | C |
| ATOM | 2618 | C | MET | B | 437 | 29.124 | 14.352 | 4.444 | 1.00 | 79.11 | B | C |
| ATOM | 2619 | O | MET | B | 437 | 28.487 | 14.669 | 3.439 | 1.00 | 79.82 | B | O |
| ATOM | 2620 | CB | MET | B | 437 | 29.388 | 11.867 | 4.636 | 1.00 | 80.86 | B | C |
| ATOM | 2621 | CG | MET | B | 437 | 28.416 | 11.504 | 3.512 | 1.00 | 82.37 | B | C |
| ATOM | 2622 | SD | MET | B | 437 | 27.440 | 10.010 | 3.839 | 1.00 | 84.37 | B | S |
| ATOM | 2623 | CE | MET | B | 437 | 26.276 | 10.004 | 2.402 | 1.00 | 84.06 | B | C |
| ATOM | 2624 | N | MET | B | 438 | 29.017 | 14.987 | 5.612 | 1.00 | 77.92 | B | N |
| ATOM | 2625 | CA | MET | B | 438 | 28.124 | 16.131 | 5.825 | 1.00 | 76.61 | B | C |
| ATOM | 2626 | C | MET | B | 438 | 28.828 | 17.470 | 5.641 | 1.00 | 75.98 | B | C |
| ATOM | 2627 | O | MET | B | 438 | 28.178 | 18.527 | 5.627 | 1.00 | 75.43 | B | O |
| ATOM | 2628 | CB | MET | B | 438 | 27.547 | 16.107 | 7.237 | 1.00 | 76.68 | B | C |
| ATOM | 2629 | CG | MET | B | 438 | 26.333 | 15.240 | 7.409 | 1.00 | 76.69 | B | C |
| ATOM | 2630 | SD | MET | B | 438 | 25.614 | 15.491 | 9.031 | 1.00 | 77.05 | B | S |
| ATOM | 2631 | CE | MET | B | 438 | 25.245 | 17.253 | 8.975 | 1.00 | 76.84 | B | C |
| ATOM | 2632 | N | ASN | B | 439 | 30.155 | 17.412 | 5.528 | 1.00 | 75.29 | B | N |
| ATOM | 2633 | CA | ASN | B | 439 | 31.000 | 18.599 | 5.362 | 1.00 | 74.30 | B | C |
| ATOM | 2634 | C | ASN | B | 439 | 30.781 | 19.630 | 6.471 | 1.00 | 72.82 | B | C |
| ATOM | 2635 | O | ASN | B | 439 | 30.382 | 20.772 | 6.209 | 1.00 | 72.40 | B | O |
| ATOM | 2636 | CB | ASN | B | 439 | 30.737 | 19.251 | 4.006 | 1.00 | 75.08 | B | C |
| ATOM | 2637 | CG | ASN | B | 439 | 31.608 | 20.455 | 3.776 | 1.00 | 75.74 | B | C |
| ATOM | 2638 | OD1 | ASN | B | 439 | 32.837 | 20.351 | 3.788 | 1.00 | 76.20 | B | O |
| ATOM | 2639 | ND2 | ASN | B | 439 | 30.983 | 21.614 | 3.580 | 1.00 | 75.88 | B | N |
| ATOM | 2640 | N | LEU | B | 440 | 31.057 | 19.224 | 7.707 | 1.00 | 70.97 | B | N |
| ATOM | 2641 | CA | LEU | B | 440 | 30.868 | 20.098 | 8.859 | 1.00 | 69.35 | B | C |
| ATOM | 2642 | C | LEU | B | 440 | 31.761 | 21.343 | 8.797 | 1.00 | 68.08 | B | C |
| ATOM | 2643 | O | LEU | B | 440 | 32.905 | 21.268 | 8.357 | 1.00 | 67.89 | B | O |
| ATOM | 2644 | CB | LEU | B | 440 | 31.138 | 19.309 | 10.148 | 1.00 | 68.99 | B | C |
| ATOM | 2645 | CG | LEU | B | 440 | 31.013 | 20.078 | 11.467 | 1.00 | 69.06 | B | C |
| ATOM | 2646 | CD1 | LEU | B | 440 | 29.611 | 20.644 | 11.600 | 1.00 | 68.40 | B | C |
| ATOM | 2647 | CD2 | LEU | B | 440 | 31.338 | 19.157 | 12.635 | 1.00 | 69.17 | B | C |
| ATOM | 2648 | N | GLN | B | 441 | 31.236 | 22.484 | 9.241 | 1.00 | 66.46 | B | N |
| ATOM | 2649 | CA | GLN | B | 441 | 32.000 | 23.736 | 9.234 | 1.00 | 64.71 | B | C |
| ATOM | 2650 | C | GLN | B | 441 | 32.568 | 24.147 | 10.593 | 1.00 | 63.38 | B | C |
| ATOM | 2651 | O | GLN | B | 441 | 31.853 | 24.206 | 11.592 | 1.00 | 63.05 | B | O |
| ATOM | 2652 | CB | GLN | B | 441 | 31.139 | 24.885 | 8.692 | 1.00 | 64.70 | B | C |
| ATOM | 2653 | CG | GLN | B | 441 | 30.716 | 24.703 | 7.243 | 1.00 | 64.38 | B | C |
| ATOM | 2654 | CD | GLN | B | 441 | 31.895 | 24.446 | 6.342 | 1.00 | 63.58 | B | C |
| ATOM | 2655 | OE1 | GLN | B | 441 | 32.747 | 25.314 | 6.167 | 1.00 | 63.64 | B | O |
| ATOM | 2656 | NE2 | GLN | B | 441 | 31.960 | 23.244 | 5.771 | 1.00 | 63.23 | B | N |
| ATOM | 2657 | N | GLY | B | 442 | 33.861 | 24.445 | 10.615 | 1.00 | 61.67 | B | N |
| ATOM | 2658 | CA | GLY | B | 442 | 34.499 | 24.853 | 11.845 | 1.00 | 60.26 | B | C |
| ATOM | 2659 | C | GLY | B | 442 | 33.614 | 25.735 | 12.696 | 1.00 | 59.40 | B | C |
| ATOM | 2660 | O | GLY | B | 442 | 33.744 | 25.750 | 13.915 | 1.00 | 59.13 | B | O |
| ATOM | 2661 | N | GLU | B | 443 | 32.709 | 26.470 | 12.060 | 1.00 | 59.08 | B | N |
| ATOM | 2662 | CA | GLU | B | 443 | 31.804 | 27.357 | 12.789 | 1.00 | 59.09 | B | C |
| ATOM | 2663 | C | GLU | B | 443 | 30.607 | 26.598 | 13.390 | 1.00 | 58.26 | B | C |
| ATOM | 2664 | O | GLU | B | 443 | 29.930 | 27.102 | 14.297 | 1.00 | 57.26 | B | O |
| ATOM | 2665 | CB | GLU | B | 443 | 31.292 | 28.484 | 11.874 | 1.00 | 60.05 | B | C |
| ATOM | 2666 | CG | GLU | B | 443 | 32.349 | 29.459 | 11.337 | 1.00 | 61.08 | B | C |
| ATOM | 2667 | CD | GLU | B | 443 | 33.144 | 28.917 | 10.148 | 1.00 | 62.01 | B | C |
| ATOM | 2668 | OE1 | GLU | B | 443 | 32.635 | 28.055 | 9.398 | 1.00 | 62.33 | B | O |
| ATOM | 2669 | OE2 | GLU | B | 443 | 34.285 | 29.375 | 9.941 | 1.00 | 63.06 | B | O |
| ATOM | 2670 | N | GLU | B | 444 | 30.349 | 25.394 | 12.879 | 1.00 | 57.62 | B | N |
| ATOM | 2671 | CA | GLU | B | 444 | 29.245 | 24.560 | 13.367 | 1.00 | 57.52 | B | C |
| ATOM | 2672 | C | GLU | B | 444 | 29.788 | 23.639 | 14.446 | 1.00 | 57.07 | B | C |
| ATOM | 2673 | O | GLU | B | 444 | 29.102 | 23.310 | 15.417 | 1.00 | 56.80 | B | O |
| ATOM | 2674 | CB | GLU | B | 444 | 28.656 | 23.715 | 12.235 | 1.00 | 57.30 | B | C |
| ATOM | 2675 | CG | GLU | B | 444 | 28.066 | 24.526 | 11.106 | 1.00 | 57.93 | B | C |
| ATOM | 2676 | CD | GLU | B | 444 | 27.627 | 23.665 | 9.936 | 1.00 | 58.33 | B | C |
| ATOM | 2677 | OE1 | GLU | B | 444 | 28.440 | 22.834 | 9.463 | 1.00 | 58.95 | B | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2678 | OE2 | GLU | B | 444 | 26.474 | 23.828 | 9.485 | 1.00 | 57.62 | B | O |
| ATOM | 2679 | N | PHE | B | 445 | 31.035 | 23.227 | 14.254 | 1.00 | 56.81 | B | N |
| ATOM | 2680 | CA | PHE | B | 445 | 31.723 | 22.361 | 15.192 | 1.00 | 56.10 | B | C |
| ATOM | 2681 | C | PHE | B | 445 | 31.796 | 23.055 | 16.560 | 1.00 | 55.35 | B | C |
| ATOM | 2682 | O | PHE | B | 445 | 31.159 | 22.617 | 17.520 | 1.00 | 55.62 | B | O |
| ATOM | 2683 | CB | PHE | B | 445 | 33.122 | 22.063 | 14.666 | 1.00 | 56.35 | B | C |
| ATOM | 2684 | CG | PHE | B | 445 | 33.971 | 21.274 | 15.613 | 1.00 | 57.30 | B | C |
| ATOM | 2685 | CD1 | PHE | B | 445 | 33.640 | 19.964 | 15.937 | 1.00 | 57.36 | B | C |
| ATOM | 2686 | CD2 | PHE | B | 445 | 35.104 | 21.842 | 16.190 | 1.00 | 57.33 | B | C |
| ATOM | 2687 | CE1 | PHE | B | 445 | 34.423 | 19.230 | 16.816 | 1.00 | 57.00 | B | C |
| ATOM | 2688 | CE2 | PHE | B | 445 | 35.890 | 21.114 | 17.068 | 1.00 | 57.22 | B | C |
| ATOM | 2689 | CZ | PHE | B | 445 | 35.547 | 19.805 | 17.382 | 1.00 | 57.11 | B | C |
| ATOM | 2690 | N | VAL | B | 446 | 32.557 | 24.140 | 16.652 | 1.00 | 54.36 | B | N |
| ATOM | 2691 | CA | VAL | B | 446 | 32.668 | 24.863 | 17.917 | 1.00 | 53.35 | B | C |
| ATOM | 2692 | C | VAL | B | 446 | 31.258 | 25.126 | 18.443 | 1.00 | 52.57 | B | C |
| ATOM | 2693 | O | VAL | B | 446 | 31.040 | 25.246 | 19.655 | 1.00 | 51.73 | B | O |
| ATOM | 2694 | CB | VAL | B | 446 | 33.412 | 26.231 | 17.748 | 1.00 | 53.43 | B | C |
| ATOM | 2695 | CG1 | VAL | B | 446 | 34.663 | 26.042 | 16.907 | 1.00 | 52.71 | B | C |
| ATOM | 2696 | CG2 | VAL | B | 446 | 32.478 | 27.290 | 17.142 | 1.00 | 52.91 | B | C |
| ATOM | 2697 | N | CYS | B | 447 | 30.305 | 25.201 | 17.511 | 1.00 | 52.05 | B | N |
| ATOM | 2698 | CA | CYS | B | 447 | 28.901 | 25.459 | 17.839 | 1.00 | 51.22 | B | C |
| ATOM | 2699 | C | CYS | B | 447 | 28.189 | 24.250 | 18.463 | 1.00 | 50.27 | B | C |
| ATOM | 2700 | O | CYS | B | 447 | 27.442 | 24.397 | 19.437 | 1.00 | 49.88 | B2 | O |
| ATOM | 2701 | CB | CYS | B | 447 | 28.146 | 25.956 | 16.594 | 1.00 | 51.72 | B | C |
| ATOM | 2702 | SG | CYS | B | 447 | 27.549 | 27.695 | 16.747 | 1.00 | 53.48 | B | S |
| ATOM | 2703 | N | LEU | B | 448 | 28.413 | 23.061 | 17.914 | 1.00 | 48.79 | B | N |
| ATOM | 2704 | CA | LEU | B | 448 | 27.801 | 21.867 | 18.484 | 1.00 | 47.67 | B | C |
| ATOM | 2705 | C | LEU | B | 448 | 28.449 | 21.642 | 19.853 | 1.00 | 47.59 | B | C |
| ATOM | 2706 | O | LEU | B | 448 | 27.771 | 21.367 | 20.857 | 1.00 | 47.46 | B | O |
| ATOM | 2707 | CB | LEU | B | 448 | 28.080 | 20.666 | 17.597 | 1.00 | 46.93 | B | C |
| ATOM | 2708 | CG | LEU | B | 448 | 27.594 | 20.758 | 16.161 | 1.00 | 46.23 | B | C |
| ATOM | 2709 | CD1 | LEU | B | 448 | 28.130 | 19.567 | 15.388 | 1.00 | 46.29 | B | C |
| ATOM | 2710 | CD2 | LEU | B | 448 | 26.072 | 20.804 | 16.133 | 1.00 | 45.82 | B | C |
| ATOM | 2711 | N | LYS | B | 449 | 29.776 | 21.779 | 19.873 | 1.00 | 46.99 | B | N |
| ATOM | 2712 | CA | LYS | B | 449 | 30.575 | 21.599 | 21.075 | 1.00 | 45.86 | B | C |
| ATOM | 2713 | C | LYS | B | 449 | 29.985 | 22.345 | 22.259 | 1.00 | 44.61 | B | C |
| ATOM | 2714 | O | LYS | B | 449 | 29.750 | 21.756 | 23.316 | 1.00 | 44.56 | B | O |
| ATOM | 2715 | CB | LYS | B | 449 | 31.999 | 22.068 | 20.812 | 1.00 | 46.30 | B | C |
| ATOM | 2716 | CG | LYS | B | 449 | 33.040 | 21.100 | 21.298 | 1.00 | 47.08 | B | C |
| ATOM | 2717 | CD | LYS | B | 449 | 34.398 | 21.410 | 20.724 | 1.00 | 47.48 | B | C |
| ATOM | 2718 | CE | LYS | B | 449 | 34.899 | 22.787 | 21.154 | 1.00 | 48.28 | B | C |
| ATOM | 2719 | NZ | LYS | B | 449 | 36.369 | 22.914 | 20.897 | 1.00 | 47.67 | B | N |
| ATOM | 2720 | N | SER | B | 450 | 29.732 | 23.637 | 22.089 | 1.00 | 43.44 | B | N |
| ATOM | 2721 | CA | SER | B | 450 | 29.151 | 24.427 | 23.176 | 1.00 | 42.55 | B | C |
| ATOM | 2722 | C | SER | B | 450 | 27.774 | 23.880 | 23.561 | 1.00 | 41.56 | B | C |
| ATOM | 2723 | O | SER | B | 450 | 27.391 | 23.943 | 24.727 | 1.00 | 41.83 | B | O |
| ATOM | 2724 | CB | SER | B | 450 | 29.028 | 25.911 | 22.785 | 1.00 | 42.28 | B | C |
| ATOM | 2725 | OG | SER | B | 450 | 30.261 | 26.416 | 22.293 | 1.00 | 42.73 | B | O |
| ATOM | 2726 | N | ILE | B | 451 | 27.017 | 23.351 | 22.601 | 1.00 | 40.30 | B | N |
| ATOM | 2727 | CA | ILE | B | 451 | 25.710 | 22.807 | 22.954 | 1.00 | 39.29 | B | C |
| ATOM | 2728 | C | ILE | B | 451 | 25.906 | 21.582 | 23.839 | 1.00 | 38.01 | B | C |
| ATOM | 2729 | O | ILE | B | 451 | 25.257 | 21.477 | 24.874 | 1.00 | 37.17 | B | O |
| ATOM | 2730 | CB | ILE | B | 451 | 24.855 | 22.425 | 21.712 | 1.00 | 39.96 | B | C |
| ATOM | 2731 | CG1 | ILE | B | 451 | 24.417 | 23.694 | 20.956 | 1.00 | 39.27 | B | C |
| ATOM | 2732 | CG2 | ILE | B | 451 | 23.589 | 21.677 | 22.168 | 1.00 | 39.72 | B | C |
| ATOM | 2733 | CD1 | ILE | B | 451 | 23.976 | 23.449 | 19.520 | 1.00 | 36.81 | B | C |
| ATOM | 2734 | N | ILE | B | 452 | 26.800 | 20.675 | 23.433 | 1.00 | 37.15 | B | N |
| ATOM | 2735 | CA | ILE | B | 452 | 27.114 | 19.474 | 24.220 | 1.00 | 37.23 | B | C |
| ATOM | 2736 | C | ILE | B | 452 | 27.349 | 19.836 | 25.698 | 1.00 | 38.23 | B | C |
| ATOM | 2737 | O | ILE | B | 452 | 26.729 | 19.282 | 26.607 | 1.00 | 37.35 | B | O |
| ATOM | 2738 | CB | ILE | B | 452 | 28.389 | 18.792 | 23.710 | 1.00 | 36.37 | B | C |
| ATOM | 2739 | CG1 | ILE | B | 452 | 28.147 | 18.223 | 22.304 | 1.00 | 35.49 | B | C |
| ATOM | 2740 | CG2 | ILE | B | 452 | 28.842 | 17.733 | 24.721 | 1.00 | 36.36 | B | C |
| ATOM | 2741 | CD1 | ILE | B | 452 | 29.232 | 17.268 | 21.798 | 1.00 | 34.10 | B | C |
| ATOM | 2742 | N | LEU | B | 453 | 28.267 | 20.772 | 25.904 | 1.00 | 39.43 | B | N |
| ATOM | 2743 | CA | LEU | B | 453 | 28.629 | 21.288 | 27.217 | 1.00 | 40.61 | B | C |
| ATOM | 2744 | C | LEU | B | 453 | 27.431 | 21.649 | 28.069 | 1.00 | 41.23 | B | C |
| ATOM | 2745 | O | LEU | B | 453 | 27.302 | 21.177 | 29.201 | 1.00 | 40.83 | B | O |
| ATOM | 2746 | CB | LEU | B | 453 | 29.480 | 22.548 | 27.054 | 1.00 | 41.31 | B | C |
| ATOM | 2747 | CG | LEU | B | 453 | 29.830 | 23.357 | 28.308 | 1.00 | 41.49 | B | C |
| ATOM | 2748 | CD1 | LEU | B | 453 | 30.706 | 22.488 | 29.205 | 1.00 | 41.32 | B | C |
| ATOM | 2749 | CD2 | LEU | B | 453 | 30.563 | 24.665 | 27.924 | 1.00 | 41.96 | B | C |
| ATOM | 2750 | N | LEU | B | 454 | 26.586 | 22.521 | 27.522 | 1.00 | 42.64 | B | N |
| ATOM | 2751 | CA | LEU | B | 454 | 25.392 | 23.007 | 28.206 | 1.00 | 44.19 | B | C |
| ATOM | 2752 | C | LEU | B | 454 | 24.255 | 22.008 | 28.198 | 1.00 | 45.49 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2753 | O | LEU | B | 454 | 23.271 | 22.181 | 28.913 | 1.00 | 46.10 | B | O |
| ATOM | 2754 | CB | LEU | B | 454 | 24.893 | 24.310 | 27.579 | 1.00 | 44.01 | B | C |
| ATOM | 2755 | CG | LEU | B | 454 | 25.763 | 25.562 | 27.658 | 1.00 | 44.04 | B | C |
| ATOM | 2756 | CD1 | LEU | B | 454 | 26.338 | 25.898 | 26.291 | 1.00 | 43.49 | B | C |
| ATOM | 2757 | CD2 | LEU | B | 454 | 24.910 | 26.710 | 28.168 | 1.00 | 43.75 | B | C |
| ATOM | 2758 | N | ASN | B | 455 | 24.371 | 20.970 | 27.382 | 1.00 | 47.04 | B | N |
| ATOM | 2759 | CA | ASN | B | 455 | 23.323 | 19.973 | 27.334 | 1.00 | 49.12 | B | C |
| ATOM | 2760 | C | ASN | B | 455 | 23.728 | 18.698 | 28.063 | 1.00 | 51.11 | B | C |
| ATOM | 2761 | O | ASN | B | 455 | 23.014 | 17.700 | 28.038 | 1.00 | 51.68 | B | O |
| ATOM | 2762 | CB | ASN | B | 455 | 22.949 | 19.662 | 25.892 | 1.00 | 47.90 | B | C |
| ATOM | 2763 | CG | ASN | B | 455 | 21.571 | 19.070 | 25.785 | 1.00 | 46.73 | B | C |
| ATOM | 2764 | OD1 | ASN | B | 455 | 20.627 | 19.572 | 26.390 | 1.00 | 45.11 | B | O |
| ATOM | 2765 | ND2 | ASN | B | 455 | 21.445 | 17.995 | 25.020 | 1.00 | 46.96 | B | N |
| ATOM | 2766 | N | SER | B | 456 | 24.881 | 18.739 | 28.717 | 1.00 | 53.45 | B | N |
| ATOM | 2767 | CA | SER | B | 456 | 25.362 | 17.597 | 29.478 | 1.00 | 55.36 | B | C |
| ATOM | 2768 | C | SER | B | 456 | 24.401 | 17.350 | 30.647 | 1.00 | 56.38 | B | C |
| ATOM | 2769 | O | SER | B | 456 | 24.096 | 16.195 | 30.984 | 1.00 | 56.32 | B | O |
| ATOM | 2770 | CB | SER | B | 456 | 26.760 | 17.885 | 30.017 | 1.00 | 56.04 | B | C |
| ATOM | 2771 | OG | SER | B | 456 | 26.746 | 19.040 | 30.836 | 1.00 | 56.90 | B | O |
| ATOM | 2772 | N | GLY | B | 457 | 23.925 | 18.445 | 31.251 | 1.00 | 57.05 | B | N |
| ATOM | 2773 | CA | GLY | B | 457 | 22.998 | 18.358 | 32.372 | 1.00 | 57.59 | B | C |
| ATOM | 2774 | C | GLY | B | 457 | 21.783 | 19.284 | 32.287 | 1.00 | 57.80 | B | C |
| ATOM | 2775 | O | GLY | B | 457 | 21.409 | 19.800 | 31.220 | 1.00 | 57.24 | B | O |
| ATOM | 2776 | N | ASP | B | 473 | 15.602 | 27.870 | 31.275 | 1.00 | 80.05 | B | N |
| ATOM | 2777 | CA | ASP | B | 473 | 16.242 | 28.898 | 32.089 | 1.00 | 80.01 | B | C |
| ATOM | 2778 | C | ASP | B | 473 | 17.279 | 29.696 | 31.294 | 1.00 | 79.67 | B | C |
| ATOM | 2779 | O | ASP | B | 473 | 17.213 | 29.789 | 30.058 | 1.00 | 79.47 | B | O |
| ATOM | 2780 | CB | ASP | B | 473 | 16.909 | 28.252 | 33.311 | 1.00 | 80.27 | B | C |
| ATOM | 2781 | CG | ASP | B | 473 | 17.717 | 27.018 | 32.949 | 1.00 | 80.55 | B | C |
| ATOM | 2782 | OD1 | ASP | B | 473 | 17.113 | 26.020 | 32.499 | 1.00 | 80.81 | B | O |
| ATOM | 2783 | OD2 | ASP | B | 473 | 18.956 | 27.048 | 33.109 | 1.00 | 80.74 | B | O |
| ATOM | 2784 | N | HIS | B | 474 | 18.228 | 30.280 | 32.021 | 1.00 | 78.95 | B | N |
| ATOM | 2785 | CA | HIS | B | 474 | 19.301 | 31.059 | 31.420 | 1.00 | 77.88 | B | C |
| ATOM | 2786 | C | HIS | B | 474 | 20.134 | 30.144 | 30.523 | 1.00 | 76.70 | B | C |
| ATOM | 2787 | O | HIS | B | 474 | 20.614 | 30.567 | 29.470 | 1.00 | 76.05 | B | O |
| ATOM | 2788 | CB | HIS | B | 474 | 20.166 | 31.673 | 32.525 | 1.00 | 78.41 | B | C |
| ATOM | 2789 | CG | HIS | B | 474 | 21.383 | 32.385 | 32.022 | 1.00 | 78.65 | B | C |
| ATOM | 2790 | ND1 | HIS | B | 474 | 22.428 | 31.730 | 31.407 | 1.00 | 78.84 | B | N |
| ATOM | 2791 | CD2 | HIS | B | 474 | 21.732 | 33.693 | 32.065 | 1.00 | 78.73 | B | C |
| ATOM | 2792 | CE1 | HIS | B | 474 | 23.369 | 32.602 | 31.095 | 1.00 | 78.85 | B | C |
| ATOM | 2793 | NE2 | HIS | B | 474 | 22.972 | 33.801 | 31.484 | 1.00 | 78.96 | B | N |
| ATOM | 2794 | N | ILE | B | 475 | 20.299 | 28.890 | 30.948 | 1.00 | 75.65 | B | N |
| ATOM | 2795 | CA | ILE | B | 475 | 21.056 | 27.909 | 30.172 | 1.00 | 74.50 | B | C |
| ATOM | 2796 | C | ILE | B | 475 | 20.379 | 27.682 | 28.822 | 1.00 | 74.06 | B | C |
| ATOM | 2797 | O | ILE | B | 475 | 21.038 | 27.644 | 27.785 | 1.00 | 73.91 | B | O |
| ATOM | 2798 | CB | ILE | B | 475 | 21.168 | 26.546 | 30.910 | 1.00 | 73.99 | B | C |
| ATOM | 2799 | CG1 | ILE | B | 475 | 22.240 | 26.617 | 32.004 | 1.00 | 73.38 | B | C |
| ATOM | 2800 | CG2 | ILE | B | 475 | 21.523 | 25.441 | 29.915 | 1.00 | 73.89 | B | C |
| ATOM | 2801 | CD1 | ILE | B | 475 | 23.677 | 26.584 | 31.478 | 1.00 | 72.74 | B | C |
| ATOM | 2802 | N | HIS | B | 476 | 19.061 | 27.524 | 28.837 | 1.00 | 73.65 | B | N |
| ATOM | 2803 | CA | HIS | B | 476 | 18.329 | 27.313 | 27.597 | 1.00 | 73.17 | B | C |
| ATOM | 2804 | C | HIS | B | 476 | 18.387 | 28.563 | 26.728 | 1.00 | 72.02 | B | C |
| ATOM | 2805 | O | HIS | B | 476 | 18.612 | 28.463 | 25.517 | 1.00 | 71.58 | B | O |
| ATOM | 2806 | CB | HIS | B | 476 | 16.882 | 26.919 | 27.897 | 1.00 | 74.47 | B | C |
| ATOM | 2807 | CG | HIS | B | 476 | 16.729 | 25.495 | 28.339 | 1.00 | 75.52 | B | C |
| ATOM | 2808 | ND1 | HIS | B | 476 | 15.649 | 25.054 | 29.072 | 1.00 | 76.10 | B | N |
| ATOM | 2809 | CD2 | HIS | B | 476 | 17.512 | 24.409 | 28.131 | 1.00 | 75.57 | B | C |
| ATOM | 2810 | CE1 | HIS | B | 476 | 15.773 | 23.758 | 29.298 | 1.00 | 76.19 | B | C |
| ATOM | 2811 | NE2 | HIS | B | 476 | 16.894 | 23.342 | 28.737 | 1.00 | 75.87 | B | N |
| ATOM | 2812 | N | ARG | B | 477 | 18.199 | 29.733 | 27.344 | 1.00 | 70.52 | B | N |
| ATOM | 2813 | CA | ARG | B | 477 | 18.261 | 31.004 | 26.615 | 1.00 | 68.93 | B | C |
| ATOM | 2814 | CB | ARG | B | 477 | 18.285 | 32.170 | 27.593 | 1.00 | 68.85 | B | C |
| ATOM | 2815 | C | ARG | B | 477 | 19.519 | 31.019 | 25.738 | 1.00 | 67.63 | B | C |
| ATOM | 2816 | O | ARG | B | 477 | 19.462 | 31.373 | 24.558 | 1.00 | 67.59 | B | O |
| ATOM | 2817 | N | VAL | B | 478 | 20.652 | 30.621 | 26.318 | 1.00 | 66.00 | B | N |
| ATOM | 2818 | CA | VAL | B | 478 | 21.913 | 30.562 | 25.578 | 1.00 | 64.18 | B | C |
| ATOM | 2819 | C | VAL | B | 478 | 21.856 | 29.415 | 24.575 | 1.00 | 62.81 | B | C |
| ATOM | 2820 | O | VAL | B | 478 | 22.415 | 29.504 | 23.488 | 1.00 | 62.47 | B | O |
| ATOM | 2821 | CB | VAL | B | 478 | 23.129 | 30.319 | 26.519 | 1.00 | 64.20 | B | C |
| ATOM | 2822 | CG1 | VAL | B | 478 | 24.420 | 30.209 | 25.699 | 1.00 | 63.47 | B | C |
| ATOM | 2823 | CG2 | VAL | B | 478 | 23.231 | 31.442 | 27.544 | 1.00 | 63.88 | B | C |
| ATOM | 2824 | N | LEU | B | 479 | 21.183 | 28.334 | 24.957 | 1.00 | 61.49 | B | N |
| ATOM | 2825 | CA | LEU | B | 479 | 21.060 | 27.175 | 24.089 | 1.00 | 60.63 | B | C |
| ATOM | 2826 | C | LEU | B | 479 | 20.245 | 27.525 | 22.849 | 1.00 | 59.97 | B | C |
| ATOM | 2827 | O | LEU | B | 479 | 20.473 | 26.975 | 21.767 | 1.00 | 59.32 | B | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2828 | CB | LEU | B | 479 | 20.438 | 25.993 | 24.856 | 1.00 | 60.37 B | | C |
| ATOM | 2829 | CG | LEU | B | 479 | 21.443 | 25.043 | 25.537 | 1.00 | 60.02 B | | C |
| ATOM | 2830 | CD1 | LEU | B | 479 | 20.706 | 24.044 | 26.402 | 1.00 | 59.82 B | | C |
| ATOM | 2831 | CD2 | LEU | B | 479 | 22.281 | 24.305 | 24.475 | 1.00 | 59.72 B | | C |
| ATOM | 2832 | N | ASP | B | 480 | 19.302 | 28.450 | 23.008 | 1.00 | 59.38 B | | N |
| ATOM | 2833 | CA | ASP | B | 480 | 18.486 | 28.893 | 21.882 | 1.00 | 59.01 B | | C |
| ATOM | 2834 | C | ASP | B | 480 | 19.328 | 29.828 | 21.023 | 1.00 | 58.62 B | | C |
| ATOM | 2835 | O | ASP | B | 480 | 19.451 | 29.630 | 19.806 | 1.00 | 58.43 B | | O |
| ATOM | 2836 | CB | ASP | B | 480 | 17.225 | 29.618 | 22.368 | 1.00 | 58.85 B | | C |
| ATOM | 2837 | CG | ASP | B | 480 | 16.148 | 28.654 | 22.857 | 1.00 | 59.01 B | | C |
| ATOM | 2838 | OD1 | ASP | B | 480 | 15.900 | 27.633 | 22.172 | 1.00 | 58.96 B | | O |
| ATOM | 2839 | OD2 | ASP | B | 480 | 15.538 | 28.918 | 23.914 | 1.00 | 58.96 B | | O |
| ATOM | 2840 | N | LYS | B | 481 | 19.923 | 30.831 | 21.667 | 1.00 | 57.83 B | | N |
| ATOM | 2841 | CA | LYS | B | 481 | 20.758 | 31.796 | 20.969 | 1.00 | 57.15 B | | C |
| ATOM | 2842 | C | LYS | B | 481 | 21.804 | 31.091 | 20.119 | 1.00 | 56.14 B | | C |
| ATOM | 2843 | O | LYS | B | 481 | 22.230 | 31.620 | 19.088 | 1.00 | 55.92 B | | O |
| ATOM | 2844 | CB | LYS | B | 481 | 21.454 | 32.718 | 21.960 | 1.00 | 57.83 B | | C |
| ATOM | 2845 | CG | LYS | B | 481 | 22.491 | 33.629 | 21.316 | 1.00 | 59.23 B | | C |
| ATOM | 2846 | CD | LYS | B | 481 | 21.887 | 34.940 | 20.830 | 1.00 | 60.43 B | | C |
| ATOM | 2847 | CE | LYS | B | 481 | 22.914 | 35.767 | 20.064 | 1.00 | 60.64 B | | C |
| ATOM | 2848 | NZ | LYS | B | 481 | 23.312 | 35.102 | 18.786 | 1.00 | 61.48 B | | N |
| ATOM | 2849 | N | ILE | B | 482 | 22.231 | 29.905 | 20.549 | 1.00 | 55.01 B | | N |
| ATOM | 2850 | CA | ILE | B | 482 | 23.221 | 29.160 | 19.777 | 1.00 | 54.09 B | | C |
| ATOM | 2851 | C | ILE | B | 482 | 22.542 | 28.460 | 18.614 | 1.00 | 54.01 B | | C |
| ATOM | 2852 | O | ILE | B | 482 | 23.182 | 28.180 | 17.600 | 1.00 | 53.72 B | | O |
| ATOM | 2853 | CB | ILE | B | 482 | 23.962 | 28.112 | 20.631 | 1.00 | 53.48 B | | C |
| ATOM | 2854 | CG1 | ILE | B | 482 | 24.673 | 28.806 | 21.795 | 1.00 | 53.26 B | | C |
| ATOM | 2855 | CG2 | ILE | B | 482 | 24.989 | 27.363 | 19.766 | 1.00 | 52.24 B | | C |
| ATOM | 2856 | CD1 | ILE | B | 482 | 25.308 | 27.858 | 22.786 | 1.00 | 52.57 B | | C |
| ATOM | 2857 | N | THR | B | 483 | 21.245 | 28.179 | 18.764 | 1.00 | 54.13 B | | N |
| ATOM | 2858 | CA | THR | B | 483 | 20.476 | 27.524 | 17.703 | 1.00 | 54.68 B | | C |
| ATOM | 2859 | C | THR | B | 483 | 20.313 | 28.540 | 16.598 | 1.00 | 53.83 B | | C |
| ATOM | 2860 | O | THR | B | 483 | 20.565 | 28.261 | 15.423 | 1.00 | 52.61 B | | O |
| ATOM | 2861 | CB | THR | B | 483 | 19.057 | 27.127 | 18.145 | 1.00 | 55.37 B | | C |
| ATOM | 2862 | OG1 | THR | B | 483 | 19.096 | 26.518 | 19.442 | 1.00 | 56.40 B | | O |
| ATOM | 2863 | CG2 | THR | B | 483 | 18.470 | 26.129 | 17.141 | 1.00 | 55.58 B | | C |
| ATOM | 2864 | N | ASP | B | 484 | 19.869 | 29.723 | 17.013 | 1.00 | 53.93 B | | N |
| ATOM | 2865 | CA | ASP | B | 484 | 19.675 | 30.851 | 16.117 | 1.00 | 54.27 B | | C |
| ATOM | 2866 | C | ASP | B | 484 | 20.989 | 31.081 | 15.373 | 1.00 | 54.82 B | | C |
| ATOM | 2867 | O | ASP | B | 484 | 20.993 | 31.327 | 14.163 | 1.00 | 55.01 B | | O |
| ATOM | 2868 | CB | ASP | B | 484 | 19.317 | 32.123 | 16.904 | 1.00 | 53.61 B | | C |
| ATOM | 2869 | CG | ASP | B | 484 | 18.072 | 31.964 | 17.775 | 1.00 | 53.09 B | | C |
| ATOM | 2870 | OD1 | ASP | B | 484 | 17.132 | 31.223 | 17.386 | 1.00 | 52.83 B | | O |
| ATOM | 2871 | OD2 | ASP | B | 484 | 18.032 | 32.614 | 18.847 | 1.00 | 52.61 B | | O |
| ATOM | 2872 | N | THR | B | 485 | 22.101 | 30.991 | 16.103 | 1.00 | 55.49 B | | N |
| ATOM | 2873 | CA | THR | B | 485 | 23.424 | 31.183 | 15.516 | 1.00 | 56.53 B | | C |
| ATOM | 2874 | C | THR | B | 485 | 23.772 | 30.118 | 14.482 | 1.00 | 58.12 B | | C |
| ATOM | 2875 | O | THR | B | 485 | 24.153 | 30.451 | 13.365 | 1.00 | 58.08 B | | O |
| ATOM | 2876 | CB | THR | B | 485 | 24.523 | 31.194 | 16.584 | 1.00 | 55.73 B | | C |
| ATOM | 2877 | OG1 | THR | B | 485 | 24.288 | 32.270 | 17.503 | 1.00 | 55.16 B | | O |
| ATOM | 2878 | CG2 | THR | B | 485 | 25.884 | 31.365 | 15.932 | 1.00 | 55.07 B | | C |
| ATOM | 2879 | N | LEU | B | 486 | 23.647 | 28.844 | 14.848 | 1.00 | 60.37 B | | N |
| ATOM | 2880 | CA | LEU | B | 486 | 23.955 | 27.764 | 13.911 | 1.00 | 62.59 B | | C |
| ATOM | 2881 | C | LEU | B | 486 | 23.138 | 27.998 | 12.651 | 1.00 | 64.36 B | | C |
| ATOM | 2882 | O | LEU | B | 486 | 23.653 | 27.875 | 11.535 | 1.00 | 64.60 B | | O |
| ATOM | 2883 | CB | LEU | B | 486 | 23.602 | 26.397 | 14.510 | 1.00 | 62.37 B | | C |
| ATOM | 2884 | CG | LEU | B | 486 | 24.755 | 25.445 | 14.863 | 1.00 | 62.68 B | | C |
| ATOM | 2885 | CD1 | LEU | B | 486 | 24.207 | 24.323 | 15.737 | 1.00 | 63.32 B | | C |
| ATOM | 2886 | CD2 | LEU | B | 486 | 25.414 | 24.874 | 13.605 | 1.00 | 62.05 B | | C |
| ATOM | 2887 | N | ILE | B | 487 | 21.865 | 28.347 | 12.834 | 1.00 | 66.25 B | | N |
| ATOM | 2888 | CA | ILE | B | 487 | 20.974 | 28.608 | 11.704 | 1.00 | 68.21 B | | C |
| ATOM | 2889 | C | ILE | B | 487 | 21.482 | 29.792 | 10.870 | 1.00 | 69.02 B | | C |
| ATOM | 2890 | O | ILE | B | 487 | 21.747 | 29.647 | 9.669 | 1.00 | 68.87 B | | O |
| ATOM | 2891 | CB | ILE | B | 487 | 19.521 | 28.902 | 12.182 | 1.00 | 68.86 B | | C |
| ATOM | 2892 | CG1 | ILE | B | 487 | 18.788 | 27.593 | 12.509 | 1.00 | 69.23 B | | C |
| ATOM | 2893 | CG2 | ILE | B | 487 | 18.766 | 29.682 | 11.110 | 1.00 | 69.73 B | | C |
| ATOM | 2894 | CD1 | ILE | B | 487 | 18.642 | 26.642 | 11.319 | 1.00 | 69.38 B | | C |
| ATOM | 2895 | N | HIS | B | 488 | 21.601 | 30.955 | 11.512 | 1.00 | 69.79 B | | N |
| ATOM | 2896 | CA | HIS | B | 488 | 22.094 | 32.175 | 10.867 | 1.00 | 70.49 B | | C |
| ATOM | 2897 | C | HIS | B | 488 | 23.324 | 31.871 | 10.006 | 1.00 | 70.42 B | | C |
| ATOM | 2898 | O | HIS | B | 488 | 23.666 | 32.622 | 9.092 | 1.00 | 70.11 B | | O |
| ATOM | 2899 | CB | HIS | B | 488 | 22.432 | 33.205 | 11.954 | 1.00 | 71.51 B | | C |
| ATOM | 2900 | CG | HIS | B | 488 | 23.340 | 34.315 | 11.507 | 1.00 | 73.05 B | | C |
| ATOM | 2901 | ND1 | HIS | B | 488 | 22.873 | 35.515 | 11.012 | 1.00 | 73.69 B | | N |
| ATOM | 2902 | CD2 | HIS | B | 488 | 24.691 | 34.418 | 11.525 | 1.00 | 73.45 B | | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2903 | CE1 | HIS | B | 488 | 23.896 | 36.310 | 10.749 | 1.00 | 73.84 | B | C |
| ATOM | 2904 | NE2 | HIS | B | 488 | 25.010 | 35.667 | 11.052 | 1.00 | 73.99 | B | N |
| ATOM | 2905 | N | LEU | B | 489 | 23.974 | 30.751 | 10.297 | 1.00 | 70.56 | B | N |
| ATOM | 2906 | CA | LEU | B | 489 | 25.157 | 30.339 | 9.560 | 1.00 | 70.69 | B | C |
| ATOM | 2907 | C | LEU | B | 489 | 24.743 | 29.539 | 8.321 | 1.00 | 70.93 | B | C |
| ATOM | 2908 | O | LEU | B | 489 | 25.246 | 29.801 | 7.226 | 1.00 | 70.95 | B | O |
| ATOM | 2909 | CB | LEU | B | 489 | 26.088 | 29.532 | 10.486 | 1.00 | 70.56 | B | C |
| ATOM | 2910 | CG | LEU | B | 489 | 26.560 | 30.233 | 11.779 | 1.00 | 70.47 | B | C |
| ATOM | 2911 | CD1 | LEU | B | 489 | 27.117 | 29.202 | 12.761 | 1.00 | 70.21 | B | C |
| ATOM | 2912 | CD2 | LEU | B | 489 | 27.599 | 31.297 | 11.461 | 1.00 | 70.54 | B | C |
| ATOM | 2913 | N | MET | B | 490 | 23.828 | 28.580 | 8.471 | 1.00 | 71.39 | B | N |
| ATOM | 2914 | CA | MET | B | 490 | 23.383 | 27.821 | 7.302 | 1.00 | 71.47 | B | C |
| ATOM | 2915 | C | MET | B | 490 | 22.713 | 28.773 | 6.328 | 1.00 | 71.66 | B | C |
| ATOM | 2916 | O | MET | B | 490 | 22.553 | 28.450 | 5.152 | 1.00 | 71.12 | B | O |
| ATOM | 2917 | CB | MET | B | 490 | 22.401 | 26.701 | 7.674 | 1.00 | 71.36 | B | C |
| ATOM | 2918 | CG | MET | B | 490 | 21.824 | 26.740 | 9.078 | 1.00 | 70.94 | B | C |
| ATOM | 2919 | SD | MET | B | 490 | 22.536 | 25.478 | 10.148 | 1.00 | 70.21 | B | S |
| ATOM | 2920 | CE | MET | B | 490 | 21.784 | 24.011 | 9.491 | 1.00 | 69.70 | B | C |
| ATOM | 2921 | N | ALA | B | 491 | 22.336 | 29.945 | 6.839 | 1.00 | 72.21 | B | N |
| ATOM | 2922 | CA | ALA | B | 491 | 21.679 | 30.995 | 6.056 | 1.00 | 72.97 | B | C |
| ATOM | 2923 | C | ALA | B | 491 | 22.640 | 31.675 | 5.089 | 1.00 | 73.47 | B | C |
| ATOM | 2924 | O | ALA | B | 491 | 22.409 | 31.691 | 3.876 | 1.00 | 73.74 | B | O |
| ATOM | 2925 | CB | ALA | B | 491 | 21.071 | 32.041 | 6.989 | 1.00 | 72.50 | B | C |
| ATOM | 2926 | N | LYS | B | 492 | 23.703 | 32.260 | 5.629 | 1.00 | 73.80 | B | N |
| ATOM | 2927 | CA | LYS | B | 492 | 24.677 | 32.911 | 4.781 | 1.00 | 74.31 | B | C |
| ATOM | 2928 | C | LYS | B | 492 | 25.351 | 31.868 | 3.896 | 1.00 | 74.51 | B | C |
| ATOM | 2929 | O | LYS | B | 492 | 25.729 | 32.155 | 2.760 | 1.00 | 74.68 | B | O |
| ATOM | 2930 | CB | LYS | B | 492 | 25.691 | 33.664 | 5.633 | 1.00 | 74.60 | B | C |
| ATOM | 2931 | CG | LYS | B | 492 | 25.012 | 34.723 | 6.490 | 1.00 | 75.62 | B | C |
| ATOM | 2932 | CD | LYS | B | 492 | 25.984 | 35.750 | 7.053 | 1.00 | 76.16 | B | C |
| ATOM | 2933 | CE | LYS | B | 492 | 25.211 | 36.959 | 7.596 | 1.00 | 76.40 | B | C |
| ATOM | 2934 | NZ | LYS | B | 492 | 26.095 | 38.008 | 8.193 | 1.00 | 76.06 | B | N |
| ATOM | 2935 | N | ALA | B | 493 | 25.479 | 30.645 | 4.397 | 1.00 | 74.77 | B | N |
| ATOM | 2936 | CA | ALA | B | 493 | 26.094 | 29.589 | 3.598 | 1.00 | 75.14 | B | C |
| ATOM | 2937 | C | ALA | B | 493 | 25.272 | 29.411 | 2.326 | 1.00 | 75.31 | B | C |
| ATOM | 2938 | O | ALA | B | 493 | 25.707 | 28.765 | 1.366 | 1.00 | 75.21 | B | O |
| ATOM | 2939 | CB | ALA | B | 493 | 26.133 | 28.279 | 4.389 | 1.00 | 75.26 | B | C |
| ATOM | 2940 | N | GLY | B | 494 | 24.079 | 30.001 | 2.331 | 1.00 | 75.50 | B | N |
| ATOM | 2941 | CA | GLY | B | 494 | 23.195 | 29.891 | 1.188 | 1.00 | 75.79 | B | C |
| ATOM | 2942 | C | GLY | B | 494 | 22.510 | 28.540 | 1.251 | 1.00 | 76.10 | B | C |
| ATOM | 2943 | O | GLY | B | 494 | 22.952 | 27.575 | 0.612 | 1.00 | 76.25 | B | O |
| ATOM | 2944 | N | LEU | B | 495 | 21.441 | 28.471 | 2.044 | 1.00 | 76.21 | B | N |
| ATOM | 2945 | CA | LEU | B | 495 | 20.680 | 27.236 | 2.231 | 1.00 | 76.23 | B | C |
| ATOM | 2946 | C | LEU | B | 495 | 19.184 | 27.534 | 2.387 | 1.00 | 75.83 | B | C |
| ATOM | 2947 | O | LEU | B | 495 | 18.795 | 28.496 | 3.068 | 1.00 | 75.38 | B | O |
| ATOM | 2948 | CB | LEU | B | 495 | 21.209 | 26.490 | 3.464 | 1.00 | 76.44 | B | C |
| ATOM | 2949 | CG | LEU | B | 495 | 21.895 | 25.130 | 3.274 | 1.00 | 76.72 | B | C |
| ATOM | 2950 | CD1 | LEU | B | 495 | 22.986 | 25.182 | 2.210 | 1.00 | 76.42 | B | C |
| ATOM | 2951 | CD2 | LEU | B | 495 | 22.477 | 24.712 | 4.621 | 1.00 | 77.12 | B | C |
| ATOM | 2952 | N | THR | B | 496 | 18.356 | 26.703 | 1.752 | 1.00 | 75.42 | B | N |
| ATOM | 2953 | CA | THR | B | 496 | 16.907 | 26.876 | 1.795 | 1.00 | 75.20 | B | C |
| ATOM | 2954 | C | THR | B | 496 | 16.372 | 26.536 | 3.180 | 1.00 | 74.92 | B | C |
| ATOM | 2955 | O | THR | B | 496 | 16.950 | 25.704 | 3.879 | 1.00 | 75.04 | B | O |
| ATOM | 2956 | CB | THR | B | 496 | 16.200 | 25.980 | 0.740 | 1.00 | 75.13 | B | C |
| ATOM | 2957 | OG1 | THR | B | 496 | 16.077 | 24.639 | 1.231 | 1.00 | 75.21 | B | O |
| ATOM | 2958 | CG2 | THR | B | 496 | 17.005 | 25.950 | −0.543 | 1.00 | 75.16 | B | C |
| ATOM | 2959 | N | LEU | B | 497 | 15.278 | 27.185 | 3.579 | 1.00 | 74.43 | B | N |
| ATOM | 2960 | CA | LEU | B | 497 | 14.688 | 26.921 | 4.887 | 1.00 | 73.73 | B | C |
| ATOM | 2961 | C | LEU | B | 497 | 14.557 | 25.425 | 5.088 | 1.00 | 72.97 | B | C |
| ATOM | 2962 | O | LEU | B | 497 | 14.748 | 24.931 | 6.192 | 1.00 | 73.25 | B | O |
| ATOM | 2963 | CB | LEU | B | 497 | 13.313 | 27.580 | 5.020 | 1.00 | 73.93 | B | C |
| ATOM | 2964 | CG | LEU | B | 497 | 13.315 | 29.097 | 5.232 | 1.00 | 74.49 | B | C |
| ATOM | 2965 | CD1 | LEU | B | 497 | 11.881 | 29.610 | 5.237 | 1.00 | 74.91 | B | C |
| ATOM | 2966 | CD2 | LEU | B | 497 | 14.014 | 29.444 | 6.543 | 1.00 | 74.46 | B | C |
| ATOM | 2967 | N | GLN | B | 498 | 14.242 | 24.702 | 4.018 | 1.00 | 72.14 | B | N |
| ATOM | 2968 | CA | GLN | B | 498 | 14.108 | 23.253 | 4.112 | 1.00 | 71.35 | B | C |
| ATOM | 2969 | C | GLN | B | 498 | 15.485 | 22.606 | 4.259 | 1.00 | 70.60 | B | C |
| ATOM | 2970 | O | GLN | B | 498 | 15.616 | 21.491 | 4.772 | 1.00 | 70.70 | B | O |
| ATOM | 2971 | CB | GLN | B | 498 | 13.417 | 22.678 | 2.878 | 1.00 | 71.46 | B | C |
| ATOM | 2972 | CG | GLN | B | 498 | 13.149 | 21.184 | 3.004 | 1.00 | 71.90 | B | C |
| ATOM | 2973 | CD | GLN | B | 498 | 12.992 | 20.501 | 1.664 | 1.00 | 72.38 | B | C |
| ATOM | 2974 | OE1 | GLN | B | 498 | 13.939 | 20.431 | 0.877 | 1.00 | 72.48 | B | O |
| ATOM | 2975 | NE2 | GLN | B | 498 | 11.793 | 19.994 | 1.393 | 1.00 | 72.10 | B | N |
| ATOM | 2976 | N | GLN | B | 499 | 16.509 | 23.302 | 3.786 | 1.00 | 69.54 | B | N |
| ATOM | 2977 | CA | GLN | B | 499 | 17.871 | 22.801 | 3.890 | 1.00 | 68.33 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 2978 | C | GLN | B | 499 | 18.429 | 23.253 | 5.228 | 1.00 | 67.24 | B | C |
| ATOM | 2979 | O | GLN | B | 499 | 19.218 | 22.548 | 5.850 | 1.00 | 66.78 | B | O |
| ATOM | 2980 | CB | GLN | B | 499 | 18.731 | 23.352 | 2.763 | 1.00 | 68.71 | B | C |
| ATOM | 2981 | CG | GLN | B | 499 | 18.270 | 22.939 | 1.390 | 1.00 | 69.04 | B | C |
| ATOM | 2982 | CD | GLN | B | 499 | 19.176 | 23.477 | 0.322 | 1.00 | 68.97 | B | C |
| ATOM | 2983 | OE1 | GLN | B | 499 | 19.458 | 24.676 | 0.285 | 1.00 | 68.62 | B | O |
| ATOM | 2984 | NE2 | GLN | B | 499 | 19.650 | 22.594 | −0.556 | 1.00 | 69.24 | B | N |
| ATOM | 2985 | N | GLN | B | 500 | 18.020 | 24.441 | 5.663 | 1.00 | 65.96 | B | N |
| ATOM | 2986 | CA | GLN | B | 500 | 18.467 | 24.946 | 6.946 | 1.00 | 64.66 | B | C |
| ATOM | 2987 | C | GLN | B | 500 | 17.930 | 23.983 | 8.000 | 1.00 | 63.75 | B | C |
| ATOM | 2988 | O | GLN | B | 500 | 18.645 | 23.082 | 8.431 | 1.00 | 64.02 | B | O |
| ATOM | 2989 | CB | GLN | B | 500 | 17.938 | 26.363 | 7.194 | 1.00 | 64.47 | B | C |
| ATOM | 2990 | CG | GLN | B | 500 | 18.295 | 27.347 | 6.085 | 1.00 | 64.65 | B | C |
| ATOM | 2991 | CD | GLN | B | 500 | 18.014 | 28.799 | 6.451 | 1.00 | 64.45 | B | C |
| ATOM | 2992 | OE1 | GLN | B | 500 | 18.054 | 29.684 | 5.596 | 1.00 | 64.09 | B | O |
| ATOM | 2993 | NE2 | GLN | B | 500 | 17.739 | 29.048 | 7.727 | 1.00 | 63.73 | B | N |
| ATOM | 2994 | N | HIS | B | 501 | 16.660 | 24.133 | 8.367 | 1.00 | 62.50 | B | N |
| ATOM | 2995 | CA | HIS | B | 501 | 16.061 | 23.277 | 9.387 | 1.00 | 61.24 | B | C |
| ATOM | 2996 | C | HIS | B | 501 | 16.320 | 21.771 | 9.263 | 1.00 | 59.77 | B | C |
| ATOM | 2997 | O | HIS | B | 501 | 16.261 | 21.062 | 10.263 | 1.00 | 59.90 | B | O |
| ATOM | 2998 | CB | HIS | B | 501 | 14.543 | 23.577 | 9.529 | 1.00 | 61.87 | B | C |
| ATOM | 2999 | CG | HIS | B | 501 | 13.656 | 22.925 | 8.501 | 1.00 | 62.65 | B | C |
| ATOM | 3000 | ND1 | HIS | B | 501 | 12.375 | 23.375 | 8.248 | 1.00 | 63.15 | B | N |
| ATOM | 3001 | CD2 | HIS | B | 501 | 13.825 | 21.829 | 7.720 | 1.00 | 62.87 | B | C |
| ATOM | 3002 | CE1 | HIS | B | 501 | 11.795 | 22.587 | 7.359 | 1.00 | 62.78 | B | C |
| ATOM | 3003 | NE2 | HIS | B | 501 | 12.653 | 21.640 | 7.023 | 1.00 | 62.94 | B | N |
| ATOM | 3004 | N | GLN | B | 502 | 16.635 | 21.286 | 8.064 | 1.00 | 58.33 | B | N |
| ATOM | 3005 | CA | GLN | B | 502 | 16.887 | 19.855 | 7.863 | 1.00 | 57.44 | B | C |
| ATOM | 3006 | C | GLN | B | 502 | 18.303 | 19.479 | 8.268 | 1.00 | 56.28 | B | C |
| ATOM | 3007 | O | GLN | B | 502 | 18.546 | 18.377 | 8.777 | 1.00 | 56.10 | B | O |
| ATOM | 3008 | CB | GLN | B | 502 | 16.671 | 19.483 | 6.398 | 1.00 | 58.57 | B | C |
| ATOM | 3009 | CG | GLN | B | 502 | 16.622 | 17.988 | 6.105 | 1.00 | 60.12 | B | C |
| ATOM | 3010 | CD | GLN | B | 502 | 16.307 | 17.722 | 4.643 | 1.00 | 61.14 | B | C |
| ATOM | 3011 | OE1 | GLN | B | 502 | 15.465 | 18.402 | 4.051 | 1.00 | 62.25 | B | O |
| ATOM | 3012 | NE2 | GLN | B | 502 | 16.974 | 16.732 | 4.056 | 1.00 | 60.68 | B | N |
| ATOM | 3013 | N | ARG | B | 503 | 19.228 | 20.409 | 8.017 | 1.00 | 54.79 | B | N |
| ATOM | 3014 | CA | ARG | B | 503 | 20.646 | 20.252 | 8.335 | 1.00 | 52.43 | B | C |
| ATOM | 3015 | C | ARG | B | 503 | 20.780 | 20.318 | 9.851 | 1.00 | 51.45 | B | C |
| ATOM | 3016 | O | ARG | B | 503 | 21.349 | 19.411 | 10.470 | 1.00 | 51.52 | B | O |
| ATOM | 3017 | CB | ARG | B | 503 | 21.464 | 21.377 | 7.671 | 1.00 | 51.80 | B | C |
| ATOM | 3018 | CG | ARG | B | 503 | 22.981 | 21.271 | 7.857 | 1.00 | 51.18 | B | C |
| ATOM | 3019 | CD | ARG | B | 503 | 23.760 | 22.354 | 7.094 | 1.00 | 50.21 | B | C |
| ATOM | 3020 | NE | ARG | B | 503 | 25.183 | 22.403 | 7.457 | 1.00 | 48.40 | B | N |
| ATOM | 3021 | CZ | ARG | B | 503 | 26.103 | 21.501 | 7.108 | 1.00 | 47.30 | B | C |
| ATOM | 3022 | NH1 | ARG | B | 503 | 25.777 | 20.451 | 6.361 | 1.00 | 46.35 | B | N |
| ATOM | 3023 | NH2 | ARG | B | 503 | 27.353 | 21.634 | 7.546 | 1.00 | 46.34 | B | N |
| ATOM | 3024 | N | LEU | B | 504 | 20.237 | 21.386 | 10.435 | 1.00 | 49.52 | B | N |
| ATOM | 3025 | CA | LEU | B | 504 | 20.256 | 21.601 | 11.875 | 1.00 | 48.70 | B | C |
| ATOM | 3026 | C | LEU | B | 504 | 19.937 | 20.307 | 12.630 | 1.00 | 49.27 | B | C |
| ATOM | 3027 | O | LEU | B | 504 | 20.597 | 19.961 | 13.608 | 1.00 | 49.95 | B | O |
| ATOM | 3028 | CB | LEU | B | 504 | 19.240 | 22.679 | 12.250 | 1.00 | 47.85 | B | C |
| ATOM | 3029 | CG | LEU | B | 504 | 18.662 | 22.652 | 13.667 | 1.00 | 47.59 | B | C |
| ATOM | 3030 | CD1 | LEU | B | 504 | 19.789 | 22.715 | 14.660 | 1.00 | 47.86 | B | C |
| ATOM | 3031 | CD2 | LEU | B | 504 | 17.722 | 23.820 | 13.882 | 1.00 | 47.23 | B | C |
| ATOM | 3032 | N | ALA | B | 505 | 18.921 | 19.595 | 12.162 | 1.00 | 49.11 | B | N |
| ATOM | 3033 | CA | ALA | B | 505 | 18.509 | 18.349 | 12.775 | 1.00 | 48.07 | B | C |
| ATOM | 3034 | C | ALA | B | 505 | 19.516 | 17.226 | 12.557 | 1.00 | 47.59 | B | C |
| ATOM | 3035 | O | ALA | B | 505 | 19.801 | 16.471 | 13.478 | 1.00 | 47.41 | B | O |
| ATOM | 3036 | CB | ALA | B | 505 | 17.146 | 17.938 | 12.229 | 1.00 | 48.47 | B | C |
| ATOM | 3037 | N | GLN | B | 506 | 20.051 | 17.098 | 11.349 | 1.00 | 47.60 | B | N |
| ATOM | 3038 | CA | GLN | B | 506 | 21.015 | 16.023 | 11.080 | 1.00 | 48.38 | B | C |
| ATOM | 3039 | C | GLN | B | 506 | 22.214 | 16.135 | 12.010 | 1.00 | 47.58 | B | C |
| ATOM | 3040 | O | GLN | B | 506 | 22.906 | 15.144 | 12.269 | 1.00 | 46.95 | B | O |
| ATOM | 3041 | CB | GLN | B | 506 | 21.534 | 16.091 | 9.646 | 1.00 | 49.71 | B | C |
| ATOM | 3042 | CG | GLN | B | 506 | 20.549 | 15.742 | 8.559 | 1.00 | 51.75 | B | C |
| ATOM | 3043 | CD | GLN | B | 506 | 20.931 | 16.405 | 7.244 | 1.00 | 53.17 | B | C |
| ATOM | 3044 | OE1 | GLN | B | 506 | 20.741 | 17.614 | 7.084 | 1.00 | 53.75 | B | O |
| ATOM | 3045 | NE2 | GLN | B | 506 | 21.491 | 15.629 | 6.306 | 1.00 | 52.32 | B | N |
| ATOM | 3046 | N | LEU | B | 507 | 22.465 | 17.362 | 12.474 | 1.00 | 46.77 | B | N |
| ATOM | 3047 | CA | LEU | B | 507 | 23.579 | 17.646 | 13.372 | 1.00 | 45.00 | B | C |
| ATOM | 3048 | C | LEU | B | 507 | 23.207 | 17.293 | 14.791 | 1.00 | 43.98 | B | C |
| ATOM | 3049 | O | LEU | B | 507 | 23.938 | 16.562 | 15.459 | 1.00 | 44.03 | B | O |
| ATOM | 3050 | CB | LEU | B | 507 | 23.960 | 19.130 | 13.327 | 1.00 | 44.50 | B | C |
| ATOM | 3051 | CG | LEU | B | 507 | 24.679 | 19.704 | 12.104 | 1.00 | 43.75 | B | C |
| ATOM | 3052 | CD1 | LEU | B | 507 | 24.959 | 21.187 | 12.338 | 1.00 | 43.01 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3053 | CD2 | LEU | B | 507 | 25.964 | 18.933 | 11.848 | 1.00 | 42.38 B | | C |
| ATOM | 3054 | N | LEU | B | 508 | 22.070 | 17.828 | 15.236 | 1.00 | 42.39 B | | N |
| ATOM | 3055 | CA | LEU | B | 508 | 21.568 | 17.609 | 16.587 | 1.00 | 41.35 B | | C |
| ATOM | 3056 | C | LEU | B | 508 | 21.242 | 16.156 | 16.917 | 1.00 | 40.60 B | | C |
| ATOM | 3057 | O | LEU | B | 508 | 21.081 | 15.807 | 18.088 | 1.00 | 40.79 B | | O |
| ATOM | 3058 | CB | LEU | B | 508 | 20.337 | 18.477 | 16.842 | 1.00 | 40.63 B | | C |
| ATOM | 3059 | CG | LEU | B | 508 | 20.548 | 19.968 | 16.599 | 1.00 | 40.72 B | | C |
| ATOM | 3060 | CD1 | LEU | B | 508 | 19.499 | 20.768 | 17.378 | 1.00 | 39.59 B | | C |
| ATOM | 3061 | CD2 | LEU | B | 508 | 21.967 | 20.356 | 17.029 | 1.00 | 40.14 B | | C |
| ATOM | 3062 | N | LEU | B | 509 | 21.150 | 15.311 | 15.895 | 1.00 | 39.43 B | | N |
| ATOM | 3063 | CA | LEU | B | 509 | 20.868 | 13.897 | 16.119 | 1.00 | 38.27 B | | C |
| ATOM | 3064 | C | LEU | B | 509 | 22.171 | 13.135 | 16.253 | 1.00 | 37.79 B | | C |
| ATOM | 3065 | O | LEU | B | 509 | 22.181 | 11.999 | 16.739 | 1.00 | 38.16 B | | O |
| ATOM | 3066 | CB | LEU | B | 509 | 20.050 | 13.311 | 14.967 | 1.00 | 37.59 B | | C |
| ATOM | 3067 | CG | LEU | B | 509 | 18.639 | 13.861 | 14.773 | 1.00 | 36.81 B | | C |
| ATOM | 3068 | CD1 | LEU | B | 509 | 18.049 | 13.250 | 13.525 | 1.00 | 36.96 B | | C |
| ATOM | 3069 | CD2 | LEU | B | 509 | 17.776 | 13.551 | 15.979 | 1.00 | 36.54 B | | C |
| ATOM | 3070 | N | ILE | B | 510 | 23.263 | 13.757 | 15.805 | 1.00 | 37.14 B | | N |
| ATOM | 3071 | CA | ILE | B | 510 | 24.606 | 13.162 | 15.879 | 1.00 | 36.85 B | | C |
| ATOM | 3072 | C | ILE | B | 510 | 25.107 | 13.257 | 17.336 | 1.00 | 36.25 B | | C |
| ATOM | 3073 | O | ILE | B | 510 | 25.941 | 12.450 | 17.769 | 1.00 | 34.82 B | | O |
| ATOM | 3074 | CB | ILE | B | 510 | 25.614 | 13.904 | 14.909 | 1.00 | 37.69 B | | C |
| ATOM | 3075 | CG1 | ILE | B | 510 | 25.212 | 13.662 | 13.448 | 1.00 | 38.65 B | | C |
| ATOM | 3076 | CG2 | ILE | B | 510 | 27.060 | 13.401 | 15.110 | 1.00 | 37.04 B | | C |
| ATOM | 3077 | CD1 | ILE | B | 510 | 25.216 | 12.191 | 13.047 | 1.00 | 39.57 B | | C |
| ATOM | 3078 | N | LEU | B | 511 | 24.590 | 14.255 | 18.066 | 1.00 | 35.45 B | | N |
| ATOM | 3079 | CA | LEU | B | 511 | 24.931 | 14.481 | 19.469 | 1.00 | 35.41 B | | C |
| ATOM | 3080 | C | LEU | B | 511 | 24.326 | 13.330 | 20.290 | 1.00 | 36.25 B | | C |
| ATOM | 3081 | O | LEU | B | 511 | 24.695 | 13.112 | 21.455 | 1.00 | 36.66 B | | O |
| ATOM | 3082 | CB | LEU | B | 511 | 24.353 | 15.814 | 19.989 | 1.00 | 33.50 B | | C |
| ATOM | 3083 | CG | LEU | B | 511 | 24.706 | 17.208 | 19.439 | 1.00 | 33.45 B | | C |
| ATOM | 3084 | CD1 | LEU | B | 511 | 24.201 | 18.270 | 20.454 | 1.00 | 33.21 B | | C |
| ATOM | 3085 | CD2 | LEU | B | 511 | 26.213 | 17.379 | 19.240 | 1.00 | 31.95 B | | C |
| ATOM | 3086 | N | SER | B | 512 | 23.385 | 12.613 | 19.674 | 1.00 | 35.92 B | | N |
| ATOM | 3087 | CA | SER | B | 512 | 22.725 | 11.482 | 20.304 | 1.00 | 36.00 B | | C |
| ATOM | 3088 | C | SER | B | 512 | 23.666 | 10.294 | 20.240 | 1.00 | 35.68 B | | C |
| ATOM | 3089 | O | SER | B | 512 | 23.743 | 9.484 | 21.166 | 1.00 | 35.82 B | | O |
| ATOM | 3090 | CB | SER | B | 512 | 21.445 | 11.132 | 19.552 | 1.00 | 36.86 B | | C |
| ATOM | 3091 | OG | SER | B | 512 | 20.323 | 11.158 | 20.408 | 1.00 | 38.06 B | | O |
| ATOM | 3092 | N | HIS | B | 513 | 24.379 | 10.196 | 19.132 | 1.00 | 34.78 B | | N |
| ATOM | 3093 | CA | HIS | B | 513 | 25.300 | 9.103 | 18.953 | 1.00 | 35.22 B | | C |
| ATOM | 3094 | C | HIS | B | 513 | 26.594 | 9.398 | 19.676 | 1.00 | 34.97 B | | C |
| ATOM | 3095 | O | HIS | B | 513 | 27.378 | 8.489 | 19.962 | 1.00 | 34.59 B | | O |
| ATOM | 3096 | CB | HIS | B | 513 | 25.575 | 8.882 | 17.478 | 1.00 | 36.04 B | | C |
| ATOM | 3097 | CG | HIS | B | 513 | 26.415 | 7.675 | 17.202 | 1.00 | 39.08 B | | C |
| ATOM | 3098 | ND1 | HIS | B | 513 | 27.796 | 7.701 | 17.241 | 1.00 | 40.64 B | | N |
| ATOM | 3099 | CD2 | HIS | B | 513 | 26.073 | 6.401 | 16.896 | 1.00 | 40.45 B | | C |
| ATOM | 3100 | CE1 | HIS | B | 513 | 28.268 | 6.498 | 16.969 | 1.00 | 40.32 B | | C |
| ATOM | 3101 | NE2 | HIS | B | 513 | 27.244 | 5.690 | 16.756 | 1.00 | 41.38 B | | N |
| ATOM | 3102 | N | ILE | B | 514 | 26.833 | 10.669 | 19.971 | 1.00 | 34.40 B | | N |
| ATOM | 3103 | CA | ILE | B | 514 | 28.064 | 11.004 | 20.651 | 1.00 | 34.32 B | | C |
| ATOM | 3104 | C | ILE | B | 514 | 27.879 | 10.674 | 22.129 | 1.00 | 34.84 B | | C |
| ATOM | 3105 | O | ILE | B | 514 | 28.827 | 10.267 | 22.802 | 1.00 | 34.93 B | | O |
| ATOM | 3106 | CB | ILE | B | 514 | 28.463 | 12.494 | 20.402 | 1.00 | 33.26 B | | C |
| ATOM | 3107 | CG1 | ILE | B | 514 | 29.020 | 12.624 | 18.977 | 1.00 | 32.81 B | | C |
| ATOM | 3108 | CG2 | ILE | B | 514 | 29.517 | 12.957 | 21.410 | 1.00 | 33.31 B | | C |
| ATOM | 3109 | CD1 | ILE | B | 514 | 29.513 | 14.005 | 18.601 | 1.00 | 31.73 B | | C |
| ATOM | 3110 | N | ARG | B | 515 | 26.649 | 10.809 | 22.614 | 1.00 | 35.34 B | | N |
| ATOM | 3111 | CA | ARG | B | 515 | 26.338 | 10.502 | 24.002 | 1.00 | 36.35 B | | C |
| ATOM | 3112 | C | ARG | B | 515 | 26.494 | 9.009 | 24.227 | 1.00 | 37.35 B | | C |
| ATOM | 3113 | O | ARG | B | 515 | 26.936 | 8.561 | 25.293 | 1.00 | 37.57 B | | O |
| ATOM | 3114 | CB | ARG | B | 515 | 24.900 | 10.866 | 24.341 | 1.00 | 35.45 B | | C |
| ATOM | 3115 | CG | ARG | B | 515 | 24.544 | 10.493 | 25.778 | 1.00 | 34.80 B | | C |
| ATOM | 3116 | CD | ARG | B | 515 | 25.143 | 11.496 | 26.727 | 1.00 | 33.13 B | | C |
| ATOM | 3117 | NE | ARG | B | 515 | 24.682 | 12.819 | 26.342 | 1.00 | 33.10 B | | N |
| ATOM | 3118 | CZ | ARG | B | 515 | 23.822 | 13.548 | 27.036 | 1.00 | 32.38 B | | C |
| ATOM | 3119 | NH1 | ARG | B | 515 | 23.325 | 13.091 | 28.176 | 1.00 | 32.70 B | | N |
| ATOM | 3120 | NH2 | ARG | B | 515 | 23.447 | 14.732 | 26.578 | 1.00 | 32.33 B | | N |
| ATOM | 3121 | N | HIS | B | 516 | 26.094 | 8.241 | 23.223 | 1.00 | 38.26 B | | N |
| ATOM | 3122 | CA | HIS | B | 516 | 26.196 | 6.796 | 23.300 | 1.00 | 39.54 B | | C |
| ATOM | 3123 | C | HIS | B | 516 | 27.676 | 6.472 | 23.462 | 1.00 | 39.65 B | | C |
| ATOM | 3124 | O | HIS | B | 516 | 28.064 | 5.699 | 24.340 | 1.00 | 39.34 B | | O |
| ATOM | 3125 | CB | HIS | B | 516 | 25.633 | 6.163 | 22.018 | 1.00 | 39.88 B | | C |
| ATOM | 3126 | CG | HIS | B | 516 | 25.511 | 4.674 | 22.076 | 1.00 | 40.26 B | | C |
| ATOM | 3127 | ND1 | HIS | B | 516 | 24.744 | 4.025 | 23.020 | 1.00 | 40.62 B | | N |

TABLE 10-continued

Structure coordinates for ERalpha-LBD/Compound 2 complex

| | # | Name | Res. | Chain | Res # | X | Y | Z | occ | B | SegID |
|---|---|---|---|---|---|---|---|---|---|---|---|
| ATOM | 3128 | CD2 | HIS | B | 516 | 26.047 | 3.705 | 21.298 | 1.00 | 40.83 B | C |
| ATOM | 3129 | CE1 | HIS | B | 516 | 24.814 | 2.721 | 22.820 | 1.00 | 41.21 B | C |
| ATOM | 3130 | NE2 | HIS | B | 516 | 25.599 | 2.500 | 21.781 | 1.00 | 41.20 B | N |
| ATOM | 3131 | N | MET | B | 517 | 28.498 | 7.098 | 22.622 | 1.00 | 40.55 B | N |
| ATOM | 3132 | CA | MET | B | 517 | 29.936 | 6.876 | 22.652 | 1.00 | 41.48 B | C |
| ATOM | 3133 | C | MET | B | 517 | 30.494 | 7.165 | 24.054 | 1.00 | 41.38 B | C |
| ATOM | 3134 | O | MET | B | 517 | 31.196 | 6.330 | 24.645 | 1.00 | 41.49 B | O |
| ATOM | 3135 | CB | MET | B | 517 | 30.628 | 7.734 | 21.576 | 1.00 | 41.94 B | C |
| ATOM | 3136 | CG | MET | B | 517 | 30.629 | 7.088 | 20.183 | 1.00 | 43.78 B | C |
| ATOM | 3137 | SD | MET | B | 517 | 31.478 | 8.054 | 18.883 | 1.00 | 45.07 B | S |
| ATOM | 3138 | CE | MET | B | 517 | 30.491 | 9.503 | 18.918 | 1.00 | 44.97 B | C |
| ATOM | 3139 | N | SER | B | 518 | 30.150 | 8.337 | 24.581 | 1.00 | 40.60 B | N |
| ATOM | 3140 | CA | SER | B | 518 | 30.576 | 8.764 | 25.904 | 1.00 | 40.56 B | C |
| ATOM | 3141 | C | SER | B | 518 | 30.131 | 7.815 | 27.028 | 1.00 | 40.65 B | C |
| ATOM | 3142 | O | SER | B | 518 | 30.850 | 7.645 | 28.012 | 1.00 | 39.28 B | O |
| ATOM | 3143 | CB | SER | B | 518 | 30.041 | 10.177 | 26.187 | 1.00 | 40.60 B | C |
| ATOM | 3144 | OG | SER | B | 518 | 30.303 | 10.573 | 27.526 | 1.00 | 40.82 B | O |
| ATOM | 3145 | N | ASN | B | 519 | 28.945 | 7.216 | 26.884 | 1.00 | 41.58 B | N |
| ATOM | 3146 | CA | ASN | B | 519 | 28.422 | 6.297 | 27.895 | 1.00 | 42.44 B | C |
| ATOM | 3147 | C | ASN | B | 519 | 29.104 | 4.945 | 27.808 | 1.00 | 43.72 B | C |
| ATOM | 3148 | O | ASN | B | 519 | 29.426 | 4.352 | 28.833 | 1.00 | 42.91 B | O |
| ATOM | 3149 | CB | ASN | B | 519 | 26.899 | 6.129 | 27.767 | 1.00 | 41.72 B | C |
| ATOM | 3150 | CG | ASN | B | 519 | 26.121 | 7.336 | 28.306 | 1.00 | 40.53 B | C |
| ATOM | 3151 | OD1 | ASN | B | 519 | 26.563 | 8.009 | 29.231 | 1.00 | 40.32 B | O |
| ATOM | 3152 | ND2 | ASN | B | 519 | 24.951 | 7.590 | 27.741 | 1.00 | 40.05 B | N |
| ATOM | 3153 | N | LYS | B | 520 | 29.328 | 4.461 | 26.589 | 1.00 | 46.32 B | N |
| ATOM | 3154 | CA | LYS | B | 520 | 30.013 | 3.183 | 26.398 | 1.00 | 49.41 B | C |
| ATOM | 3155 | C | LYS | B | 520 | 31.489 | 3.436 | 26.704 | 1.00 | 51.70 B | C |
| ATOM | 3156 | O | LYS | B | 520 | 32.254 | 2.504 | 26.993 | 1.00 | 52.18 B | O |
| ATOM | 3157 | CB | LYS | B | 520 | 29.883 | 2.686 | 24.951 | 1.00 | 49.32 B | C |
| ATOM | 3158 | CG | LYS | B | 520 | 28.454 | 2.549 | 24.446 | 1.00 | 49.62 B | C |
| ATOM | 3159 | CD | LYS | B | 520 | 28.062 | 1.096 | 24.167 | 1.00 | 50.01 B | C |
| ATOM | 3160 | CE | LYS | B | 520 | 27.831 | 0.298 | 25.453 | 1.00 | 50.16 B | C |
| ATOM | 3161 | NZ | LYS | B | 520 | 26.558 | −0.479 | 25.402 | 1.00 | 49.95 B | N |
| ATOM | 3162 | N | GLY | B | 521 | 31.881 | 4.706 | 26.628 | 1.00 | 53.71 B | N |
| ATOM | 3163 | CA | GLY | B | 521 | 33.253 | 5.083 | 26.910 | 1.00 | 56.19 B | C |
| ATOM | 3164 | C | GLY | B | 521 | 33.508 | 5.086 | 28.404 | 1.00 | 58.00 B | C |
| ATOM | 3165 | O | GLY | B | 521 | 34.447 | 4.452 | 28.876 | 1.00 | 57.59 B | O |
| ATOM | 3166 | N | MET | B | 522 | 32.675 | 5.810 | 29.148 | 1.00 | 60.42 B | N |
| ATOM | 3167 | CA | MET | B | 522 | 32.814 | 5.879 | 30.598 | 1.00 | 62.97 B | C |
| ATOM | 3168 | C | MET | B | 522 | 32.239 | 4.654 | 31.279 | 1.00 | 64.95 B | C |
| ATOM | 3169 | O | MET | B | 522 | 31.642 | 4.736 | 32.360 | 1.00 | 64.81 B | O |
| ATOM | 3170 | CB | MET | B | 522 | 32.157 | 7.143 | 31.149 | 1.00 | 62.72 B | C |
| ATOM | 3171 | CG | MET | B | 522 | 33.089 | 8.323 | 31.188 | 1.00 | 62.95 B | C |
| ATOM | 3172 | SD | MET | B | 522 | 32.389 | 9.626 | 32.174 | 1.00 | 64.96 B | S |
| ATOM | 3173 | CE | MET | B | 522 | 31.026 | 10.171 | 31.117 | 1.00 | 64.27 B | C |
| ATOM | 3174 | N | GLU | B | 523 | 32.408 | 3.527 | 30.604 | 1.00 | 67.73 B | N |
| ATOM | 3175 | CA | GLU | B | 523 | 32.294 | 2.105 | 30.910 | 1.00 | 70.41 B | C |
| ATOM | 3176 | C | GLU | B | 523 | 33.628 | 1.389 | 30.714 | 1.00 | 72.28 B | C |
| ATOM | 3177 | O | GLU | B | 523 | 34.054 | 0.572 | 31.519 | 1.00 | 72.32 B | O |
| ATOM | 3178 | CB | GLU | B | 523 | 31.243 | 1.499 | 29.980 | 1.00 | 70.61 B | C |
| ATOM | 3179 | CG | GLU | B | 523 | 30.299 | 0.547 | 30.716 | 1.00 | 71.89 B | C |
| ATOM | 3180 | CD | GLU | B | 523 | 29.395 | −0.130 | 29.714 | 1.00 | 72.79 B | C |
| ATOM | 3181 | OE1 | GLU | B | 523 | 28.526 | 0.533 | 29.171 | 1.00 | 73.01 B | O |
| ATOM | 3182 | OE2 | GLU | B | 523 | 29.577 | −1.320 | 29.472 | 1.00 | 73.48 B | O |
| ATOM | 3183 | N | HIS | B | 524 | 34.282 | 1.688 | 29.576 | 1.00 | 74.65 B | N |
| ATOM | 3184 | CA | HIS | B | 524 | 35.601 | 1.117 | 29.340 | 1.00 | 76.85 B | C |
| ATOM | 3185 | C | HIS | B | 524 | 36.516 | 1.393 | 30.535 | 1.00 | 78.11 B | C |
| ATOM | 3186 | O | HIS | B | 524 | 37.185 | 0.520 | 31.068 | 1.00 | 78.11 B | O |
| ATOM | 3187 | CB | HIS | B | 524 | 36.172 | 1.798 | 28.090 | 1.00 | 77.60 B | C |
| ATOM | 3188 | CG | HIS | B | 524 | 37.102 | 0.866 | 27.347 | 1.00 | 78.70 B | C |
| ATOM | 3189 | ND1 | HIS | B | 524 | 36.745 | −0.383 | 26.954 | 1.00 | 79.31 B | N |
| ATOM | 3190 | CD2 | HIS | B | 524 | 38.348 | 1.166 | 26.782 | 1.00 | 78.77 B | C |
| ATOM | 3191 | CE1 | HIS | B | 524 | 37.744 | −0.816 | 26.161 | 1.00 | 79.46 B | C |
| ATOM | 3192 | NE2 | HIS | B | 524 | 38.716 | 0.092 | 26.039 | 1.00 | 79.00 B | N |
| ATOM | 3193 | N | LEU | B | 525 | 36.542 | 2.676 | 30.933 | 1.00 | 79.72 B | N |
| ATOM | 3194 | CA | LEU | B | 525 | 37.426 | 3.097 | 32.014 | 1.00 | 81.66 B | C |
| ATOM | 3195 | C | LEU | B | 525 | 37.099 | 2.445 | 33.363 | 1.00 | 83.17 B | C |
| ATOM | 3196 | O | LEU | B | 525 | 37.969 | 1.998 | 34.100 | 1.00 | 83.68 B | O |
| ATOM | 3197 | CB | LEU | B | 525 | 37.344 | 4.618 | 32.113 | 1.00 | 81.54 B | C |
| ATOM | 3198 | CG | LEU | B | 525 | 37.482 | 5.280 | 30.739 | 1.00 | 81.44 B | C |
| ATOM | 3199 | CD1 | LEU | B | 525 | 37.503 | 6.804 | 30.816 | 1.00 | 81.42 B | C |
| ATOM | 3200 | CD2 | LEU | B | 525 | 38.765 | 4.869 | 30.013 | 1.00 | 81.14 B | C |
| ATOM | 3201 | N | TYR | B | 526 | 35.798 | 2.444 | 33.707 | 1.00 | 84.60 B | N |
| ATOM | 3202 | CA | TYR | B | 526 | 35.404 | 1.965 | 35.031 | 1.00 | 85.83 B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3203 | C | TYR | B | 526 | 35.898 | 0.543 | 35.295 | 1.00 | 86.14 | B | C |
| ATOM | 3204 | O | TYR | B | 526 | 36.579 | 0.266 | 36.273 | 1.00 | 86.73 | B | O |
| ATOM | 3205 | CB | TYR | B | 526 | 33.879 | 2.090 | 35.203 | 1.00 | 86.70 | B | C |
| ATOM | 3206 | CG | TYR | B | 526 | 33.887 | 3.518 | 35.619 | 1.00 | 88.22 | B | C |
| ATOM | 3207 | CD1 | TYR | B | 526 | 35.097 | 4.024 | 35.142 | 1.00 | 89.23 | B | C |
| ATOM | 3208 | CD2 | TYR | B | 526 | 32.901 | 4.395 | 36.062 | 1.00 | 88.97 | B | C |
| ATOM | 3209 | CE1 | TYR | B | 526 | 35.316 | 5.394 | 35.110 | 1.00 | 89.85 | B | C |
| ATOM | 3210 | CE2 | TYR | B | 526 | 33.123 | 5.764 | 36.040 | 1.00 | 89.77 | B | C |
| ATOM | 3211 | CZ | TYR | B | 526 | 34.334 | 6.261 | 35.552 | 1.00 | 90.00 | B | C |
| ATOM | 3212 | OH | TYR | B | 526 | 34.548 | 7.626 | 35.532 | 1.00 | 90.05 | B | O |
| ATOM | 3213 | N | PRO | B | 535 | 37.600 | 12.482 | 41.665 | 1.00 | 78.46 | B | N |
| ATOM | 3214 | CA | PRO | B | 535 | 38.967 | 12.956 | 41.402 | 1.00 | 78.01 | B | C |
| ATOM | 3215 | C | PRO | B | 535 | 38.973 | 14.110 | 40.402 | 1.00 | 77.43 | B | C |
| ATOM | 3216 | O | PRO | B | 535 | 39.847 | 14.980 | 40.428 | 1.00 | 77.37 | B | O |
| ATOM | 3217 | CB | PRO | B | 535 | 39.659 | 11.725 | 40.813 | 1.00 | 78.43 | B | C |
| ATOM | 3218 | CG | PRO | B | 535 | 38.891 | 10.571 | 41.388 | 1.00 | 78.90 | B | C |
| ATOM | 3219 | CD | PRO | B | 535 | 37.460 | 11.055 | 41.319 | 1.00 | 78.59 | B | C |
| ATOM | 3220 | N | LEU | B | 536 | 37.978 | 14.101 | 39.524 | 1.00 | 76.54 | B | N |
| ATOM | 3221 | CA | LEU | B | 536 | 37.864 | 15.098 | 38.480 | 1.00 | 75.75 | B | C |
| ATOM | 3222 | C | LEU | B | 536 | 37.289 | 16.424 | 38.961 | 1.00 | 75.28 | B | C |
| ATOM | 3223 | O | LEU | B | 536 | 37.495 | 17.457 | 38.331 | 1.00 | 74.71 | B | O |
| ATOM | 3224 | CB | LEU | B | 536 | 37.010 | 14.529 | 37.347 | 1.00 | 75.75 | B | C |
| ATOM | 3225 | CG | LEU | B | 536 | 37.485 | 14.804 | 35.917 | 1.00 | 75.93 | B | C |
| ATOM | 3226 | CD1 | LEU | B | 536 | 37.528 | 13.488 | 35.136 | 1.00 | 75.87 | B | C |
| ATOM | 3227 | CD2 | LEU | B | 536 | 36.566 | 15.825 | 35.243 | 1.00 | 74.93 | B | C |
| ATOM | 3228 | N | TYR | B | 537 | 36.572 | 16.397 | 40.078 | 1.00 | 75.23 | B | N |
| ATOM | 3229 | CA | TYR | B | 537 | 35.980 | 17.619 | 40.614 | 1.00 | 75.14 | B | C |
| ATOM | 3230 | C | TYR | B | 537 | 37.018 | 18.501 | 41.309 | 1.00 | 74.55 | B | C |
| ATOM | 3231 | O | TYR | B | 537 | 36.748 | 19.670 | 41.586 | 1.00 | 74.34 | B | O |
| ATOM | 3232 | CB | TYR | B | 537 | 34.842 | 17.277 | 41.581 | 1.00 | 75.83 | B | C |
| ATOM | 3233 | CG | TYR | B | 537 | 35.258 | 16.369 | 42.714 | 1.00 | 76.57 | B | C |
| ATOM | 3234 | CD1 | TYR | B | 537 | 35.681 | 16.892 | 43.941 | 1.00 | 76.56 | B | C |
| ATOM | 3235 | CD2 | TYR | B | 537 | 35.250 | 14.980 | 42.553 | 1.00 | 76.93 | B | C |
| ATOM | 3236 | CE1 | TYR | B | 537 | 36.085 | 16.050 | 44.984 | 1.00 | 76.80 | B | C |
| ATOM | 3237 | CE2 | TYR | B | 537 | 35.654 | 14.130 | 43.586 | 1.00 | 77.00 | B | C |
| ATOM | 3238 | CZ | TYR | B | 537 | 36.071 | 14.669 | 44.796 | 1.00 | 77.10 | B | C |
| ATOM | 3239 | OH | TYR | B | 537 | 36.482 | 13.822 | 45.804 | 1.00 | 77.67 | B | O |
| ATOM | 3240 | N | ASP | B | 538 | 38.198 | 17.940 | 41.583 | 1.00 | 73.77 | B | N |
| ATOM | 3241 | CA | ASP | B | 538 | 39.286 | 18.683 | 42.230 | 1.00 | 73.14 | B | C |
| ATOM | 3242 | C | ASP | B | 538 | 39.976 | 19.592 | 41.204 | 1.00 | 72.24 | B | C |
| ATOM | 3243 | O | ASP | B | 538 | 40.239 | 20.771 | 41.472 | 1.00 | 71.71 | B | O |
| ATOM | 3244 | CB | ASP | B | 538 | 40.316 | 17.715 | 42.853 | 1.00 | 73.88 | B | C |
| ATOM | 3245 | CG | ASP | B | 538 | 40.030 | 17.402 | 44.338 | 1.00 | 74.54 | B | C |
| ATOM | 3246 | OD1 | ASP | B | 538 | 40.094 | 18.334 | 45.171 | 1.00 | 74.83 | B | O |
| ATOM | 3247 | OD2 | ASP | B | 538 | 39.749 | 16.227 | 44.680 | 1.00 | 74.80 | B | O |
| ATOM | 3248 | N | LEU | B | 539 | 40.275 | 19.040 | 40.029 | 1.00 | 71.36 | B | N |
| ATOM | 3249 | CA | LEU | B | 539 | 40.905 | 19.822 | 38.970 | 1.00 | 70.48 | B | C |
| ATOM | 3250 | C | LEU | B | 539 | 39.898 | 20.874 | 38.475 | 1.00 | 70.50 | B | C |
| ATOM | 3251 | O | LEU | B | 539 | 40.212 | 22.065 | 38.376 | 1.00 | 69.85 | B | O |
| ATOM | 3252 | CB | LEU | B | 539 | 41.334 | 18.899 | 37.823 | 1.00 | 69.36 | B | C |
| ATOM | 3253 | CG | LEU | B | 539 | 41.709 | 19.512 | 36.465 | 1.00 | 68.18 | B | C |
| ATOM | 3254 | CD1 | LEU | B | 539 | 42.800 | 20.544 | 36.631 | 1.00 | 67.52 | B | C |
| ATOM | 3255 | CD2 | LEU | B | 539 | 42.161 | 18.408 | 35.520 | 1.00 | 67.56 | B | C |
| ATOM | 3256 | N | LEU | B | 540 | 38.681 | 20.421 | 38.189 | 1.00 | 70.78 | B | N |
| ATOM | 3257 | CA | LEU | B | 540 | 37.618 | 21.298 | 37.711 | 1.00 | 71.37 | B | C |
| ATOM | 3258 | C | LEU | B | 540 | 37.467 | 22.464 | 38.676 | 1.00 | 71.92 | B | C |
| ATOM | 3259 | O | LEU | B | 540 | 37.547 | 23.628 | 38.277 | 1.00 | 71.84 | B | O |
| ATOM | 3260 | CB | LEU | B | 540 | 36.294 | 20.522 | 37.607 | 1.00 | 70.59 | B | C |
| ATOM | 3261 | CG | LEU | B | 540 | 36.272 | 19.359 | 36.599 | 1.00 | 70.29 | B | C |
| ATOM | 3262 | CD1 | LEU | B | 540 | 35.056 | 18.495 | 36.820 | 1.00 | 70.02 | B | C |
| ATOM | 3263 | CD2 | LEU | B | 540 | 36.280 | 19.898 | 35.185 | 1.00 | 70.19 | B | C |
| ATOM | 3264 | N | LEU | B | 541 | 37.269 | 22.129 | 39.949 | 1.00 | 72.86 | B | N |
| ATOM | 3265 | CA | LEU | B | 541 | 37.095 | 23.106 | 41.023 | 1.00 | 73.63 | B | C |
| ATOM | 3266 | C | LEU | B | 541 | 38.150 | 24.207 | 40.993 | 1.00 | 74.21 | B | C |
| ATOM | 3267 | O | LEU | B | 541 | 37.851 | 25.372 | 40.725 | 1.00 | 74.06 | B | O |
| ATOM | 3268 | CB | LEU | B | 541 | 37.163 | 22.392 | 42.373 | 1.00 | 73.34 | B | C |
| ATOM | 3269 | CG | LEU | B | 541 | 35.994 | 22.522 | 43.348 | 1.00 | 73.40 | B | C |
| ATOM | 3270 | CD1 | LEU | B | 541 | 36.124 | 21.440 | 44.421 | 1.00 | 73.10 | B | C |
| ATOM | 3271 | CD2 | LEU | B | 541 | 35.968 | 23.924 | 43.959 | 1.00 | 73.09 | B | C |
| ATOM | 3272 | N | GLU | B | 542 | 39.385 | 23.821 | 41.278 | 1.00 | 75.35 | B | N |
| ATOM | 3273 | CA | GLU | B | 542 | 40.489 | 24.755 | 41.316 | 1.00 | 76.82 | B | C |
| ATOM | 3274 | C | GLU | B | 542 | 40.710 | 25.447 | 39.981 | 1.00 | 77.80 | B | C |
| ATOM | 3275 | O | GLU | B | 542 | 41.236 | 26.562 | 39.940 | 1.00 | 77.95 | B | O |
| ATOM | 3276 | CB | GLU | B | 542 | 41.740 | 24.017 | 41.759 | 1.00 | 77.14 | B | C |
| ATOM | 3277 | CG | GLU | B | 542 | 42.961 | 24.250 | 40.915 | 1.00 | 77.59 | B | C |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3278 | CD | GLU | B | 542 | 43.865 | 23.035 | 40.922 | 1.00 | 78.35 | B | C |
| ATOM | 3279 | OE1 | GLU | B | 542 | 43.442 | 21.991 | 40.372 | 1.00 | 78.10 | B | O |
| ATOM | 3280 | OE2 | GLU | B | 542 | 44.984 | 23.119 | 41.484 | 1.00 | 78.89 | B | O |
| ATOM | 3281 | N | MET | B | 543 | 40.305 | 24.795 | 38.894 | 1.00 | 78.75 | B | N |
| ATOM | 3282 | CA | MET | B | 543 | 40.460 | 25.381 | 37.561 | 1.00 | 79.67 | B | C |
| ATOM | 3283 | C | MET | B | 543 | 39.333 | 26.383 | 37.257 | 1.00 | 80.14 | B | C |
| ATOM | 3284 | O | MET | B | 543 | 39.510 | 27.305 | 36.449 | 1.00 | 79.79 | B | O |
| ATOM | 3285 | CB | MET | B | 543 | 40.493 | 24.276 | 36.494 | 1.00 | 80.16 | B | C |
| ATOM | 3286 | CG | MET | B | 543 | 41.857 | 24.058 | 35.859 | 1.00 | 80.86 | B | C |
| ATOM | 3287 | SD | MET | B | 543 | 42.127 | 25.010 | 34.340 | 1.00 | 82.16 | B | S |
| ATOM | 3288 | CE | MET | B | 543 | 41.923 | 26.703 | 34.908 | 1.00 | 81.80 | B | C |
| ATOM | 3289 | N | LEU | B | 544 | 38.186 | 26.213 | 37.918 | 1.00 | 80.62 | B | N |
| ATOM | 3290 | CA | LEU | B | 544 | 37.039 | 27.100 | 37.711 | 1.00 | 81.03 | B | C |
| ATOM | 3291 | C | LEU | B | 544 | 37.089 | 28.373 | 38.564 | 1.00 | 81.89 | B | C |
| ATOM | 3292 | O | LEU | B | 544 | 36.707 | 29.451 | 38.096 | 1.00 | 81.68 | B | O |
| ATOM | 3293 | CB | LEU | B | 544 | 35.725 | 26.345 | 37.962 | 1.00 | 79.90 | B | C |
| ATOM | 3294 | CG | LEU | B | 544 | 35.396 | 25.237 | 36.958 | 1.00 | 78.86 | B | C |
| ATOM | 3295 | CD1 | LEU | B | 544 | 33.985 | 24.727 | 37.196 | 1.00 | 78.49 | B | C |
| ATOM | 3296 | CD2 | LEU | B | 544 | 35.525 | 25.778 | 35.541 | 1.00 | 78.54 | B | C |
| ATOM | 3297 | N | ASP | B | 545 | 37.555 | 28.261 | 39.808 | 1.00 | 82.95 | B | N |
| ATOM | 3298 | CA | ASP | B | 545 | 37.644 | 29.444 | 40.657 | 1.00 | 83.85 | B | C |
| ATOM | 3299 | C | ASP | B | 545 | 38.753 | 30.349 | 40.114 | 1.00 | 84.37 | B | C |
| ATOM | 3300 | O | ASP | B | 545 | 38.521 | 31.529 | 39.854 | 1.00 | 84.67 | B | O |
| ATOM | 3301 | CB | ASP | B | 545 | 37.933 | 29.070 | 42.111 | 1.00 | 83.84 | B | C |
| ATOM | 3302 | CG | ASP | B | 545 | 37.698 | 30.238 | 43.064 | 1.00 | 84.14 | B | C |
| ATOM | 3303 | OD1 | ASP | B | 545 | 36.588 | 30.818 | 43.023 | 1.00 | 83.88 | B | O |
| ATOM | 3304 | OD2 | ASP | B | 545 | 38.610 | 30.579 | 43.851 | 1.00 | 84.14 | B | O |
| ATOM | 3305 | N | ALA | B | 546 | 39.946 | 29.783 | 39.928 | 1.00 | 84.98 | B | N |
| ATOM | 3306 | CA | ALA | B | 546 | 41.093 | 30.517 | 39.388 | 1.00 | 85.66 | B | C |
| ATOM | 3307 | C | ALA | B | 546 | 40.700 | 31.414 | 38.206 | 1.00 | 86.13 | B | C |
| ATOM | 3308 | O | ALA | B | 546 | 40.738 | 32.662 | 38.357 | 1.00 | 86.27 | B | O |
| ATOM | 3309 | CB | ALA | B | 546 | 42.180 | 29.533 | 38.947 | 1.00 | 85.60 | B | C |
| ATOM | 3310 | OXT | ALA | B | 546 | 40.356 | 30.859 | 37.135 | 1.00 | 86.58 | B | O |
| TER | 3311 | | ALA | B | 546 | | | | | | | |
| ATOM | 3312 | O | HOH | W | 1 | 6.616 | 1.990 | 26.422 | 1.00 | 62.61 | W | O |
| ATOM | 3313 | O | HOH | W | 2 | 39.420 | 16.713 | 21.685 | 1.00 | 35.80 | W | O |
| ATOM | 3314 | O | HOH | W | 3 | −5.821 | 1.620 | 27.591 | 1.00 | 12.60 | W | O |
| ATOM | 3315 | O | HOH | W | 4 | 6.282 | 3.093 | 23.580 | 1.00 | 36.55 | W | O |
| ATOM | 3316 | O | HOH | W | 5 | 1.031 | 0.766 | 28.949 | 1.00 | 28.08 | W | O |
| ATOM | 3317 | O | HOH | W | 6 | −1.993 | −7.318 | 26.765 | 1.00 | 2.00 | W | O |
| ATOM | 3318 | O | HOH | W | 7 | 16.771 | 2.092 | 23.217 | 1.00 | 16.71 | W | O |
| ATOM | 3319 | O | HOH | W | 8 | 17.019 | 2.444 | 15.541 | 1.00 | 43.64 | W | O |
| ATOM | 3320 | O | HOH | W | 9 | 24.336 | 9.006 | 12.863 | 1.00 | 30.12 | W | O |
| ATOM | 3321 | O | HOH | W | 10 | 24.261 | 15.545 | 23.596 | 1.00 | 20.36 | W | O |
| ATOM | 3322 | O | HOH | W | 11 | 21.576 | 15.248 | 30.051 | 1.00 | 49.80 | W | O |
| ATOM | 3323 | O | HOH | W | 12 | 35.572 | 26.561 | 20.456 | 1.00 | 9.26 | W | O |
| ATOM | 3324 | O | HOH | W | 13 | 38.540 | 19.732 | 20.019 | 1.00 | 21.04 | W | O |
| ATOM | 3325 | O | HOH | W | 14 | −5.412 | −8.837 | 34.482 | 1.00 | 45.91 | W | O |
| ATOM | 3326 | O | HOH | W | 15 | 2.208 | 5.048 | 25.082 | 1.00 | 32.03 | W | O |
| ATOM | 3327 | O | HOH | W | 16 | −0.989 | 9.732 | 21.431 | 1.00 | 22.15 | W | O |
| ATOM | 3328 | O | HOH | W | 17 | 3.737 | 6.567 | 16.038 | 1.00 | 32.59 | W | O |
| ATOM | 3329 | O | HOH | W | 18 | 5.237 | 3.133 | 19.299 | 1.00 | 13.15 | W | O |
| ATOM | 3330 | O | HOH | W | 19 | 5.670 | 12.226 | 35.549 | 1.00 | 26.18 | W | O |
| ATOM | 3331 | O | HOH | W | 20 | 9.735 | 26.361 | 26.531 | 1.00 | 51.28 | W | O |
| ATOM | 3332 | O | HOH | W | 21 | 13.414 | 26.349 | 9.078 | 1.00 | 58.01 | W | O |
| ATOM | 3333 | O | HOH | W | 22 | 27.812 | 8.520 | 33.983 | 1.00 | 44.37 | W | O |
| ATOM | 3334 | O | HOH | W | 23 | 28.703 | 9.909 | 29.073 | 1.00 | 17.83 | W | O |
| ATOM | 3335 | O | HOH | W | 24 | 18.405 | 12.660 | 31.845 | 1.00 | 29.55 | W | O |
| ATOM | 3336 | O | HOH | W | 25 | 21.097 | 2.480 | 23.252 | 1.00 | 29.73 | W | O |
| ATOM | 3337 | O | HOH | W | 26 | 22.335 | 1.166 | 26.425 | 1.00 | 37.92 | W | O |
| ATOM | 3338 | O | HOH | W | 27 | 19.293 | −9.491 | 35.226 | 1.00 | 29.40 | W | O |
| ATOM | 3339 | O | HOH | W | 28 | 19.368 | −7.237 | 37.257 | 1.00 | 30.35 | W | O |
| ATOM | 3340 | O | HOH | W | 29 | 19.894 | −10.520 | 38.745 | 1.00 | 36.47 | W | O |
| ATOM | 3341 | O | HOH | W | 30 | 34.228 | −1.440 | 26.257 | 1.00 | 38.40 | W | O |
| ATOM | 3342 | O | HOH | W | 31 | 53.762 | 18.520 | 23.907 | 1.00 | 11.65 | W | O |
| ATOM | 3343 | O | HOH | W | 32 | 38.131 | 9.669 | 11.164 | 1.00 | 58.77 | W | O |
| ATOM | 3344 | O | HOH | W | 33 | 27.201 | 24.350 | 5.916 | 1.00 | 29.41 | W | O |
| ATOM | 3345 | O | HOH | W | 34 | 22.785 | 21.508 | 3.661 | 1.00 | 45.48 | W | O |
| ATOM | 3346 | O | HOH | W | 35 | 24.075 | 21.960 | −2.139 | 1.00 | 25.69 | W | O |
| ATOM | 3347 | O | HOH | W | 36 | 27.925 | 25.285 | −3.132 | 1.00 | 58.01 | W | O |
| ATOM | 3348 | O | HOH | W | 37 | 28.308 | 27.218 | −1.453 | 1.00 | 28.78 | W | O |
| ATOM | 3349 | O | HOH | W | 38 | 25.955 | 26.997 | −1.007 | 1.00 | 34.74 | W | O |
| ATOM | 3350 | O | HOH | W | 39 | 31.511 | 8.345 | 38.443 | 1.00 | 33.24 | W | O |
| ATOM | 3351 | O | HOH | W | 40 | 34.529 | 9.647 | 40.896 | 1.00 | 33.94 | W | O |
| ATOM | 3352 | O | HOH | W | 41 | 24.665 | 36.439 | 25.124 | 1.00 | 30.47 | W | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3353 | O | HOH | W | 42 | 30.953 | 36.100 | 28.619 | 1.00 | 46.95 | W | O |
| ATOM | 3354 | O | HOH | W | 43 | 26.625 | 37.296 | 27.179 | 1.00 | 24.97 | W | O |
| ATOM | 3355 | O | HOH | W | 44 | 5.989 | 7.527 | −1.763 | 1.00 | 35.64 | W | O |
| ATOM | 3356 | O | HOH | W | 45 | 8.005 | 5.050 | −1.718 | 1.00 | 32.20 | W | O |
| ATOM | 3357 | O | HOH | W | 46 | 8.798 | 3.105 | −3.343 | 1.00 | 34.34 | W | O |
| ATOM | 3358 | O | HOH | W | 47 | 6.861 | 1.939 | 5.704 | 1.00 | 28.48 | W | O |
| ATOM | 3359 | O | HOH | W | 48 | 7.144 | −1.672 | −0.808 | 1.00 | 57.81 | W | O |
| ATOM | 3360 | O | HOH | W | 49 | 10.918 | 10.975 | 3.171 | 1.00 | 34.54 | W | O |
| ATOM | 3361 | O | HOH | W | 50 | 46.848 | −6.879 | 19.916 | 1.00 | 55.91 | W | O |
| ATOM | 3362 | O | HOH | W | 51 | 12.892 | 13.878 | 44.766 | 1.00 | 49.87 | W | O |
| ATOM | 3363 | O | HOH | W | 52 | 13.448 | 16.065 | 43.862 | 1.00 | 41.35 | W | O |
| ATOM | 3364 | O | HOH | W | 53 | 15.480 | 15.270 | 41.619 | 1.00 | 47.41 | W | O |
| ATOM | 3365 | O | HOH | W | 54 | 23.110 | −0.161 | 20.397 | 1.00 | 32.85 | W | O |
| ATOM | 3366 | O | HOH | W | 55 | 21.316 | 16.675 | 36.656 | 1.00 | 33.54 | W | O |
| ATOM | 3367 | O | HOH | W | 56 | 26.287 | 3.189 | 28.843 | 1.00 | 35.19 | W | O |
| ATOM | 3368 | O | HOH | W | 57 | 3.971 | −0.285 | 22.159 | 1.00 | 17.55 | W | O |
| ATOM | 3369 | O | HOH | W | 58 | −0.893 | −7.294 | 24.607 | 1.00 | 31.21 | W | O |
| ATOM | 3370 | O | HOH | W | 59 | 12.124 | −6.921 | 42.456 | 1.00 | 31.98 | W | O |
| ATOM | 3371 | O | HOH | W | 60 | 17.301 | −15.220 | 40.505 | 1.00 | 45.55 | W | O |
| ATOM | 3372 | O | HOH | W | 61 | 18.104 | −13.256 | 42.320 | 1.00 | 37.94 | W | O |
| ATOM | 3373 | O | HOH | W | 62 | 15.133 | −13.791 | 32.864 | 1.00 | 45.33 | W | O |
| ATOM | 3374 | O | HOH | W | 63 | 45.247 | 16.625 | 20.535 | 1.00 | 23.95 | W | O |
| ATOM | 3375 | O | HOH | W | 64 | 44.108 | 37.578 | 34.812 | 1.00 | 25.60 | W | O |
| ATOM | 3376 | O | HOH | W | 65 | 5.600 | 18.711 | 41.701 | 1.00 | 24.10 | W | O |
| ATOM | 3377 | O | HOH | W | 66 | 6.367 | −0.303 | 47.824 | 1.00 | 26.09 | W | O |
| ATOM | 3378 | O | HOH | W | 67 | 28.757 | −2.874 | 6.968 | 1.00 | 45.07 | W | O |
| ATOM | 3379 | O | HOH | W | 68 | 28.254 | −5.350 | 10.006 | 1.00 | 37.55 | W | O |
| ATOM | 3380 | O | HOH | W | 69 | 49.711 | 21.467 | 28.396 | 1.00 | 19.45 | W | O |
| ATOM | 3381 | O | HOH | W | 70 | 3.834 | 1.904 | 49.049 | 1.00 | 32.00 | W | O |
| ATOM | 3382 | O | HOH | W | 71 | 12.585 | 35.908 | 14.550 | 1.00 | 30.75 | W | O |
| ATOM | 3383 | O | HOH | W | 72 | 23.662 | 8.496 | 35.017 | 1.00 | 34.12 | W | O |
| ATOM | 3384 | O | HOH | W | 73 | 1.854 | −9.295 | 46.367 | 1.00 | 38.49 | W | O |
| ATOM | 3385 | O | HOH | W | 74 | 16.996 | 25.375 | 41.316 | 1.00 | 46.26 | W | O |
| ATOM | 3386 | O | HOH | W | 75 | 28.435 | 5.284 | 20.699 | 1.00 | 51.41 | W | O |
| ATOM | 3387 | O | HOH | W | 76 | 31.339 | 34.305 | 4.604 | 1.00 | 47.26 | W | O |
| ATOM | 3388 | O | HOH | W | 77 | 43.209 | 36.903 | 38.192 | 1.00 | 40.56 | W | O |
| ATOM | 3389 | O | HOH | W | 78 | 18.534 | 8.166 | 18.201 | 1.00 | 21.71 | W | O |
| ATOM | 3390 | O | HOH | W | 79 | 19.257 | −17.750 | 43.319 | 1.00 | 49.46 | W | O |
| ATOM | 3391 | O | HOH | W | 80 | 4.548 | −15.020 | 27.393 | 1.00 | 35.16 | W | O |
| ATOM | 3392 | O | HOH | W | 81 | 37.891 | 37.741 | 14.334 | 1.00 | 28.47 | W | O |
| ATOM | 3393 | O | HOH | W | 82 | 19.555 | 6.021 | −3.469 | 1.00 | 41.81 | W | O |
| ATOM | 3394 | O | HOH | W | 83 | 13.160 | 38.556 | 28.946 | 1.00 | 42.47 | W | O |
| ATOM | 3395 | O | HOH | W | 84 | 16.111 | −1.404 | 48.455 | 1.00 | 23.81 | W | O |
| ATOM | 3396 | O | HOH | W | 85 | 36.480 | 8.405 | 9.683 | 1.00 | 54.82 | W | O |
| ATOM | 3397 | O | HOH | W | 86 | −5.399 | 11.875 | 11.431 | 1.00 | 31.63 | W | O |
| ATOM | 3398 | O | HOH | W | 87 | 46.331 | 34.561 | 29.060 | 1.00 | 33.82 | W | O |
| ATOM | 3399 | O | HOH | W | 88 | 17.381 | 13.193 | 38.445 | 1.00 | 34.15 | W | O |
| ATOM | 3400 | O | HOH | W | 89 | 29.865 | 0.288 | 3.291 | 1.00 | 26.03 | W | O |
| ATOM | 3401 | O | HOH | W | 90 | 5.840 | 27.514 | 21.177 | 1.00 | 31.41 | W | O |
| ATOM | 3402 | O | HOH | W | 91 | 54.962 | 16.049 | 23.364 | 1.00 | 41.98 | W | O |
| ATOM | 3403 | O | HOH | W | 92 | −3.615 | 12.554 | 5.180 | 1.00 | 23.80 | W | O |
| ATOM | 3404 | O | HOH | W | 93 | 12.453 | 26.483 | 43.131 | 1.00 | 34.43 | W | O |
| ATOM | 3405 | O | HOH | W | 94 | 41.972 | 29.690 | 19.741 | 1.00 | 36.86 | W | O |
| ATOM | 3406 | O | HOH | W | 95 | 18.293 | −13.215 | 45.009 | 1.00 | 32.97 | W | O |
| ATOM | 3407 | O | HOH | W | 96 | 10.012 | 26.686 | 5.797 | 1.00 | 36.17 | W | O |
| ATOM | 3408 | O | HOH | W | 97 | −0.948 | 2.487 | 41.360 | 1.00 | 45.62 | W | O |
| ATOM | 3409 | O | HOH | W | 98 | 27.187 | 0.707 | 9.726 | 1.00 | 31.68 | W | O |
| ATOM | 3410 | O | HOH | W | 99 | −2.994 | −3.671 | 10.429 | 1.00 | 52.08 | W | O |
| ATOM | 3411 | O | HOH | W | 100 | 26.106 | −1.698 | 12.043 | 1.00 | 21.52 | W | O |
| ATOM | 3412 | O | HOH | W | 101 | 25.679 | −0.186 | 14.451 | 1.00 | 32.91 | W | O |
| ATOM | 3413 | O | HOH | W | 102 | 26.238 | 1.847 | 13.110 | 1.00 | 36.46 | W | O |
| ATOM | 3414 | O | HOH | W | 103 | 21.921 | −3.789 | 17.655 | 1.00 | 25.13 | W | O |
| ATOM | 3415 | O | HOH | W | 104 | 25.159 | −4.436 | 17.508 | 1.00 | 53.25 | W | O |
| ATOM | 3416 | O | HOH | W | 105 | 22.242 | −8.386 | 9.467 | 1.00 | 29.86 | W | O |
| ATOM | 3417 | O | HOH | W | 106 | 21.908 | −12.759 | 8.872 | 1.00 | 34.18 | W | O |
| ATOM | 3418 | O | HOH | W | 107 | 21.434 | −16.111 | 4.629 | 1.00 | 41.28 | W | O |
| ATOM | 3419 | O | HOH | W | 108 | −2.907 | −13.049 | 44.414 | 1.00 | 30.16 | W | O |
| ATOM | 3420 | O | HOH | W | 109 | −0.126 | −13.651 | 44.027 | 1.00 | 34.20 | W | O |
| ATOM | 3421 | O | HOH | W | 110 | −4.280 | −9.444 | 54.210 | 1.00 | 37.30 | W | O |
| ATOM | 3422 | O | HOH | W | 111 | −6.729 | −10.645 | 54.918 | 1.00 | 43.11 | W | O |
| ATOM | 3423 | O | HOH | W | 112 | −1.542 | −9.713 | 50.342 | 1.00 | 48.54 | W | O |
| ATOM | 3424 | O | HOH | W | 113 | −0.887 | 3.470 | 48.555 | 1.00 | 40.94 | W | O |
| ATOM | 3425 | O | HOH | W | 114 | 6.375 | 2.534 | 55.249 | 1.00 | 46.63 | W | O |
| ATOM | 3426 | O | HOH | W | 115 | 1.971 | −14.567 | 32.704 | 1.00 | 35.50 | W | O |
| ATOM | 3427 | O | HOH | W | 116 | 1.743 | 1.689 | 24.959 | 1.00 | 30.92 | W | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3428 | O | HOH | W | 117 | −0.139 | −0.886 | 44.717 | 1.00 | 40.59 | W | O |
| ATOM | 3429 | O | HOH | W | 118 | 0.916 | −2.559 | 48.745 | 1.00 | 46.72 | W | O |
| ATOM | 3430 | O | HOH | W | 119 | 9.947 | 3.243 | 49.696 | 1.00 | 53.06 | W | O |
| ATOM | 3431 | O | HOH | W | 120 | 15.147 | 8.977 | 45.117 | 1.00 | 36.12 | W | O |
| ATOM | 3432 | O | HOH | W | 121 | 20.215 | 18.879 | 37.211 | 1.00 | 37.08 | W | O |
| ATOM | 3433 | O | HOH | W | 122 | 19.867 | 19.619 | 34.326 | 1.00 | 56.02 | W | O |
| ATOM | 3434 | O | HOH | W | 123 | 17.296 | 25.755 | 20.837 | 1.00 | 29.17 | W | O |
| ATOM | 3435 | O | HOH | W | 124 | 24.794 | 16.970 | 25.644 | 1.00 | 38.85 | W | O |
| ATOM | 3436 | O | HOH | W | 125 | 23.888 | 8.296 | 15.260 | 1.00 | 44.98 | W | O |
| ATOM | 3437 | O | HOH | W | 126 | 16.997 | 22.931 | 24.791 | 1.00 | 46.27 | W | O |
| ATOM | 3438 | O | HOH | W | 127 | 16.999 | 20.205 | 28.703 | 1.00 | 42.25 | W | O |
| ATOM | 3439 | O | HOH | W | 128 | 14.299 | 27.213 | 26.342 | 1.00 | 47.41 | W | O |
| ATOM | 3440 | O | HOH | W | 129 | 13.962 | 29.676 | 29.021 | 1.00 | 44.74 | W | O |
| ATOM | 3441 | O | HOH | W | 130 | 9.837 | −12.752 | 21.380 | 1.00 | 29.81 | W | O |
| ATOM | 3442 | O | HOH | W | 131 | 19.479 | −10.794 | 15.591 | 1.00 | 27.67 | W | O |
| ATOM | 3443 | O | HOH | W | 132 | 10.112 | −5.869 | 11.094 | 1.00 | 46.01 | W | O |
| ATOM | 3444 | O | HOH | W | 133 | 5.850 | 1.393 | 21.300 | 1.00 | 24.93 | W | O |
| ATOM | 3445 | O | HOH | W | 134 | 4.687 | 5.090 | 23.228 | 1.00 | 32.16 | W | O |
| ATOM | 3446 | O | HOH | W | 135 | 12.643 | −7.745 | 28.490 | 1.00 | 52.18 | W | O |
| ATOM | 3447 | O | HOH | W | 136 | 14.128 | −7.548 | 30.513 | 1.00 | 47.97 | W | O |
| ATOM | 3448 | O | HOH | W | 137 | 16.206 | −9.477 | 30.623 | 1.00 | 44.64 | W | O |
| ATOM | 3449 | O | HOH | W | 138 | 15.325 | −12.125 | 30.795 | 1.00 | 39.50 | W | O |
| ATOM | 3450 | O | HOH | W | 139 | 17.541 | −14.127 | 29.779 | 1.00 | 55.43 | W | O |
| ATOM | 3451 | O | HOH | W | 140 | 11.870 | −12.470 | 29.712 | 1.00 | 41.38 | W | O |
| ATOM | 3452 | O | HOH | W | 141 | 10.876 | −12.714 | 27.322 | 1.00 | 31.03 | W | O |
| ATOM | 3453 | O | HOH | W | 142 | 9.217 | −21.047 | 30.535 | 1.00 | 40.07 | W | O |
| ATOM | 3454 | O | HOH | W | 143 | 5.177 | −8.919 | 16.234 | 1.00 | 47.67 | W | O |
| ATOM | 3455 | O | HOH | W | 144 | 42.186 | 15.613 | 36.965 | 1.00 | 51.41 | W | O |
| ATOM | 3456 | O | HOH | W | 145 | 3.524 | 9.362 | 48.993 | 1.00 | 40.52 | W | O |
| ATOM | 3457 | O | HOH | W | 146 | 49.550 | 3.039 | 12.553 | 1.00 | 54.20 | W | O |
| ATOM | 3458 | O | HOH | W | 147 | 48.385 | −1.991 | 19.707 | 1.00 | 44.91 | W | O |
| ATOM | 3459 | O | HOH | W | 148 | 22.135 | 23.729 | −2.670 | 1.00 | 32.91 | W | O |
| ATOM | 3460 | O | HOH | W | 149 | 25.649 | 20.661 | −1.052 | 1.00 | 32.57 | W | O |
| ATOM | 3461 | O | HOH | W | 150 | 23.484 | 17.334 | 4.921 | 1.00 | 33.19 | W | O |
| ATOM | 3462 | O | HOH | W | 151 | 23.066 | 16.772 | 0.087 | 1.00 | 62.43 | W | O |
| ATOM | 3463 | O | HOH | W | 152 | 15.463 | 16.820 | 1.694 | 1.00 | 36.38 | W | O |
| ATOM | 3464 | O | HOH | W | 153 | 30.317 | 27.269 | −0.562 | 1.00 | 52.08 | W | O |
| ATOM | 3465 | O | HOH | W | 154 | 28.306 | 30.027 | −2.274 | 1.00 | 47.95 | W | O |
| ATOM | 3466 | O | HOH | W | 155 | 24.989 | 32.148 | −0.965 | 1.00 | 54.13 | W | O |
| ATOM | 3467 | O | HOH | W | 156 | 32.169 | 37.778 | 3.875 | 1.00 | 58.61 | W | O |
| ATOM | 3468 | O | HOH | W | 157 | 13.191 | 36.298 | 5.915 | 1.00 | 45.17 | W | O |
| ATOM | 3469 | O | HOH | W | 158 | 9.921 | −6.856 | 5.770 | 1.00 | 41.04 | W | O |
| ATOM | 3470 | O | HOH | W | 159 | 12.779 | −11.044 | 3.525 | 1.00 | 50.55 | W | O |
| ATOM | 3471 | O | HOH | W | 160 | 10.871 | 11.401 | 43.473 | 1.00 | 67.60 | W | O |
| ATOM | 3472 | O | HOH | W | 161 | 2.428 | 19.618 | 40.350 | 1.00 | 51.52 | W | O |
| ATOM | 3473 | O | HOH | W | 162 | 24.841 | 5.806 | 34.275 | 1.00 | 37.19 | W | O |
| ATOM | 3474 | O | HOH | W | 163 | 36.638 | −1.185 | 34.282 | 1.00 | 45.94 | W | O |
| ATOM | 3475 | O | HOH | W | 164 | 40.791 | −0.922 | 30.142 | 1.00 | 48.68 | W | O |
| ATOM | 3476 | O | HOH | W | 165 | 18.155 | −11.172 | 22.401 | 1.00 | 55.12 | W | O |
| ATOM | 3477 | O | HOH | W | 166 | 20.563 | −12.551 | 19.508 | 1.00 | 37.29 | W | O |
| ATOM | 3478 | O | HOH | W | 167 | 22.920 | −4.816 | 24.095 | 1.00 | 45.38 | W | O |
| ATOM | 3479 | O | HOH | W | 168 | 23.641 | −3.466 | 21.333 | 1.00 | 59.26 | W | O |
| ATOM | 3480 | O | HOH | W | 169 | 35.609 | 13.783 | 40.120 | 1.00 | 46.99 | W | O |
| ATOM | 3481 | O | HOH | W | 170 | −3.439 | −7.166 | 32.556 | 1.00 | 34.59 | W | O |
| ATOM | 3482 | O | HOH | W | 171 | −4.626 | −6.690 | 30.550 | 1.00 | 43.68 | W | O |
| ATOM | 3483 | O | HOH | W | 172 | 0.101 | −6.049 | 38.990 | 1.00 | 52.74 | W | O |
| ATOM | 3484 | O | HOH | W | 173 | 9.987 | −4.321 | 45.025 | 1.00 | 43.43 | W | O |
| ATOM | 3485 | O | HOH | W | 174 | 14.493 | −3.895 | 44.817 | 1.00 | 38.49 | W | O |
| ATOM | 3486 | O | HOH | W | 175 | 53.116 | 11.194 | 13.682 | 1.00 | 57.33 | W | O |
| ATOM | 3487 | O | HOH | W | 176 | 55.394 | 12.707 | 14.576 | 1.00 | 58.12 | W | O |
| ATOM | 3488 | O | HOH | W | 177 | 55.981 | 8.917 | 13.494 | 1.00 | 59.59 | W | O |
| ATOM | 3489 | O | HOH | W | 178 | 51.678 | 8.781 | 13.549 | 1.00 | 63.80 | W | O |
| ATOM | 3490 | O | HOH | W | 179 | 54.744 | 16.041 | 13.908 | 1.00 | 51.05 | W | O |
| ATOM | 3491 | O | HOH | W | 180 | 52.718 | 18.170 | 12.653 | 1.00 | 60.85 | W | O |
| ATOM | 3492 | O | HOH | W | 181 | 50.998 | 18.396 | 9.982 | 1.00 | 57.81 | W | O |
| ATOM | 3493 | O | HOH | W | 182 | 48.158 | 17.495 | 10.701 | 1.00 | 37.79 | W | O |
| ATOM | 3494 | O | HOH | W | 183 | 48.198 | 18.596 | 12.500 | 1.00 | 45.68 | W | O |
| ATOM | 3495 | O | HOH | W | 184 | 14.625 | −10.774 | 27.905 | 1.00 | 48.91 | W | O |
| ATOM | 3496 | O | HOH | W | 185 | 12.684 | −8.342 | 26.124 | 1.00 | 75.83 | W | O |
| ATOM | 3497 | O | HOH | W | 186 | 14.494 | −7.815 | 24.938 | 1.00 | 60.33 | W | O |
| ATOM | 3498 | O | HOH | W | 187 | 16.518 | −7.725 | 25.888 | 1.00 | 77.63 | W | O |
| ATOM | 3499 | O | HOH | W | 188 | 17.707 | −6.957 | 28.003 | 1.00 | 69.87 | W | O |
| ATOM | 3500 | O | HOH | W | 189 | 18.452 | −7.246 | 26.198 | 1.00 | 70.59 | W | O |
| ATOM | 3501 | O | HOH | W | 190 | 38.391 | −0.173 | 35.296 | 1.00 | 62.35 | W | O |
| ATOM | 3502 | O | HOH | W | 191 | 42.304 | 0.294 | 36.211 | 1.00 | 56.56 | W | O |

TABLE 10-continued

Structure coordinates for ERalpha-LBD/Compound 2 complex

| | # | Name | Res. | Chain | Res # | X | Y | Z | occ | B | SegID | |
|---|---|---|---|---|---|---|---|---|---|---|---|---|
| ATOM | 3503 | O | HOH | W | 192 | 40.833 | 1.750 | 34.254 | 1.00 | 52.36 | W | O |
| ATOM | 3504 | O | HOH | W | 193 | 42.374 | 4.718 | 32.166 | 1.00 | 51.94 | W | O |
| ATOM | 3505 | O | HOH | W | 194 | 41.272 | 6.298 | 34.010 | 1.00 | 59.49 | W | O |
| ATOM | 3506 | O | HOH | W | 195 | 44.297 | 3.746 | 43.942 | 1.00 | 46.56 | W | O |
| ATOM | 3507 | O | HOH | W | 196 | 40.796 | 8.301 | 33.300 | 1.00 | 66.27 | W | O |
| ATOM | 3508 | O | HOH | W | 197 | 39.009 | 10.241 | 38.457 | 1.00 | 61.33 | W | O |
| ATOM | 3509 | O | HOH | W | 198 | 37.921 | 10.242 | 36.162 | 1.00 | 60.42 | W | O |
| ATOM | 3510 | O | HOH | W | 199 | 43.853 | 18.983 | 21.471 | 1.00 | 55.77 | W | O |
| ATOM | 3511 | O | HOH | W | 200 | 36.954 | 22.119 | 24.982 | 1.00 | 40.42 | W | O |
| ATOM | 3512 | O | HOH | W | 201 | 38.871 | 20.315 | 24.194 | 1.00 | 53.21 | W | O |
| ATOM | 3513 | O | HOH | W | 202 | 38.060 | 19.076 | 22.826 | 1.00 | 55.69 | W | O |
| ATOM | 3514 | O | HOH | W | 203 | 40.437 | 20.699 | 24.783 | 1.00 | 61.23 | W | O |
| ATOM | 3515 | O | HOH | W | 204 | 39.504 | 24.381 | 14.904 | 1.00 | 33.72 | W | O |
| ATOM | 3516 | O | HOH | W | 205 | 51.115 | 6.282 | 6.270 | 1.00 | 42.53 | W | O |
| ATOM | 3517 | O | HOH | W | 207 | 51.470 | 4.625 | 10.983 | 1.00 | 69.98 | W | O |
| ATOM | 3518 | O | HOH | W | 208 | −6.837 | −10.130 | 41.729 | 1.00 | 68.40 | W | O |
| ATOM | 3519 | O | HOH | W | 209 | −3.530 | −11.849 | 46.277 | 1.00 | 58.44 | W | O |
| ATOM | 3520 | O | HOH | W | 210 | −8.613 | −10.367 | 47.063 | 1.00 | 50.93 | W | O |
| ATOM | 3521 | O | HOH | W | 211 | 53.971 | 8.468 | 21.837 | 1.00 | 48.86 | W | O |
| ATOM | 3522 | O | HOH | W | 212 | 55.183 | 3.235 | 21.483 | 1.00 | 47.58 | W | O |
| ATOM | 3523 | O | HOH | W | 213 | 56.630 | 3.649 | 23.756 | 1.00 | 60.21 | W | O |
| ATOM | 3524 | O | HOH | W | 214 | 54.787 | 4.239 | 27.738 | 1.00 | 49.35 | W | O |
| ATOM | 3525 | O | HOH | W | 215 | 56.878 | 5.064 | 29.179 | 1.00 | 63.29 | W | O |
| ATOM | 3526 | O | HOH | W | 216 | 57.127 | 5.093 | 32.021 | 1.00 | 58.56 | W | O |
| ATOM | 3527 | O | HOH | W | 217 | 57.815 | 1.447 | 32.130 | 1.00 | 63.51 | W | O |
| ATOM | 3528 | O | HOH | W | 218 | 56.328 | 1.146 | 29.708 | 1.00 | 64.81 | W | O |
| ATOM | 3529 | O | HOH | W | 219 | 56.419 | −0.280 | 27.916 | 1.00 | 58.80 | W | O |
| ATOM | 3530 | O | HOH | W | 220 | 31.206 | 30.519 | 40.575 | 1.00 | 73.87 | W | O |
| ATOM | 3531 | O | HOH | W | 221 | 33.450 | 31.265 | 37.544 | 1.00 | 58.62 | W | O |
| ATOM | 3532 | O | HOH | W | 222 | 38.726 | 33.763 | 42.724 | 1.00 | 51.03 | W | O |
| ATOM | 3533 | O | HOH | W | 223 | 40.911 | 34.144 | 41.656 | 1.00 | 40.29 | W | O |
| ATOM | 3534 | O | HOH | W | 224 | 43.344 | 29.123 | 36.328 | 1.00 | 54.66 | W | O |
| ATOM | 3535 | O | HOH | W | 225 | 45.020 | 24.574 | 37.518 | 1.00 | 56.10 | W | O |
| ATOM | 3536 | O | HOH | W | 226 | −6.021 | 1.718 | 13.376 | 1.00 | 54.09 | W | O |
| TER | 3537 | | HOH | W | 226 | | | | | | | |
| ATOM | 3538 | C1 | 132 | A | 1 | 12.606 | 0.987 | 36.558 | 1.00 | 73.26 | A2 | C |
| ATOM | 3539 | C2 | 132 | A | 1 | 12.416 | 1.343 | 35.217 | 1.00 | 73.12 | A2 | C |
| ATOM | 3540 | C3 | 132 | A | 1 | 12.376 | 0.351 | 34.204 | 1.00 | 73.19 | A2 | C |
| ATOM | 3541 | C4 | 132 | A | 1 | 12.536 | −1.032 | 34.553 | 1.00 | 73.10 | A2 | C |
| ATOM | 3542 | C5 | 132 | A | 1 | 12.723 | −1.368 | 35.909 | 1.00 | 73.30 | A2 | C |
| ATOM | 3543 | C6 | 132 | A | 1 | 12.756 | −0.371 | 36.909 | 1.00 | 73.45 | A2 | C |
| ATOM | 3544 | N11 | 132 | A | 1 | 12.187 | 0.684 | 32.858 | 1.00 | 72.85 | A2 | N |
| ATOM | 3545 | C12 | 132 | A | 1 | 12.986 | −0.134 | 31.855 | 1.00 | 72.83 | A2 | C |
| ATOM | 3546 | C13 | 132 | A | 1 | 12.744 | −1.610 | 32.102 | 1.00 | 73.01 | A2 | C |
| ATOM | 3547 | C14 | 132 | A | 1 | 12.506 | −2.060 | 33.446 | 1.00 | 73.07 | A2 | C |
| ATOM | 3548 | C15 | 132 | A | 1 | 12.725 | −2.506 | 31.016 | 1.00 | 73.16 | A2 | C |
| ATOM | 3549 | C16 | 132 | A | 1 | 12.468 | −3.865 | 31.260 | 1.00 | 73.45 | A2 | C |
| ATOM | 3550 | C17 | 132 | A | 1 | 12.229 | −4.343 | 32.570 | 1.00 | 73.31 | A2 | C |
| ATOM | 3551 | C18 | 132 | A | 1 | 12.250 | −3.439 | 33.657 | 1.00 | 73.24 | A2 | C |
| ATOM | 3552 | S22 | 132 | A | 1 | 11.329 | 1.584 | 31.932 | 1.00 | 71.97 | A2 | S |
| ATOM | 3553 | C23 | 132 | A | 1 | 9.758 | 0.896 | 31.354 | 1.00 | 72.06 | A2 | C |
| ATOM | 3554 | C24 | 132 | A | 1 | 9.558 | −0.462 | 31.744 | 1.00 | 71.58 | A2 | C |
| ATOM | 3555 | C25 | 132 | A | 1 | 8.396 | −1.167 | 31.346 | 1.00 | 71.25 | A2 | C |
| ATOM | 3556 | C26 | 132 | A | 1 | 7.432 | −0.528 | 30.548 | 1.00 | 71.23 | A2 | C |
| ATOM | 3557 | C27 | 132 | A | 1 | 7.623 | 0.821 | 30.143 | 1.00 | 71.54 | A2 | C |
| ATOM | 3558 | C28 | 132 | A | 1 | 8.782 | 1.532 | 30.539 | 1.00 | 71.74 | A2 | C |
| ATOM | 3559 | O33 | 132 | A | 1 | 12.069 | 1.969 | 30.752 | 1.00 | 73.34 | A2 | O |
| ATOM | 3560 | O34 | 132 | A | 1 | 10.962 | 2.618 | 32.850 | 1.00 | 71.79 | A2 | O |
| ATOM | 3561 | O35 | 132 | A | 1 | 6.303 | −1.217 | 30.155 | 1.00 | 71.40 | A2 | O |
| ATOM | 3562 | F36 | 132 | A | 1 | 12.441 | −4.723 | 30.235 | 1.00 | 73.35 | A2 | F |
| ATOM | 3563 | C38 | 132 | A | 1 | 14.495 | 0.223 | 31.912 | 1.00 | 72.96 | A2 | C |
| TER | 3564 | | 132 | A | 1 | | | | | | | |
| ATOM | 3565 | C1 | 132 | B | 1 | 40.522 | 4.159 | 23.224 | 1.00 | 76.73 | B2 | C |
| ATOM | 3566 | C2 | 132 | B | 1 | 39.710 | 5.283 | 23.234 | 1.00 | 75.93 | B2 | C |
| ATOM | 3567 | C3 | 132 | B | 1 | 39.706 | 6.160 | 24.357 | 1.00 | 75.78 | B2 | C |
| ATOM | 3568 | C4 | 132 | B | 1 | 40.524 | 5.904 | 25.487 | 1.00 | 76.08 | B2 | C |
| ATOM | 3569 | C5 | 132 | B | 1 | 41.338 | 4.770 | 25.464 | 1.00 | 76.38 | B2 | C |
| ATOM | 3570 | C6 | 132 | B | 1 | 41.341 | 3.915 | 24.351 | 1.00 | 76.42 | B2 | C |
| ATOM | 3571 | N11 | 132 | B | 1 | 38.923 | 7.259 | 24.378 | 1.00 | 75.80 | B2 | N |
| ATOM | 3572 | C12 | 132 | B | 1 | 38.214 | 7.554 | 25.711 | 1.00 | 75.91 | B2 | C |
| ATOM | 3573 | C13 | 132 | B | 1 | 39.272 | 7.658 | 26.798 | 1.00 | 75.42 | B2 | C |
| ATOM | 3574 | C14 | 132 | B | 1 | 40.449 | 6.847 | 26.669 | 1.00 | 75.60 | B2 | C |
| ATOM | 3575 | C15 | 132 | B | 1 | 39.105 | 8.536 | 27.890 | 1.00 | 74.78 | B2 | C |
| ATOM | 3576 | C16 | 132 | B | 1 | 40.128 | 8.607 | 28.859 | 1.00 | 74.25 | B2 | C |
| ATOM | 3577 | C17 | 132 | B | 1 | 41.302 | 7.833 | 28.747 | 1.00 | 74.65 | B2 | C |

TABLE 10-continued

Structure coordinates for ERalpha-LBD/Compound 2 complex

|      | #    | Name | Res. | Chain | Res # | X      | Y      | Z      | occ  | B     | SegID |   |
|------|------|------|------|-------|-------|--------|--------|--------|------|-------|-------|---|
| ATOM | 3578 | C18  | 132  | B     | 1     | 41.450 | 6.957  | 27.652 | 1.00 | 75.32 | B2    | C |
| ATOM | 3579 | S22  | 132  | B     | 1     | 38.586 | 8.453  | 23.468 | 1.00 | 75.83 | B2    | S |
| ATOM | 3580 | C23  | 132  | B     | 1     | 39.632 | 9.935  | 23.540 | 1.00 | 75.88 | B2    | C |
| ATOM | 3581 | C24  | 132  | B     | 1     | 40.671 | 9.897  | 24.513 | 1.00 | 75.77 | B2    | C |
| ATOM | 3582 | C25  | 132  | B     | 1     | 41.543 | 11.012 | 24.674 | 1.00 | 75.75 | B2    | C |
| ATOM | 3583 | C26  | 132  | B     | 1     | 41.360 | 12.162 | 23.871 | 1.00 | 75.73 | B2    | C |
| ATOM | 3584 | C27  | 132  | B     | 1     | 40.326 | 12.207 | 22.922 | 1.00 | 75.92 | B2    | C |
| ATOM | 3585 | C28  | 132  | B     | 1     | 39.468 | 11.104 | 22.757 | 1.00 | 75.97 | B2    | C |
| ATOM | 3586 | O33  | 132  | B     | 1     | 37.216 | 8.864  | 23.612 | 1.00 | 76.50 | B2    | O |
| ATOM | 3587 | O34  | 132  | B     | 1     | 38.986 | 7.869  | 22.211 | 1.00 | 75.68 | B2    | O |
| ATOM | 3588 | O35  | 132  | B     | 1     | 42.191 | 13.243 | 24.018 | 1.00 | 76.24 | B2    | O |
| ATOM | 3589 | F36  | 132  | B     | 1     | 39.987 | 9.426  | 29.904 | 1.00 | 74.26 | B2    | F |
| ATOM | 3590 | C38  | 132  | B     | 1     | 37.163 | 6.446  | 26.067 | 1.00 | 76.47 | B2    | C |
| TER  | 3591 |      | 132  | B     | 1     |        |        |        |      |       |       |   |

Other embodiments are in the claims.

What is claimed is:

1. A method of designing or selecting a candidate agent that interacts with an estrogen receptor alpha (ERα), comprising:
   (a) utilizing the X-ray three-dimensional coordinates of a complex of an ERα ligand binding domain and a ligand according to Table 9 or Table 10, ± a root mean square deviation for alpha carbon atoms of not more than 1.5 Å, to generate a three-dimensional model, wherein the ligand is 4-[1-allyl-7-(trifluoromethyl)-1H-indazol-3-yl]benzene-1,3-diol) (Compound 1) or 4-[(8-Fluoro-6-methylphenanthridin-5(6H)-yl)sulfonyl]phenol) (Compound 2), and wherein the ligand is capable of forming one or more of the following interactions with the ERα ligand binding domain:
      (i) hydroxyl group of the A ring of Compound 1 forms hydrogen bonds with the side chains of Glu353 and Arg394 of SEQ ID NO:1,
      (ii) the hydroxyl group of Compound 2 forms hydrogen bonds with the side chain of Glu353 of SEQ ID NO:1,
      (iii) the phenyl group of Compound 1 and Compound 2 interacts with Phe404 of SEQ ID NO:1;
      (iv) Compound 1 and 2 interact indirectly with Phe425 and His524 of SEQ ID NO:1;
      (v) the indazole group of Compound 1 and the phenanthridine group of Compound 2 form hydrophobic interactions with the ERα ligand binding domain; or
      (vi) the allyl group of Compound 1 and the phenanthroline group of Compound 2 interact with Met421 of SEQ ID NO:1;
   (b) identifying the amino acid residues forming the ligand binding pocket of the ERα ligand binding domain from the three-dimensional model in step (a) in order to generate a three-dimensional representation of the ligand binding pocket of ERα, wherein the ligand binding pocket comprises amino acids Glu353, Arg394, Phe404, Met421, Phe425 and His524 of SEQ ID NO: 1, according to Table 9 or 10 ± a root mean square deviation for alpha carbon atoms of not more than 1.5 Å; and wherein said three-dimensional representation of the ligand binding pocket optionally has the ligand from step (a) present or absent;
   (c) employing said three-dimensional representation from step (b) to design or select said candidate agent such that the interactions from step (a) are maintained between the candidate agent and the ERα ligand binding pocket;
   (d) contacting said candidate agent with said ERα ligand binding domain to determine the ability of said candidate agent to interact or bind said ERα ligand binding domain;
   whereby the detection of the ability of said candidate agent to interact or bind said ERα ligand binding domain, thereby identifies said candidate agent as an agent that interacts with the ERα.

2. The method of claim 1, further comprising synthesizing the candidate agent.

3. The method of claim 1, wherein the design or selection of step (c) comprises determining a fit between the structural coordinates of the amino acids of the ERα ligand binding domain and a three-dimensional structure of the candidate agent.

4. The method of claim 1, wherein the design or selection step comprises altering a computer-displayed representation of the three-dimensional structure of the candidate agent in the three-dimensional model.

5. The method of claim 1, wherein the ligand inhibits NFκB transcriptional activity and does not stimulate proliferation of mouse or uterine tissue.

6. The method of claim 1 further comprising altering a computer-displayed representation of the ligand of the model.

7. The method of claim 6, wherein altering the computer-displayed representation of the ligand comprises changing the structural coordinates of the ligand.

8. The method of claim 6, wherein altering the computer-displayed representation of the ligand comprises changing the chemical structure of the ligand.

9. The method of claim 6, wherein altering the computer-displayed representation of the ligand comprises superimposing the three-dimensional structure of the candidate agent over the computer-displayed representation of the ligand.

10. The method of claim 1, wherein the ligand binding domain of the estrogen receptor alpha comprises amino acids Ser301 to Ser554 of SEQ ID NO:1.

11. The method of claim 1, wherein estrogen receptor alpha comprises the amino acid sequence of SEQ ID NO:1.

12. The method of claim 1, wherein the candidate agent inhibits NFκB transcriptional activity.

13. The method of claim 1, wherein the ligand has anti-rheumatic activity.

14. The method of claim 1, wherein the structural coordinates of the ligand and the ERα ligand binding domain are according to Tables 9 or 10, +/− a root mean square deviation for alpha carbon atoms of not more than 1.0 Å.

15. The method of claim 1, wherein the structural coordinates of the ligand and the ERα ligand binding domain are according to Tables 9 or 10, +/− a root mean square deviation for alpha carbon atoms of not more than 0.5 Å.

16. The method of claim 1, wherein the candidate agent is a ligand of the estrogen receptor alpha (ERα) having the structure of the formula:

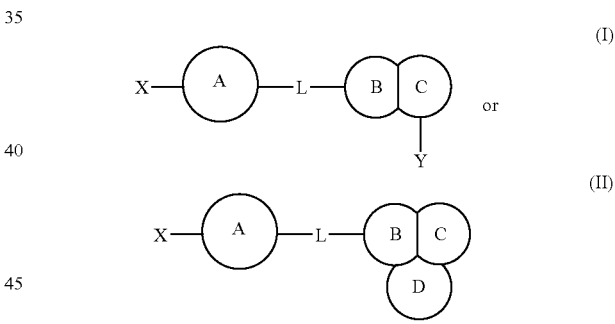

wherein A, B, C, and D represent ring systems; rings B and C of compound I are fused rings, and ring B has at least one nitrogen; rings B, C and D of compound II are fused rings, wherein ring B is fused to ring C and ring C is fused to ring D, or rings C and D are each fused to ring B; L is a linker moiety selected from the group consisting of a direct chemical bond, a sulfonyl, an alkyl, an alkenyl, and an alkynyl; X is a substituent of ring A; Y of compound I includes a carbon chain of not more than ten carbon atoms; rings A, B and C of compounds I and II and ring D of compound II are each independently formed of at least four atoms, and one or more atoms in rings A, B, or C are independently heteroatoms.

17. The method of claim 16, wherein rings B and C of compound I form an indazole.

18. The method of claim 16, wherein rings B, C, and D of compound II form a phenanthridine.

19. A method of designing or selecting a candidate agent that interacts with an estrogen receptor alpha (ERα), comprising:

(a) utilizing the X-ray three-dimensional coordinates of a complex of the ERα ligand binding domain and a ligand according to Table 9, ± a root mean square deviation for alpha carbon atoms of not more than 1.5 Å, to generate a three-dimensional model, wherein the ligand is 4-[1-allyl-7-(trifluoromethyl)-1H-indazol-3-yl]benzene-1,3-diol) (Compound 1), and wherein the ligand is capable of forming one or more of the following interactions with the ERα ligand binding domain:
(i) hydroxyl group of the A ring of Compound 1 forms hydrogen bonds with the side chains of Glu353 and Arg394 of SEQ ID NO:1,
(ii) the phenyl group of Compound 1 interacts with Phe404 of SEQ ID NO:1;
(iii) Compound 1 interacts indirectly with Phe425 and His524 of SEQ ID NO:1;
(iv) the indazole group of Compound 1 form hydrophobic interactions with the ERα ligand binding domain; or
(v) the allyl group of Compound 1 interacts with Met421 of SEQ ID NO:1;
(b) identifying the amino acid residues forming the ligand binding pocket of the ERα ligand binding domain from the three-dimensional model in step (a) in order to generate a three-dimensional representation of the ligand binding pocket of ERα, wherein the ligand binding pocket comprises amino acids Glu353, Arg394, Phe404, Met421, Phe425 and His524 of SEQ ID NO: 1, according to Table 9 ± a root mean square deviation for alpha carbon atoms of not more than 1.5Å; and wherein said three-dimensional representation of the ligand binding pocket optionally has the ligand from step (a) present or absent;
(c) employing said three-dimensional representation from step (b) to design or select said candidate agent such that the interactions from step (a) are maintained between the candidate agent and the ERα ligand binding pocket;
(d) synthesizing the candidate agent; and
(e) contacting said candidate agent with said ERα ligand binding domain to determine the ability of said candidate agent to interact or bind said ERα ligand binding domain;
whereby the detection of the ability of said candidate agent to interact or bind said ERα ligand binding domain, thereby identifies said candidate agent as an agent that interacts with the ERα.

20. A method of designing or selecting a candidate agent that interacts with an estrogen receptor alpha (ERα), comprising:
(a) utilizing the X-ray three-dimensional coordinates of a complex of the ERα ligand binding domain and a ligand according to Table 10, ± a root mean square deviation for alpha carbon atoms of not more than 1.5 Å, to generate a three-dimensional model, wherein the ligand is 4-[(8-Fluoro-6-methylphenanthridin-5(6H)-yl)sulfonyl]phenol) (Compound 2), and wherein the ligand is capable of forming one or more of the following interactions with the ERα ligand binding domain:
(i) the hydroxyl group of Compound 2 forms hydrogen bonds with the side chain of Glu353 of SEQ ID NO:1,
(ii) the phenyl group of Compound 2 interacts with Phe404 of SEQ ID NO:1;
(iii) Compound 2 interacts indirectly with Phe425 and His524 of SEQ ID NO: 1;
(iv) the phenanthridine group of Compound 2 forms hydrophobic interactions with the ERα ligand binding domain; or
(v) the phenanthroline group of Compound 2 interact with Met421 of SEQ ID NO:1;
(b) identifying the amino acid residues forming the ligand binding pocket of the ERα ligand binding domain from the three-dimensional model in step (a) in order to generate a three-dimensional representation of the ligand binding pocket of ERα, wherein the ligand binding pocket comprises amino acids Glu353, Arg394, Phe404, Met421, Phe425 and His524 of SEQ ID NO: 1, according to Table 10 ± a root mean square deviation for alpha carbon atoms of not more than 1.5 Å; and wherein said three-dimensional representation of the ligand binding pocket optionally has the ligand from step (a) present or absent;
(c) employing said three-dimensional representation from step (b) to design or select said candidate agent such that the interactions from step (a) are maintained between the candidate agent and the ERα ligand binding pocket;
(d) synthesizing the candidate agent; and
(e) contacting said candidate agent with said ERα ligand binding domain to determine the ability of said candidate agent to interact or bind said ERα ligand binding domain;
whereby the detection of the ability of said candidate agent to interact or bind said ERα ligand binding domain, thereby identifies said candidate agent as an agent that interacts with the ERα.

21. The method of any of claim 1, 19 or 20, further comprising obtaining the agent.

22. The method of claim 21, further comprising detecting the ability of the agent to bind in vitro or in vivo to the ligand binding domain of the estrogen receptor alpha.

23. A method of designing or selecting an agent that interacts with an estrogen receptor alpha (ERα), comprising:
(a) providing a three-dimensional structure of a complex comprising a human ERα ligand binding domain and 4-[1-allyl-7-(trifluoromethyl)-1H-indazol-3-yl]benzene-1,3-diol) (Compound 1), said three-dimensional structure being obtained by subjecting a co-crystal comprising the ERα ligand binding domain in complex with Compound 1, wherein said ERα ligand binding domain comprises the amino acid sequence of SEQ ID NO:1, and said co-crystal is characterized by space group C2, with dimensions unit cell dimensions a=104.80 Å, b=54.12 Å, c=97.10 Å, α=γ=90° C. and β=104.8°, to X-ray diffraction and collecting data sufficient to determine the three-dimensional structure of said complex;
(b) generating a three-dimensional model from the three-dimensional structure of said complex;
(c) identifying the amino acid residues forming the ligand binding pocket of the ERα ligand binding domain from the three-dimensional model in step (b) in order to generate a three-dimensional representation of the ligand binding pocket of ERα, wherein the ligand binding pocket comprises amino acids Glu353, Arg394, Phe404, Met421, Phe425 and His524 of SEQ ID NO: 1, according to Table 9 ± a root mean square deviation for alpha carbon atoms of not more than 1.5 Å; and wherein said three-dimensional representation of the ligand binding pocket optionally has the ligand from step (a) present or absent;
(d) employing said three dimensional representation from step (c) to design or select said candidate agent; and
(e) contacting said candidate agent with said ERα ligand binding domain to determine the ability of said candidate agent to interact or bind said ERα ligand binding domain;

whereby the detection of the ability of said candidate agent to interact or bind said ERα ligand binding domain thereby identifies said candidate agent as an agent that interacts with the ERα.

24. A method of designing or selecting an agent that interacts with an estrogen receptor alpha (ERα), comprising:
(a) providing a three-dimensional structure of a complex comprising a human ERα ligand binding domain and 4-[(8-Fluoro-6-methylphenanthridin-5(6H)-yl)sulfonyl]phenol) (Compound 2), said three-dimensional structure being obtained by subjecting a co-crystal comprising the ERα ligand binding domain in complex with Compound 2, wherein said ERα ligand binding domain comprises the amino acid sequence of SEQ ID NO:1, and said co-crystal is characterized by space group C2, with dimensions unit cell dimensions a=105.128 Å, b=52.927 Å, c=95.534 Å, and β=113.247°, to X-ray diffraction and collecting data sufficient to determine the three-dimensional structure of said complex;
(b) generating a three-dimensional model from the three-dimensional structure of said complex;
(c) identifying the amino acid residues forming the ligand binding pocket of the ERα ligand binding domain from the three-dimensional model in step (b) in order to generate a three-dimensional representation of the ligand binding pocket of ERα, wherein the ligand binding pocket comprises amino acids Glu353, Arg394, Phe404, Met421, Phe425 and His524 of SEQ ID NO: 1, according to Table 10 ± a root mean square deviation for alpha carbon atoms of not more than 1.5 Å; and wherein said three-dimensional representation of the ligand binding pocket optionally has the ligand from step (a) present or absent;
(d) employing said three dimensional representation from step (c) to design or select said candidate agent;
(e) contacting said candidate agent with said ERα ligand binding domain to determine the ability of said candidate agent to interact or bind said ERα ligand binding domain;
whereby the detection of the ability of said candidate agent to interact or bind said ERα ligand binding domain thereby identifies said candidate agent as an agent that interacts with the ERα.

25. The method of claim 23, further comprising synthesizing said candidate agent.

26. The method of claim 24, further comprising synthesizing said candidate agent.

27. The method of claim 25 or 26, further comprising detecting the ability of the candidate agent to bind in vitro or in vivo to the ligand binding domain of the estrogen receptor alpha.

28. The method of claim 16, wherein the candidate agent is a ligand of the estrogen receptor alpha (ERα) having the structure of the formula:

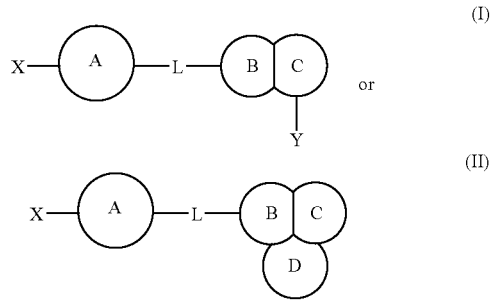

wherein A of the ligand is selected from the group consisting of a phenyl, a thiophene, a pyrrole, and a methyl-pyrrole; B of the ligand comprises at least one nitrogen atom; and X is selected from the group consisting of a hydroxy substituent, an amino substituent, a cyano substituent, a nitro substituent, a sulfur-containing substituent, and amido substituent, and an oxo substituent.

* * * * *